United States Patent
Cusack et al.

(10) Patent No.: US 9,783,794 B2
(45) Date of Patent: *Oct. 10, 2017

(54) INFLUENZA A 2009 PANDEMIC H1N1 POLYPEPTIDE FRAGMENTS COMPRISING ENDONUCLEASE ACTIVITY AND THEIR USE

(71) Applicant: European Molecular Biology Laboratory (EMBL), Heidelberg (DE)

(72) Inventors: Stephen Cusack, Seyssinet-Pariset (FR); Eva Kowalinski, Hirschberg (DE); Chloe Zubieta, Le Fontanil-Cornillon (FR)

(73) Assignee: European Molecular Biology Laboratory (EMBL), Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/751,634

(22) Filed: Jun. 26, 2015

(65) Prior Publication Data

US 2016/0053241 A1 Feb. 25, 2016

Related U.S. Application Data

(62) Division of application No. 13/635,064, filed as application No. PCT/EP2011/001274 on Mar. 15, 2011, now Pat. No. 9,181,307.

(60) Provisional application No. 61/340,335, filed on Mar. 16, 2010.

(51) Int. Cl.
| | |
|---|---|
| *C12N 9/22* | (2006.01) |
| *A61K 31/33* | (2006.01) |
| *C07K 14/005* | (2006.01) |
| *C07D 211/32* | (2006.01) |
| *C07D 211/96* | (2006.01) |
| *C07D 311/62* | (2006.01) |
| *C07H 19/10* | (2006.01) |
| *C07K 16/40* | (2006.01) |
| *G06F 19/16* | (2011.01) |
| *A61K 38/00* | (2006.01) |

(52) U.S. Cl.
CPC .............. *C12N 9/22* (2013.01); *A61K 31/33* (2013.01); *C07D 211/32* (2013.01); *C07D 211/96* (2013.01); *C07D 311/62* (2013.01); *C07H 19/10* (2013.01); *C07K 14/005* (2013.01); *C07K 16/40* (2013.01); *G06F 19/16* (2013.01); *A61K 38/00* (2013.01); *C07K 2299/00* (2013.01); *C07K 2317/34* (2013.01); *C12N 2760/16122* (2013.01)

(58) Field of Classification Search
None
See application file for complete search history.

(56) References Cited

U.S. PATENT DOCUMENTS

2005/0143402 A1   6/2005   Cheetham et al.

FOREIGN PATENT DOCUMENTS

| JP | 2013-521786 | 6/2013 |
| WO | 2011/113579 | 9/2011 |

OTHER PUBLICATIONS

Obayashi et al. (The structural basis for an essential subunit interaction in influenza virus RNA polymerase, Nature, vol. 454, No. 28, 2008, pp. 1127-1132).*
Dias et al., "The cap-snatching endonuclease of influenza virus polymerase resides in the PA subunit", Nature, 2009, vol. 458, p. 914-918.
Garten et al., "Antigenic and Genetic Characteristics of Swine-Origin 2009 A(H1N1) Influenza Viruses Circulating in Humans", Science, 2009, vol. 325, p. 197-201.
Garten et al., "Supporting Online Material for Antigenic and Genetic Characteristics of Swine-Origin 2009 A(H1N1) In", Science, 2009. Retrieved from the Internet: http://www.sciencemag.org/content/325/593.
Mizutani et al., "Systematic study on crystal-contact engineering of diphthine synthase: influence of mutations at crystal-packing regions on X-ray diffraction quality", Acta Cryst. 2008, D64, p. 1020-1033.
Gerloff et al., Sep. 1, 2009; "SubName: Full-Polymerase acidic protein; flags: Fragment:"; XP002637949, retrieved from EBI accession No. UNIPROT: C6HOY9; database accession No. C6HOY9; compound.
Eshagi et al., Oct. 3, 2009; "Subname: Full+Polymerase PA; Flags: Fragment;", XP002637950, retrieved from EBI accession No. UNIPROT: C8CTT5; Database accession No. C8CTT5; compound.
Garten, R. J. et al., "Antigenic and Genetic Characteristics of Swine-Origin 2009 A(H1N1) Influenza Viruses Circulating in Humans," Science, 2009, 325, 197-201.

(Continued)

*Primary Examiner* — Suzanne M Noakes
*Assistant Examiner* — Jae W Lee
(74) *Attorney, Agent, or Firm* — Barnes & Thornburg LLP

(57) ABSTRACT

The present invention relates to polypeptide fragments comprising an amino-terminal fragment of the PA subunit of a viral RNA-dependent RNA polymerase possessing endonuclease activity, wherein the PA subunit is from Influenza A 2009 pandemic H1N1 virus or is a variant thereof. This invention also relates to (i) crystals of the polypeptide fragments which are suitable for structure determination of the polypeptide fragments using X-ray crystallography and (ii) computational methods using the structural coordinates of the polypeptide to screen for and design compounds that modulate, preferably inhibit the endonucleolytically active site within the polypeptide fragment. In addition, this invention relates to methods of identifying compounds that bind to the PA polypeptide fragments possessing endonuclease activity and preferably inhibit the endonucleolytic activity, as well as the compounds themselves. Preferably, the compounds are identifiable by the methods disclosed herein or the pharmaceutical compositions are producible by the methods disclosed herein.

14 Claims, 209 Drawing Sheets

(56) References Cited

OTHER PUBLICATIONS

Kuzuhara, X et al., "Green tea catchhins inhibit the endonuclease activity of influenza A virus RNA polymerase," PLOS Currents, 2009, XP002637952.
Hayden, F., "Developing New Antiviral Agents for Influenza Treatment: What Does the Future Hold?" Clinical Infection Diseases, 2009, 48, Suppl. 1, S3-S13.
Sleeman, K. et al., "In Vitro Antiviral Activity of Favipiravir (T-705) against Drug-Resistance Influenza and 2009 A(H1N1) Viruses," Antimicrobial Agents and Chemotherapy, 2010, 54, 2517-2524.
Zhao, C. et al., "Nucleoside Monophosphate Complex Structures of the Endonuclease Domain from the Influenza Virus Polymerase PA Subunit Reveal the Substrate Binding Site inside the Catalytic Center," Journal of Virology, 2009, 83, 9024-9030.
Dias, A. et al., "The cap-snatching endonuclease of influenza virus polymerase resides in the PA subunit," Nature, 2009, 458, 914-918.
Nistal-Villan, E. et al., "New prospects for the rational design of antivirals," Nature Medicine, 2009, 15, 1253-1254.
Hastings, J.C. et al., "Anti-influenza virus activities of 4-substituted 2,4-dioxobutanoic acid inhibitors," Antimicrobial Agents and Chemotherapy, 1996, 40, 1304-1307.
Wienceck, J., "New Strategies for Protein Crystal Growth," Ann. Rev. Biomed. Eng., 1, 505-534.

Dubois, R. et al., "Structural and Biochemical Basis for Development of Influenza Virus Inhibitors Targeting the PA Endonuclease," PLOT Pathogens, 2012, 8, 1-13.
Nakazawa, M. et al., "PA subunit of RNA polymerase as a promising target for anti-influenza virus agents," Antiviral Res., 2008, 78, 194-201.
Thathaisong, U. et al., "Human monoclonal single chain antibodies (HuScFv) that bind to the polymerase proteins of influenza A virus," Asian Pac. J. Allergy Immunol., 2008, 26, 23-35.
Yuan, P. et al., "Crystal structure of an avian influenza polymerase $PA_N$ reveals an endonuclease active site," Nature, 2009, 458, 909-913.
Liu, Y. et al., "Structure-function studies of the influenza virus RNA polymerase PA subunit," Science in China Series C: Life Sciences, 2009, 52, 450-458.
Hara, K. et al., "Amino acid residues in the N-terminal region of the PA subunit of influenza A virus RNA polymerase play a critical role in protein stability, endonuclease activity, cap binding, and virion RNA promoter binding," J. Virology, 2006, 80, 7789-7798.
International Search Report and Written Opinion prepared for PCT/EP2011/001274, mailed Jun. 19, 2012, 23 pages.
Tomassini et al., 1994, Inhibition of Cap (m7GpppXm)-Dependent Endonuclease of Influenza Virus by 4-Substituted 2, 4-Dioxobutanoic Acid Compounds, Antimicrobial Agents and Chemotherapy, vol. 38, No. 12., pp. 2827-2837.

\* cited by examiner

```
Native H1N1 polypeptide fragment (Chain A)
HEADER      ----                                           XX-XXX-XX   xxxx
COMPND      ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.10
REMARK   3   RESOLUTION RANGE LOW  (ANGSTROMS) :  20.00
REMARK   3   DATA CUTOFF            (SIGMA(F)) :  NONE
REMARK   3   COMPLETENESS FOR RANGE        (%) :  98.97
REMARK   3   NUMBER OF REFLECTIONS             :  63279
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE     (WORKING + TEST SET) :  0.22341
REMARK   3   R VALUE            (WORKING SET) :  0.22159
REMARK   3   FREE R VALUE                     :  0.26801
REMARK   3   FREE R VALUE TEST SET SIZE   (%) :  4.0
REMARK   3   FREE R VALUE TEST SET COUNT      :  2639
REMARK   3
REMARK   3  FIT IN THE HIGHEST RESOLUTION BIN.
REMARK   3   TOTAL NUMBER OF BINS USED           :       20
REMARK   3   BIN RESOLUTION RANGE HIGH           :    2.100
REMARK   3   BIN RESOLUTION RANGE LOW            :    2.154
REMARK   3   REFLECTION IN BIN     (WORKING SET) :     4547
REMARK   3   BIN COMPLETENESS (WORKING+TEST) (%) :    97.48
REMARK   3   BIN R VALUE           (WORKING SET) :    0.248
REMARK   3   BIN FREE R VALUE SET COUNT          :      204
REMARK   3   BIN FREE R VALUE                    :    0.291
REMARK   3
REMARK   3  NUMBER OF NON-HYDROGEN ATOMS USED IN REFINEMENT.
REMARK   3   ALL ATOMS              :     6568
REMARK   3
REMARK   3  B VALUES.
REMARK   3   FROM WILSON PLOT           (A**2) : NULL
REMARK   3   MEAN B VALUE      (OVERALL, A**2) :  33.980
REMARK   3   OVERALL ANISOTROPIC B VALUE.
REMARK   3    B11 (A**2) :    0.00
REMARK   3    B22 (A**2) :    0.04
REMARK   3    B33 (A**2) :   -0.04
REMARK   3    B12 (A**2) :    0.00
REMARK   3    B13 (A**2) :   -0.02
REMARK   3    B23 (A**2) :    0.00
REMARK   3
REMARK   3  ESTIMATED OVERALL COORDINATE ERROR.
REMARK   3   ESU BASED ON R VALUE                       (A): 0.199
REMARK   3   ESU BASED ON FREE R VALUE                  (A): 0.184
REMARK   3   ESU BASED ON MAXIMUM LIKELIHOOD            (A): 0.131
REMARK   3   ESU FOR B VALUES BASED ON MAXIMUM LIKELIHOOD (A**2): 4.762
REMARK   3
REMARK   3 CORRELATION COEFFICIENTS.
REMARK   3   CORRELATION COEFFICIENT FO-FC      :  0.928
REMARK   3   CORRELATION COEFFICIENT FO-FC FREE :  0.893
REMARK   3
REMARK   3 RMS DEVIATIONS FROM IDEAL VALUES        COUNT    RMS    WEIGHT
```

FIG. 1A

```
REMARK   3   BOND LENGTHS REFINED ATOMS       (A):  6502 ; 0.026 ; 0.022
REMARK   3   BOND ANGLES REFINED ATOMS  (DEGREES):  8730 ; 2.114 ; 1.941
REMARK   3   TORSION ANGLES, PERIOD 1   (DEGREES):   758 ; 7.213 ; 5.000
REMARK   3   TORSION ANGLES, PERIOD 2   (DEGREES):   346 ;35.310 ;33.526
REMARK   3   TORSION ANGLES, PERIOD 3   (DEGREES):  1222 ;19.330 ;15.000
REMARK   3   TORSION ANGLES, PERIOD 4   (DEGREES):    56 ;20.187 ;15.000
REMARK   3   CHIRAL-CENTER RESTRAINTS       (A**3):   938 ; 0.155 ; 0.200
REMARK   3   GENERAL PLANES REFINED ATOMS     (A):  4900 ; 0.012 ; 0.020
REMARK   3
REMARK   3   ISOTROPIC THERMAL FACTOR RESTRAINTS.   COUNT   RMS    WEIGHT
REMARK   3   MAIN-CHAIN BOND REFINED ATOMS  (A**2):  3820 ; 1.364 ; 1.500
REMARK   3   MAIN-CHAIN ANGLE REFINED ATOMS (A**2):  6192 ; 2.379 ; 2.000
REMARK   3   SIDE-CHAIN BOND REFINED ATOMS  (A**2):  2682 ; 3.867 ; 3.000
REMARK   3   SIDE-CHAIN ANGLE REFINED ATOMS (A**2):  2538 ; 5.937 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  : NULL
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS    :   1.40
REMARK   3   ION PROBE RADIUS    :   0.80
REMARK   3   SHRINKAGE RADIUS    :   0.80
REMARK   3
REMARK   3  OTHER REFINEMENT REMARKS:
REMARK   3   U VALUES       : REFINED INDIVIDUALLY
REMARK   3
LINKR           GLU A   64                 ASN A   69                    gap
LINKR           GLU C   64                 ASN C   69                    gap
LINKR           ILE C  138                 ASN C  142                    gap
LINKR           GLU B   64                 ASN B   69                    gap
LINKR           GLU D   64                 ASN D   69                    gap
LINKR           ILE D  138                 ASN D  142                    gap
CRYST1  263.630   66.240   66.320  90.00  95.98  90.00 C 1 2 1
SCALE1     0.003793  0.000000  0.000397    0.00000
SCALE2     0.000000  0.015097  0.000000    0.00000
SCALE3     0.000000  0.000000  0.015161    0.00000
ATOM      1  N   GLY A  -2     106.920  36.113 -16.120  1.00 42.11           N
ATOM      2  CA  GLY A  -2     107.197  36.607 -14.722  1.00 42.42           C
ATOM      3  C   GLY A  -2     106.306  37.763 -14.247  1.00 42.64           C
ATOM      4  O   GLY A  -2     106.398  38.220 -13.071  1.00 42.95           O
ATOM      5  N   MET A  -1     105.422  38.235 -15.136  1.00 42.19           N
ATOM      6  CA  MET A  -1     104.454  39.289 -14.808  1.00 41.62           C
ATOM      7  CB  MET A  -1     103.457  39.402 -15.946  1.00 42.52           C
ATOM      8  CG  MET A  -1     102.421  40.555 -15.917  1.00 47.58           C
ATOM      9  SD  MET A  -1     100.922  40.056 -16.866  1.00 59.76           S
ATOM     10  CE  MET A  -1      99.977  39.071 -15.666  1.00 58.22           C
ATOM     11  C   MET A  -1     103.711  38.952 -13.499  1.00 40.62           C
ATOM     12  O   MET A  -1     103.430  39.841 -12.678  1.00 38.80           O
ATOM     13  N   ALA A   0     103.391  37.665 -13.306  1.00 38.62           N
ATOM     14  CA  ALA A   0     102.561  37.313 -12.164  1.00 37.98           C
ATOM     15  CB  ALA A   0     102.144  35.841 -12.242  1.00 38.44           C
ATOM     16  C   ALA A   0     103.311  37.598 -10.850  1.00 35.87           C
ATOM     17  O   ALA A   0     102.751  38.144  -9.897  1.00 34.89           O
```

FIG. 1B

```
ATOM   18  N    MET A  1     104.590  37.247 -10.790  1.00 33.89           N
ATOM   19  CA   MET A  1     105.271  37.492  -9.543  1.00 33.49           C
ATOM   20  CB   MET A  1     106.518  36.611  -9.384  1.00 34.19           C
ATOM   21  CG   MET A  1     107.436  37.038  -8.233  1.00 33.79           C
ATOM   22  SD   MET A  1     106.782  36.651  -6.599  1.00 37.21           S
ATOM   23  CE   MET A  1     107.366  34.945  -6.546  1.00 34.04           C
ATOM   24  C    MET A  1     105.561  38.983  -9.344  1.00 32.13           C
ATOM   25  O    MET A  1     105.475  39.490  -8.218  1.00 30.65           O
ATOM   26  N    GLU A  2     105.805  39.692 -10.432  1.00 32.04           N
ATOM   27  CA   GLU A  2     106.093  41.143 -10.347  1.00 33.26           C
ATOM   28  CB   GLU A  2     106.453  41.711 -11.741  1.00 34.23           C
ATOM   29  CG   GLU A  2     106.964  43.179 -11.676  1.00 37.06           C
ATOM   30  CD   GLU A  2     106.799  44.010 -13.027  1.00 43.24           C
ATOM   31  OE1  GLU A  2     106.583  43.427 -14.154  1.00 36.15           O
ATOM   32  OE2  GLU A  2     106.889  45.274 -12.911  1.00 44.58           O
ATOM   33  C    GLU A  2     104.889  41.897  -9.827  1.00 33.56           C
ATOM   34  O    GLU A  2     105.031  42.794  -9.016  1.00 34.09           O
ATOM   35  N    ASP A  3     103.706  41.593 -10.377  1.00 33.72           N
ATOM   36  CA   ASP A  3     102.423  42.039  -9.798  1.00 34.07           C
ATOM   37  CB   ASP A  3     101.300  41.380 -10.599  1.00 36.24           C
ATOM   38  CG   ASP A  3     101.268  41.859 -12.022  1.00 39.95           C
ATOM   39  OD1  ASP A  3     102.165  42.658 -12.371  1.00 46.54           O
ATOM   40  OD2  ASP A  3     100.368  41.438 -12.778  1.00 46.06           O
ATOM   41  C    ASP A  3     102.185  41.651  -8.323  1.00 32.78           C
ATOM   42  O    ASP A  3     101.657  42.422  -7.544  1.00 31.80           O
ATOM   43  N    PHE A  4     102.489  40.415  -7.950  1.00 31.44           N
ATOM   44  CA   PHE A  4     102.310  40.074  -6.547  1.00 30.67           C
ATOM   45  CB   PHE A  4     102.654  38.598  -6.293  1.00 30.24           C
ATOM   46  CG   PHE A  4     102.680  38.280  -4.850  1.00 29.43           C
ATOM   47  CD1  PHE A  4     101.477  38.056  -4.165  1.00 30.86           C
ATOM   48  CE1  PHE A  4     101.487  37.848  -2.742  1.00 30.63           C
ATOM   49  CZ   PHE A  4     102.726  37.837  -2.039  1.00 29.79           C
ATOM   50  CE2  PHE A  4     103.933  38.077  -2.737  1.00 30.85           C
ATOM   51  CD2  PHE A  4     103.872  38.292  -4.150  1.00 26.32           C
ATOM   52  C    PHE A  4     103.170  40.984  -5.646  1.00 29.79           C
ATOM   53  O    PHE A  4     102.736  41.450  -4.558  1.00 30.94           O
ATOM   54  N    VAL A  5     104.420  41.216  -6.064  1.00 30.48           N
ATOM   55  CA   VAL A  5     105.391  41.980  -5.260  1.00 29.36           C
ATOM   56  CB   VAL A  5     106.750  41.975  -5.963  1.00 29.08           C
ATOM   57  CG1  VAL A  5     107.689  42.974  -5.341  1.00 30.12           C
ATOM   58  CG2  VAL A  5     107.379  40.663  -5.854  1.00 28.29           C
ATOM   59  C    VAL A  5     104.893  43.391  -5.079  1.00 30.37           C
ATOM   60  O    VAL A  5     104.839  43.988  -3.974  1.00 29.91           O
ATOM   61  N    ARG A  6     104.447  43.938  -6.185  1.00 31.19           N
ATOM   62  CA   ARG A  6     103.939  45.319  -6.118  1.00 33.22           C
ATOM   63  CB   ARG A  6     103.770  45.939  -7.538  1.00 32.70           C
ATOM   64  CG   ARG A  6     105.082  46.029  -8.302  1.00 32.45           C
ATOM   65  CD   ARG A  6     104.899  46.627  -9.647  1.00 35.90           C
ATOM   66  NE   ARG A  6     106.156  46.609 -10.372  1.00 38.38           N
ATOM   67  CZ   ARG A  6     107.124  47.499 -10.167  1.00 39.22           C
ATOM   68  NH1  ARG A  6     106.951  48.504  -9.313  1.00 38.07           N
ATOM   69  NH2  ARG A  6     108.242  47.408 -10.846  1.00 39.11           N
ATOM   70  C    ARG A  6     102.703  45.545  -5.228  1.00 32.81           C
ATOM   71  O    ARG A  6     102.496  46.644  -4.772  1.00 33.19           O
ATOM   72  N    GLN A  7     101.881  44.519  -4.973  1.00 33.24           N
ATOM   73  CA   GLN A  7     100.780  44.711  -4.058  1.00 32.91           C
ATOM   74  CB   GLN A  7      99.476  44.128  -4.612  1.00 33.20           C
ATOM   75  CG   GLN A  7      99.463  42.611  -4.729  1.00 37.26           C
ATOM   76  CD   GLN A  7      98.171  42.066  -5.417  1.00 48.45           C
ATOM   77  OE1  GLN A  7      97.277  42.847  -5.795  1.00 50.00           O
ATOM   78  NE2  GLN A  7      98.102  40.727  -5.626  1.00 48.29           N
ATOM   79  C    GLN A  7     101.079  44.182  -2.654  1.00 33.62           C
ATOM   80  O    GLN A  7     100.299  44.397  -1.770  1.00 32.93           O
```

FIG. 1C

| | | | | | | | | | | |
|---|---|---|---|---|---|---|---|---|---|---|
| ATOM | 81 | N | CYS | A | 8 | 102.177 | 43.440 | -2.474 | 1.00 33.35 | N |
| ATOM | 82 | CA | CYS | A | 8 | 102.481 | 42.866 | -1.192 | 1.00 33.91 | C |
| ATOM | 83 | CB | CYS | A | 8 | 103.316 | 41.566 | -1.329 | 1.00 32.63 | C |
| ATOM | 84 | SG | CYS | A | 8 | 103.610 | 40.718 | 0.309 | 1.00 39.98 | S |
| ATOM | 85 | C | CYS | A | 8 | 103.208 | 43.872 | -0.253 | 1.00 33.14 | C |
| ATOM | 86 | O | CYS | A | 8 | 102.930 | 43.932 | 0.938 | 1.00 33.37 | O |
| ATOM | 87 | N | PHE | A | 9 | 104.104 | 44.667 | -0.814 | 1.00 31.55 | N |
| ATOM | 88 | CA | PHE | A | 9 | 105.010 | 45.524 | -0.030 | 1.00 30.40 | C |
| ATOM | 89 | CB | PHE | A | 9 | 106.448 | 45.248 | -0.499 | 1.00 27.69 | C |
| ATOM | 90 | CG | PHE | A | 9 | 106.903 | 43.833 | -0.211 | 1.00 25.63 | C |
| ATOM | 91 | CD1 | PHE | A | 9 | 107.353 | 43.466 | 1.062 | 1.00 26.07 | C |
| ATOM | 92 | CE1 | PHE | A | 9 | 107.793 | 42.130 | 1.319 | 1.00 27.24 | C |
| ATOM | 93 | CZ | PHE | A | 9 | 107.717 | 41.166 | 0.272 | 1.00 23.99 | C |
| ATOM | 94 | CE2 | PHE | A | 9 | 107.294 | 41.550 | -0.973 | 1.00 23.73 | C |
| ATOM | 95 | CD2 | PHE | A | 9 | 106.831 | 42.891 | -1.179 | 1.00 21.08 | C |
| ATOM | 96 | C | PHE | A | 9 | 104.685 | 47.015 | -0.164 | 1.00 29.41 | C |
| ATOM | 97 | O | PHE | A | 9 | 104.147 | 47.376 | -1.159 | 1.00 30.84 | O |
| ATOM | 98 | N | ASN | A | 10 | 105.003 | 47.836 | 0.845 | 1.00 31.48 | N |
| ATOM | 99 | CA | ASN | A | 10 | 104.954 | 49.343 | 0.796 | 1.00 32.81 | C |
| ATOM | 100 | CB | ASN | A | 10 | 106.003 | 49.954 | 1.744 | 1.00 33.17 | C |
| ATOM | 101 | CG | ASN | A | 10 | 105.617 | 49.821 | 3.046 | 1.00 37.36 | C |
| ATOM | 102 | OD1 | ASN | A | 10 | 104.483 | 49.355 | 3.258 | 1.00 47.16 | O |
| ATOM | 103 | ND2 | ASN | A | 10 | 106.489 | 50.111 | 3.990 | 1.00 40.42 | N |
| ATOM | 104 | C | ASN | A | 10 | 105.505 | 49.853 | -0.488 | 1.00 31.88 | C |
| ATOM | 105 | O | ASN | A | 10 | 106.470 | 49.265 | -0.938 | 1.00 32.03 | O |
| ATOM | 106 | N | PRO | A | 11 | 105.010 | 51.024 | -0.977 | 1.00 31.02 | N |
| ATOM | 107 | CA | PRO | A | 11 | 105.727 | 51.649 | -2.085 | 1.00 29.85 | C |
| ATOM | 108 | CB | PRO | A | 11 | 104.879 | 52.908 | -2.416 | 1.00 29.84 | C |
| ATOM | 109 | CG | PRO | A | 11 | 103.380 | 52.433 | -2.010 | 1.00 32.11 | C |
| ATOM | 110 | CD | PRO | A | 11 | 103.694 | 51.680 | -0.689 | 1.00 32.04 | C |
| ATOM | 111 | C | PRO | A | 11 | 107.203 | 52.062 | -1.713 | 1.00 28.66 | C |
| ATOM | 112 | O | PRO | A | 11 | 107.988 | 52.180 | -2.609 | 1.00 27.80 | O |
| ATOM | 113 | N | MET | A | 12 | 107.494 | 52.332 | -0.437 | 1.00 25.87 | N |
| ATOM | 114 | CA | MET | A | 12 | 108.820 | 52.670 | 0.038 | 1.00 28.94 | C |
| ATOM | 115 | CB | MET | A | 12 | 108.774 | 53.099 | 1.545 | 1.00 30.09 | C |
| ATOM | 116 | CG | MET | A | 12 | 110.174 | 53.272 | 2.135 | 1.00 37.54 | C |
| ATOM | 117 | SD | MET | A | 12 | 110.304 | 53.494 | 3.953 | 1.00 56.33 | S |
| ATOM | 118 | CE | MET | A | 12 | 109.646 | 51.934 | 4.573 | 1.00 50.08 | C |
| ATOM | 119 | C | MET | A | 12 | 109.771 | 51.479 | -0.139 | 1.00 26.98 | C |
| ATOM | 120 | O | MET | A | 12 | 110.867 | 51.607 | -0.653 | 1.00 25.63 | O |
| ATOM | 121 | N | ILE | A | 13 | 109.308 | 50.300 | 0.239 | 1.00 26.06 | N |
| ATOM | 122 | CA | ILE | A | 13 | 110.072 | 49.065 | 0.002 | 1.00 25.53 | C |
| ATOM | 123 | CB | ILE | A | 13 | 109.369 | 47.853 | 0.646 | 1.00 26.04 | C |
| ATOM | 124 | CG1 | ILE | A | 13 | 109.158 | 48.098 | 2.166 | 1.00 27.13 | C |
| ATOM | 125 | CD1 | ILE | A | 13 | 110.363 | 48.591 | 2.856 | 1.00 31.35 | C |
| ATOM | 126 | CG2 | ILE | A | 13 | 110.138 | 46.504 | 0.450 | 1.00 23.46 | C |
| ATOM | 127 | C | ILE | A | 13 | 110.272 | 48.842 | -1.508 | 1.00 25.48 | C |
| ATOM | 128 | O | ILE | A | 13 | 111.392 | 48.579 | -1.975 | 1.00 24.10 | O |
| ATOM | 129 | N | VAL | A | 14 | 109.210 | 48.994 | -2.276 | 1.00 25.92 | N |
| ATOM | 130 | CA | VAL | A | 14 | 109.285 | 48.591 | -3.719 | 1.00 25.96 | C |
| ATOM | 131 | CB | VAL | A | 14 | 107.930 | 48.586 | -4.414 | 1.00 25.30 | C |
| ATOM | 132 | CG1 | VAL | A | 14 | 108.071 | 48.477 | -5.978 | 1.00 26.39 | C |
| ATOM | 133 | CG2 | VAL | A | 14 | 106.973 | 47.441 | -3.805 | 1.00 27.53 | C |
| ATOM | 134 | C | VAL | A | 14 | 110.296 | 49.496 | -4.433 | 1.00 25.98 | C |
| ATOM | 135 | O | VAL | A | 14 | 111.114 | 49.020 | -5.291 | 1.00 23.87 | O |
| ATOM | 136 | N | GLU | A | 15 | 110.274 | 50.764 | -4.043 | 1.00 25.35 | N |
| ATOM | 137 | CA | GLU | A | 15 | 111.147 | 51.772 | -4.683 | 1.00 27.71 | C |
| ATOM | 138 | CB | GLU | A | 15 | 110.803 | 53.205 | -4.179 | 1.00 27.39 | C |
| ATOM | 139 | CG | GLU | A | 15 | 111.648 | 54.380 | -4.744 | 1.00 33.50 | C |
| ATOM | 140 | CD | GLU | A | 15 | 110.861 | 55.741 | -4.786 | 1.00 39.08 | C |
| ATOM | 141 | OE1 | GLU | A | 15 | 110.621 | 56.357 | -3.718 | 1.00 37.10 | O |
| ATOM | 142 | OE2 | GLU | A | 15 | 110.448 | 56.155 | -5.906 | 1.00 44.04 | O |
| ATOM | 143 | C | GLU | A | 15 | 112.612 | 51.454 | -4.349 | 1.00 27.40 | C |

FIG. 1D

```
ATOM  144  O    GLU A  15   113.381  51.391   -5.271  1.00 29.50      O
ATOM  145  N    LEU A  16   112.953  51.231   -3.059  1.00 26.00      N
ATOM  146  CA   LEU A  16   114.324  50.797   -2.607  1.00 25.66      C
ATOM  147  CB   LEU A  16   114.463  50.615   -1.022  1.00 24.84      C
ATOM  148  CG   LEU A  16   114.470  51.912   -0.120  1.00 28.10      C
ATOM  149  CD1  LEU A  16   114.169  51.812    1.363  1.00 24.50      C
ATOM  150  CD2  LEU A  16   115.819  52.795   -0.228  1.00 27.58      C
ATOM  151  C    LEU A  16   114.825  49.601   -3.355  1.00 25.50      C
ATOM  152  O    LEU A  16   115.972  49.577   -3.769  1.00 25.71      O
ATOM  153  N    ALA A  17   113.952  48.600   -3.540  1.00 23.82      N
ATOM  154  CA   ALA A  17   114.260  47.399   -4.263  1.00 23.96      C
ATOM  155  CB   ALA A  17   113.053  46.340   -4.077  1.00 23.48      C
ATOM  156  C    ALA A  17   114.552  47.651   -5.768  1.00 23.90      C
ATOM  157  O    ALA A  17   115.585  47.145   -6.326  1.00 22.52      O
ATOM  158  N    GLU A  18   113.709  48.454   -6.433  1.00 23.41      N
ATOM  159  CA   GLU A  18   113.972  48.771   -7.837  1.00 25.58      C
ATOM  160  CB   GLU A  18   112.837  49.559   -8.481  1.00 27.82      C
ATOM  161  CG   GLU A  18   111.423  48.914   -8.429  1.00 29.86      C
ATOM  162  CD   GLU A  18   110.354  49.936   -8.798  1.00 35.01      C
ATOM  163  OE1  GLU A  18   110.439  51.101   -8.318  1.00 42.13      O
ATOM  164  OE2  GLU A  18   109.441  49.604   -9.572  1.00 37.55      O
ATOM  165  C    GLU A  18   115.299  49.595   -7.982  1.00 26.84      C
ATOM  166  O    GLU A  18   116.003  49.428   -8.947  1.00 27.35      O
ATOM  167  N    LYS A  19   115.580  50.489   -7.035  1.00 27.67      N
ATOM  168  CA   LYS A  19   116.789  51.304   -7.104  1.00 30.64      C
ATOM  169  CB   LYS A  19   116.835  52.322   -5.956  1.00 29.91      C
ATOM  170  CG   LYS A  19   115.802  53.446   -6.099  1.00 36.63      C
ATOM  171  CD   LYS A  19   115.807  54.399   -4.881  1.00 36.59      C
ATOM  172  CE   LYS A  19   115.309  55.763   -5.323  1.00 42.22      C
ATOM  173  NZ   LYS A  19   115.724  56.847   -4.358  1.00 43.08      N
ATOM  174  C    LYS A  19   117.988  50.373   -6.987  1.00 29.27      C
ATOM  175  O    LYS A  19   118.927  50.487   -7.800  1.00 29.84      O
ATOM  176  N    ALA A  20   117.913  49.420   -6.044  1.00 28.62      N
ATOM  177  CA   ALA A  20   119.038  48.541   -5.829  1.00 29.09      C
ATOM  178  CB   ALA A  20   118.866  47.679   -4.563  1.00 28.93      C
ATOM  179  C    ALA A  20   119.296  47.714   -7.075  1.00 29.58      C
ATOM  180  O    ALA A  20   120.446  47.526   -7.525  1.00 28.61      O
ATOM  181  N    MET A  21   118.227  47.198   -7.633  1.00 30.20      N
ATOM  182  CA   MET A  21   118.381  46.327   -8.765  1.00 31.07      C
ATOM  183  CB   MET A  21   117.115  45.554   -9.068  1.00 29.96      C
ATOM  184  CG   MET A  21   116.890  44.360   -8.192  1.00 28.70      C
ATOM  185  SD   MET A  21   115.271  43.605   -8.539  1.00 30.60      S
ATOM  186  CE   MET A  21   115.692  42.772  -10.043  1.00 32.06      C
ATOM  187  C    MET A  21   118.829  47.125  -10.007  1.00 32.07      C
ATOM  188  O    MET A  21   119.651  46.628  -10.738  1.00 32.00      O
ATOM  189  N    LYS A  22   118.302  48.331  -10.227  1.00 32.88      N
ATOM  190  CA   LYS A  22   118.768  49.175  -11.353  1.00 34.41      C
ATOM  191  CB   LYS A  22   118.000  50.488  -11.432  1.00 33.51      C
ATOM  192  CG   LYS A  22   118.217  51.117  -12.801  1.00 40.97      C
ATOM  193  CD   LYS A  22   117.597  52.548  -12.899  1.00 47.64      C
ATOM  194  CE   LYS A  22   118.111  53.312  -14.126  1.00 48.65      C
ATOM  195  NZ   LYS A  22   117.521  54.691  -14.031  1.00 51.01      N
ATOM  196  C    LYS A  22   120.280  49.525  -11.283  1.00 33.38      C
ATOM  197  O    LYS A  22   121.009  49.461  -12.294  1.00 33.44      O
ATOM  198  N    GLU A  23   120.718  49.860  -10.082  1.00 33.00      N
ATOM  199  CA   GLU A  23   122.076  50.205   -9.764  1.00 33.25      C
ATOM  200  CB   GLU A  23   122.188  50.431   -8.248  1.00 33.36      C
ATOM  201  CG   GLU A  23   123.655  50.643   -7.695  1.00 39.45      C
ATOM  202  CD   GLU A  23   124.099  52.084   -7.546  1.00 42.41      C
ATOM  203  OE1  GLU A  23   123.884  52.865   -8.486  1.00 47.54      O
ATOM  204  OE2  GLU A  23   124.663  52.456   -6.467  1.00 45.45      O
ATOM  205  C    GLU A  23   123.119  49.160  -10.244  1.00 32.51      C
ATOM  206  O    GLU A  23   124.209  49.559  -10.663  1.00 33.04      O
```

FIG. 1E

```
ATOM    207  N    TYR A  24     122.798  47.854 -10.190  1.00 31.10           N
ATOM    208  CA   TYR A  24     123.737  46.822 -10.622  1.00 30.25           C
ATOM    209  CB   TYR A  24     124.091  45.813  -9.509  1.00 29.88           C
ATOM    210  CG   TYR A  24     124.517  46.501  -8.232  1.00 30.66           C
ATOM    211  CD1  TYR A  24     125.845  47.015  -8.087  1.00 28.09           C
ATOM    212  CE1  TYR A  24     126.245  47.603  -6.969  1.00 28.22           C
ATOM    213  CZ   TYR A  24     125.308  47.835  -5.957  1.00 34.66           C
ATOM    214  OH   TYR A  24     125.704  48.479  -4.834  1.00 34.37           O
ATOM    215  CE2  TYR A  24     123.989  47.384  -6.070  1.00 31.70           C
ATOM    216  CD2  TYR A  24     123.617  46.730  -7.235  1.00 29.48           C
ATOM    217  C    TYR A  24     123.221  46.146 -11.871  1.00 31.20           C
ATOM    218  O    TYR A  24     123.556  45.006 -12.127  1.00 30.08           O
ATOM    219  N    GLY A  25     122.392  46.858 -12.632  1.00 31.07           N
ATOM    220  CA   GLY A  25     121.974  46.381 -13.945  1.00 34.02           C
ATOM    221  C    GLY A  25     120.985  45.184 -13.877  1.00 34.74           C
ATOM    222  O    GLY A  25     120.931  44.376 -14.757  1.00 35.69           O
ATOM    223  N    GLU A  26     120.251  45.020 -12.800  1.00 34.56           N
ATOM    224  CA   GLU A  26     119.269  43.951 -12.808  1.00 35.34           C
ATOM    225  CB   GLU A  26     119.283  43.228 -11.465  1.00 33.83           C
ATOM    226  CG   GLU A  26     120.503  42.336 -11.172  1.00 32.93           C
ATOM    227  CD   GLU A  26     120.790  42.208  -9.664  1.00 33.15           C
ATOM    228  OE1  GLU A  26     120.240  43.008  -8.868  1.00 35.33           O
ATOM    229  OE2  GLU A  26     121.564  41.330  -9.234  1.00 37.78           O
ATOM    230  C    GLU A  26     117.884  44.567 -13.123  1.00 36.09           C
ATOM    231  O    GLU A  26     117.529  45.645 -12.584  1.00 36.21           O
ATOM    232  N    ASP A  27     117.067  43.894 -13.939  1.00 35.84           N
ATOM    233  CA   ASP A  27     115.737  44.450 -14.258  1.00 36.21           C
ATOM    234  CB   ASP A  27     115.489  44.325 -15.767  1.00 36.31           C
ATOM    235  CG   ASP A  27     114.170  44.955 -16.193  1.00 39.03           C
ATOM    236  OD1  ASP A  27     113.361  45.405 -15.312  1.00 43.45           O
ATOM    237  OD2  ASP A  27     113.942  44.994 -17.416  1.00 37.86           O
ATOM    238  C    ASP A  27     114.571  43.748 -13.484  1.00 36.73           C
ATOM    239  O    ASP A  27     114.350  42.541 -13.682  1.00 34.87           O
ATOM    240  N    PRO A  28     113.814  44.494 -12.625  1.00 36.93           N
ATOM    241  CA   PRO A  28     112.786  43.801 -11.812  1.00 37.09           C
ATOM    242  CB   PRO A  28     112.158  44.951 -11.003  1.00 36.98           C
ATOM    243  CG   PRO A  28     113.296  45.905 -10.848  1.00 38.10           C
ATOM    244  CD   PRO A  28     113.970  45.897 -12.196  1.00 36.43           C
ATOM    245  C    PRO A  28     111.710  43.016 -12.617  1.00 37.10           C
ATOM    246  O    PRO A  28     111.159  42.070 -12.091  1.00 37.74           O
ATOM    247  N    LYS A  29     111.459  43.375 -13.882  1.00 37.20           N
ATOM    248  CA   LYS A  29     110.421  42.731 -14.707  1.00 37.12           C
ATOM    249  CB   LYS A  29     110.063  43.605 -15.891  1.00 37.66           C
ATOM    250  CG   LYS A  29     109.449  44.938 -15.509  1.00 38.59           C
ATOM    251  CD   LYS A  29     109.174  45.767 -16.782  1.00 43.47           C
ATOM    252  CE   LYS A  29     108.421  47.016 -16.418  1.00 41.22           C
ATOM    253  NZ   LYS A  29     108.888  47.398 -15.082  1.00 43.48           N
ATOM    254  C    LYS A  29     110.909  41.363 -15.153  1.00 36.54           C
ATOM    255  O    LYS A  29     110.125  40.456 -15.431  1.00 35.83           O
ATOM    256  N    ILE A  30     112.225  41.197 -15.146  1.00 35.98           N
ATOM    257  CA   ILE A  30     112.794  39.948 -15.564  1.00 36.07           C
ATOM    258  CB   ILE A  30     113.893  40.186 -16.641  1.00 37.76           C
ATOM    259  CG1  ILE A  30     113.335  41.004 -17.846  1.00 37.27           C
ATOM    260  CD1  ILE A  30     114.434  41.663 -18.646  1.00 38.51           C
ATOM    261  CG2  ILE A  30     114.643  38.790 -17.038  1.00 37.36           C
ATOM    262  C    ILE A  30     113.258  39.054 -14.380  1.00 35.15           C
ATOM    263  O    ILE A  30     112.998  37.819 -14.335  1.00 34.62           O
ATOM    264  N    GLU A  31     113.966  39.627 -13.428  1.00 32.56           N
ATOM    265  CA   GLU A  31     114.387  38.810 -12.285  1.00 31.04           C
ATOM    266  CB   GLU A  31     115.813  39.228 -11.847  1.00 31.30           C
ATOM    267  CG   GLU A  31     116.857  38.566 -12.666  1.00 33.30           C
ATOM    268  CD   GLU A  31     118.271  39.046 -12.332  1.00 34.64           C
ATOM    269  OE1  GLU A  31     118.964  38.310 -11.587  1.00 38.54           O
```

FIG. 1F

| | | | | | | | | | |
|---|---|---|---|---|---|---|---|---|---|
| ATOM | 270 | OE2 | GLU | A | 31 | 118.688 | 40.120 | -12.828 | 1.00 38.37 | O |
| ATOM | 271 | C | GLU | A | 31 | 113.349 | 38.971 | -11.201 | 1.00 29.15 | C |
| ATOM | 272 | O | GLU | A | 31 | 113.592 | 39.601 | -10.208 | 1.00 29.02 | O |
| ATOM | 273 | N | THR | A | 32 | 112.159 | 38.405 | -11.408 | 1.00 28.35 | N |
| ATOM | 274 | CA | THR | A | 32 | 111.080 | 38.662 | -10.529 | 1.00 25.14 | C |
| ATOM | 275 | CB | THR | A | 32 | 109.691 | 38.308 | -11.199 | 1.00 26.11 | C |
| ATOM | 276 | OG1 | THR | A | 32 | 109.722 | 36.935 | -11.584 | 1.00 23.73 | O |
| ATOM | 277 | CG2 | THR | A | 32 | 109.484 | 39.127 | -12.468 | 1.00 26.65 | C |
| ATOM | 278 | C | THR | A | 32 | 111.241 | 37.956 | -9.206 | 1.00 24.47 | C |
| ATOM | 279 | O | THR | A | 32 | 110.782 | 38.481 | -8.214 | 1.00 22.40 | O |
| ATOM | 280 | N | ASN | A | 33 | 111.914 | 36.783 | -9.146 | 1.00 25.61 | N |
| ATOM | 281 | CA | ASN | A | 33 | 112.121 | 36.141 | -7.851 | 1.00 25.65 | C |
| ATOM | 282 | CB | ASN | A | 33 | 112.519 | 34.640 | -7.967 | 1.00 27.21 | C |
| ATOM | 283 | CG | ASN | A | 33 | 111.359 | 33.816 | -8.499 | 1.00 28.50 | C |
| ATOM | 284 | OD1 | ASN | A | 33 | 111.547 | 33.021 | -9.402 | 1.00 36.25 | O |
| ATOM | 285 | ND2 | ASN | A | 33 | 110.153 | 34.146 | -8.082 | 1.00 22.48 | N |
| ATOM | 286 | C | ASN | A | 33 | 113.141 | 36.898 | -6.983 | 1.00 24.71 | C |
| ATOM | 287 | O | ASN | A | 33 | 112.991 | 37.015 | -5.750 | 1.00 23.62 | O |
| ATOM | 288 | N | LYS | A | 34 | 114.163 | 37.395 | -7.653 | 1.00 24.60 | N |
| ATOM | 289 | CA | LYS | A | 34 | 115.119 | 38.352 | -7.043 | 1.00 25.52 | C |
| ATOM | 290 | CB | LYS | A | 34 | 116.271 | 38.653 | -8.013 | 1.00 25.03 | C |
| ATOM | 291 | CG | LYS | A | 34 | 117.398 | 39.618 | -7.386 | 1.00 31.00 | C |
| ATOM | 292 | CD | LYS | A | 34 | 118.579 | 39.745 | -8.336 | 1.00 37.80 | C |
| ATOM | 293 | CE | LYS | A | 34 | 119.522 | 38.493 | -8.233 | 1.00 38.22 | C |
| ATOM | 294 | NZ | LYS | A | 34 | 120.773 | 38.795 | -9.012 | 1.00 39.96 | N |
| ATOM | 295 | C | LYS | A | 34 | 114.430 | 39.650 | -6.544 | 1.00 24.86 | C |
| ATOM | 296 | O | LYS | A | 34 | 114.581 | 40.044 | -5.351 | 1.00 25.65 | O |
| ATOM | 297 | N | PHE | A | 35 | 113.654 | 40.297 | -7.417 | 1.00 24.43 | N |
| ATOM | 298 | CA | PHE | A | 35 | 112.809 | 41.415 | -6.937 | 1.00 24.24 | C |
| ATOM | 299 | CB | PHE | A | 35 | 111.793 | 41.709 | -8.025 | 1.00 25.49 | C |
| ATOM | 300 | CG | PHE | A | 35 | 111.020 | 42.979 | -7.844 | 1.00 27.31 | C |
| ATOM | 301 | CD1 | PHE | A | 35 | 111.564 | 44.076 | -7.167 | 1.00 23.80 | C |
| ATOM | 302 | CE1 | PHE | A | 35 | 110.818 | 45.286 | -7.086 | 1.00 28.99 | C |
| ATOM | 303 | CZ | PHE | A | 35 | 109.554 | 45.385 | -7.706 | 1.00 24.27 | C |
| ATOM | 304 | CE2 | PHE | A | 35 | 109.038 | 44.301 | -8.395 | 1.00 26.04 | C |
| ATOM | 305 | CD2 | PHE | A | 35 | 109.749 | 43.104 | -8.447 | 1.00 26.96 | C |
| ATOM | 306 | C | PHE | A | 35 | 112.117 | 41.127 | -5.567 | 1.00 23.64 | C |
| ATOM | 307 | O | PHE | A | 35 | 112.262 | 41.855 | -4.606 | 1.00 20.80 | O |
| ATOM | 308 | N | ALA | A | 36 | 111.394 | 40.012 | -5.464 | 1.00 25.29 | N |
| ATOM | 309 | CA | ALA | A | 36 | 110.791 | 39.587 | -4.203 | 1.00 23.01 | C |
| ATOM | 310 | CB | ALA | A | 36 | 109.813 | 38.378 | -4.474 | 1.00 23.96 | C |
| ATOM | 311 | C | ALA | A | 36 | 111.694 | 39.296 | -3.030 | 1.00 22.15 | C |
| ATOM | 312 | O | ALA | A | 36 | 111.330 | 39.570 | -1.885 | 1.00 21.47 | O |
| ATOM | 313 | N | ALA | A | 37 | 112.884 | 38.739 | -3.270 | 1.00 22.04 | N |
| ATOM | 314 | CA | ALA | A | 37 | 113.718 | 38.343 | -2.202 | 1.00 19.77 | C |
| ATOM | 315 | CB | ALA | A | 37 | 114.948 | 37.380 | -2.703 | 1.00 19.56 | C |
| ATOM | 316 | C | ALA | A | 37 | 114.287 | 39.694 | -1.688 | 1.00 21.30 | C |
| ATOM | 317 | O | ALA | A | 37 | 114.417 | 39.867 | -0.467 | 1.00 20.64 | O |
| ATOM | 318 | N | ILE | A | 38 | 114.531 | 40.644 | -2.583 | 1.00 20.77 | N |
| ATOM | 319 | CA | ILE | A | 38 | 115.086 | 42.013 | -2.119 | 1.00 21.63 | C |
| ATOM | 320 | CB | ILE | A | 38 | 115.527 | 42.981 | -3.290 | 1.00 22.23 | C |
| ATOM | 321 | CG1 | ILE | A | 38 | 116.592 | 42.401 | -4.242 | 1.00 26.72 | C |
| ATOM | 322 | CD1 | ILE | A | 38 | 117.648 | 41.799 | -3.507 | 1.00 29.37 | C |
| ATOM | 323 | CG2 | ILE | A | 38 | 116.050 | 44.370 | -2.694 | 1.00 18.26 | C |
| ATOM | 324 | C | ILE | A | 38 | 114.066 | 42.755 | -1.191 | 1.00 21.39 | C |
| ATOM | 325 | O | ILE | A | 38 | 114.369 | 43.176 | -0.038 | 1.00 21.05 | O |
| ATOM | 326 | N | CYS | A | 39 | 112.804 | 42.802 | -1.656 | 1.00 23.05 | N |
| ATOM | 327 | CA | CYS | A | 39 | 111.754 | 43.498 | -0.877 | 1.00 23.02 | C |
| ATOM | 328 | CB | CYS | A | 39 | 110.359 | 43.473 | -1.615 | 1.00 21.00 | C |
| ATOM | 329 | SG | CYS | A | 39 | 110.343 | 44.408 | -3.128 | 1.00 27.59 | S |
| ATOM | 330 | C | CYS | A | 39 | 111.592 | 42.888 | 0.464 | 1.00 22.06 | C |
| ATOM | 331 | O | CYS | A | 39 | 111.417 | 43.620 | 1.437 | 1.00 20.89 | O |
| ATOM | 332 | N | THR | A | 40 | 111.577 | 41.546 | 0.512 | 1.00 22.10 | N |

FIG. 1G

```
ATOM    333  CA   THR A  40     111.449  40.812   1.751  1.00 21.04           C
ATOM    334  CB   THR A  40     111.403  39.228   1.509  1.00 23.25           C
ATOM    335  OG1  THR A  40     110.391  38.893   0.580  1.00 21.80           O
ATOM    336  CG2  THR A  40     110.932  38.491   2.814  1.00 22.85           C
ATOM    337  C    THR A  40     112.565  41.111   2.745  1.00 21.93           C
ATOM    338  O    THR A  40     112.354  41.300   3.949  1.00 21.15           O
ATOM    339  N    HIS A  41     113.798  41.021   2.247  1.00 21.54           N
ATOM    340  CA   HIS A  41     114.916  41.325   3.035  1.00 21.49           C
ATOM    341  CB   HIS A  41     116.177  41.157   2.212  1.00 22.12           C
ATOM    342  CG   HIS A  41     117.403  41.340   3.023  1.00 26.08           C
ATOM    343  ND1  HIS A  41     118.143  42.501   2.989  1.00 25.08           N
ATOM    344  CE1  HIS A  41     119.173  42.389   3.804  1.00 19.14           C
ATOM    345  NE2  HIS A  41     119.130  41.191   4.359  1.00 28.46           N
ATOM    346  CD2  HIS A  41     118.049  40.501   3.866  1.00 26.32           C
ATOM    347  C    HIS A  41     114.820  42.781   3.560  1.00 19.08           C
ATOM    348  O    HIS A  41     114.944  43.029   4.764  1.00 14.92           O
ATOM    349  N    LEU A  42     114.527  43.705   2.637  1.00 20.28           N
ATOM    350  CA   LEU A  42     114.220  45.068   3.084  1.00 20.07           C
ATOM    351  CB   LEU A  42     113.991  46.070   1.930  1.00 20.76           C
ATOM    352  CG   LEU A  42     115.136  46.439   0.970  1.00 22.35           C
ATOM    353  CD1  LEU A  42     114.681  46.964  -0.436  1.00 20.75           C
ATOM    354  CD2  LEU A  42     116.058  47.459   1.643  1.00 27.69           C
ATOM    355  C    LEU A  42     113.148  45.111   4.139  1.00 19.88           C
ATOM    356  O    LEU A  42     113.377  45.702   5.223  1.00 17.77           O
ATOM    357  N    GLU A  43     111.997  44.439   3.908  1.00 21.82           N
ATOM    358  CA   GLU A  43     110.892  44.570   4.900  1.00 20.65           C
ATOM    359  CB   GLU A  43     109.515  43.943   4.470  1.00 22.30           C
ATOM    360  CG   GLU A  43     108.430  45.007   4.881  1.00 25.46           C
ATOM    361  CD   GLU A  43     107.038  44.589   4.789  1.00 37.53           C
ATOM    362  OE1  GLU A  43     106.699  43.527   5.324  1.00 41.59           O
ATOM    363  OE2  GLU A  43     106.226  45.379   4.206  1.00 48.75           O
ATOM    364  C    GLU A  43     111.317  44.055   6.219  1.00 20.03           C
ATOM    365  O    GLU A  43     111.061  44.669   7.268  1.00 22.15           O
ATOM    366  N    VAL A  44     112.035  42.931   6.233  1.00 19.16           N
ATOM    367  CA   VAL A  44     112.503  42.424   7.522  1.00 18.30           C
ATOM    368  CB   VAL A  44     113.201  41.005   7.320  1.00 19.74           C
ATOM    369  CG1  VAL A  44     113.865  40.613   8.652  1.00 20.11           C
ATOM    370  CG2  VAL A  44     112.076  39.996   6.816  1.00 21.24           C
ATOM    371  C    VAL A  44     113.420  43.346   8.326  1.00 19.87           C
ATOM    372  O    VAL A  44     113.315  43.462   9.570  1.00 19.37           O
ATOM    373  N    CYS A  45     114.348  43.995   7.624  1.00 20.59           N
ATOM    374  CA   CYS A  45     115.312  44.966   8.259  1.00 22.34           C
ATOM    375  CB   CYS A  45     116.368  45.493   7.237  1.00 21.83           C
ATOM    376  SG   CYS A  45     117.587  44.252   6.771  1.00 26.82           S
ATOM    377  C    CYS A  45     114.582  46.155   8.912  1.00 21.91           C
ATOM    378  O    CYS A  45     114.729  46.408  10.111  1.00 22.11           O
ATOM    379  N    PHE A  46     113.714  46.794   8.155  1.00 22.73           N
ATOM    380  CA   PHE A  46     112.823  47.796   8.764  1.00 24.28           C
ATOM    381  CB   PHE A  46     111.922  48.394   7.735  1.00 24.77           C
ATOM    382  CG   PHE A  46     112.628  49.239   6.744  1.00 29.86           C
ATOM    383  CD1  PHE A  46     113.030  50.553   7.089  1.00 36.82           C
ATOM    384  CE1  PHE A  46     113.665  51.350   6.139  1.00 35.81           C
ATOM    385  CZ   PHE A  46     113.882  50.840   4.858  1.00 38.37           C
ATOM    386  CE2  PHE A  46     113.469  49.607   4.518  1.00 36.57           C
ATOM    387  CD2  PHE A  46     112.820  48.803   5.465  1.00 31.36           C
ATOM    388  C    PHE A  46     111.983  47.338   9.940  1.00 23.58           C
ATOM    389  O    PHE A  46     111.850  48.077  10.902  1.00 24.26           O
ATOM    390  N    MET A  47     111.348  46.156   9.874  1.00 23.87           N
ATOM    391  CA   MET A  47     110.578  45.664  11.039  1.00 23.27           C
ATOM    392  CB   MET A  47     109.832  44.332  10.639  1.00 24.23           C
ATOM    393  CG   MET A  47     108.665  44.510   9.651  1.00 23.95           C
ATOM    394  SD   MET A  47     107.762  42.932   9.293  1.00 32.59           S
ATOM    395  CE   MET A  47     106.999  42.762  10.891  1.00 24.89           C
```

FIG. 1H

| ATOM | 396 | C   | MET A | 47 | 111.372 | 45.397 | 12.307 | 1.00 | 23.14 | C |
|------|-----|-----|-------|----|---------|--------|--------|------|-------|---|
| ATOM | 397 | O   | MET A | 47 | 110.901 | 45.537 | 13.467 | 1.00 | 21.96 | O |
| ATOM | 398 | N   | TYR A | 48 | 112.606 | 44.958 | 12.091 | 1.00 | 22.19 | N |
| ATOM | 399 | CA  | TYR A | 48 | 113.462 | 44.585 | 13.136 | 1.00 | 21.11 | C |
| ATOM | 400 | CB  | TYR A | 48 | 114.754 | 44.010 | 12.506 | 1.00 | 19.64 | C |
| ATOM | 401 | CG  | TYR A | 48 | 115.615 | 43.198 | 13.444 | 1.00 | 19.63 | C |
| ATOM | 402 | CD1 | TYR A | 48 | 115.667 | 41.797 | 13.347 | 1.00 | 23.15 | C |
| ATOM | 403 | CE1 | TYR A | 48 | 116.517 | 41.048 | 14.189 | 1.00 | 20.73 | C |
| ATOM | 404 | CZ  | TYR A | 48 | 117.274 | 41.635 | 15.172 | 1.00 | 23.31 | C |
| ATOM | 405 | OH  | TYR A | 48 | 118.038 | 40.821 | 16.043 | 1.00 | 21.51 | O |
| ATOM | 406 | CE2 | TYR A | 48 | 117.231 | 43.047 | 15.333 | 1.00 | 20.56 | C |
| ATOM | 407 | CD2 | TYR A | 48 | 116.385 | 43.803 | 14.470 | 1.00 | 23.79 | C |
| ATOM | 408 | C   | TYR A | 48 | 113.713 | 45.865 | 13.963 | 1.00 | 23.18 | C |
| ATOM | 409 | O   | TYR A | 48 | 113.791 | 45.866 | 15.205 | 1.00 | 20.86 | O |
| ATOM | 410 | N   | SER A | 49 | 113.743 | 46.972 | 13.247 | 1.00 | 25.22 | N |
| ATOM | 411 | CA  | SER A | 49 | 114.167 | 48.218 | 13.852 | 1.00 | 28.76 | C |
| ATOM | 412 | CB  | SER A | 49 | 114.856 | 49.040 | 12.790 | 1.00 | 28.94 | C |
| ATOM | 413 | OG  | SER A | 49 | 113.912 | 49.388 | 11.783 | 1.00 | 32.93 | O |
| ATOM | 414 | C   | SER A | 49 | 112.932 | 48.981 | 14.418 | 1.00 | 30.63 | C |
| ATOM | 415 | O   | SER A | 49 | 113.077 | 49.678 | 15.395 | 1.00 | 29.11 | O |
| ATOM | 416 | N   | ASP A | 50 | 111.739 | 48.749 | 13.839 | 1.00 | 31.70 | N |
| ATOM | 417 | CA  | ASP A | 50 | 110.465 | 49.377 | 14.301 | 1.00 | 33.27 | C |
| ATOM | 418 | CB  | ASP A | 50 | 109.215 | 48.604 | 13.749 | 1.00 | 33.14 | C |
| ATOM | 419 | CG  | ASP A | 50 | 108.724 | 49.144 | 12.449 | 1.00 | 36.94 | C |
| ATOM | 420 | OD1 | ASP A | 50 | 109.142 | 50.281 | 12.102 | 1.00 | 42.74 | O |
| ATOM | 421 | OD2 | ASP A | 50 | 107.939 | 48.427 | 11.747 | 1.00 | 37.80 | O |
| ATOM | 422 | C   | ASP A | 50 | 110.310 | 49.429 | 15.819 | 1.00 | 32.77 | C |
| ATOM | 423 | O   | ASP A | 50 | 110.406 | 48.411 | 16.493 | 1.00 | 33.85 | O |
| ATOM | 424 | N   | PHE A | 51 | 110.074 | 50.610 | 16.369 | 1.00 | 32.76 | N |
| ATOM | 425 | CA  | PHE A | 51 | 109.477 | 50.740 | 17.743 | 1.00 | 31.19 | C |
| ATOM | 426 | CB  | PHE A | 51 | 108.442 | 49.613 | 18.063 | 1.00 | 32.43 | C |
| ATOM | 427 | CG  | PHE A | 51 | 107.329 | 49.501 | 17.083 | 1.00 | 33.43 | C |
| ATOM | 428 | CD1 | PHE A | 51 | 106.787 | 50.656 | 16.473 | 1.00 | 38.68 | C |
| ATOM | 429 | CE1 | PHE A | 51 | 105.755 | 50.565 | 15.527 | 1.00 | 39.63 | C |
| ATOM | 430 | CZ  | PHE A | 51 | 105.235 | 49.277 | 15.189 | 1.00 | 40.25 | C |
| ATOM | 431 | CE2 | PHE A | 51 | 105.777 | 48.108 | 15.807 | 1.00 | 41.18 | C |
| ATOM | 432 | CD2 | PHE A | 51 | 106.831 | 48.242 | 16.736 | 1.00 | 38.51 | C |
| ATOM | 433 | C   | PHE A | 51 | 110.494 | 50.683 | 18.813 | 1.00 | 29.39 | C |
| ATOM | 434 | O   | PHE A | 51 | 110.116 | 50.767 | 19.986 | 1.00 | 28.70 | O |
| ATOM | 435 | N   | HIS A | 52 | 111.768 | 50.444 | 18.458 | 1.00 | 28.72 | N |
| ATOM | 436 | CA  | HIS A | 52 | 112.796 | 50.265 | 19.472 | 1.00 | 27.24 | C |
| ATOM | 437 | CB  | HIS A | 52 | 113.687 | 49.063 | 19.164 | 1.00 | 27.74 | C |
| ATOM | 438 | CG  | HIS A | 52 | 112.950 | 47.754 | 19.087 | 1.00 | 29.30 | C |
| ATOM | 439 | ND1 | HIS A | 52 | 112.717 | 46.977 | 20.198 | 1.00 | 29.47 | N |
| ATOM | 440 | CE1 | HIS A | 52 | 112.012 | 45.913 | 19.844 | 1.00 | 33.01 | C |
| ATOM | 441 | NE2 | HIS A | 52 | 111.839 | 45.940 | 18.528 | 1.00 | 33.69 | N |
| ATOM | 442 | CD2 | HIS A | 52 | 112.405 | 47.092 | 18.032 | 1.00 | 28.21 | C |
| ATOM | 443 | C   | HIS A | 52 | 113.665 | 51.545 | 19.614 | 1.00 | 28.97 | C |
| ATOM | 444 | O   | HIS A | 52 | 114.308 | 52.025 | 18.646 | 1.00 | 25.35 | O |
| ATOM | 445 | N   | PHE A | 53 | 113.718 | 52.019 | 20.842 | 1.00 | 30.92 | N |
| ATOM | 446 | CA  | PHE A | 53 | 114.325 | 53.320 | 21.167 | 1.00 | 34.45 | C |
| ATOM | 447 | CB  | PHE A | 53 | 113.222 | 54.406 | 21.335 | 1.00 | 34.83 | C |
| ATOM | 448 | CG  | PHE A | 53 | 112.563 | 54.748 | 20.068 | 1.00 | 35.99 | C |
| ATOM | 449 | CD1 | PHE A | 53 | 113.166 | 55.609 | 19.183 | 1.00 | 40.04 | C |
| ATOM | 450 | CE1 | PHE A | 53 | 112.583 | 55.880 | 17.958 | 1.00 | 40.10 | C |
| ATOM | 451 | CZ  | PHE A | 53 | 111.395 | 55.278 | 17.608 | 1.00 | 40.74 | C |
| ATOM | 452 | CE2 | PHE A | 53 | 110.781 | 54.386 | 18.481 | 1.00 | 39.70 | C |
| ATOM | 453 | CD2 | PHE A | 53 | 111.375 | 54.112 | 19.698 | 1.00 | 42.11 | C |
| ATOM | 454 | C   | PHE A | 53 | 115.141 | 53.254 | 22.408 | 1.00 | 35.34 | C |
| ATOM | 455 | O   | PHE A | 53 | 114.946 | 52.398 | 23.229 | 1.00 | 37.62 | O |
| ATOM | 456 | N   | ILE A | 54 | 116.126 | 54.137 | 22.520 | 1.00 | 39.00 | N |
| ATOM | 457 | CA  | ILE A | 54 | 116.812 | 54.358 | 23.775 | 1.00 | 40.31 | C |
| ATOM | 458 | CB  | ILE A | 54 | 118.338 | 54.234 | 23.570 | 1.00 | 42.04 | C |

FIG. 1I

```
ATOM  459  CG1  ILE A  54   118.734  52.738  23.535  1.00 40.76      C
ATOM  460  CD1  ILE A  54   119.572  52.504  22.328  1.00 39.39      C
ATOM  461  CG2  ILE A  54   119.145  55.027  24.592  1.00 36.99      C
ATOM  462  C    ILE A  54   116.403  55.764  24.163  1.00 42.94      C
ATOM  463  O    ILE A  54   116.412  56.662  23.336  1.00 42.66      O
ATOM  464  N    ASP A  55   116.017  55.963  25.410  1.00 45.93      N
ATOM  465  CA   ASP A  55   115.441  57.267  25.756  1.00 49.47      C
ATOM  466  CB   ASP A  55   114.317  57.120  26.780  1.00 50.32      C
ATOM  467  CG   ASP A  55   114.802  56.476  28.097  1.00 51.50      C
ATOM  468  OD1  ASP A  55   114.018  55.762  28.748  1.00 52.94      O
ATOM  469  OD2  ASP A  55   115.973  56.681  28.482  1.00 53.29      O
ATOM  470  C    ASP A  55   116.505  58.213  26.277  1.00 51.12      C
ATOM  471  O    ASP A  55   117.702  58.051  25.994  1.00 51.23      O
ATOM  472  N    GLU A  56   116.047  59.174  27.071  1.00 53.58      N
ATOM  473  CA   GLU A  56   116.852  60.286  27.601  1.00 55.53      C
ATOM  474  CB   GLU A  56   115.889  61.333  28.161  1.00 56.20      C
ATOM  475  CG   GLU A  56   114.414  60.990  27.806  1.00 57.21      C
ATOM  476  CD   GLU A  56   113.486  61.253  28.921  1.00 59.52      C
ATOM  477  OE1  GLU A  56   112.285  61.089  28.689  1.00 61.14      O
ATOM  478  OE2  GLU A  56   113.938  61.631  30.033  1.00 63.69      O
ATOM  479  C    GLU A  56   117.785  59.810  28.713  1.00 56.99      C
ATOM  480  O    GLU A  56   118.983  60.144  28.750  1.00 58.03      O
ATOM  481  N    ARG A  57   117.226  59.025  29.615  1.00 58.21      N
ATOM  482  CA   ARG A  57   117.955  58.472  30.722  1.00 59.56      C
ATOM  483  CB   ARG A  57   116.976  58.077  31.858  1.00 59.94      C
ATOM  484  CG   ARG A  57   115.743  59.025  32.020  1.00 63.90      C
ATOM  485  CD   ARG A  57   115.248  59.206  33.478  1.00 68.93      C
ATOM  486  NE   ARG A  57   116.099  60.116  34.274  1.00 72.68      N
ATOM  487  CZ   ARG A  57   116.324  60.006  35.596  1.00 74.39      C
ATOM  488  NH1  ARG A  57   115.758  59.027  36.307  1.00 74.29      N
ATOM  489  NH2  ARG A  57   117.119  60.878  36.224  1.00 73.92      N
ATOM  490  C    ARG A  57   118.808  57.287  30.215  1.00 59.66      C
ATOM  491  O    ARG A  57   119.564  56.694  30.983  1.00 59.63      O
ATOM  492  N    GLY A  58   118.660  56.937  28.929  1.00 59.68      N
ATOM  493  CA   GLY A  58   119.575  56.030  28.225  1.00 59.05      C
ATOM  494  C    GLY A  58   119.293  54.534  28.200  1.00 59.03      C
ATOM  495  O    GLY A  58   120.222  53.716  27.981  1.00 58.74      O
ATOM  496  N    GLU A  59   118.037  54.152  28.416  1.00 58.42      N
ATOM  497  CA   GLU A  59   117.682  52.717  28.360  1.00 58.36      C
ATOM  498  CB   GLU A  59   117.211  52.146  29.716  1.00 58.91      C
ATOM  499  CG   GLU A  59   116.727  53.161  30.735  1.00 60.56      C
ATOM  500  CD   GLU A  59   117.838  54.105  31.246  1.00 62.98      C
ATOM  501  OE1  GLU A  59   117.462  55.219  31.670  1.00 62.31      O
ATOM  502  OE2  GLU A  59   119.064  53.757  31.222  1.00 62.07      O
ATOM  503  C    GLU A  59   116.715  52.380  27.230  1.00 57.44      C
ATOM  504  O    GLU A  59   115.942  53.243  26.786  1.00 56.78      O
ATOM  505  N    SER A  60   116.776  51.127  26.773  1.00 56.20      N
ATOM  506  CA   SER A  60   115.984  50.691  25.616  1.00 56.01      C
ATOM  507  CB   SER A  60   116.631  49.510  24.903  1.00 55.49      C
ATOM  508  OG   SER A  60   116.990  48.533  25.856  1.00 56.45      O
ATOM  509  C    SER A  60   114.578  50.335  26.005  1.00 55.06      C
ATOM  510  O    SER A  60   114.366  49.481  26.850  1.00 54.75      O
ATOM  511  N    ILE A  61   113.632  51.000  25.351  1.00 55.19      N
ATOM  512  CA   ILE A  61   112.190  50.864  25.610  1.00 54.35      C
ATOM  513  CB   ILE A  61   111.631  52.139  26.278  1.00 54.74      C
ATOM  514  CG1  ILE A  61   111.996  53.371  25.450  1.00 55.79      C
ATOM  515  CD1  ILE A  61   111.169  54.621  25.788  1.00 58.32      C
ATOM  516  CG2  ILE A  61   112.126  52.292  27.748  1.00 55.82      C
ATOM  517  C    ILE A  61   111.436  50.639  24.292  1.00 53.30      C
ATOM  518  O    ILE A  61   111.963  50.958  23.211  1.00 51.29      O
ATOM  519  N    ILE A  62   110.203  50.123  24.398  1.00 52.71      N
ATOM  520  CA   ILE A  62   109.306  49.964  23.248  1.00 52.41      C
ATOM  521  CB   ILE A  62   108.640  48.535  23.194  1.00 52.13      C
```

FIG. 1J

```
ATOM   522  CG1 ILE A   62      109.725  47.431  23.123  1.00 52.63           C
ATOM   523  CD1 ILE A   62      109.325  46.065  23.710  1.00 47.97           C
ATOM   524  CG2 ILE A   62      107.749  48.398  21.973  1.00 51.39           C
ATOM   525  C   ILE A   62      108.287  51.122  23.174  1.00 52.81           C
ATOM   526  O   ILE A   62      107.639  51.442  24.160  1.00 52.03           O
ATOM   527  N   VAL A   63      108.208  51.760  22.003  1.00 53.12           N
ATOM   528  CA  VAL A   63      107.306  52.875  21.725  1.00 54.51           C
ATOM   529  CB  VAL A   63      108.119  54.201  21.551  1.00 54.25           C
ATOM   530  CG1 VAL A   63      107.251  55.318  20.983  1.00 55.15           C
ATOM   531  CG2 VAL A   63      108.783  54.618  22.834  1.00 52.54           C
ATOM   532  C   VAL A   63      106.592  52.591  20.400  1.00 55.49           C
ATOM   533  O   VAL A   63      107.255  52.429  19.414  1.00 55.99           O
ATOM   534  N   GLU A   64      105.262  52.597  20.353  1.00 57.01           N
ATOM   535  CA  GLU A   64      104.527  52.232  19.134  1.00 58.58           C
ATOM   536  CB  GLU A   64      103.499  51.142  19.456  1.00 59.63           C
ATOM   537  CG  GLU A   64      104.074  50.011  20.315  1.00 62.16           C
ATOM   538  CD  GLU A   64      103.900  48.633  19.697  1.00 65.82           C
ATOM   539  OE1 GLU A   64      102.788  48.326  19.205  1.00 66.64           O
ATOM   540  OE2 GLU A   64      104.888  47.848  19.727  1.00 68.44           O
ATOM   541  C   GLU A   64      103.847  53.350  18.334  1.00 58.80           C
ATOM   542  O   GLU A   64      103.720  54.477  18.787  1.00 58.79           O
ATOM   543  N   ASN A   69      108.491  60.891  20.150  1.00 47.33           N
ATOM   544  CA  ASN A   69      108.881  61.505  21.428  1.00 49.37           C
ATOM   545  CB  ASN A   69      108.591  60.477  22.512  1.00 49.40           C
ATOM   546  CG  ASN A   69      109.061  60.887  23.884  1.00 52.60           C
ATOM   547  OD1 ASN A   69      109.932  61.749  24.046  1.00 54.70           O
ATOM   548  ND2 ASN A   69      108.517  60.206  24.901  1.00 54.58           N
ATOM   549  C   ASN A   69      110.358  62.047  21.403  1.00 49.37           C
ATOM   550  O   ASN A   69      111.311  61.289  21.601  1.00 50.10           O
ATOM   551  N   ALA A   70      110.527  63.352  21.135  1.00 49.25           N
ATOM   552  CA  ALA A   70      111.761  63.913  20.517  1.00 47.76           C
ATOM   553  CB  ALA A   70      111.534  65.425  20.191  1.00 48.77           C
ATOM   554  C   ALA A   70      113.182  63.655  21.163  1.00 47.17           C
ATOM   555  O   ALA A   70      114.244  63.836  20.515  1.00 46.79           O
ATOM   556  N   LEU A   71      113.226  63.215  22.420  1.00 45.43           N
ATOM   557  CA  LEU A   71      114.508  62.950  23.061  1.00 44.08           C
ATOM   558  CB  LEU A   71      114.449  63.312  24.533  1.00 43.97           C
ATOM   559  CG  LEU A   71      114.368  64.799  24.880  1.00 42.01           C
ATOM   560  CD1 LEU A   71      114.114  64.902  26.375  1.00 38.92           C
ATOM   561  CD2 LEU A   71      115.669  65.502  24.496  1.00 38.65           C
ATOM   562  C   LEU A   71      115.005  61.520  22.932  1.00 44.74           C
ATOM   563  O   LEU A   71      116.169  61.231  23.154  1.00 44.38           O
ATOM   564  N   LEU A   72      114.135  60.595  22.587  1.00 45.46           N
ATOM   565  CA  LEU A   72      114.654  59.244  22.453  1.00 46.52           C
ATOM   566  CB  LEU A   72      113.571  58.194  22.706  1.00 47.21           C
ATOM   567  CG  LEU A   72      112.105  58.530  22.676  1.00 49.53           C
ATOM   568  CD1 LEU A   72      111.594  58.547  21.240  1.00 49.94           C
ATOM   569  CD2 LEU A   72      111.461  57.436  23.473  1.00 53.22           C
ATOM   570  C   LEU A   72      115.385  59.064  21.113  1.00 45.34           C
ATOM   571  O   LEU A   72      115.002  59.701  20.102  1.00 45.79           O
ATOM   572  N   LYS A   73      116.449  58.242  21.160  1.00 43.11           N
ATOM   573  CA  LYS A   73      117.261  57.828  19.997  1.00 42.14           C
ATOM   574  CB  LYS A   73      118.730  57.715  20.418  1.00 42.49           C
ATOM   575  CG  LYS A   73      119.729  57.159  19.308  1.00 45.81           C
ATOM   576  CD  LYS A   73      121.142  56.826  19.913  1.00 48.57           C
ATOM   577  CE  LYS A   73      122.229  56.680  18.853  1.00 50.87           C
ATOM   578  NZ  LYS A   73      122.068  57.614  17.676  1.00 52.28           N
ATOM   579  C   LYS A   73      116.832  56.429  19.509  1.00 39.34           C
ATOM   580  O   LYS A   73      116.624  55.549  20.340  1.00 37.81           O
ATOM   581  N   HIS A   74      116.725  56.284  18.185  1.00 36.23           N
ATOM   582  CA  HIS A   74      116.502  55.024  17.496  1.00 35.73           C
ATOM   583  CB  HIS A   74      116.736  55.212  15.975  1.00 36.37           C
ATOM   584  CG  HIS A   74      115.507  55.632  15.206  1.00 40.54           C
```

FIG. 1K

```
ATOM    585  ND1 HIS A  74     114.560  54.727  14.750  1.00 41.72      N
ATOM    586  CE1 HIS A  74     113.624  55.374  14.072  1.00 43.42      C
ATOM    587  NE2 HIS A  74     113.941  56.663  14.051  1.00 42.94      N
ATOM    588  CD2 HIS A  74     115.101  56.854  14.768  1.00 37.66      C
ATOM    589  C   HIS A  74     117.493  53.972  18.008  1.00 32.26      C
ATOM    590  O   HIS A  74     118.724  54.233  18.054  1.00 31.60      O
ATOM    591  N   ARG A  75     116.995  52.810  18.408  1.00 29.08      N
ATOM    592  CA  ARG A  75     117.904  51.718  18.901  1.00 27.67      C
ATOM    593  CB  ARG A  75     117.146  50.597  19.648  1.00 28.19      C
ATOM    594  CG  ARG A  75     118.139  49.532  20.388  1.00 27.31      C
ATOM    595  CD  ARG A  75     117.422  48.267  20.769  1.00 31.20      C
ATOM    596  NE  ARG A  75     118.389  47.181  21.055  1.00 31.60      N
ATOM    597  CZ  ARG A  75     118.065  46.050  21.678  1.00 32.06      C
ATOM    598  NH1 ARG A  75     116.800  45.873  22.074  1.00 30.78      N
ATOM    599  NH2 ARG A  75     118.991  45.101  21.920  1.00 33.97      N
ATOM    600  C   ARG A  75     118.873  51.139  17.802  1.00 26.98      C
ATOM    601  O   ARG A  75     120.051  50.868  18.087  1.00 28.42      O
ATOM    602  N   PHE A  76     118.391  51.028  16.573  1.00 26.49      N
ATOM    603  CA  PHE A  76     119.110  50.428  15.442  1.00 26.90      C
ATOM    604  CB  PHE A  76     118.263  49.299  14.823  1.00 26.78      C
ATOM    605  CG  PHE A  76     117.963  48.158  15.786  1.00 27.51      C
ATOM    606  CD1 PHE A  76     118.977  47.227  16.147  1.00 27.11      C
ATOM    607  CE1 PHE A  76     118.710  46.166  17.101  1.00 20.93      C
ATOM    608  CZ  PHE A  76     117.443  46.075  17.647  1.00 21.48      C
ATOM    609  CE2 PHE A  76     116.419  47.006  17.277  1.00 23.38      C
ATOM    610  CD2 PHE A  76     116.679  48.017  16.371  1.00 26.20      C
ATOM    611  C   PHE A  76     119.438  51.511  14.394  1.00 27.87      C
ATOM    612  O   PHE A  76     118.580  52.340  14.081  1.00 28.54      O
ATOM    613  N   GLU A  77     120.673  51.562  13.909  1.00 25.24      N
ATOM    614  CA  GLU A  77     120.965  52.250  12.656  1.00 26.74      C
ATOM    615  CB  GLU A  77     122.473  52.499  12.640  1.00 26.83      C
ATOM    616  CG  GLU A  77     123.077  53.793  12.198  1.00 32.19      C
ATOM    617  CD  GLU A  77     122.239  55.065  12.460  1.00 30.31      C
ATOM    618  OE1 GLU A  77     121.468  55.454  11.582  1.00 35.51      O
ATOM    619  OE2 GLU A  77     122.386  55.638  13.515  1.00 32.50      O
ATOM    620  C   GLU A  77     120.659  51.218  11.560  1.00 25.79      C
ATOM    621  O   GLU A  77     121.008  50.031  11.734  1.00 24.39      O
ATOM    622  N   ILE A  78     120.125  51.657  10.419  1.00 24.55      N
ATOM    623  CA  ILE A  78     119.883  50.760   9.347  1.00 25.64      C
ATOM    624  CB  ILE A  78     118.448  50.859   8.776  1.00 25.37      C
ATOM    625  CG1 ILE A  78     117.389  50.439   9.853  1.00 30.17      C
ATOM    626  CD1 ILE A  78     116.483  51.585  10.530  1.00 34.64      C
ATOM    627  CG2 ILE A  78     118.333  49.789   7.709  1.00 27.85      C
ATOM    628  C   ILE A  78     120.886  51.000   8.209  1.00 26.64      C
ATOM    629  O   ILE A  78     121.053  52.149   7.781  1.00 26.38      O
ATOM    630  N   ILE A  79     121.516  49.922   7.699  1.00 23.83      N
ATOM    631  CA  ILE A  79     122.585  50.100   6.764  1.00 22.98      C
ATOM    632  CB  ILE A  79     123.951  49.382   7.310  1.00 23.51      C
ATOM    633  CG1 ILE A  79     124.300  49.862   8.720  1.00 22.81      C
ATOM    634  CD1 ILE A  79     125.273  48.966   9.523  1.00 26.88      C
ATOM    635  CG2 ILE A  79     125.077  49.497   6.306  1.00 20.50      C
ATOM    636  C   ILE A  79     122.134  49.641   5.382  1.00 23.00      C
ATOM    637  O   ILE A  79     122.437  50.247   4.395  1.00 21.80      O
ATOM    638  N   GLU A  80     121.459  48.508   5.329  1.00 23.94      N
ATOM    639  CA  GLU A  80     120.755  48.052   4.174  1.00 25.99      C
ATOM    640  CB  GLU A  80     119.922  46.837   4.593  1.00 26.50      C
ATOM    641  CG  GLU A  80     119.194  46.095   3.498  1.00 30.22      C
ATOM    642  CD  GLU A  80     120.088  45.520   2.424  1.00 36.91      C
ATOM    643  OE1 GLU A  80     121.264  45.170   2.689  1.00 42.16      O
ATOM    644  OE2 GLU A  80     119.593  45.383   1.292  1.00 42.25      O
ATOM    645  C   GLU A  80     119.812  49.178   3.708  1.00 26.68      C
ATOM    646  O   GLU A  80     119.318  49.987   4.538  1.00 26.87      O
ATOM    647  N   GLY A  81     119.597  49.256   2.409  1.00 25.00      N
```

FIG. 1L

```
ATOM    648  CA  GLY A  81     118.737  50.303   1.848  1.00 25.66           C
ATOM    649  C   GLY A  81     119.566  51.452   1.296  1.00 27.49           C
ATOM    650  O   GLY A  81     119.066  52.211   0.524  1.00 28.91           O
ATOM    651  N   ARG A  82     120.832  51.578   1.679  1.00 25.71           N
ATOM    652  CA  ARG A  82     121.684  52.695   1.153  1.00 27.02           C
ATOM    653  CB  ARG A  82     122.514  53.299   2.254  1.00 22.81           C
ATOM    654  CG  ARG A  82     121.735  53.488   3.594  1.00 25.76           C
ATOM    655  CD  ARG A  82     122.605  54.074   4.702  1.00 22.32           C
ATOM    656  NE  ARG A  82     121.858  54.133   5.980  1.00 29.84           N
ATOM    657  CZ  ARG A  82     121.140  55.205   6.347  1.00 32.60           C
ATOM    658  NH1 ARG A  82     121.107  56.262   5.544  1.00 28.57           N
ATOM    659  NH2 ARG A  82     120.443  55.215   7.487  1.00 31.43           N
ATOM    660  C   ARG A  82     122.618  52.221   0.049  1.00 28.24           C
ATOM    661  O   ARG A  82     122.981  51.039  -0.045  1.00 26.51           O
ATOM    662  N   ASP A  83     123.044  53.156  -0.769  1.00 29.07           N
ATOM    663  CA  ASP A  83     123.972  52.797  -1.821  1.00 29.79           C
ATOM    664  CB  ASP A  83     123.922  53.845  -2.938  1.00 29.55           C
ATOM    665  CG  ASP A  83     124.780  55.113  -2.614  1.00 36.23           C
ATOM    666  OD1 ASP A  83     125.172  55.334  -1.455  1.00 43.86           O
ATOM    667  OD2 ASP A  83     125.064  55.914  -3.547  1.00 43.76           O
ATOM    668  C   ASP A  83     125.365  52.596  -1.157  1.00 27.22           C
ATOM    669  O   ASP A  83     125.540  52.902   0.023  1.00 25.99           O
ATOM    670  N   ARG A  84     126.342  52.064  -1.890  1.00 24.65           N
ATOM    671  CA  ARG A  84     127.605  51.719  -1.219  1.00 24.50           C
ATOM    672  CB  ARG A  84     128.518  50.936  -2.190  1.00 23.17           C
ATOM    673  CG  ARG A  84     127.913  49.574  -2.510  1.00 27.83           C
ATOM    674  CD  ARG A  84     128.382  48.423  -1.562  1.00 30.58           C
ATOM    675  NE  ARG A  84     128.176  47.187  -2.298  1.00 33.27           N
ATOM    676  CZ  ARG A  84     126.990  46.558  -2.387  1.00 38.36           C
ATOM    677  NH1 ARG A  84     125.928  47.080  -1.785  1.00 37.14           N
ATOM    678  NH2 ARG A  84     126.826  45.443  -3.131  1.00 37.61           N
ATOM    679  C   ARG A  84     128.344  52.887  -0.497  1.00 23.58           C
ATOM    680  O   ARG A  84     128.793  52.747   0.634  1.00 22.35           O
ATOM    681  N   ILE A  85     128.393  54.067  -1.117  1.00 25.70           N
ATOM    682  CA  ILE A  85     129.092  55.228  -0.509  1.00 24.40           C
ATOM    683  CB  ILE A  85     129.068  56.423  -1.444  1.00 26.28           C
ATOM    684  CG1 ILE A  85     129.783  56.105  -2.761  1.00 29.93           C
ATOM    685  CD1 ILE A  85     131.106  55.591  -2.555  1.00 34.08           C
ATOM    686  CG2 ILE A  85     129.755  57.666  -0.783  1.00 27.71           C
ATOM    687  C   ILE A  85     128.439  55.558   0.809  1.00 24.36           C
ATOM    688  O   ILE A  85     129.097  55.567   1.824  1.00 24.48           O
ATOM    689  N   MET A  86     127.095  55.709   0.842  1.00 25.64           N
ATOM    690  CA  MET A  86     126.443  56.186   2.028  1.00 24.45           C
ATOM    691  CB  MET A  86     124.953  56.436   1.752  1.00 25.98           C
ATOM    692  CG  MET A  86     124.689  57.628   0.955  1.00 32.14           C
ATOM    693  SD  MET A  86     125.740  59.004   1.491  1.00 44.80           S
ATOM    694  CE  MET A  86     126.135  59.636  -0.158  1.00 38.55           C
ATOM    695  C   MET A  86     126.494  55.177   3.117  1.00 23.73           C
ATOM    696  O   MET A  86     126.565  55.531   4.305  1.00 23.45           O
ATOM    697  N   ALA A  87     126.314  53.902   2.754  1.00 23.19           N
ATOM    698  CA  ALA A  87     126.461  52.825   3.766  1.00 22.63           C
ATOM    699  CB  ALA A  87     126.153  51.381   3.070  1.00 19.72           C
ATOM    700  C   ALA A  87     127.746  52.775   4.552  1.00 19.18           C
ATOM    701  O   ALA A  87     127.800  52.676   5.791  1.00 20.92           O
ATOM    702  N   TRP A  88     128.831  52.786   3.828  1.00 22.50           N
ATOM    703  CA  TRP A  88     130.159  52.751   4.434  1.00 20.36           C
ATOM    704  CB  TRP A  88     131.225  52.618   3.346  1.00 20.71           C
ATOM    705  CG  TRP A  88     131.428  51.252   2.946  1.00 23.65           C
ATOM    706  CD1 TRP A  88     131.074  50.665   1.793  1.00 23.39           C
ATOM    707  NE1 TRP A  88     131.408  49.330   1.845  1.00 24.15           N
ATOM    708  CE2 TRP A  88     131.949  49.051   3.075  1.00 20.66           C
ATOM    709  CD2 TRP A  88     131.937  50.224   3.805  1.00 22.48           C
ATOM    710  CE3 TRP A  88     132.494  50.242   5.105  1.00 24.89           C
```

FIG. 1M

```
ATOM    711  CZ3 TRP A  88     132.986  49.032   5.640  1.00 28.04           C
ATOM    712  CH2 TRP A  88     132.913  47.838   4.886  1.00 24.59           C
ATOM    713  CZ2 TRP A  88     132.421  47.823   3.601  1.00 23.83           C
ATOM    714  C   TRP A  88     130.333  54.119   5.133  1.00 21.55           C
ATOM    715  O   TRP A  88     131.074  54.202   6.097  1.00 21.31           O
ATOM    716  N   THR A  89     129.641  55.157   4.669  1.00 22.55           N
ATOM    717  CA  THR A  89     129.718  56.470   5.431  1.00 23.74           C
ATOM    718  CB  THR A  89     129.028  57.623   4.642  1.00 23.90           C
ATOM    719  OG1 THR A  89     129.757  57.813   3.440  1.00 26.28           O
ATOM    720  CG2 THR A  89     129.005  58.954   5.435  1.00 27.11           C
ATOM    721  C   THR A  89     129.071  56.316   6.765  1.00 21.64           C
ATOM    722  O   THR A  89     129.604  56.792   7.778  1.00 24.13           O
ATOM    723  N   VAL A  90     127.938  55.606   6.802  1.00 20.19           N
ATOM    724  CA  VAL A  90     127.269  55.366   8.099  1.00 21.17           C
ATOM    725  CB  VAL A  90     125.840  54.848   7.772  1.00 21.45           C
ATOM    726  CG1 VAL A  90     125.136  54.314   8.980  1.00 23.14           C
ATOM    727  CG2 VAL A  90     125.006  56.025   7.161  1.00 25.54           C
ATOM    728  C   VAL A  90     128.118  54.410   8.956  1.00 20.25           C
ATOM    729  O   VAL A  90     128.440  54.638  10.117  1.00 22.52           O
ATOM    730  N   VAL A  91     128.523  53.290   8.384  1.00 20.69           N
ATOM    731  CA  VAL A  91     129.428  52.423   9.157  1.00 21.28           C
ATOM    732  CB  VAL A  91     129.899  51.253   8.315  1.00 18.74           C
ATOM    733  CG1 VAL A  91     131.108  50.627   9.004  1.00 21.12           C
ATOM    734  CG2 VAL A  91     128.642  50.226   8.134  1.00 18.85           C
ATOM    735  C   VAL A  91     130.663  53.199   9.694  1.00 22.68           C
ATOM    736  O   VAL A  91     131.080  52.976  10.816  1.00 23.09           O
ATOM    737  N   ASN A  92     131.267  54.060   8.895  1.00 24.25           N
ATOM    738  CA  ASN A  92     132.554  54.763   9.373  1.00 26.98           C
ATOM    739  CB  ASN A  92     133.244  55.584   8.261  1.00 26.36           C
ATOM    740  CG  ASN A  92     133.911  54.759   7.173  1.00 32.55           C
ATOM    741  OD1 ASN A  92     134.164  53.518   7.296  1.00 40.81           O
ATOM    742  ND2 ASN A  92     134.184  55.436   6.044  1.00 33.67           N
ATOM    743  C   ASN A  92     132.182  55.736  10.512  1.00 27.38           C
ATOM    744  O   ASN A  92     132.840  55.867  11.497  1.00 28.44           O
ATOM    745  N   SER A  93     131.056  56.388  10.382  1.00 28.83           N
ATOM    746  CA  SER A  93     130.588  57.280  11.476  1.00 29.39           C
ATOM    747  CB  SER A  93     129.422  58.157  10.960  1.00 29.20           C
ATOM    748  OG  SER A  93     128.668  58.681  12.031  1.00 36.15           O
ATOM    749  C   SER A  93     130.223  56.530  12.703  1.00 27.81           C
ATOM    750  O   SER A  93     130.458  56.998  13.829  1.00 27.63           O
ATOM    751  N   ILE A  94     129.682  55.314  12.531  1.00 27.52           N
ATOM    752  CA  ILE A  94     129.370  54.491  13.683  1.00 24.71           C
ATOM    753  CB  ILE A  94     128.529  53.258  13.280  1.00 26.27           C
ATOM    754  CG1 ILE A  94     127.159  53.670  12.712  1.00 24.93           C
ATOM    755  CD1 ILE A  94     126.349  52.474  12.155  1.00 23.61           C
ATOM    756  CG2 ILE A  94     128.351  52.417  14.523  1.00 24.62           C
ATOM    757  C   ILE A  94     130.622  53.978  14.398  1.00 25.53           C
ATOM    758  O   ILE A  94     130.719  53.958  15.632  1.00 25.48           O
ATOM    759  N   CYS A  95     131.591  53.501  13.653  1.00 24.91           N
ATOM    760  CA  CYS A  95     132.861  53.178  14.281  1.00 28.68           C
ATOM    761  CB  CYS A  95     133.812  52.447  13.302  1.00 27.47           C
ATOM    762  SG  CYS A  95     132.943  50.957  12.676  1.00 33.60           S
ATOM    763  C   CYS A  95     133.542  54.397  15.039  1.00 30.70           C
ATOM    764  O   CYS A  95     134.003  54.243  16.159  1.00 32.47           O
ATOM    765  N   ASN A  96     133.455  55.606  14.517  1.00 31.17           N
ATOM    766  CA  ASN A  96     133.886  56.772  15.342  1.00 34.29           C
ATOM    767  CB  ASN A  96     133.859  58.056  14.510  1.00 34.06           C
ATOM    768  CG  ASN A  96     134.879  58.038  13.453  1.00 37.04           C
ATOM    769  OD1 ASN A  96     135.975  57.501  13.686  1.00 45.12           O
ATOM    770  ND2 ASN A  96     134.545  58.544  12.256  1.00 37.27           N
ATOM    771  C   ASN A  96     133.119  57.009  16.625  1.00 34.55           C
ATOM    772  O   ASN A  96     133.709  57.374  17.648  1.00 37.18           O
ATOM    773  N   THR A  97     131.801  56.806  16.590  1.00 34.97           N
```

FIG. 1N

```
ATOM   774  CA   THR A  97     130.957  57.079  17.746  1.00 33.78           C
ATOM   775  CB   THR A  97     129.505  56.848  17.350  1.00 34.91           C
ATOM   776  OG1  THR A  97     129.269  57.549  16.135  1.00 38.47           O
ATOM   777  CG2  THR A  97     128.484  57.284  18.448  1.00 30.89           C
ATOM   778  C    THR A  97     131.237  56.141  18.888  1.00 34.63           C
ATOM   779  O    THR A  97     131.252  56.583  20.069  1.00 35.31           O
ATOM   780  N    THR A  98     131.383  54.845  18.578  1.00 32.27           N
ATOM   781  CA   THR A  98     131.299  53.823  19.602  1.00 32.11           C
ATOM   782  CB   THR A  98     130.294  52.634  19.277  1.00 34.31           C
ATOM   783  OG1  THR A  98     130.817  51.901  18.172  1.00 29.27           O
ATOM   784  CG2  THR A  98     128.798  53.106  18.997  1.00 32.15           C
ATOM   785  C    THR A  98     132.658  53.191  19.764  1.00 30.79           C
ATOM   786  O    THR A  98     132.964  52.655  20.828  1.00 29.82           O
ATOM   787  N    GLY A  99     133.451  53.245  18.722  1.00 30.71           N
ATOM   788  CA   GLY A  99     134.799  52.674  18.770  1.00 33.01           C
ATOM   789  C    GLY A  99     134.797  51.167  18.530  1.00 33.78           C
ATOM   790  O    GLY A  99     135.782  50.441  18.851  1.00 35.21           O
ATOM   791  N    VAL A 100     133.676  50.700  17.984  1.00 32.38           N
ATOM   792  CA   VAL A 100     133.510  49.319  17.605  1.00 31.73           C
ATOM   793  CB   VAL A 100     132.022  49.029  17.297  1.00 30.21           C
ATOM   794  CG1  VAL A 100     131.627  49.696  15.965  1.00 29.23           C
ATOM   795  CG2  VAL A 100     131.741  47.503  17.320  1.00 33.80           C
ATOM   796  C    VAL A 100     134.357  49.027  16.375  1.00 29.68           C
ATOM   797  O    VAL A 100     134.462  49.843  15.509  1.00 27.97           O
ATOM   798  N    GLU A 101     134.979  47.847  16.348  1.00 30.40           N
ATOM   799  CA   GLU A 101     135.787  47.408  15.230  1.00 29.78           C
ATOM   800  CB   GLU A 101     136.290  45.985  15.510  1.00 30.19           C
ATOM   801  CG   GLU A 101     137.453  45.557  14.676  1.00 35.18           C
ATOM   802  CD   GLU A 101     138.065  44.217  15.194  1.00 41.01           C
ATOM   803  OE1  GLU A 101     137.468  43.156  14.899  1.00 34.44           O
ATOM   804  OE2  GLU A 101     139.115  44.265  15.898  1.00 43.44           O
ATOM   805  C    GLU A 101     134.980  47.455  13.928  1.00 28.95           C
ATOM   806  O    GLU A 101     133.789  47.037  13.866  1.00 27.32           O
ATOM   807  N    LYS A 102     135.599  48.025  12.910  1.00 26.95           N
ATOM   808  CA   LYS A 102     134.976  48.090  11.614  1.00 26.95           C
ATOM   809  CB   LYS A 102     135.659  49.128  10.752  1.00 27.08           C
ATOM   810  CG   LYS A 102     134.920  49.455   9.444  1.00 31.11           C
ATOM   811  CD   LYS A 102     135.721  50.466   8.606  1.00 37.88           C
ATOM   812  CE   LYS A 102     136.068  51.667   9.490  1.00 39.44           C
ATOM   813  NZ   LYS A 102     136.109  52.904   8.671  1.00 42.90           N
ATOM   814  C    LYS A 102     134.956  46.701  10.898  1.00 26.48           C
ATOM   815  O    LYS A 102     135.966  46.025  10.814  1.00 24.28           O
ATOM   816  N    PRO A 103     133.785  46.282  10.424  1.00 26.52           N
ATOM   817  CA   PRO A 103     133.661  44.977   9.755  1.00 26.25           C
ATOM   818  CB   PRO A 103     132.158  44.681   9.835  1.00 26.53           C
ATOM   819  CG   PRO A 103     131.493  46.120   9.778  1.00 26.84           C
ATOM   820  CD   PRO A 103     132.546  47.089  10.386  1.00 25.64           C
ATOM   821  C    PRO A 103     134.096  45.225   8.301  1.00 27.05           C
ATOM   822  O    PRO A 103     134.032  46.371   7.832  1.00 26.40           O
ATOM   823  N    LYS A 104     134.549  44.169   7.636  1.00 26.71           N
ATOM   824  CA   LYS A 104     135.044  44.181   6.243  1.00 29.35           C
ATOM   825  CB   LYS A 104     136.008  42.980   6.066  1.00 28.99           C
ATOM   826  CG   LYS A 104     137.325  43.212   6.750  1.00 29.89           C
ATOM   827  CD   LYS A 104     138.216  41.953   6.664  1.00 34.14           C
ATOM   828  CE   LYS A 104     139.444  42.210   7.460  1.00 33.97           C
ATOM   829  NZ   LYS A 104     140.592  41.452   6.906  1.00 38.04           N
ATOM   830  C    LYS A 104     134.007  44.126   5.126  1.00 28.96           C
ATOM   831  O    LYS A 104     134.283  44.443   3.946  1.00 29.54           O
ATOM   832  N    PHE A 105     132.312  43.720   5.479  1.00 29.04           N
ATOM   833  CA   PHE A 105     131.708  43.743   4.520  1.00 30.31           C
ATOM   834  CB   PHE A 105     131.232  42.302   4.442  1.00 31.46           C
ATOM   835  CG   PHE A 105     130.672  41.867   5.705  1.00 36.41           C
ATOM   836  CD1  PHE A 105     129.290  41.812   5.879  1.00 45.29           C
```

FIG. 10

```
ATOM    837  CE1 PHE A 105     128.735  41.454   7.116  1.00 44.10           C
ATOM    838  CZ  PHE A 105     129.571  41.201   8.191  1.00 44.12           C
ATOM    839  CE2 PHE A 105     130.936  41.266   8.054  1.00 41.63           C
ATOM    840  CD2 PHE A 105     131.505  41.619   6.801  1.00 42.87           C
ATOM    841  C   PHE A 105     130.586  44.579   5.147  1.00 27.91           C
ATOM    842  O   PHE A 105     130.584  44.743   6.344  1.00 28.94           O
ATOM    843  N   LEU A 106     129.619  45.052   4.377  1.00 26.08           N
ATOM    844  CA  LEU A 106     128.495  45.800   4.948  1.00 25.85           C
ATOM    845  CB  LEU A 106     127.801  46.539   3.813  1.00 25.11           C
ATOM    846  CG  LEU A 106     128.658  47.729   3.333  1.00 28.47           C
ATOM    847  CD1 LEU A 106     128.032  48.268   2.020  1.00 25.00           C
ATOM    848  CD2 LEU A 106     128.789  48.852   4.393  1.00 26.80           C
ATOM    849  C   LEU A 106     127.459  44.873   5.625  1.00 23.67           C
ATOM    850  O   LEU A 106     126.841  44.064   4.979  1.00 22.75           O
ATOM    851  N   PRO A 107     127.239  45.006   6.911  1.00 21.65           N
ATOM    852  CA  PRO A 107     126.107  44.250   7.445  1.00 21.50           C
ATOM    853  CB  PRO A 107     126.495  44.050   8.916  1.00 21.01           C
ATOM    854  CG  PRO A 107     127.423  45.181   9.206  1.00 25.92           C
ATOM    855  CD  PRO A 107     127.928  45.804   7.929  1.00 23.21           C
ATOM    856  C   PRO A 107     124.772  45.074   7.337  1.00 20.47           C
ATOM    857  O   PRO A 107     124.819  46.181   6.787  1.00 21.40           O
ATOM    858  N   ASP A 108     123.683  44.651   7.994  1.00 18.13           N
ATOM    859  CA  ASP A 108     122.347  45.269   7.759  1.00 19.87           C
ATOM    860  CB  ASP A 108     121.259  44.137   7.728  1.00 18.23           C
ATOM    861  CG  ASP A 108     121.537  43.177   6.613  1.00 19.12           C
ATOM    862  OD1 ASP A 108     121.573  43.526   5.408  1.00 22.66           O
ATOM    863  OD2 ASP A 108     121.803  42.066   6.937  1.00 27.04           O
ATOM    864  C   ASP A 108     121.958  46.266   8.763  1.00 18.51           C
ATOM    865  O   ASP A 108     121.254  47.171   8.421  1.00 24.12           O
ATOM    866  N   LEU A 109     122.239  45.992  10.017  1.00 20.09           N
ATOM    867  CA  LEU A 109     121.941  46.871  11.117  1.00 20.75           C
ATOM    868  CB  LEU A 109     120.740  46.364  11.965  1.00 22.01           C
ATOM    869  CG  LEU A 109     119.437  46.024  11.201  1.00 23.61           C
ATOM    870  CD1 LEU A 109     118.556  44.988  11.897  1.00 25.56           C
ATOM    871  CD2 LEU A 109     118.659  47.297  10.951  1.00 21.63           C
ATOM    872  C   LEU A 109     123.145  47.077  12.052  1.00 21.13           C
ATOM    873  O   LEU A 109     124.139  46.248  12.116  1.00 19.84           O
ATOM    874  N   TYR A 110     123.026  48.139  12.862  1.00 18.38           N
ATOM    875  CA  TYR A 110     123.835  48.314  14.042  1.00 18.86           C
ATOM    876  CB  TYR A 110     124.738  49.545  13.875  1.00 19.35           C
ATOM    877  CG  TYR A 110     125.608  49.673  15.059  1.00 20.54           C
ATOM    878  CD1 TYR A 110     126.630  48.755  15.253  1.00 21.69           C
ATOM    879  CE1 TYR A 110     127.368  48.772  16.386  1.00 20.34           C
ATOM    880  CZ  TYR A 110     127.138  49.755  17.370  1.00 27.19           C
ATOM    881  OH  TYR A 110     127.959  49.778  18.497  1.00 27.25           O
ATOM    882  CE2 TYR A 110     126.072  50.662  17.228  1.00 22.47           C
ATOM    883  CD2 TYR A 110     125.331  50.614  16.071  1.00 25.73           C
ATOM    884  C   TYR A 110     122.965  48.494  15.278  1.00 20.38           C
ATOM    885  O   TYR A 110     121.993  49.249  15.278  1.00 20.57           O
ATOM    886  N   ASP A 111     123.326  47.857  16.358  1.00 20.65           N
ATOM    887  CA  ASP A 111     122.465  47.877  17.553  1.00 24.59           C
ATOM    888  CB  ASP A 111     122.243  46.427  18.028  1.00 23.42           C
ATOM    889  CG  ASP A 111     121.488  46.310  19.310  1.00 23.58           C
ATOM    890  OD1 ASP A 111     121.168  47.299  19.907  1.00 21.89           O
ATOM    891  OD2 ASP A 111     121.136  45.158  19.712  1.00 27.24           O
ATOM    892  C   ASP A 111     123.179  48.671  18.613  1.00 24.74           C
ATOM    893  O   ASP A 111     124.200  48.229  19.054  1.00 25.21           O
ATOM    894  N   TYR A 112     122.633  49.832  19.006  1.00 26.40           N
ATOM    895  CA  TYR A 112     123.326  50.766  19.956  1.00 26.77           C
ATOM    896  CB  TYR A 112     122.802  52.196  19.880  1.00 26.44           C
ATOM    897  CG  TYR A 112     123.312  52.933  18.711  1.00 27.42           C
ATOM    898  CD1 TYR A 112     122.503  53.117  17.629  1.00 30.73           C
ATOM    899  CE1 TYR A 112     122.937  53.801  16.512  1.00 34.75           C
```

FIG. 1P

```
ATOM    900  CZ   TYR A 112     124.251  54.322  16.463  1.00 29.86           C
ATOM    901  OH   TYR A 112     124.579  54.954  15.262  1.00 29.23           O
ATOM    902  CE2  TYR A 112     125.107  54.156  17.518  1.00 27.39           C
ATOM    903  CD2  TYR A 112     124.638  53.490  18.682  1.00 31.22           C
ATOM    904  C    TYR A 112     123.159  50.289  21.370  1.00 27.89           C
ATOM    905  O    TYR A 112     123.926  50.687  22.261  1.00 27.99           O
ATOM    906  N    LYS A 113     122.240  49.359  21.605  1.00 29.22           N
ATOM    907  CA   LYS A 113     122.257  48.819  22.955  1.00 30.96           C
ATOM    908  CB   LYS A 113     120.919  48.223  23.365  1.00 32.31           C
ATOM    909  CG   LYS A 113     120.822  47.797  24.848  1.00 34.11           C
ATOM    910  CD   LYS A 113     119.778  46.717  24.972  1.00 42.13           C
ATOM    911  CE   LYS A 113     119.274  46.559  26.400  1.00 44.42           C
ATOM    912  NZ   LYS A 113     118.071  45.698  26.322  1.00 49.89           N
ATOM    913  C    LYS A 113     123.360  47.770  23.156  1.00 32.96           C
ATOM    914  O    LYS A 113     124.047  47.810  24.178  1.00 33.42           O
ATOM    915  N    GLU A 114     123.467  46.766  22.276  1.00 32.57           N
ATOM    916  CA   GLU A 114     124.380  45.593  22.565  1.00 32.04           C
ATOM    917  CB   GLU A 114     123.857  44.308  21.919  1.00 31.51           C
ATOM    918  CG   GLU A 114     122.469  43.836  22.471  1.00 31.86           C
ATOM    919  CD   GLU A 114     122.625  43.183  23.815  1.00 37.94           C
ATOM    920  OE1  GLU A 114     123.781  42.998  24.277  1.00 39.64           O
ATOM    921  OE2  GLU A 114     121.613  42.818  24.429  1.00 43.07           O
ATOM    922  C    GLU A 114     125.756  45.954  22.026  1.00 32.14           C
ATOM    923  O    GLU A 114     126.747  45.271  22.266  1.00 32.02           O
ATOM    924  N    ASN A 115     125.775  47.077  21.311  1.00 31.99           N
ATOM    925  CA   ASN A 115     126.875  47.553  20.497  1.00 31.56           C
ATOM    926  CB   ASN A 115     127.980  48.185  21.360  1.00 31.25           C
ATOM    927  CG   ASN A 115     127.597  49.552  21.871  1.00 34.17           C
ATOM    928  OD1  ASN A 115     127.374  49.713  23.065  1.00 37.89           O
ATOM    929  ND2  ASN A 115     127.557  50.553  20.990  1.00 32.94           N
ATOM    930  C    ASN A 115     127.467  46.562  19.507  1.00 29.75           C
ATOM    931  O    ASN A 115     128.653  46.329  19.520  1.00 29.27           O
ATOM    932  N    ARG A 116     126.652  45.951  18.676  1.00 28.67           N
ATOM    933  CA   ARG A 116     127.218  45.144  17.602  1.00 25.74           C
ATOM    934  CB   ARG A 116     127.204  43.671  18.025  1.00 27.34           C
ATOM    935  CG   ARG A 116     125.776  43.205  18.372  1.00 28.20           C
ATOM    936  CD   ARG A 116     125.710  42.102  19.438  1.00 25.80           C
ATOM    937  NE   ARG A 116     124.300  41.665  19.571  1.00 25.41           N
ATOM    938  CZ   ARG A 116     123.820  40.823  20.499  1.00 26.84           C
ATOM    939  NH1  ARG A 116     124.610  40.265  21.384  1.00 27.39           N
ATOM    940  NH2  ARG A 116     122.533  40.505  20.531  1.00 28.58           N
ATOM    941  C    ARG A 116     126.453  45.415  16.312  1.00 24.65           C
ATOM    942  O    ARG A 116     125.378  45.966  16.325  1.00 22.53           O
ATOM    943  N    PHE A 117     127.092  45.123  15.189  1.00 22.12           N
ATOM    944  CA   PHE A 117     126.475  45.053  13.958  1.00 22.26           C
ATOM    945  CB   PHE A 117     127.492  45.108  12.829  1.00 21.72           C
ATOM    946  CG   PHE A 117     128.183  46.450  12.698  1.00 22.55           C
ATOM    947  CD1  PHE A 117     127.539  47.474  12.101  1.00 19.09           C
ATOM    948  CE1  PHE A 117     128.182  48.769  11.990  1.00 27.35           C
ATOM    949  CZ   PHE A 117     129.423  49.008  12.467  1.00 22.15           C
ATOM    950  CE2  PHE A 117     130.137  47.972  13.055  1.00 21.26           C
ATOM    951  CD2  PHE A 117     129.485  46.651  13.152  1.00 19.95           C
ATOM    952  C    PHE A 117     125.675  43.719  13.875  1.00 22.96           C
ATOM    953  O    PHE A 117     125.989  42.731  14.541  1.00 25.10           O
ATOM    954  N    ILE A 118     124.686  43.712  13.003  1.00 24.15           N
ATOM    955  CA   ILE A 118     123.789  42.546  12.755  1.00 21.86           C
ATOM    956  CB   ILE A 118     122.370  42.822  13.179  1.00 22.55           C
ATOM    957  CG1  ILE A 118     122.365  43.631  14.455  1.00 26.73           C
ATOM    958  CD1  ILE A 118     121.691  43.061  15.549  1.00 35.89           C
ATOM    959  CG2  ILE A 118     121.456  41.470  13.204  1.00 19.31           C
ATOM    960  C    ILE A 118     123.741  42.310  11.267  1.00 20.89           C
ATOM    961  O    ILE A 118     123.533  43.232  10.474  1.00 17.21           O
ATOM    962  N    GLU A 119     123.915  41.039  10.902  1.00 20.10           N
```

FIG. 1Q

```
ATOM    963  CA   GLU A 119     123.743  40.632   9.559  1.00 20.80           C
ATOM    964  CB   GLU A 119     124.965  39.722   9.159  1.00 21.09           C
ATOM    965  CG   GLU A 119     124.703  38.961   7.898  1.00 26.34           C
ATOM    966  CD   GLU A 119     124.413  39.937   6.720  1.00 29.79           C
ATOM    967  OE1  GLU A 119     125.044  41.001   6.633  1.00 35.89           O
ATOM    968  OE2  GLU A 119     123.570  39.648   5.878  1.00 30.35           O
ATOM    969  C    GLU A 119     122.435  39.871   9.626  1.00 21.24           C
ATOM    970  O    GLU A 119     122.242  38.967  10.425  1.00 18.50           O
ATOM    971  N    ILE A 120     121.492  40.283   8.801  1.00 23.72           N
ATOM    972  CA   ILE A 120     120.180  39.652   8.763  1.00 23.23           C
ATOM    973  CB   ILE A 120     119.058  40.710   8.511  1.00 23.83           C
ATOM    974  CG1  ILE A 120     118.935  41.682   9.709  1.00 23.83           C
ATOM    975  CD1  ILE A 120     118.508  40.916  10.991  1.00 22.81           C
ATOM    976  CG2  ILE A 120     117.745  39.983   8.239  1.00 20.21           C
ATOM    977  C    ILE A 120     120.097  38.700   7.609  1.00 23.86           C
ATOM    978  O    ILE A 120     120.582  38.993   6.526  1.00 22.92           O
ATOM    979  N    GLY A 121     119.426  37.560   7.803  1.00 25.01           N
ATOM    980  CA   GLY A 121     119.232  36.658   6.659  1.00 24.61           C
ATOM    981  C    GLY A 121     117.769  36.223   6.636  1.00 23.18           C
ATOM    982  O    GLY A 121     117.158  36.076   7.665  1.00 22.81           O
ATOM    983  N    VAL A 122     117.223  36.109   5.445  1.00 24.10           N
ATOM    984  CA   VAL A 122     115.869  35.612   5.177  1.00 23.11           C
ATOM    985  CB   VAL A 122     114.904  36.735   4.643  1.00 22.67           C
ATOM    986  CG1  VAL A 122     113.495  36.113   4.539  1.00 22.36           C
ATOM    987  CG2  VAL A 122     114.848  37.914   5.619  1.00 19.79           C
ATOM    988  C    VAL A 122     115.975  34.511   4.140  1.00 23.74           C
ATOM    989  O    VAL A 122     116.410  34.746   3.015  1.00 24.81           O
ATOM    990  N    THR A 123     115.576  33.293   4.514  1.00 24.85           N
ATOM    991  CA   THR A 123     115.754  32.159   3.617  1.00 24.26           C
ATOM    992  CB   THR A 123     116.843  31.104   4.163  1.00 25.22           C
ATOM    993  OG1  THR A 123     116.857  29.972   3.288  1.00 27.18           O
ATOM    994  CG2  THR A 123     116.491  30.621   5.538  1.00 23.74           C
ATOM    995  C    THR A 123     114.448  31.426   3.377  1.00 23.31           C
ATOM    996  O    THR A 123     113.616  31.321   4.267  1.00 21.78           O
ATOM    997  N    ARG A 124     114.303  30.903   2.163  1.00 25.09           N
ATOM    998  CA   ARG A 124     113.220  29.963   1.794  1.00 27.08           C
ATOM    999  CB   ARG A 124     112.892  30.113   0.287  1.00 25.27           C
ATOM   1000  CG   ARG A 124     112.201  31.455  -0.079  1.00 28.12           C
ATOM   1001  CD   ARG A 124     113.240  32.483  -0.446  1.00 25.39           C
ATOM   1002  NE   ARG A 124     113.468  32.338  -1.876  1.00 29.12           N
ATOM   1003  CZ   ARG A 124     114.397  32.959  -2.571  1.00 31.04           C
ATOM   1004  NH1  ARG A 124     115.255  33.762  -1.985  1.00 32.81           N
ATOM   1005  NH2  ARG A 124     114.455  32.774  -3.864  1.00 29.63           N
ATOM   1006  C    ARG A 124     113.643  28.482   2.045  1.00 29.45           C
ATOM   1007  O    ARG A 124     112.879  27.552   1.718  1.00 30.42           O
ATOM   1008  N    ARG A 125     114.888  28.255   2.451  1.00 30.37           N
ATOM   1009  CA   ARG A 125     115.335  26.867   2.766  1.00 33.50           C
ATOM   1010  CB   ARG A 125     116.751  26.608   2.296  1.00 33.86           C
ATOM   1011  CG   ARG A 125     117.004  26.792   0.812  1.00 38.17           C
ATOM   1012  CD   ARG A 125     118.397  27.434   0.639  1.00 38.05           C
ATOM   1013  NE   ARG A 125     119.447  26.467   1.022  1.00 43.50           N
ATOM   1014  CZ   ARG A 125     120.717  26.763   1.272  1.00 44.97           C
ATOM   1015  NH1  ARG A 125     121.145  28.022   1.221  1.00 45.26           N
ATOM   1016  NH2  ARG A 125     121.564  25.796   1.614  1.00 47.76           N
ATOM   1017  C    ARG A 125     115.280  26.654   4.273  1.00 32.67           C
ATOM   1018  O    ARG A 125     114.366  27.065   4.950  1.00 36.32           O
ATOM   1019  N    GLU A 126     116.260  26.030   4.840  1.00 33.04           N
ATOM   1020  CA   GLU A 126     116.131  25.695   6.247  1.00 31.85           C
ATOM   1021  CB   GLU A 126     116.552  24.241   6.397  1.00 33.19           C
ATOM   1022  CG   GLU A 126     116.246  23.646   7.743  1.00 36.91           C
ATOM   1023  CD   GLU A 126     117.399  23.846   8.698  1.00 42.26           C
ATOM   1024  OE1  GLU A 126     117.112  24.348   9.850  1.00 42.79           O
ATOM   1025  OE2  GLU A 126     118.570  23.493   8.309  1.00 37.69           O
```

FIG. 1R

```
ATOM   1026  C    GLU A 126     116.982   26.678    7.037  1.00 30.31           C
ATOM   1027  O    GLU A 126     118.039   27.091    6.585  1.00 30.05           O
ATOM   1028  N    VAL A 127     116.535   27.044    8.221  1.00 29.36           N
ATOM   1029  CA   VAL A 127     117.161   28.084    8.983  1.00 29.64           C
ATOM   1030  CB   VAL A 127     116.200   28.526   10.146  1.00 31.07           C
ATOM   1031  CG1  VAL A 127     116.721   28.187   11.511  1.00 30.66           C
ATOM   1032  CG2  VAL A 127     115.922   29.997   10.064  1.00 31.21           C
ATOM   1033  C    VAL A 127     118.629   27.726    9.380  1.00 29.43           C
ATOM   1034  O    VAL A 127     119.588   28.550    9.175  1.00 27.52           O
ATOM   1035  N    HIS A 128     118.820   26.487    9.881  1.00 27.13           N
ATOM   1036  CA   HIS A 128     120.123   26.064   10.345  1.00 28.16           C
ATOM   1037  CB   HIS A 128     120.010   24.701   11.160  1.00 28.60           C
ATOM   1038  CG   HIS A 128     121.196   24.418   12.014  1.00 29.94           C
ATOM   1039  ND1  HIS A 128     121.352   23.250   12.720  1.00 29.01           N
ATOM   1040  CE1  HIS A 128     122.490   23.294   13.383  1.00 30.53           C
ATOM   1041  NE2  HIS A 128     123.126   24.397   13.048  1.00 30.25           N
ATOM   1042  CD2  HIS A 128     122.351   25.109   12.178  1.00 32.97           C
ATOM   1043  C    HIS A 128     121.228   26.123    9.271  1.00 27.06           C
ATOM   1044  O    HIS A 128     122.275   26.768    9.459  1.00 27.42           O
ATOM   1045  N    ILE A 129     120.983   25.497    8.144  1.00 27.67           N
ATOM   1046  CA   ILE A 129     121.965   25.389    7.084  1.00 29.76           C
ATOM   1047  CB   ILE A 129     121.637   24.267    6.007  1.00 32.02           C
ATOM   1048  CG1  ILE A 129     122.898   23.958    5.225  1.00 31.34           C
ATOM   1049  CD1  ILE A 129     122.711   22.950    4.122  1.00 43.21           C
ATOM   1050  CG2  ILE A 129     120.493   24.647    5.091  1.00 32.48           C
ATOM   1051  C    ILE A 129     122.298   26.739    6.458  1.00 28.92           C
ATOM   1052  O    ILE A 129     123.477   27.029    6.174  1.00 26.57           O
ATOM   1053  N    TYR A 130     121.289   27.595    6.383  1.00 26.94           N
ATOM   1054  CA   TYR A 130     121.513   28.921    5.944  1.00 27.00           C
ATOM   1055  CB   TYR A 130     120.146   29.665    5.719  1.00 25.76           C
ATOM   1056  CG   TYR A 130     120.335   30.993    5.027  1.00 28.67           C
ATOM   1057  CD1  TYR A 130     120.631   31.052    3.684  1.00 29.98           C
ATOM   1058  CE1  TYR A 130     120.841   32.281    3.053  1.00 35.41           C
ATOM   1059  CZ   TYR A 130     120.726   33.473    3.752  1.00 28.23           C
ATOM   1060  OH   TYR A 130     120.908   34.640    3.064  1.00 34.08           O
ATOM   1061  CE2  TYR A 130     120.464   33.445    5.095  1.00 29.64           C
ATOM   1062  CD2  TYR A 130     120.256   32.197    5.729  1.00 29.56           C
ATOM   1063  C    TYR A 130     122.417   29.647    6.924  1.00 25.09           C
ATOM   1064  O    TYR A 130     123.366   30.256    6.504  1.00 25.63           O
ATOM   1065  N    TYR A 131     122.148   29.514    8.217  1.00 23.85           N
ATOM   1066  CA   TYR A 131     122.915   30.114    9.217  1.00 23.89           C
ATOM   1067  CB   TYR A 131     122.348   29.743   10.620  1.00 24.32           C
ATOM   1068  CG   TYR A 131     123.233   30.277   11.701  1.00 27.01           C
ATOM   1069  CD1  TYR A 131     123.019   31.548   12.222  1.00 30.13           C
ATOM   1070  CE1  TYR A 131     123.857   32.084   13.168  1.00 30.19           C
ATOM   1071  CZ   TYR A 131     124.958   31.387   13.583  1.00 37.38           C
ATOM   1072  OH   TYR A 131     125.783   31.979   14.511  1.00 42.12           O
ATOM   1073  CE2  TYR A 131     125.244   30.121   13.066  1.00 36.83           C
ATOM   1074  CD2  TYR A 131     124.360   29.559   12.141  1.00 34.49           C
ATOM   1075  C    TYR A 131     124.433   29.754    9.052  1.00 26.44           C
ATOM   1076  O    TYR A 131     125.349   30.661    9.187  1.00 24.68           O
ATOM   1077  N    LEU A 132     124.689   28.462    8.769  1.00 25.67           N
ATOM   1078  CA   LEU A 132     126.054   27.902    8.775  1.00 27.57           C
ATOM   1079  CB   LEU A 132     126.081   26.337    8.684  1.00 26.28           C
ATOM   1080  CG   LEU A 132     125.458   25.542    9.824  1.00 23.94           C
ATOM   1081  CD1  LEU A 132     125.611   23.951    9.620  1.00 26.89           C
ATOM   1082  CD2  LEU A 132     126.083   25.979   11.185  1.00 23.18           C
ATOM   1083  C    LEU A 132     126.737   28.483    7.586  1.00 28.21           C
ATOM   1084  O    LEU A 132     127.853   29.013    7.725  1.00 28.68           O
ATOM   1085  N    GLU A 133     126.040   28.488    6.450  1.00 29.62           N
ATOM   1086  CA   GLU A 133     126.633   29.063    5.258  1.00 32.24           C
ATOM   1087  CB   GLU A 133     125.763   28.842    4.087  1.00 31.82           C
ATOM   1088  CG   GLU A 133     125.769   27.365    3.691  1.00 37.61           C
```

FIG. 1S

```
ATOM   1089  CD   GLU A 133     124.755  27.093   2.605  1.00 43.83           C
ATOM   1090  OE1  GLU A 133     124.067  28.032   2.161  1.00 48.18           O
ATOM   1091  OE2  GLU A 133     124.630  25.929   2.186  1.00 51.10           O
ATOM   1092  C    GLU A 133     126.946  30.562   5.418  1.00 33.05           C
ATOM   1093  O    GLU A 133     127.993  31.019   4.947  1.00 32.39           O
ATOM   1094  N    LYS A 134     126.101  31.295   6.162  1.00 34.52           N
ATOM   1095  CA   LYS A 134     126.379  32.722   6.436  1.00 36.37           C
ATOM   1096  CB   LYS A 134     125.146  33.484   6.952  1.00 35.60           C
ATOM   1097  CG   LYS A 134     124.347  34.204   5.875  1.00 40.77           C
ATOM   1098  CD   LYS A 134     124.789  35.662   5.801  1.00 43.36           C
ATOM   1099  CE   LYS A 134     123.626  36.588   5.423  1.00 42.20           C
ATOM   1100  NZ   LYS A 134     123.671  37.059   3.981  1.00 36.67           N
ATOM   1101  C    LYS A 134     127.544  32.916   7.384  1.00 36.06           C
ATOM   1102  O    LYS A 134     128.350  33.835   7.170  1.00 36.67           O
ATOM   1103  N    ALA A 135     127.605  32.108   8.444  1.00 37.11           N
ATOM   1104  CA   ALA A 135     128.692  32.198   9.444  1.00 38.75           C
ATOM   1105  CB   ALA A 135     128.355  31.440  10.690  1.00 37.18           C
ATOM   1106  C    ALA A 135     130.071  31.789   8.888  1.00 40.80           C
ATOM   1107  O    ALA A 135     131.118  32.394   9.238  1.00 40.99           O
ATOM   1108  N    ASN A 136     130.082  30.792   8.015  1.00 41.49           N
ATOM   1109  CA   ASN A 136     131.282  30.511   7.203  1.00 44.23           C
ATOM   1110  CB   ASN A 136     130.978  29.413   6.190  1.00 43.80           C
ATOM   1111  CG   ASN A 136     132.208  28.676   5.747  1.00 45.24           C
ATOM   1112  OD1  ASN A 136     132.593  28.745   4.586  1.00 50.31           O
ATOM   1113  ND2  ASN A 136     132.836  27.969   6.661  1.00 45.35           N
ATOM   1114  C    ASN A 136     131.772  31.732   6.423  1.00 45.73           C
ATOM   1115  O    ASN A 136     132.936  32.097   6.496  1.00 46.33           O
ATOM   1116  N    LYS A 137     130.851  32.360   5.692  1.00 47.91           N
ATOM   1117  CA   LYS A 137     131.163  33.359   4.682  1.00 50.18           C
ATOM   1118  CB   LYS A 137     129.972  33.541   3.743  1.00 50.21           C
ATOM   1119  CG   LYS A 137     130.224  34.510   2.650  1.00 52.51           C
ATOM   1120  CD   LYS A 137     128.981  35.312   2.356  1.00 56.82           C
ATOM   1121  CE   LYS A 137     129.306  36.494   1.421  1.00 57.58           C
ATOM   1122  NZ   LYS A 137     128.066  37.179   0.927  1.00 58.58           N
ATOM   1123  C    LYS A 137     131.576  34.685   5.309  1.00 51.35           C
ATOM   1124  O    LYS A 137     132.452  35.375   4.790  1.00 50.74           O
ATOM   1125  N    ILE A 138     130.943  35.037   6.427  1.00 53.13           N
ATOM   1126  CA   ILE A 138     131.298  36.251   7.154  1.00 54.46           C
ATOM   1127  CB   ILE A 138     130.359  36.547   8.370  1.00 53.81           C
ATOM   1128  CG1  ILE A 138     129.005  37.052   7.925  1.00 52.73           C
ATOM   1129  CD1  ILE A 138     128.232  37.686   9.077  1.00 50.31           C
ATOM   1130  CG2  ILE A 138     130.945  37.615   9.255  1.00 55.84           C
ATOM   1131  C    ILE A 138     132.680  35.968   7.664  1.00 55.71           C
ATOM   1132  O    ILE A 138     133.659  36.551   7.163  1.00 56.60           O
ATOM   1133  N    LYS A 139     132.748  35.063   8.646  1.00 56.77           N
ATOM   1134  CA   LYS A 139     133.969  34.720   9.358  1.00 57.96           C
ATOM   1135  CB   LYS A 139     135.003  34.034   8.452  1.00 58.98           C
ATOM   1136  CG   LYS A 139     135.190  32.534   8.752  1.00 59.51           C
ATOM   1137  CD   LYS A 139     136.671  32.152   8.904  1.00 59.96           C
ATOM   1138  CE   LYS A 139     136.873  30.618   8.745  1.00 59.03           C
ATOM   1139  NZ   LYS A 139     138.018  30.068   9.494  1.00 58.17           N
ATOM   1140  C    LYS A 139     134.590  35.885  10.132  1.00 58.82           C
ATOM   1141  O    LYS A 139     135.804  35.895  10.379  1.00 58.81           O
ATOM   1142  N    SER A 140     133.747  36.858  10.516  1.00 58.84           N
ATOM   1143  CA   SER A 140     134.048  37.754  11.654  1.00 58.34           C
ATOM   1144  CB   SER A 140     134.033  39.253  11.295  1.00 58.21           C
ATOM   1145  OG   SER A 140     133.098  39.582  10.279  1.00 57.99           O
ATOM   1146  C    SER A 140     133.161  37.454  12.878  1.00 57.93           C
ATOM   1147  O    SER A 140     131.926  37.491  12.797  1.00 58.35           O
ATOM   1148  N    GLU A 141     133.820  37.121  13.991  1.00 57.36           N
ATOM   1149  CA   GLU A 141     133.186  36.838  15.301  1.00 56.53           C
ATOM   1150  CB   GLU A 141     134.214  36.164  16.278  1.00 56.69           C
ATOM   1151  CG   GLU A 141     133.666  35.616  17.664  1.00 57.49           C
```

FIG. 1T

```
ATOM   1152  CD   GLU A 141     133.195  34.108  17.687  1.00 57.93           C
ATOM   1153  OE1  GLU A 141     132.589  33.608  16.703  1.00 56.39           O
ATOM   1154  OE2  GLU A 141     133.406  33.435  18.732  1.00 56.13           O
ATOM   1155  C    GLU A 141     132.594  38.166  15.846  1.00 55.02           C
ATOM   1156  O    GLU A 141     131.938  38.210  16.907  1.00 55.80           O
ATOM   1157  N    ASN A 142     132.823  39.234  15.089  1.00 51.90           N
ATOM   1158  CA   ASN A 142     132.262  40.534  15.388  1.00 50.18           C
ATOM   1159  CB   ASN A 142     132.830  41.557  14.397  1.00 51.86           C
ATOM   1160  CG   ASN A 142     134.368  41.496  14.299  1.00 58.45           C
ATOM   1161  OD1  ASN A 142     135.054  41.091  15.263  1.00 64.09           O
ATOM   1162  ND2  ASN A 142     134.916  41.892  13.133  1.00 62.16           N
ATOM   1163  C    ASN A 142     130.746  40.552  15.262  1.00 45.54           C
ATOM   1164  O    ASN A 142     130.008  40.846  16.204  1.00 44.71           O
ATOM   1165  N    THR A 143     130.333  40.242  14.057  1.00 40.26           N
ATOM   1166  CA   THR A 143     129.026  40.551  13.569  1.00 37.76           C
ATOM   1167  CB   THR A 143     129.107  40.626  12.037  1.00 37.80           C
ATOM   1168  OG1  THR A 143     130.010  41.669  11.695  1.00 41.40           O
ATOM   1169  CG2  THR A 143     127.772  40.969  11.397  1.00 38.66           C
ATOM   1170  C    THR A 143     128.064  39.445  13.980  1.00 34.31           C
ATOM   1171  O    THR A 143     128.274  38.308  13.565  1.00 31.88           O
ATOM   1172  N    HIS A 144     127.001  39.808  14.725  1.00 31.19           N
ATOM   1173  CA   HIS A 144     125.919  38.897  15.139  1.00 28.43           C
ATOM   1174  CB   HIS A 144     125.062  39.636  16.150  1.00 29.67           C
ATOM   1175  CG   HIS A 144     124.470  38.772  17.203  1.00 27.10           C
ATOM   1176  ND1  HIS A 144     125.215  38.173  18.194  1.00 27.40           N
ATOM   1177  CE1  HIS A 144     124.434  37.442  18.957  1.00 25.64           C
ATOM   1178  NE2  HIS A 144     123.203  37.552  18.497  1.00 29.95           N
ATOM   1179  CD2  HIS A 144     123.192  38.433  17.442  1.00 28.08           C
ATOM   1180  C    HIS A 144     125.077  38.498  13.918  1.00 27.35           C
ATOM   1181  O    HIS A 144     124.945  39.259  12.970  1.00 26.80           O
ATOM   1182  N    ILE A 145     124.501  37.298  13.903  1.00 26.07           N
ATOM   1183  CA   ILE A 145     123.781  36.900  12.707  1.00 24.79           C
ATOM   1184  CB   ILE A 145     124.475  35.688  11.994  1.00 25.87           C
ATOM   1185  CG1  ILE A 145     125.841  36.096  11.450  1.00 24.90           C
ATOM   1186  CD1  ILE A 145     126.765  34.892  11.080  1.00 27.25           C
ATOM   1187  CG2  ILE A 145     123.588  35.132  10.892  1.00 22.14           C
ATOM   1188  C    ILE A 145     122.389  36.514  13.162  1.00 22.86           C
ATOM   1189  O    ILE A 145     122.240  35.954  14.192  1.00 20.58           O
ATOM   1190  N    HIS A 146     121.371  36.947  12.453  1.00 22.20           N
ATOM   1191  CA   HIS A 146     120.014  36.580  12.820  1.00 22.79           C
ATOM   1192  CB   HIS A 146     119.324  37.715  13.590  1.00 22.24           C
ATOM   1193  CG   HIS A 146     118.098  37.311  14.323  1.00 20.41           C
ATOM   1194  ND1  HIS A 146     117.700  37.911  15.504  1.00 21.91           N
ATOM   1195  CE1  HIS A 146     116.567  37.362  15.908  1.00 18.49           C
ATOM   1196  NE2  HIS A 146     116.244  36.403  15.054  1.00 21.16           N
ATOM   1197  CD2  HIS A 146     117.152  36.383  14.028  1.00 19.39           C
ATOM   1198  C    HIS A 146     119.288  36.240  11.555  1.00 22.31           C
ATOM   1199  O    HIS A 146     119.186  37.079  10.613  1.00 20.78           O
ATOM   1200  N    ILE A 147     118.811  34.998  11.522  1.00 22.70           N
ATOM   1201  CA   ILE A 147     118.213  34.362  10.313  1.00 21.45           C
ATOM   1202  CB   ILE A 147     118.817  33.003   9.982  1.00 22.08           C
ATOM   1203  CG1  ILE A 147     120.356  33.072   9.878  1.00 25.84           C
ATOM   1204  CD1  ILE A 147     120.868  34.126   8.883  1.00 22.00           C
ATOM   1205  CG2  ILE A 147     118.274  32.466   8.631  1.00 22.00           C
ATOM   1206  C    ILE A 147     116.739  34.130  10.508  1.00 21.15           C
ATOM   1207  O    ILE A 147     116.317  33.706  11.542  1.00 21.00           O
ATOM   1208  N    PHE A 148     115.925  34.446   9.510  1.00 20.82           N
ATOM   1209  CA   PHE A 148     114.485  34.142   9.641  1.00 20.72           C
ATOM   1210  CB   PHE A 148     113.612  35.452   9.555  1.00 19.83           C
ATOM   1211  CG   PHE A 148     113.771  36.320  10.733  1.00 21.73           C
ATOM   1212  CD1  PHE A 148     113.122  36.025  11.903  1.00 20.89           C
ATOM   1213  CE1  PHE A 148     113.223  36.844  13.044  1.00 23.63           C
ATOM   1214  CZ   PHE A 148     114.105  37.934  13.023  1.00 22.51           C
```

FIG. 1U

```
ATOM   1215  CE2 PHE A 148     114.818  38.209  11.823  1.00 18.18           C
ATOM   1216  CD2 PHE A 148     114.629  37.415  10.688  1.00 20.44           C
ATOM   1217  C   PHE A 148     114.085  33.290   8.533  1.00 20.52           C
ATOM   1218  O   PHE A 148     114.632  33.433   7.470  1.00 21.54           O
ATOM   1219  N   SER A 149     113.049  32.454   8.725  1.00 24.56           N
ATOM   1220  CA  SER A 149     112.560  31.700   7.605  1.00 26.69           C
ATOM   1221  CB  SER A 149     112.827  30.194   7.820  1.00 24.67           C
ATOM   1222  OG  SER A 149     111.719  29.628   8.427  1.00 27.98           O
ATOM   1223  C   SER A 149     111.052  32.032   7.379  1.00 27.64           C
ATOM   1224  O   SER A 149     110.435  32.628   8.256  1.00 29.66           O
ATOM   1225  N   PHE A 150     110.502  31.661   6.224  1.00 29.30           N
ATOM   1226  CA  PHE A 150     109.056  31.796   5.863  1.00 31.71           C
ATOM   1227  CB  PHE A 150     108.920  31.651   4.336  1.00 32.58           C
ATOM   1228  CG  PHE A 150     109.451  32.832   3.576  1.00 29.17           C
ATOM   1229  CD1 PHE A 150     108.601  33.893   3.258  1.00 21.99           C
ATOM   1230  CE1 PHE A 150     109.069  34.990   2.562  1.00 26.89           C
ATOM   1231  CZ  PHE A 150     110.440  35.024   2.191  1.00 23.00           C
ATOM   1232  CE2 PHE A 150     111.250  33.977   2.462  1.00 24.93           C
ATOM   1233  CD2 PHE A 150     110.761  32.865   3.158  1.00 28.36           C
ATOM   1234  C   PHE A 150     108.102  30.774   6.487  1.00 33.92           C
ATOM   1235  O   PHE A 150     106.884  30.819   6.299  1.00 33.98           O
ATOM   1236  N   THR A 151     108.669  29.835   7.222  1.00 35.95           N
ATOM   1237  CA  THR A 151     107.916  28.803   7.911  1.00 36.83           C
ATOM   1238  CB  THR A 151     108.551  27.462   7.578  1.00 37.62           C
ATOM   1239  OG1 THR A 151     108.019  26.533   8.506  1.00 45.95           O
ATOM   1240  CG2 THR A 151     110.062  27.511   7.753  1.00 35.76           C
ATOM   1241  C   THR A 151     107.844  29.067   9.444  1.00 36.33           C
ATOM   1242  O   THR A 151     107.544  28.184  10.264  1.00 35.35           O
ATOM   1243  N   GLY A 152     108.168  30.304   9.834  1.00 36.00           N
ATOM   1244  CA  GLY A 152     108.131  30.669  11.247  1.00 33.94           C
ATOM   1245  C   GLY A 152     109.344  30.408  12.101  1.00 32.46           C
ATOM   1246  O   GLY A 152     109.262  30.382  13.352  1.00 32.26           O
ATOM   1247  N   GLU A 153     110.489  30.183  11.487  1.00 30.42           N
ATOM   1248  CA  GLU A 153     111.610  29.822  12.359  1.00 30.30           C
ATOM   1249  CB  GLU A 153     112.237  28.530  11.878  1.00 30.48           C
ATOM   1250  CG  GLU A 153     111.125  27.502  11.689  1.00 38.02           C
ATOM   1251  CD  GLU A 153     111.659  26.100  11.590  1.00 44.11           C
ATOM   1252  OE1 GLU A 153     112.880  25.930  11.336  1.00 48.04           O
ATOM   1253  OE2 GLU A 153     110.849  25.166  11.813  1.00 51.52           O
ATOM   1254  C   GLU A 153     112.638  30.916  12.344  1.00 27.40           C
ATOM   1255  O   GLU A 153     112.682  31.707  11.385  1.00 25.25           O
ATOM   1256  N   GLU A 154     113.482  30.926  13.384  1.00 27.06           N
ATOM   1257  CA  GLU A 154     114.687  31.835  13.399  1.00 26.77           C
ATOM   1258  CB  GLU A 154     114.439  33.092  14.206  1.00 25.11           C
ATOM   1259  CG  GLU A 154     113.856  32.751  15.637  1.00 27.82           C
ATOM   1260  CD  GLU A 154     113.414  33.966  16.435  1.00 32.69           C
ATOM   1261  OE1 GLU A 154     113.886  35.109  16.175  1.00 33.69           O
ATOM   1262  OE2 GLU A 154     112.630  33.784  17.372  1.00 36.65           O
ATOM   1263  C   GLU A 154     115.871  31.096  13.981  1.00 25.56           C
ATOM   1264  O   GLU A 154     115.698  30.175  14.779  1.00 24.36           O
ATOM   1265  N   MET A 155     117.073  31.517  13.591  1.00 23.57           N
ATOM   1266  CA  MET A 155     118.275  31.107  14.316  1.00 23.80           C
ATOM   1267  CB  MET A 155     119.017  30.054  13.568  1.00 21.29           C
ATOM   1268  CG  MET A 155     120.178  29.493  14.390  1.00 29.12           C
ATOM   1269  SD  MET A 155     120.809  27.962  13.614  1.00 35.15           S
ATOM   1270  CE  MET A 155     119.387  26.985  14.088  1.00 36.95           C
ATOM   1271  C   MET A 155     119.240  32.283  14.463  1.00 23.67           C
ATOM   1272  O   MET A 155     119.507  32.977  13.466  1.00 22.85           O
ATOM   1273  N   ALA A 156     119.788  32.461  15.651  1.00 21.76           N
ATOM   1274  CA  ALA A 156     120.684  33.626  15.895  1.00 25.54           C
ATOM   1275  CB  ALA A 156     119.924  34.733  16.666  1.00 24.12           C
ATOM   1276  C   ALA A 156     121.901  33.240  16.657  1.00 25.34           C
ATOM   1277  O   ALA A 156     121.836  32.399  17.563  1.00 28.10           O
```

FIG. 1V

```
ATOM   1278  N   THR A 157     123.010  33.882  16.335  1.00 26.62           N
ATOM   1279  CA  THR A 157     124.237  33.748  17.093  1.00 25.56           C
ATOM   1280  CB  THR A 157     125.146  34.995  16.863  1.00 26.58           C
ATOM   1281  OG1 THR A 157     125.352  35.125  15.482  1.00 23.30           O
ATOM   1282  CG2 THR A 157     126.478  34.814  17.590  1.00 25.53           C
ATOM   1283  C   THR A 157     124.091  33.556  18.581  1.00 27.17           C
ATOM   1284  O   THR A 157     123.459  34.338  19.285  1.00 26.05           O
ATOM   1285  N   LYS A 158     124.743  32.500  19.068  1.00 29.56           N
ATOM   1286  CA  LYS A 158     124.823  32.154  20.498  1.00 30.33           C
ATOM   1287  CB  LYS A 158     125.674  33.157  21.305  1.00 30.65           C
ATOM   1288  CG  LYS A 158     127.097  33.113  21.036  1.00 35.27           C
ATOM   1289  CD  LYS A 158     127.744  32.251  22.154  1.00 44.59           C
ATOM   1290  CE  LYS A 158     129.262  32.191  22.003  1.00 45.76           C
ATOM   1291  NZ  LYS A 158     129.668  31.511  20.776  1.00 49.48           N
ATOM   1292  C   LYS A 158     123.497  32.018  21.144  1.00 30.12           C
ATOM   1293  O   LYS A 158     123.440  32.030  22.369  1.00 30.20           O
ATOM   1294  N   ALA A 159     122.461  31.768  20.339  1.00 30.87           N
ATOM   1295  CA  ALA A 159     121.068  31.752  20.835  1.00 31.80           C
ATOM   1296  CB  ALA A 159     120.807  30.529  21.784  1.00 30.34           C
ATOM   1297  C   ALA A 159     120.681  33.100  21.526  1.00 30.61           C
ATOM   1298  O   ALA A 159     119.897  33.152  22.461  1.00 31.33           O
ATOM   1299  N   ASP A 160     121.237  34.191  21.050  1.00 31.03           N
ATOM   1300  CA  ASP A 160     120.860  35.488  21.584  1.00 28.96           C
ATOM   1301  CB  ASP A 160     122.167  36.184  22.013  1.00 30.00           C
ATOM   1302  CG  ASP A 160     121.986  37.598  22.394  1.00 30.68           C
ATOM   1303  OD1 ASP A 160     120.823  38.120  22.280  1.00 34.16           O
ATOM   1304  OD2 ASP A 160     123.012  38.196  22.784  1.00 29.55           O
ATOM   1305  C   ASP A 160     120.009  36.152  20.461  1.00 28.49           C
ATOM   1306  O   ASP A 160     120.462  36.486  19.347  1.00 29.35           O
ATOM   1307  N   TYR A 161     118.725  36.218  20.757  1.00 29.19           N
ATOM   1308  CA  TYR A 161     117.719  36.613  19.837  1.00 28.85           C
ATOM   1309  CB  TYR A 161     116.422  35.696  19.949  1.00 29.41           C
ATOM   1310  CG  TYR A 161     116.766  34.353  19.404  1.00 30.32           C
ATOM   1311  CD1 TYR A 161     116.680  34.086  18.045  1.00 32.04           C
ATOM   1312  CE1 TYR A 161     117.078  32.826  17.505  1.00 33.00           C
ATOM   1313  CZ  TYR A 161     117.657  31.836  18.367  1.00 37.47           C
ATOM   1314  OH  TYR A 161     118.174  30.617  17.871  1.00 35.26           O
ATOM   1315  CE2 TYR A 161     117.781  32.115  19.726  1.00 37.19           C
ATOM   1316  CD2 TYR A 161     117.354  33.369  20.239  1.00 35.58           C
ATOM   1317  C   TYR A 161     117.517  38.162  19.756  1.00 28.13           C
ATOM   1318  O   TYR A 161     116.714  38.643  18.946  1.00 27.44           O
ATOM   1319  N   THR A 162     118.291  38.914  20.561  1.00 27.88           N
ATOM   1320  CA  THR A 162     118.344  40.387  20.519  1.00 27.05           C
ATOM   1321  CB  THR A 162     118.830  40.940  19.129  1.00 25.80           C
ATOM   1322  OG1 THR A 162     120.196  40.513  18.949  1.00 26.05           O
ATOM   1323  CG2 THR A 162     118.809  42.529  19.044  1.00 22.66           C
ATOM   1324  C   THR A 162     117.031  40.999  20.943  1.00 28.86           C
ATOM   1325  O   THR A 162     117.013  41.670  21.937  1.00 29.35           O
ATOM   1326  N   LEU A 163     115.939  40.702  20.221  1.00 29.90           N
ATOM   1327  CA  LEU A 163     114.665  41.426  20.384  1.00 30.80           C
ATOM   1328  CB  LEU A 163     113.992  41.496  19.049  1.00 29.73           C
ATOM   1329  CG  LEU A 163     114.635  42.351  17.947  1.00 29.60           C
ATOM   1330  CD1 LEU A 163     113.788  42.182  16.648  1.00 24.71           C
ATOM   1331  CD2 LEU A 163     114.736  43.834  18.370  1.00 24.30           C
ATOM   1332  C   LEU A 163     113.745  40.735  21.355  1.00 32.39           C
ATOM   1333  O   LEU A 163     114.014  39.588  21.701  1.00 33.64           O
ATOM   1334  N   ASP A 164     112.655  41.372  21.789  1.00 33.97           N
ATOM   1335  CA  ASP A 164     111.723  40.634  22.689  1.00 35.55           C
ATOM   1336  CB  ASP A 164     110.623  41.549  23.225  1.00 37.24           C
ATOM   1337  CG  ASP A 164     110.066  42.424  22.132  1.00 37.16           C
ATOM   1338  OD1 ASP A 164     110.872  43.169  21.565  1.00 35.69           O
ATOM   1339  OD2 ASP A 164     108.862  42.341  21.811  1.00 42.57           O
ATOM   1340  C   ASP A 164     111.057  39.628  21.797  1.00 35.46           C
```

FIG. 1W

```
ATOM   1341  O   ASP A 164     111.129  39.739  20.550  1.00 33.31           O
ATOM   1342  N   GLU A 165     110.353  38.685  22.412  1.00 35.82           N
ATOM   1343  CA  GLU A 165     109.581  37.697  21.661  1.00 36.75           C
ATOM   1344  CB  GLU A 165     108.911  36.782  22.671  1.00 38.41           C
ATOM   1345  CG  GLU A 165     109.814  35.841  23.310  1.00 45.07           C
ATOM   1346  CD  GLU A 165     109.125  34.490  23.450  1.00 52.54           C
ATOM   1347  OE1 GLU A 165     109.135  33.762  22.414  1.00 49.98           O
ATOM   1348  OE2 GLU A 165     108.578  34.195  24.565  1.00 48.11           O
ATOM   1349  C   GLU A 165     108.455  38.274  20.768  1.00 36.08           C
ATOM   1350  O   GLU A 165     108.118  37.715  19.701  1.00 35.12           O
ATOM   1351  N   GLU A 166     107.838  39.360  21.228  1.00 35.44           N
ATOM   1352  CA  GLU A 166     106.673  39.888  20.535  1.00 35.56           C
ATOM   1353  CB  GLU A 166     105.890  40.878  21.461  1.00 37.07           C
ATOM   1354  CG  GLU A 166     104.381  40.608  21.543  1.00 40.70           C
ATOM   1355  CD  GLU A 166     103.566  41.902  21.668  1.00 50.09           C
ATOM   1356  OE1 GLU A 166     102.959  42.361  20.658  1.00 53.45           O
ATOM   1357  OE2 GLU A 166     103.543  42.482  22.782  1.00 53.92           O
ATOM   1358  C   GLU A 166     107.097  40.512  19.186  1.00 33.77           C
ATOM   1359  O   GLU A 166     106.529  40.193  18.146  1.00 33.36           O
ATOM   1360  N   SER A 167     108.124  41.380  19.194  1.00 32.33           N
ATOM   1361  CA  SER A 167     108.760  41.843  17.954  1.00 29.96           C
ATOM   1362  CB  SER A 167     109.984  42.656  18.349  1.00 30.89           C
ATOM   1363  OG  SER A 167     109.643  43.712  19.240  1.00 29.23           O
ATOM   1364  C   SER A 167     109.198  40.756  16.927  1.00 27.93           C
ATOM   1365  O   SER A 167     108.985  40.860  15.781  1.00 29.09           O
ATOM   1366  N   ARG A 168     109.866  39.728  17.374  1.00 28.03           N
ATOM   1367  CA  ARG A 168     110.277  38.638  16.572  1.00 26.71           C
ATOM   1368  CB  ARG A 168     111.057  37.736  17.489  1.00 27.66           C
ATOM   1369  CG  ARG A 168     112.520  38.077  17.586  1.00 30.76           C
ATOM   1370  CD  ARG A 168     113.230  36.889  18.088  1.00 31.97           C
ATOM   1371  NE  ARG A 168     113.062  36.916  19.479  1.00 35.28           N
ATOM   1372  CZ  ARG A 168     113.127  35.894  20.326  1.00 37.96           C
ATOM   1373  NH1 ARG A 168     113.318  34.662  19.930  1.00 36.85           N
ATOM   1374  NH2 ARG A 168     112.992  36.172  21.626  1.00 34.61           N
ATOM   1375  C   ARG A 168     109.086  37.833  16.017  1.00 25.51           C
ATOM   1376  O   ARG A 168     109.130  37.375  14.851  1.00 23.96           O
ATOM   1377  N   ALA A 169     108.046  37.640  16.847  1.00 25.04           N
ATOM   1378  CA  ALA A 169     106.794  36.943  16.382  1.00 26.61           C
ATOM   1379  CB  ALA A 169     105.772  36.680  17.583  1.00 26.61           C
ATOM   1380  C   ALA A 169     106.136  37.715  15.276  1.00 27.19           C
ATOM   1381  O   ALA A 169     105.585  37.110  14.369  1.00 28.22           O
ATOM   1382  N   ARG A 170     106.184  39.066  15.345  1.00 26.67           N
ATOM   1383  CA  ARG A 170     105.587  39.967  14.346  1.00 26.51           C
ATOM   1384  CB  ARG A 170     105.845  41.413  14.818  1.00 27.54           C
ATOM   1385  CG  ARG A 170     104.818  42.492  14.422  1.00 31.56           C
ATOM   1386  CD  ARG A 170     105.348  43.878  14.934  1.00 37.15           C
ATOM   1387  NE  ARG A 170     105.402  44.889  13.855  1.00 45.81           N
ATOM   1388  CZ  ARG A 170     106.505  45.478  13.347  1.00 48.22           C
ATOM   1389  NH1 ARG A 170     107.711  45.195  13.818  1.00 43.46           N
ATOM   1390  NH2 ARG A 170     106.386  46.405  12.366  1.00 48.54           N
ATOM   1391  C   ARG A 170     106.295  39.794  12.979  1.00 25.43           C
ATOM   1392  O   ARG A 170     105.658  39.670  11.938  1.00 26.10           O
ATOM   1393  N   ILE A 171     107.628  39.687  13.008  1.00 22.73           N
ATOM   1394  CA  ILE A 171     108.357  39.356  11.786  1.00 22.29           C
ATOM   1395  CB  ILE A 171     109.877  39.514  11.963  1.00 20.69           C
ATOM   1396  CG1 ILE A 171     110.223  40.994  12.215  1.00 20.55           C
ATOM   1397  CD1 ILE A 171     111.587  41.116  12.878  1.00 24.73           C
ATOM   1398  CG2 ILE A 171     110.649  39.013  10.625  1.00 17.15           C
ATOM   1399  C   ILE A 171     108.092  37.925  11.224  1.00 24.02           C
ATOM   1400  O   ILE A 171     107.930  37.775  10.032  1.00 22.47           O
ATOM   1401  N   LYS A 172     108.210  36.894  12.073  1.00 26.04           N
ATOM   1402  CA  LYS A 172     107.944  35.495  11.671  1.00 27.04           C
ATOM   1403  CB  LYS A 172     108.159  34.558  12.842  1.00 26.24           C
```

FIG. 1X

| | | | | | | | | | |
|---|---|---|---|---|---|---|---|---|---|
| ATOM | 1404 | CG | LYS | A | 172 | 109.602 | 34.325 | 13.140 | 1.00 30.50 | C |
| ATOM | 1405 | CD | LYS | A | 172 | 109.812 | 33.378 | 14.336 | 1.00 34.18 | C |
| ATOM | 1406 | CE | LYS | A | 172 | 109.383 | 33.989 | 15.642 | 1.00 34.48 | C |
| ATOM | 1407 | NZ | LYS | A | 172 | 110.181 | 33.278 | 16.690 | 1.00 34.27 | N |
| ATOM | 1408 | C | LYS | A | 172 | 106.510 | 35.365 | 11.131 | 1.00 27.01 | C |
| ATOM | 1409 | O | LYS | A | 172 | 106.262 | 34.685 | 10.141 | 1.00 28.03 | O |
| ATOM | 1410 | N | THR | A | 173 | 105.565 | 36.060 | 11.743 | 1.00 29.93 | N |
| ATOM | 1411 | CA | THR | A | 173 | 104.151 | 36.102 | 11.217 | 1.00 30.29 | C |
| ATOM | 1412 | CB | THR | A | 173 | 103.260 | 36.717 | 12.246 | 1.00 31.89 | C |
| ATOM | 1413 | OG1 | THR | A | 173 | 103.316 | 35.332 | 13.368 | 1.00 33.85 | O |
| ATOM | 1414 | CG2 | THR | A | 173 | 101.752 | 36.862 | 11.757 | 1.00 31.43 | C |
| ATOM | 1415 | C | THR | A | 173 | 104.004 | 36.764 | 9.840 | 1.00 30.75 | C |
| ATOM | 1416 | O | THR | A | 173 | 103.257 | 36.293 | 8.986 | 1.00 30.39 | O |
| ATOM | 1417 | N | ARG | A | 174 | 104.784 | 37.817 | 9.583 | 1.00 30.40 | N |
| ATOM | 1418 | CA | ARG | A | 174 | 104.700 | 38.466 | 8.324 | 1.00 28.17 | C |
| ATOM | 1419 | CB | ARG | A | 174 | 105.447 | 39.811 | 8.340 | 1.00 29.56 | C |
| ATOM | 1420 | CG | ARG | A | 174 | 105.689 | 40.402 | 6.958 | 1.00 30.31 | C |
| ATOM | 1421 | CD | ARG | A | 174 | 104.403 | 41.001 | 6.402 | 1.00 37.43 | C |
| ATOM | 1422 | NE | ARG | A | 174 | 104.725 | 41.826 | 5.245 | 1.00 35.70 | N |
| ATOM | 1423 | CZ | ARG | A | 174 | 103.943 | 42.058 | 4.186 | 1.00 41.01 | C |
| ATOM | 1424 | NH1 | ARG | A | 174 | 102.730 | 41.533 | 4.072 | 1.00 40.42 | N |
| ATOM | 1425 | NH2 | ARG | A | 174 | 104.392 | 42.854 | 3.219 | 1.00 39.63 | N |
| ATOM | 1426 | C | ARG | A | 174 | 105.223 | 37.586 | 7.221 | 1.00 26.53 | C |
| ATOM | 1427 | O | ARG | A | 174 | 104.617 | 37.512 | 6.216 | 1.00 25.92 | O |
| ATOM | 1428 | N | LEU | A | 175 | 106.377 | 36.942 | 7.408 | 1.00 26.25 | N |
| ATOM | 1429 | CA | LEU | A | 175 | 106.986 | 36.062 | 6.409 | 1.00 24.97 | C |
| ATOM | 1430 | CB | LEU | A | 175 | 108.353 | 35.565 | 6.936 | 1.00 23.61 | C |
| ATOM | 1431 | CG | LEU | A | 175 | 109.369 | 36.726 | 7.147 | 1.00 24.02 | C |
| ATOM | 1432 | CD1 | LEU | A | 175 | 110.717 | 36.198 | 7.619 | 1.00 21.67 | C |
| ATOM | 1433 | CD2 | LEU | A | 175 | 109.528 | 37.491 | 5.821 | 1.00 16.97 | C |
| ATOM | 1434 | C | LEU | A | 175 | 106.039 | 34.849 | 6.077 | 1.00 25.23 | C |
| ATOM | 1435 | O | LEU | A | 175 | 105.838 | 34.478 | 4.885 | 1.00 22.05 | O |
| ATOM | 1436 | N | PHE | A | 176 | 105.467 | 34.329 | 7.125 | 1.00 25.41 | N |
| ATOM | 1437 | CA | PHE | A | 176 | 104.505 | 33.154 | 7.078 | 1.00 28.69 | C |
| ATOM | 1438 | CB | PHE | A | 176 | 104.077 | 32.744 | 8.510 | 1.00 28.11 | C |
| ATOM | 1439 | CG | PHE | A | 176 | 103.256 | 31.438 | 8.550 | 1.00 32.78 | C |
| ATOM | 1440 | CD1 | PHE | A | 176 | 103.901 | 30.210 | 8.560 | 1.00 34.00 | C |
| ATOM | 1441 | CE1 | PHE | A | 176 | 103.144 | 28.991 | 8.607 | 1.00 38.40 | C |
| ATOM | 1442 | CZ | PHE | A | 176 | 101.757 | 29.043 | 8.620 | 1.00 35.28 | C |
| ATOM | 1443 | CE2 | PHE | A | 176 | 101.095 | 30.272 | 8.627 | 1.00 36.37 | C |
| ATOM | 1444 | CD2 | PHE | A | 176 | 101.857 | 31.471 | 8.598 | 1.00 31.25 | C |
| ATOM | 1445 | C | PHE | A | 176 | 103.309 | 33.559 | 6.232 | 1.00 27.87 | C |
| ATOM | 1446 | O | PHE | A | 176 | 102.995 | 32.929 | 5.255 | 1.00 29.43 | O |
| ATOM | 1447 | N | THR | A | 177 | 102.720 | 34.703 | 6.523 | 1.00 30.69 | N |
| ATOM | 1448 | CA | THR | A | 177 | 101.618 | 35.269 | 5.710 | 1.00 30.39 | C |
| ATOM | 1449 | CB | THR | A | 177 | 101.209 | 36.530 | 6.331 | 1.00 31.43 | C |
| ATOM | 1450 | OG1 | THR | A | 177 | 101.167 | 36.272 | 7.727 | 1.00 38.77 | O |
| ATOM | 1451 | CG2 | THR | A | 177 | 99.780 | 37.023 | 5.913 | 1.00 31.72 | C |
| ATOM | 1452 | C | THR | A | 177 | 102.021 | 35.506 | 4.257 | 1.00 30.26 | C |
| ATOM | 1453 | O | THR | A | 177 | 101.218 | 35.221 | 3.347 | 1.00 31.11 | O |
| ATOM | 1454 | N | ILE | A | 178 | 103.254 | 35.951 | 3.992 | 1.00 27.30 | N |
| ATOM | 1455 | CA | ILE | A | 178 | 103.698 | 36.128 | 2.561 | 1.00 25.45 | C |
| ATOM | 1456 | CB | ILE | A | 178 | 105.101 | 36.843 | 2.401 | 1.00 23.58 | C |
| ATOM | 1457 | CG1 | ILE | A | 178 | 105.036 | 38.269 | 2.985 | 1.00 25.77 | C |
| ATOM | 1458 | CD1 | ILE | A | 178 | 106.506 | 38.868 | 3.316 | 1.00 23.14 | C |
| ATOM | 1459 | CG2 | ILE | A | 178 | 105.652 | 36.759 | 0.910 | 1.00 19.72 | C |
| ATOM | 1460 | C | ILE | A | 178 | 103.831 | 34.824 | 1.794 | 1.00 26.04 | C |
| ATOM | 1461 | O | ILE | A | 178 | 103.546 | 34.773 | 0.598 | 1.00 26.19 | O |
| ATOM | 1462 | N | ARG | A | 179 | 104.374 | 33.800 | 2.436 | 1.00 25.98 | N |
| ATOM | 1463 | CA | ARG | A | 179 | 104.498 | 32.508 | 1.824 | 1.00 27.03 | C |
| ATOM | 1464 | CB | ARG | A | 179 | 105.217 | 31.554 | 2.765 | 1.00 26.80 | C |
| ATOM | 1465 | CG | ARG | A | 179 | 105.288 | 30.121 | 2.260 | 1.00 27.93 | C |
| ATOM | 1466 | CD | ARG | A | 179 | 105.910 | 29.169 | 3.249 | 1.00 32.90 | C |

FIG. 1Y

```
ATOM   1467  NE   ARG A 179     105.117  29.142   4.463  1.00 44.55           N
ATOM   1468  CZ   ARG A 179     104.068  28.335   4.659  1.00 45.92           C
ATOM   1469  NH1  ARG A 179     103.690  27.477   3.711  1.00 43.01           N
ATOM   1470  NH2  ARG A 179     103.392  28.411   5.794  1.00 44.90           N
ATOM   1471  C    ARG A 179     103.091  31.921   1.556  1.00 29.37           C
ATOM   1472  O    ARG A 179     102.828  31.432   0.429  1.00 28.76           O
ATOM   1473  N    GLN A 180     102.213  31.937   2.576  1.00 29.72           N
ATOM   1474  CA   GLN A 180     100.786  31.496   2.340  1.00 33.09           C
ATOM   1475  CB   GLN A 180      99.884  31.807   3.496  1.00 31.60           C
ATOM   1476  CG   GLN A 180      99.988  30.864   4.596  1.00 38.26           C
ATOM   1477  CD   GLN A 180      99.076  31.268   5.703  1.00 44.59           C
ATOM   1478  OE1  GLN A 180      99.076  32.430   6.120  1.00 45.64           O
ATOM   1479  NE2  GLN A 180      98.244  30.333   6.164  1.00 45.94           N
ATOM   1480  C    GLN A 180     100.189  32.226   1.136  1.00 33.43           C
ATOM   1481  O    GLN A 180      99.525  31.619   0.324  1.00 35.33           O
ATOM   1482  N    GLU A 181     100.398  33.542   1.038  1.00 33.86           N
ATOM   1483  CA   GLU A 181      99.844  34.326  -0.061  1.00 32.37           C
ATOM   1484  CB   GLU A 181     100.030  35.836   0.174  1.00 34.20           C
ATOM   1485  CG   GLU A 181      99.071  36.445   1.211  1.00 39.61           C
ATOM   1486  CD   GLU A 181      97.556  36.514   0.781  1.00 47.38           C
ATOM   1487  OE1  GLU A 181      97.189  36.466  -0.439  1.00 49.01           O
ATOM   1488  OE2  GLU A 181      96.703  36.659   1.706  1.00 52.25           O
ATOM   1489  C    GLU A 181     100.425  33.870  -1.386  1.00 31.75           C
ATOM   1490  O    GLU A 181      99.660  33.574  -2.336  1.00 30.87           O
ATOM   1491  N    MET A 182     101.754  33.723  -1.448  1.00 29.72           N
ATOM   1492  CA   MET A 182     102.383  33.124  -2.637  1.00 28.02           C
ATOM   1493  CB   MET A 182     103.892  32.991  -2.427  1.00 27.79           C
ATOM   1494  CG   MET A 182     104.633  34.344  -2.260  1.00 29.70           C
ATOM   1495  SD   MET A 182     106.417  34.208  -2.460  1.00 29.37           S
ATOM   1496  CE   MET A 182     106.663  33.894  -4.197  1.00 36.51           C
ATOM   1497  C    MET A 182     101.819  31.722  -2.981  1.00 26.97           C
ATOM   1498  O    MET A 182     101.676  31.353  -4.157  1.00 24.81           O
ATOM   1499  N    ALA A 183     101.626  30.914  -1.967  1.00 26.40           N
ATOM   1500  CA   ALA A 183     101.298  29.487  -2.171  1.00 28.90           C
ATOM   1501  CB   ALA A 183     101.454  28.606  -0.815  1.00 27.54           C
ATOM   1502  C    ALA A 183      99.868  29.428  -2.749  1.00 30.70           C
ATOM   1503  O    ALA A 183      99.632  28.742  -3.748  1.00 33.28           O
ATOM   1504  N    SER A 184      98.967  30.212  -2.178  1.00 31.25           N
ATOM   1505  CA   SER A 184      97.610  30.432  -2.739  1.00 31.98           C
ATOM   1506  CB   SER A 184      96.876  31.462  -1.907  1.00 31.89           C
ATOM   1507  OG   SER A 184      96.797  30.826  -0.617  1.00 35.96           O
ATOM   1508  C    SER A 184      97.563  30.745  -4.221  1.00 31.47           C
ATOM   1509  O    SER A 184      96.784  30.128  -4.988  1.00 29.22           O
ATOM   1510  N    ARG A 185      98.491  31.588  -4.658  1.00 31.19           N
ATOM   1511  CA   ARG A 185      98.608  31.897  -6.085  1.00 31.27           C
ATOM   1512  CB   ARG A 185      99.111  33.334  -6.291  1.00 32.55           C
ATOM   1513  CG   ARG A 185      98.169  34.391  -5.760  1.00 29.13           C
ATOM   1514  CD   ARG A 185      98.996  35.663  -5.456  1.00 27.62           C
ATOM   1515  NE   ARG A 185      98.198  36.845  -5.103  1.00 24.61           N
ATOM   1516  CZ   ARG A 185      97.702  37.075  -3.886  1.00 29.07           C
ATOM   1517  NH1  ARG A 185      97.901  36.222  -2.922  1.00 24.68           N
ATOM   1518  NH2  ARG A 185      97.002  38.179  -3.619  1.00 32.34           N
ATOM   1519  C    ARG A 185      99.554  30.935  -6.764  1.00 31.46           C
ATOM   1520  O    ARG A 185      99.934  31.156  -7.904  1.00 33.55           O
ATOM   1521  N    SER A 186      99.936  29.850  -6.100  1.00 31.68           N
ATOM   1522  CA   SER A 186     100.956  28.920  -6.680  1.00 32.11           C
ATOM   1523  CB   SER A 186     100.287  27.806  -7.480  1.00 32.50           C
ATOM   1524  OG   SER A 186     100.162  28.137  -8.820  1.00 38.14           O
ATOM   1525  C    SER A 186     102.269  29.583  -7.301  1.00 32.44           C
ATOM   1526  O    SER A 186     102.794  29.286  -8.441  1.00 30.76           O
ATOM   1527  N    LEU A 187     102.813  30.479  -6.485  1.00 31.52           N
ATOM   1528  CA   LEU A 187     103.988  31.198  -6.814  1.00 32.49           C
ATOM   1529  CB   LEU A 187     103.760  32.704  -6.634  1.00 31.67           C
```

FIG. 1Z

```
ATOM   1530  CG   LEU A 187     102.934  33.440  -7.724  1.00 34.94           C
ATOM   1531  CD1  LEU A 187     102.652  34.952  -7.322  1.00 34.90           C
ATOM   1532  CD2  LEU A 187     103.593  33.337  -9.078  1.00 34.12           C
ATOM   1533  C    LEU A 187     105.110  30.753  -5.930  1.00 32.67           C
ATOM   1534  O    LEU A 187     106.272  31.115  -6.181  1.00 32.59           O
ATOM   1535  N    TRP A 188     104.770  29.948  -4.926  1.00 31.57           N
ATOM   1536  CA   TRP A 188     105.672  29.686  -3.860  1.00 33.33           C
ATOM   1537  CB   TRP A 188     104.935  29.227  -2.575  1.00 32.39           C
ATOM   1538  CG   TRP A 188     105.893  28.718  -1.582  1.00 33.07           C
ATOM   1539  CD1  TRP A 188     106.086  27.410  -1.226  1.00 35.84           C
ATOM   1540  NE1  TRP A 188     107.081  27.299  -0.286  1.00 31.40           N
ATOM   1541  CE2  TRP A 188     107.583  28.545  -0.011  1.00 32.33           C
ATOM   1542  CD2  TRP A 188     106.849  29.482  -0.820  1.00 32.66           C
ATOM   1543  CE3  TRP A 188     107.160  30.862  -0.725  1.00 30.49           C
ATOM   1544  CZ3  TRP A 188     108.189  31.262   0.175  1.00 23.09           C
ATOM   1545  CH2  TRP A 188     108.904  30.308   0.949  1.00 28.37           C
ATOM   1546  CZ2  TRP A 188     108.601  28.941   0.886  1.00 26.38           C
ATOM   1547  C    TRP A 188     106.777  28.710  -4.257  1.00 33.89           C
ATOM   1548  O    TRP A 188     107.960  28.953  -4.003  1.00 33.34           O
ATOM   1549  N    ASP A 189     106.398  27.610  -4.889  1.00 34.35           N
ATOM   1550  CA   ASP A 189     107.384  26.648  -5.317  1.00 34.70           C
ATOM   1551  CB   ASP A 189     106.643  25.448  -5.915  1.00 36.28           C
ATOM   1552  CG   ASP A 189     107.547  24.255  -6.183  1.00 43.70           C
ATOM   1553  OD1  ASP A 189     108.521  23.999  -5.400  1.00 48.58           O
ATOM   1554  OD2  ASP A 189     107.273  23.560  -7.213  1.00 51.52           O
ATOM   1555  C    ASP A 189     108.442  27.253  -6.285  1.00 35.16           C
ATOM   1556  O    ASP A 189     109.611  26.867  -6.264  1.00 35.34           O
ATOM   1557  N    SER A 190     108.043  28.161  -7.168  1.00 34.10           N
ATOM   1558  CA   SER A 190     109.005  28.833  -8.018  1.00 34.32           C
ATOM   1559  CB   SER A 190     108.278  29.654  -9.058  1.00 33.89           C
ATOM   1560  OG   SER A 190     109.280  30.065  -9.990  1.00 41.67           O
ATOM   1561  C    SER A 190     109.971  29.771  -7.237  1.00 33.71           C
ATOM   1562  O    SER A 190     111.170  29.851  -7.500  1.00 33.55           O
ATOM   1563  N    PHE A 191     109.429  30.490  -6.278  1.00 33.61           N
ATOM   1564  CA   PHE A 191     110.246  31.346  -5.409  1.00 33.24           C
ATOM   1565  CB   PHE A 191     109.323  32.260  -4.637  1.00 30.51           C
ATOM   1566  CG   PHE A 191     110.012  33.216  -3.692  1.00 24.21           C
ATOM   1567  CD1  PHE A 191     110.874  34.201  -4.165  1.00 27.54           C
ATOM   1568  CE1  PHE A 191     111.429  35.157  -3.278  1.00 26.58           C
ATOM   1569  CZ   PHE A 191     111.150  35.091  -1.901  1.00 22.84           C
ATOM   1570  CE2  PHE A 191     110.268  34.130  -1.439  1.00 27.35           C
ATOM   1571  CD2  PHE A 191     109.722  33.185  -2.360  1.00 21.84           C
ATOM   1572  C    PHE A 191     111.122  30.528  -4.454  1.00 34.72           C
ATOM   1573  O    PHE A 191     112.264  30.884  -4.212  1.00 34.69           O
ATOM   1574  N    ARG A 192     110.581  29.462  -3.862  1.00 37.55           N
ATOM   1575  CA   ARG A 192     111.446  28.585  -3.085  1.00 39.47           C
ATOM   1576  CB   ARG A 192     110.653  27.506  -2.313  1.00 40.04           C
ATOM   1577  CG   ARG A 192     111.539  26.596  -1.374  1.00 43.76           C
ATOM   1578  CD   ARG A 192     110.760  25.562  -0.517  1.00 44.57           C
ATOM   1579  NE   ARG A 192     109.696  24.935  -1.286  1.00 51.11           N
ATOM   1580  CZ   ARG A 192     109.851  24.024  -2.255  1.00 52.22           C
ATOM   1581  NH1  ARG A 192     111.055  23.557  -2.583  1.00 53.29           N
ATOM   1582  NH2  ARG A 192     108.777  23.579  -2.897  1.00 52.31           N
ATOM   1583  C    ARG A 192     112.573  28.025  -3.965  1.00 40.71           C
ATOM   1584  O    ARG A 192     113.765  28.151  -3.596  1.00 41.21           O
ATOM   1585  N    GLN A 193     112.244  27.501  -5.151  1.00 41.42           N
ATOM   1586  CA   GLN A 193     113.278  26.837  -5.989  1.00 41.77           C
ATOM   1587  CB   GLN A 193     112.681  26.081  -7.152  1.00 41.08           C
ATOM   1588  CG   GLN A 193     111.610  25.146  -6.682  1.00 46.62           C
ATOM   1589  CD   GLN A 193     112.115  23.826  -6.160  1.00 52.45           C
ATOM   1590  OE1  GLN A 193     113.110  23.758  -5.408  1.00 55.27           O
ATOM   1591  NE2  GLN A 193     111.411  22.745  -6.537  1.00 53.32           N
ATOM   1592  C    GLN A 193     114.399  27.698  -6.519  1.00 41.51           C
```

FIG. 1AA

```
ATOM   1593  O    GLN A 193     115.491  27.185  -6.745  1.00 40.65           O
ATOM   1594  N    SER A 194     114.130  28.981  -6.739  1.00 41.28           N
ATOM   1595  CA   SER A 194     115.136  29.862  -7.274  1.00 42.17           C
ATOM   1596  CB   SER A 194     114.482  31.132  -7.846  1.00 42.35           C
ATOM   1597  OG   SER A 194     113.938  31.877  -6.778  1.00 42.42           O
ATOM   1598  C    SER A 194     116.207  30.223  -6.202  1.00 42.12           C
ATOM   1599  O    SER A 194     117.230  30.768  -6.528  1.00 41.95           O
ATOM   1600  N    GLU A 195     115.983  29.933  -4.926  1.00 43.28           N
ATOM   1601  CA   GLU A 195     117.016  30.275  -3.927  1.00 44.25           C
ATOM   1602  CB   GLU A 195     116.525  30.078  -2.478  1.00 43.64           C
ATOM   1603  CG   GLU A 195     117.634  30.320  -1.461  1.00 44.63           C
ATOM   1604  CD   GLU A 195     117.166  30.739  -0.095  1.00 44.42           C
ATOM   1605  OE1  GLU A 195     117.981  30.661   0.829  1.00 41.25           O
ATOM   1606  OE2  GLU A 195     116.000  31.174   0.068  1.00 46.92           O
ATOM   1607  C    GLU A 195     118.368  29.554  -4.156  1.00 44.00           C
ATOM   1608  O    GLU A 195     118.374  28.347  -4.469  1.00 45.08           O
ATOM   1609  MN   MN  A 901     121.549  40.494   5.133  1.00 44.36          MN
ATOM   1610  MG   MG  A 902     122.916  43.816   3.714  1.00 40.56          MG
ATOM   6389  OH2  WAT A 901     122.045  42.811  18.783  1.00 26.44      A    O
ATOM   6392  OH2  WAT A 902     119.887  38.331  17.323  1.00 26.18      A    O
ATOM   6394  OH2  WAT A 903     110.707  45.442  15.972  1.00 27.34      A    O
ATOM   6395  OH2  WAT A 904     123.764  46.193   3.887  1.00 25.43      A    O
ATOM   6396  OH2  WAT A 904     118.775  46.035  -1.122  1.00 33.31      A    O
ATOM   6397  OH2  WAT A 905     118.343  33.451   0.684  1.00 39.92      A    O
ATOM   6399  OH2  WAT A 906     127.719  38.320  18.733  1.00 33.07      A    O
ATOM   6400  OH2  WAT A 907     101.260  28.674   4.136  1.00 44.78      A    O
ATOM   6402  OH2  WAT A 908     108.131  51.963  -7.683  1.00 40.55      A    O
ATOM   6403  OH2  WAT A 909     120.504  30.149   0.243  1.00 35.40      A    O
ATOM   6404  OH2  WAT A 910     119.491  54.349  10.527  1.00 25.13      A    O
ATOM   6405  OH2  WAT A 911     112.965  34.751  24.069  1.00 47.07      A    O
ATOM   6406  OH2  WAT A 912     120.559  43.926  -6.265  1.00 43.93      A    O
ATOM   6407  OH2  WAT A 913     126.036  24.176   3.064  1.00 49.41      A    O
ATOM   6408  OH2  WAT A 914     117.926  41.407 -15.080  1.00 48.12      A    O
ATOM   6409  OH2  WAT A 915     125.405  36.981  22.518  1.00 43.66      A    O
ATOM   6410  OH2  WAT A 916     124.778  42.688   4.758  1.00 29.14      A    O
ATOM   6411  OH2  WAT A 917     104.308  44.947 -12.185  1.00 56.88      A    O
ATOM   6412  OH2  WAT A 918     107.575  32.972  -8.947  1.00 64.71      A    O
ATOM   6413  OH2  WAT A 919     119.018  43.026  23.298  1.00 44.05      A    O
ATOM   6415  OH2  WAT A 920     125.055  50.783  24.110  1.00 45.48      A    O
END
```

FIG. 1AB

```
H1N1 polypeptide fragment (Chain A) with bound EMBL-
R05-3
HEADER    ----                                          XX-XXX-9-   xxxx
COMPND    ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.50
REMARK   3   RESOLUTION RANGE LOW  (ANGSTROMS) :  89.10
REMARK   3   DATA CUTOFF            (SIGMA(F)) : NONE
REMARK   3   COMPLETENESS FOR RANGE        (%) :  99.04
REMARK   3   NUMBER OF REFLECTIONS             :  28997
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.20822
REMARK   3   R VALUE            (WORKING SET) : 0.20459
REMARK   3   FREE R VALUE                     : 0.27625
REMARK   3   FREE R VALUE TEST SET SIZE   (%) : 5.1
REMARK   3   FREE R VALUE TEST SET COUNT      : 1545
REMARK   3
REMARK   3  FIT IN THE HIGHEST RESOLUTION BIN.
REMARK   3   TOTAL NUMBER OF BINS USED           :     20
REMARK   3   BIN RESOLUTION RANGE HIGH           :  2.502
REMARK   3   BIN RESOLUTION RANGE LOW            :  2.567
REMARK   3   REFLECTION IN BIN    (WORKING SET) :   1968
REMARK   3   BIN COMPLETENESS (WORKING+TEST) (%) :  93.65
REMARK   3   BIN R VALUE          (WORKING SET) :  0.268
REMARK   3   BIN FREE R VALUE SET COUNT          :    113
REMARK   3   BIN FREE R VALUE                    :  0.378
REMARK   3
REMARK   3  NUMBER OF NON-HYDROGEN ATOMS USED IN REFINEMENT.
REMARK   3   ALL ATOMS         :      6523
REMARK   3
REMARK   3  B VALUES.
REMARK   3   FROM WILSON PLOT          (A**2) : NULL
REMARK   3   MEAN B VALUE      (OVERALL, A**2) : 29.083
REMARK   3   OVERALL ANISOTROPIC B VALUE.
REMARK   3    B11 (A**2) :     0.24
REMARK   3    B22 (A**2) :    -0.24
REMARK   3    B33 (A**2) :     0.00
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                      (A):  0.783
REMARK   3   ESU BASED ON FREE R VALUE                 (A):  0.335
REMARK   3   ESU BASED ON MAXIMUM LIKELIHOOD           (A):  0.240
REMARK   3   ESU FOR B VALUES BASED ON MAXIMUM LIKELIHOOD (A**2): 23.556
REMARK   3
REMARK   3 CORRELATION COEFFICIENTS.
REMARK   3   CORRELATION COEFFICIENT FO-FC      :  0.937
REMARK   3   CORRELATION COEFFICIENT FO-FC FREE :  0.891
REMARK   3
```

FIG. 2A

```
REMARK   3  RMS DEVIATIONS FROM IDEAL VALUES          COUNT    RMS    WEIGHT
REMARK   3   BOND LENGTHS REFINED ATOMS        (A):  6520 ; 0.016 ; 0.022
REMARK   3   BOND LENGTHS OTHERS               (A):  4574 ; 0.001 ; 0.020
REMARK   3   BOND ANGLES REFINED ATOMS   (DEGREES):  8769 ; 1.513 ; 1.974
REMARK   3   BOND ANGLES OTHERS          (DEGREES): 11027 ; 0.893 ; 3.000
REMARK   3   TORSION ANGLES, PERIOD 1    (DEGREES):   741 ; 6.052 ; 5.000
REMARK   3   TORSION ANGLES, PERIOD 2    (DEGREES):   332 ;35.152 ;23.373
REMARK   3   TORSION ANGLES, PERIOD 3    (DEGREES):  1193 ;19.051 ;15.000
REMARK   3   TORSION ANGLES, PERIOD 4    (DEGREES):    55 ;19.093 ;15.000
REMARK   3   CHIRAL-CENTER RESTRAINTS       (A**3):   920 ; 0.086 ; 0.200
REMARK   3   GENERAL PLANES REFINED ATOMS      (A):  7058 ; 0.006 ; 0.020
REMARK   3   GENERAL PLANES OTHERS             (A):  1441 ; 0.001 ; 0.020
REMARK   3
REMARK   3  ISOTROPIC THERMAL FACTOR RESTRAINTS.     COUNT    RMS    WEIGHT
REMARK   3   MAIN-CHAIN BOND REFINED ATOMS  (A**2):  3740 ; 0.632 ; 1.500
REMARK   3   MAIN-CHAIN BOND OTHER ATOMS    (A**2):  1503 ; 0.123 ; 1.500
REMARK   3   MAIN-CHAIN ANGLE REFINED ATOMS (A**2):  6055 ; 1.173 ; 2.000
REMARK   3   SIDE-CHAIN BOND REFINED ATOMS  (A**2):  2780 ; 1.839 ; 3.000
REMARK   3   SIDE-CHAIN ANGLE REFINED ATOMS (A**2):  2714 ; 2.962 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  :    4
REMARK   3   ATOM RECORD CONTAINS SUM OF TLS AND RESIDUAL B FACTORS
REMARK   3
REMARK   3   TLS GROUP :    1
REMARK   3    NUMBER OF COMPONENTS GROUP :    4
REMARK   3    COMPONENTS        C SSSEQI   TO   C SSSEQI
REMARK   3    RESIDUE RANGE :   A    -2        A    194
REMARK   3    RESIDUE RANGE :   A   901        A    902
REMARK   3    RESIDUE RANGE :   A   401        A    404
REMARK   3    RESIDUE RANGE :   A   801        A    801
REMARK   3    ORIGIN FOR THE GROUP (A): -18.7820 -18.3467  15.6409
REMARK   3    T TENSOR
REMARK   3      T11:   0.0626 T22:   0.0601
REMARK   3      T33:   0.0370 T12:   0.0477
REMARK   3      T13:   0.0061 T23:  -0.0096
REMARK   3    L TENSOR
REMARK   3      L11:   3.8491 L22:   3.1615
REMARK   3      L33:   2.2199 L12:   0.4794
REMARK   3      L13:   0.2562 L23:  -0.2521
REMARK   3    S TENSOR
REMARK   3      S11:   0.0271 S12:  -0.0426 S13:   0.3012
REMARK   3      S21:   0.1037 S22:   0.0068 S23:   0.2311
REMARK   3      S31:  -0.2046 S32:   0.0173 S33:  -0.0339
REMARK   3
REMARK   3   TLS GROUP :    2
REMARK   3    NUMBER OF COMPONENTS GROUP :    4
REMARK   3    COMPONENTS        C SSSEQI   TO   C SSSEQI
REMARK   3    RESIDUE RANGE :   B    -2        B    193
REMARK   3    RESIDUE RANGE :   B   901        B    902
REMARK   3    RESIDUE RANGE :   B   401        B    404
REMARK   3    RESIDUE RANGE :   B   801        B    801
REMARK   3    ORIGIN FOR THE GROUP (A):  -9.5592 -43.9684  15.4406
REMARK   3    T TENSOR
REMARK   3      T11:   0.0655 T22:   0.0616
REMARK   3      T33:   0.0284 T12:   0.0424
```

FIG. 2B

```
REMARK   3         T13:  -0.0096 T23:    0.0116
REMARK   3      L TENSOR
REMARK   3         L11:   3.5209 L22:    2.7524
REMARK   3         L33:   2.1675 L12:    0.0213
REMARK   3         L13:  -0.8001 L23:    0.2855
REMARK   3      S TENSOR
REMARK   3         S11:   0.0173 S12:   -0.0992 S13:   -0.2131
REMARK   3         S21:   0.1239 S22:   -0.0222 S23:   -0.2049
REMARK   3         S31:   0.2223 S32:   -0.0015 S33:    0.0049
REMARK   3
REMARK   3     TLS GROUP :     3
REMARK   3     NUMBER OF COMPONENTS GROUP :     4
REMARK   3     COMPONENTS        C SSSEQI    TO   C SSSEQI
REMARK   3     RESIDUE RANGE :   C      0          C    195
REMARK   3     RESIDUE RANGE :   C    901          C    902
REMARK   3     RESIDUE RANGE :   C    401          C    403
REMARK   3     RESIDUE RANGE :   C    801          C    801
REMARK   3     ORIGIN FOR THE GROUP (A):  -4.3952 -15.1378  52.3445
REMARK   3      T TENSOR
REMARK   3         T11:   0.0906 T22:    0.0725
REMARK   3         T33:   0.0515 T12:   -0.0225
REMARK   3         T13:  -0.0351 T23:   -0.0026
REMARK   3      L TENSOR
REMARK   3         L11:   3.4910 L22:    2.7740
REMARK   3         L33:   2.4480 L12:    1.0609
REMARK   3         L13:  -0.2109 L23:   -1.3961
REMARK   3      S TENSOR
REMARK   3         S11:  -0.0152 S12:    0.1383 S13:   -0.1047
REMARK   3         S21:  -0.2065 S22:   -0.0565 S23:   -0.0793
REMARK   3         S31:   0.1206 S32:    0.1449 S33:    0.0717
REMARK   3
REMARK   3     TLS GROUP :     4
REMARK   3     NUMBER OF COMPONENTS GROUP :     4
REMARK   3     COMPONENTS        C SSSEQI    TO   C SSSEQI
REMARK   3     RESIDUE RANGE :   D      0          D    195
REMARK   3     RESIDUE RANGE :   D    901          D    902
REMARK   3     RESIDUE RANGE :   D    401          D    403
REMARK   3     RESIDUE RANGE :   D    801          D    801
REMARK   3     ORIGIN FOR THE GROUP (A): -21.2945 -45.7592  51.4140
REMARK   3      T TENSOR
REMARK   3         T11:   0.1308 T22:    0.1190
REMARK   3         T33:   0.0216 T12:   -0.0416
REMARK   3         T13:  -0.0097 T23:    0.0186
REMARK   3      L TENSOR
REMARK   3         L11:   3.6692 L22:    2.1484
REMARK   3         L33:   2.5225 L12:   -0.2058
REMARK   3         L13:  -0.3579 L23:    1.1039
REMARK   3      S TENSOR
REMARK   3         S11:   0.0541 S12:    0.3685 S13:   -0.0165
REMARK   3         S21:  -0.1313 S22:   -0.0722 S23:    0.0569
REMARK   3         S31:   0.0558 S32:   -0.2205 S33:    0.0181
REMARK   3
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS   :  1.40
REMARK   3   ION PROBE RADIUS   :  0.80
REMARK   3   SHRINKAGE RADIUS   :  0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : WITH TLS ADDED
```

FIG. 2C

```
REMARK   3
LINKR           GLU A  64              LEU A  71           gap
LINKR           LYS A 137              LYS A 142           gap
LINKR           GLU B  64              LEU B  71           gap
LINKR           PHE D  51              LEU D  72           gap
CRYST1   54.570  122.540  129.780  90.00  90.00  90.00 P 21 21 21
SCALE1      0.018325  0.000000  0.000000        0.00000
SCALE2      0.000000  0.008161  0.000000        0.00000
SCALE3      0.000000  0.000000  0.007705        0.00000
ATOM      1  N   GLY A  -2     -38.519 -32.846  21.771  1.00 50.75           A   N
ATOM      2  CA  GLY A  -2     -37.114 -32.422  21.506  1.00 47.67           A   C
ATOM      3  C   GLY A  -2     -36.272 -33.439  20.743  1.00 46.67           A   C
ATOM      4  O   GLY A  -2     -35.234 -33.069  20.155  1.00 45.44           A   O
ATOM      5  N   MET A  -1     -36.681 -34.712  20.738  1.00 47.85           A   N
ATOM      6  CA  MET A  -1     -35.956 -35.754  19.979  1.00 46.83           A   C
ATOM      7  CB  MET A  -1     -36.686 -37.113  20.044  1.00 49.48           A   C
ATOM      8  C   MET A  -1     -35.726 -35.349  18.511  1.00 44.43           A   C
ATOM      9  O   MET A  -1     -34.666 -35.599  17.955  1.00 43.39           A   O
ATOM     10  N   ALA A   0     -36.720 -34.719  17.900  1.00 44.28           A   N
ATOM     11  CA  ALA A   0     -36.655 -34.339  16.497  1.00 42.51           A   C
ATOM     12  CB  ALA A   0     -37.986 -33.694  16.075  1.00 43.78           A   C
ATOM     13  C   ALA A   0     -35.474 -33.389  16.265  1.00 39.35           A   C
ATOM     14  O   ALA A   0     -34.733 -33.539  15.297  1.00 38.08           A   O
ATOM     15  N   MET A   1     -35.292 -32.433  17.169  1.00 38.01           A   N
ATOM     16  CA  MET A   1     -34.191 -31.470  17.075  1.00 35.93           A   C
ATOM     17  CB  MET A   1     -34.381 -30.323  18.074  1.00 35.54           A   C
ATOM     18  CG  MET A   1     -33.244 -29.325  18.087  1.00 34.33           A   C
ATOM     19  SD  MET A   1     -33.022 -28.423  16.534  1.00 33.65           A   S
ATOM     20  CE  MET A   1     -33.808 -26.859  16.941  1.00 31.82           A   C
ATOM     21  C   MET A   1     -32.846 -32.119  17.336  1.00 34.49           A   C
ATOM     22  O   MET A   1     -31.846 -31.792  16.687  1.00 32.19           A   O
ATOM     23  N   GLU A   2     -32.812 -33.015  18.317  1.00 35.64           A   N
ATOM     24  CA  GLU A   2     -31.568 -33.679  18.636  1.00 34.77           A   C
ATOM     25  CB  GLU A   2     -31.717 -34.578  19.855  1.00 36.86           A   C
ATOM     26  CG  GLU A   2     -30.425 -34.762  20.606  1.00 37.45           A   C
ATOM     27  CD  GLU A   2     -30.412 -36.006  21.476  1.00 43.71           A   C
ATOM     28  OE1 GLU A   2     -31.509 -36.429  21.931  1.00 47.97           A   O
ATOM     29  OE2 GLU A   2     -29.299 -36.551  21.719  1.00 43.85           A   O
ATOM     30  C   GLU A   2     -31.147 -34.488  17.419  1.00 34.14           A   C
ATOM     31  O   GLU A   2     -29.985 -34.482  17.006  1.00 32.33           A   O
ATOM     32  N   ASP A   3     -32.100 -35.177  16.818  1.00 34.95           A   N
ATOM     33  CA  ASP A   3     -31.771 -35.929  15.636  1.00 34.86           A   C
ATOM     34  CB  ASP A   3     -32.951 -36.772  15.208  1.00 38.04           A   C
ATOM     35  CG  ASP A   3     -33.054 -38.043  16.010  1.00 42.67           A   C
ATOM     36  OD1 ASP A   3     -33.714 -38.974  15.522  1.00 48.58           A   O
ATOM     37  OD2 ASP A   3     -32.445 -38.125  17.107  1.00 45.54           A   O
ATOM     38  C   ASP A   3     -31.316 -34.990  14.532  1.00 31.91           A   C
ATOM     39  O   ASP A   3     -30.341 -35.265  13.839  1.00 30.97           A   O
ATOM     40  N   PHE A   4     -32.002 -33.866  14.402  1.00 29.93           A   N
ATOM     41  CA  PHE A   4     -31.671 -32.913  13.370  1.00 27.51           A   C
ATOM     42  CB  PHE A   4     -32.603 -31.719  13.404  1.00 26.94           A   C
ATOM     43  CG  PHE A   4     -32.205 -30.665  12.461  1.00 25.87           A   C
ATOM     44  CD1 PHE A   4     -32.405 -30.843  11.101  1.00 27.98           A   C
ATOM     45  CE1 PHE A   4     -31.974 -29.878  10.188  1.00 29.31           A   C
ATOM     46  CZ  PHE A   4     -31.333 -28.704  10.653  1.00 26.48           A   C
ATOM     47  CE2 PHE A   4     -31.116 -28.546  11.995  1.00 24.77           A   C
ATOM     48  CD2 PHE A   4     -31.549 -29.527  12.901  1.00 24.87           A   C
ATOM     49  C   PHE A   4     -30.251 -32.415  13.524  1.00 24.87           A   C
ATOM     50  O   PHE A   4     -29.479 -32.359  12.569  1.00 24.18           A   O
ATOM     51  N   VAL A   5     -29.915 -32.020  14.731  1.00 23.79           A   N
ATOM     52  CA  VAL A   5     -28.585 -31.554  14.998  1.00 21.57           A   C
ATOM     53  CB  VAL A   5     -28.420 -31.160  16.467  1.00 21.39           A   C
ATOM     54  CG1 VAL A   5     -26.932 -31.024  16.833  1.00 20.32           A   C
```

FIG. 2D

```
ATOM   55  CG2 VAL A   5      -29.181 -29.876  16.730  1.00 17.95      A    C
ATOM   56  C   VAL A   5      -27.576 -32.599  14.597  1.00 21.42      A    C
ATOM   57  O   VAL A   5      -26.613 -32.293  13.908  1.00 20.79      A    O
ATOM   58  N   ARG A   6      -27.802 -33.839  14.981  1.00 23.52      A    N
ATOM   59  CA  ARG A   6      -26.811 -34.885  14.715  1.00 24.60      A    C
ATOM   60  CB  ARG A   6      -27.158 -36.180  15.456  1.00 26.20      A    C
ATOM   61  CG  ARG A   6      -26.996 -35.977  16.943  1.00 26.38      A    C
ATOM   62  CD  ARG A   6      -27.362 -37.122  17.837  1.00 30.58      A    C
ATOM   63  NE  ARG A   6      -27.377 -36.649  19.238  1.00 33.78      A    N
ATOM   64  CZ  ARG A   6      -26.311 -36.377  20.015  1.00 33.11      A    C
ATOM   65  NH1 ARG A   6      -25.067 -36.568  19.606  1.00 31.54      A    N
ATOM   66  NH2 ARG A   6      -26.501 -35.918  21.251  1.00 34.64      A    N
ATOM   67  C   ARG A   6      -26.637 -35.086  13.226  1.00 25.83      A    C
ATOM   68  O   ARG A   6      -25.550 -35.332  12.782  1.00 26.84      A    O
ATOM   69  N   GLN A   7      -27.688 -34.913  12.440  1.00 27.44      A    N
ATOM   70  CA  GLN A   7      -27.585 -35.097  11.014  1.00 28.35      A    C
ATOM   71  CB  GLN A   7      -28.937 -35.504  10.426  1.00 30.34      A    C
ATOM   72  CG  GLN A   7      -29.292 -36.929  10.705  1.00 33.32      A    C
ATOM   73  CD  GLN A   7      -30.564 -37.407  10.001  1.00 36.08      A    C
ATOM   74  OE1 GLN A   7      -31.086 -36.771   9.079  1.00 33.80      A    O
ATOM   75  NE2 GLN A   7      -31.054 -38.562  10.441  1.00 38.66      A    N
ATOM   76  C   GLN A   7      -27.085 -33.861  10.297  1.00 27.47      A    C
ATOM   77  O   GLN A   7      -26.649 -33.939   9.153  1.00 29.12      A    O
ATOM   78  N   CYS A   8      -27.169 -32.707  10.931  1.00 25.80      A    N
ATOM   79  CA  CYS A   8      -26.876 -31.460  10.242  1.00 24.20      A    C
ATOM   80  CB  CYS A   8      -27.829 -30.402  10.771  1.00 24.13      A    C
ATOM   81  SG  CYS A   8      -27.679 -28.858  10.002  1.00 25.78      A    S
ATOM   82  C   CYS A   8      -25.417 -30.998  10.402  1.00 21.96      A    C
ATOM   83  O   CYS A   8      -24.829 -30.431   9.482  1.00 20.81      A    O
ATOM   84  N   PHE A   9      -24.837 -31.210  11.576  1.00 20.93      A    N
ATOM   85  CA  PHE A   9      -23.491 -30.717  11.835  1.00 19.41      A    C
ATOM   86  CB  PHE A   9      -23.416 -29.960  13.156  1.00 18.35      A    C
ATOM   87  CG  PHE A   9      -24.257 -28.764  13.175  1.00 17.85      A    C
ATOM   88  CD1 PHE A   9      -23.801 -27.582  12.635  1.00 18.20      A    C
ATOM   89  CE1 PHE A   9      -24.604 -26.492  12.606  1.00 17.55      A    C
ATOM   90  CZ  PHE A   9      -25.904 -26.553  13.103  1.00 15.93      A    C
ATOM   91  CE2 PHE A   9      -26.372 -27.703  13.609  1.00 16.98      A    C
ATOM   92  CD2 PHE A   9      -25.555 -28.820  13.641  1.00 19.53      A    C
ATOM   93  C   PHE A   9      -22.526 -31.860  11.827  1.00 20.11      A    C
ATOM   94  O   PHE A   9      -22.891 -32.984  12.129  1.00 22.44      A    O
ATOM   95  N   ASN A  10      -21.297 -31.556  11.425  1.00 19.59      A    N
ATOM   96  CA  ASN A  10      -20.165 -32.464  11.531  1.00 19.31      A    C
ATOM   97  CB  ASN A  10      -18.866 -31.678  11.312  1.00 18.53      A    C
ATOM   98  CG  ASN A  10      -17.725 -32.563  11.032  1.00 20.99      A    C
ATOM   99  OD1 ASN A  10      -17.170 -33.208  11.931  1.00 25.13      A    O
ATOM  100  ND2 ASN A  10      -17.353 -32.633   9.776  1.00 22.16      A    N
ATOM  101  C   ASN A  10      -20.111 -33.072  12.918  1.00 17.98      A    C
ATOM  102  O   ASN A  10      -20.383 -32.396  13.895  1.00 16.58      A    O
ATOM  103  N   PRO A  11      -19.758 -34.337  13.005  1.00 18.37      A    N
ATOM  104  CA  PRO A  11      -19.655 -34.938  14.315  1.00 19.57      A    C
ATOM  105  CB  PRO A  11      -19.239 -36.371  14.006  1.00 20.39      A    C
ATOM  106  CG  PRO A  11      -19.666 -36.594  12.648  1.00 20.94      A    C
ATOM  107  CD  PRO A  11      -19.656 -35.334  11.929  1.00 19.75      A    C
ATOM  108  C   PRO A  11      -18.625 -34.259  15.224  1.00 19.98      A    C
ATOM  109  O   PRO A  11      -18.788 -34.265  16.440  1.00 19.39      A    O
ATOM  110  N   MET A  12      -17.592 -33.656  14.626  1.00 20.46      A    N
ATOM  111  CA  MET A  12      -16.610 -32.943  15.400  1.00 20.47      A    C
ATOM  112  CB  MET A  12      -15.419 -32.504  14.542  1.00 20.73      A    C
ATOM  113  CG  MET A  12      -14.529 -33.634  14.064  1.00 24.64      A    C
ATOM  114  SD  MET A  12      -13.560 -33.183  12.568  1.00 32.34      A    S
ATOM  115  CE  MET A  12      -12.195 -32.490  13.401  1.00 30.42      A    C
ATOM  116  C   MET A  12      -17.276 -31.757  16.087  1.00 18.94      A    C
ATOM  117  O   MET A  12      -17.098 -31.579  17.289  1.00 19.31      A    O
```

FIG. 2E

```
ATOM    118  N    ILE A   13     -18.059 -30.970  15.346  1.00 17.39           A    N
ATOM    119  CA   ILE A   13     -18.776 -29.809  15.909  1.00 15.91           A    C
ATOM    120  CB   ILE A   13     -19.720 -29.184  14.906  1.00 16.36           A    C
ATOM    121  CG1  ILE A   13     -18.967 -28.565  13.733  1.00 16.97           A    C
ATOM    122  CD1  ILE A   13     -17.918 -27.616  14.160  1.00 19.34           A    C
ATOM    123  CG2  ILE A   13     -20.622 -28.130  15.569  1.00 14.69           A    C
ATOM    124  C    ILE A   13     -19.675 -30.251  17.064  1.00 16.26           A    C
ATOM    125  O    ILE A   13     -19.704 -29.615  18.131  1.00 15.30           A    O
ATOM    126  N    VAL A   14     -20.368 -31.360  16.834  1.00 16.18           A    N
ATOM    127  CA   VAL A   14     -21.317 -31.891  17.777  1.00 17.15           A    C
ATOM    128  CB   VAL A   14     -22.166 -32.995  17.123  1.00 18.61           A    C
ATOM    129  CG1  VAL A   14     -23.052 -33.625  18.133  1.00 20.90           A    C
ATOM    130  CG2  VAL A   14     -23.022 -32.419  15.921  1.00 17.70           A    C
ATOM    131  C    VAL A   14     -20.612 -32.385  19.039  1.00 18.00           A    C
ATOM    132  O    VAL A   14     -21.056 -32.099  20.145  1.00 18.86           A    O
ATOM    133  N    GLU A   15     -19.501 -33.105  18.899  1.00 18.33           A    N
ATOM    134  CA   GLU A   15     -18.707 -33.444  20.067  1.00 18.94           A    C
ATOM    135  CB   GLU A   15     -17.487 -34.258  19.697  1.00 19.34           A    C
ATOM    136  CG   GLU A   15     -17.805 -35.639  19.181  1.00 22.29           A    C
ATOM    137  CD   GLU A   15     -16.685 -36.607  19.410  1.00 23.71           A    C
ATOM    138  OE1  GLU A   15     -15.565 -36.170  19.714  1.00 27.78           A    O
ATOM    139  OE2  GLU A   15     -16.922 -37.813  19.333  1.00 27.67           A    O
ATOM    140  C    GLU A   15     -18.272 -32.198  20.886  1.00 18.08           A    C
ATOM    141  O    GLU A   15     -18.275 -32.237  22.124  1.00 18.57           A    O
ATOM    142  N    LEU A   16     -17.898 -31.114  20.211  1.00 17.01           A    N
ATOM    143  CA   LEU A   16     -17.514 -29.873  20.928  1.00 16.98           A    C
ATOM    144  CB   LEU A   16     -16.799 -28.848  20.041  1.00 15.14           A    C
ATOM    145  CG   LEU A   16     -15.438 -29.310  19.469  1.00 16.38           A    C
ATOM    146  CD1  LEU A   16     -15.069 -28.378  18.317  1.00 13.21           A    C
ATOM    147  CD2  LEU A   16     -14.281 -29.384  20.520  1.00 14.19           A    C
ATOM    148  C    LEU A   16     -18.713 -29.249  21.589  1.00 16.38           A    C
ATOM    149  O    LEU A   16     -18.609 -28.816  22.706  1.00 18.12           A    O
ATOM    150  N    ALA A   17     -19.859 -29.246  20.923  1.00 15.62           A    N
ATOM    151  CA   ALA A   17     -21.048 -28.606  21.489  1.00 15.78           A    C
ATOM    152  CB   ALA A   17     -22.204 -28.590  20.509  1.00 14.60           A    C
ATOM    153  C    ALA A   17     -21.452 -29.312  22.780  1.00 17.05           A    C
ATOM    154  O    ALA A   17     -21.773 -28.662  23.741  1.00 17.12           A    O
ATOM    155  N    GLU A   18     -21.403 -30.642  22.776  1.00 17.83           A    N
ATOM    156  CA   GLU A   18     -21.733 -31.453  23.930  1.00 19.84           A    C
ATOM    157  CB   GLU A   18     -21.597 -32.942  23.584  1.00 21.03           A    C
ATOM    158  CG   GLU A   18     -22.694 -33.505  22.703  1.00 21.16           A    C
ATOM    159  CD   GLU A   18     -22.538 -34.988  22.429  1.00 22.58           A    C
ATOM    160  OE1  GLU A   18     -21.430 -35.493  22.704  1.00 22.98           A    O
ATOM    161  OE2  GLU A   18     -23.504 -35.639  21.927  1.00 23.47           A    O
ATOM    162  C    GLU A   18     -20.858 -31.138  25.150  1.00 20.89           A    C
ATOM    163  O    GLU A   18     -21.352 -31.123  26.296  1.00 21.49           A    O
ATOM    164  N    LYS A   19     -19.568 -30.897  24.915  1.00 20.66           A    N
ATOM    165  CA   LYS A   19     -18.627 -30.577  26.037  1.00 21.79           A    C
ATOM    166  CB   LYS A   19     -17.169 -30.693  25.605  1.00 20.61           A    C
ATOM    167  CG   LYS A   19     -16.773 -32.098  25.329  1.00 21.87           A    C
ATOM    168  CD   LYS A   19     -15.479 -32.193  24.532  1.00 21.08           A    C
ATOM    169  CE   LYS A   19     -15.017 -33.678  24.362  1.00 23.20           A    C
ATOM    170  NZ   LYS A   19     -14.869 -34.470  25.633  1.00 22.35           A    N
ATOM    171  C    LYS A   19     -18.893 -29.162  26.519  1.00 21.37           A    C
ATOM    172  O    LYS A   19     -18.859 -28.877  27.739  1.00 23.73           A    O
ATOM    173  N    ALA A   20     -19.193 -28.307  25.555  1.00 18.73           A    N
ATOM    174  CA   ALA A   20     -19.483 -26.929  25.837  1.00 19.32           A    C
ATOM    175  CB   ALA A   20     -19.753 -26.157  24.557  1.00 16.73           A    C
ATOM    176  C    ALA A   20     -20.672 -26.878  26.769  1.00 20.89           A    C
ATOM    177  O    ALA A   20     -20.591 -26.270  27.823  1.00 23.74           A    O
ATOM    178  N    MET A   21     -21.739 -27.574  26.426  1.00 20.70           A    N
ATOM    179  CA   MET A   21     -22.901 -27.563  27.251  1.00 22.97           A    C
ATOM    180  CB   MET A   21     -24.045 -28.281  26.556  1.00 23.11           A    C
```

FIG. 2F

```
ATOM    181  CG  MET A  21     -24.530 -27.534  25.314  1.00 23.06           A  C
ATOM    182  SD  MET A  21     -26.174 -28.016  24.724  1.00 26.35           A  S
ATOM    183  CE  MET A  21     -27.199 -27.416  26.072  1.00 25.56           A  C
ATOM    184  C   MET A  21     -22.639 -28.118  28.648  1.00 25.25           A  C
ATOM    185  O   MET A  21     -23.143 -27.574  29.638  1.00 26.92           A  O
ATOM    186  N   LYS A  22     -21.829 -29.165  28.730  1.00 26.13           A  N
ATOM    187  CA  LYS A  22     -21.489 -29.773  30.020  1.00 29.17           A  C
ATOM    188  CB  LYS A  22     -20.665 -31.035  29.833  1.00 29.20           A  C
ATOM    189  CG  LYS A  22     -20.517 -31.813  31.101  1.00 33.11           A  C
ATOM    190  CD  LYS A  22     -19.465 -32.898  30.998  1.00 36.31           A  C
ATOM    191  CE  LYS A  22     -19.953 -34.225  31.598  1.00 40.17           A  C
ATOM    192  NZ  LYS A  22     -18.954 -35.315  31.374  1.00 42.12           A  N
ATOM    193  C   LYS A  22     -20.763 -28.783  30.952  1.00 30.09           A  C
ATOM    194  O   LYS A  22     -21.119 -28.665  32.135  1.00 31.19           A  O
ATOM    195  N   GLU A  23     -19.802 -28.060  30.376  1.00 28.37           A  N
ATOM    196  CA  GLU A  23     -19.168 -26.908  31.013  1.00 29.67           A  C
ATOM    197  CB  GLU A  23     -18.219 -26.222  30.021  1.00 27.78           A  C
ATOM    198  CG  GLU A  23     -17.129 -25.370  30.606  1.00 28.78           A  C
ATOM    199  CD  GLU A  23     -16.143 -24.850  29.545  1.00 28.63           A  C
ATOM    200  OE1 GLU A  23     -16.335 -25.079  28.335  1.00 29.68           A  O
ATOM    201  OE2 GLU A  23     -15.164 -24.176  29.913  1.00 31.53           A  O
ATOM    202  C   GLU A  23     -20.241 -25.922  31.488  1.00 31.64           A  C
ATOM    203  O   GLU A  23     -20.312 -25.584  32.697  1.00 33.74           A  O
ATOM    204  N   TYR A  24     -21.131 -25.515  30.575  1.00 30.64           A  N
ATOM    205  CA  TYR A  24     -22.137 -24.519  30.947  1.00 32.37           A  C
ATOM    206  CB  TYR A  24     -22.914 -23.970  29.754  1.00 31.23           A  C
ATOM    207  CG  TYR A  24     -22.085 -23.591  28.586  1.00 28.21           A  C
ATOM    208  CD1 TYR A  24     -22.619 -23.581  27.330  1.00 26.36           A  C
ATOM    209  CE1 TYR A  24     -21.845 -23.230  26.230  1.00 27.39           A  C
ATOM    210  CZ  TYR A  24     -20.518 -22.910  26.417  1.00 27.75           A  C
ATOM    211  OH  TYR A  24     -19.693 -22.577  25.369  1.00 24.23           A  O
ATOM    212  CE2 TYR A  24     -19.981 -22.934  27.672  1.00 28.48           A  C
ATOM    213  CD2 TYR A  24     -20.760 -23.265  28.742  1.00 29.94           A  C
ATOM    214  C   TYR A  24     -23.148 -25.039  31.950  1.00 35.13           A  C
ATOM    215  O   TYR A  24     -23.948 -24.251  32.413  1.00 36.84           A  O
ATOM    216  N   GLY A  25     -23.104 -26.338  32.278  1.00 36.28           A  N
ATOM    217  CA  GLY A  25     -24.021 -26.966  33.237  1.00 38.88           A  C
ATOM    218  C   GLY A  25     -25.284 -27.483  32.568  1.00 38.95           A  C
ATOM    219  O   GLY A  25     -26.202 -27.884  33.219  1.00 40.13           A  O
ATOM    220  N   GLU A  26     -25.307 -27.494  31.244  1.00 37.74           A  N
ATOM    221  CA  GLU A  26     -26.493 -27.858  30.501  1.00 38.12           A  C
ATOM    222  CB  GLU A  26     -26.690 -26.821  29.421  1.00 36.54           A  C
ATOM    223  CG  GLU A  26     -27.092 -25.451  30.032  1.00 39.91           A  C
ATOM    224  CD  GLU A  26     -26.490 -24.262  29.316  1.00 39.81           A  C
ATOM    225  OE1 GLU A  26     -25.942 -24.435  28.211  1.00 42.01           A  O
ATOM    226  OE2 GLU A  26     -26.558 -23.144  29.859  1.00 41.95           A  O
ATOM    227  C   GLU A  26     -26.427 -29.266  29.914  1.00 37.96           A  C
ATOM    228  O   GLU A  26     -25.342 -29.803  29.727  1.00 37.23           A  O
ATOM    229  N   ASP A  27     -27.606 -29.849  29.667  1.00 39.12           A  N
ATOM    230  CA  ASP A  27     -27.764 -31.177  29.082  1.00 39.25           A  C
ATOM    231  CB  ASP A  27     -28.707 -32.025  29.928  1.00 42.22           A  C
ATOM    232  CG  ASP A  27     -28.894 -33.440  29.376  1.00 44.32           A  C
ATOM    233  OD1 ASP A  27     -28.229 -33.814  28.376  1.00 44.76           A  O
ATOM    234  OD2 ASP A  27     -29.714 -34.196  29.947  1.00 47.21           A  O
ATOM    235  C   ASP A  27     -28.343 -31.030  27.681  1.00 37.87           A  C
ATOM    236  O   ASP A  27     -29.436 -30.489  27.520  1.00 38.80           A  O
ATOM    237  N   PRO A  28     -27.615 -31.499  26.654  1.00 36.28           A  N
ATOM    238  CA  PRO A  28     -28.056 -31.269  25.280  1.00 35.00           A  C
ATOM    239  CB  PRO A  28     -26.913 -31.846  24.438  1.00 33.33           A  C
ATOM    240  CG  PRO A  28     -26.148 -32.681  25.355  1.00 34.90           A  C
ATOM    241  CD  PRO A  28     -26.269 -32.079  26.693  1.00 35.29           A  C
ATOM    242  C   PRO A  28     -29.369 -31.931  24.904  1.00 36.56           A  C
ATOM    243  O   PRO A  28     -30.044 -31.465  23.979  1.00 35.66           A  O
```

FIG. 2G

```
ATOM    244  N    LYS A  29     -29.713 -33.017  25.594  1.00 38.93      A   N
ATOM    245  CA   LYS A  29     -30.986 -33.706  25.356  1.00 41.06      A   C
ATOM    246  CB   LYS A  29     -30.915 -35.149  25.867  1.00 43.29      A   C
ATOM    247  CG   LYS A  29     -30.426 -36.155  24.825  1.00 44.43      A   C
ATOM    248  CD   LYS A  29     -30.115 -37.532  25.440  1.00 50.57      A   C
ATOM    249  CE   LYS A  29     -30.527 -38.696  24.510  1.00 53.55      A   C
ATOM    250  NZ   LYS A  29     -29.737 -38.688  23.223  1.00 52.09      A   N
ATOM    251  C    LYS A  29     -32.161 -32.960  25.989  1.00 42.43      A   C
ATOM    252  O    LYS A  29     -33.291 -33.106  25.551  1.00 43.23      A   O
ATOM    253  N    ILE A  30     -31.887 -32.178  27.030  1.00 43.17      A   N
ATOM    254  CA   ILE A  30     -32.903 -31.342  27.663  1.00 45.15      A   C
ATOM    255  CB   ILE A  30     -32.619 -31.102  29.193  1.00 47.04      A   C
ATOM    256  CG1  ILE A  30     -32.764 -32.417  29.971  1.00 49.74      A   C
ATOM    257  CD1  ILE A  30     -32.450 -32.330  31.480  1.00 51.74      A   C
ATOM    258  CG2  ILE A  30     -33.596 -30.095  29.790  1.00 48.66      A   C
ATOM    259  C    ILE A  30     -32.980 -30.027  26.885  1.00 43.30      A   C
ATOM    260  O    ILE A  30     -34.012 -29.715  26.307  1.00 42.91      A   O
ATOM    261  N    GLU A  31     -31.865 -29.293  26.823  1.00 41.69      A   N
ATOM    262  CA   GLU A  31     -31.827 -27.955  26.167  1.00 39.92      A   C
ATOM    263  CB   GLU A  31     -30.974 -26.960  26.983  1.00 39.98      A   C
ATOM    264  CG   GLU A  31     -31.647 -26.570  28.318  1.00 44.32      A   C
ATOM    265  CD   GLU A  31     -31.051 -25.334  28.993  1.00 47.24      A   C
ATOM    266  OE1  GLU A  31     -31.081 -24.241  28.380  1.00 48.73      A   O
ATOM    267  OE2  GLU A  31     -30.601 -25.446  30.163  1.00 49.73      A   O
ATOM    268  C    GLU A  31     -31.419 -28.051  24.693  1.00 36.66      A   C
ATOM    269  O    GLU A  31     -30.393 -27.509  24.240  1.00 34.58      A   O
ATOM    270  N    THR A  32     -32.268 -28.748  23.947  1.00 36.29      A   N
ATOM    271  CA   THR A  32     -32.001 -29.045  22.555  1.00 34.03      A   C
ATOM    272  CB   THR A  32     -33.077 -29.979  21.957  1.00 35.51      A   C
ATOM    273  OG1  THR A  32     -34.351 -29.327  21.960  1.00 38.58      A   O
ATOM    274  CG2  THR A  32     -33.179 -31.259  22.746  1.00 36.42      A   C
ATOM    275  C    THR A  32     -31.864 -27.790  21.697  1.00 31.73      A   C
ATOM    276  O    THR A  32     -31.005 -27.753  20.813  1.00 30.28      A   O
ATOM    277  N    ASN A  33     -32.667 -26.755  21.954  1.00 31.40      A   N
ATOM    278  CA   ASN A  33     -32.523 -25.511  21.179  1.00 29.99      A   C
ATOM    279  CB   ASN A  33     -33.665 -24.495  21.407  1.00 31.18      A   C
ATOM    280  CG   ASN A  33     -34.978 -24.895  20.728  1.00 33.33      A   C
ATOM    281  OD1  ASN A  33     -36.075 -24.692  21.273  1.00 38.17      A   O
ATOM    282  ND2  ASN A  33     -34.878 -25.464  19.548  1.00 34.83      A   N
ATOM    283  C    ASN A  33     -31.173 -24.825  21.406  1.00 28.09      A   C
ATOM    284  O    ASN A  33     -30.518 -24.410  20.464  1.00 26.28      A   O
ATOM    285  N    LYS A  34     -30.766 -24.683  22.652  1.00 28.62      A   N
ATOM    286  CA   LYS A  34     -29.479 -24.117  22.917  1.00 28.25      A   C
ATOM    287  CB   LYS A  34     -29.251 -23.923  24.416  1.00 30.26      A   C
ATOM    288  CG   LYS A  34     -27.921 -23.202  24.718  1.00 31.82      A   C
ATOM    289  CD   LYS A  34     -27.857 -22.715  26.179  1.00 36.92      A   C
ATOM    290  CE   LYS A  34     -26.500 -22.043  26.503  1.00 37.85      A   C
ATOM    291  NZ   LYS A  34     -26.418 -21.555  27.963  1.00 39.77      A   N
ATOM    292  C    LYS A  34     -28.386 -24.993  22.313  1.00 26.26      A   C
ATOM    293  O    LYS A  34     -27.344 -24.489  21.962  1.00 25.42      A   O
ATOM    294  N    PHE A  35     -28.625 -26.303  22.226  1.00 26.66      A   N
ATOM    295  CA   PHE A  35     -27.695 -27.259  21.570  1.00 25.28      A   C
ATOM    296  CB   PHE A  35     -28.263 -28.688  21.714  1.00 26.97      A   C
ATOM    297  CG   PHE A  35     -27.340 -29.815  21.283  1.00 26.72      A   C
ATOM    298  CD1  PHE A  35     -25.971 -29.792  21.536  1.00 28.20      A   C
ATOM    299  CE1  PHE A  35     -25.145 -30.864  21.151  1.00 26.51      A   C
ATOM    300  CZ   PHE A  35     -25.696 -31.956  20.545  1.00 28.02      A   C
ATOM    301  CE2  PHE A  35     -27.089 -31.996  20.296  1.00 27.80      A   C
ATOM    302  CD2  PHE A  35     -27.882 -30.953  20.689  1.00 27.70      A   C
ATOM    303  C    PHE A  35     -27.484 -26.888  20.106  1.00 23.16      A   C
ATOM    304  O    PHE A  35     -26.327 -26.742  19.678  1.00 21.73      A   O
ATOM    305  N    ALA A  36     -28.584 -26.693  19.365  1.00 22.28      A   N
ATOM    306  CA   ALA A  36     -28.507 -26.232  17.959  1.00 21.27      A   C
```

FIG. 2H

```
ATOM   307  CB   ALA A  36     -29.875 -26.152  17.307  1.00 21.28      A    C
ATOM   308  C    ALA A  36     -27.784 -24.891  17.805  1.00 20.58      A    C
ATOM   309  O    ALA A  36     -26.921 -24.739  16.907  1.00 19.84      A    O
ATOM   310  N    ALA A  37     -28.121 -23.929  18.662  1.00 20.34      A    N
ATOM   311  CA   ALA A  37     -27.501 -22.604  18.566  1.00 20.81      A    C
ATOM   312  CB   ALA A  37     -28.131 -21.587  19.582  1.00 20.93      A    C
ATOM   313  C    ALA A  37     -25.998 -22.715  18.814  1.00 19.61      A    C
ATOM   314  O    ALA A  37     -25.194 -22.007  18.204  1.00 19.55      A    O
ATOM   315  N    ILE A  38     -25.623 -23.573  19.743  1.00 19.45      A    N
ATOM   316  CA   ILE A  38     -24.243 -23.656  20.083  1.00 19.17      A    C
ATOM   317  CB   ILE A  38     -24.019 -24.341  21.439  1.00 20.89      A    C
ATOM   318  CG1  ILE A  38     -24.493 -23.419  22.551  1.00 21.15      A    C
ATOM   319  CD1  ILE A  38     -24.610 -24.148  23.852  1.00 24.96      A    C
ATOM   320  CG2  ILE A  38     -22.500 -24.733  21.641  1.00 18.93      A    C
ATOM   321  C    ILE A  38     -23.488 -24.341  18.960  1.00 17.60      A    C
ATOM   322  O    ILE A  38     -22.420 -23.884  18.630  1.00 17.30      A    O
ATOM   323  N    CYS A  39     -24.028 -25.414  18.373  1.00 17.62      A    N
ATOM   324  CA   CYS A  39     -23.441 -25.979  17.137  1.00 16.85      A    C
ATOM   325  CB   CYS A  39     -24.222 -27.186  16.634  1.00 18.19      A    C
ATOM   326  SG   CYS A  39     -24.155 -28.635  17.642  1.00 15.81      A    S
ATOM   327  C    CYS A  39     -23.377 -24.965  15.982  1.00 16.18      A    C
ATOM   328  O    CYS A  39     -22.406 -24.910  15.261  1.00 16.46      A    O
ATOM   329  N    THR A  40     -24.384 -24.137  15.825  1.00 16.58      A    N
ATOM   330  CA   THR A  40     -24.388 -23.191  14.721  1.00 16.57      A    C
ATOM   331  CB   THR A  40     -25.731 -22.469  14.608  1.00 17.81      A    C
ATOM   332  OG1  THR A  40     -26.813 -23.438  14.570  1.00 17.65      A    O
ATOM   333  CG2  THR A  40     -25.734 -21.609  13.345  1.00 17.88      A    C
ATOM   334  C    THR A  40     -23.269 -22.186  14.865  1.00 16.76      A    C
ATOM   335  O    THR A  40     -22.500 -21.963  13.946  1.00 18.19      A    O
ATOM   336  N    HIS A  41     -23.156 -21.591  16.039  1.00 17.23      A    N
ATOM   337  CA   HIS A  41     -22.100 -20.648  16.340  1.00 16.15      A    C
ATOM   338  CB   HIS A  41     -22.220 -20.238  17.784  1.00 16.60      A    C
ATOM   339  CG   HIS A  41     -21.284 -19.148  18.190  1.00 15.39      A    C
ATOM   340  ND1  HIS A  41     -20.070 -19.397  18.797  1.00 12.33      A    N
ATOM   341  CE1  HIS A  41     -19.486 -18.246  19.071  1.00 14.61      A    C
ATOM   342  NE2  HIS A  41     -20.268 -17.264  18.666  1.00 14.41      A    N
ATOM   343  CD2  HIS A  41     -21.403 -17.803  18.114  1.00 14.71      A    C
ATOM   344  C    HIS A  41     -20.726 -21.233  16.102  1.00 16.02      A    C
ATOM   345  O    HIS A  41     -19.892 -20.616  15.439  1.00 16.87      A    O
ATOM   346  N    LEU A  42     -20.475 -22.422  16.625  1.00 16.35      A    N
ATOM   347  CA   LEU A  42     -19.175 -23.073  16.432  1.00 15.82      A    C
ATOM   348  CB   LEU A  42     -19.107 -24.409  17.136  1.00 16.48      A    C
ATOM   349  CG   LEU A  42     -18.593 -24.388  18.590  1.00 18.28      A    C
ATOM   350  CD1  LEU A  42     -19.483 -25.258  19.436  1.00 20.28      A    C
ATOM   351  CD2  LEU A  42     -17.168 -24.838  18.695  1.00 13.65      A    C
ATOM   352  C    LEU A  42     -18.942 -23.273  14.959  1.00 15.64      A    C
ATOM   353  O    LEU A  42     -17.877 -22.885  14.470  1.00 16.50      A    O
ATOM   354  N    GLU A  43     -19.936 -23.776  14.211  1.00 15.26      A    N
ATOM   355  CA   GLU A  43     -19.687 -23.932  12.796  1.00 16.02      A    C
ATOM   356  CB   GLU A  43     -20.840 -24.582  12.009  1.00 18.04      A    C
ATOM   357  CG   GLU A  43     -20.263 -25.433  10.859  1.00 20.41      A    C
ATOM   358  CD   GLU A  43     -21.292 -26.232  10.118  1.00 26.88      A    C
ATOM   359  OE1  GLU A  43     -22.217 -25.602   9.579  1.00 26.20      A    O
ATOM   360  OE2  GLU A  43     -21.148 -27.495  10.049  1.00 33.05      A    O
ATOM   361  C    GLU A  43     -19.272 -22.616  12.131  1.00 15.14      A    C
ATOM   362  O    GLU A  43     -18.337 -22.594  11.351  1.00 14.71      A    O
ATOM   363  N    VAL A  44     -19.940 -21.521  12.470  1.00 14.64      A    N
ATOM   364  CA   VAL A  44     -19.607 -20.259  11.868  1.00 14.99      A    C
ATOM   365  CB   VAL A  44     -20.672 -19.222  12.222  1.00 16.08      A    C
ATOM   366  CG1  VAL A  44     -20.278 -17.844  11.727  1.00 15.24      A    C
ATOM   367  CG2  VAL A  44     -22.015 -19.641  11.610  1.00 16.62      A    C
ATOM   368  C    VAL A  44     -18.174 -19.808  12.219  1.00 15.20      A    C
ATOM   369  O    VAL A  44     -17.426 -19.405  11.340  1.00 15.01      A    O
```

FIG. 2I

```
ATOM    370  N    CYS A  45     -17.787 -19.943  13.492  1.00 15.02      A    N
ATOM    371  CA   CYS A  45     -16.418 -19.703  13.917  1.00 15.09      A    C
ATOM    372  CB   CYS A  45     -16.237 -20.043  15.393  1.00 15.14      A    C
ATOM    373  SG   CYS A  45     -17.126 -18.860  16.494  1.00 17.74      A    S
ATOM    374  C    CYS A  45     -15.405 -20.476  13.081  1.00 15.35      A    C
ATOM    375  O    CYS A  45     -14.442 -19.893  12.640  1.00 14.54      A    O
ATOM    376  N    PHE A  46     -15.616 -21.780  12.877  1.00 16.14      A    N
ATOM    377  CA   PHE A  46     -14.668 -22.606  12.105  1.00 16.71      A    C
ATOM    378  CB   PHE A  46     -14.859 -24.095  12.351  1.00 16.76      A    C
ATOM    379  CG   PHE A  46     -14.377 -24.544  13.710  1.00 18.56      A    C
ATOM    380  CD1  PHE A  46     -13.031 -24.565  14.013  1.00 16.99      A    C
ATOM    381  CE1  PHE A  46     -12.581 -24.945  15.277  1.00 18.86      A    C
ATOM    382  CZ   PHE A  46     -13.459 -25.320  16.246  1.00 18.27      A    C
ATOM    383  CE2  PHE A  46     -14.819 -25.313  15.967  1.00 21.68      A    C
ATOM    384  CD2  PHE A  46     -15.279 -24.934  14.699  1.00 20.78      A    C
ATOM    385  C    PHE A  46     -14.764 -22.334  10.620  1.00 17.91      A    C
ATOM    386  O    PHE A  46     -13.767 -22.384   9.909  1.00 18.58      A    O
ATOM    387  N    MET A  47     -15.958 -22.029  10.132  1.00 18.70      A    N
ATOM    388  CA   MET A  47     -16.070 -21.621   8.740  1.00 19.52      A    C
ATOM    389  CB   MET A  47     -17.515 -21.445   8.333  1.00 19.81      A    C
ATOM    390  CG   MET A  47     -18.260 -22.739   8.144  1.00 20.59      A    C
ATOM    391  SD   MET A  47     -19.892 -22.374   7.501  1.00 21.22      A    S
ATOM    392  CE   MET A  47     -19.486 -22.150   5.806  1.00 22.09      A    C
ATOM    393  C    MET A  47     -15.321 -20.325   8.506  1.00 19.33      A    C
ATOM    394  O    MET A  47     -14.673 -20.161   7.502  1.00 20.61      A    O
ATOM    395  N    TYR A  48     -15.412 -19.408   9.445  1.00 19.41      A    N
ATOM    396  CA   TYR A  48     -14.788 -18.082   9.295  1.00 20.50      A    C
ATOM    397  CB   TYR A  48     -15.066 -17.243  10.560  1.00 19.66      A    C
ATOM    398  CG   TYR A  48     -14.976 -15.735  10.449  1.00 19.41      A    C
ATOM    399  CD1  TYR A  48     -16.121 -14.956  10.339  1.00 18.97      A    C
ATOM    400  CE1  TYR A  48     -16.057 -13.595  10.270  1.00 18.30      A    C
ATOM    401  CZ   TYR A  48     -14.851 -12.956  10.353  1.00 18.88      A    C
ATOM    402  OH   TYR A  48     -14.814 -11.588  10.293  1.00 19.64      A    O
ATOM    403  CE2  TYR A  48     -13.696 -13.678  10.485  1.00 20.51      A    C
ATOM    404  CD2  TYR A  48     -13.764 -15.075  10.553  1.00 21.06      A    C
ATOM    405  C    TYR A  48     -13.268 -18.297   9.048  1.00 21.22      A    C
ATOM    406  O    TYR A  48     -12.646 -17.587   8.249  1.00 21.95      A    O
ATOM    407  N    SER A  49     -12.715 -19.323   9.700  1.00 20.73      A    N
ATOM    408  CA   SER A  49     -11.292 -19.622   9.643  1.00 21.92      A    C
ATOM    409  CB   SER A  49     -10.869 -20.369  10.904  1.00 21.47      A    C
ATOM    410  OG   SER A  49      -9.881 -21.354  10.617  1.00 24.24      A    O
ATOM    411  C    SER A  49     -10.851 -20.398   8.404  1.00 22.71      A    C
ATOM    412  O    SER A  49      -9.750 -20.200   7.938  1.00 23.74      A    O
ATOM    413  N    ASP A  50     -11.697 -21.284   7.891  1.00 23.37      A    N
ATOM    414  CA   ASP A  50     -11.408 -22.051   6.690  1.00 25.48      A    C
ATOM    415  CB   ASP A  50     -12.703 -22.647   6.137  1.00 26.38      A    C
ATOM    416  CG   ASP A  50     -13.187 -23.856   6.916  1.00 26.94      A    C
ATOM    417  OD1  ASP A  50     -12.375 -24.528   7.527  1.00 27.01      A    O
ATOM    418  OD2  ASP A  50     -14.401 -24.151   6.884  1.00 32.80      A    O
ATOM    419  C    ASP A  50     -10.777 -21.232   5.556  1.00 27.02      A    C
ATOM    420  O    ASP A  50     -11.207 -20.127   5.236  1.00 27.66      A    O
ATOM    421  N    PHE A  51      -9.762 -21.795   4.928  1.00 28.32      A    N
ATOM    422  CA   PHE A  51      -9.218 -21.253   3.680  1.00 30.00      A    C
ATOM    423  CB   PHE A  51     -10.300 -20.841   2.666  1.00 30.77      A    C
ATOM    424  CG   PHE A  51     -11.406 -21.809   2.519  1.00 31.84      A    C
ATOM    425  CD1  PHE A  51     -11.146 -23.165   2.385  1.00 35.15      A    C
ATOM    426  CE1  PHE A  51     -12.193 -24.068   2.237  1.00 35.39      A    C
ATOM    427  CZ   PHE A  51     -13.507 -23.603   2.208  1.00 34.54      A    C
ATOM    428  CE2  PHE A  51     -13.766 -22.247   2.328  1.00 32.66      A    C
ATOM    429  CD2  PHE A  51     -12.723 -21.364   2.486  1.00 32.53      A    C
ATOM    430  C    PHE A  51      -8.333 -20.059   3.851  1.00 29.55      A    C
ATOM    431  O    PHE A  51      -7.718 -19.646   2.868  1.00 31.06      A    O
ATOM    432  N    HIS A  52      -8.270 -19.511   5.063  1.00 27.47      A    N
```

FIG. 2J

```
ATOM    433  CA  HIS A  52      -7.437 -18.330   5.348  1.00 27.94      A  C
ATOM    434  CB  HIS A  52      -8.231 -17.342   6.196  1.00 26.83      A  C
ATOM    435  CG  HIS A  52      -9.395 -16.764   5.476  1.00 28.10      A  C
ATOM    436  ND1 HIS A  52      -9.269 -15.736   4.564  1.00 30.46      A  N
ATOM    437  CE1 HIS A  52     -10.456 -15.446   4.067  1.00 30.64      A  C
ATOM    438  NE2 HIS A  52     -11.344 -16.264   4.609  1.00 29.75      A  N
ATOM    439  CD2 HIS A  52     -10.704 -17.111   5.478  1.00 27.35      A  C
ATOM    440  C   HIS A  52      -6.104 -18.662   6.022  1.00 27.57      A  C
ATOM    441  O   HIS A  52      -6.058 -19.355   7.020  1.00 26.50      A  O
ATOM    442  N   PHE A  53      -5.007 -18.188   5.445  1.00 28.94      A  N
ATOM    443  CA  PHE A  53      -3.668 -18.522   5.950  1.00 28.70      A  C
ATOM    444  CB  PHE A  53      -3.054 -19.634   5.084  1.00 30.26      A  C
ATOM    445  CG  PHE A  53      -3.883 -20.872   5.043  1.00 27.97      A  C
ATOM    446  CD1 PHE A  53      -3.801 -21.797   6.065  1.00 26.02      A  C
ATOM    447  CE1 PHE A  53      -4.595 -22.938   6.040  1.00 27.12      A  C
ATOM    448  CZ  PHE A  53      -5.502 -23.147   4.976  1.00 27.38      A  C
ATOM    449  CE2 PHE A  53      -5.603 -22.220   3.978  1.00 26.47      A  C
ATOM    450  CD2 PHE A  53      -4.796 -21.080   4.012  1.00 28.15      A  C
ATOM    451  C   PHE A  53      -2.755 -17.319   5.991  1.00 29.18      A  C
ATOM    452  O   PHE A  53      -3.152 -16.225   5.633  1.00 28.10      A  O
ATOM    453  N   ILE A  54      -1.540 -17.540   6.474  1.00 30.67      A  N
ATOM    454  CA  ILE A  54      -0.461 -16.534   6.439  1.00 33.09      A  C
ATOM    455  CB  ILE A  54      -0.171 -16.011   7.871  1.00 32.95      A  C
ATOM    456  CG1 ILE A  54      -1.306 -15.081   8.306  1.00 32.29      A  C
ATOM    457  CD1 ILE A  54      -1.222 -14.731   9.768  1.00 33.16      A  C
ATOM    458  CG2 ILE A  54       1.171 -15.266   7.959  1.00 34.00      A  C
ATOM    459  C   ILE A  54       0.781 -17.171   5.828  1.00 35.14      A  C
ATOM    460  O   ILE A  54       1.062 -18.342   6.078  1.00 34.60      A  O
ATOM    461  N   ASP A  55       1.509 -16.409   5.018  1.00 38.12      A  N
ATOM    462  CA  ASP A  55       2.678 -16.934   4.304  1.00 40.92      A  C
ATOM    463  CB  ASP A  55       2.691 -16.424   2.857  1.00 42.73      A  C
ATOM    464  CG  ASP A  55       3.250 -15.033   2.723  1.00 44.02      A  C
ATOM    465  OD1 ASP A  55       3.704 -14.675   1.612  1.00 45.40      A  O
ATOM    466  OD2 ASP A  55       3.246 -14.302   3.725  1.00 43.03      A  O
ATOM    467  C   ASP A  55       3.943 -16.580   5.094  1.00 43.06      A  C
ATOM    468  O   ASP A  55       3.813 -16.109   6.219  1.00 41.80      A  O
ATOM    469  N   GLU A  56       5.138 -16.801   4.538  1.00 46.51      A  N
ATOM    470  CA  GLU A  56       6.377 -16.603   5.303  1.00 49.50      A  C
ATOM    471  CB  GLU A  56       7.627 -17.215   4.620  1.00 53.21      A  C
ATOM    472  CG  GLU A  56       7.558 -18.663   4.150  1.00 54.84      A  C
ATOM    473  CD  GLU A  56       7.256 -19.677   5.256  1.00 56.52      A  C
ATOM    474  OE1 GLU A  56       6.878 -19.298   6.393  1.00 56.80      A  O
ATOM    475  OE2 GLU A  56       7.376 -20.889   4.971  1.00 59.29      A  O
ATOM    476  C   GLU A  56       6.732 -15.157   5.629  1.00 51.05      A  C
ATOM    477  O   GLU A  56       7.622 -14.945   6.451  1.00 52.87      A  O
ATOM    478  N   ARG A  57       6.115 -14.171   4.976  1.00 51.60      A  N
ATOM    479  CA  ARG A  57       6.412 -12.744   5.257  1.00 52.92      A  C
ATOM    480  CB  ARG A  57       6.699 -11.942   3.961  1.00 55.63      A  C
ATOM    481  CG  ARG A  57       8.197 -11.818   3.571  1.00 60.48      A  C
ATOM    482  CD  ARG A  57       8.607 -10.393   3.084  1.00 63.64      A  C
ATOM    483  NE  ARG A  57      10.012 -10.323   2.632  1.00 68.09      A  N
ATOM    484  CZ  ARG A  57      10.738  -9.198   2.526  1.00 72.13      A  C
ATOM    485  NH1 ARG A  57      10.205  -8.021   2.853  1.00 72.40      A  N
ATOM    486  NH2 ARG A  57      12.011  -9.233   2.095  1.00 74.08      A  N
ATOM    487  C   ARG A  57       5.298 -12.055   6.052  1.00 50.34      A  C
ATOM    488  O   ARG A  57       5.345 -10.841   6.256  1.00 52.01      A  O
ATOM    489  N   GLY A  58       4.301 -12.811   6.496  1.00 46.96      A  N
ATOM    490  CA  GLY A  58       3.133 -12.227   7.169  1.00 44.46      A  C
ATOM    491  C   GLY A  58       1.970 -11.773   6.285  1.00 43.35      A  C
ATOM    492  O   GLY A  58       0.990 -11.190   6.778  1.00 41.65      A  O
ATOM    493  N   GLU A  59       2.051 -12.058   4.989  1.00 43.75      A  N
ATOM    494  CA  GLU A  59       0.999 -11.670   4.052  1.00 43.17      A  C
ATOM    495  CB  GLU A  59       1.551 -11.641   2.604  1.00 46.48      A  C
```

FIG. 2K

```
ATOM  496  CG   GLU A  59      2.920 -10.834   2.475  1.00 51.44      A  C
ATOM  497  CD   GLU A  59      3.599 -10.849   1.058  1.00 57.39      A  C
ATOM  498  OE1  GLU A  59      4.797 -11.237   0.973  1.00 60.23      A  O
ATOM  499  OE2  GLU A  59      2.962 -10.439   0.048  1.00 58.61      A  O
ATOM  500  C    GLU A  59     -0.177 -12.635   4.223  1.00 39.22      A  C
ATOM  501  O    GLU A  59      0.008 -13.845   4.367  1.00 37.74      A  O
ATOM  502  N    SER A  60     -1.389 -12.098   4.273  1.00 37.25      A  N
ATOM  503  CA   SER A  60     -2.576 -12.951   4.386  1.00 34.87      A  C
ATOM  504  CB   SER A  60     -3.782 -12.167   4.899  1.00 33.32      A  C
ATOM  505  OG   SER A  60     -4.110 -11.118   3.999  1.00 36.85      A  O
ATOM  506  C    SER A  60     -2.858 -13.579   3.026  1.00 35.08      A  C
ATOM  507  O    SER A  60     -2.465 -13.038   1.996  1.00 37.89      A  O
ATOM  508  N    ILE A  61     -3.507 -14.729   3.023  1.00 33.23      A  N
ATOM  509  CA   ILE A  61     -3.706 -15.477   1.805  1.00 34.51      A  C
ATOM  510  CB   ILE A  61     -2.431 -16.291   1.448  1.00 36.25      A  C
ATOM  511  CG1  ILE A  61     -2.151 -17.423   2.422  1.00 34.55      A  C
ATOM  512  CD1  ILE A  61     -0.658 -17.912   2.382  1.00 34.18      A  C
ATOM  513  CG2  ILE A  61     -1.208 -15.397   1.466  1.00 39.05      A  C
ATOM  514  C    ILE A  61     -4.945 -16.371   1.847  1.00 33.17      A  C
ATOM  515  O    ILE A  61     -5.222 -17.023   2.846  1.00 30.98      A  O
ATOM  516  N    ILE A  62     -5.677 -16.400   0.737  1.00 35.18      A  N
ATOM  517  CA   ILE A  62     -6.905 -17.171   0.617  1.00 34.43      A  C
ATOM  518  CB   ILE A  62     -8.055 -16.309   0.032  1.00 35.05      A  C
ATOM  519  CG1  ILE A  62     -8.295 -15.087   0.940  1.00 34.22      A  C
ATOM  520  CD1  ILE A  62     -9.396 -14.138   0.465  1.00 34.75      A  C
ATOM  521  CG2  ILE A  62     -9.336 -17.160  -0.173  1.00 30.76      A  C
ATOM  522  C    ILE A  62     -6.646 -18.353  -0.293  1.00 37.27      A  C
ATOM  523  O    ILE A  62     -6.224 -18.164  -1.429  1.00 37.86      A  O
ATOM  524  N    VAL A  63     -6.936 -19.562   0.221  1.00 38.57      A  N
ATOM  525  CA   VAL A  63     -6.563 -20.838  -0.426  1.00 41.42      A  C
ATOM  526  CB   VAL A  63     -5.277 -21.378   0.201  1.00 41.01      A  C
ATOM  527  CG1  VAL A  63     -4.850 -22.657  -0.492  1.00 43.16      A  C
ATOM  528  CG2  VAL A  63     -4.173 -20.337   0.137  1.00 42.58      A  C
ATOM  529  C    VAL A  63     -7.619 -21.947  -0.270  1.00 42.62      A  C
ATOM  530  O    VAL A  63     -7.934 -22.335   0.869  1.00 40.60      A  O
ATOM  531  N    GLU A  64     -8.126 -22.494  -1.393  1.00 46.80      A  N
ATOM  532  CA   GLU A  64     -9.155 -23.586  -1.356  1.00 47.65      A  C
ATOM  533  CB   GLU A  64     -9.568 -24.028  -2.768  1.00 50.96      A  C
ATOM  534  CG   GLU A  64    -10.681 -23.204  -3.401  1.00 54.65      A  C
ATOM  535  CD   GLU A  64    -11.841 -22.925  -2.443  1.00 56.63      A  C
ATOM  536  OE1  GLU A  64    -12.296 -23.875  -1.733  1.00 58.48      A  O
ATOM  537  OE2  GLU A  64    -12.277 -21.744  -2.396  1.00 56.99      A  O
ATOM  538  C    GLU A  64     -8.729 -24.829  -0.565  1.00 47.56      A  C
ATOM  539  O    GLU A  64     -8.195 -25.801  -1.128  1.00 50.63      A  O
ATOM  540  N    LEU A  71      0.780 -27.601   4.107  1.00 40.62      A  N
ATOM  541  CA   LEU A  71      0.706 -27.176   5.491  1.00 38.62      A  C
ATOM  542  CB   LEU A  71      1.727 -27.947   6.335  1.00 40.34      A  C
ATOM  543  CG   LEU A  71      1.696 -29.475   6.258  1.00 41.81      A  C
ATOM  544  CD1  LEU A  71      2.947 -30.014   6.868  1.00 44.76      A  C
ATOM  545  CD2  LEU A  71      0.486 -30.066   6.934  1.00 38.80      A  C
ATOM  546  C    LEU A  71      1.037 -25.700   5.576  1.00 37.67      A  C
ATOM  547  O    LEU A  71      2.038 -25.272   5.015  1.00 39.52      A  O
ATOM  548  N    LEU A  72      0.218 -24.939   6.303  1.00 34.72      A  N
ATOM  549  CA   LEU A  72      0.293 -23.478   6.293  1.00 34.00      A  C
ATOM  550  CB   LEU A  72     -0.677 -22.963   5.250  1.00 33.74      A  C
ATOM  551  CG   LEU A  72     -0.154 -23.121   3.834  1.00 36.99      A  C
ATOM  552  CD1  LEU A  72     -1.230 -22.825   2.806  1.00 37.53      A  C
ATOM  553  CD2  LEU A  72      1.057 -22.236   3.666  1.00 39.80      A  C
ATOM  554  C    LEU A  72     -0.075 -22.869   7.618  1.00 31.35      A  C
ATOM  555  O    LEU A  72     -0.939 -23.406   8.274  1.00 30.25      A  O
ATOM  556  N    LYS A  73      0.537 -21.744   8.018  1.00 31.38      A  N
ATOM  557  CA   LYS A  73      0.094 -21.078   9.284  1.00 29.65      A  C
ATOM  558  CB   LYS A  73      0.986 -19.934   9.753  1.00 30.49      A  C
```

FIG. 2L

| | | | | | | | | | | |
|---|---|---|---|---|---|---|---|---|---|---|
|ATOM|559|CG|LYS|A|73|2.505|-20.207|9.780|1.00 36.77|A C|
|ATOM|560|CD|LYS|A|73|3.335|-18.896|9.514|1.00 40.46|A C|
|ATOM|561|CE|LYS|A|73|4.764|-19.184|9.082|1.00 45.72|A C|
|ATOM|562|NZ|LYS|A|73|5.681|-17.976|9.164|1.00 48.12|A N|
|ATOM|563|C|LYS|A|73|-1.326|-20.529|9.101|1.00 26.75|A C|
|ATOM|564|O|LYS|A|73|-1.584|-19.752|8.168|1.00 26.71|A O|
|ATOM|565|N|HIS|A|74|-2.227|-20.952|9.984|1.00 24.13|A N|
|ATOM|566|CA|HIS|A|74|-3.587|-20.426|10.037|1.00 22.22|A C|
|ATOM|567|CB|HIS|A|74|-4.400|-21.157|11.104|1.00 20.82|A C|
|ATOM|568|CG|HIS|A|74|-4.543|-22.609|10.823|1.00 20.84|A C|
|ATOM|569|ND1|HIS|A|74|-5.595|-23.114|10.104|1.00 22.21|A N|
|ATOM|570|CE1|HIS|A|74|-5.427|-24.414|9.934|1.00 23.54|A C|
|ATOM|571|NE2|HIS|A|74|-4.292|-24.764|10.508|1.00 25.28|A N|
|ATOM|572|CD2|HIS|A|74|-3.714|-23.649|11.061|1.00 24.28|A C|
|ATOM|573|C|HIS|A|74|-3.581|-18.936|10.306|1.00 21.52|A C|
|ATOM|574|O|HIS|A|74|-2.757|-18.435|11.003|1.00 21.20|A O|
|ATOM|575|N|ARG|A|75|-4.502|-18.231|9.694|1.00 21.50|A N|
|ATOM|576|CA|ARG|A|75|-4.653|-16.795|9.915|1.00 22.33|A C|
|ATOM|577|CB|ARG|A|75|-5.450|-16.180|8.769|1.00 22.31|A C|
|ATOM|578|CG|ARG|A|75|-6.043|-14.849|9.140|1.00 22.69|A C|
|ATOM|579|CD|ARG|A|75|-6.460|-14.042|7.949|1.00 21.24|A C|
|ATOM|580|NE|ARG|A|75|-6.703|-12.682|8.377|1.00 22.56|A N|
|ATOM|581|CZ|ARG|A|75|-7.319|-11.749|7.665|1.00 20.85|A C|
|ATOM|582|NH1|ARG|A|75|-7.727|-11.987|6.437|1.00 20.39|A N|
|ATOM|583|NH2|ARG|A|75|-7.473|-10.554|8.187|1.00 20.76|A N|
|ATOM|584|C|ARG|A|75|-5.327|-16.464|11.265|1.00 21.79|A C|
|ATOM|585|O|ARG|A|75|-4.933|-15.502|11.947|1.00 21.64|A O|
|ATOM|586|N|PHE|A|76|-6.331|-17.275|11.620|1.00 20.73|A N|
|ATOM|587|CA|PHE|A|76|-7.072|-17.142|12.853|1.00 19.96|A C|
|ATOM|588|CB|PHE|A|76|-8.539|-17.227|12.544|1.00 19.36|A C|
|ATOM|589|CG|PHE|A|76|-8.984|-16.151|11.630|1.00 19.43|A C|
|ATOM|590|CD1|PHE|A|76|-9.156|-14.874|12.108|1.00 17.29|A C|
|ATOM|591|CE1|PHE|A|76|-9.549|-13.897|11.273|1.00 18.02|A C|
|ATOM|592|CZ|PHE|A|76|-9.699|-14.147|9.960|1.00 16.62|A C|
|ATOM|593|CE2|PHE|A|76|-9.507|-15.392|9.471|1.00 17.48|A C|
|ATOM|594|CD2|PHE|A|76|-9.145|-16.390|10.284|1.00 15.87|A C|
|ATOM|595|C|PHE|A|76|-6.752|-18.191|13.890|1.00 20.94|A C|
|ATOM|596|O|PHE|A|76|-6.583|-19.374|13.560|1.00 21.39|A O|
|ATOM|597|N|GLU|A|77|-6.618|-17.727|15.137|1.00 21.91|A N|
|ATOM|598|CA|GLU|A|77|-6.633|-18.584|16.312|1.00 22.56|A C|
|ATOM|599|CB|GLU|A|77|-5.908|-17.926|17.491|1.00 24.24|A C|
|ATOM|600|CG|GLU|A|77|-5.729|-18.834|18.705|1.00 26.42|A C|
|ATOM|601|CD|GLU|A|77|-4.756|-19.978|18.430|1.00 30.22|A C|
|ATOM|602|OE1|GLU|A|77|-5.206|-21.124|18.406|1.00 31.63|A O|
|ATOM|603|OE2|GLU|A|77|-3.552|-19.738|18.202|1.00 31.88|A O|
|ATOM|604|C|GLU|A|77|-8.102|-18.715|16.650|1.00 21.64|A C|
|ATOM|605|O|GLU|A|77|-8.823|-17.732|16.647|1.00 21.72|A O|
|ATOM|606|N|ILE|A|78|-8.558|-19.925|16.906|1.00 21.21|A N|
|ATOM|607|CA|ILE|A|78|-9.928|-20.126|17.216|1.00 20.18|A C|
|ATOM|608|CB|ILE|A|78|-10.510|-21.255|16.434|1.00 19.64|A C|
|ATOM|609|CG1|ILE|A|78|-10.391|-20.885|14.944|1.00 21.24|A C|
|ATOM|610|CD1|ILE|A|78|-11.000|-21.853|13.936|1.00 19.74|A C|
|ATOM|611|CG2|ILE|A|78|-11.950|-21.442|16.840|1.00 18.74|A C|
|ATOM|612|C|ILE|A|78|-10.017|-20.332|18.692|1.00 20.84|A C|
|ATOM|613|O|ILE|A|78|-9.512|-21.303|19.244|1.00 22.65|A O|
|ATOM|614|N|ILE|A|79|-10.648|-19.365|19.332|1.00 20.69|A N|
|ATOM|615|CA|ILE|A|79|-10.717|-19.308|20.744|1.00 20.49|A C|
|ATOM|616|CB|ILE|A|79|-10.499|-17.831|21.182|1.00 22.28|A C|
|ATOM|617|CG1|ILE|A|79|-9.000|-17.525|21.056|1.00 22.60|A C|
|ATOM|618|CD1|ILE|A|79|-8.683|-16.112|20.954|1.00 25.33|A C|
|ATOM|619|CG2|ILE|A|79|-10.990|-17.572|22.645|1.00 22.37|A C|
|ATOM|620|C|ILE|A|79|-11.993|-19.931|21.248|1.00 19.31|A C|
|ATOM|621|O|ILE|A|79|-11.981|-20.617|22.240|1.00 19.59|A O|

FIG. 2M

```
ATOM    622  N    GLU A  80     -13.101 -19.702  20.559  1.00 18.55          A    N
ATOM    623  CA   GLU A  80     -14.381 -20.338  20.905  1.00 17.71          A    C
ATOM    624  CB   GLU A  80     -15.449 -19.912  19.891  1.00 17.46          A    C
ATOM    625  CG   GLU A  80     -16.834 -20.518  20.077  1.00 17.47          A    C
ATOM    626  CD   GLU A  80     -17.323 -20.267  21.447  1.00 18.77          A    C
ATOM    627  OE1  GLU A  80     -18.077 -19.282  21.682  1.00 20.03          A    O
ATOM    628  OE2  GLU A  80     -16.879 -21.023  22.314  1.00 20.21          A    O
ATOM    629  C    GLU A  80     -14.160 -21.813  20.796  1.00 16.77          A    C
ATOM    630  O    GLU A  80     -13.317 -22.234  20.002  1.00 18.28          A    O
ATOM    631  N    GLY A  81     -14.923 -22.610  21.527  1.00 16.42          A    N
ATOM    632  CA   GLY A  81     -14.783 -24.090  21.495  1.00 15.55          A    C
ATOM    633  C    GLY A  81     -13.843 -24.656  22.577  1.00 16.45          A    C
ATOM    634  O    GLY A  81     -14.004 -25.781  23.006  1.00 15.16          A    O
ATOM    635  N    ARG A  82     -12.840 -23.896  23.016  1.00 16.78          A    N
ATOM    636  CA   ARG A  82     -11.977 -24.394  24.083  1.00 18.58          A    C
ATOM    637  CB   ARG A  82     -10.622 -23.738  24.022  1.00 19.00          A    C
ATOM    638  CG   ARG A  82     -10.049 -23.729  22.614  1.00 19.26          A    C
ATOM    639  CD   ARG A  82      -8.529 -23.885  22.602  1.00 22.10          A    C
ATOM    640  NE   ARG A  82      -8.005 -22.974  21.612  1.00 25.14          A    N
ATOM    641  CZ   ARG A  82      -6.847 -23.067  20.983  1.00 26.07          A    C
ATOM    642  NH1  ARG A  82      -5.999 -24.041  21.196  1.00 27.20          A    N
ATOM    643  NH2  ARG A  82      -6.553 -22.143  20.102  1.00 30.40          A    N
ATOM    644  C    ARG A  82     -12.616 -24.133  25.422  1.00 19.88          A    C
ATOM    645  O    ARG A  82     -13.398 -23.203  25.550  1.00 19.50          A    O
ATOM    646  N    ASP A  83     -12.275 -24.921  26.433  1.00 21.92          A    N
ATOM    647  CA   ASP A  83     -12.786 -24.616  27.761  1.00 24.32          A    C
ATOM    648  CB   ASP A  83     -12.585 -25.758  28.765  1.00 26.49          A    C
ATOM    649  CG   ASP A  83     -11.182 -25.822  29.354  1.00 31.14          A    C
ATOM    650  OD1  ASP A  83     -10.667 -24.822  29.928  1.00 33.34          A    O
ATOM    651  OD2  ASP A  83     -10.611 -26.931  29.282  1.00 36.31          A    O
ATOM    652  C    ASP A  83     -12.254 -23.284  28.253  1.00 24.76          A    C
ATOM    653  O    ASP A  83     -11.265 -22.766  27.757  1.00 25.46          A    O
ATOM    654  N    ARG A  84     -12.946 -22.719  29.229  1.00 25.80          A    N
ATOM    655  CA   ARG A  84     -12.758 -21.329  29.595  1.00 25.68          A    C
ATOM    656  CB   ARG A  84     -13.786 -21.013  30.654  1.00 26.96          A    C
ATOM    657  CG   ARG A  84     -14.026 -19.572  30.952  1.00 26.70          A    C
ATOM    658  CD   ARG A  84     -14.977 -19.507  32.125  1.00 27.20          A    C
ATOM    659  NE   ARG A  84     -15.605 -18.207  32.234  1.00 28.48          A    N
ATOM    660  CZ   ARG A  84     -16.536 -17.884  33.131  1.00 29.36          A    C
ATOM    661  NH1  ARG A  84     -16.944 -18.771  34.030  1.00 32.29          A    N
ATOM    662  NH2  ARG A  84     -17.047 -16.654  33.141  1.00 27.99          A    N
ATOM    663  C    ARG A  84     -11.321 -20.999  30.053  1.00 26.98          A    C
ATOM    664  O    ARG A  84     -10.717 -20.042  29.585  1.00 26.80          A    O
ATOM    665  N    ILE A  85     -10.753 -21.804  30.931  1.00 28.79          A    N
ATOM    666  CA   ILE A  85      -9.381 -21.570  31.389  1.00 30.65          A    C
ATOM    667  CB   ILE A  85      -8.975 -22.501  32.572  1.00 33.18          A    C
ATOM    668  CG1  ILE A  85      -9.972 -22.386  33.742  1.00 34.22          A    C
ATOM    669  CD1  ILE A  85     -10.276 -20.971  34.143  1.00 36.07          A    C
ATOM    670  CG2  ILE A  85      -7.536 -22.207  33.036  1.00 33.46          A    C
ATOM    671  C    ILE A  85      -8.362 -21.729  30.248  1.00 30.41          A    C
ATOM    672  O    ILE A  85      -7.439 -20.926  30.107  1.00 30.66          A    O
ATOM    673  N    MET A  86      -8.516 -22.757  29.429  1.00 30.29          A    N
ATOM    674  CA   MET A  86      -7.646 -22.911  28.260  1.00 30.11          A    C
ATOM    675  CB   MET A  86      -8.004 -24.163  27.482  1.00 30.47          A    C
ATOM    676  CG   MET A  86      -7.168 -24.362  26.203  1.00 34.57          A    C
ATOM    677  SD   MET A  86      -5.456 -24.872  26.581  1.00 47.42          A    S
ATOM    678  CE   MET A  86      -5.822 -26.631  26.898  1.00 46.36          A    C
ATOM    679  C    MET A  86      -7.825 -21.735  27.348  1.00 27.47          A    C
ATOM    680  O    MET A  86      -6.861 -21.180  26.817  1.00 27.61          A    O
ATOM    681  N    ALA A  87      -9.070 -21.336  27.172  1.00 25.40          A    N
ATOM    682  CA   ALA A  87      -9.361 -20.172  26.327  1.00 24.02          A    C
ATOM    683  CB   ALA A  87     -10.873 -19.921  26.269  1.00 22.34          A    C
ATOM    684  C    ALA A  87      -8.607 -18.914  26.793  1.00 24.83          A    C
```

FIG. 2N

| | | | | | | | | | | | |
|---|---|---|---|---|---|---|---|---|---|---|---|
| ATOM | 685 | O | ALA | A | 87 | -7.987 | -18.218 | 26.014 | 1.00 | 23.73 | A | O |
| ATOM | 686 | N | TRP | A | 88 | -8.647 | -18.625 | 28.085 | 1.00 | 27.46 | A | N |
| ATOM | 687 | CA | TRP | A | 88 | -7.946 | -17.454 | 28.569 | 1.00 | 29.09 | A | C |
| ATOM | 688 | CB | TRP | A | 88 | -8.407 | -17.101 | 29.971 | 1.00 | 31.42 | A | C |
| ATOM | 689 | CG | TRP | A | 88 | -9.623 | -16.265 | 29.969 | 1.00 | 32.23 | A | C |
| ATOM | 690 | CD1 | TRP | A | 88 | -10.857 | -16.633 | 30.385 | 1.00 | 33.83 | A | C |
| ATOM | 691 | NE1 | TRP | A | 88 | -11.745 | -15.602 | 30.219 | 1.00 | 32.94 | A | N |
| ATOM | 692 | CE2 | TRP | A | 88 | -11.083 | -14.529 | 29.688 | 1.00 | 33.49 | A | C |
| ATOM | 693 | CD2 | TRP | A | 88 | -9.741 | -14.913 | 29.508 | 1.00 | 34.13 | A | C |
| ATOM | 694 | CE3 | TRP | A | 88 | -8.839 | -13.980 | 28.978 | 1.00 | 35.66 | A | C |
| ATOM | 695 | CZ3 | TRP | A | 88 | -9.316 | -12.705 | 28.639 | 1.00 | 35.71 | A | C |
| ATOM | 696 | CH2 | TRP | A | 88 | -10.660 | -12.365 | 28.823 | 1.00 | 33.86 | A | C |
| ATOM | 697 | CZ2 | TRP | A | 88 | -11.554 | -13.253 | 29.348 | 1.00 | 33.51 | A | C |
| ATOM | 698 | C | TRP | A | 88 | -6.409 | -17.585 | 28.478 | 1.00 | 30.02 | A | C |
| ATOM | 699 | O | TRP | A | 88 | -5.725 | -16.568 | 28.292 | 1.00 | 30.77 | A | O |
| ATOM | 700 | N | THR | A | 89 | -5.870 | -18.801 | 28.592 | 1.00 | 29.92 | A | N |
| ATOM | 701 | CA | THR | A | 89 | -4.419 | -18.982 | 28.499 | 1.00 | 31.72 | A | C |
| ATOM | 702 | CB | THR | A | 89 | -3.922 | -20.431 | 28.725 | 1.00 | 32.18 | A | C |
| ATOM | 703 | OG1 | THR | A | 89 | -4.511 | -20.990 | 29.897 | 1.00 | 34.56 | A | O |
| ATOM | 704 | CG2 | THR | A | 89 | -2.441 | -20.421 | 28.932 | 1.00 | 33.82 | A | C |
| ATOM | 705 | C | THR | A | 89 | -3.976 | -18.587 | 27.112 | 1.00 | 30.66 | A | C |
| ATOM | 706 | O | THR | A | 89 | -3.028 | -17.815 | 26.947 | 1.00 | 31.67 | A | O |
| ATOM | 707 | N | VAL | A | 90 | -4.688 | -19.094 | 26.113 | 1.00 | 28.11 | A | N |
| ATOM | 708 | CA | VAL | A | 90 | -4.388 | -18.728 | 24.754 | 1.00 | 26.92 | A | C |
| ATOM | 709 | CB | VAL | A | 90 | -5.294 | -19.455 | 23.731 | 1.00 | 24.83 | A | C |
| ATOM | 710 | CG1 | VAL | A | 90 | -5.039 | -18.911 | 22.355 | 1.00 | 23.93 | A | C |
| ATOM | 711 | CG2 | VAL | A | 90 | -5.008 | -20.967 | 23.732 | 1.00 | 22.64 | A | C |
| ATOM | 712 | C | VAL | A | 90 | -4.487 | -17.233 | 24.571 | 1.00 | 27.87 | A | C |
| ATOM | 713 | O | VAL | A | 90 | -3.602 | -16.610 | 23.989 | 1.00 | 28.85 | A | O |
| ATOM | 714 | N | VAL | A | 91 | -5.544 | -16.640 | 25.110 | 1.00 | 28.70 | A | N |
| ATOM | 715 | CA | VAL | A | 91 | -5.738 | -15.192 | 24.986 | 1.00 | 29.04 | A | C |
| ATOM | 716 | CB | VAL | A | 91 | -7.113 | -14.736 | 25.578 | 1.00 | 28.96 | A | C |
| ATOM | 717 | CG1 | VAL | A | 91 | -7.179 | -13.211 | 25.701 | 1.00 | 29.25 | A | C |
| ATOM | 718 | CG2 | VAL | A | 91 | -8.253 | -15.289 | 24.744 | 1.00 | 23.50 | A | C |
| ATOM | 719 | C | VAL | A | 91 | -4.578 | -14.460 | 25.646 | 1.00 | 31.68 | A | C |
| ATOM | 720 | O | VAL | A | 91 | -3.904 | -13.687 | 25.012 | 1.00 | 32.87 | A | O |
| ATOM | 721 | N | ASN | A | 92 | -4.312 | -14.717 | 26.906 | 1.00 | 33.65 | A | N |
| ATOM | 722 | CA | ASN | A | 92 | -3.200 | -14.029 | 27.542 | 1.00 | 36.86 | A | C |
| ATOM | 723 | CB | ASN | A | 92 | -3.006 | -14.539 | 28.970 | 1.00 | 38.97 | A | C |
| ATOM | 724 | CG | ASN | A | 92 | -4.119 | -14.106 | 29.903 | 1.00 | 39.87 | A | C |
| ATOM | 725 | OD1 | ASN | A | 92 | -4.844 | -13.152 | 29.628 | 1.00 | 39.13 | A | O |
| ATOM | 726 | ND2 | ASN | A | 92 | -4.251 | -14.814 | 31.030 | 1.00 | 42.69 | A | N |
| ATOM | 727 | C | ASN | A | 92 | -1.881 | -14.130 | 26.760 | 1.00 | 37.28 | A | C |
| ATOM | 728 | O | ASN | A | 92 | -1.149 | -13.159 | 26.606 | 1.00 | 38.40 | A | O |
| ATOM | 729 | N | SER | A | 93 | -1.588 | -15.307 | 26.247 | 1.00 | 36.94 | A | N |
| ATOM | 730 | CA | SER | A | 93 | -0.337 | -15.503 | 25.521 | 1.00 | 38.34 | A | C |
| ATOM | 731 | CB | SER | A | 93 | -0.124 | -16.968 | 25.192 | 1.00 | 37.18 | A | C |
| ATOM | 732 | OG | SER | A | 93 | 0.898 | -17.026 | 24.224 | 1.00 | 40.28 | A | O |
| ATOM | 733 | C | SER | A | 93 | -0.206 | -14.687 | 24.223 | 1.00 | 37.33 | A | C |
| ATOM | 734 | O | SER | A | 93 | 0.896 | -14.256 | 23.872 | 1.00 | 39.36 | A | O |
| ATOM | 735 | N | ILE | A | 94 | -1.320 | -14.509 | 23.522 | 1.00 | 34.69 | A | N |
| ATOM | 736 | CA | ILE | A | 94 | -1.373 | -13.709 | 22.305 | 1.00 | 33.75 | A | C |
| ATOM | 737 | CB | ILE | A | 94 | -2.770 | -13.817 | 21.632 | 1.00 | 31.25 | A | C |
| ATOM | 738 | CG1 | ILE | A | 94 | -2.839 | -15.093 | 20.798 | 1.00 | 27.80 | A | C |
| ATOM | 739 | CD1 | ILE | A | 94 | -4.235 | -15.666 | 20.631 | 1.00 | 21.21 | A | C |
| ATOM | 740 | CG2 | ILE | A | 94 | -3.058 | -12.605 | 20.773 | 1.00 | 32.33 | A | C |
| ATOM | 741 | C | ILE | A | 94 | -1.081 | -12.275 | 22.647 | 1.00 | 35.87 | A | C |
| ATOM | 742 | O | ILE | A | 94 | -0.264 | -11.609 | 22.000 | 1.00 | 37.38 | A | O |
| ATOM | 743 | N | CYS | A | 95 | -1.739 | -11.799 | 23.688 | 1.00 | 36.60 | A | N |
| ATOM | 744 | CA | CYS | A | 95 | -1.440 | -10.478 | 24.220 | 1.00 | 39.22 | A | C |
| ATOM | 745 | CB | CYS | A | 95 | -2.417 | -10.153 | 25.342 | 1.00 | 39.48 | A | C |
| ATOM | 746 | SG | CYS | A | 95 | -4.117 | -10.039 | 24.773 | 1.00 | 36.90 | A | S |
| ATOM | 747 | C | CYS | A | 95 | 0.006 | -10.357 | 24.717 | 1.00 | 42.33 | A | C |

FIG. 20

| | | | | | | | | | | |
|---|---|---|---|---|---|---|---|---|---|---|
|ATOM|748|O|CYS|A|95|0.619|-9.297|24.611|1.00 44.48|A O|
|ATOM|749|N|ASN|A|96|0.547|-11.433|25.273|1.00 43.48|A N|
|ATOM|750|CA|ASN|A|96|1.951|-11.440|25.730|1.00 46.80|A C|
|ATOM|751|CB|ASN|A|96|2.222|-12.687|26.595|1.00 47.81|A C|
|ATOM|752|CG|ASN|A|96|3.569|-13.345|26.293|1.00 50.31|A C|
|ATOM|753|OD1|ASN|A|96|4.614|-12.854|26.714|1.00 53.01|A O|
|ATOM|754|ND2|ASN|A|96|3.541|-14.465|25.552|1.00 50.84|A N|
|ATOM|755|C|ASN|A|96|2.908|-11.383|24.539|1.00 46.83|A C|
|ATOM|756|O|ASN|A|96|3.914|-10.667|24.543|1.00 47.99|A O|
|ATOM|757|N|THR|A|97|2.566|-12.151|23.512|1.00 44.55|A N|
|ATOM|758|CA|THR|A|97|3.365|-12.206|22.307|1.00 44.73|A C|
|ATOM|759|CB|THR|A|97|2.979|-13.441|21.449|1.00 42.72|A C|
|ATOM|760|OG1|THR|A|97|3.603|-14.611|21.987|1.00 43.16|A O|
|ATOM|761|CG2|THR|A|97|3.409|-13.268|19.979|1.00 43.11|A C|
|ATOM|762|C|THR|A|97|3.229|-10.954|21.442|1.00 44.68|A C|
|ATOM|763|O|THR|A|97|4.108|-10.694|20.634|1.00 46.45|A O|
|ATOM|764|N|THR|A|98|2.138|-10.197|21.557|1.00 43.17|A N|
|ATOM|765|CA|THR|A|98|1.885|-9.140|20.559|1.00 42.50|A C|
|ATOM|766|CB|THR|A|98|0.774|-9.528|19.530|1.00 40.02|A C|
|ATOM|767|OG1|THR|A|98|-0.519|-9.388|20.127|1.00 39.65|A O|
|ATOM|768|CG2|THR|A|98|0.928|-10.950|19.005|1.00 38.10|A C|
|ATOM|769|C|THR|A|98|1.486|-7.800|21.107|1.00 43.20|A C|
|ATOM|770|O|THR|A|98|1.238|-6.912|20.329|1.00 43.28|A O|
|ATOM|771|N|GLY|A|99|1.389|-7.637|22.418|1.00 44.05|A N|
|ATOM|772|CA|GLY|A|99|1.029|-6.339|22.989|1.00 45.96|A C|
|ATOM|773|C|GLY|A|99|-0.395|-5.842|22.772|1.00 44.86|A C|
|ATOM|774|O|GLY|A|99|-0.725|-4.728|23.166|1.00 46.20|A O|
|ATOM|775|N|VAL|A|100|-1.249|-6.637|22.134|1.00 42.66|A N|
|ATOM|776|CA|VAL|A|100|-2.643|-6.255|22.034|1.00 42.24|A C|
|ATOM|777|CB|VAL|A|100|-3.438|-7.106|21.022|1.00 39.82|A C|
|ATOM|778|CG1|VAL|A|100|-2.855|-8.495|20.861|1.00 39.65|A C|
|ATOM|779|CG2|VAL|A|100|-4.899|-7.208|21.447|1.00 38.69|A C|
|ATOM|780|C|VAL|A|100|-3.235|-6.366|23.438|1.00 43.13|A C|
|ATOM|781|O|VAL|A|100|-2.872|-7.245|24.213|1.00 42.09|A O|
|ATOM|782|N|GLU|A|101|-4.123|-5.448|23.782|1.00 44.88|A N|
|ATOM|783|CA|GLU|A|101|-4.626|-5.412|25.143|1.00 46.74|A C|
|ATOM|784|CB|GLU|A|101|-5.175|-4.039|25.489|1.00 49.49|A C|
|ATOM|785|CG|GLU|A|101|-4.014|-3.037|25.794|1.00 54.31|A C|
|ATOM|786|CD|GLU|A|101|-4.266|-1.646|25.254|1.00 57.93|A C|
|ATOM|787|OE1|GLU|A|101|-5.005|-1.523|24.244|1.00 57.00|A O|
|ATOM|788|OE2|GLU|A|101|-3.716|-0.677|25.837|1.00 62.35|A O|
|ATOM|789|C|GLU|A|101|-5.652|-6.488|25.328|1.00 44.56|A C|
|ATOM|790|O|GLU|A|101|-6.359|-6.857|24.382|1.00 42.09|A O|
|ATOM|791|N|LYS|A|102|-5.682|-7.027|26.543|1.00 45.57|A N|
|ATOM|792|CA|LYS|A|102|-6.553|-8.133|26.874|1.00 43.83|A C|
|ATOM|793|CB|LYS|A|102|-6.235|-8.668|28.282|1.00 45.87|A C|
|ATOM|794|CG|LYS|A|102|-4.899|-9.419|28.386|1.00 48.08|A C|
|ATOM|795|CD|LYS|A|102|-4.396|-9.528|29.870|1.00 53.47|A C|
|ATOM|796|CE|LYS|A|102|-3.050|-10.282|29.960|1.00 54.41|A C|
|ATOM|797|NZ|LYS|A|102|-2.405|-10.204|31.304|1.00 58.67|A N|
|ATOM|798|C|LYS|A|102|-7.998|-7.644|26.787|1.00 42.94|A C|
|ATOM|799|O|LYS|A|102|-8.318|-6.529|27.206|1.00 44.44|A O|
|ATOM|800|N|PRO|A|103|-8.867|-8.451|26.179|1.00 40.32|A N|
|ATOM|801|CA|PRO|A|103|-10.274|-8.104|26.212|1.00 40.13|A C|
|ATOM|802|CB|PRO|A|103|-10.868|-9.008|25.150|1.00 37.14|A C|
|ATOM|803|CG|PRO|A|103|-9.912|-10.159|25.048|1.00 35.56|A C|
|ATOM|804|CD|PRO|A|103|-8.594|-9.592|25.285|1.00 37.55|A C|
|ATOM|805|C|PRO|A|103|-10.846|-8.406|27.590|1.00 41.44|A C|
|ATOM|806|O|PRO|A|103|-10.265|-9.206|28.325|1.00 41.12|A O|
|ATOM|807|N|LYS|A|104|-11.945|-7.741|27.949|1.00 42.91|A N|
|ATOM|808|CA|LYS|A|104|-12.576|-7.967|29.253|1.00 44.59|A C|
|ATOM|809|CB|LYS|A|104|-13.456|-6.777|29.690|1.00 47.61|A C|
|ATOM|810|CG|LYS|A|104|-12.841|-5.357|29.568|1.00 50.39|A C|

FIG. 2P

```
ATOM    811  CD  LYS A 104     -11.857   -5.015  30.699  1.00 54.21      A    C
ATOM    812  CE  LYS A 104     -11.561   -3.510  30.765  1.00 57.22      A    C
ATOM    813  NZ  LYS A 104     -11.294   -3.031  32.157  1.00 60.01      A    N
ATOM    814  C   LYS A 104     -13.412   -9.259  29.189  1.00 42.20      A    C
ATOM    815  O   LYS A 104     -13.539   -9.955  30.193  1.00 42.76      A    O
ATOM    816  N   PHE A 105     -13.931   -9.590  27.999  1.00 39.21      A    N
ATOM    817  CA  PHE A 105     -14.756  -10.787  27.779  1.00 36.79      A    C
ATOM    818  CB  PHE A 105     -16.162  -10.349  27.320  1.00 36.78      A    C
ATOM    819  CG  PHE A 105     -16.887   -9.470  28.335  1.00 40.39      A    C
ATOM    820  CD1 PHE A 105     -16.614   -8.096  28.421  1.00 44.91      A    C
ATOM    821  CE1 PHE A 105     -17.246   -7.272  29.373  1.00 46.44      A    C
ATOM    822  CZ  PHE A 105     -18.166   -7.831  30.239  1.00 48.49      A    C
ATOM    823  CE2 PHE A 105     -18.455   -9.211  30.158  1.00 46.08      A    C
ATOM    824  CD2 PHE A 105     -17.809  -10.014  29.221  1.00 41.49      A    C
ATOM    825  C   PHE A 105     -14.095  -11.734  26.748  1.00 33.83      A    C
ATOM    826  O   PHE A 105     -13.360  -11.287  25.888  1.00 33.24      A    O
ATOM    827  N   LEU A 106     -14.347  -13.038  26.822  1.00 31.90      A    N
ATOM    828  CA  LEU A 106     -13.744  -13.971  25.863  1.00 29.47      A    C
ATOM    829  CB  LEU A 106     -14.042  -15.425  26.188  1.00 28.98      A    C
ATOM    830  CG  LEU A 106     -13.058  -16.172  27.051  1.00 31.59      A    C
ATOM    831  CD1 LEU A 106     -13.528  -17.616  27.085  1.00 31.44      A    C
ATOM    832  CD2 LEU A 106     -11.653  -16.028  26.468  1.00 32.35      A    C
ATOM    833  C   LEU A 106     -14.282  -13.777  24.473  1.00 27.08      A    C
ATOM    834  O   LEU A 106     -15.483  -13.754  24.300  1.00 26.62      A    O
ATOM    835  N   PRO A 107     -13.394  -13.686  23.471  1.00 25.12      A    N
ATOM    836  CA  PRO A 107     -13.859  -13.629  22.115  1.00 23.06      A    C
ATOM    837  CB  PRO A 107     -12.793  -12.792  21.395  1.00 23.11      A    C
ATOM    838  CG  PRO A 107     -11.723  -12.584  22.338  1.00 25.26      A    C
ATOM    839  CD  PRO A 107     -11.973  -13.328  23.581  1.00 25.96      A    C
ATOM    840  C   PRO A 107     -13.938  -15.002  21.507  1.00 21.48      A    C
ATOM    841  O   PRO A 107     -13.809  -16.013  22.183  1.00 21.22      A    O
ATOM    842  N   ASP A 108     -14.123  -15.023  20.204  1.00 20.33      A    N
ATOM    843  CA  ASP A 108     -14.236  -16.238  19.495  1.00 19.01      A    C
ATOM    844  CB  ASP A 108     -15.438  -16.120  18.591  1.00 18.62      A    C
ATOM    845  CG  ASP A 108     -16.728  -16.017  19.366  1.00 19.88      A    C
ATOM    846  OD1 ASP A 108     -16.888  -16.782  20.339  1.00 18.38      A    O
ATOM    847  OD2 ASP A 108     -17.604  -15.211  18.966  1.00 24.12      A    O
ATOM    848  C   ASP A 108     -12.983  -16.537  18.696  1.00 19.17      A    C
ATOM    849  O   ASP A 108     -12.559  -17.702  18.649  1.00 19.01      A    O
ATOM    850  N   LEU A 109     -12.424  -15.498  18.052  1.00 19.50      A    N
ATOM    851  CA  LEU A 109     -11.235  -15.604  17.208  1.00 19.30      A    C
ATOM    852  CB  LEU A 109     -11.620  -15.460  15.746  1.00 19.03      A    C
ATOM    853  CG  LEU A 109     -12.797  -16.288  15.245  1.00 18.60      A    C
ATOM    854  CD1 LEU A 109     -13.247  -15.809  13.877  1.00 17.11      A    C
ATOM    855  CD2 LEU A 109     -12.423  -17.774  15.181  1.00 16.39      A    C
ATOM    856  C   LEU A 109     -10.172  -14.527  17.507  1.00 20.42      A    C
ATOM    857  O   LEU A 109     -10.419  -13.529  18.150  1.00 20.87      A    O
ATOM    858  N   TYR A 110      -8.971  -14.772  17.024  1.00 21.17      A    N
ATOM    859  CA  TYR A 110      -7.913  -13.768  17.009  1.00 23.18      A    C
ATOM    860  CB  TYR A 110      -6.738  -14.110  17.960  1.00 23.21      A    C
ATOM    861  CG  TYR A 110      -5.687  -13.026  17.906  1.00 24.16      A    C
ATOM    862  CD1 TYR A 110      -5.849  -11.845  18.609  1.00 23.79      A    C
ATOM    863  CE1 TYR A 110      -4.906  -10.826  18.532  1.00 26.68      A    C
ATOM    864  CZ  TYR A 110      -3.776  -10.973  17.733  1.00 27.84      A    C
ATOM    865  OH  TYR A 110      -2.839   -9.941  17.665  1.00 31.95      A    O
ATOM    866  CE2 TYR A 110      -3.591  -12.146  17.017  1.00 25.34      A    C
ATOM    867  CD2 TYR A 110      -4.546  -13.162  17.105  1.00 24.55      A    C
ATOM    868  C   TYR A 110      -7.424  -13.740  15.567  1.00 23.58      A    C
ATOM    869  O   TYR A 110      -7.307  -14.798  14.936  1.00 23.79      A    O
ATOM    870  N   ASP A 111      -7.129  -12.552  15.057  1.00 24.83      A    N
ATOM    871  CA  ASP A 111      -6.707  -12.396  13.663  1.00 25.09      A    C
ATOM    872  CB  ASP A 111      -7.500  -11.282  12.952  1.00 24.86      A    C
ATOM    873  CG  ASP A 111      -7.183  -11.204  11.449  1.00 27.30      A    C
```

FIG. 2Q

```
ATOM    874  OD1 ASP A 111      -6.028 -11.502  11.071  1.00 29.01           A    O
ATOM    875  OD2 ASP A 111      -8.060 -10.821  10.634  1.00 26.97           A    O
ATOM    876  C   ASP A 111      -5.228 -12.097  13.679  1.00 25.63           A    C
ATOM    877  O   ASP A 111      -4.824 -11.018  14.063  1.00 27.34           A    O
ATOM    878  N   TYR A 112      -4.411 -13.044  13.259  1.00 25.27           A    N
ATOM    879  CA  TYR A 112      -2.948 -12.830  13.295  1.00 26.62           A    C
ATOM    880  CB  TYR A 112      -2.197 -14.151  13.144  1.00 25.93           A    C
ATOM    881  CG  TYR A 112      -2.257 -15.085  14.339  1.00 23.97           A    C
ATOM    882  CD1 TYR A 112      -2.984 -16.261  14.283  1.00 22.17           A    C
ATOM    883  CE1 TYR A 112      -3.018 -17.121  15.342  1.00 20.62           A    C
ATOM    884  CZ  TYR A 112      -2.325 -16.820  16.473  1.00 21.62           A    C
ATOM    885  OH  TYR A 112      -2.389 -17.695  17.511  1.00 22.57           A    O
ATOM    886  CE2 TYR A 112      -1.596 -15.676  16.569  1.00 22.89           A    C
ATOM    887  CD2 TYR A 112      -1.558 -14.815  15.505  1.00 24.02           A    C
ATOM    888  C   TYR A 112      -2.437 -11.792  12.266  1.00 28.99           A    C
ATOM    889  O   TYR A 112      -1.330 -11.242  12.444  1.00 31.17           A    O
ATOM    890  N   LYS A 113      -3.238 -11.515  11.226  1.00 28.59           A    N
ATOM    891  CA  LYS A 113      -2.947 -10.439  10.271  1.00 30.80           A    C
ATOM    892  CB  LYS A 113      -3.686 -10.624   8.939  1.00 30.21           A    C
ATOM    893  CG  LYS A 113      -3.282  -9.610   7.850  1.00 33.82           A    C
ATOM    894  CD  LYS A 113      -4.537  -8.999   7.173  1.00 35.86           A    C
ATOM    895  CE  LYS A 113      -4.288  -8.270   5.800  1.00 38.22           A    C
ATOM    896  NZ  LYS A 113      -5.496  -8.425   4.841  1.00 36.89           A    N
ATOM    897  C   LYS A 113      -3.273  -9.053  10.824  1.00 31.90           A    C
ATOM    898  O   LYS A 113      -2.399  -8.180  10.816  1.00 34.68           A    O
ATOM    899  N   GLU A 114      -4.513  -8.831  11.276  1.00 30.94           A    N
ATOM    900  CA  GLU A 114      -4.925  -7.508  11.744  1.00 31.98           A    C
ATOM    901  CB  GLU A 114      -6.413  -7.294  11.580  1.00 31.77           A    C
ATOM    902  CG  GLU A 114      -6.916  -7.307  10.146  1.00 34.31           A    C
ATOM    903  CD  GLU A 114      -6.555  -6.075   9.344  1.00 39.25           A    C
ATOM    904  OE1 GLU A 114      -5.598  -5.336   9.680  1.00 43.46           A    O
ATOM    905  OE2 GLU A 114      -7.240  -5.858   8.331  1.00 44.48           A    O
ATOM    906  C   GLU A 114      -4.606  -7.285  13.188  1.00 32.10           A    C
ATOM    907  O   GLU A 114      -4.784  -6.180  13.686  1.00 34.06           A    O
ATOM    908  N   ASN A 115      -4.130  -8.322  13.863  1.00 30.43           A    N
ATOM    909  CA  ASN A 115      -3.846  -8.254  15.264  1.00 30.57           A    C
ATOM    910  CB  ASN A 115      -2.616  -7.395  15.519  1.00 33.23           A    C
ATOM    911  CG  ASN A 115      -1.344  -8.024  14.985  1.00 34.24           A    C
ATOM    912  OD1 ASN A 115      -0.663  -7.433  14.140  1.00 33.21           A    O
ATOM    913  ND2 ASN A 115      -0.995  -9.215  15.505  1.00 31.29           A    N
ATOM    914  C   ASN A 115      -5.047  -7.743  16.062  1.00 29.97           A    C
ATOM    915  O   ASN A 115      -4.970  -6.708  16.720  1.00 31.48           A    O
ATOM    916  N   ARG A 116      -6.159  -8.468  16.000  1.00 27.44           A    N
ATOM    917  CA  ARG A 116      -7.314  -8.126  16.829  1.00 27.17           A    C
ATOM    918  CB  ARG A 116      -8.155  -7.025  16.188  1.00 27.75           A    C
ATOM    919  CG  ARG A 116      -8.476  -7.291  14.774  1.00 27.44           A    C
ATOM    920  CD  ARG A 116      -9.170  -6.152  14.091  1.00 30.15           A    C
ATOM    921  NE  ARG A 116      -9.810  -6.632  12.870  1.00 29.20           A    N
ATOM    922  CZ  ARG A 116     -10.027  -5.896  11.790  1.00 31.42           A    C
ATOM    923  NH1 ARG A 116      -9.663  -4.630  11.758  1.00 33.58           A    N
ATOM    924  NH2 ARG A 116     -10.612  -6.445  10.728  1.00 31.88           A    N
ATOM    925  C   ARG A 116      -8.162  -9.331  17.129  1.00 24.70           A    C
ATOM    926  O   ARG A 116      -8.163 -10.278  16.391  1.00 23.44           A    O
ATOM    927  N   PHE A 117      -8.857  -9.295  18.255  1.00 24.79           A    N
ATOM    928  CA  PHE A 117      -9.746 -10.369  18.621  1.00 22.59           A    C
ATOM    929  CB  PHE A 117      -9.951 -10.402  20.131  1.00 23.08           A    C
ATOM    930  CG  PHE A 117      -8.780 -10.915  20.873  1.00 21.97           A    C
ATOM    931  CD1 PHE A 117      -8.537 -12.266  20.941  1.00 21.70           A    C
ATOM    932  CE1 PHE A 117      -7.421 -12.756  21.606  1.00 21.64           A    C
ATOM    933  CZ  PHE A 117      -6.547 -11.891  22.193  1.00 22.64           A    C
ATOM    934  CE2 PHE A 117      -6.756 -10.536  22.104  1.00 23.09           A    C
ATOM    935  CD2 PHE A 117      -7.861 -10.056  21.431  1.00 24.35           A    C
ATOM    936  C   PHE A 117     -11.015 -10.067  17.950  1.00 22.46           A    C
```

FIG. 2R

```
ATOM    937  O   PHE A 117     -11.314  -8.915  17.702  1.00 24.46      A  O
ATOM    938  N   ILE A 118     -11.785 -11.093  17.665  1.00 21.99      A  N
ATOM    939  CA  ILE A 118     -13.081 -10.925  17.000  1.00 21.97      A  C
ATOM    940  CB  ILE A 118     -13.107 -11.586  15.575  1.00 20.98      A  C
ATOM    941  CG1 ILE A 118     -11.979 -11.073  14.702  1.00 22.82      A  C
ATOM    942  CD1 ILE A 118     -11.952 -11.700  13.359  1.00 22.50      A  C
ATOM    943  CG2 ILE A 118     -14.426 -11.316  14.873  1.00 21.92      A  C
ATOM    944  C   ILE A 118     -14.124 -11.637  17.833  1.00 21.02      A  C
ATOM    945  O   ILE A 118     -13.886 -12.749  18.283  1.00 19.24      A  O
ATOM    946  N   GLU A 119     -15.269 -10.987  18.028  1.00 22.25      A  N
ATOM    947  CA  GLU A 119     -16.474 -11.626  18.595  1.00 22.01      A  C
ATOM    948  CB  GLU A 119     -17.155 -10.674  19.607  1.00 24.47      A  C
ATOM    949  CG  GLU A 119     -18.537 -11.103  20.127  1.00 25.86      A  C
ATOM    950  CD  GLU A 119     -18.518 -12.466  20.786  1.00 27.75      A  C
ATOM    951  OE1 GLU A 119     -17.833 -12.584  21.810  1.00 31.85      A  O
ATOM    952  OE2 GLU A 119     -19.191 -13.409  20.311  1.00 28.17      A  O
ATOM    953  C   GLU A 119     -17.424 -11.954  17.445  1.00 20.38      A  C
ATOM    954  O   GLU A 119     -17.764 -11.065  16.633  1.00 20.55      A  O
ATOM    955  N   ILE A 120     -17.830 -13.222  17.338  1.00 18.50      A  N
ATOM    956  CA  ILE A 120     -18.763 -13.625  16.277  1.00 17.22      A  C
ATOM    957  CB  ILE A 120     -18.403 -14.968  15.633  1.00 15.29      A  C
ATOM    958  CG1 ILE A 120     -17.023 -14.936  14.951  1.00 14.77      A  C
ATOM    959  CD1 ILE A 120     -16.962 -14.259  13.705  1.00 14.15      A  C
ATOM    960  CG2 ILE A 120     -19.444 -15.378  14.609  1.00 13.20      A  C
ATOM    961  C   ILE A 120     -20.147 -13.733  16.862  1.00 17.93      A  C
ATOM    962  O   ILE A 120     -20.367 -14.459  17.816  1.00 18.28      A  O
ATOM    963  N   GLY A 121     -21.076 -12.999  16.289  1.00 19.46      A  N
ATOM    964  CA  GLY A 121     -22.500 -13.163  16.588  1.00 21.04      A  C
ATOM    965  C   GLY A 121     -23.265 -13.921  15.507  1.00 21.01      A  C
ATOM    966  O   GLY A 121     -23.040 -13.718  14.329  1.00 19.79      A  O
ATOM    967  N   VAL A 122     -24.136 -14.835  15.942  1.00 22.40      A  N
ATOM    968  CA  VAL A 122     -25.161 -15.416  15.092  1.00 23.38      A  C
ATOM    969  CB  VAL A 122     -24.883 -16.900  14.793  1.00 22.81      A  C
ATOM    970  CG1 VAL A 122     -25.964 -17.442  13.871  1.00 23.86      A  C
ATOM    971  CG2 VAL A 122     -23.449 -17.119  14.174  1.00 18.25      A  C
ATOM    972  C   VAL A 122     -26.488 -15.262  15.820  1.00 25.57      A  C
ATOM    973  O   VAL A 122     -26.645 -15.798  16.910  1.00 26.52      A  O
ATOM    974  N   THR A 123     -27.423 -14.514  15.226  1.00 27.67      A  N
ATOM    975  CA  THR A 123     -28.718 -14.194  15.833  1.00 29.23      A  C
ATOM    976  CB  THR A 123     -28.847 -12.652  16.054  1.00 31.50      A  C
ATOM    977  OG1 THR A 123     -30.020 -12.357  16.811  1.00 31.34      A  O
ATOM    978  CG2 THR A 123     -28.867 -11.877  14.715  1.00 30.26      A  C
ATOM    979  C   THR A 123     -29.918 -14.655  14.992  1.00 31.33      A  C
ATOM    980  O   THR A 123     -29.984 -14.442  13.779  1.00 31.78      A  O
ATOM    981  N   ARG A 124     -30.882 -15.274  15.659  1.00 33.15      A  N
ATOM    982  CA  ARG A 124     -32.177 -15.560  15.080  1.00 35.18      A  C
ATOM    983  CB  ARG A 124     -32.967 -16.550  15.942  1.00 36.29      A  C
ATOM    984  CG  ARG A 124     -32.343 -17.936  16.226  1.00 37.15      A  C
ATOM    985  CD  ARG A 124     -31.628 -17.978  17.599  1.00 41.14      A  C
ATOM    986  NE  ARG A 124     -32.035 -19.077  18.492  1.00 43.21      A  N
ATOM    987  CZ  ARG A 124     -31.433 -19.385  19.645  1.00 41.99      A  C
ATOM    988  NH1 ARG A 124     -30.369 -18.711  20.062  1.00 40.67      A  N
ATOM    989  NH2 ARG A 124     -31.894 -20.386  20.385  1.00 43.27      A  N
ATOM    990  C   ARG A 124     -32.992 -14.271  14.962  1.00 37.37      A  C
ATOM    991  O   ARG A 124     -34.028 -14.246  14.289  1.00 38.57      A  O
ATOM    992  N   ARG A 125     -32.532 -13.201  15.602  1.00 38.17      A  N
ATOM    993  CA  ARG A 125     -33.250 -11.912  15.562  1.00 41.22      A  C
ATOM    994  CB  ARG A 125     -33.016 -11.156  16.881  1.00 42.21      A  C
ATOM    995  CG  ARG A 125     -33.484 -11.919  18.115  1.00 42.07      A  C
ATOM    996  CD  ARG A 125     -33.430 -11.057  19.354  1.00 41.85      A  C
ATOM    997  NE  ARG A 125     -32.101 -11.061  19.940  1.00 39.46      A  N
ATOM    998  CZ  ARG A 125     -31.717 -10.316  20.975  1.00 40.24      A  C
ATOM    999  NH1 ARG A 125     -32.553  -9.477  21.576  1.00 41.40      A  N
```

FIG. 2S

```
ATOM   1000  NH2 ARG A 125     -30.471 -10.416  21.416  1.00 39.37      A    N
ATOM   1001  C   ARG A 125     -32.890 -11.034  14.344  1.00 41.74      A    C
ATOM   1002  O   ARG A 125     -32.536 -11.537  13.279  1.00 41.77      A    O
ATOM   1003  N   GLU A 126     -33.043  -9.726  14.478  1.00 43.70      A    N
ATOM   1004  CA  GLU A 126     -32.568  -8.784  13.477  1.00 44.15      A    C
ATOM   1005  CB  GLU A 126     -33.614  -7.682  13.251  1.00 47.73      A    C
ATOM   1006  CG  GLU A 126     -34.960  -8.194  12.678  1.00 50.38      A    C
ATOM   1007  CD  GLU A 126     -36.171  -7.860  13.566  1.00 54.94      A    C
ATOM   1008  OE1 GLU A 126     -37.209  -7.382  13.042  1.00 56.33      A    O
ATOM   1009  OE2 GLU A 126     -36.080  -8.084  14.796  1.00 55.82      A    O
ATOM   1010  C   GLU A 126     -31.270  -8.217  14.007  1.00 42.39      A    C
ATOM   1011  O   GLU A 126     -31.133  -7.997  15.203  1.00 42.57      A    O
ATOM   1012  N   VAL A 127     -30.320  -7.974  13.119  1.00 40.95      A    N
ATOM   1013  CA  VAL A 127     -28.908  -7.865  13.506  1.00 38.67      A    C
ATOM   1014  CB  VAL A 127     -28.023  -8.137  12.283  1.00 37.45      A    C
ATOM   1015  CG1 VAL A 127     -26.599  -8.400  12.690  1.00 36.34      A    C
ATOM   1016  CG2 VAL A 127     -28.501  -9.351  11.567  1.00 37.25      A    C
ATOM   1017  C   VAL A 127     -28.456  -6.546  14.155  1.00 39.69      A    C
ATOM   1018  O   VAL A 127     -27.370  -6.476  14.724  1.00 38.67      A    O
ATOM   1019  N   HIS A 128     -29.246  -5.487  14.077  1.00 41.75      A    N
ATOM   1020  CA  HIS A 128     -28.804  -4.238  14.686  1.00 43.30      A    C
ATOM   1021  CB  HIS A 128     -29.461  -3.024  14.044  1.00 46.76      A    C
ATOM   1022  CG  HIS A 128     -29.172  -2.870  12.586  1.00 49.58      A    C
ATOM   1023  ND1 HIS A 128     -27.886  -2.823  12.078  1.00 50.91      A    N
ATOM   1024  CE1 HIS A 128     -27.947  -2.669  10.764  1.00 52.55      A    C
ATOM   1025  NE2 HIS A 128     -29.219  -2.606  10.407  1.00 52.49      A    N
ATOM   1026  CD2 HIS A 128     -30.005  -2.719  11.526  1.00 51.47      A    C
ATOM   1027  C   HIS A 128     -29.102  -4.272  16.175  1.00 42.90      A    C
ATOM   1028  O   HIS A 128     -28.302  -3.779  16.976  1.00 42.72      A    O
ATOM   1029  N   ILE A 129     -30.265  -4.831  16.526  1.00 42.28      A    N
ATOM   1030  CA  ILE A 129     -30.622  -5.086  17.910  1.00 42.49      A    C
ATOM   1031  CB  ILE A 129     -31.942  -5.844  18.030  1.00 42.88      A    C
ATOM   1032  CG1 ILE A 129     -33.113  -4.987  17.541  1.00 45.10      A    C
ATOM   1033  CD1 ILE A 129     -34.357  -5.759  17.263  1.00 43.33      A    C
ATOM   1034  CG2 ILE A 129     -32.214  -6.231  19.484  1.00 42.58      A    C
ATOM   1035  C   ILE A 129     -29.554  -5.914  18.614  1.00 40.65      A    C
ATOM   1036  O   ILE A 129     -29.225  -5.642  19.755  1.00 41.71      A    O
ATOM   1037  N   TYR A 130     -29.009  -6.911  17.925  1.00 38.48      A    N
ATOM   1038  CA  TYR A 130     -28.003  -7.757  18.481  1.00 36.89      A    C
ATOM   1039  CB  TYR A 130     -27.874  -9.022  17.646  1.00 34.64      A    C
ATOM   1040  CG  TYR A 130     -27.085 -10.161  18.286  1.00 33.81      A    C
ATOM   1041  CD1 TYR A 130     -27.724 -11.168  18.999  1.00 34.44      A    C
ATOM   1042  CE1 TYR A 130     -26.983 -12.229  19.580  1.00 33.80      A    C
ATOM   1043  CZ  TYR A 130     -25.602 -12.273  19.435  1.00 31.71      A    C
ATOM   1044  OH  TYR A 130     -24.883 -13.300  20.008  1.00 34.72      A    O
ATOM   1045  CE2 TYR A 130     -24.945 -11.296  18.738  1.00 30.52      A    C
ATOM   1046  CD2 TYR A 130     -25.683 -10.239  18.161  1.00 33.43      A    C
ATOM   1047  C   TYR A 130     -26.689  -6.982  18.554  1.00 37.66      A    C
ATOM   1048  O   TYR A 130     -26.065  -6.922  19.609  1.00 37.62      A    O
ATOM   1049  N   TYR A 131     -26.283  -6.362  17.449  1.00 38.85      A    N
ATOM   1050  CA  TYR A 131     -25.057  -5.536  17.428  1.00 39.75      A    C
ATOM   1051  CB  TYR A 131     -24.949  -4.739  16.125  1.00 40.66      A    C
ATOM   1052  CG  TYR A 131     -23.663  -3.937  15.975  1.00 41.87      A    C
ATOM   1053  CD1 TYR A 131     -22.590  -4.462  15.294  1.00 41.42      A    C
ATOM   1054  CE1 TYR A 131     -21.422  -3.749  15.131  1.00 42.24      A    C
ATOM   1055  CZ  TYR A 131     -21.305  -2.482  15.642  1.00 45.27      A    C
ATOM   1056  OH  TYR A 131     -20.104  -1.845  15.437  1.00 48.27      A    O
ATOM   1057  CE2 TYR A 131     -22.352  -1.901  16.328  1.00 46.24      A    C
ATOM   1058  CD2 TYR A 131     -23.535  -2.633  16.489  1.00 47.24      A    C
ATOM   1059  C   TYR A 131     -25.030  -4.556  18.583  1.00 42.12      A    C
ATOM   1060  O   TYR A 131     -24.006  -4.341  19.191  1.00 42.27      A    O
ATOM   1061  N   LEU A 132     -26.173  -3.965  18.871  1.00 44.85      A    N
ATOM   1062  CA  LEU A 132     -26.271  -2.966  19.915  1.00 47.90      A    C
```

FIG. 2T

```
ATOM   1063  CB  LEU A 132     -27.627  -2.268  19.808  1.00 49.90      A  C
ATOM   1064  CG  LEU A 132     -27.693  -0.843  20.312  1.00 51.56      A  C
ATOM   1065  CD1 LEU A 132     -26.648  -0.015  19.587  1.00 49.52      A  C
ATOM   1066  CD2 LEU A 132     -29.101  -0.304  20.116  1.00 50.10      A  C
ATOM   1067  C   LEU A 132     -26.056  -3.567  21.318  1.00 48.76      A  C
ATOM   1068  O   LEU A 132     -25.314  -3.020  22.128  1.00 49.84      A  O
ATOM   1069  N   GLU A 133     -26.692  -4.694  21.601  1.00 48.84      A  N
ATOM   1070  CA  GLU A 133     -26.417  -5.423  22.836  1.00 49.90      A  C
ATOM   1071  CB  GLU A 133     -27.192  -6.722  22.873  1.00 48.99      A  C
ATOM   1072  CG  GLU A 133     -28.610  -6.601  23.299  1.00 51.22      A  C
ATOM   1073  CD  GLU A 133     -29.343  -7.876  23.013  1.00 52.45      A  C
ATOM   1074  OE1 GLU A 133     -28.665  -8.899  22.723  1.00 49.60      A  O
ATOM   1075  OE2 GLU A 133     -30.598  -7.868  23.056  1.00 57.45      A  O
ATOM   1076  C   GLU A 133     -24.955  -5.813  23.018  1.00 49.20      A  C
ATOM   1077  O   GLU A 133     -24.449  -5.734  24.127  1.00 50.95      A  O
ATOM   1078  N   LYS A 134     -24.297  -6.267  21.954  1.00 47.52      A  N
ATOM   1079  CA  LYS A 134     -22.918  -6.716  22.056  1.00 47.13      A  C
ATOM   1080  CB  LYS A 134     -22.558  -7.669  20.891  1.00 44.61      A  C
ATOM   1081  CG  LYS A 134     -22.998  -9.141  21.101  1.00 43.57      A  C
ATOM   1082  CD  LYS A 134     -21.871 -10.003  21.754  1.00 45.33      A  C
ATOM   1083  CE  LYS A 134     -22.122 -11.557  21.705  1.00 45.28      A  C
ATOM   1084  NZ  LYS A 134     -22.353 -12.203  23.073  1.00 45.74      A  N
ATOM   1085  C   LYS A 134     -21.950  -5.537  22.122  1.00 49.73      A  C
ATOM   1086  O   LYS A 134     -21.005  -5.538  22.921  1.00 50.25      A  O
ATOM   1087  N   ALA A 135     -22.182  -4.530  21.283  1.00 52.31      A  N
ATOM   1088  CA  ALA A 135     -21.353  -3.310  21.276  1.00 54.81      A  C
ATOM   1089  CB  ALA A 135     -21.736  -2.399  20.115  1.00 55.85      A  C
ATOM   1090  C   ALA A 135     -21.457  -2.556  22.588  1.00 58.36      A  C
ATOM   1091  O   ALA A 135     -20.439  -2.167  23.167  1.00 59.43      A  O
ATOM   1092  N   ASN A 136     -22.685  -2.378  23.070  1.00 61.08      A  N
ATOM   1093  CA  ASN A 136     -22.929  -1.712  24.364  1.00 64.99      A  C
ATOM   1094  CB  ASN A 136     -24.377  -1.159  24.420  1.00 67.57      A  C
ATOM   1095  CG  ASN A 136     -24.486   0.173  25.172  1.00 71.94      A  C
ATOM   1096  OD1 ASN A 136     -23.947   0.334  26.267  1.00 73.57      A  O
ATOM   1097  ND2 ASN A 136     -25.205   1.124  24.584  1.00 74.29      A  N
ATOM   1098  C   ASN A 136     -22.626  -2.663  25.547  1.00 64.87      A  C
ATOM   1099  O   ASN A 136     -23.192  -2.523  26.637  1.00 66.98      A  O
ATOM   1100  N   LYS A 137     -21.753  -3.642  25.287  1.00 62.92      A  N
ATOM   1101  CA  LYS A 137     -21.091  -4.487  26.291  1.00 62.98      A  C
ATOM   1102  CB  LYS A 137     -21.868  -5.794  26.524  1.00 61.42      A  C
ATOM   1103  CG  LYS A 137     -20.983  -7.050  26.706  1.00 60.28      A  C
ATOM   1104  CD  LYS A 137     -21.811  -8.308  27.033  1.00 61.08      A  C
ATOM   1105  CE  LYS A 137     -20.950  -9.431  27.631  1.00 60.58      A  C
ATOM   1106  NZ  LYS A 137     -21.576 -10.052  28.854  1.00 62.60      A  N
ATOM   1107  C   LYS A 137     -19.678  -4.792  25.772  1.00 61.38      A  C
ATOM   1108  O   LYS A 137     -18.679  -4.392  26.375  1.00 63.57      A  O
ATOM   1109  N   LYS A 142     -11.808  -2.879  22.186  1.00 43.60      A  N
ATOM   1110  CA  LYS A 142     -11.035  -2.973  20.927  1.00 43.07      A  C
ATOM   1111  CB  LYS A 142      -9.535  -2.721  21.167  1.00 44.52      A  C
ATOM   1112  CG  LYS A 142      -9.273  -1.639  22.197  1.00 50.43      A  C
ATOM   1113  CD  LYS A 142      -7.911  -0.934  22.018  1.00 54.90      A  C
ATOM   1114  CE  LYS A 142      -7.775   0.176  23.065  1.00 59.58      A  C
ATOM   1115  NZ  LYS A 142      -6.575   1.060  22.900  1.00 65.00      A  N
ATOM   1116  C   LYS A 142     -11.199  -4.308  20.200  1.00 39.25      A  C
ATOM   1117  O   LYS A 142     -10.560  -4.536  19.177  1.00 37.65      A  O
ATOM   1118  N   THR A 143     -12.028  -5.189  20.752  1.00 37.84      A  N
ATOM   1119  CA  THR A 143     -12.468  -6.430  20.084  1.00 34.92      A  C
ATOM   1120  CB  THR A 143     -13.329  -7.261  21.015  1.00 34.29      A  C
ATOM   1121  OG1 THR A 143     -12.507  -7.867  22.019  1.00 36.56      A  O
ATOM   1122  CG2 THR A 143     -14.084  -8.332  20.238  1.00 32.44      A  C
ATOM   1123  C   THR A 143     -13.379  -6.123  18.937  1.00 33.76      A  C
ATOM   1124  O   THR A 143     -14.347  -5.412  19.119  1.00 35.42      A  O
ATOM   1125  N   HIS A 144     -13.103  -6.683  17.768  1.00 31.58      A  N
```

FIG. 2U

```
ATOM   1126  CA   HIS A 144     -13.879   -6.389   16.570  1.00 30.64        A  C
ATOM   1127  CB   HIS A 144     -13.013   -6.690   15.353  1.00 30.26        A  C
ATOM   1128  CG   HIS A 144     -13.421   -5.965   14.116  1.00 31.02        A  C
ATOM   1129  ND1  HIS A 144     -12.924   -4.723   13.789  1.00 33.31        A  N
ATOM   1130  CE1  HIS A 144     -13.450   -4.331   12.645  1.00 35.40        A  C
ATOM   1131  NE2  HIS A 144     -14.265   -5.278   12.215  1.00 34.11        A  N
ATOM   1132  CD2  HIS A 144     -14.258   -6.314   13.115  1.00 30.72        A  C
ATOM   1133  C    HIS A 144     -15.124   -7.274   16.582  1.00 28.60        A  C
ATOM   1134  O    HIS A 144     -15.026   -8.452   16.869  1.00 27.93        A  O
ATOM   1135  N    ILE A 145     -16.295   -6.707   16.316  1.00 29.03        A  N
ATOM   1136  CA   ILE A 145     -17.565   -7.456   16.324  1.00 27.56        A  C
ATOM   1137  CB   ILE A 145     -18.682   -6.671   17.081  1.00 29.24        A  C
ATOM   1138  CG1  ILE A 145     -18.243   -6.290   18.498  1.00 30.10        A  C
ATOM   1139  CD1  ILE A 145     -19.218   -5.350   19.228  1.00 31.54        A  C
ATOM   1140  CG2  ILE A 145     -19.970   -7.472   17.144  1.00 28.53        A  C
ATOM   1141  C    ILE A 145     -18.030   -7.718   14.877  1.00 27.06        A  C
ATOM   1142  O    ILE A 145     -18.013   -6.809   14.037  1.00 29.01        A  O
ATOM   1143  N    HIS A 146     -18.444   -8.949   14.591  1.00 24.85        A  N
ATOM   1144  CA   HIS A 146     -19.029   -9.311   13.301  1.00 23.84        A  C
ATOM   1145  CB   HIS A 146     -17.994  -10.107   12.522  1.00 22.81        A  C
ATOM   1146  CG   HIS A 146     -18.276  -10.241   11.063  1.00 23.36        A  C
ATOM   1147  ND1  HIS A 146     -17.269  -10.235   10.117  1.00 24.62        A  N
ATOM   1148  CE1  HIS A 146     -17.794  -10.383    8.918  1.00 24.66        A  C
ATOM   1149  NE2  HIS A 146     -19.104  -10.480    9.049  1.00 25.22        A  N
ATOM   1150  CD2  HIS A 146     -19.431  -10.402   10.383  1.00 23.16        A  C
ATOM   1151  C    HIS A 146     -20.263  -10.181   13.583  1.00 22.82        A  C
ATOM   1152  O    HIS A 146     -20.167  -11.214   14.220  1.00 21.58        A  O
ATOM   1153  N    ILE A 147     -21.403   -9.755   13.078  1.00 23.29        A  N
ATOM   1154  CA   ILE A 147     -22.685  -10.383   13.305  1.00 22.31        A  C
ATOM   1155  CB   ILE A 147     -23.736   -9.332   13.702  1.00 24.10        A  C
ATOM   1156  CG1  ILE A 147     -23.437   -8.797   15.093  1.00 25.27        A  C
ATOM   1157  CD1  ILE A 147     -22.925   -9.868   16.011  1.00 22.49        A  C
ATOM   1158  CG2  ILE A 147     -25.135   -9.925   13.604  1.00 24.13        A  C
ATOM   1159  C    ILE A 147     -23.234  -10.928   12.029  1.00 22.12        A  C
ATOM   1160  O    ILE A 147     -23.261  -10.211   11.034  1.00 22.47        A  O
ATOM   1161  N    PHE A 148     -23.741  -12.165   12.087  1.00 21.33        A  N
ATOM   1162  CA   PHE A 148     -24.475  -12.782   10.996  1.00 21.67        A  C
ATOM   1163  CB   PHE A 148     -23.814  -14.079   10.669  1.00 19.74        A  C
ATOM   1164  CG   PHE A 148     -22.506  -13.942    9.994  1.00 20.45        A  C
ATOM   1165  CD1  PHE A 148     -22.446  -13.717    8.628  1.00 20.06        A  C
ATOM   1166  CE1  PHE A 148     -21.248  -13.646    7.974  1.00 18.84        A  C
ATOM   1167  CZ   PHE A 148     -20.100  -13.800    8.653  1.00 19.15        A  C
ATOM   1168  CE2  PHE A 148     -20.122  -14.040   10.047  1.00 18.95        A  C
ATOM   1169  CD2  PHE A 148     -21.312  -14.120   10.705  1.00 19.37        A  C
ATOM   1170  C    PHE A 148     -25.892  -13.119   11.417  1.00 22.61        A  C
ATOM   1171  O    PHE A 148     -26.097  -13.387   12.577  1.00 23.73        A  O
ATOM   1172  N    SER A 149     -26.854  -13.137   10.496  1.00 24.41        A  N
ATOM   1173  CA   SER A 149     -28.223  -13.595   10.804  1.00 26.40        A  C
ATOM   1174  CB   SER A 149     -29.250  -12.547   10.442  1.00 28.65        A  C
ATOM   1175  OG   SER A 149     -29.568  -12.615    9.073  1.00 31.05        A  O
ATOM   1176  C    SER A 149     -28.569  -14.877   10.062  1.00 26.57        A  C
ATOM   1177  O    SER A 149     -27.817  -15.306    9.191  1.00 27.76        A  O
ATOM   1178  N    PHE A 150     -29.694  -15.502   10.418  1.00 27.04        A  N
ATOM   1179  CA   PHE A 150     -30.184  -16.660    9.682  1.00 26.50        A  C
ATOM   1180  CB   PHE A 150     -31.136  -17.518   10.528  1.00 26.32        A  C
ATOM   1181  CG   PHE A 150     -30.440  -18.335   11.527  1.00 23.45        A  C
ATOM   1182  CD1  PHE A 150     -30.021  -19.627   11.220  1.00 21.13        A  C
ATOM   1183  CE1  PHE A 150     -29.343  -20.366   12.119  1.00 16.81        A  C
ATOM   1184  CZ   PHE A 150     -28.995  -19.828   13.358  1.00 19.31        A  C
ATOM   1185  CE2  PHE A 150     -29.371  -18.548   13.692  1.00 20.69        A  C
ATOM   1186  CD2  PHE A 150     -30.111  -17.802   12.762  1.00 24.45        A  C
ATOM   1187  C    PHE A 150     -30.879  -16.220    8.395  1.00 28.91        A  C
ATOM   1188  O    PHE A 150     -31.139  -17.065    7.529  1.00 29.34        A  O
```

FIG. 2V

```
ATOM   1189  N    THR A 151     -31.211 -14.928   8.278  1.00 30.40           A  N
ATOM   1190  CA   THR A 151     -31.908 -14.417   7.104  1.00 32.32           A  C
ATOM   1191  CB   THR A 151     -33.014 -13.405   7.505  1.00 34.26           A  C
ATOM   1192  OG1  THR A 151     -32.547 -12.574   8.564  1.00 33.56           A  O
ATOM   1193  CG2  THR A 151     -34.259 -14.132   7.964  1.00 34.11           A  C
ATOM   1194  C    THR A 151     -30.993 -13.796   6.056  1.00 33.29           A  C
ATOM   1195  O    THR A 151     -31.453 -13.156   5.135  1.00 36.54           A  O
ATOM   1196  N    GLY A 152     -29.695 -13.973   6.181  1.00 32.92           A  N
ATOM   1197  CA   GLY A 152     -28.760 -13.482   5.169  1.00 33.43           A  C
ATOM   1198  C    GLY A 152     -28.133 -12.114   5.396  1.00 34.12           A  C
ATOM   1199  O    GLY A 152     -27.382 -11.663   4.543  1.00 35.73           A  O
ATOM   1200  N    GLU A 153     -28.431 -11.442   6.507  1.00 33.78           A  N
ATOM   1201  CA   GLU A 153     -27.876 -10.114   6.768  1.00 34.81           A  C
ATOM   1202  CB   GLU A 153     -28.876  -9.227   7.503  1.00 36.84           A  C
ATOM   1203  CG   GLU A 153     -30.088  -8.814   6.698  1.00 40.70           A  C
ATOM   1204  CD   GLU A 153     -31.271  -8.468   7.591  1.00 45.04           A  C
ATOM   1205  OE1  GLU A 153     -31.626  -9.335   8.431  1.00 42.84           A  O
ATOM   1206  OE2  GLU A 153     -31.849  -7.338   7.450  1.00 49.64           A  O
ATOM   1207  C    GLU A 153     -26.615 -10.218   7.613  1.00 32.76           A  C
ATOM   1208  O    GLU A 153     -26.390 -11.227   8.288  1.00 30.70           A  O
ATOM   1209  N    GLU A 154     -25.785  -9.178   7.574  1.00 33.09           A  N
ATOM   1210  CA   GLU A 154     -24.577  -9.155   8.394  1.00 31.82           A  C
ATOM   1211  CB   GLU A 154     -23.393  -9.824   7.671  1.00 30.31           A  C
ATOM   1212  CG   GLU A 154     -22.914  -9.031   6.469  1.00 33.94           A  C
ATOM   1213  CD   GLU A 154     -21.598  -9.499   5.860  1.00 35.24           A  C
ATOM   1214  OE1  GLU A 154     -20.734 -10.113   6.543  1.00 33.20           A  O
ATOM   1215  OE2  GLU A 154     -21.429  -9.195   4.666  1.00 38.99           A  O
ATOM   1216  C    GLU A 154     -24.219  -7.737   8.780  1.00 32.97           A  C
ATOM   1217  O    GLU A 154     -24.552  -6.800   8.070  1.00 34.72           A  O
ATOM   1218  N    MET A 155     -23.545  -7.575   9.915  1.00 32.59           A  N
ATOM   1219  CA   MET A 155     -22.881  -6.303  10.196  1.00 34.59           A  C
ATOM   1220  CB   MET A 155     -23.861  -5.263  10.735  1.00 37.18           A  C
ATOM   1221  CG   MET A 155     -24.313  -5.424  12.146  1.00 39.53           A  C
ATOM   1222  SD   MET A 155     -25.553  -4.136  12.466  1.00 50.66           A  S
ATOM   1223  CE   MET A 155     -26.996  -4.967  11.774  1.00 46.78           A  C
ATOM   1224  C    MET A 155     -21.626  -6.435  11.063  1.00 32.52           A  C
ATOM   1225  O    MET A 155     -21.516  -7.341  11.854  1.00 29.62           A  O
ATOM   1226  N    ALA A 156     -20.694  -5.502  10.885  1.00 33.66           A  N
ATOM   1227  CA   ALA A 156     -19.379  -5.591  11.500  1.00 32.99           A  C
ATOM   1228  CB   ALA A 156     -18.440  -6.221  10.549  1.00 31.69           A  C
ATOM   1229  C    ALA A 156     -18.843  -4.229  11.958  1.00 35.67           A  C
ATOM   1230  O    ALA A 156     -19.040  -3.223  11.280  1.00 38.97           A  O
ATOM   1231  N    THR A 157     -18.163  -4.197  13.106  1.00 35.16           A  N
ATOM   1232  CA   THR A 157     -17.575  -2.967  13.600  1.00 37.13           A  C
ATOM   1233  CB   THR A 157     -16.562  -3.220  14.764  1.00 36.63           A  C
ATOM   1234  OG1  THR A 157     -17.229  -3.077  16.026  1.00 39.19           A  O
ATOM   1235  CG2  THR A 157     -15.445  -2.196  14.763  1.00 38.72           A  C
ATOM   1236  C    THR A 157     -16.884  -2.237  12.468  1.00 38.18           A  C
ATOM   1237  O    THR A 157     -16.137  -2.844  11.730  1.00 36.37           A  O
ATOM   1238  N    LYS A 158     -17.158  -0.933  12.348  1.00 41.09           A  N
ATOM   1239  CA   LYS A 158     -16.553  -0.062  11.354  1.00 43.23           A  C
ATOM   1240  CB   LYS A 158     -15.025  -0.009  11.536  1.00 43.59           A  C
ATOM   1241  CG   LYS A 158     -14.535   0.841  12.715  1.00 47.25           A  C
ATOM   1242  CD   LYS A 158     -13.015   0.665  12.924  1.00 49.55           A  C
ATOM   1243  CE   LYS A 158     -12.343   1.858  13.643  1.00 53.50           A  C
ATOM   1244  NZ   LYS A 158     -12.056   1.562  15.084  1.00 52.93           A  N
ATOM   1245  C    LYS A 158     -16.883  -0.409   9.905  1.00 42.65           A  C
ATOM   1246  O    LYS A 158     -16.308   0.167   8.998  1.00 45.29           A  O
ATOM   1247  N    ALA A 159     -17.805  -1.328   9.674  1.00 40.71           A  N
ATOM   1248  CA   ALA A 159     -18.094  -1.836   8.312  1.00 40.55           A  C
ATOM   1249  CB   ALA A 159     -18.549  -0.720   7.402  1.00 42.47           A  C
ATOM   1250  C    ALA A 159     -16.900  -2.619   7.699  1.00 39.14           A  C
ATOM   1251  O    ALA A 159     -16.752  -2.729   6.466  1.00 39.69           A  O
```

FIG. 2W

```
ATOM   1252  N    ASP A 160     -16.077  -3.173   8.587  1.00 37.02           A    N
ATOM   1253  CA   ASP A 160     -14.924  -3.970   8.218  1.00 35.61           A    C
ATOM   1254  CB   ASP A 160     -13.694  -3.549   9.046  1.00 35.96           A    C
ATOM   1255  CG   ASP A 160     -12.406  -4.237   8.608  1.00 34.75           A    C
ATOM   1256  OD1  ASP A 160     -12.434  -5.102   7.716  1.00 32.77           A    O
ATOM   1257  OD2  ASP A 160     -11.341  -3.907   9.175  1.00 37.58           A    O
ATOM   1258  C    ASP A 160     -15.259  -5.438   8.450  1.00 33.02           A    C
ATOM   1259  O    ASP A 160     -15.233  -5.937   9.596  1.00 30.79           A    O
ATOM   1260  N    TYR A 161     -15.542  -6.139   7.355  1.00 32.31           A    N
ATOM   1261  CA   TYR A 161     -16.011  -7.499   7.467  1.00 30.28           A    C
ATOM   1262  CB   TYR A 161     -17.033  -7.779   6.381  1.00 30.73           A    C
ATOM   1263  CG   TYR A 161     -18.186  -6.817   6.446  1.00 34.16           A    C
ATOM   1264  CD1  TYR A 161     -19.245  -7.035   7.322  1.00 34.14           A    C
ATOM   1265  CE1  TYR A 161     -20.320  -6.158   7.390  1.00 36.01           A    C
ATOM   1266  CZ   TYR A 161     -20.338  -5.032   6.595  1.00 40.45           A    C
ATOM   1267  OH   TYR A 161     -21.402  -4.162   6.699  1.00 45.76           A    O
ATOM   1268  CE2  TYR A 161     -19.291  -4.770   5.712  1.00 41.25           A    C
ATOM   1269  CD2  TYR A 161     -18.215  -5.665   5.645  1.00 39.08           A    C
ATOM   1270  C    TYR A 161     -14.869  -8.494   7.451  1.00 28.89           A    C
ATOM   1271  O    TYR A 161     -15.106  -9.712   7.375  1.00 26.31           A    O
ATOM   1272  N    THR A 162     -13.639  -7.975   7.557  1.00 29.48           A    N
ATOM   1273  CA   THR A 162     -12.439  -8.801   7.625  1.00 29.16           A    C
ATOM   1274  CB   THR A 162     -12.433  -9.684   8.868  1.00 26.95           A    C
ATOM   1275  OG1  THR A 162     -12.638  -8.877  10.017  1.00 27.65           A    O
ATOM   1276  CG2  THR A 162     -11.095 -10.413   9.014  1.00 27.47           A    C
ATOM   1277  C    THR A 162     -12.217  -9.696   6.403  1.00 29.42           A    C
ATOM   1278  O    THR A 162     -11.279  -9.486   5.663  1.00 31.31           A    O
ATOM   1279  N    LEU A 163     -13.067 -10.705   6.215  1.00 29.00           A    N
ATOM   1280  CA   LEU A 163     -12.918 -11.681   5.124  1.00 28.99           A    C
ATOM   1281  CB   LEU A 163     -13.864 -12.867   5.305  1.00 26.83           A    C
ATOM   1282  CG   LEU A 163     -13.694 -13.727   6.560  1.00 24.81           A    C
ATOM   1283  CD1  LEU A 163     -14.813 -14.756   6.672  1.00 17.75           A    C
ATOM   1284  CD2  LEU A 163     -12.293 -14.373   6.544  1.00 24.21           A    C
ATOM   1285  C    LEU A 163     -13.271 -11.053   3.814  1.00 31.29           A    C
ATOM   1286  O    LEU A 163     -13.794  -9.958   3.782  1.00 34.30           A    O
ATOM   1287  N    ASP A 164     -13.000 -11.774   2.738  1.00 31.82           A    N
ATOM   1288  CA   ASP A 164     -13.570 -11.497   1.415  1.00 33.23           A    C
ATOM   1289  CB   ASP A 164     -12.836 -12.353   0.375  1.00 33.86           A    C
ATOM   1290  CG   ASP A 164     -12.879 -13.837   0.723  1.00 31.15           A    C
ATOM   1291  OD1  ASP A 164     -12.646 -14.181   1.920  1.00 22.95           A    O
ATOM   1292  OD2  ASP A 164     -13.190 -14.635  -0.192  1.00 30.23           A    O
ATOM   1293  C    ASP A 164     -15.059 -11.840   1.351  1.00 32.77           A    C
ATOM   1294  O    ASP A 164     -15.611 -12.492   2.244  1.00 30.52           A    O
ATOM   1295  N    GLU A 165     -15.687 -11.452   0.245  1.00 35.33           A    N
ATOM   1296  CA   GLU A 165     -17.135 -11.620   0.060  1.00 35.80           A    C
ATOM   1297  CB   GLU A 165     -17.621 -10.754  -1.098  1.00 39.00           A    C
ATOM   1298  CG   GLU A 165     -17.718  -9.290  -0.680  1.00 42.20           A    C
ATOM   1299  CD   GLU A 165     -17.909  -8.328  -1.841  1.00 47.50           A    C
ATOM   1300  OE1  GLU A 165     -19.041  -8.247  -2.387  1.00 51.13           A    O
ATOM   1301  OE2  GLU A 165     -16.929  -7.628  -2.177  1.00 47.82           A    O
ATOM   1302  C    GLU A 165     -17.584 -13.082  -0.086  1.00 34.46           A    C
ATOM   1303  O    GLU A 165     -18.644 -13.461   0.441  1.00 33.54           A    O
ATOM   1304  N    GLU A 166     -16.778 -13.904  -0.758  1.00 33.94           A    N
ATOM   1305  CA   GLU A 166     -17.147 -15.309  -0.988  1.00 32.81           A    C
ATOM   1306  CB   GLU A 166     -16.138 -15.997  -1.909  1.00 33.94           A    C
ATOM   1307  CG   GLU A 166     -16.477 -15.868  -3.354  1.00 40.06           A    C
ATOM   1308  CD   GLU A 166     -17.695 -16.674  -3.717  1.00 42.03           A    C
ATOM   1309  OE1  GLU A 166     -18.699 -16.036  -4.118  1.00 43.59           A    O
ATOM   1310  OE2  GLU A 166     -17.654 -17.930  -3.578  1.00 40.54           A    O
ATOM   1311  C    GLU A 166     -17.236 -16.105   0.302  1.00 29.15           A    C
ATOM   1312  O    GLU A 166     -18.157 -16.895   0.491  1.00 27.59           A    O
ATOM   1313  N    SER A 167     -16.234 -15.926   1.152  1.00 27.33           A    N
ATOM   1314  CA   SER A 167     -16.229 -16.533   2.450  1.00 25.51           A    C
```

FIG. 2X

```
ATOM   1315  CB   SER A 167     -14.930 -16.159   3.196  1.00 25.59      A    C
ATOM   1316  OG   SER A 167     -13.773 -16.490   2.425  1.00 26.87      A    O
ATOM   1317  C    SER A 167     -17.481 -16.111   3.241  1.00 24.17      A    C
ATOM   1318  O    SER A 167     -18.175 -16.931   3.813  1.00 22.43      A    O
ATOM   1319  N    ARG A 168     -17.816 -14.830   3.199  1.00 25.85      A    N
ATOM   1320  CA   ARG A 168     -19.049 -14.335   3.861  1.00 25.35      A    C
ATOM   1321  CB   ARG A 168     -19.076 -12.826   3.853  1.00 26.28      A    C
ATOM   1322  CG   ARG A 168     -17.933 -12.273   4.684  1.00 27.62      A    C
ATOM   1323  CD   ARG A 168     -18.113 -10.808   4.963  1.00 30.07      A    C
ATOM   1324  NE   ARG A 168     -17.401  -9.988   4.007  1.00 33.04      A    N
ATOM   1325  CZ   ARG A 168     -17.931  -8.996   3.302  1.00 36.55      A    C
ATOM   1326  NH1  ARG A 168     -19.205  -8.665   3.410  1.00 34.96      A    N
ATOM   1327  NH2  ARG A 168     -17.148  -8.314   2.483  1.00 40.96      A    N
ATOM   1328  C    ARG A 168     -20.346 -14.895   3.293  1.00 25.33      A    C
ATOM   1329  O    ARG A 168     -21.255 -15.244   4.039  1.00 24.28      A    O
ATOM   1330  N    ALA A 169     -20.419 -14.997   1.983  1.00 26.69      A    N
ATOM   1331  CA   ALA A 169     -21.601 -15.479   1.328  1.00 27.83      A    C
ATOM   1332  CB   ALA A 169     -21.462 -15.252  -0.141  1.00 30.58      A    C
ATOM   1333  C    ALA A 169     -21.770 -16.952   1.608  1.00 27.84      A    C
ATOM   1334  O    ALA A 169     -22.874 -17.450   1.708  1.00 27.83      A    O
ATOM   1335  N    ARG A 170     -20.649 -17.659   1.686  1.00 27.97      A    N
ATOM   1336  CA   ARG A 170     -20.652 -19.049   2.079  1.00 27.76      A    C
ATOM   1337  CB   ARG A 170     -19.208 -19.559   2.086  1.00 27.38      A    C
ATOM   1338  CG   ARG A 170     -18.994 -20.951   2.580  1.00 29.26      A    C
ATOM   1339  CD   ARG A 170     -17.511 -21.395   2.298  1.00 35.11      A    C
ATOM   1340  NE   ARG A 170     -17.249 -22.811   2.599  1.00 36.75      A    N
ATOM   1341  CZ   ARG A 170     -16.789 -23.292   3.757  1.00 38.06      A    C
ATOM   1342  NH1  ARG A 170     -16.502 -22.488   4.783  1.00 36.34      A    N
ATOM   1343  NH2  ARG A 170     -16.611 -24.609   3.888  1.00 39.67      A    N
ATOM   1344  C    ARG A 170     -21.321 -19.263   3.462  1.00 25.65      A    C
ATOM   1345  O    ARG A 170     -22.153 -20.168   3.610  1.00 26.74      A    O
ATOM   1346  N    ILE A 171     -20.959 -18.453   4.454  1.00 23.34      A    N
ATOM   1347  CA   ILE A 171     -21.528 -18.581   5.815  1.00 21.38      A    C
ATOM   1348  CB   ILE A 171     -20.724 -17.757   6.872  1.00 20.28      A    C
ATOM   1349  CG1  ILE A 171     -19.253 -18.186   6.935  1.00 20.15      A    C
ATOM   1350  CD1  ILE A 171     -18.357 -17.285   7.730  1.00 19.43      A    C
ATOM   1351  CG2  ILE A 171     -21.302 -17.951   8.245  1.00 19.43      A    C
ATOM   1352  C    ILE A 171     -23.017 -18.141   5.869  1.00 21.64      A    C
ATOM   1353  O    ILE A 171     -23.864 -18.852   6.423  1.00 20.45      A    O
ATOM   1354  N    LYS A 172     -23.316 -16.980   5.288  1.00 21.99      A    N
ATOM   1355  CA   LYS A 172     -24.699 -16.519   5.112  1.00 23.19      A    C
ATOM   1356  CB   LYS A 172     -24.717 -15.260   4.268  1.00 25.29      A    C
ATOM   1357  CG   LYS A 172     -24.311 -13.997   5.005  1.00 26.28      A    C
ATOM   1358  CD   LYS A 172     -24.515 -12.763   4.124  1.00 29.81      A    C
ATOM   1359  CE   LYS A 172     -23.230 -12.281   3.458  1.00 30.35      A    C
ATOM   1360  NZ   LYS A 172     -23.272 -10.797   3.295  1.00 34.17      A    N
ATOM   1361  C    LYS A 172     -25.619 -17.547   4.436  1.00 23.68      A    C
ATOM   1362  O    LYS A 172     -26.742 -17.750   4.851  1.00 23.47      A    O
ATOM   1363  N    THR A 173     -25.133 -18.165   3.372  1.00 24.52      A    N
ATOM   1364  CA   THR A 173     -25.788 -19.315   2.754  1.00 25.18      A    C
ATOM   1365  CB   THR A 173     -25.002 -19.806   1.553  1.00 26.05      A    C
ATOM   1366  OG1  THR A 173     -25.177 -18.867   0.500  1.00 25.67      A    O
ATOM   1367  CG2  THR A 173     -25.501 -21.177   1.095  1.00 27.22      A    C
ATOM   1368  C    THR A 173     -25.999 -20.487   3.707  1.00 23.67      A    C
ATOM   1369  O    THR A 173     -27.134 -20.937   3.915  1.00 23.84      A    O
ATOM   1370  N    ARG A 174     -24.927 -20.987   4.292  1.00 22.32      A    N
ATOM   1371  CA   ARG A 174     -25.076 -22.077   5.292  1.00 21.02      A    C
ATOM   1372  CB   ARG A 174     -23.743 -22.347   5.954  1.00 19.66      A    C
ATOM   1373  CG   ARG A 174     -23.755 -23.374   7.102  1.00 19.80      A    C
ATOM   1374  CD   ARG A 174     -24.160 -24.739   6.651  1.00 19.79      A    C
ATOM   1375  NE   ARG A 174     -23.943 -25.723   7.712  1.00 20.94      A    N
ATOM   1376  CZ   ARG A 174     -24.575 -26.887   7.812  1.00 21.39      A    C
ATOM   1377  NH1  ARG A 174     -25.469 -27.228   6.914  1.00 24.70      A    N
```

FIG. 2Y

| | | | | | | | | | | |
|---|---|---|---|---|---|---|---|---|---|---|
| ATOM | 1378 | NH2 | ARG | A | 174 | -24.338 | -27.697 | 8.830 | 1.00 21.74 | A | N |
| ATOM | 1379 | C | ARG | A | 174 | -26.159 | -21.801 | 6.364 | 1.00 20.47 | A | C |
| ATOM | 1380 | O | ARG | A | 174 | -26.930 | -22.688 | 6.717 | 1.00 22.09 | A | O |
| ATOM | 1381 | N | LEU | A | 175 | -26.230 | -20.572 | 6.860 | 1.00 19.74 | A | N |
| ATOM | 1382 | CA | LEU | A | 175 | -27.168 | -20.197 | 7.923 | 1.00 18.80 | A | C |
| ATOM | 1383 | CB | LEU | A | 175 | -26.799 | -18.832 | 8.467 | 1.00 18.24 | A | C |
| ATOM | 1384 | CG | LEU | A | 175 | -25.526 | -18.838 | 9.316 | 1.00 16.34 | A | C |
| ATOM | 1385 | CD1 | LEU | A | 175 | -25.099 | -17.421 | 9.637 | 1.00 15.42 | A | C |
| ATOM | 1386 | CD2 | LEU | A | 175 | -25.756 | -19.624 | 10.574 | 1.00 11.76 | A | C |
| ATOM | 1387 | C | LEU | A | 175 | -28.596 | -20.173 | 7.409 | 1.00 20.46 | A | C |
| ATOM | 1388 | O | LEU | A | 175 | -29.533 | -20.652 | 8.063 | 1.00 20.52 | A | O |
| ATOM | 1389 | N | PHE | A | 176 | -28.754 | -19.600 | 6.227 | 1.00 21.77 | A | N |
| ATOM | 1390 | CA | PHE | A | 176 | -30.021 | -19.600 | 5.549 | 1.00 23.48 | A | C |
| ATOM | 1391 | CB | PHE | A | 176 | -29.906 | -18.837 | 4.240 | 1.00 25.28 | A | C |
| ATOM | 1392 | CG | PHE | A | 176 | -31.208 | -18.645 | 3.558 | 1.00 26.90 | A | C |
| ATOM | 1393 | CD1 | PHE | A | 176 | -31.952 | -17.509 | 3.783 | 1.00 28.37 | A | C |
| ATOM | 1394 | CE1 | PHE | A | 176 | -33.206 | -17.345 | 3.166 | 1.00 31.59 | A | C |
| ATOM | 1395 | CZ | PHE | A | 176 | -33.697 | -18.328 | 2.334 | 1.00 31.69 | A | C |
| ATOM | 1396 | CE2 | PHE | A | 176 | -32.946 | -19.476 | 2.110 | 1.00 30.52 | A | C |
| ATOM | 1397 | CD2 | PHE | A | 176 | -31.722 | -19.633 | 2.730 | 1.00 27.45 | A | C |
| ATOM | 1398 | C | PHE | A | 176 | -30.513 | -21.035 | 5.323 | 1.00 23.97 | A | C |
| ATOM | 1399 | O | PHE | A | 176 | -31.675 | -21.334 | 5.533 | 1.00 24.81 | A | O |
| ATOM | 1400 | N | THR | A | 177 | -29.617 | -21.929 | 4.940 | 1.00 23.73 | A | N |
| ATOM | 1401 | CA | THR | A | 177 | -29.978 | -23.323 | 4.688 | 1.00 24.64 | A | C |
| ATOM | 1402 | CB | THR | A | 177 | -28.798 | -24.073 | 4.026 | 1.00 24.41 | A | C |
| ATOM | 1403 | OG1 | THR | A | 177 | -28.493 | -23.455 | 2.773 | 1.00 27.31 | A | O |
| ATOM | 1404 | CG2 | THR | A | 177 | -29.122 | -25.522 | 3.789 | 1.00 24.94 | A | C |
| ATOM | 1405 | C | THR | A | 177 | -30.381 | -24.014 | 5.991 | 1.00 24.04 | A | C |
| ATOM | 1406 | O | THR | A | 177 | -31.293 | -24.814 | 6.010 | 1.00 24.79 | A | O |
| ATOM | 1407 | N | ILE | A | 178 | -29.689 | -23.706 | 7.089 | 1.00 22.92 | A | N |
| ATOM | 1408 | CA | ILE | A | 178 | -30.005 | -24.332 | 8.367 | 1.00 21.84 | A | C |
| ATOM | 1409 | CB | ILE | A | 178 | -29.032 | -23.921 | 9.493 | 1.00 20.44 | A | C |
| ATOM | 1410 | CG1 | ILE | A | 178 | -27.674 | -24.610 | 9.258 | 1.00 20.61 | A | C |
| ATOM | 1411 | CD1 | ILE | A | 178 | -26.467 | -24.066 | 10.079 | 1.00 19.02 | A | C |
| ATOM | 1412 | CG2 | ILE | A | 178 | -29.610 | -24.329 | 10.830 | 1.00 17.28 | A | C |
| ATOM | 1413 | C | ILE | A | 178 | -31.407 | -23.974 | 8.746 | 1.00 23.42 | A | C |
| ATOM | 1414 | O | ILE | A | 178 | -32.105 | -24.773 | 9.346 | 1.00 23.94 | A | O |
| ATOM | 1415 | N | ARG | A | 179 | -31.831 | -22.772 | 8.346 | 1.00 24.37 | A | N |
| ATOM | 1416 | CA | ARG | A | 179 | -33.143 | -22.284 | 8.686 | 1.00 25.71 | A | C |
| ATOM | 1417 | CB | ARG | A | 179 | -33.206 | -20.771 | 8.492 | 1.00 26.10 | A | C |
| ATOM | 1418 | CG | ARG | A | 179 | -34.586 | -20.143 | 8.572 | 1.00 26.15 | A | C |
| ATOM | 1419 | CD | ARG | A | 179 | -34.391 | -18.643 | 8.699 | 1.00 25.26 | A | C |
| ATOM | 1420 | NE | ARG | A | 179 | -35.601 | -17.834 | 8.687 | 1.00 27.38 | A | N |
| ATOM | 1421 | CZ | ARG | A | 179 | -36.290 | -17.499 | 7.589 | 1.00 28.24 | A | C |
| ATOM | 1422 | NH1 | ARG | A | 179 | -35.918 | -17.966 | 6.401 | 1.00 27.05 | A | N |
| ATOM | 1423 | NH2 | ARG | A | 179 | -37.359 | -16.695 | 7.682 | 1.00 28.26 | A | N |
| ATOM | 1424 | C | ARG | A | 179 | -34.232 | -22.999 | 7.901 | 1.00 27.95 | A | C |
| ATOM | 1425 | O | ARG | A | 179 | -35.230 | -23.401 | 8.488 | 1.00 28.79 | A | O |
| ATOM | 1426 | N | GLN | A | 180 | -34.035 | -23.139 | 6.592 | 1.00 29.37 | A | N |
| ATOM | 1427 | CA | GLN | A | 180 | -34.993 | -23.845 | 5.723 | 1.00 32.45 | A | C |
| ATOM | 1428 | CB | GLN | A | 180 | -34.444 | -24.033 | 4.301 | 1.00 33.31 | A | C |
| ATOM | 1429 | CG | GLN | A | 180 | -34.436 | -22.794 | 3.393 | 1.00 35.31 | A | C |
| ATOM | 1430 | CD | GLN | A | 180 | -34.070 | -23.140 | 1.895 | 1.00 38.64 | A | C |
| ATOM | 1431 | OE1 | GLN | A | 180 | -33.029 | -23.787 | 1.631 | 1.00 36.28 | A | O |
| ATOM | 1432 | NE2 | GLN | A | 180 | -34.917 | -22.690 | 0.934 | 1.00 33.57 | A | N |
| ATOM | 1433 | C | GLN | A | 180 | -35.241 | -25.219 | 6.295 | 1.00 32.96 | A | C |
| ATOM | 1434 | O | GLN | A | 180 | -36.373 | -25.620 | 6.512 | 1.00 33.91 | A | O |
| ATOM | 1435 | N | GLU | A | 181 | -34.145 | -25.924 | 6.565 | 1.00 32.68 | A | N |
| ATOM | 1436 | CA | GLU | A | 181 | -34.206 | -27.318 | 6.994 | 1.00 33.70 | A | C |
| ATOM | 1437 | CB | GLU | A | 181 | -32.813 | -27.901 | 7.128 | 1.00 32.17 | A | C |
| ATOM | 1438 | CG | GLU | A | 181 | -31.988 | -27.873 | 5.832 | 1.00 34.86 | A | C |
| ATOM | 1439 | CD | GLU | A | 181 | -32.544 | -28.754 | 4.719 | 1.00 41.94 | A | C |
| ATOM | 1440 | OE1 | GLU | A | 181 | -33.685 | -29.295 | 4.852 | 1.00 42.23 | A | O |

FIG. 2Z

```
ATOM   1441  OE2 GLU A 181     -31.820 -28.884   3.689  1.00 45.95           A  O
ATOM   1442  C   GLU A 181     -34.966 -27.485   8.299  1.00 33.82           A  C
ATOM   1443  O   GLU A 181     -35.753 -28.421   8.444  1.00 35.45           A  O
ATOM   1444  N   MET A 182     -34.737 -26.564   9.232  1.00 31.80           A  N
ATOM   1445  CA  MET A 182     -35.500 -26.543  10.455  1.00 31.53           A  C
ATOM   1446  CB  MET A 182     -34.948 -25.490  11.412  1.00 30.23           A  C
ATOM   1447  CG  MET A 182     -33.702 -25.929  12.115  1.00 26.42           A  C
ATOM   1448  SD  MET A 182     -33.111 -24.639  13.192  1.00 26.48           A  S
ATOM   1449  CE  MET A 182     -31.606 -25.384  13.838  1.00 19.66           A  C
ATOM   1450  C   MET A 182     -36.956 -26.261  10.181  1.00 33.86           A  C
ATOM   1451  O   MET A 182     -37.825 -26.948  10.709  1.00 35.48           A  O
ATOM   1452  N   ALA A 183     -37.223 -25.233   9.380  1.00 34.28           A  N
ATOM   1453  CA  ALA A 183     -38.584 -24.850   9.071  1.00 36.44           A  C
ATOM   1454  CB  ALA A 183     -38.602 -23.665   8.145  1.00 36.72           A  C
ATOM   1455  C   ALA A 183     -39.331 -26.046   8.471  1.00 38.62           A  C
ATOM   1456  O   ALA A 183     -40.399 -26.393   8.949  1.00 40.80           A  O
ATOM   1457  N   SER A 184     -38.748 -26.689   7.457  1.00 38.62           A  N
ATOM   1458  CA  SER A 184     -39.262 -27.958   6.867  1.00 40.39           A  C
ATOM   1459  CB  SER A 184     -38.225 -28.565   5.919  1.00 39.77           A  C
ATOM   1460  OG  SER A 184     -38.112 -27.806   4.727  1.00 42.27           A  O
ATOM   1461  C   SER A 184     -39.602 -29.046   7.868  1.00 40.03           A  C
ATOM   1462  O   SER A 184     -40.507 -29.828   7.668  1.00 41.57           A  O
ATOM   1463  N   ARG A 185     -38.827 -29.117   8.925  1.00 38.25           A  N
ATOM   1464  CA  ARG A 185     -38.988 -30.148   9.937  1.00 38.93           A  C
ATOM   1465  CB  ARG A 185     -37.600 -30.608  10.376  1.00 37.10           A  C
ATOM   1466  CG  ARG A 185     -36.863 -31.340   9.246  1.00 38.89           A  C
ATOM   1467  CD  ARG A 185     -35.378 -31.600   9.541  1.00 39.89           A  C
ATOM   1468  NE  ARG A 185     -34.823 -32.547   8.571  1.00 43.99           A  N
ATOM   1469  CZ  ARG A 185     -34.592 -32.289   7.275  1.00 46.58           A  C
ATOM   1470  NH1 ARG A 185     -34.817 -31.080   6.741  1.00 46.22           A  N
ATOM   1471  NH2 ARG A 185     -34.114 -33.257   6.499  1.00 47.51           A  N
ATOM   1472  C   ARG A 185     -39.851 -29.644  11.112  1.00 39.09           A  C
ATOM   1473  O   ARG A 185     -39.839 -30.216  12.220  1.00 38.87           A  O
ATOM   1474  N   SER A 186     -40.617 -28.589  10.814  1.00 38.98           A  N
ATOM   1475  CA  SER A 186     -41.364 -27.775  11.774  1.00 39.02           A  C
ATOM   1476  CB  SER A 186     -42.787 -28.318  11.970  1.00 42.25           A  C
ATOM   1477  OG  SER A 186     -42.858 -29.255  13.014  1.00 43.17           A  O
ATOM   1478  C   SER A 186     -40.638 -27.562  13.087  1.00 36.41           A  C
ATOM   1479  O   SER A 186     -41.217 -27.708  14.141  1.00 37.30           A  O
ATOM   1480  N   LEU A 187     -39.369 -27.185  12.993  1.00 33.31           A  N
ATOM   1481  CA  LEU A 187     -38.513 -26.960  14.150  1.00 31.65           A  C
ATOM   1482  CB  LEU A 187     -37.232 -27.804  14.027  1.00 29.58           A  C
ATOM   1483  CG  LEU A 187     -37.318 -29.320  14.224  1.00 31.16           A  C
ATOM   1484  CD1 LEU A 187     -35.913 -29.921  14.157  1.00 26.69           A  C
ATOM   1485  CD2 LEU A 187     -38.056 -29.719  15.547  1.00 31.38           A  C
ATOM   1486  C   LEU A 187     -38.081 -25.506  14.335  1.00 30.61           A  C
ATOM   1487  O   LEU A 187     -37.476 -25.176  15.341  1.00 28.40           A  O
ATOM   1488  N   TRP A 188     -38.393 -24.641  13.374  1.00 32.06           A  N
ATOM   1489  CA  TRP A 188     -37.838 -23.293  13.380  1.00 32.09           A  C
ATOM   1490  CB  TRP A 188     -37.803 -22.720  11.964  1.00 32.52           A  C
ATOM   1491  CG  TRP A 188     -37.354 -21.281  11.890  1.00 32.48           A  C
ATOM   1492  CD1 TRP A 188     -38.137 -20.203  11.622  1.00 33.85           A  C
ATOM   1493  NE1 TRP A 188     -37.378 -19.054  11.638  1.00 34.60           A  N
ATOM   1494  CE2 TRP A 188     -36.080 -19.384  11.910  1.00 30.05           A  C
ATOM   1495  CD2 TRP A 188     -36.024 -20.775  12.069  1.00 30.38           A  C
ATOM   1496  CE3 TRP A 188     -34.789 -21.363  12.359  1.00 31.15           A  C
ATOM   1497  CZ3 TRP A 188     -33.659 -20.545  12.464  1.00 26.54           A  C
ATOM   1498  CH2 TRP A 188     -33.761 -19.174  12.298  1.00 27.22           A  C
ATOM   1499  CZ2 TRP A 188     -34.963 -18.576  12.035  1.00 29.26           A  C
ATOM   1500  C   TRP A 188     -38.592 -22.381  14.351  1.00 33.95           A  C
ATOM   1501  O   TRP A 188     -37.981 -21.702  15.167  1.00 34.22           A  O
ATOM   1502  N   ASP A 189     -39.905 -22.378  14.297  1.00 36.86           A  N
ATOM   1503  CA  ASP A 189     -40.679 -21.561  15.217  1.00 39.20           A  C
```

FIG. 2AA

```
ATOM   1504  CB  ASP A 189     -42.171 -21.874  15.115  1.00 42.44       A    C
ATOM   1505  CG  ASP A 189     -42.760 -21.466  13.773  1.00 43.79       A    C
ATOM   1506  OD1 ASP A 189     -42.109 -20.684  13.047  1.00 43.56       A    O
ATOM   1507  OD2 ASP A 189     -43.866 -21.932  13.438  1.00 46.72       A    O
ATOM   1508  C   ASP A 189     -40.181 -21.706  16.642  1.00 39.03       A    C
ATOM   1509  O   ASP A 189     -39.831 -20.714  17.255  1.00 39.50       A    O
ATOM   1510  N   SER A 190     -40.099 -22.928  17.158  1.00 39.41       A    N
ATOM   1511  CA  SER A 190     -39.605 -23.130  18.516  1.00 39.55       A    C
ATOM   1512  CB  SER A 190     -39.674 -24.615  18.903  1.00 39.97       A    C
ATOM   1513  OG  SER A 190     -38.850 -24.924  20.035  1.00 39.28       A    O
ATOM   1514  C   SER A 190     -38.180 -22.573  18.712  1.00 37.78       A    C
ATOM   1515  O   SER A 190     -37.877 -22.011  19.766  1.00 38.13       A    O
ATOM   1516  N   PHE A 191     -37.323 -22.707  17.704  1.00 36.14       A    N
ATOM   1517  CA  PHE A 191     -35.919 -22.295  17.825  1.00 34.76       A    C
ATOM   1518  CB  PHE A 191     -35.126 -22.858  16.649  1.00 32.56       A    C
ATOM   1519  CG  PHE A 191     -33.655 -22.577  16.699  1.00 28.05       A    C
ATOM   1520  CD1 PHE A 191     -32.859 -23.145  17.673  1.00 26.10       A    C
ATOM   1521  CE1 PHE A 191     -31.509 -22.927  17.724  1.00 22.35       A    C
ATOM   1522  CZ  PHE A 191     -30.897 -22.142  16.782  1.00 23.35       A    C
ATOM   1523  CE2 PHE A 191     -31.668 -21.568  15.776  1.00 27.43       A    C
ATOM   1524  CD2 PHE A 191     -33.055 -21.800  15.742  1.00 27.43       A    C
ATOM   1525  C   PHE A 191     -35.752 -20.780  17.869  1.00 36.67       A    C
ATOM   1526  O   PHE A 191     -34.854 -20.263  18.533  1.00 36.41       A    O
ATOM   1527  N   ARG A 192     -36.633 -20.090  17.157  1.00 39.71       A    N
ATOM   1528  CA  ARG A 192     -36.670 -18.634  17.075  1.00 41.72       A    C
ATOM   1529  CB  ARG A 192     -37.507 -18.260  15.838  1.00 43.43       A    C
ATOM   1530  CG  ARG A 192     -37.926 -16.796  15.732  1.00 46.86       A    C
ATOM   1531  CD  ARG A 192     -36.756 -15.946  15.341  1.00 46.92       A    C
ATOM   1532  NE  ARG A 192     -37.181 -14.578  15.048  1.00 51.32       A    N
ATOM   1533  CZ  ARG A 192     -37.150 -13.558  15.906  1.00 53.74       A    C
ATOM   1534  NH1 ARG A 192     -36.720 -13.721  17.156  1.00 54.57       A    N
ATOM   1535  NH2 ARG A 192     -37.564 -12.358  15.508  1.00 56.15       A    N
ATOM   1536  C   ARG A 192     -37.283 -17.993  18.339  1.00 44.52       A    C
ATOM   1537  O   ARG A 192     -36.831 -16.940  18.808  1.00 44.73       A    O
ATOM   1538  N   GLN A 193     -38.349 -18.607  18.847  1.00 46.67       A    N
ATOM   1539  CA  GLN A 193     -38.993 -18.146  20.062  1.00 49.61       A    C
ATOM   1540  CB  GLN A 193     -40.376 -18.822  20.220  1.00 53.00       A    C
ATOM   1541  CG  GLN A 193     -41.410 -18.323  19.172  1.00 56.38       A    C
ATOM   1542  CD  GLN A 193     -42.784 -18.976  19.287  1.00 63.04       A    C
ATOM   1543  OE1 GLN A 193     -43.723 -18.396  19.867  1.00 69.39       A    O
ATOM   1544  NE2 GLN A 193     -42.922 -20.177  18.716  1.00 63.68       A    N
ATOM   1545  C   GLN A 193     -38.107 -18.317  21.310  1.00 48.43       A    C
ATOM   1546  O   GLN A 193     -38.182 -17.532  22.240  1.00 49.72       A    O
ATOM   1547  N   SER A 194     -37.237 -19.316  21.319  1.00 46.39       A    N
ATOM   1548  CA  SER A 194     -36.257 -19.433  22.392  1.00 45.38       A    C
ATOM   1549  CB  SER A 194     -35.786 -20.875  22.548  1.00 44.24       A    C
ATOM   1550  OG  SER A 194     -34.552 -21.076  21.874  1.00 41.52       A    O
ATOM   1551  C   SER A 194     -35.082 -18.537  22.058  1.00 43.11       A    C
ATOM   1552  O   SER A 194     -34.156 -18.430  22.842  1.00 42.28       A    O
ATOM   1553  MN  MN  A 901     -19.730 -15.353  19.652  1.00 24.66       A   MN
ATOM   1554  MN  MN  A 902     -17.636 -17.125  22.275  1.00 27.74       A   MN
ATOM   1555  S   SO4 A 401     -16.315 -14.270  29.711  1.00 49.62       A    S
ATOM   1556  O1  SO4 A 401     -16.679 -14.563  28.329  1.00 47.34       A    O
ATOM   1557  O2  SO4 A 401     -15.179 -13.353  29.695  1.00 50.25       A    O
ATOM   1558  O3  SO4 A 401     -15.826 -15.471  30.411  1.00 48.00       A    O
ATOM   1559  O4  SO4 A 401     -17.503 -13.682  30.326  1.00 48.14       A    O
ATOM   1560  S   SO4 A 402     -37.933 -15.252  10.914  1.00 51.77       A    S
ATOM   1561  O1  SO4 A 402     -36.726 -15.591  10.198  1.00 48.67       A    O
ATOM   1562  O2  SO4 A 402     -37.598 -14.973  12.305  1.00 52.29       A    O
ATOM   1563  O3  SO4 A 402     -38.880 -16.367  10.883  1.00 54.48       A    O
ATOM   1564  O4  SO4 A 402     -38.557 -14.070  10.323  1.00 54.14       A    O
ATOM   1565  S   SO4 A 403     -34.546 -25.119  24.645  1.00 54.24       A    S
ATOM   1566  O1  SO4 A 403     -33.134 -24.717  24.606  1.00 44.33       A    O
```

FIG. 2AB

```
ATOM  1567  O2   SO4 A 403    -34.970 -25.344  26.041  1.00 57.26      A    O
ATOM  1568  O3   SO4 A 403    -34.671 -26.397  23.918  1.00 53.36      A    O
ATOM  1569  O4   SO4 A 403    -35.509 -24.120  24.115  1.00 53.43      A    O
ATOM  1570  S    SO4 A 404    -30.517 -14.816  19.351  1.00 49.29      A    S
ATOM  1571  O1   SO4 A 404    -30.690 -15.206  17.973  1.00 46.82      A    O
ATOM  1572  O2   SO4 A 404    -29.139 -15.139  19.746  1.00 46.81      A    O
ATOM  1573  O3   SO4 A 404    -31.523 -15.523  20.160  1.00 50.01      A    O
ATOM  1574  O4   SO4 A 404    -30.727 -13.368  19.479  1.00 51.58      A    O
ATOM  1575  CL   ci3 A 801    -25.090 -19.946  21.321  1.00 48.41      A    CL
ATOM  1576  CZB  ci3 A 801    -23.772 -19.842  22.519  1.00 35.75      A    C
ATOM  1577  CEB  ci3 A 801    -22.456 -19.789  22.057  1.00 31.41      A    C
ATOM  1578  CDB  ci3 A 801    -21.432 -19.704  22.992  1.00 29.45      A    C
ATOM  1579  CEA  ci3 A 801    -24.083 -19.829  23.882  1.00 34.17      A    C
ATOM  1580  CDA  ci3 A 801    -23.041 -19.743  24.796  1.00 31.84      A    C
ATOM  1581  CGA  ci3 A 801    -21.728 -19.682  24.352  1.00 29.22      A    C
ATOM  1582  CO   ci3 A 801    -20.601 -19.560  25.340  1.00 30.06      A    C
ATOM  1583  CF   ci3 A 801    -20.221 -18.093  25.621  1.00 30.88      A    C
ATOM  1584  CB   ci3 A 801    -19.972 -17.347  24.313  1.00 28.20      A    C
ATOM  1585  CM   ci3 A 801    -21.054 -16.681  23.533  1.00 27.21      A    C
ATOM  1586  CA   ci3 A 801    -20.840 -16.187  22.287  1.00 26.30      A    C
ATOM  1587  CE   ci3 A 801    -21.950 -15.566  21.577  1.00 27.57      A    C
ATOM  1588  OAO  ci3 A 801    -21.803 -15.292  20.358  1.00 26.92      A    O
ATOM  1589  OAN  ci3 A 801    -23.004 -15.296  22.220  1.00 30.71      A    O
ATOM  1590  O14  ci3 A 801    -19.652 -16.189  21.691  1.00 22.31      A    O
ATOM  1591  O13  ci3 A 801    -18.834 -17.336  23.871  1.00 25.98      A    O
ATOM  1592  CG   ci3 A 801    -21.392 -17.444  26.404  1.00 30.85      A    C
ATOM  1593  CK   ci3 A 801    -21.031 -16.189  27.199  1.00 33.96      A    C
ATOM  1594  CI   ci3 A 801    -19.573 -16.130  27.627  1.00 35.23      A    C
ATOM  1595  NJ   ci3 A 801    -19.034 -17.502  27.735  1.00 35.00      A    N
ATOM  1596  CH   ci3 A 801    -18.884 -18.064  26.396  1.00 30.47      A    C
ATOM  1597  CP   ci3 A 801    -17.731 -17.546  28.491  1.00 38.12      A    C
ATOM  1598  CGB  ci3 A 801    -17.631 -18.891  29.181  1.00 38.25      A    C
ATOM  1599  CD1  ci3 A 801    -16.977 -19.953  28.555  1.00 36.44      A    C
ATOM  1600  CE1  ci3 A 801    -16.943 -21.187  29.173  1.00 36.89      A    C
ATOM  1601  CZ   ci3 A 801    -17.557 -21.372  30.401  1.00 37.89      A    C
ATOM  1602  CE2  ci3 A 801    -18.218 -20.318  31.023  1.00 41.22      A    C
ATOM  1603  CD2  ci3 A 801    -18.257 -19.072  30.405  1.00 40.70      A    C
ATOM  6409  OH2  WAT A 903    -10.601  -9.091  11.772  1.00 32.57      A    O
ATOM  6410  OH2  WAT A 904    -14.901  -8.548  10.607  1.00 16.35      A    O
ATOM  6412  OH2  WAT A 905    -17.002 -19.982  -5.112  1.00 42.22      A    O
ATOM  6414  OH2  WAT A 906    -17.378 -15.047  22.418  1.00 22.40      A    O
ATOM  6416  OH2  WAT A 907    -18.289 -26.989   9.464  1.00 32.93      A    O
ATOM  6417  OH2  WAT A 908     -6.835 -22.198  16.683  1.00 23.51      A    O
ATOM  6418  OH2  WAT A 909    -18.589 -34.825  23.372  1.00 31.96      A    O
ATOM  6420  OH2  WAT A 910    -14.376 -25.985   8.906  1.00 29.63      A    O
ATOM  6421  OH2  WAT A 911    -37.599 -11.578  18.813  1.00 42.67      A    O
ATOM  6422  OH2  WAT A 912    -15.925 -27.185  26.775  1.00 29.68      A    O
ATOM  6423  OH2  WAT A 913    -25.317 -39.185  20.346  1.00 31.82      A    O
END
```

FIG. 2AC

```
H1N1 polypeptide fragment (Chain D) with bound EMBL-
R05-3
HEADER       ----                                           XX-XXX-9-   xxxx
COMPND       ---
REMARK    3
REMARK    3 REFINEMENT.
REMARK    3   PROGRAM      : REFMAC 5.5.0102
REMARK    3   AUTHORS      : MURSHUDOV,VAGIN,DODSON
REMARK    3
REMARK    3    REFINEMENT TARGET : MAXIMUM LIKELIHOOD
REMARK    3
REMARK    3  DATA USED IN REFINEMENT.
REMARK    3   RESOLUTION RANGE HIGH (ANGSTROMS) :    2.50
REMARK    3   RESOLUTION RANGE LOW  (ANGSTROMS) :   89.10
REMARK    3   DATA CUTOFF            (SIGMA(F)) :    NONE
REMARK    3   COMPLETENESS FOR RANGE        (%) :   99.04
REMARK    3   NUMBER OF REFLECTIONS             :   28997
REMARK    3
REMARK    3  FIT TO DATA USED IN REFINEMENT.
REMARK    3   CROSS-VALIDATION METHOD          : THROUGHOUT
REMARK    3   FREE R VALUE TEST SET SELECTION  : RANDOM
REMARK    3   R VALUE     (WORKING + TEST SET) : 0.20822
REMARK    3   R VALUE            (WORKING SET) : 0.20459
REMARK    3   FREE R VALUE                     : 0.27625
REMARK    3   FREE R VALUE TEST SET SIZE   (%) : 5.1
REMARK    3   FREE R VALUE TEST SET COUNT      : 1545
REMARK    3
REMARK    3  FIT IN THE HIGHEST RESOLUTION BIN.
REMARK    3   TOTAL NUMBER OF BINS USED           :      20
REMARK    3   BIN RESOLUTION RANGE HIGH           :   2.502
REMARK    3   BIN RESOLUTION RANGE LOW            :   2.567
REMARK    3   REFLECTION IN BIN     (WORKING SET) :    1968
REMARK    3   BIN COMPLETENESS (WORKING+TEST) (%) :   93.65
REMARK    3   BIN R VALUE           (WORKING SET) :   0.268
REMARK    3   BIN FREE R VALUE SET COUNT          :     113
REMARK    3   BIN FREE R VALUE                    :   0.378
REMARK    3
REMARK    3  NUMBER OF NON-HYDROGEN ATOMS USED IN REFINEMENT.
REMARK    3   ALL ATOMS            :     6523
REMARK    3
REMARK    3  B VALUES.
REMARK    3   FROM WILSON PLOT           (A**2) : NULL
REMARK    3   MEAN B VALUE      (OVERALL, A**2) : 29.083
REMARK    3   OVERALL ANISOTROPIC B VALUE.
REMARK    3    B11 (A**2) :    0.24
REMARK    3    B22 (A**2) :   -0.24
REMARK    3    B33 (A**2) :    0.00
REMARK    3    B12 (A**2) :    0.00
REMARK    3    B13 (A**2) :    0.00
REMARK    3    B23 (A**2) :    0.00
REMARK    3
REMARK    3  ESTIMATED OVERALL COORDINATE ERROR.
REMARK    3   ESU BASED ON R VALUE                      (A): 0.783
REMARK    3   ESU BASED ON FREE R VALUE                 (A): 0.335
REMARK    3   ESU BASED ON MAXIMUM LIKELIHOOD           (A): 0.240
REMARK    3   ESU FOR B VALUES BASED ON MAXIMUM LIKELIHOOD (A**2): 23.556
REMARK    3
REMARK    3 CORRELATION COEFFICIENTS.
REMARK    3   CORRELATION COEFFICIENT FO-FC      : 0.937
REMARK    3   CORRELATION COEFFICIENT FO-FC FREE : 0.891
REMARK    3
```

FIG. 3A

```
REMARK   3  RMS DEVIATIONS FROM IDEAL VALUES          COUNT    RMS    WEIGHT
REMARK   3   BOND LENGTHS REFINED ATOMS      (A):      6520 ; 0.016 ; 0.022
REMARK   3   BOND LENGTHS OTHERS             (A):      4574 ; 0.001 ; 0.020
REMARK   3   BOND ANGLES REFINED ATOMS (DEGREES):      8769 ; 1.513 ; 1.974
REMARK   3   BOND ANGLES OTHERS        (DEGREES):     11027 ; 0.893 ; 3.000
REMARK   3   TORSION ANGLES, PERIOD 1  (DEGREES):       741 ; 6.052 ; 5.000
REMARK   3   TORSION ANGLES, PERIOD 2  (DEGREES):       332 ;35.152 ;23.373
REMARK   3   TORSION ANGLES, PERIOD 3  (DEGREES):      1193 ;19.051 ;15.000
REMARK   3   TORSION ANGLES, PERIOD 4  (DEGREES):        55 ;19.093 ;15.000
REMARK   3   CHIRAL-CENTER RESTRAINTS     (A**3):       920 ; 0.086 ; 0.200
REMARK   3   GENERAL PLANES REFINED ATOMS    (A):      7058 ; 0.006 ; 0.020
REMARK   3   GENERAL PLANES OTHERS           (A):      1441 ; 0.001 ; 0.020
REMARK   3
REMARK   3  ISOTROPIC THERMAL FACTOR RESTRAINTS.      COUNT    RMS    WEIGHT
REMARK   3   MAIN-CHAIN BOND REFINED ATOMS  (A**2):    3740 ; 0.632 ; 1.500
REMARK   3   MAIN-CHAIN BOND OTHER ATOMS    (A**2):    1503 ; 0.123 ; 1.500
REMARK   3   MAIN-CHAIN ANGLE REFINED ATOMS (A**2):    6055 ; 1.173 ; 2.000
REMARK   3   SIDE-CHAIN BOND REFINED ATOMS  (A**2):    2780 ; 1.839 ; 3.000
REMARK   3   SIDE-CHAIN ANGLE REFINED ATOMS (A**2):    2714 ; 2.962 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  :    4
REMARK   3   ATOM RECORD CONTAINS SUM OF TLS AND RESIDUAL B FACTORS
REMARK   3
REMARK   3   TLS GROUP :    1
REMARK   3    NUMBER OF COMPONENTS GROUP :    4
REMARK   3    COMPONENTS        C SSSEQI   TO   C SSSEQI
REMARK   3    RESIDUE RANGE :   A     -2        A    194
REMARK   3    RESIDUE RANGE :   A    901        A    902
REMARK   3    RESIDUE RANGE :   A    401        A    404
REMARK   3    RESIDUE RANGE :   A    801        A    801
REMARK   3    ORIGIN FOR THE GROUP (A): -18.7820 -18.3467  15.6409
REMARK   3    T TENSOR
REMARK   3      T11:   0.0626 T22:   0.0601
REMARK   3      T33:   0.0370 T12:   0.0477
REMARK   3      T13:   0.0061 T23:  -0.0096
REMARK   3    L TENSOR
REMARK   3      L11:   3.8491 L22:   3.1615
REMARK   3      L33:   2.2199 L12:   0.4794
REMARK   3      L13:   0.2562 L23:  -0.2521
REMARK   3    S TENSOR
REMARK   3      S11:   0.0271 S12:  -0.0426 S13:   0.3012
REMARK   3      S21:   0.1037 S22:   0.0068 S23:   0.2311
REMARK   3      S31:  -0.2046 S32:   0.0173 S33:  -0.0339
REMARK   3
REMARK   3   TLS GROUP :    2
REMARK   3    NUMBER OF COMPONENTS GROUP :    4
REMARK   3    COMPONENTS        C SSSEQI   TO   C SSSEQI
REMARK   3    RESIDUE RANGE :   B     -2        B    193
REMARK   3    RESIDUE RANGE :   B    901        B    902
REMARK   3    RESIDUE RANGE :   B    401        B    404
REMARK   3    RESIDUE RANGE :   B    801        B    801
REMARK   3    ORIGIN FOR THE GROUP (A):  -9.5592 -43.9684  15.4406
REMARK   3    T TENSOR
REMARK   3      T11:   0.0655 T22:   0.0616
REMARK   3      T33:   0.0284 T12:   0.0424
```

FIG. 3B

```
REMARK   3       T13:   -0.0096 T23:    0.0116
REMARK   3     L TENSOR
REMARK   3       L11:    3.5209 L22:    2.7524
REMARK   3       L33:    2.1675 L12:    0.0213
REMARK   3       L13:   -0.8001 L23:    0.2855
REMARK   3     S TENSOR
REMARK   3       S11:    0.0173 S12:   -0.0992 S13:   -0.2131
REMARK   3       S21:    0.1239 S22:   -0.0222 S23:   -0.2049
REMARK   3       S31:    0.2223 S32:   -0.0015 S33:    0.0049
REMARK   3
REMARK   3    TLS GROUP :    3
REMARK   3     NUMBER OF COMPONENTS GROUP :    4
REMARK   3     COMPONENTS        C SSSEQI    TO   C SSSEQI
REMARK   3     RESIDUE RANGE :   C      0           C    195
REMARK   3     RESIDUE RANGE :   C    901           C    902
REMARK   3     RESIDUE RANGE :   C    401           C    403
REMARK   3     RESIDUE RANGE :   C    801           C    801
REMARK   3     ORIGIN FOR THE GROUP (A):  -4.3952 -15.1378  52.3445
REMARK   3     T TENSOR
REMARK   3       T11:    0.0906 T22:    0.0725
REMARK   3       T33:    0.0515 T12:   -0.0225
REMARK   3       T13:   -0.0351 T23:   -0.0026
REMARK   3     L TENSOR
REMARK   3       L11:    3.4910 L22:    2.7740
REMARK   3       L33:    2.4480 L12:    1.0609
REMARK   3       L13:   -0.2109 L23:   -1.3961
REMARK   3     S TENSOR
REMARK   3       S11:   -0.0152 S12:    0.1383 S13:   -0.1047
REMARK   3       S21:   -0.2065 S22:   -0.0565 S23:   -0.0793
REMARK   3       S31:    0.1206 S32:    0.1449 S33:    0.0717
REMARK   3
REMARK   3    TLS GROUP :    4
REMARK   3     NUMBER OF COMPONENTS GROUP :    4
REMARK   3     COMPONENTS        C SSSEQI    TO   C SSSEQI
REMARK   3     RESIDUE RANGE :   D      0           D    195
REMARK   3     RESIDUE RANGE :   D    901           D    902
REMARK   3     RESIDUE RANGE :   D    401           D    403
REMARK   3     RESIDUE RANGE :   D    801           D    801
REMARK   3     ORIGIN FOR THE GROUP (A): -21.2945 -45.7592  51.4140
REMARK   3     T TENSOR
REMARK   3       T11:    0.1308 T22:    0.1190
REMARK   3       T33:    0.0216 T12:   -0.0416
REMARK   3       T13:   -0.0097 T23:    0.0186
REMARK   3     L TENSOR
REMARK   3       L11:    3.6692 L22:    2.1484
REMARK   3       L33:    2.5225 L12:   -0.2058
REMARK   3       L13:   -0.3579 L23:    1.1039
REMARK   3     S TENSOR
REMARK   3       S11:    0.0541 S12:    0.3685 S13:   -0.0165
REMARK   3       S21:   -0.1313 S22:   -0.0722 S23:    0.0569
REMARK   3       S31:    0.0558 S32:   -0.2205 S33:    0.0181
REMARK   3
REMARK   3
REMARK   3   BULK SOLVENT MODELLING.
REMARK   3    METHOD USED : MASK
REMARK   3    PARAMETERS FOR MASK CALCULATION
REMARK   3    VDW PROBE RADIUS   :  1.40
REMARK   3    ION PROBE RADIUS   :  0.80
REMARK   3    SHRINKAGE RADIUS   :  0.80
REMARK   3
REMARK   3   OTHER REFINEMENT REMARKS:
REMARK   3   HYDROGENS HAVE BEEN ADDED IN THE RIDING POSITIONS
REMARK   3   U VALUES      : WITH TLS ADDED
```

FIG. 3C

```
REMARK    3
LINKR              GLU A   64                LEU A   71           gap
LINKR              LYS A  137                LYS A  142           gap
LINKR              GLU B   64                LEU B   71           gap
LINKR              PHE D   51                LEU D   72           gap
CRYST1   54.570  122.540  129.780  90.00  90.00  90.00 P 21 21 21
SCALE1      0.018325  0.000000  0.000000        0.00000
SCALE2      0.000000  0.008161  0.000000        0.00000
SCALE3      0.000000  0.000000  0.007705        0.00000
ATOM   9666  N   ALA D   0     -43.744 -40.288  53.969  1.00 42.23           N
ATOM   9667  CA  ALA D   0     -43.826 -41.746  53.723  1.00 42.48           C
ATOM   9669  CB  ALA D   0     -44.635 -42.041  52.466  1.00 44.64           C
ATOM   9673  C   ALA D   0     -42.411 -42.327  53.631  1.00 39.94           C
ATOM   9674  O   ALA D   0     -42.069 -43.247  54.364  1.00 38.22           O
ATOM   9678  N   MET D   1     -41.574 -41.775  52.762  1.00 39.94           N
ATOM   9679  CA  MET D   1     -40.208 -42.297  52.608  1.00 38.00           C
ATOM   9681  CB  MET D   1     -39.385 -41.479  51.609  1.00 37.81           C
ATOM   9684  CG  MET D   1     -37.883 -41.908  51.505  1.00 36.08           C
ATOM   9687  SD  MET D   1     -37.557 -43.690  51.304  1.00 35.33           S
ATOM   9688  CE  MET D   1     -37.104 -43.712  49.542  1.00 33.59           C
ATOM   9692  C   MET D   1     -39.499 -42.281  53.930  1.00 36.72           C
ATOM   9693  O   MET D   1     -38.809 -43.255  54.296  1.00 34.99           O
ATOM   9695  N   GLU D   2     -39.684 -41.184  54.655  1.00 37.51           N
ATOM   9696  CA  GLU D   2     -39.021 -41.017  55.936  1.00 37.19           C
ATOM   9698  CB  GLU D   2     -39.021 -39.545  56.373  1.00 37.65           C
ATOM   9701  CG  GLU D   2     -40.358 -38.993  56.715  1.00 42.68           C
ATOM   9704  CD  GLU D   2     -40.452 -37.507  56.461  1.00 48.57           C
ATOM   9705  OE1 GLU D   2     -39.625 -36.753  57.036  1.00 48.70           O
ATOM   9706  OE2 GLU D   2     -41.364 -37.102  55.684  1.00 52.95           O
ATOM   9707  C   GLU D   2     -39.638 -41.929  56.992  1.00 38.02           C
ATOM   9708  O   GLU D   2     -38.994 -42.264  57.988  1.00 36.83           O
ATOM   9710  N   ASP D   3     -40.875 -42.351  56.777  1.00 40.21           N
ATOM   9711  CA  ASP D   3     -41.445 -43.362  57.652  1.00 42.06           C
ATOM   9713  CB  ASP D   3     -42.955 -43.488  57.446  1.00 45.00           C
ATOM   9716  CG  ASP D   3     -43.727 -42.487  58.282  1.00 47.81           C
ATOM   9717  OD1 ASP D   3     -44.705 -42.891  58.951  1.00 52.73           O
ATOM   9718  OD2 ASP D   3     -43.329 -41.299  58.308  1.00 49.71           O
ATOM   9719  C   ASP D   3     -40.740 -44.703  57.451  1.00 41.14           C
ATOM   9720  O   ASP D   3     -40.297 -45.335  58.401  1.00 40.50           O
ATOM   9722  N   PHE D   4     -40.629 -45.111  56.198  1.00 41.26           N
ATOM   9723  CA  PHE D   4     -39.893 -46.304  55.833  1.00 40.45           C
ATOM   9725  CB  PHE D   4     -39.854 -46.397  54.306  1.00 41.06           C
ATOM   9728  CG  PHE D   4     -39.038 -47.530  53.785  1.00 40.10           C
ATOM   9729  CD1 PHE D   4     -39.498 -48.817  53.876  1.00 42.36           C
ATOM   9731  CE1 PHE D   4     -38.755 -49.853  53.391  1.00 42.25           C
ATOM   9733  CZ  PHE D   4     -37.537 -49.606  52.790  1.00 39.59           C
ATOM   9735  CE2 PHE D   4     -37.081 -48.333  52.693  1.00 37.73           C
ATOM   9737  CD2 PHE D   4     -37.822 -47.301  53.194  1.00 38.13           C
ATOM   9739  C   PHE D   4     -38.470 -46.315  56.422  1.00 37.45           C
ATOM   9740  O   PHE D   4     -38.050 -47.289  57.045  1.00 37.05           O
ATOM   9742  N   VAL D   5     -37.735 -45.233  56.236  1.00 35.56           N
ATOM   9743  CA  VAL D   5     -36.353 -45.167  56.743  1.00 32.58           C
ATOM   9745  CB  VAL D   5     -35.720 -43.789  56.472  1.00 31.10           C
ATOM   9747  CG1 VAL D   5     -34.368 -43.645  57.192  1.00 26.65           C
ATOM   9751  CG2 VAL D   5     -35.563 -43.593  54.986  1.00 29.67           C
ATOM   9755  C   VAL D   5     -36.279 -45.502  58.238  1.00 32.77           C
ATOM   9756  O   VAL D   5     -35.536 -46.386  58.650  1.00 30.97           O
ATOM   9758  N   ARG D   6     -37.078 -44.802  59.025  1.00 34.64           N
ATOM   9759  CA  ARG D   6     -37.118 -44.976  60.476  1.00 36.17           C
ATOM   9761  CB  ARG D   6     -38.070 -43.960  61.098  1.00 37.98           C
ATOM   9764  CG  ARG D   6     -37.498 -42.587  61.222  1.00 37.05           C
ATOM   9767  CD  ARG D   6     -38.492 -41.688  61.893  1.00 41.18           C
ATOM   9770  NE  ARG D   6     -38.293 -40.344  61.389  1.00 43.18           N
```

FIG. 3D

```
ATOM   9772  CZ   ARG D   6    -39.242 -39.439  61.206  1.00 45.47           C
ATOM   9773  NH1  ARG D   6    -40.521 -39.687  61.506  1.00 46.55           N
ATOM   9776  NH2  ARG D   6    -38.881 -38.264  60.705  1.00 47.08           N
ATOM   9779  C    ARG D   6    -37.577 -46.329  60.974  1.00 37.73           C
ATOM   9780  O    ARG D   6    -37.069 -46.825  61.964  1.00 37.69           O
ATOM   9782  N    GLN D   7    -38.554 -46.910  60.312  1.00 39.94           N
ATOM   9783  CA   GLN D   7    -39.108 -48.160  60.775  1.00 42.97           C
ATOM   9785  CB   GLN D   7    -40.601 -48.276  60.363  1.00 45.71           C
ATOM   9788  CG   GLN D   7    -41.532 -47.252  61.074  1.00 47.44           C
ATOM   9791  CD   GLN D   7    -42.881 -47.051  60.382  1.00 50.85           C
ATOM   9792  OE1  GLN D   7    -43.048 -47.342  59.187  1.00 51.31           O
ATOM   9793  NE2  GLN D   7    -43.855 -46.557  61.144  1.00 52.57           N
ATOM   9796  C    GLN D   7    -38.283 -49.373  60.290  1.00 42.96           C
ATOM   9797  O    GLN D   7    -38.309 -50.430  60.930  1.00 44.30           O
ATOM   9799  N    CYS D   8    -37.524 -49.212  59.201  1.00 41.61           N
ATOM   9800  CA   CYS D   8    -36.845 -50.356  58.550  1.00 41.17           C
ATOM   9802  CB   CYS D   8    -37.336 -50.455  57.106  1.00 42.02           C
ATOM   9805  SG   CYS D   8    -39.125 -51.002  57.072  1.00 49.42           S
ATOM   9807  C    CYS D   8    -35.289 -50.444  58.667  1.00 37.81           C
ATOM   9808  O    CYS D   8    -34.747 -51.549  58.799  1.00 38.30           O
ATOM   9810  N    PHE D   9    -34.586 -49.309  58.670  1.00 34.43           N
ATOM   9811  CA   PHE D   9    -33.153 -49.292  58.933  1.00 31.22           C
ATOM   9813  CB   PHE D   9    -32.532 -47.993  58.442  1.00 29.82           C
ATOM   9816  CG   PHE D   9    -32.317 -47.945  56.971  1.00 30.28           C
ATOM   9817  CD1  PHE D   9    -31.160 -48.507  56.406  1.00 29.51           C
ATOM   9819  CE1  PHE D   9    -30.955 -48.468  55.052  1.00 29.38           C
ATOM   9821  CZ   PHE D   9    -31.885 -47.848  54.240  1.00 30.60           C
ATOM   9823  CE2  PHE D   9    -33.036 -47.274  54.796  1.00 31.63           C
ATOM   9825  CD2  PHE D   9    -33.240 -47.322  56.148  1.00 30.27           C
ATOM   9827  C    PHE D   9    -32.868 -49.358  60.415  1.00 30.46           C
ATOM   9828  O    PHE D   9    -33.641 -48.830  61.199  1.00 29.72           O
ATOM   9830  N    ASN D  10    -31.711 -49.919  60.783  1.00 29.56           N
ATOM   9831  CA   ASN D  10    -31.223 -49.875  62.181  1.00 29.84           C
ATOM   9833  CB   ASN D  10    -29.789 -50.423  62.334  1.00 29.38           C
ATOM   9836  CG   ASN D  10    -29.417 -50.679  63.808  1.00 32.78           C
ATOM   9837  OD1  ASN D  10    -28.584 -49.985  64.391  1.00 33.24           O
ATOM   9838  ND2  ASN D  10    -30.092 -51.642  64.426  1.00 37.50           N
ATOM   9841  C    ASN D  10    -31.259 -48.452  62.736  1.00 28.42           C
ATOM   9842  O    ASN D  10    -30.713 -47.556  62.145  1.00 26.91           O
ATOM   9844  N    PRO D  11    -31.894 -48.248  63.893  1.00 29.78           N
ATOM   9845  CA   PRO D  11    -32.022 -46.899  64.426  1.00 29.42           C
ATOM   9847  CB   PRO D  11    -32.778 -47.109  65.735  1.00 31.22           C
ATOM   9850  CG   PRO D  11    -32.696 -48.551  66.006  1.00 32.47           C
ATOM   9853  CD   PRO D  11    -32.683 -49.204  64.682  1.00 31.29           C
ATOM   9856  C    PRO D  11    -30.721 -46.161  64.698  1.00 28.64           C
ATOM   9857  O    PRO D  11    -30.733 -44.934  64.695  1.00 28.47           O
ATOM   9858  N    MET D  12    -29.613 -46.864  64.938  1.00 28.31           N
ATOM   9859  CA   MET D  12    -28.340 -46.174  65.046  1.00 27.14           C
ATOM   9861  CB   MET D  12    -27.211 -47.052  65.620  1.00 28.43           C
ATOM   9864  CG   MET D  12    -25.942 -46.240  66.000  1.00 30.14           C
ATOM   9867  SD   MET D  12    -24.670 -47.181  66.898  1.00 39.52           S
ATOM   9868  CE   MET D  12    -24.080 -48.285  65.615  1.00 33.57           C
ATOM   9872  C    MET D  12    -27.954 -45.600  63.685  1.00 24.11           C
ATOM   9873  O    MET D  12    -27.434 -44.483  63.592  1.00 22.48           O
ATOM   9875  N    ILE D  13    -28.217 -46.340  62.623  1.00 22.82           N
ATOM   9876  CA   ILE D  13    -27.957 -45.798  61.277  1.00 21.13           C
ATOM   9878  CB   ILE D  13    -28.282 -46.818  60.180  1.00 21.15           C
ATOM   9880  CG1  ILE D  13    -27.559 -48.164  60.439  1.00 22.92           C
ATOM   9883  CD1  ILE D  13    -26.162 -48.280  59.976  1.00 22.54           C
ATOM   9887  CG2  ILE D  13    -27.908 -46.264  58.834  1.00 21.35           C
ATOM   9891  C    ILE D  13    -28.780 -44.493  61.069  1.00 20.44           C
ATOM   9892  O    ILE D  13    -28.261 -43.449  60.691  1.00 18.18           O
ATOM   9894  N    VAL D  14    -30.059 -44.530  61.409  1.00 21.13           N
```

FIG. 3E

```
ATOM   9895  CA   VAL D  14     -30.915 -43.373  61.162  1.00 21.32           C
ATOM   9897  CB   VAL D  14     -32.383 -43.744  61.439  1.00 22.38           C
ATOM   9899  CG1  VAL D  14     -33.291 -42.582  61.199  1.00 22.67           C
ATOM   9903  CG2  VAL D  14     -32.770 -44.906  60.544  1.00 22.26           C
ATOM   9907  C    VAL D  14     -30.424 -42.122  61.940  1.00 21.19           C
ATOM   9908  O    VAL D  14     -30.270 -41.032  61.358  1.00 21.33           O
ATOM   9910  N    GLU D  15     -30.120 -42.295  63.219  1.00 20.98           N
ATOM   9911  CA   GLU D  15     -29.554 -41.196  64.023  1.00 21.19           C
ATOM   9913  CB   GLU D  15     -29.379 -41.592  65.488  1.00 21.42           C
ATOM   9916  CG   GLU D  15     -30.688 -41.998  66.134  1.00 22.70           C
ATOM   9919  CD   GLU D  15     -30.697 -41.975  67.651  1.00 23.66           C
ATOM   9920  OE1  GLU D  15     -29.608 -41.922  68.247  1.00 23.41           O
ATOM   9921  OE2  GLU D  15     -31.818 -41.979  68.240  1.00 24.95           O
ATOM   9922  C    GLU D  15     -28.229 -40.679  63.457  1.00 20.49           C
ATOM   9923  O    GLU D  15     -28.042 -39.487  63.309  1.00 20.63           O
ATOM   9925  N    LEU D  16     -27.324 -41.572  63.092  1.00 20.12           N
ATOM   9926  CA   LEU D  16     -26.090 -41.128  62.498  1.00 19.69           C
ATOM   9928  CB   LEU D  16     -25.121 -42.306  62.234  1.00 18.98           C
ATOM   9931  CG   LEU D  16     -24.589 -43.000  63.499  1.00 20.75           C
ATOM   9933  CD1  LEU D  16     -23.898 -44.384  63.221  1.00 19.34           C
ATOM   9937  CD2  LEU D  16     -23.664 -42.088  64.271  1.00 18.92           C
ATOM   9941  C    LEU D  16     -26.394 -40.349  61.218  1.00 19.34           C
ATOM   9942  O    LEU D  16     -25.783 -39.320  60.959  1.00 20.59           O
ATOM   9944  N    ALA D  17     -27.331 -40.825  60.413  1.00 19.68           N
ATOM   9945  CA   ALA D  17     -27.665 -40.117  59.176  1.00 19.28           C
ATOM   9947  CB   ALA D  17     -28.687 -40.846  58.422  1.00 19.11           C
ATOM   9951  C    ALA D  17     -28.141 -38.702  59.515  1.00 20.15           C
ATOM   9952  O    ALA D  17     -27.655 -37.747  58.933  1.00 20.22           O
ATOM   9954  N    GLU D  18     -29.044 -38.580  60.495  1.00 20.95           N
ATOM   9955  CA   GLU D  18     -29.559 -37.270  60.937  1.00 22.10           C
ATOM   9957  CB   GLU D  18     -30.542 -37.451  62.089  1.00 22.35           C
ATOM   9960  CG   GLU D  18     -31.852 -37.995  61.539  1.00 23.65           C
ATOM   9963  CD   GLU D  18     -32.872 -38.424  62.579  1.00 23.56           C
ATOM   9964  OE1  GLU D  18     -32.635 -38.282  63.816  1.00 22.31           O
ATOM   9965  OE2  GLU D  18     -33.921 -38.927  62.120  1.00 22.14           O
ATOM   9966  C    GLU D  18     -28.479 -36.281  61.339  1.00 22.50           C
ATOM   9967  O    GLU D  18     -28.573 -35.090  61.117  1.00 23.22           O
ATOM   9969  N    LYS D  19     -27.449 -36.815  61.944  1.00 22.77           N
ATOM   9970  CA   LYS D  19     -26.388 -36.040  62.512  1.00 23.69           C
ATOM   9972  CB   LYS D  19     -25.739 -36.864  63.640  1.00 23.72           C
ATOM   9975  CG   LYS D  19     -24.295 -36.630  63.926  1.00 26.03           C
ATOM   9978  CD   LYS D  19     -23.485 -37.830  63.387  1.00 31.54           C
ATOM   9981  CE   LYS D  19     -22.122 -37.897  64.017  1.00 30.79           C
ATOM   9984  NZ   LYS D  19     -22.425 -37.752  65.450  1.00 34.24           N
ATOM   9988  C    LYS D  19     -25.442 -35.568  61.392  1.00 23.07           C
ATOM   9989  O    LYS D  19     -25.033 -34.394  61.393  1.00 23.91           O
ATOM   9991  N    ALA D  20     -25.173 -36.432  60.405  1.00 21.96           N
ATOM   9992  CA   ALA D  20     -24.408 -36.023  59.199  1.00 21.27           C
ATOM   9994  CB   ALA D  20     -24.177 -37.195  58.261  1.00 19.62           C
ATOM   9998  C    ALA D  20     -25.145 -34.932  58.459  1.00 22.50           C
ATOM   9999  O    ALA D  20     -24.530 -33.945  58.057  1.00 23.54           O
ATOM  10001  N    MET D  21     -26.454 -35.078  58.287  1.00 22.08           N
ATOM  10002  CA   MET D  21     -27.139 -34.153  57.419  1.00 23.85           C
ATOM  10004  CB   MET D  21     -28.550 -34.648  57.081  1.00 24.83           C
ATOM  10007  CG   MET D  21     -28.562 -35.883  56.178  1.00 23.06           C
ATOM  10010  SD   MET D  21     -30.208 -36.181  55.543  1.00 25.52           S
ATOM  10011  CE   MET D  21     -30.405 -34.936  54.278  1.00 23.85           C
ATOM  10015  C    MET D  21     -27.151 -32.759  58.072  1.00 25.63           C
ATOM  10016  O    MET D  21     -26.965 -31.709  57.414  1.00 24.63           O
ATOM  10018  N    LYS D  22     -27.315 -32.764  59.384  1.00 26.67           N
ATOM  10019  CA   LYS D  22     -27.262 -31.533  60.125  1.00 29.19           C
ATOM  10021  CB   LYS D  22     -27.631 -31.763  61.581  1.00 29.37           C
ATOM  10024  CG   LYS D  22     -27.945 -30.463  62.321  1.00 32.41           C
```

FIG. 3F

```
ATOM  10027  CD   LYS D  22     -27.654 -30.623  63.809  1.00 34.28           C
ATOM  10030  CE   LYS D  22     -28.397 -29.596  64.657  1.00 37.41           C
ATOM  10033  NZ   LYS D  22     -28.723 -30.168  66.029  1.00 38.83           N
ATOM  10037  C    LYS D  22     -25.847 -30.929  59.999  1.00 29.62           C
ATOM  10038  O    LYS D  22     -25.714 -29.723  59.864  1.00 30.17           O
ATOM  10040  N    GLU D  23     -24.810 -31.769  60.010  1.00 28.79           N
ATOM  10041  CA   GLU D  23     -23.445 -31.255  59.948  1.00 29.93           C
ATOM  10043  CB   GLU D  23     -22.383 -32.306  60.318  1.00 27.88           C
ATOM  10046  CG   GLU D  23     -21.000 -31.683  60.382  1.00 28.69           C
ATOM  10049  CD   GLU D  23     -19.856 -32.640  60.726  1.00 28.62           C
ATOM  10050  OE1  GLU D  23     -20.069 -33.857  60.801  1.00 27.71           O
ATOM  10051  OE2  GLU D  23     -18.713 -32.153  60.915  1.00 30.05           O
ATOM  10052  C    GLU D  23     -23.158 -30.661  58.568  1.00 31.93           C
ATOM  10053  O    GLU D  23     -22.455 -29.652  58.463  1.00 33.71           O
ATOM  10055  N    TYR D  24     -23.689 -31.287  57.521  1.00 32.32           N
ATOM  10056  CA   TYR D  24     -23.511 -30.802  56.156  1.00 34.10           C
ATOM  10058  CB   TYR D  24     -23.915 -31.911  55.182  1.00 34.13           C
ATOM  10061  CG   TYR D  24     -23.264 -31.887  53.817  1.00 37.55           C
ATOM  10062  CD1  TYR D  24     -21.901 -32.077  53.674  1.00 39.42           C
ATOM  10064  CE1  TYR D  24     -21.291 -32.071  52.413  1.00 42.57           C
ATOM  10066  CZ   TYR D  24     -22.067 -31.890  51.263  1.00 45.24           C
ATOM  10067  OH   TYR D  24     -21.483 -31.874  50.005  1.00 45.86           O
ATOM  10069  CE2  TYR D  24     -23.442 -31.704  51.382  1.00 45.57           C
ATOM  10071  CD2  TYR D  24     -24.032 -31.707  52.660  1.00 42.99           C
ATOM  10073  C    TYR D  24     -24.353 -29.534  55.934  1.00 35.56           C
ATOM  10074  O    TYR D  24     -23.924 -28.601  55.276  1.00 37.31           O
ATOM  10076  N    GLY D  25     -25.528 -29.483  56.531  1.00 35.78           N
ATOM  10077  CA   GLY D  25     -26.395 -28.286  56.459  1.00 37.89           C
ATOM  10080  C    GLY D  25     -27.640 -28.642  55.691  1.00 38.22           C
ATOM  10081  O    GLY D  25     -28.171 -27.865  54.923  1.00 40.85           O
ATOM  10083  N    GLU D  26     -28.100 -29.860  55.889  1.00 36.62           N
ATOM  10084  CA   GLU D  26     -29.216 -30.368  55.147  1.00 36.54           C
ATOM  10086  CB   GLU D  26     -28.728 -31.297  54.037  1.00 35.78           C
ATOM  10089  CG   GLU D  26     -28.267 -30.507  52.806  1.00 39.21           C
ATOM  10092  CD   GLU D  26     -27.755 -31.388  51.661  1.00 42.65           C
ATOM  10093  OE1  GLU D  26     -27.414 -32.574  51.914  1.00 42.60           O
ATOM  10094  OE2  GLU D  26     -27.671 -30.886  50.504  1.00 44.18           O
ATOM  10095  C    GLU D  26     -30.176 -31.030  56.102  1.00 34.71           C
ATOM  10096  O    GLU D  26     -29.799 -31.550  57.155  1.00 33.55           O
ATOM  10098  N    ASP D  27     -31.436 -30.972  55.718  1.00 34.93           N
ATOM  10099  CA   ASP D  27     -32.533 -31.242  56.617  1.00 34.36           C
ATOM  10101  CB   ASP D  27     -33.468 -30.046  56.599  1.00 36.60           C
ATOM  10104  CG   ASP D  27     -34.666 -30.235  57.465  1.00 37.11           C
ATOM  10105  OD1  ASP D  27     -34.719 -31.229  58.237  1.00 33.25           O
ATOM  10106  OD2  ASP D  27     -35.568 -29.380  57.339  1.00 38.21           O
ATOM  10107  C    ASP D  27     -33.260 -32.520  56.195  1.00 32.76           C
ATOM  10108  O    ASP D  27     -33.975 -32.514  55.192  1.00 33.20           O
ATOM  10110  N    PRO D  28     -33.097 -33.613  56.979  1.00 30.71           N
ATOM  10111  CA   PRO D  28     -33.693 -34.964  56.762  1.00 29.60           C
ATOM  10113  CB   PRO D  28     -33.410 -35.671  58.072  1.00 28.32           C
ATOM  10116  CG   PRO D  28     -32.216 -35.031  58.588  1.00 28.02           C
ATOM  10119  CD   PRO D  28     -32.369 -33.572  58.256  1.00 29.71           C
ATOM  10122  C    PRO D  28     -35.201 -34.995  56.518  1.00 31.33           C
ATOM  10123  O    PRO D  28     -35.720 -35.992  56.050  1.00 30.93           O
ATOM  10124  N    LYS D  29     -35.885 -33.910  56.861  1.00 33.67           N
ATOM  10125  CA   LYS D  29     -37.317 -33.805  56.717  1.00 36.61           C
ATOM  10127  CB   LYS D  29     -37.895 -32.820  57.771  1.00 38.38           C
ATOM  10130  CG   LYS D  29     -37.638 -33.247  59.255  1.00 38.09           C
ATOM  10133  CD   LYS D  29     -38.534 -32.522  60.257  1.00 42.26           C
ATOM  10136  CE   LYS D  29     -38.149 -31.035  60.476  1.00 44.88           C
ATOM  10139  NZ   LYS D  29     -39.205 -30.289  61.265  1.00 46.07           N
ATOM  10143  C    LYS D  29     -37.697 -33.376  55.302  1.00 38.14           C
ATOM  10144  O    LYS D  29     -38.811 -33.656  54.857  1.00 40.07           O
```

FIG. 3G

```
ATOM  10146  N    ILE D  30     -36.776 -32.711  54.605  1.00 38.09           N
ATOM  10147  CA   ILE D  30     -37.045 -32.136  53.276  1.00 39.99           C
ATOM  10149  CB   ILE D  30     -36.452 -30.689  53.091  1.00 41.14           C
ATOM  10151  CG1  ILE D  30     -36.755 -29.803  54.323  1.00 41.83           C
ATOM  10154  CD1  ILE D  30     -36.556 -28.257  54.131  1.00 41.98           C
ATOM  10158  CG2  ILE D  30     -36.977 -30.055  51.811  1.00 42.65           C
ATOM  10162  C    ILE D  30     -36.482 -33.062  52.215  1.00 38.96           C
ATOM  10163  O    ILE D  30     -37.216 -33.486  51.355  1.00 40.45           O
ATOM  10165  N    GLU D  31     -35.193 -33.391  52.276  1.00 37.35           N
ATOM  10166  CA   GLU D  31     -34.630 -34.347  51.314  1.00 37.00           C
ATOM  10168  CB   GLU D  31     -33.268 -33.937  50.740  1.00 36.92           C
ATOM  10171  CG   GLU D  31     -32.339 -33.221  51.659  1.00 38.57           C
ATOM  10174  CD   GLU D  31     -32.386 -31.714  51.462  1.00 43.67           C
ATOM  10175  OE1  GLU D  31     -32.638 -31.297  50.303  1.00 44.42           O
ATOM  10176  OE2  GLU D  31     -32.146 -30.960  52.454  1.00 46.22           O
ATOM  10177  C    GLU D  31     -34.588 -35.756  51.871  1.00 34.98           C
ATOM  10178  O    GLU D  31     -33.546 -36.283  52.277  1.00 33.32           O
ATOM  10180  N    THR D  32     -35.758 -36.371  51.833  1.00 35.60           N
ATOM  10181  CA   THR D  32     -35.983 -37.656  52.449  1.00 34.06           C
ATOM  10183  CB   THR D  32     -37.495 -37.919  52.629  1.00 35.97           C
ATOM  10185  OG1  THR D  32     -38.114 -38.072  51.351  1.00 37.69           O
ATOM  10187  CG2  THR D  32     -38.164 -36.762  53.366  1.00 37.68           C
ATOM  10191  C    THR D  32     -35.349 -38.792  51.650  1.00 32.30           C
ATOM  10192  O    THR D  32     -34.923 -39.782  52.240  1.00 30.42           O
ATOM  10194  N    ASN D  33     -35.301 -38.676  50.319  1.00 32.61           N
ATOM  10195  CA   ASN D  33     -34.591 -39.666  49.519  1.00 31.15           C
ATOM  10197  CB   ASN D  33     -34.827 -39.467  48.040  1.00 33.44           C
ATOM  10200  CG   ASN D  33     -36.189 -39.899  47.608  1.00 34.80           C
ATOM  10201  OD1  ASN D  33     -36.819 -39.228  46.799  1.00 39.60           O
ATOM  10202  ND2  ASN D  33     -36.658 -41.026  48.136  1.00 33.49           N
ATOM  10205  C    ASN D  33     -33.115 -39.624  49.769  1.00 29.11           C
ATOM  10206  O    ASN D  33     -32.489 -40.655  49.935  1.00 27.88           O
ATOM  10208  N    LYS D  34     -32.547 -38.430  49.813  1.00 29.41           N
ATOM  10209  CA   LYS D  34     -31.142 -38.308  50.129  1.00 28.21           C
ATOM  10211  CB   LYS D  34     -30.685 -36.841  50.113  1.00 28.89           C
ATOM  10214  CG   LYS D  34     -29.159 -36.732  50.245  1.00 30.84           C
ATOM  10217  CD   LYS D  34     -28.664 -35.330  50.430  1.00 35.84           C
ATOM  10220  CE   LYS D  34     -28.678 -34.517  49.139  1.00 39.72           C
ATOM  10223  NZ   LYS D  34     -28.615 -33.039  49.462  1.00 42.40           N
ATOM  10227  C    LYS D  34     -30.853 -38.954  51.496  1.00 26.41           C
ATOM  10228  O    LYS D  34     -29.826 -39.616  51.681  1.00 24.92           O
ATOM  10230  N    PHE D  35     -31.773 -38.754  52.433  1.00 27.00           N
ATOM  10231  CA   PHE D  35     -31.710 -39.310  53.794  1.00 26.20           C
ATOM  10233  CB   PHE D  35     -32.997 -38.912  54.530  1.00 27.70           C
ATOM  10236  CG   PHE D  35     -33.103 -39.356  55.973  1.00 27.64           C
ATOM  10237  CD1  PHE D  35     -32.016 -39.362  56.825  1.00 28.06           C
ATOM  10239  CE1  PHE D  35     -32.162 -39.707  58.160  1.00 28.17           C
ATOM  10241  CZ   PHE D  35     -33.412 -40.027  58.668  1.00 29.11           C
ATOM  10243  CE2  PHE D  35     -34.497 -40.000  57.850  1.00 30.48           C
ATOM  10245  CD2  PHE D  35     -34.347 -39.651  56.504  1.00 30.63           C
ATOM  10247  C    PHE D  35     -31.613 -40.801  53.742  1.00 25.62           C
ATOM  10248  O    PHE D  35     -30.766 -41.401  54.404  1.00 24.89           O
ATOM  10250  N    ALA D  36     -32.489 -41.403  52.941  1.00 26.66           N
ATOM  10251  CA   ALA D  36     -32.503 -42.855  52.776  1.00 26.23           C
ATOM  10253  CB   ALA D  36     -33.708 -43.277  51.909  1.00 27.86           C
ATOM  10257  C    ALA D  36     -31.202 -43.356  52.156  1.00 24.54           C
ATOM  10258  O    ALA D  36     -30.794 -44.490  52.374  1.00 23.31           O
ATOM  10260  N    ALA D  37     -30.574 -42.504  51.362  1.00 24.52           N
ATOM  10261  CA   ALA D  37     -29.330 -42.846  50.686  1.00 23.98           C
ATOM  10263  CB   ALA D  37     -29.086 -41.896  49.513  1.00 25.43           C
ATOM  10267  C    ALA D  37     -28.148 -42.820  51.646  1.00 22.17           C
ATOM  10268  O    ALA D  37     -27.306 -43.741  51.620  1.00 21.11           O
ATOM  10270  N    ILE D  38     -28.078 -41.781  52.489  1.00 21.44           N
```

FIG. 3H

```
ATOM  10271  CA  ILE D  38     -26.988 -41.695  53.486  1.00 19.80           C
ATOM  10273  CB  ILE D  38     -27.074 -40.459  54.436  1.00 20.43           C
ATOM  10275  CG1 ILE D  38     -27.497 -39.173  53.694  1.00 22.08           C
ATOM  10278  CD1 ILE D  38     -26.572 -38.696  52.677  1.00 19.46           C
ATOM  10282  CG2 ILE D  38     -25.730 -40.183  55.094  1.00 18.32           C
ATOM  10286  C   ILE D  38     -27.060 -42.979  54.330  1.00 18.70           C
ATOM  10287  O   ILE D  38     -26.034 -43.648  54.553  1.00 17.98           O
ATOM  10289  N   CYS D  39     -28.281 -43.322  54.756  1.00 18.57           N
ATOM  10290  CA  CYS D  39     -28.554 -44.527  55.519  1.00 18.83           C
ATOM  10292  CB  CYS D  39     -30.055 -44.670  55.812  1.00 20.70           C
ATOM  10295  SG  CYS D  39     -30.745 -43.590  57.057  1.00 21.43           S
ATOM  10297  C   CYS D  39     -28.085 -45.808  54.854  1.00 18.65           C
ATOM  10298  O   CYS D  39     -27.428 -46.631  55.472  1.00 18.45           O
ATOM  10300  N   THR D  40     -28.470 -46.001  53.607  1.00 19.58           N
ATOM  10301  CA  THR D  40     -28.016 -47.158  52.836  1.00 19.90           C
ATOM  10303  CB  THR D  40     -28.596 -47.114  51.402  1.00 20.83           C
ATOM  10305  OG1 THR D  40     -30.003 -47.226  51.483  1.00 21.62           O
ATOM  10307  CG2 THR D  40     -28.081 -48.251  50.572  1.00 22.06           C
ATOM  10311  C   THR D  40     -26.516 -47.169  52.728  1.00 18.58           C
ATOM  10312  O   THR D  40     -25.867 -48.184  52.954  1.00 18.19           O
ATOM  10314  N   HIS D  41     -25.972 -46.022  52.383  1.00 18.27           N
ATOM  10315  CA  HIS D  41     -24.535 -45.919  52.216  1.00 18.96           C
ATOM  10317  CB  HIS D  41     -24.162 -44.509  51.727  1.00 18.85           C
ATOM  10320  CG  HIS D  41     -22.694 -44.302  51.546  1.00 19.60           C
ATOM  10321  ND1 HIS D  41     -21.892 -43.818  52.549  1.00 20.02           N
ATOM  10323  CE1 HIS D  41     -20.650 -43.719  52.105  1.00 19.91           C
ATOM  10325  NE2 HIS D  41     -20.616 -44.137  50.854  1.00 17.66           N
ATOM  10327  CD2 HIS D  41     -21.880 -44.515  50.482  1.00 20.23           C
ATOM  10329  C   HIS D  41     -23.796 -46.287  53.513  1.00 18.49           C
ATOM  10330  O   HIS D  41     -22.793 -47.038  53.512  1.00 17.36           O
ATOM  10332  N   LEU D  42     -24.315 -45.764  54.617  1.00 18.90           N
ATOM  10333  CA  LEU D  42     -23.714 -46.022  55.901  1.00 19.08           C
ATOM  10335  CB  LEU D  42     -24.482 -45.275  56.976  1.00 19.96           C
ATOM  10338  CG  LEU D  42     -23.787 -44.208  57.816  1.00 19.37           C
ATOM  10340  CD1 LEU D  42     -24.802 -43.486  58.707  1.00 20.36           C
ATOM  10344  CD2 LEU D  42     -22.770 -44.860  58.655  1.00 16.31           C
ATOM  10348  C   LEU D  42     -23.769 -47.522  56.157  1.00 19.94           C
ATOM  10349  O   LEU D  42     -22.758 -48.181  56.493  1.00 19.58           O
ATOM  10351  N   GLU D  43     -24.964 -48.064  55.978  1.00 21.11           N
ATOM  10352  CA  GLU D  43     -25.174 -49.489  56.197  1.00 22.45           C
ATOM  10354  CB  GLU D  43     -26.585 -49.907  55.788  1.00 23.52           C
ATOM  10357  CG  GLU D  43     -26.990 -51.187  56.491  1.00 25.98           C
ATOM  10360  CD  GLU D  43     -28.452 -51.501  56.433  1.00 27.97           C
ATOM  10361  OE1 GLU D  43     -29.112 -51.234  55.406  1.00 26.25           O
ATOM  10362  OE2 GLU D  43     -28.939 -52.063  57.436  1.00 33.45           O
ATOM  10363  C   GLU D  43     -24.109 -50.353  55.495  1.00 22.17           C
ATOM  10364  O   GLU D  43     -23.495 -51.220  56.129  1.00 23.22           O
ATOM  10366  N   VAL D  44     -23.845 -50.059  54.225  1.00 20.97           N
ATOM  10367  CA  VAL D  44     -22.829 -50.767  53.455  1.00 20.76           C
ATOM  10369  CB  VAL D  44     -22.747 -50.236  52.001  1.00 21.10           C
ATOM  10371  CG1 VAL D  44     -21.596 -50.880  51.261  1.00 19.31           C
ATOM  10375  CG2 VAL D  44     -24.083 -50.463  51.276  1.00 20.55           C
ATOM  10379  C   VAL D  44     -21.441 -50.623  54.049  1.00 20.53           C
ATOM  10380  O   VAL D  44     -20.686 -51.583  54.193  1.00 20.00           O
ATOM  10382  N   CYS D  45     -21.099 -49.395  54.382  1.00 21.02           N
ATOM  10383  CA  CYS D  45     -19.834 -49.130  55.042  1.00 20.47           C
ATOM  10385  CB  CYS D  45     -19.735 -47.663  55.360  1.00 19.81           C
ATOM  10388  SG  CYS D  45     -19.327 -46.656  53.924  1.00 21.21           S
ATOM  10390  C   CYS D  45     -19.700 -49.991  56.289  1.00 21.62           C
ATOM  10391  O   CYS D  45     -18.667 -50.628  56.486  1.00 21.60           O
ATOM  10393  N   PHE D  46     -20.761 -50.085  57.100  1.00 23.35           N
ATOM  10394  CA  PHE D  46     -20.687 -50.910  58.331  1.00 24.64           C
ATOM  10396  CB  PHE D  46     -21.878 -50.685  59.269  1.00 25.68           C
```

FIG. 3I

```
ATOM  10399  CG   PHE D  46     -21.906 -49.321  59.949  1.00 25.78           C
ATOM  10400  CD1  PHE D  46     -20.901 -48.370  59.754  1.00 26.01           C
ATOM  10402  CE1  PHE D  46     -20.942 -47.123  60.374  1.00 24.14           C
ATOM  10404  CZ   PHE D  46     -21.975 -46.826  61.219  1.00 27.52           C
ATOM  10406  CE2  PHE D  46     -22.993 -47.768  61.440  1.00 28.91           C
ATOM  10408  CD2  PHE D  46     -22.946 -49.005  60.802  1.00 28.79           C
ATOM  10410  C    PHE D  46     -20.599 -52.378  58.016  1.00 25.86           C
ATOM  10411  O    PHE D  46     -19.946 -53.116  58.729  1.00 27.29           O
ATOM  10413  N    MET D  47     -21.259 -52.820  56.953  1.00 26.86           N
ATOM  10414  CA   MET D  47     -21.237 -54.239  56.605  1.00 27.62           C
ATOM  10416  CB   MET D  47     -22.374 -54.557  55.656  1.00 27.79           C
ATOM  10419  CG   MET D  47     -23.783 -54.442  56.256  1.00 27.80           C
ATOM  10422  SD   MET D  47     -25.051 -54.624  54.977  1.00 28.52           S
ATOM  10423  CE   MET D  47     -25.144 -56.385  54.790  1.00 26.66           C
ATOM  10427  C    MET D  47     -19.872 -54.607  56.001  1.00 28.44           C
ATOM  10428  O    MET D  47     -19.314 -55.665  56.270  1.00 30.45           O
ATOM  10430  N    TYR D  48     -19.316 -53.716  55.209  1.00 27.99           N
ATOM  10431  CA   TYR D  48     -18.041 -53.979  54.548  1.00 28.75           C
ATOM  10433  CB   TYR D  48     -17.686 -52.763  53.698  1.00 26.89           C
ATOM  10436  CG   TYR D  48     -16.758 -52.996  52.536  1.00 25.04           C
ATOM  10437  CD1  TYR D  48     -17.229 -52.955  51.233  1.00 22.51           C
ATOM  10439  CE1  TYR D  48     -16.374 -53.117  50.174  1.00 22.19           C
ATOM  10441  CZ   TYR D  48     -15.017 -53.284  50.406  1.00 22.27           C
ATOM  10442  OH   TYR D  48     -14.123 -53.423  49.359  1.00 20.04           O
ATOM  10444  CE2  TYR D  48     -14.537 -53.312  51.696  1.00 22.33           C
ATOM  10446  CD2  TYR D  48     -15.390 -53.142  52.736  1.00 22.26           C
ATOM  10448  C    TYR D  48     -16.923 -54.267  55.564  1.00 30.28           C
ATOM  10449  O    TYR D  48     -16.102 -55.148  55.359  1.00 30.57           O
ATOM  10451  N    SER D  49     -16.940 -53.520  56.665  1.00 32.17           N
ATOM  10452  CA   SER D  49     -15.913 -53.570  57.701  1.00 33.79           C
ATOM  10454  CB   SER D  49     -15.547 -52.156  58.126  1.00 32.57           C
ATOM  10457  OG   SER D  49     -16.671 -51.468  58.644  1.00 33.19           O
ATOM  10459  C    SER D  49     -16.277 -54.362  58.936  1.00 36.43           C
ATOM  10460  O    SER D  49     -15.519 -54.341  59.887  1.00 37.68           O
ATOM  10462  N    ASP D  50     -17.373 -55.108  58.909  1.00 39.33           N
ATOM  10463  CA   ASP D  50     -17.880 -55.781  60.113  1.00 43.16           C
ATOM  10465  CB   ASP D  50     -16.997 -56.959  60.564  1.00 45.40           C
ATOM  10468  CG   ASP D  50     -17.060 -58.140  59.652  1.00 48.53           C
ATOM  10469  OD1  ASP D  50     -17.132 -57.970  58.406  1.00 50.84           O
ATOM  10470  OD2  ASP D  50     -16.997 -59.256  60.209  1.00 52.08           O
ATOM  10471  C    ASP D  50     -17.928 -54.809  61.294  1.00 44.06           C
ATOM  10472  O    ASP D  50     -17.318 -55.083  62.341  1.00 45.39           O
ATOM  10474  N    PHE D  51     -18.596 -53.672  61.140  1.00 44.11           N
ATOM  10475  CA   PHE D  51     -18.733 -52.774  62.265  1.00 45.34           C
ATOM  10477  CB   PHE D  51     -19.413 -51.465  61.880  1.00 44.40           C
ATOM  10480  CG   PHE D  51     -19.350 -50.415  62.961  1.00 45.30           C
ATOM  10481  CD1  PHE D  51     -18.210 -49.654  63.126  1.00 45.52           C
ATOM  10483  CE1  PHE D  51     -18.129 -48.671  64.109  1.00 46.41           C
ATOM  10485  CZ   PHE D  51     -19.185 -48.445  64.930  1.00 47.67           C
ATOM  10487  CE2  PHE D  51     -20.361 -49.214  64.792  1.00 48.92           C
ATOM  10489  CD2  PHE D  51     -20.428 -50.194  63.810  1.00 48.18           C
ATOM  10491  C    PHE D  51     -19.529 -53.458  63.369  1.00 47.33           C
ATOM  10492  O    PHE D  51     -19.133 -53.403  64.534  1.00 49.18           O
ATOM  10494  N    LEU D  72      -8.988 -59.570  68.353  1.00 62.22           N
ATOM  10495  CA   LEU D  72      -7.685 -59.041  67.935  1.00 61.49           C
ATOM  10497  CB   LEU D  72      -6.727 -60.192  67.578  1.00 63.65           C
ATOM  10503  C    LEU D  72      -7.868 -58.041  66.775  1.00 57.74           C
ATOM  10504  O    LEU D  72      -8.975 -57.563  66.543  1.00 55.53           O
ATOM  10506  N    LYS D  73      -6.786 -57.733  66.057  1.00 57.15           N
ATOM  10507  CA   LYS D  73      -6.736 -56.583  65.121  1.00 53.86           C
ATOM  10509  CB   LYS D  73      -5.376 -56.532  64.419  1.00 54.25           C
ATOM  10516  C    LYS D  73      -7.845 -56.542  64.052  1.00 51.43           C
ATOM  10517  O    LYS D  73      -7.982 -57.483  63.247  1.00 52.46           O
```

FIG. 3J

```
ATOM  10519  N    HIS D  74    -8.613 -55.445  64.058  1.00 48.14    N
ATOM  10520  CA   HIS D  74    -9.609 -55.141  63.024  1.00 45.20    C
ATOM  10522  CB   HIS D  74   -10.452 -53.911  63.423  1.00 44.05    C
ATOM  10525  CG   HIS D  74   -11.816 -54.246  63.931  1.00 46.72    C
ATOM  10526  ND1  HIS D  74   -12.961 -53.969  63.211  1.00 48.52    N
ATOM  10528  CE1  HIS D  74   -14.017 -54.392  63.890  1.00 50.46    C
ATOM  10530  NE2  HIS D  74   -13.599 -54.911  65.036  1.00 50.71    N
ATOM  10532  CD2  HIS D  74   -12.227 -54.832  65.086  1.00 50.66    C
ATOM  10534  C    HIS D  74    -8.909 -54.831  61.704  1.00 42.43    C
ATOM  10535  O    HIS D  74    -7.868 -54.168  61.688  1.00 42.74    O
ATOM  10537  N    ARG D  75    -9.504 -55.274  60.600  1.00 39.37    N
ATOM  10538  CA   ARG D  75    -8.914 -55.112  59.267  1.00 36.90    C
ATOM  10540  CB   ARG D  75    -9.436 -56.203  58.324  1.00 37.10    C
ATOM  10543  CG   ARG D  75    -8.603 -56.342  57.055  1.00 37.23    C
ATOM  10546  CD   ARG D  75    -9.457 -56.636  55.837  1.00 36.66    C
ATOM  10549  NE   ARG D  75    -8.772 -56.330  54.579  1.00 35.46    N
ATOM  10551  CZ   ARG D  75    -8.711 -57.130  53.530  1.00 35.68    C
ATOM  10552  NH1  ARG D  75    -9.288 -58.308  53.557  1.00 39.50    N
ATOM  10555  NH2  ARG D  75    -8.075 -56.748  52.435  1.00 36.83    N
ATOM  10558  C    ARG D  75    -9.201 -53.748  58.635  1.00 33.06    C
ATOM  10559  O    ARG D  75    -8.428 -53.250  57.839  1.00 32.65    O
ATOM  10561  N    PHE D  76   -10.342 -53.179  58.968  1.00 30.04    N
ATOM  10562  CA   PHE D  76   -10.749 -51.923  58.418  1.00 27.04    C
ATOM  10564  CB   PHE D  76   -12.051 -52.065  57.653  1.00 25.51    C
ATOM  10567  CG   PHE D  76   -11.973 -52.997  56.503  1.00 26.10    C
ATOM  10568  CD1  PHE D  76   -11.380 -52.598  55.315  1.00 27.18    C
ATOM  10570  CE1  PHE D  76   -11.297 -53.457  54.243  1.00 27.93    C
ATOM  10572  CZ   PHE D  76   -11.850 -54.733  54.349  1.00 29.41    C
ATOM  10574  CE2  PHE D  76   -12.459 -55.132  55.539  1.00 27.69    C
ATOM  10576  CD2  PHE D  76   -12.522 -54.275  56.589  1.00 27.12    C
ATOM  10578  C    PHE D  76   -10.954 -50.896  59.514  1.00 25.51    C
ATOM  10579  O    PHE D  76   -11.418 -51.203  60.603  1.00 25.09    O
ATOM  10581  N    GLU D  77   -10.637 -49.658  59.177  1.00 23.99    N
ATOM  10582  CA   GLU D  77   -11.040 -48.536  59.984  1.00 22.86    C
ATOM  10584  CB   GLU D  77    -9.923 -47.533  60.100  1.00 22.90    C
ATOM  10587  CG   GLU D  77   -10.155 -46.566  61.199  1.00 24.13    C
ATOM  10590  CD   GLU D  77   -10.005 -47.194  62.564  1.00 24.46    C
ATOM  10591  OE1  GLU D  77   -10.944 -47.054  63.363  1.00 24.01    O
ATOM  10592  OE2  GLU D  77    -8.951 -47.818  62.818  1.00 24.25    O
ATOM  10593  C    GLU D  77   -12.195 -47.861  59.327  1.00 21.32    C
ATOM  10594  O    GLU D  77   -12.161 -47.520  58.140  1.00 20.30    O
ATOM  10596  N    ILE D  78   -13.221 -47.629  60.106  1.00 21.06    N
ATOM  10597  CA   ILE D  78   -14.332 -46.868  59.608  1.00 20.39    C
ATOM  10599  CB   ILE D  78   -15.625 -47.313  60.225  1.00 20.73    C
ATOM  10601  CG1  ILE D  78   -16.764 -46.594  59.514  1.00 20.45    C
ATOM  10604  CD1  ILE D  78   -18.005 -47.339  59.587  1.00 23.42    C
ATOM  10608  CG2  ILE D  78   -15.625 -47.074  61.765  1.00 22.46    C
ATOM  10612  C    ILE D  78   -14.160 -45.366  59.809  1.00 20.01    C
ATOM  10613  O    ILE D  78   -13.989 -44.868  60.935  1.00 21.07    O
ATOM  10615  N    ILE D  79   -14.248 -44.659  58.690  1.00 19.15    N
ATOM  10616  CA   ILE D  79   -14.168 -43.205  58.622  1.00 19.24    C
ATOM  10618  CB   ILE D  79   -13.202 -42.819  57.517  1.00 19.30    C
ATOM  10620  CG1  ILE D  79   -11.923 -43.646  57.696  1.00 19.42    C
ATOM  10623  CD1  ILE D  79   -10.818 -43.290  56.753  1.00 20.67    C
ATOM  10627  CG2  ILE D  79   -12.971 -41.316  57.501  1.00 18.20    C
ATOM  10631  C    ILE D  79   -15.549 -42.574  58.354  1.00 19.33    C
ATOM  10632  O    ILE D  79   -15.887 -41.600  58.954  1.00 19.03    O
ATOM  10634  N    GLU D  80   -16.356 -43.149  57.461  1.00 19.90    N
ATOM  10635  CA   GLU D  80   -17.688 -42.609  57.226  1.00 20.03    C
ATOM  10637  CB   GLU D  80   -18.371 -43.365  56.112  1.00 20.46    C
ATOM  10640  CG   GLU D  80   -19.783 -42.877  55.740  1.00 22.53    C
ATOM  10643  CD   GLU D  80   -19.834 -41.429  55.297  1.00 24.88    C
ATOM  10644  OE1  GLU D  80   -19.476 -41.133  54.134  1.00 25.39    O
```

FIG. 3K

| ATOM | 10645 | OE2 | GLU | D | 80 | -20.263 | -40.589 | 56.121 | 1.00 | 28.04 | O |
| ATOM | 10646 | C | GLU | D | 80 | -18.547 | -42.701 | 58.474 | 1.00 | 20.31 | C |
| ATOM | 10647 | O | GLU | D | 80 | -18.439 | -43.671 | 59.272 | 1.00 | 19.98 | O |
| ATOM | 10649 | N | GLY | D | 81 | -19.433 | -41.719 | 58.639 | 1.00 | 19.99 | N |
| ATOM | 10650 | CA | GLY | D | 81 | -20.310 | -41.684 | 59.847 | 1.00 | 20.15 | C |
| ATOM | 10653 | C | GLY | D | 81 | -19.778 | -40.859 | 61.010 | 1.00 | 19.72 | C |
| ATOM | 10654 | O | GLY | D | 81 | -20.521 | -40.465 | 61.894 | 1.00 | 19.53 | O |
| ATOM | 10656 | N | ARG | D | 82 | -18.476 | -40.593 | 61.008 | 1.00 | 19.30 | N |
| ATOM | 10657 | CA | ARG | D | 82 | -17.893 | -39.720 | 61.984 | 1.00 | 19.10 | C |
| ATOM | 10659 | CB | ARG | D | 82 | -16.391 | -39.967 | 62.067 | 1.00 | 19.08 | C |
| ATOM | 10662 | CG | ARG | D | 82 | -16.014 | -41.396 | 62.380 | 1.00 | 17.27 | C |
| ATOM | 10665 | CD | ARG | D | 82 | -14.519 | -41.518 | 62.552 | 1.00 | 14.54 | C |
| ATOM | 10668 | NE | ARG | D | 82 | -14.086 | -42.877 | 62.911 | 1.00 | 14.56 | N |
| ATOM | 10670 | CZ | ARG | D | 82 | -13.823 | -43.303 | 64.148 | 1.00 | 13.61 | C |
| ATOM | 10671 | NH1 | ARG | D | 82 | -13.948 | -42.519 | 65.204 | 1.00 | 15.62 | N |
| ATOM | 10674 | NH2 | ARG | D | 82 | -13.405 | -44.526 | 64.340 | 1.00 | 12.88 | N |
| ATOM | 10677 | C | ARG | D | 82 | -18.192 | -38.308 | 61.500 | 1.00 | 19.49 | C |
| ATOM | 10678 | O | ARG | D | 82 | -18.533 | -38.138 | 60.332 | 1.00 | 19.61 | O |
| ATOM | 10680 | N | ASP | D | 83 | -18.071 | -37.314 | 62.384 | 1.00 | 19.86 | N |
| ATOM | 10681 | CA | ASP | D | 83 | -18.101 | -35.904 | 61.974 | 1.00 | 20.68 | C |
| ATOM | 10683 | CB | ASP | D | 83 | -18.485 | -34.971 | 63.140 | 1.00 | 21.42 | C |
| ATOM | 10686 | CG | ASP | D | 83 | -17.410 | -34.885 | 64.211 | 1.00 | 24.02 | C |
| ATOM | 10687 | OD1 | ASP | D | 83 | -16.378 | -35.559 | 64.132 | 1.00 | 23.95 | O |
| ATOM | 10688 | OD2 | ASP | D | 83 | -17.600 | -34.115 | 65.164 | 1.00 | 31.98 | O |
| ATOM | 10689 | C | ASP | D | 83 | -16.762 | -35.510 | 61.352 | 1.00 | 20.10 | C |
| ATOM | 10690 | O | ASP | D | 83 | -15.842 | -36.299 | 61.338 | 1.00 | 19.28 | O |
| ATOM | 10692 | N | ARG | D | 84 | -16.667 | -34.305 | 60.805 | 1.00 | 21.08 | N |
| ATOM | 10693 | CA | ARG | D | 84 | -15.442 | -33.924 | 60.105 | 1.00 | 22.29 | C |
| ATOM | 10695 | CB | ARG | D | 84 | -15.539 | -32.562 | 59.426 | 1.00 | 23.52 | C |
| ATOM | 10698 | CG | ARG | D | 84 | -16.045 | -32.627 | 58.025 | 1.00 | 24.81 | C |
| ATOM | 10701 | CD | ARG | D | 84 | -15.979 | -31.268 | 57.376 | 1.00 | 28.72 | C |
| ATOM | 10704 | NE | ARG | D | 84 | -16.599 | -31.255 | 56.049 | 1.00 | 29.44 | N |
| ATOM | 10706 | CZ | ARG | D | 84 | -17.745 | -30.644 | 55.749 | 1.00 | 34.75 | C |
| ATOM | 10707 | NH1 | ARG | D | 84 | -18.437 | -29.962 | 56.664 | 1.00 | 35.56 | N |
| ATOM | 10710 | NH2 | ARG | D | 84 | -18.219 | -30.712 | 54.508 | 1.00 | 38.55 | N |
| ATOM | 10713 | C | ARG | D | 84 | -14.217 | -33.954 | 61.023 | 1.00 | 23.32 | C |
| ATOM | 10714 | O | ARG | D | 84 | -13.200 | -34.470 | 60.592 | 1.00 | 22.67 | O |
| ATOM | 10716 | N | ILE | D | 85 | -14.331 | -33.411 | 62.256 | 1.00 | 24.56 | N |
| ATOM | 10717 | CA | ILE | D | 85 | -13.209 | -33.378 | 63.193 | 1.00 | 25.89 | C |
| ATOM | 10719 | CB | ILE | D | 85 | -13.525 | -32.829 | 64.645 | 1.00 | 27.33 | C |
| ATOM | 10721 | CG1 | ILE | D | 85 | -14.337 | -31.515 | 64.671 | 1.00 | 28.71 | C |
| ATOM | 10724 | CD1 | ILE | D | 85 | -13.825 | -30.448 | 63.852 | 1.00 | 30.00 | C |
| ATOM | 10728 | CG2 | ILE | D | 85 | -12.250 | -32.574 | 65.397 | 1.00 | 27.41 | C |
| ATOM | 10732 | C | ILE | D | 85 | -12.639 | -34.789 | 63.354 | 1.00 | 24.91 | C |
| ATOM | 10733 | O | ILE | D | 85 | -11.464 | -35.009 | 63.114 | 1.00 | 24.68 | O |
| ATOM | 10735 | N | MET | D | 86 | -13.488 | -35.746 | 63.708 | 1.00 | 24.04 | N |
| ATOM | 10736 | CA | MET | D | 86 | -13.014 | -37.100 | 64.055 | 1.00 | 23.40 | C |
| ATOM | 10738 | CB | MET | D | 86 | -14.109 | -37.901 | 64.751 | 1.00 | 23.09 | C |
| ATOM | 10741 | CG | MET | D | 86 | -14.446 | -37.396 | 66.160 | 1.00 | 25.62 | C |
| ATOM | 10744 | SD | MET | D | 86 | -13.047 | -37.633 | 67.305 | 1.00 | 33.11 | S |
| ATOM | 10745 | CE | MET | D | 86 | -12.658 | -35.921 | 67.695 | 1.00 | 33.18 | C |
| ATOM | 10749 | C | MET | D | 86 | -12.518 | -37.836 | 62.845 | 1.00 | 22.08 | C |
| ATOM | 10750 | O | MET | D | 86 | -11.575 | -38.617 | 62.911 | 1.00 | 23.02 | O |
| ATOM | 10752 | N | ALA | D | 87 | -13.144 | -37.555 | 61.728 | 1.00 | 21.02 | N |
| ATOM | 10753 | CA | ALA | D | 87 | -12.770 | -38.159 | 60.481 | 1.00 | 20.27 | C |
| ATOM | 10755 | CB | ALA | D | 87 | -13.755 | -37.749 | 59.381 | 1.00 | 20.12 | C |
| ATOM | 10759 | C | ALA | D | 87 | -11.375 | -37.725 | 60.121 | 1.00 | 20.58 | C |
| ATOM | 10760 | O | ALA | D | 87 | -10.568 | -38.536 | 59.689 | 1.00 | 20.94 | O |
| ATOM | 10762 | N | TRP | D | 88 | -11.080 | -36.444 | 60.293 | 1.00 | 20.70 | N |
| ATOM | 10763 | CA | TRP | D | 88 | -9.729 | -35.967 | 60.022 | 1.00 | 21.71 | C |
| ATOM | 10765 | CB | TRP | D | 88 | -9.714 | -34.447 | 59.754 | 1.00 | 22.79 | C |
| ATOM | 10768 | CG | TRP | D | 88 | -10.114 | -34.159 | 58.336 | 1.00 | 25.39 | C |
| ATOM | 10769 | CD1 | TRP | D | 88 | -11.238 | -33.502 | 57.883 | 1.00 | 25.70 | C |

FIG. 3L

```
ATOM  10771  NE1  TRP  D  88   -11.249  -33.475  56.503  1.00  25.62        N
ATOM  10773  CE2  TRP  D  88   -10.141  -34.138  56.048  1.00  29.04        C
ATOM  10774  CD2  TRP  D  88    -9.410  -34.584  57.171  1.00  27.97        C
ATOM  10775  CE3  TRP  D  88    -8.252  -35.321  56.968  1.00  28.64        C
ATOM  10777  CZ3  TRP  D  88    -7.853  -35.581  55.679  1.00  30.95        C
ATOM  10779  CH2  TRP  D  88    -8.589  -35.129  54.588  1.00  29.78        C
ATOM  10781  CZ2  TRP  D  88    -9.734  -34.406  54.751  1.00  31.24        C
ATOM  10783  C    TRP  D  88    -8.699  -36.410  61.099  1.00  21.12        C
ATOM  10784  O    TRP  D  88    -7.528  -36.681  60.783  1.00  21.20        O
ATOM  10786  N    THR  D  89    -9.145  -36.494  62.342  1.00  19.96        N
ATOM  10787  CA   THR  D  89    -8.341  -37.070  63.389  1.00  20.95        C
ATOM  10789  CB   THR  D  89    -9.075  -37.070  64.748  1.00  21.64        C
ATOM  10791  OG1  THR  D  89    -9.567  -35.747  65.050  1.00  21.71        O
ATOM  10793  CG2  THR  D  89    -8.128  -37.555  65.842  1.00  18.21        C
ATOM  10797  C    THR  D  89    -7.936  -38.515  63.015  1.00  20.70        C
ATOM  10798  O    THR  D  89    -6.748  -38.846  63.018  1.00  21.58        O
ATOM  10800  N    VAL  D  90    -8.905  -39.356  62.651  1.00  18.90        N
ATOM  10801  CA   VAL  D  90    -8.575  -40.751  62.300  1.00  18.68        C
ATOM  10803  CB   VAL  D  90    -9.819  -41.654  62.157  1.00  17.20        C
ATOM  10805  CG1  VAL  D  90    -9.392  -43.035  61.644  1.00  16.28        C
ATOM  10809  CG2  VAL  D  90   -10.556  -41.763  63.533  1.00  17.37        C
ATOM  10813  C    VAL  D  90    -7.723  -40.901  61.045  1.00  18.56        C
ATOM  10814  O    VAL  D  90    -6.818  -41.728  61.018  1.00  20.06        O
ATOM  10816  N    VAL  D  91    -8.012  -40.135  59.999  1.00  18.11        N
ATOM  10817  CA   VAL  D  91    -7.185  -40.195  58.801  1.00  18.28        C
ATOM  10819  CB   VAL  D  91    -7.840  -39.460  57.632  1.00  17.88        C
ATOM  10821  CG1  VAL  D  91    -6.850  -39.230  56.491  1.00  18.37        C
ATOM  10825  CG2  VAL  D  91    -9.047  -40.250  57.133  1.00  16.26        C
ATOM  10829  C    VAL  D  91    -5.761  -39.677  59.076  1.00  20.42        C
ATOM  10830  O    VAL  D  91    -4.800  -40.221  58.558  1.00  21.57        O
ATOM  10832  N    ASN  D  92    -5.620  -38.655  59.910  1.00  21.56        N
ATOM  10833  CA   ASN  D  92    -4.294  -38.161  60.254  1.00  23.76        C
ATOM  10835  CB   ASN  D  92    -4.374  -36.861  61.085  1.00  24.40        C
ATOM  10838  CG   ASN  D  92    -4.752  -35.655  60.246  1.00  23.60        C
ATOM  10839  OD1  ASN  D  92    -4.652  -35.695  59.022  1.00  23.35        O
ATOM  10840  ND2  ASN  D  92    -5.182  -34.580  60.893  1.00  20.20        N
ATOM  10843  C    ASN  D  92    -3.456  -39.205  60.995  1.00  24.53        C
ATOM  10844  O    ASN  D  92    -2.258  -39.351  60.731  1.00  25.65        O
ATOM  10846  N    SER  D  93    -4.091  -39.916  61.918  1.00  23.92        N
ATOM  10847  CA   SER  D  93    -3.397  -40.927  62.700  1.00  25.43        C
ATOM  10849  CB   SER  D  93    -4.262  -41.322  63.899  1.00  25.34        C
ATOM  10852  OG   SER  D  93    -4.094  -42.677  64.262  1.00  27.29        O
ATOM  10854  C    SER  D  93    -2.976  -42.152  61.844  1.00  25.59        C
ATOM  10855  O    SER  D  93    -1.891  -42.666  61.994  1.00  27.01        O
ATOM  10857  N    ILE  D  94    -3.829  -42.604  60.940  1.00  24.37        N
ATOM  10858  CA   ILE  D  94    -3.470  -43.674  60.013  1.00  24.56        C
ATOM  10860  CB   ILE  D  94    -4.665  -44.037  59.110  1.00  23.03        C
ATOM  10862  CG1  ILE  D  94    -5.766  -44.709  59.916  1.00  21.15        C
ATOM  10865  CD1  ILE  D  94    -7.088  -44.664  59.194  1.00  22.77        C
ATOM  10869  CG2  ILE  D  94    -4.246  -44.899  58.001  1.00  20.27        C
ATOM  10873  C    ILE  D  94    -2.319  -43.268  59.094  1.00  26.61        C
ATOM  10874  O    ILE  D  94    -1.409  -44.082  58.777  1.00  26.98        O
ATOM  10876  N    CYS  D  95    -2.351  -42.015  58.654  1.00  27.05        N
ATOM  10877  CA   CYS  D  95    -1.315  -41.541  57.743  1.00  28.72        C
ATOM  10879  CB   CYS  D  95    -1.733  -40.233  57.066  1.00  28.26        C
ATOM  10882  SG   CYS  D  95    -3.036  -40.558  55.823  1.00  29.35        S
ATOM  10884  C    CYS  D  95     0.047  -41.465  58.430  1.00  30.59        C
ATOM  10885  O    CYS  D  95     1.036  -41.931  57.884  1.00  31.72        O
ATOM  10887  N    ASN  D  96     0.095  -40.899  59.630  1.00  32.04        N
ATOM  10888  CA   ASN  D  96     1.373  -40.730  60.360  1.00  34.51        C
ATOM  10890  CB   ASN  D  96     1.190  -39.935  61.652  1.00  35.40        C
ATOM  10893  CG   ASN  D  96     0.683  -38.513  61.430  1.00  35.47        C
ATOM  10894  OD1  ASN  D  96     1.257  -37.749  60.662  1.00  36.94        O
```

FIG. 3M

```
ATOM  10895  ND2 ASN D  96     -0.367 -38.144  62.158  1.00 31.66      N
ATOM  10898  C   ASN D  96      1.979 -42.084  60.744  1.00 35.23      C
ATOM  10899  O   ASN D  96      3.201 -42.216  60.885  1.00 37.25      O
ATOM  10901  N   THR D  97      1.098 -43.074  60.879  1.00 33.72      N
ATOM  10902  CA  THR D  97      1.429 -44.410  61.351  1.00 34.39      C
ATOM  10904  CB  THR D  97      0.212 -45.029  62.077  1.00 32.39      C
ATOM  10906  OG1 THR D  97      0.184 -44.535  63.412  1.00 34.63      O
ATOM  10908  CG2 THR D  97      0.316 -46.501  62.150  1.00 33.78      C
ATOM  10912  C   THR D  97      1.898 -45.352  60.241  1.00 34.38      C
ATOM  10913  O   THR D  97      2.930 -45.982  60.378  1.00 36.17      O
ATOM  10915  N   THR D  98      1.113 -45.477  59.174  1.00 32.90      N
ATOM  10916  CA  THR D  98      1.442 -46.372  58.079  1.00 33.46      C
ATOM  10918  CB  THR D  98      0.196 -46.880  57.315  1.00 31.74      C
ATOM  10920  OG1 THR D  98     -0.621 -45.767  56.926  1.00 33.13      O
ATOM  10922  CG2 THR D  98     -0.632 -47.860  58.190  1.00 31.22      C
ATOM  10926  C   THR D  98      2.344 -45.678  57.097  1.00 34.36      C
ATOM  10927  O   THR D  98      3.120 -46.332  56.437  1.00 35.52      O
ATOM  10929  N   GLY D  99      2.254 -44.353  57.007  1.00 34.38      N
ATOM  10930  CA  GLY D  99      3.077 -43.598  56.082  1.00 35.61      C
ATOM  10933  C   GLY D  99      2.447 -43.529  54.709  1.00 35.08      C
ATOM  10934  O   GLY D  99      3.098 -43.099  53.774  1.00 36.15      O
ATOM  10936  N   VAL D 100      1.181 -43.940  54.578  1.00 33.53      N
ATOM  10937  CA  VAL D 100      0.446 -43.707  53.338  1.00 33.15      C
ATOM  10939  CB  VAL D 100     -0.897 -44.437  53.297  1.00 31.43      C
ATOM  10941  CG1 VAL D 100     -1.698 -43.934  52.103  1.00 31.38      C
ATOM  10945  CG2 VAL D 100     -0.684 -45.952  53.178  1.00 32.18      C
ATOM  10949  C   VAL D 100      0.153 -42.229  53.108  1.00 33.44      C
ATOM  10950  O   VAL D 100     -0.201 -41.489  54.032  1.00 33.23      O
ATOM  10952  N   GLU D 101      0.305 -41.815  51.860  1.00 34.85      N
ATOM  10953  CA  GLU D 101     -0.086 -40.489  51.389  1.00 35.66      C
ATOM  10955  CB  GLU D 101     -0.106 -40.511  49.840  1.00 37.08      C
ATOM  10958  CG  GLU D 101     -0.914 -39.393  49.144  1.00 39.86      C
ATOM  10961  CD  GLU D 101     -0.412 -39.071  47.734  1.00 44.29      C
ATOM  10962  OE1 GLU D 101     -1.173 -38.473  46.951  1.00 46.95      O
ATOM  10963  OE2 GLU D 101      0.747 -39.395  47.404  1.00 48.84      O
ATOM  10964  C   GLU D 101     -1.435 -40.057  51.975  1.00 33.15      C
ATOM  10965  O   GLU D 101     -2.332 -40.858  52.193  1.00 31.25      O
ATOM  10967  N   LYS D 102     -1.577 -38.783  52.272  1.00 33.92      N
ATOM  10968  CA  LYS D 102     -2.842 -38.311  52.856  1.00 32.27      C
ATOM  10970  CB  LYS D 102     -2.650 -37.072  53.743  1.00 32.89      C
ATOM  10973  CG  LYS D 102     -3.710 -36.947  54.865  1.00 30.89      C
ATOM  10976  CD  LYS D 102     -3.414 -35.816  55.873  1.00 31.22      C
ATOM  10979  CE  LYS D 102     -2.233 -36.142  56.783  1.00 32.10      C
ATOM  10982  NZ  LYS D 102     -2.088 -35.330  58.041  1.00 31.25      N
ATOM  10986  C   LYS D 102     -3.802 -38.016  51.723  1.00 31.74      C
ATOM  10987  O   LYS D 102     -3.455 -37.334  50.775  1.00 32.47      O
ATOM  10989  N   PRO D 103     -5.007 -38.572  51.799  1.00 30.57      N
ATOM  10990  CA  PRO D 103     -5.992 -38.255  50.801  1.00 30.52      C
ATOM  10992  CB  PRO D 103     -7.100 -39.262  51.080  1.00 28.44      C
ATOM  10995  CG  PRO D 103     -6.982 -39.583  52.491  1.00 27.57      C
ATOM  10998  CD  PRO D 103     -5.582 -39.356  52.903  1.00 29.57      C
ATOM  11001  C   PRO D 103     -6.455 -36.820  50.996  1.00 31.35      C
ATOM  11002  O   PRO D 103     -6.427 -36.328  52.118  1.00 30.64      O
ATOM  11003  N   LYS D 104     -6.837 -36.154  49.905  1.00 33.01      N
ATOM  11004  CA  LYS D 104     -7.235 -34.730  49.952  1.00 34.29      C
ATOM  11006  CB  LYS D 104     -6.745 -33.978  48.702  1.00 36.54      C
ATOM  11009  CG  LYS D 104     -5.224 -34.077  48.450  1.00 38.95      C
ATOM  11012  CD  LYS D 104     -4.859 -33.499  47.086  1.00 41.60      C
ATOM  11015  CE  LYS D 104     -3.634 -34.185  46.474  1.00 43.82      C
ATOM  11018  NZ  LYS D 104     -3.371 -33.689  45.065  1.00 45.63      N
ATOM  11022  C   LYS D 104     -8.757 -34.561  50.121  1.00 32.74      C
ATOM  11023  O   LYS D 104     -9.277 -33.458  50.014  1.00 34.40      O
ATOM  11025  N   PHE D 105     -9.449 -35.661  50.381  1.00 30.39      N
```

FIG. 3N

```
ATOM  11026  CA   PHE D 105     -10.880 -35.666 50.700  1.00 29.29           C
ATOM  11028  CB   PHE D 105     -11.697 -36.031 49.455  1.00 29.63           C
ATOM  11031  CG   PHE D 105     -11.755 -37.523 49.184  1.00 31.64           C
ATOM  11032  CD1  PHE D 105     -12.926 -38.259 49.447  1.00 33.99           C
ATOM  11034  CE1  PHE D 105     -12.991 -39.670 49.202  1.00 31.96           C
ATOM  11036  CZ   PHE D 105     -11.869 -40.337 48.715  1.00 31.31           C
ATOM  11038  CE2  PHE D 105     -10.695 -39.608 48.440  1.00 32.98           C
ATOM  11040  CD2  PHE D 105     -10.640 -38.211 48.684  1.00 33.57           C
ATOM  11042  C    PHE D 105     -11.081 -36.740 51.769  1.00 26.05           C
ATOM  11043  O    PHE D 105     -10.225 -37.590 51.932  1.00 24.89           O
ATOM  11045  N    LEU D 106     -12.192 -36.736 52.489  1.00 24.17           N
ATOM  11046  CA   LEU D 106     -12.481 -37.890 53.384  1.00 22.29           C
ATOM  11048  CB   LEU D 106     -13.461 -37.503 54.469  1.00 20.83           C
ATOM  11051  CG   LEU D 106     -12.891 -36.516 55.478  1.00 21.62           C
ATOM  11053  CD1  LEU D 106     -14.026 -36.112 56.402  1.00 20.23           C
ATOM  11057  CD2  LEU D 106     -11.704 -37.104 56.260  1.00 20.68           C
ATOM  11061  C    LEU D 106     -13.007 -39.151 52.657  1.00 21.28           C
ATOM  11062  O    LEU D 106     -14.085 -39.106 52.103  1.00 21.19           O
ATOM  11064  N    PRO D 107     -12.254 -40.281 52.685  1.00 21.24           N
ATOM  11065  CA   PRO D 107     -12.745 -41.625 52.272  1.00 20.47           C
ATOM  11067  CB   PRO D 107     -11.494 -42.507 52.344  1.00 20.82           C
ATOM  11070  CG   PRO D 107     -10.355 -41.601 52.365  1.00 22.49           C
ATOM  11073  CD   PRO D 107     -10.811 -40.316 52.990  1.00 22.15           C
ATOM  11076  C    PRO D 107     -13.778 -42.225 53.215  1.00 19.49           C
ATOM  11077  O    PRO D 107     -14.140 -41.620 54.189  1.00 19.91           O
ATOM  11078  N    ASP D 108     -14.210 -43.444 52.956  1.00 19.04           N
ATOM  11079  CA   ASP D 108     -15.120 -44.105 53.873  1.00 18.39           C
ATOM  11081  CB   ASP D 108     -16.179 -44.797 53.063  1.00 18.10           C
ATOM  11084  CG   ASP D 108     -16.958 -43.811 52.180  1.00 17.67           C
ATOM  11085  OD1  ASP D 108     -17.461 -42.812 52.747  1.00 12.43           O
ATOM  11086  OD2  ASP D 108     -17.082 -44.059 50.948  1.00 15.59           O
ATOM  11087  C    ASP D 108     -14.459 -45.090 54.849  1.00 18.94           C
ATOM  11088  O    ASP D 108     -14.894 -45.163 56.000  1.00 18.33           O
ATOM  11090  N    LEU D 109     -13.419 -45.799 54.379  1.00 19.03           N
ATOM  11091  CA   LEU D 109     -12.735 -46.843 55.105  1.00 19.62           C
ATOM  11093  CB   LEU D 109     -13.223 -48.210 54.645  1.00 20.13           C
ATOM  11096  CG   LEU D 109     -14.645 -48.661 54.995  1.00 22.03           C
ATOM  11098  CD1  LEU D 109     -14.814 -50.120 54.632  1.00 23.58           C
ATOM  11102  CD2  LEU D 109     -15.000 -48.417 56.472  1.00 21.73           C
ATOM  11106  C    LEU D 109     -11.243 -46.820 54.823  1.00 20.51           C
ATOM  11107  O    LEU D 109     -10.836 -46.332 53.758  1.00 20.97           O
ATOM  11109  N    TYR D 110     -10.452 -47.322 55.788  1.00 20.70           N
ATOM  11110  CA   TYR D 110      -9.052 -47.655 55.604  1.00 22.01           C
ATOM  11112  CB   TYR D 110      -8.138 -46.893 56.586  1.00 22.47           C
ATOM  11115  CG   TYR D 110      -6.704 -47.186 56.285  1.00 21.12           C
ATOM  11116  CD1  TYR D 110      -6.098 -46.644 55.163  1.00 20.26           C
ATOM  11118  CE1  TYR D 110      -4.802 -46.948 54.836  1.00 22.71           C
ATOM  11120  CZ   TYR D 110      -4.054 -47.811 55.645  1.00 23.66           C
ATOM  11121  OH   TYR D 110      -2.751 -48.111 55.294  1.00 26.81           O
ATOM  11123  CE2  TYR D 110      -4.623 -48.366 56.755  1.00 22.33           C
ATOM  11125  CD2  TYR D 110      -5.974 -48.061 57.060  1.00 22.26           C
ATOM  11127  C    TYR D 110      -8.840 -49.177 55.803  1.00 24.15           C
ATOM  11128  O    TYR D 110      -9.313 -49.743 56.807  1.00 23.87           O
ATOM  11130  N    ASP D 111      -8.119 -49.806 54.860  1.00 25.63           N
ATOM  11131  CA   ASP D 111      -7.811 -51.247 54.881  1.00 27.51           C
ATOM  11133  CB   ASP D 111      -7.919 -51.810 53.474  1.00 28.12           C
ATOM  11136  CG   ASP D 111      -7.706 -53.315 53.415  1.00 30.82           C
ATOM  11137  OD1  ASP D 111      -7.171 -53.906 54.379  1.00 34.77           O
ATOM  11138  OD2  ASP D 111      -8.074 -53.920 52.383  1.00 31.66           O
ATOM  11139  C    ASP D 111      -6.390 -51.502 55.353  1.00 29.31           C
ATOM  11140  O    ASP D 111      -5.446 -51.110 54.686  1.00 29.40           O
ATOM  11142  N    TYR D 112      -6.234 -52.194 56.474  1.00 30.68           N
ATOM  11143  CA   TYR D 112      -4.904 -52.410 57.049  1.00 32.66           C
```

FIG. 30

```
ATOM  11145 CB   TYR D 112      -4.993 -52.715  58.546  1.00 33.52           C
ATOM  11148 CG   TYR D 112      -5.365 -51.527  59.389  1.00 34.28           C
ATOM  11149 CD1  TYR D 112      -6.594 -51.485  60.059  1.00 35.69           C
ATOM  11151 CE1  TYR D 112      -6.955 -50.373  60.857  1.00 35.35           C
ATOM  11153 CZ   TYR D 112      -6.066 -49.301  61.000  1.00 37.04           C
ATOM  11154 OH   TYR D 112      -6.441 -48.225  61.804  1.00 38.71           O
ATOM  11156 CE2  TYR D 112      -4.817 -49.329  60.354  1.00 35.88           C
ATOM  11158 CD2  TYR D 112      -4.479 -50.447  59.553  1.00 36.05           C
ATOM  11160 C    TYR D 112      -4.101 -53.511  56.361  1.00 33.66           C
ATOM  11161 O    TYR D 112      -2.872 -53.497  56.395  1.00 34.40           O
ATOM  11163 N    LYS D 113      -4.789 -54.474  55.759  1.00 33.94           N
ATOM  11164 CA   LYS D 113      -4.108 -55.570  55.065  1.00 35.12           C
ATOM  11166 CB   LYS D 113      -5.068 -56.728  54.794  1.00 35.57           C
ATOM  11169 CG   LYS D 113      -4.367 -58.023  54.310  1.00 39.16           C
ATOM  11172 CD   LYS D 113      -5.202 -58.748  53.260  1.00 41.19           C
ATOM  11175 CE   LYS D 113      -4.423 -59.843  52.580  1.00 44.54           C
ATOM  11178 NZ   LYS D 113      -4.163 -60.984  53.505  1.00 47.74           N
ATOM  11182 C    LYS D 113      -3.490 -55.077  53.758  1.00 34.66           C
ATOM  11183 O    LYS D 113      -2.354 -55.437  53.450  1.00 36.20           O
ATOM  11185 N    GLU D 114      -4.232 -54.254  53.013  1.00 32.70           N
ATOM  11186 CA   GLU D 114      -3.830 -53.798  51.669  1.00 33.14           C
ATOM  11188 CB   GLU D 114      -5.057 -53.764  50.742  1.00 32.77           C
ATOM  11191 CG   GLU D 114      -5.564 -55.147  50.299  1.00 34.95           C
ATOM  11194 CD   GLU D 114      -4.604 -55.862  49.358  1.00 39.59           C
ATOM  11195 OE1  GLU D 114      -3.997 -55.162  48.498  1.00 42.17           O
ATOM  11196 OE2  GLU D 114      -4.466 -57.111  49.471  1.00 40.13           O
ATOM  11197 C    GLU D 114      -3.164 -52.423  51.689  1.00 32.17           C
ATOM  11198 O    GLU D 114      -2.580 -51.978  50.701  1.00 31.87           O
ATOM  11200 N    ASN D 115      -3.268 -51.776  52.841  1.00 31.58           N
ATOM  11201 CA   ASN D 115      -2.694 -50.464  53.133  1.00 31.82           C
ATOM  11203 CB   ASN D 115      -1.173 -50.546  53.354  1.00 33.95           C
ATOM  11206 CG   ASN D 115      -0.818 -50.884  54.821  1.00 36.60           C
ATOM  11207 OD1  ASN D 115       0.074 -51.697  55.063  1.00 40.72           O
ATOM  11208 ND2  ASN D 115      -1.534 -50.273  55.799  1.00 32.45           N
ATOM  11211 C    ASN D 115      -3.095 -49.327  52.204  1.00 30.47           C
ATOM  11212 O    ASN D 115      -2.262 -48.590  51.665  1.00 31.43           O
ATOM  11214 N    ARG D 116      -4.396 -49.152  52.100  1.00 28.23           N
ATOM  11215 CA   ARG D 116      -4.973 -48.147  51.227  1.00 27.72           C
ATOM  11217 CB   ARG D 116      -5.085 -48.730  49.824  1.00 27.48           C
ATOM  11220 CG   ARG D 116      -6.036 -49.926  49.729  1.00 27.69           C
ATOM  11223 CD   ARG D 116      -5.969 -50.567  48.377  1.00 28.30           C
ATOM  11226 NE   ARG D 116      -6.766 -51.783  48.296  1.00 28.86           N
ATOM  11228 CZ   ARG D 116      -6.607 -52.743  47.380  1.00 29.74           C
ATOM  11229 NH1  ARG D 116      -5.662 -52.658  46.449  1.00 29.18           N
ATOM  11232 NH2  ARG D 116      -7.380 -53.822  47.422  1.00 30.56           N
ATOM  11235 C    ARG D 116      -6.352 -47.732  51.756  1.00 25.96           C
ATOM  11236 O    ARG D 116      -7.055 -48.528  52.357  1.00 26.03           O
ATOM  11238 N    PHE D 117      -6.736 -46.492  51.555  1.00 25.82           N
ATOM  11239 CA   PHE D 117      -8.116 -46.094  51.840  1.00 24.79           C
ATOM  11241 CB   PHE D 117      -8.251 -44.574  51.892  1.00 25.21           C
ATOM  11244 CG   PHE D 117      -7.588 -43.959  53.084  1.00 26.40           C
ATOM  11245 CD1  PHE D 117      -8.269 -43.860  54.293  1.00 25.80           C
ATOM  11247 CE1  PHE D 117      -7.655 -43.305  55.397  1.00 29.23           C
ATOM  11249 CZ   PHE D 117      -6.325 -42.848  55.302  1.00 30.05           C
ATOM  11251 CE2  PHE D 117      -5.637 -42.944  54.103  1.00 29.22           C
ATOM  11253 CD2  PHE D 117      -6.268 -43.508  53.000  1.00 28.74           C
ATOM  11255 C    PHE D 117      -9.040 -46.617  50.760  1.00 24.69           C
ATOM  11256 O    PHE D 117      -8.602 -46.928  49.643  1.00 24.86           O
ATOM  11258 N    ILE D 118     -10.322 -46.706  51.114  1.00 23.62           N
ATOM  11259 CA   ILE D 118     -11.383 -47.101  50.188  1.00 23.01           C
ATOM  11261 CB   ILE D 118     -12.052 -48.393  50.629  1.00 22.85           C
ATOM  11263 CG1  ILE D 118     -11.035 -49.514  50.753  1.00 24.26           C
ATOM  11266 CD1  ILE D 118     -11.595 -50.697  51.505  1.00 26.62           C
```

FIG. 3P

```
ATOM  11270  CG2 ILE D 118    -13.117 -48.790  49.662  1.00 21.80           C
ATOM  11274  C   ILE D 118    -12.490 -46.062  50.143  1.00 22.17           C
ATOM  11275  O   ILE D 118    -12.931 -45.573  51.194  1.00 20.78           O
ATOM  11277  N   GLU D 119    -12.925 -45.733  48.922  1.00 22.67           N
ATOM  11278  CA  GLU D 119    -14.179 -45.016  48.696  1.00 22.16           C
ATOM  11280  CB  GLU D 119    -13.965 -43.863  47.709  1.00 22.98           C
ATOM  11283  CG  GLU D 119    -15.186 -42.998  47.364  1.00 24.76           C
ATOM  11286  CD  GLU D 119    -15.959 -42.482  48.562  1.00 26.12           C
ATOM  11287  OE1 GLU D 119    -15.316 -42.302  49.598  1.00 29.20           O
ATOM  11288  OE2 GLU D 119    -17.200 -42.236  48.484  1.00 27.45           O
ATOM  11289  C   GLU D 119    -15.235 -46.008  48.205  1.00 21.91           C
ATOM  11290  O   GLU D 119    -15.050 -46.661  47.158  1.00 22.57           O
ATOM  11292  N   ILE D 120    -16.304 -46.132  48.999  1.00 20.63           N
ATOM  11293  CA  ILE D 120    -17.486 -46.922  48.699  1.00 20.54           C
ATOM  11295  CB  ILE D 120    -18.163 -47.392  49.967  1.00 20.44           C
ATOM  11297  CG1 ILE D 120    -17.237 -48.288  50.814  1.00 21.06           C
ATOM  11300  CD1 ILE D 120    -17.494 -49.775  50.641  1.00 20.07           C
ATOM  11304  CG2 ILE D 120    -19.440 -48.140  49.641  1.00 20.24           C
ATOM  11308  C   ILE D 120    -18.519 -46.080  47.980  1.00 21.10           C
ATOM  11309  O   ILE D 120    -18.717 -44.922  48.305  1.00 21.73           O
ATOM  11311  N   GLY D 121    -19.175 -46.668  46.992  1.00 22.15           N
ATOM  11312  CA  GLY D 121    -20.267 -46.021  46.258  1.00 22.76           C
ATOM  11315  C   GLY D 121    -21.515 -46.901  46.236  1.00 22.95           C
ATOM  11316  O   GLY D 121    -21.410 -48.124  46.174  1.00 23.35           O
ATOM  11318  N   VAL D 122    -22.685 -46.276  46.337  1.00 22.92           N
ATOM  11319  CA  VAL D 122    -23.966 -46.955  46.221  1.00 23.71           C
ATOM  11321  CB  VAL D 122    -24.682 -47.087  47.573  1.00 22.99           C
ATOM  11323  CG1 VAL D 122    -25.852 -48.092  47.449  1.00 25.65           C
ATOM  11327  CG2 VAL D 122    -23.737 -47.507  48.633  1.00 20.66           C
ATOM  11331  C   VAL D 122    -24.851 -46.186  45.264  1.00 25.15           C
ATOM  11332  O   VAL D 122    -25.250 -45.081  45.547  1.00 25.16           O
ATOM  11334  N   THR D 123    -25.138 -46.772  44.115  1.00 27.83           N
ATOM  11335  CA  THR D 123    -25.885 -46.091  43.046  1.00 29.95           C
ATOM  11337  CB  THR D 123    -24.998 -45.920  41.763  1.00 31.02           C
ATOM  11339  OG1 THR D 123    -25.690 -45.154  40.762  1.00 32.09           O
ATOM  11341  CG2 THR D 123    -24.587 -47.255  41.193  1.00 30.85           C
ATOM  11345  C   THR D 123    -27.182 -46.844  42.701  1.00 32.09           C
ATOM  11346  O   THR D 123    -27.222 -48.060  42.638  1.00 31.54           O
ATOM  11348  N   ARG D 124    -28.239 -46.090  42.473  1.00 34.91           N
ATOM  11349  CA  ARG D 124    -29.484 -46.633  41.967  1.00 38.00           C
ATOM  11351  CB  ARG D 124    -30.655 -45.745  42.412  1.00 39.13           C
ATOM  11354  CG  ARG D 124    -30.968 -45.808  43.917  1.00 38.96           C
ATOM  11357  CD  ARG D 124    -30.222 -44.751  44.710  1.00 39.84           C
ATOM  11360  NE  ARG D 124    -30.923 -43.475  44.825  1.00 42.41           N
ATOM  11362  CZ  ARG D 124    -30.373 -42.346  45.288  1.00 45.57           C
ATOM  11363  NH1 ARG D 124    -29.096 -42.307  45.684  1.00 45.12           N
ATOM  11366  NH2 ARG D 124    -31.105 -41.232  45.360  1.00 48.31           N
ATOM  11369  C   ARG D 124    -29.454 -46.736  40.438  1.00 40.77           C
ATOM  11370  O   ARG D 124    -30.433 -47.186  39.816  1.00 42.13           O
ATOM  11372  N   ARG D 125    -28.335 -46.314  39.847  1.00 41.57           N
ATOM  11373  CA  ARG D 125    -28.208 -46.174  38.395  1.00 45.03           C
ATOM  11375  CB  ARG D 125    -27.855 -44.719  38.005  1.00 46.02           C
ATOM  11378  CG  ARG D 125    -28.510 -43.614  38.832  1.00 48.87           C
ATOM  11381  CD  ARG D 125    -28.243 -42.204  38.247  1.00 53.76           C
ATOM  11384  NE  ARG D 125    -29.113 -41.923  37.088  1.00 60.75           N
ATOM  11386  CZ  ARG D 125    -28.865 -41.024  36.129  1.00 64.34           C
ATOM  11387  NH1 ARG D 125    -27.764 -40.268  36.175  1.00 65.11           N
ATOM  11390  NH2 ARG D 125    -29.722 -40.884  35.116  1.00 65.65           N
ATOM  11393  C   ARG D 125    -27.124 -47.151  37.894  1.00 44.97           C
ATOM  11394  O   ARG D 125    -26.933 -48.222  38.473  1.00 44.28           O
ATOM  11396  N   GLU D 126    -26.406 -46.786  36.831  1.00 46.10           N
ATOM  11397  CA  GLU D 126    -25.518 -47.722  36.180  1.00 46.17           C
ATOM  11399  CB  GLU D 126    -25.428 -47.422  34.691  1.00 49.13           C
```

FIG. 3Q

```
ATOM  11402  CG   GLU D 126     -24.992 -48.616  33.849  1.00 51.00           C
ATOM  11405  CD   GLU D 126     -23.490 -48.805  33.849  1.00 50.01           C
ATOM  11406  OE1  GLU D 126     -22.998 -49.964  33.883  1.00 50.63           O
ATOM  11407  OE2  GLU D 126     -22.803 -47.774  33.843  1.00 47.97           O
ATOM  11408  C    GLU D 126     -24.158 -47.682  36.864  1.00 43.96           C
ATOM  11409  O    GLU D 126     -23.516 -46.618  36.986  1.00 43.49           O
ATOM  11411  N    VAL D 127     -23.726 -48.870  37.290  1.00 42.11           N
ATOM  11412  CA   VAL D 127     -22.574 -49.031  38.166  1.00 39.12           C
ATOM  11414  CB   VAL D 127     -22.497 -50.506  38.648  1.00 38.93           C
ATOM  11416  CG1  VAL D 127     -21.698 -51.387  37.667  1.00 40.52           C
ATOM  11420  CG2  VAL D 127     -21.964 -50.603  40.064  1.00 36.45           C
ATOM  11424  C    VAL D 127     -21.266 -48.577  37.499  1.00 38.61           C
ATOM  11425  O    VAL D 127     -20.306 -48.303  38.167  1.00 37.48           O
ATOM  11427  N    HIS D 128     -21.242 -48.461  36.186  1.00 39.10           N
ATOM  11428  CA   HIS D 128     -20.037 -48.056  35.492  1.00 39.49           C
ATOM  11430  CB   HIS D 128     -20.093 -48.585  34.040  1.00 42.49           C
ATOM  11433  CG   HIS D 128     -18.768 -48.912  33.446  1.00 42.48           C
ATOM  11434  ND1  HIS D 128     -18.624 -49.851  32.449  1.00 45.75           N
ATOM  11436  CE1  HIS D 128     -17.355 -49.922  32.090  1.00 46.12           C
ATOM  11438  NE2  HIS D 128     -16.665 -49.074  32.834  1.00 45.23           N
ATOM  11440  CD2  HIS D 128     -17.528 -48.427  33.689  1.00 42.92           C
ATOM  11442  C    HIS D 128     -19.835 -46.522  35.502  1.00 38.84           C
ATOM  11443  O    HIS D 128     -18.779 -46.043  35.854  1.00 37.66           O
ATOM  11445  N    ILE D 129     -20.836 -45.745  35.102  1.00 39.76           N
ATOM  11446  CA   ILE D 129     -20.624 -44.305  34.995  1.00 39.99           C
ATOM  11448  CB   ILE D 129     -21.637 -43.549  34.038  1.00 42.72           C
ATOM  11450  CG1  ILE D 129     -22.787 -42.906  34.785  1.00 42.83           C
ATOM  11453  CD1  ILE D 129     -23.882 -42.403  33.834  1.00 47.90           C
ATOM  11457  CG2  ILE D 129     -22.180 -44.452  32.918  1.00 44.46           C
ATOM  11461  C    ILE D 129     -20.539 -43.701  36.390  1.00 37.06           C
ATOM  11462  O    ILE D 129     -19.853 -42.703  36.588  1.00 37.31           O
ATOM  11464  N    TYR D 130     -21.191 -44.327  37.364  1.00 34.61           N
ATOM  11465  CA   TYR D 130     -21.031 -43.926  38.737  1.00 31.96           C
ATOM  11467  CB   TYR D 130     -22.055 -44.615  39.650  1.00 31.69           C
ATOM  11470  CG   TYR D 130     -22.158 -43.979  41.017  1.00 28.18           C
ATOM  11471  CD1  TYR D 130     -22.982 -42.892  41.235  1.00 30.14           C
ATOM  11473  CE1  TYR D 130     -23.097 -42.296  42.509  1.00 31.16           C
ATOM  11475  CZ   TYR D 130     -22.359 -42.797  43.562  1.00 29.86           C
ATOM  11476  OH   TYR D 130     -22.439 -42.223  44.797  1.00 31.44           O
ATOM  11478  CE2  TYR D 130     -21.530 -43.882  43.367  1.00 29.97           C
ATOM  11480  CD2  TYR D 130     -21.431 -44.467  42.078  1.00 29.02           C
ATOM  11482  C    TYR D 130     -19.644 -44.194  39.260  1.00 30.26           C
ATOM  11483  O    TYR D 130     -19.095 -43.342  39.896  1.00 30.16           O
ATOM  11485  N    TYR D 131     -19.062 -45.362  39.028  1.00 30.19           N
ATOM  11486  CA   TYR D 131     -17.605 -45.521  39.293  1.00 29.83           C
ATOM  11488  CB   TYR D 131     -17.011 -46.781  38.667  1.00 31.00           C
ATOM  11491  CG   TYR D 131     -15.520 -47.025  38.964  1.00 30.49           C
ATOM  11492  CD1  TYR D 131     -15.123 -47.845  40.001  1.00 29.21           C
ATOM  11494  CE1  TYR D 131     -13.787 -48.093  40.250  1.00 28.88           C
ATOM  11496  CZ   TYR D 131     -12.829 -47.526  39.450  1.00 30.39           C
ATOM  11497  OH   TYR D 131     -11.494 -47.764  39.703  1.00 32.25           O
ATOM  11499  CE2  TYR D 131     -13.192 -46.721  38.414  1.00 30.93           C
ATOM  11501  CD2  TYR D 131     -14.524 -46.480  38.170  1.00 32.61           C
ATOM  11503  C    TYR D 131     -16.809 -44.378  38.745  1.00 31.11           C
ATOM  11504  O    TYR D 131     -15.954 -43.877  39.423  1.00 30.80           O
ATOM  11506  N    LEU D 132     -17.052 -44.002  37.495  1.00 34.01           N
ATOM  11507  CA   LEU D 132     -16.241 -42.985  36.851  1.00 36.05           C
ATOM  11509  CB   LEU D 132     -16.518 -42.969  35.353  1.00 38.96           C
ATOM  11512  CG   LEU D 132     -16.149 -44.222  34.546  1.00 40.94           C
ATOM  11514  CD1  LEU D 132     -16.564 -44.059  33.102  1.00 43.11           C
ATOM  11518  CD2  LEU D 132     -14.660 -44.537  34.600  1.00 42.31           C
ATOM  11522  C    LEU D 132     -16.472 -41.602  37.468  1.00 36.06           C
ATOM  11523  O    LEU D 132     -15.515 -40.839  37.641  1.00 35.93           O
```

FIG. 3R

```
ATOM  11525  N   GLU D 133     -17.722 -41.294  37.820  1.00 36.17           N
ATOM  11526  CA  GLU D 133     -18.037 -40.016  38.447  1.00 36.93           C
ATOM  11528  CB  GLU D 133     -19.534 -39.861  38.735  1.00 36.22           C
ATOM  11531  CG  GLU D 133     -20.284 -39.334  37.514  1.00 39.74           C
ATOM  11534  CD  GLU D 133     -21.813 -39.546  37.514  1.00 42.20           C
ATOM  11535  OE1 GLU D 133     -22.374 -40.317  38.341  1.00 43.64           O
ATOM  11536  OE2 GLU D 133     -22.468 -38.930  36.646  1.00 44.27           O
ATOM  11537  C   GLU D 133     -17.234 -39.931  39.710  1.00 35.85           C
ATOM  11538  O   GLU D 133     -16.646 -38.914  40.034  1.00 36.14           O
ATOM  11540  N   LYS D 134     -17.157 -41.042  40.402  1.00 35.38           N
ATOM  11541  CA  LYS D 134     -16.385 -41.078  41.609  1.00 34.94           C
ATOM  11543  CB  LYS D 134     -16.693 -42.358  42.375  1.00 33.62           C
ATOM  11546  CG  LYS D 134     -17.970 -42.261  43.165  1.00 33.21           C
ATOM  11549  CD  LYS D 134     -17.774 -41.405  44.446  1.00 32.64           C
ATOM  11552  CE  LYS D 134     -18.893 -41.629  45.489  1.00 31.69           C
ATOM  11555  NZ  LYS D 134     -20.059 -40.724  45.291  1.00 32.12           N
ATOM  11559  C   LYS D 134     -14.905 -40.931  41.346  1.00 36.35           C
ATOM  11560  O   LYS D 134     -14.268 -40.107  41.971  1.00 35.94           O
ATOM  11562  N   ALA D 135     -14.357 -41.708  40.416  1.00 38.90           N
ATOM  11563  CA  ALA D 135     -12.962 -41.529  40.015  1.00 41.34           C
ATOM  11565  CB  ALA D 135     -12.616 -42.413  38.834  1.00 42.63           C
ATOM  11569  C   ALA D 135     -12.726 -40.056  39.683  1.00 44.50           C
ATOM  11570  O   ALA D 135     -11.825 -39.431  40.239  1.00 45.52           O
ATOM  11572  N   ASN D 136     -13.561 -39.493  38.812  1.00 47.13           N
ATOM  11573  CA  ASN D 136     -13.468 -38.066  38.459  1.00 49.96           C
ATOM  11575  CB  ASN D 136     -14.446 -37.761  37.310  1.00 52.17           C
ATOM  11578  CG  ASN D 136     -14.197 -36.428  36.664  1.00 54.64           C
ATOM  11579  OD1 ASN D 136     -14.484 -35.376  37.234  1.00 55.02           O
ATOM  11580  ND2 ASN D 136     -13.693 -36.463  35.447  1.00 58.23           N
ATOM  11583  C   ASN D 136     -13.689 -37.074  39.637  1.00 49.63           C
ATOM  11584  O   ASN D 136     -13.053 -36.020  39.670  1.00 50.64           O
ATOM  11586  N   LYS D 137     -14.578 -37.392  40.582  1.00 48.40           N
ATOM  11587  CA  LYS D 137     -14.800 -36.505  41.741  1.00 48.61           C
ATOM  11589  CB  LYS D 137     -16.046 -36.882  42.570  1.00 47.09           C
ATOM  11592  CG  LYS D 137     -17.384 -36.410  42.011  1.00 49.77           C
ATOM  11595  CD  LYS D 137     -18.519 -36.729  42.986  1.00 50.24           C
ATOM  11598  CE  LYS D 137     -19.838 -37.158  42.292  1.00 52.04           C
ATOM  11601  NZ  LYS D 137     -20.535 -38.202  43.127  1.00 49.80           N
ATOM  11605  C   LYS D 137     -13.594 -36.581  42.645  1.00 47.94           C
ATOM  11606  O   LYS D 137     -12.992 -35.566  42.967  1.00 48.99           O
ATOM  11608  N   ILE D 138     -13.283 -37.817  43.038  1.00 46.97           N
ATOM  11609  CA  ILE D 138     -12.137 -38.207  43.882  1.00 46.02           C
ATOM  11611  CB  ILE D 138     -11.884 -39.782  43.782  1.00 45.48           C
ATOM  11613  CG1 ILE D 138     -11.407 -40.362  45.098  1.00 43.83           C
ATOM  11616  CD1 ILE D 138     -10.806 -41.741  44.940  1.00 44.28           C
ATOM  11620  CG2 ILE D 138     -10.864 -40.175  42.636  1.00 46.83           C
ATOM  11624  C   ILE D 138     -10.819 -37.539  43.533  1.00 47.32           C
ATOM  11625  O   ILE D 138     -10.232 -36.854  44.355  1.00 46.85           O
ATOM  11627  N   LYS D 139     -10.370 -37.773  42.300  1.00 49.38           N
ATOM  11628  CA  LYS D 139      -8.969 -37.566  41.858  1.00 51.15           C
ATOM  11630  CB  LYS D 139      -8.797 -36.150  41.274  1.00 53.55           C
ATOM  11633  CG  LYS D 139      -9.849 -35.824  40.186  1.00 55.21           C
ATOM  11636  CD  LYS D 139      -9.567 -34.523  39.410  1.00 59.03           C
ATOM  11639  CE  LYS D 139     -10.178 -34.545  37.977  1.00 61.27           C
ATOM  11642  NZ  LYS D 139      -9.700 -33.421  37.089  1.00 62.12           N
ATOM  11646  C   LYS D 139      -7.875 -37.929  42.907  1.00 50.02           C
ATOM  11647  O   LYS D 139      -6.806 -37.343  42.928  1.00 51.38           O
ATOM  11649  N   SER D 140      -8.153 -38.900  43.772  1.00 47.96           N
ATOM  11650  CA  SER D 140      -7.090 -39.597  44.478  1.00 47.54           C
ATOM  11652  CB  SER D 140      -7.418 -39.879  45.952  1.00 45.45           C
ATOM  11655  OG  SER D 140      -6.869 -38.866  46.802  1.00 47.29           O
ATOM  11657  C   SER D 140      -6.888 -40.872  43.697  1.00 47.59           C
ATOM  11658  O   SER D 140      -7.683 -41.827  43.758  1.00 46.48           O
```

FIG. 3S

```
ATOM  11660  N    GLU D 141      -5.812 -40.878  42.935  1.00 49.10           N
ATOM  11661  CA   GLU D 141      -5.473 -42.033  42.145  1.00 49.51           C
ATOM  11663  CB   GLU D 141      -4.329 -41.686  41.188  1.00 52.84           C
ATOM  11666  CG   GLU D 141      -4.623 -40.504  40.223  1.00 55.81           C
ATOM  11669  CD   GLU D 141      -3.350 -39.799  39.748  1.00 60.59           C
ATOM  11670  OE1  GLU D 141      -2.370 -39.703  40.541  1.00 59.44           O
ATOM  11671  OE2  GLU D 141      -3.338 -39.331  38.577  1.00 64.77           O
ATOM  11672  C    GLU D 141      -5.096 -43.228  43.038  1.00 47.18           C
ATOM  11673  O    GLU D 141      -5.123 -44.369  42.561  1.00 47.70           O
ATOM  11675  N    LYS D 142      -4.748 -42.953  44.310  1.00 44.44           N
ATOM  11676  CA   LYS D 142      -4.318 -43.960  45.287  1.00 41.79           C
ATOM  11678  CB   LYS D 142      -3.197 -43.400  46.174  1.00 42.46           C
ATOM  11681  CG   LYS D 142      -1.833 -43.467  45.558  1.00 45.67           C
ATOM  11684  CD   LYS D 142      -0.773 -42.972  46.526  1.00 48.23           C
ATOM  11687  CE   LYS D 142       0.471 -42.481  45.782  1.00 52.26           C
ATOM  11690  NZ   LYS D 142       1.619 -42.223  46.691  1.00 54.00           N
ATOM  11694  C    LYS D 142      -5.439 -44.408  46.210  1.00 38.54           C
ATOM  11695  O    LYS D 142      -5.199 -45.189  47.155  1.00 38.05           O
ATOM  11697  N    THR D 143      -6.653 -43.914  45.998  1.00 35.44           N
ATOM  11698  CA   THR D 143      -7.769 -44.426  46.790  1.00 32.64           C
ATOM  11700  CB   THR D 143      -8.637 -43.276  47.372  1.00 31.53           C
ATOM  11702  OG1  THR D 143      -7.937 -42.683  48.477  1.00 32.38           O
ATOM  11704  CG2  THR D 143      -9.957 -43.761  47.873  1.00 29.73           C
ATOM  11708  C    THR D 143      -8.549 -45.499  45.999  1.00 31.14           C
ATOM  11709  O    THR D 143      -8.950 -45.289  44.877  1.00 32.45           O
ATOM  11711  N    HIS D 144      -8.725 -46.665  46.603  1.00 29.03           N
ATOM  11712  CA   HIS D 144      -9.411 -47.770  45.983  1.00 28.06           C
ATOM  11714  CB   HIS D 144      -9.064 -49.078  46.713  1.00 28.24           C
ATOM  11717  CG   HIS D 144      -9.145 -50.287  45.836  1.00 31.06           C
ATOM  11718  ND1  HIS D 144      -8.135 -50.636  44.957  1.00 33.84           N
ATOM  11720  CE1  HIS D 144      -8.503 -51.716  44.286  1.00 35.06           C
ATOM  11722  NE2  HIS D 144      -9.711 -52.075  44.695  1.00 33.08           N
ATOM  11724  CD2  HIS D 144     -10.140 -51.189  45.652  1.00 30.89           C
ATOM  11726  C    HIS D 144     -10.907 -47.467  46.043  1.00 26.18           C
ATOM  11727  O    HIS D 144     -11.419 -47.074  47.086  1.00 24.25           O
ATOM  11729  N    ILE D 145     -11.572 -47.594  44.897  1.00 25.76           N
ATOM  11730  CA   ILE D 145     -12.998 -47.343  44.750  1.00 24.45           C
ATOM  11732  CB   ILE D 145     -13.258 -46.514  43.496  1.00 26.08           C
ATOM  11734  CG1  ILE D 145     -12.229 -45.400  43.356  1.00 25.87           C
ATOM  11737  CD1  ILE D 145     -12.577 -44.397  42.255  1.00 25.33           C
ATOM  11741  CG2  ILE D 145     -14.708 -45.949  43.488  1.00 26.68           C
ATOM  11745  C    ILE D 145     -13.778 -48.666  44.591  1.00 24.08           C
ATOM  11746  O    ILE D 145     -13.437 -49.479  43.740  1.00 23.81           O
ATOM  11748  N    HIS D 146     -14.789 -48.889  45.444  1.00 23.05           N
ATOM  11749  CA   HIS D 146     -15.740 -50.013  45.295  1.00 22.78           C
ATOM  11751  CB   HIS D 146     -15.656 -50.947  46.495  1.00 22.61           C
ATOM  11754  CG   HIS D 146     -16.166 -52.328  46.222  1.00 23.08           C
ATOM  11755  ND1  HIS D 146     -15.623 -53.444  46.814  1.00 21.87           N
ATOM  11757  CE1  HIS D 146     -16.245 -54.521  46.356  1.00 26.01           C
ATOM  11759  NE2  HIS D 146     -17.165 -54.144  45.491  1.00 23.82           N
ATOM  11761  CD2  HIS D 146     -17.127 -52.776  45.379  1.00 25.01           C
ATOM  11763  C    HIS D 146     -17.170 -49.487  45.202  1.00 21.76           C
ATOM  11764  O    HIS D 146     -17.636 -48.842  46.124  1.00 18.96           O
ATOM  11766  N    ILE D 147     -17.849 -49.762  44.086  1.00 23.08           N
ATOM  11767  CA   ILE D 147     -19.234 -49.308  43.860  1.00 23.28           C
ATOM  11769  CB   ILE D 147     -19.415 -48.614  42.478  1.00 24.67           C
ATOM  11771  CG1  ILE D 147     -18.401 -47.489  42.263  1.00 24.03           C
ATOM  11774  CD1  ILE D 147     -18.472 -46.342  43.263  1.00 19.12           C
ATOM  11778  CG2  ILE D 147     -20.857 -48.076  42.297  1.00 24.14           C
ATOM  11782  C    ILE D 147     -20.165 -50.505  43.830  1.00 24.12           C
ATOM  11783  O    ILE D 147     -19.914 -51.444  43.083  1.00 25.47           O
ATOM  11785  N    PHE D 148     -21.241 -50.454  44.606  1.00 23.56           N
ATOM  11786  CA   PHE D 148     -22.360 -51.407  44.483  1.00 24.84           C
```

FIG. 3T

```
ATOM  11788  CB   PHE D 148     -22.716 -51.970  45.864  1.00 23.78           C
ATOM  11791  CG   PHE D 148     -21.571 -52.676  46.594  1.00 22.59           C
ATOM  11792  CD1  PHE D 148     -21.463 -54.076  46.574  1.00 22.09           C
ATOM  11794  CE1  PHE D 148     -20.453 -54.719  47.262  1.00 21.46           C
ATOM  11796  CZ   PHE D 148     -19.549 -53.993  48.016  1.00 20.38           C
ATOM  11798  CE2  PHE D 148     -19.640 -52.618  48.051  1.00 20.15           C
ATOM  11800  CD2  PHE D 148     -20.664 -51.963  47.358  1.00 20.22           C
ATOM  11802  C    PHE D 148     -23.656 -50.753  43.900  1.00 26.39           C
ATOM  11803  O    PHE D 148     -23.899 -49.553  44.096  1.00 25.58           O
ATOM  11805  N    SER D 149     -24.478 -51.535  43.181  1.00 28.44           N
ATOM  11806  CA   SER D 149     -25.842 -51.116  42.828  1.00 30.01           C
ATOM  11808  CB   SER D 149     -26.071 -51.275  41.343  1.00 32.27           C
ATOM  11811  OG   SER D 149     -26.391 -52.618  41.063  1.00 33.41           O
ATOM  11813  C    SER D 149     -26.932 -51.918  43.537  1.00 31.21           C
ATOM  11814  O    SER D 149     -26.674 -52.961  44.154  1.00 31.25           O
ATOM  11816  N    PHE D 150     -28.174 -51.453  43.413  1.00 33.01           N
ATOM  11817  CA   PHE D 150     -29.310 -52.140  44.055  1.00 34.21           C
ATOM  11819  CB   PHE D 150     -30.490 -51.192  44.299  1.00 34.37           C
ATOM  11822  CG   PHE D 150     -30.293 -50.220  45.430  1.00 32.20           C
ATOM  11823  CD1  PHE D 150     -30.872 -50.447  46.678  1.00 33.43           C
ATOM  11825  CE1  PHE D 150     -30.707 -49.527  47.736  1.00 31.51           C
ATOM  11827  CZ   PHE D 150     -29.985 -48.355  47.520  1.00 29.65           C
ATOM  11829  CE2  PHE D 150     -29.435 -48.122  46.270  1.00 29.66           C
ATOM  11831  CD2  PHE D 150     -29.598 -49.043  45.237  1.00 30.34           C
ATOM  11833  C    PHE D 150     -29.733 -53.318  43.172  1.00 37.08           C
ATOM  11834  O    PHE D 150     -30.488 -54.203  43.597  1.00 39.31           O
ATOM  11836  N    THR D 151     -29.237 -53.316  41.944  1.00 37.93           N
ATOM  11837  CA   THR D 151     -29.475 -54.382  40.987  1.00 40.29           C
ATOM  11839  CB   THR D 151     -29.445 -53.790  39.592  1.00 41.72           C
ATOM  11841  OG1  THR D 151     -30.615 -52.988  39.432  1.00 44.28           O
ATOM  11843  CG2  THR D 151     -29.450 -54.850  38.538  1.00 45.90           C
ATOM  11847  C    THR D 151     -28.453 -55.509  41.088  1.00 39.97           C
ATOM  11848  O    THR D 151     -28.538 -56.471  40.342  1.00 41.39           O
ATOM  11850  N    GLY D 152     -27.475 -55.389  41.994  1.00 37.82           N
ATOM  11851  CA   GLY D 152     -26.586 -56.510  42.304  1.00 37.91           C
ATOM  11854  C    GLY D 152     -25.234 -56.528  41.602  1.00 38.15           C
ATOM  11855  O    GLY D 152     -24.396 -57.391  41.888  1.00 38.24           O
ATOM  11857  N    GLU D 153     -25.000 -55.593  40.683  1.00 38.24           N
ATOM  11858  CA   GLU D 153     -23.694 -55.481  40.052  1.00 37.93           C
ATOM  11860  CB   GLU D 153     -23.787 -54.776  38.705  1.00 39.85           C
ATOM  11863  CG   GLU D 153     -24.753 -55.455  37.727  1.00 44.05           C
ATOM  11866  CD   GLU D 153     -26.037 -54.678  37.487  1.00 46.05           C
ATOM  11867  OE1  GLU D 153     -26.495 -54.637  36.320  1.00 50.88           O
ATOM  11868  OE2  GLU D 153     -26.588 -54.102  38.449  1.00 47.02           O
ATOM  11869  C    GLU D 153     -22.757 -54.734  40.975  1.00 35.05           C
ATOM  11870  O    GLU D 153     -23.154 -54.237  42.028  1.00 33.81           O
ATOM  11872  N    GLU D 154     -21.489 -54.690  40.595  1.00 34.47           N
ATOM  11873  CA   GLU D 154     -20.494 -54.026  41.392  1.00 31.77           C
ATOM  11875  CB   GLU D 154     -20.081 -54.860  42.616  1.00 30.63           C
ATOM  11878  CG   GLU D 154     -19.738 -56.313  42.287  1.00 32.09           C
ATOM  11881  CD   GLU D 154     -18.984 -57.063  43.387  1.00 31.57           C
ATOM  11882  OE1  GLU D 154     -18.518 -56.458  44.358  1.00 29.03           O
ATOM  11883  OE2  GLU D 154     -18.856 -58.300  43.279  1.00 35.08           O
ATOM  11884  C    GLU D 154     -19.317 -53.779  40.515  1.00 32.16           C
ATOM  11885  O    GLU D 154     -19.078 -54.510  39.565  1.00 33.55           O
ATOM  11887  N    MET D 155     -18.585 -52.730  40.846  1.00 30.95           N
ATOM  11888  CA   MET D 155     -17.350 -52.436  40.183  1.00 31.44           C
ATOM  11890  CB   MET D 155     -17.578 -51.383  39.109  1.00 32.43           C
ATOM  11893  CG   MET D 155     -16.393 -51.223  38.197  1.00 35.00           C
ATOM  11896  SD   MET D 155     -16.867 -50.320  36.753  1.00 40.80           S
ATOM  11897  CE   MET D 155     -17.791 -51.525  35.789  1.00 42.22           C
ATOM  11901  C    MET D 155     -16.342 -51.935  41.195  1.00 29.60           C
ATOM  11902  O    MET D 155     -16.703 -51.211  42.099  1.00 27.86           O
```

FIG. 3U

```
ATOM  11904  N    ALA D 156     -15.078 -52.315  40.997  1.00 30.56           N
ATOM  11905  CA   ALA D 156     -13.969 -51.891  41.826  1.00 29.48           C
ATOM  11907  CB   ALA D 156     -13.675 -52.944  42.876  1.00 29.13           C
ATOM  11911  C    ALA D 156     -12.708 -51.611  41.016  1.00 31.16           C
ATOM  11912  O    ALA D 156     -12.519 -52.122  39.910  1.00 31.47           O
ATOM  11914  N    THR D 157     -11.839 -50.796  41.617  1.00 31.56           N
ATOM  11915  CA   THR D 157     -10.532 -50.468  41.045  1.00 33.49           C
ATOM  11917  CB   THR D 157      -9.737 -49.560  41.981  1.00 32.23           C
ATOM  11919  OG1  THR D 157     -10.409 -48.315  42.028  1.00 30.99           O
ATOM  11921  CG2  THR D 157      -8.301 -49.306  41.483  1.00 32.10           C
ATOM  11925  C    THR D 157      -9.719 -51.701  40.677  1.00 35.89           C
ATOM  11926  O    THR D 157      -9.507 -52.605  41.490  1.00 36.07           O
ATOM  11928  N    LYS D 158      -9.316 -51.728  39.414  1.00 38.94           N
ATOM  11929  CA   LYS D 158      -8.505 -52.802  38.848  1.00 41.36           C
ATOM  11931  CB   LYS D 158      -7.070 -52.708  39.414  1.00 41.62           C
ATOM  11934  CG   LYS D 158      -6.554 -51.241  39.333  1.00 43.71           C
ATOM  11937  CD   LYS D 158      -5.045 -50.999  39.535  1.00 46.85           C
ATOM  11940  CE   LYS D 158      -4.748 -49.470  39.465  1.00 47.67           C
ATOM  11943  NZ   LYS D 158      -3.283 -49.088  39.519  1.00 50.10           N
ATOM  11947  C    LYS D 158      -9.160 -54.158  39.062  1.00 41.16           C
ATOM  11948  O    LYS D 158      -8.485 -55.151  39.158  1.00 43.22           O
ATOM  11950  N    ALA D 159     -10.486 -54.189  39.108  1.00 40.46           N
ATOM  11951  CA   ALA D 159     -11.268 -55.416  39.361  1.00 40.58           C
ATOM  11953  CB   ALA D 159     -11.213 -56.348  38.173  1.00 42.48           C
ATOM  11957  C    ALA D 159     -10.873 -56.156  40.647  1.00 39.88           C
ATOM  11958  O    ALA D 159     -11.089 -57.364  40.768  1.00 40.90           O
ATOM  11960  N    ASP D 160     -10.336 -55.407  41.610  1.00 38.43           N
ATOM  11961  CA   ASP D 160      -9.890 -55.944  42.873  1.00 37.41           C
ATOM  11963  CB   ASP D 160      -8.547 -55.312  43.223  1.00 37.65           C
ATOM  11966  CG   ASP D 160      -8.065 -55.705  44.585  1.00 38.77           C
ATOM  11967  OD1  ASP D 160      -8.821 -56.408  45.306  1.00 40.38           O
ATOM  11968  OD2  ASP D 160      -6.931 -55.309  44.931  1.00 41.04           O
ATOM  11969  C    ASP D 160     -10.955 -55.596  43.902  1.00 35.17           C
ATOM  11970  O    ASP D 160     -11.085 -54.445  44.328  1.00 34.28           O
ATOM  11972  N    TYR D 161     -11.730 -56.592  44.302  1.00 35.04           N
ATOM  11973  CA   TYR D 161     -12.921 -56.359  45.111  1.00 32.90           C
ATOM  11975  CB   TYR D 161     -14.026 -57.334  44.746  1.00 33.82           C
ATOM  11978  CG   TYR D 161     -14.434 -57.273  43.317  1.00 33.31           C
ATOM  11979  CD1  TYR D 161     -15.229 -56.236  42.853  1.00 31.18           C
ATOM  11981  CE1  TYR D 161     -15.625 -56.178  41.540  1.00 32.44           C
ATOM  11983  CZ   TYR D 161     -15.229 -57.176  40.677  1.00 33.70           C
ATOM  11984  OH   TYR D 161     -15.612 -57.130  39.382  1.00 35.47           O
ATOM  11986  CE2  TYR D 161     -14.455 -58.224  41.112  1.00 34.45           C
ATOM  11988  CD2  TYR D 161     -14.057 -58.266  42.432  1.00 34.07           C
ATOM  11990  C    TYR D 161     -12.662 -56.503  46.566  1.00 31.85           C
ATOM  11991  O    TYR D 161     -13.606 -56.565  47.346  1.00 30.83           O
ATOM  11993  N    THR D 162     -11.390 -56.591  46.933  1.00 32.70           N
ATOM  11994  CA   THR D 162     -10.966 -56.531  48.344  1.00 32.03           C
ATOM  11996  CB   THR D 162     -11.282 -55.156  49.000  1.00 29.88           C
ATOM  11998  OG1  THR D 162     -10.363 -54.165  48.511  1.00 28.97           O
ATOM  12000  CG2  THR D 162     -11.161 -55.228  50.511  1.00 29.13           C
ATOM  12004  C    THR D 162     -11.586 -57.653  49.151  1.00 32.99           C
ATOM  12005  O    THR D 162     -10.868 -58.530  49.620  1.00 34.69           O
ATOM  12007  N    LEU D 163     -12.905 -57.629  49.327  1.00 32.51           N
ATOM  12008  CA   LEU D 163     -13.568 -58.687  50.077  1.00 33.68           C
ATOM  12010  CB   LEU D 163     -14.964 -58.261  50.535  1.00 32.44           C
ATOM  12013  CG   LEU D 163     -15.030 -57.082  51.492  1.00 30.24           C
ATOM  12015  CD1  LEU D 163     -16.449 -56.801  51.991  1.00 25.53           C
ATOM  12019  CD2  LEU D 163     -14.106 -57.371  52.667  1.00 31.84           C
ATOM  12023  C    LEU D 163     -13.672 -60.008  49.301  1.00 36.23           C
ATOM  12024  O    LEU D 163     -13.398 -60.094  48.098  1.00 36.84           O
ATOM  12026  N    ASP D 164     -14.059 -61.038  50.041  1.00 37.83           N
ATOM  12027  CA   ASP D 164     -14.443 -62.316  49.471  1.00 40.28           C
```

FIG. 3V

```
ATOM  12029  CB   ASP D 164     -14.249 -63.472  50.467  1.00 42.34           C
ATOM  12032  CG   ASP D 164     -14.901 -63.212  51.811  1.00 42.62           C
ATOM  12033  OD1  ASP D 164     -15.120 -62.040  52.192  1.00 44.72           O
ATOM  12034  OD2  ASP D 164     -15.165 -64.194  52.509  1.00 46.90           O
ATOM  12035  C    ASP D 164     -15.885 -62.221  49.044  1.00 39.83           C
ATOM  12036  O    ASP D 164     -16.593 -61.273  49.416  1.00 38.82           O
ATOM  12038  N    GLU D 165     -16.311 -63.212  48.263  1.00 41.32           N
ATOM  12039  CA   GLU D 165     -17.567 -63.140  47.544  1.00 40.77           C
ATOM  12041  CB   GLU D 165     -17.654 -64.257  46.506  1.00 43.41           C
ATOM  12044  CG   GLU D 165     -18.683 -64.001  45.418  1.00 44.17           C
ATOM  12047  CD   GLU D 165     -18.903 -65.185  44.510  1.00 46.19           C
ATOM  12048  OE1  GLU D 165     -19.776 -65.094  43.633  1.00 47.41           O
ATOM  12049  OE2  GLU D 165     -18.216 -66.204  44.670  1.00 48.74           O
ATOM  12050  C    GLU D 165     -18.747 -63.177  48.495  1.00 40.26           C
ATOM  12051  O    GLU D 165     -19.741 -62.489  48.270  1.00 39.60           O
ATOM  12053  N    GLU D 166     -18.653 -63.942  49.573  1.00 40.83           N
ATOM  12054  CA   GLU D 166     -19.790 -64.022  50.485  1.00 40.94           C
ATOM  12056  CB   GLU D 166     -19.599 -65.125  51.529  1.00 43.13           C
ATOM  12059  CG   GLU D 166     -20.791 -65.319  52.506  1.00 45.95           C
ATOM  12062  CD   GLU D 166     -22.078 -65.877  51.858  1.00 50.29           C
ATOM  12063  OE1  GLU D 166     -22.171 -66.009  50.606  1.00 50.97           O
ATOM  12064  OE2  GLU D 166     -23.010 -66.205  52.626  1.00 51.77           O
ATOM  12065  C    GLU D 166     -20.091 -62.675  51.140  1.00 37.79           C
ATOM  12066  O    GLU D 166     -21.250 -62.254  51.215  1.00 37.49           O
ATOM  12068  N    SER D 167     -19.056 -61.985  51.593  1.00 35.47           N
ATOM  12069  CA   SER D 167     -19.264 -60.717  52.288  1.00 32.81           C
ATOM  12071  CB   SER D 167     -17.928 -60.183  52.787  1.00 31.40           C
ATOM  12074  OG   SER D 167     -17.219 -61.233  53.390  1.00 33.27           O
ATOM  12076  C    SER D 167     -19.944 -59.713  51.359  1.00 30.85           C
ATOM  12077  O    SER D 167     -20.846 -58.998  51.746  1.00 29.35           O
ATOM  12079  N    ARG D 168     -19.489 -59.702  50.121  1.00 30.86           N
ATOM  12080  CA   ARG D 168     -20.066 -58.886  49.062  1.00 30.41           C
ATOM  12082  CB   ARG D 168     -19.164 -58.963  47.825  1.00 31.30           C
ATOM  12085  CG   ARG D 168     -17.836 -58.296  48.081  1.00 32.31           C
ATOM  12088  CD   ARG D 168     -17.017 -58.318  46.847  1.00 35.25           C
ATOM  12091  NE   ARG D 168     -16.365 -59.603  46.702  1.00 37.68           N
ATOM  12093  CZ   ARG D 168     -16.173 -60.231  45.554  1.00 39.01           C
ATOM  12094  NH1  ARG D 168     -16.605 -59.722  44.405  1.00 39.11           N
ATOM  12097  NH2  ARG D 168     -15.549 -61.387  45.571  1.00 40.93           N
ATOM  12100  C    ARG D 168     -21.453 -59.339  48.669  1.00 30.59           C
ATOM  12101  O    ARG D 168     -22.302 -58.531  48.329  1.00 29.77           O
ATOM  12103  N    ALA D 169     -21.663 -60.645  48.676  1.00 31.96           N
ATOM  12104  CA   ALA D 169     -22.969 -61.179  48.373  1.00 33.14           C
ATOM  12106  CB   ALA D 169     -22.915 -62.688  48.264  1.00 35.23           C
ATOM  12110  C    ALA D 169     -23.929 -60.724  49.466  1.00 32.14           C
ATOM  12111  O    ALA D 169     -25.034 -60.291  49.188  1.00 31.42           O
ATOM  12113  N    ARG D 170     -23.459 -60.826  50.707  1.00 32.02           N
ATOM  12114  CA   ARG D 170     -24.132 -60.280  51.876  1.00 31.46           C
ATOM  12116  CB   ARG D 170     -23.161 -60.383  53.070  1.00 31.70           C
ATOM  12119  CG   ARG D 170     -23.797 -60.563  54.447  1.00 35.80           C
ATOM  12122  CD   ARG D 170     -22.767 -60.868  55.577  1.00 40.47           C
ATOM  12125  NE   ARG D 170     -23.113 -60.108  56.800  1.00 43.77           N
ATOM  12127  CZ   ARG D 170     -22.692 -58.866  57.092  1.00 43.38           C
ATOM  12128  NH1  ARG D 170     -21.856 -58.206  56.291  1.00 42.86           N
ATOM  12131  NH2  ARG D 170     -23.111 -58.266  58.208  1.00 43.95           N
ATOM  12134  C    ARG D 170     -24.631 -58.816  51.617  1.00 29.01           C
ATOM  12135  O    ARG D 170     -25.827 -58.536  51.758  1.00 28.41           O
ATOM  12137  N    ILE D 171     -23.720 -57.919  51.195  1.00 26.61           N
ATOM  12138  CA   ILE D 171     -24.065 -56.524  50.845  1.00 24.48           C
ATOM  12140  CB   ILE D 171     -22.804 -55.702  50.470  1.00 23.29           C
ATOM  12142  CG1  ILE D 171     -21.945 -55.422  51.718  1.00 22.42           C
ATOM  12145  CD1  ILE D 171     -20.487 -55.094  51.434  1.00 20.75           C
ATOM  12149  CG2  ILE D 171     -23.196 -54.388  49.761  1.00 19.72           C
```

FIG. 3W

```
ATOM  12153  C    ILE D 171     -25.014 -56.426  49.658  1.00 25.42           C
ATOM  12154  O    ILE D 171     -25.955 -55.624  49.676  1.00 24.89           O
ATOM  12156  N    LYS D 172     -24.750 -57.210  48.608  1.00 26.05           N
ATOM  12157  CA   LYS D 172     -25.603 -57.169  47.405  1.00 26.90           C
ATOM  12159  CB   LYS D 172     -25.069 -58.090  46.321  1.00 27.55           C
ATOM  12162  CG   LYS D 172     -23.887 -57.524  45.619  1.00 25.13           C
ATOM  12165  CD   LYS D 172     -23.084 -58.574  44.968  1.00 24.07           C
ATOM  12168  CE   LYS D 172     -21.815 -58.049  44.332  1.00 21.74           C
ATOM  12171  NZ   LYS D 172     -20.948 -59.188  43.839  1.00 23.23           N
ATOM  12175  C    LYS D 172     -27.062 -57.514  47.702  1.00 28.33           C
ATOM  12176  O    LYS D 172     -27.975 -56.849  47.220  1.00 28.52           O
ATOM  12178  N    THR D 173     -27.257 -58.552  48.496  1.00 29.69           N
ATOM  12179  CA   THR D 173     -28.576 -58.968  48.956  1.00 31.84           C
ATOM  12181  CB   THR D 173     -28.464 -60.226  49.823  1.00 33.15           C
ATOM  12183  OG1  THR D 173     -27.880 -61.258  49.032  1.00 34.28           O
ATOM  12185  CG2  THR D 173     -29.843 -60.669  50.345  1.00 33.68           C
ATOM  12189  C    THR D 173     -29.289 -57.907  49.782  1.00 31.15           C
ATOM  12190  O    THR D 173     -30.498 -57.705  49.654  1.00 32.04           O
ATOM  12192  N    ARG D 174     -28.544 -57.256  50.649  1.00 30.04           N
ATOM  12193  CA   ARG D 174     -29.115 -56.194  51.437  1.00 30.11           C
ATOM  12195  CB   ARG D 174     -28.042 -55.625  52.370  1.00 28.34           C
ATOM  12198  CG   ARG D 174     -28.506 -54.573  53.312  1.00 29.41           C
ATOM  12201  CD   ARG D 174     -29.703 -55.049  54.057  1.00 35.70           C
ATOM  12204  NE   ARG D 174     -29.949 -54.288  55.282  1.00 40.26           N
ATOM  12206  CZ   ARG D 174     -31.112 -53.730  55.618  1.00 44.12           C
ATOM  12207  NH1  ARG D 174     -32.169 -53.849  54.822  1.00 48.17           N
ATOM  12210  NH2  ARG D 174     -31.235 -53.063  56.766  1.00 43.20           N
ATOM  12213  C    ARG D 174     -29.722 -55.115  50.507  1.00 30.42           C
ATOM  12214  O    ARG D 174     -30.853 -54.703  50.709  1.00 31.19           O
ATOM  12216  N    LEU D 175     -28.992 -54.687  49.472  1.00 30.45           N
ATOM  12217  CA   LEU D 175     -29.503 -53.639  48.567  1.00 31.20           C
ATOM  12219  CB   LEU D 175     -28.390 -53.039  47.693  1.00 29.88           C
ATOM  12222  CG   LEU D 175     -27.208 -52.478  48.499  1.00 27.58           C
ATOM  12224  CD1  LEU D 175     -25.939 -52.327  47.659  1.00 26.06           C
ATOM  12228  CD2  LEU D 175     -27.591 -51.180  49.173  1.00 23.45           C
ATOM  12232  C    LEU D 175     -30.640 -54.205  47.715  1.00 34.22           C
ATOM  12233  O    LEU D 175     -31.663 -53.547  47.485  1.00 34.49           O
ATOM  12235  N    PHE D 176     -30.458 -55.450  47.301  1.00 36.30           N
ATOM  12236  CA   PHE D 176     -31.491 -56.191  46.646  1.00 39.61           C
ATOM  12238  CB   PHE D 176     -31.066 -57.664  46.476  1.00 41.55           C
ATOM  12241  CG   PHE D 176     -31.824 -58.402  45.399  1.00 44.53           C
ATOM  12242  CD1  PHE D 176     -31.396 -58.351  44.082  1.00 46.61           C
ATOM  12244  CE1  PHE D 176     -32.089 -59.032  43.068  1.00 49.41           C
ATOM  12246  CZ   PHE D 176     -33.222 -59.778  43.387  1.00 51.85           C
ATOM  12248  CE2  PHE D 176     -33.662 -59.831  44.716  1.00 50.56           C
ATOM  12250  CD2  PHE D 176     -32.956 -59.143  45.709  1.00 47.43           C
ATOM  12252  C    PHE D 176     -32.765 -56.063  47.470  1.00 40.89           C
ATOM  12253  O    PHE D 176     -33.791 -55.556  46.972  1.00 42.53           O
ATOM  12255  N    THR D 177     -32.691 -56.486  48.734  1.00 40.51           N
ATOM  12256  CA   THR D 177     -33.829 -56.398  49.651  1.00 40.93           C
ATOM  12258  CB   THR D 177     -33.437 -56.873  51.089  1.00 40.82           C
ATOM  12260  OG1  THR D 177     -33.513 -58.302  51.144  1.00 43.04           O
ATOM  12262  CG2  THR D 177     -34.361 -56.310  52.154  1.00 41.08           C
ATOM  12266  C    THR D 177     -34.415 -54.985  49.687  1.00 39.49           C
ATOM  12267  O    THR D 177     -35.598 -54.814  49.442  1.00 41.04           O
ATOM  12269  N    ILE D 178     -33.591 -53.977  49.964  1.00 36.71           N
ATOM  12270  CA   ILE D 178     -34.092 -52.598  50.165  1.00 35.43           C
ATOM  12272  CB   ILE D 178     -32.947 -51.593  50.459  1.00 32.62           C
ATOM  12274  CG1  ILE D 178     -32.364 -51.798  51.861  1.00 31.58           C
ATOM  12277  CD1  ILE D 178     -30.876 -51.395  52.009  1.00 27.36           C
ATOM  12281  CG2  ILE D 178     -33.426 -50.201  50.367  1.00 31.39           C
ATOM  12285  C    ILE D 178     -34.928 -52.103  48.978  1.00 37.06           C
ATOM  12286  O    ILE D 178     -35.981 -51.521  49.163  1.00 38.29           O
```

FIG. 3X

| | | | | | | | | | | |
|---|---|---|---|---|---|---|---|---|---|---|
|ATOM|12288|N|ARG|D|179|-34.465|-52.362|47.764|1.00 37.72|N|
|ATOM|12289|CA|ARG|D|179|-35.134|-51.888|46.552|1.00 39.49|C|
|ATOM|12291|CB|ARG|D|179|-34.224|-52.137|45.326|1.00 39.85|C|
|ATOM|12294|CG|ARG|D|179|-34.933|-52.378|43.996|1.00 43.52|C|
|ATOM|12297|CD|ARG|D|179|-33.963|-52.193|42.820|1.00 46.15|C|
|ATOM|12300|NE|ARG|D|179|-34.013|-53.225|41.789|1.00 48.57|N|
|ATOM|12302|CZ|ARG|D|179|-35.036|-53.443|40.964|1.00 53.40|C|
|ATOM|12303|NH1|ARG|D|179|-36.163|-52.737|41.050|1.00 54.73|N|
|ATOM|12306|NH2|ARG|D|179|-34.940|-54.399|40.047|1.00 55.92|N|
|ATOM|12309|C|ARG|D|179|-36.472|-52.582|46.357|1.00 41.99|C|
|ATOM|12310|O|ARG|D|179|-37.454|-51.963|45.953|1.00 43.26|O|
|ATOM|12312|N|GLN|D|180|-36.486|-53.886|46.615|1.00 42.75|N|
|ATOM|12313|CA|GLN|D|180|-37.699|-54.661|46.512|1.00 45.40|C|
|ATOM|12315|CB|GLN|D|180|-37.391|-56.167|46.567|1.00 46.64|C|
|ATOM|12318|CG|GLN|D|180|-36.582|-56.600|45.324|1.00 48.36|C|
|ATOM|12321|CD|GLN|D|180|-36.702|-58.061|44.959|1.00 51.64|C|
|ATOM|12322|OE1|GLN|D|180|-36.816|-58.917|45.830|1.00 54.29|O|
|ATOM|12323|NE2|GLN|D|180|-36.638|-58.357|43.658|1.00 52.43|N|
|ATOM|12326|C|GLN|D|180|-38.722|-54.231|47.551|1.00 45.54|C|
|ATOM|12327|O|GLN|D|180|-39.897|-54.173|47.248|1.00 47.32|O|
|ATOM|12329|N|GLU|D|181|-38.281|-53.890|48.751|1.00 44.02|N|
|ATOM|12330|CA|GLU|D|181|-39.214|-53.434|49.762|1.00 45.40|C|
|ATOM|12332|CB|GLU|D|181|-38.611|-53.525|51.167|1.00 44.53|C|
|ATOM|12335|CG|GLU|D|181|-38.563|-54.951|51.731|1.00 47.63|C|
|ATOM|12338|CD|GLU|D|181|-39.835|-55.755|51.459|1.00 53.66|C|
|ATOM|12339|OE1|GLU|D|181|-40.837|-55.553|52.194|1.00 57.27|O|
|ATOM|12340|OE2|GLU|D|181|-39.835|-56.577|50.504|1.00 56.33|O|
|ATOM|12341|C|GLU|D|181|-39.727|-52.029|49.464|1.00 44.92|C|
|ATOM|12342|O|GLU|D|181|-40.911|-51.768|49.636|1.00 46.40|O|
|ATOM|12344|N|MET|D|182|-38.847|-51.147|49.001|1.00 43.02|N|
|ATOM|12345|CA|MET|D|182|-39.246|-49.807|48.527|1.00 43.23|C|
|ATOM|12347|CB|MET|D|182|-38.039|-48.995|48.052|1.00 41.07|C|
|ATOM|12350|CG|MET|D|182|-37.247|-48.310|49.111|1.00 38.22|C|
|ATOM|12353|SD|MET|D|182|-35.864|-47.434|48.358|1.00 37.92|S|
|ATOM|12354|CE|MET|D|182|-35.329|-46.346|49.672|1.00 39.82|C|
|ATOM|12358|C|MET|D|182|-40.222|-49.913|47.360|1.00 46.23|C|
|ATOM|12359|O|MET|D|182|-41.181|-49.138|47.281|1.00 47.86|O|
|ATOM|12361|N|ALA|D|183|-39.959|-50.850|46.447|1.00 46.98|N|
|ATOM|12362|CA|ALA|D|183|-40.876|-51.133|45.364|1.00 50.19|C|
|ATOM|12364|CB|ALA|D|183|-40.294|-52.210|44.447|1.00 50.69|C|
|ATOM|12368|C|ALA|D|183|-42.259|-51.556|45.914|1.00 52.99|C|
|ATOM|12369|O|ALA|D|183|-43.299|-51.073|45.450|1.00 55.13|O|
|ATOM|12371|N|SER|D|184|-42.262|-52.416|46.933|1.00 52.96|N|
|ATOM|12372|CA|SER|D|184|-43.499|-52.938|47.521|1.00 55.63|C|
|ATOM|12374|CB|SER|D|184|-43.193|-54.013|48.584|1.00 55.48|C|
|ATOM|12377|OG|SER|D|184|-42.547|-55.152|48.004|1.00 56.61|O|
|ATOM|12379|C|SER|D|184|-44.380|-51.846|48.119|1.00 55.96|C|
|ATOM|12380|O|SER|D|184|-45.520|-52.095|48.476|1.00 58.00|O|
|ATOM|12382|N|ARG|D|185|-43.839|-50.638|48.238|1.00 54.34|N|
|ATOM|12383|CA|ARG|D|185|-44.605|-49.485|48.690|1.00 54.82|C|
|ATOM|12385|CB|ARG|D|185|-44.085|-49.027|50.032|1.00 53.02|C|
|ATOM|12388|CG|ARG|D|185|-44.408|-49.994|51.138|1.00 56.42|C|
|ATOM|12391|CD|ARG|D|185|-43.287|-50.982|51.402|1.00 57.87|C|
|ATOM|12394|NE|ARG|D|185|-43.227|-51.331|52.818|1.00 61.18|N|
|ATOM|12396|CZ|ARG|D|185|-42.389|-52.213|53.364|1.00 62.75|C|
|ATOM|12397|NH1|ARG|D|185|-41.510|-52.831|52.611|1.00 61.78|N|
|ATOM|12400|NH2|ARG|D|185|-42.442|-52.414|54.687|1.00 63.46|N|
|ATOM|12403|C|ARG|D|185|-44.523|-48.342|47.717|1.00 54.23|C|
|ATOM|12404|O|ARG|D|185|-44.808|-47.210|48.079|1.00 53.61|O|
|ATOM|12406|N|SER|D|186|-44.142|-48.650|46.479|1.00 54.48|N|
|ATOM|12407|CA|SER|D|186|-43.914|-47.647|45.437|1.00 54.60|C|
|ATOM|12409|CB|SER|D|186|-45.242|-47.355|44.712|1.00 58.29|C|
|ATOM|12412|OG|SER|D|186|-46.327|-47.327|45.620|1.00 59.32|O|

FIG. 3Y

| | | | | | | | | | |
|---|---|---|---|---|---|---|---|---|---|
| ATOM | 12414 | C | SER | D | 186 | -43.221 | -46.354 | 45.933 | 1.00 52.16 | C |
| ATOM | 12415 | O | SER | D | 186 | -43.622 | -45.242 | 45.592 | 1.00 52.94 | O |
| ATOM | 12417 | N | LEU | D | 187 | -42.183 | -46.516 | 46.745 | 1.00 49.04 | N |
| ATOM | 12418 | CA | LEU | D | 187 | -41.310 | -45.408 | 47.108 | 1.00 47.26 | C |
| ATOM | 12420 | CB | LEU | D | 187 | -40.807 | -45.581 | 48.556 | 1.00 45.01 | C |
| ATOM | 12423 | CG | LEU | D | 187 | -41.824 | -45.524 | 49.702 | 1.00 44.89 | C |
| ATOM | 12425 | CD1 | LEU | D | 187 | -41.312 | -46.318 | 50.907 | 1.00 41.69 | C |
| ATOM | 12429 | CD2 | LEU | D | 187 | -42.142 | -44.076 | 50.072 | 1.00 43.58 | C |
| ATOM | 12433 | C | LEU | D | 187 | -40.098 | -45.340 | 46.148 | 1.00 46.50 | C |
| ATOM | 12434 | O | LEU | D | 187 | -39.372 | -44.318 | 46.097 | 1.00 45.52 | O |
| ATOM | 12436 | N | TRP | D | 188 | -39.895 | -46.429 | 45.403 | 1.00 46.79 | N |
| ATOM | 12437 | CA | TRP | D | 188 | -38.670 | -46.662 | 44.648 | 1.00 46.35 | C |
| ATOM | 12439 | CB | TRP | D | 188 | -38.595 | -48.134 | 44.219 | 1.00 46.60 | C |
| ATOM | 12442 | CG | TRP | D | 188 | -37.524 | -48.411 | 43.236 | 1.00 44.64 | C |
| ATOM | 12443 | CD1 | TRP | D | 188 | -37.670 | -48.633 | 41.909 | 1.00 45.46 | C |
| ATOM | 12445 | NE1 | TRP | D | 188 | -36.449 | -48.864 | 41.319 | 1.00 43.84 | N |
| ATOM | 12447 | CE2 | TRP | D | 188 | -35.477 | -48.781 | 42.279 | 1.00 43.71 | C |
| ATOM | 12448 | CD2 | TRP | D | 188 | -36.125 | -48.484 | 43.505 | 1.00 43.13 | C |
| ATOM | 12449 | CE3 | TRP | D | 188 | -35.352 | -48.352 | 44.664 | 1.00 38.00 | C |
| ATOM | 12451 | CZ3 | TRP | D | 188 | -33.974 | -48.502 | 44.564 | 1.00 38.57 | C |
| ATOM | 12453 | CH2 | TRP | D | 188 | -33.347 | -48.788 | 43.328 | 1.00 37.48 | C |
| ATOM | 12455 | CZ2 | TRP | D | 188 | -34.076 | -48.921 | 42.178 | 1.00 41.08 | C |
| ATOM | 12457 | C | TRP | D | 188 | -38.505 | -45.769 | 43.411 | 1.00 48.51 | C |
| ATOM | 12458 | O | TRP | D | 188 | -37.491 | -45.093 | 43.241 | 1.00 47.29 | O |
| ATOM | 12460 | N | ASP | D | 189 | -39.491 | -45.785 | 42.530 | 1.00 52.50 | N |
| ATOM | 12461 | CA | ASP | D | 189 | -39.354 | -45.062 | 41.291 | 1.00 55.01 | C |
| ATOM | 12463 | CB | ASP | D | 189 | -40.665 | -45.133 | 40.491 | 1.00 58.57 | C |
| ATOM | 12466 | CG | ASP | D | 189 | -40.778 | -46.429 | 39.657 | 1.00 61.60 | C |
| ATOM | 12467 | OD1 | ASP | D | 189 | -41.897 | -46.992 | 39.549 | 1.00 64.37 | O |
| ATOM | 12468 | OD2 | ASP | D | 189 | -39.744 | -46.885 | 39.099 | 1.00 62.98 | O |
| ATOM | 12469 | C | ASP | D | 189 | -38.828 | -43.629 | 41.558 | 1.00 54.43 | C |
| ATOM | 12470 | O | ASP | D | 189 | -37.881 | -43.184 | 40.912 | 1.00 54.40 | O |
| ATOM | 12472 | N | SER | D | 190 | -39.388 | -42.954 | 42.557 | 1.00 54.60 | N |
| ATOM | 12473 | CA | SER | D | 190 | -38.973 | -41.596 | 42.941 | 1.00 54.39 | C |
| ATOM | 12475 | CB | SER | D | 190 | -39.994 | -41.040 | 43.952 | 1.00 54.76 | C |
| ATOM | 12478 | OG | SER | D | 190 | -39.508 | -39.894 | 44.627 | 1.00 54.38 | O |
| ATOM | 12480 | C | SER | D | 190 | -37.524 | -41.552 | 43.510 | 1.00 51.92 | C |
| ATOM | 12481 | O | SER | D | 190 | -36.734 | -40.639 | 43.207 | 1.00 51.62 | O |
| ATOM | 12483 | N | PHE | D | 191 | -37.204 | -42.541 | 44.341 | 1.00 50.22 | N |
| ATOM | 12484 | CA | PHE | D | 191 | -35.854 | -42.756 | 44.860 | 1.00 48.23 | C |
| ATOM | 12486 | CB | PHE | D | 191 | -35.847 | -44.033 | 45.717 | 1.00 46.68 | C |
| ATOM | 12489 | CG | PHE | D | 191 | -34.596 | -44.245 | 46.522 | 1.00 43.90 | C |
| ATOM | 12490 | CD1 | PHE | D | 191 | -34.231 | -43.357 | 47.530 | 1.00 43.04 | C |
| ATOM | 12492 | CE1 | PHE | D | 191 | -33.093 | -43.575 | 48.302 | 1.00 39.26 | C |
| ATOM | 12494 | CZ | PHE | D | 191 | -32.314 | -44.701 | 48.076 | 1.00 38.81 | C |
| ATOM | 12496 | CE2 | PHE | D | 191 | -32.664 | -45.597 | 47.081 | 1.00 40.47 | C |
| ATOM | 12498 | CD2 | PHE | D | 191 | -33.806 | -45.376 | 46.316 | 1.00 43.34 | C |
| ATOM | 12500 | C | PHE | D | 191 | -34.831 | -42.881 | 43.715 | 1.00 48.87 | C |
| ATOM | 12501 | O | PHE | D | 191 | -33.759 | -42.277 | 43.774 | 1.00 47.49 | O |
| ATOM | 12503 | N | ARG | D | 192 | -35.170 | -43.663 | 42.684 | 1.00 50.96 | N |
| ATOM | 12504 | CA | ARG | D | 192 | -34.286 | -43.844 | 41.533 | 1.00 51.76 | C |
| ATOM | 12506 | CB | ARG | D | 192 | -34.829 | -44.929 | 40.592 | 1.00 53.96 | C |
| ATOM | 12509 | CG | ARG | D | 192 | -34.006 | -45.207 | 39.298 | 1.00 55.98 | C |
| ATOM | 12512 | CD | ARG | D | 192 | -34.956 | -45.213 | 38.047 | 1.00 61.20 | C |
| ATOM | 12515 | NE | ARG | D | 192 | -34.263 | -45.335 | 36.761 | 1.00 63.86 | N |
| ATOM | 12517 | CZ | ARG | D | 192 | -34.812 | -45.098 | 35.566 | 1.00 68.34 | C |
| ATOM | 12518 | NH1 | ARG | D | 192 | -36.079 | -44.704 | 35.452 | 1.00 72.04 | N |
| ATOM | 12521 | NH2 | ARG | D | 192 | -34.085 | -45.246 | 34.463 | 1.00 69.34 | N |
| ATOM | 12524 | C | ARG | D | 192 | -34.138 | -42.515 | 40.817 | 1.00 52.89 | C |
| ATOM | 12525 | O | ARG | D | 192 | -33.030 | -42.076 | 40.537 | 1.00 51.34 | O |
| ATOM | 12527 | N | GLN | D | 193 | -35.259 | -41.854 | 40.561 | 1.00 55.49 | N |
| ATOM | 12528 | CA | GLN | D | 193 | -35.243 | -40.655 | 39.736 | 1.00 58.03 | C |
| ATOM | 12530 | CB | GLN | D | 193 | -36.667 | -40.178 | 39.419 | 1.00 60.99 | C |

FIG. 3Z

```
ATOM  12533  CG   GLN D 193     -37.538 -41.162  38.574  1.00 64.09           C
ATOM  12536  CD   GLN D 193     -36.980 -41.497  37.178  1.00 67.02           C
ATOM  12537  OE1  GLN D 193     -35.836 -41.171  36.836  1.00 67.05           O
ATOM  12538  NE2  GLN D 193     -37.804 -42.162  36.368  1.00 70.31           N
ATOM  12541  C    GLN D 193     -34.431 -39.508  40.329  1.00 57.02           C
ATOM  12542  O    GLN D 193     -34.048 -38.602  39.593  1.00 59.00           O
ATOM  12544  N    SER D 194     -34.135 -39.551  41.628  1.00 54.66           N
ATOM  12545  CA   SER D 194     -33.509 -38.399  42.304  1.00 53.79           C
ATOM  12547  CB   SER D 194     -34.262 -38.101  43.609  1.00 52.88           C
ATOM  12550  OG   SER D 194     -34.037 -39.109  44.572  1.00 50.44           O
ATOM  12552  C    SER D 194     -31.981 -38.449  42.575  1.00 51.71           C
ATOM  12553  O    SER D 194     -31.426 -37.492  43.110  1.00 51.24           O
ATOM  12555  N    GLU D 195     -31.288 -39.526  42.219  1.00 51.03           N
ATOM  12556  CA   GLU D 195     -29.820 -39.502  42.293  1.00 49.61           C
ATOM  12558  CB   GLU D 195     -29.223 -40.869  41.978  1.00 48.86           C
ATOM  12561  CG   GLU D 195     -27.737 -40.968  42.412  1.00 47.74           C
ATOM  12564  CD   GLU D 195     -27.161 -42.354  42.238  1.00 47.16           C
ATOM  12565  OE1  GLU D 195     -27.716 -43.298  42.831  1.00 46.61           O
ATOM  12566  OE2  GLU D 195     -26.154 -42.499  41.509  1.00 49.24           O
ATOM  12567  C    GLU D 195     -29.199 -38.442  41.365  1.00 51.23           C
ATOM  12568  O    GLU D 195     -29.595 -38.298  40.196  1.00 53.99           O
ATOM  12570  MN   MN  D 901     -18.745 -43.295  49.760  1.00 26.31          MN
ATOM  12571  MN   MN  D 902     -17.803 -40.957  52.434  1.00 34.52          MN
ATOM  12572  CL   ci3 D 801     -25.956 -34.127  53.753  1.00 54.96          CL
ATOM  12573  CZB  ci3 D 801     -24.690 -35.342  53.444  1.00 43.18           C
ATOM  12574  CEB  ci3 D 801     -24.448 -35.727  52.134  1.00 40.81           C
ATOM  12576  CDB  ci3 D 801     -23.468 -36.666  51.878  1.00 39.27           C
ATOM  12578  CEA  ci3 D 801     -23.981 -35.856  54.527  1.00 40.07           C
ATOM  12580  CDA  ci3 D 801     -22.996 -36.797  54.275  1.00 39.18           C
ATOM  12582  CGA  ci3 D 801     -22.734 -37.200  52.949  1.00 38.70           C
ATOM  12583  CO   ci3 D 801     -21.646 -38.221  52.689  1.00 35.86           C
ATOM  12586  CF   ci3 D 801     -20.316 -37.614  52.180  1.00 33.98           C
ATOM  12587  CB   ci3 D 801     -19.651 -38.848  51.627  1.00 29.61           C
ATOM  12588  CM   ci3 D 801     -20.220 -39.457  50.399  1.00 26.51           C
ATOM  12590  CA   ci3 D 801     -19.959 -40.717  49.992  1.00 25.57           C
ATOM  12591  CE   ci3 D 801     -20.655 -41.205  48.791  1.00 25.30           C
ATOM  12592  OAO  ci3 D 801     -20.599 -42.397  48.496  1.00 25.52           O
ATOM  12593  OAN  ci3 D 801     -21.313 -40.438  48.064  1.00 27.12           O
ATOM  12594  O14  ci3 D 801     -19.090 -41.503  50.630  1.00 22.81           O
ATOM  12596  O13  ci3 D 801     -18.745 -39.389  52.269  1.00 30.18           O
ATOM  12597  CG   ci3 D 801     -20.543 -36.526  51.115  1.00 36.49           C
ATOM  12600  CK   ci3 D 801     -19.310 -35.745  50.632  1.00 37.77           C
ATOM  12603  CI   ci3 D 801     -18.302 -35.444  51.736  1.00 36.98           C
ATOM  12606  NJ   ci3 D 801     -18.837 -35.721  53.085  1.00 38.68           N
ATOM  12608  CH   ci3 D 801     -19.477 -37.051  53.325  1.00 35.02           C
ATOM  12611  CP   ci3 D 801     -17.773 -35.502  54.121  1.00 40.12           C
ATOM  12614  CGB  ci3 D 801     -18.471 -35.119  55.413  1.00 42.33           C
ATOM  12615  CD1  ci3 D 801     -18.172 -35.778  56.596  1.00 42.90           C
ATOM  12617  CE1  ci3 D 801     -18.862 -35.438  57.757  1.00 44.15           C
ATOM  12619  CZ   ci3 D 801     -19.840 -34.427  57.731  1.00 46.06           C
ATOM  12621  CE2  ci3 D 801     -20.145 -33.764  56.556  1.00 44.97           C
ATOM  12623  CD2  ci3 D 801     -19.452 -34.112  55.402  1.00 44.58           C
ATOM  12625  S    SO4 D 401     -14.624 -34.192  52.148  1.00 66.16           S
ATOM  12626  O1   SO4 D 401     -15.155 -35.548  52.307  1.00 64.30           O
ATOM  12627  O2   SO4 D 401     -13.212 -34.208  52.533  1.00 66.20           O
ATOM  12628  O3   SO4 D 401     -15.314 -33.237  53.026  1.00 65.34           O
ATOM  12629  O4   SO4 D 401     -14.788 -33.791  50.731  1.00 67.19           O
ATOM  12630  S    SO4 D 402     -34.392 -49.793  38.082  1.00 77.20           S
ATOM  12631  O1   SO4 D 402     -33.781 -48.467  38.166  1.00 76.12           O
ATOM  12632  O2   SO4 D 402     -35.849 -49.595  38.009  1.00 78.54           O
ATOM  12633  O3   SO4 D 402     -34.050 -50.591  39.265  1.00 74.06           O
ATOM  12634  O4   SO4 D 402     -33.880 -50.461  36.875  1.00 77.77           O
ATOM  12635  S    SO4 D 403     -34.859 -35.764  47.792  1.00 71.04           S
```

FIG. 3AA

```
ATOM  12636  O1   SO4 D 403     -33.707 -36.216  48.593  1.00 64.37           O
ATOM  12637  O2   SO4 D 403     -34.918 -34.295  47.851  1.00 72.70           O
ATOM  12638  O3   SO4 D 403     -36.136 -36.311  48.281  1.00 70.86           O
ATOM  12639  O4   SO4 D 403     -34.737 -36.186  46.387  1.00 71.30           O
ATOM   6464  OH2  WAT D 903     -12.713 -53.361  46.394  1.00 18.08      D    O
ATOM   6466  OH2  WAT D 904     -23.583 -42.624  54.397  1.00 21.49      D    O
ATOM   6469  OH2  WAT D 905     -16.273 -40.780  51.257  1.00 25.68      D    O
ATOM   6470  OH2  WAT D 906     -17.996 -39.513  48.206  1.00 59.37      D    O
ATOM   6473  OH2  WAT D 907     -36.072 -38.721  60.846  1.00 29.20      D    O
ATOM   6474  OH2  WAT D 908     -13.932 -51.948  62.527  1.00 59.26      D    O
ATOM   6476  OH2  WAT D 909     -13.424 -32.315  54.842  1.00 28.40      D    O
ATOM   6477  OH2  WAT D 910     -16.728 -40.455  54.280  1.00 20.53      D    O
ATOM   6479  OH2  WAT D 911     -21.321 -49.827  31.532  1.00 61.32      D    O
END
```

FIG. 3AB

```
H1N1 polypeptide fragment (Chain A) with bound EMBL-
R05-2
HEADER       ----                                        XX-XXX-XX   xxxx
COMPND       ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.07
REMARK   3   RESOLUTION RANGE LOW  (ANGSTROMS) :  43.96
REMARK   3   DATA CUTOFF            (SIGMA(F)) :   NONE
REMARK   3   COMPLETENESS FOR RANGE        (%) :  83.72
REMARK   3   NUMBER OF REFLECTIONS             :  42925
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE     (WORKING + TEST SET) : 0.20756
REMARK   3   R VALUE            (WORKING SET) : 0.20470
REMARK   3   FREE R VALUE                     : 0.25936
REMARK   3   FREE R VALUE TEST SET SIZE   (%) : 5.2
REMARK   3   FREE R VALUE TEST SET COUNT      : 2363
REMARK   3
REMARK   3  FIT IN THE HIGHEST RESOLUTION BIN.
REMARK   3   TOTAL NUMBER OF BINS USED           :     20
REMARK   3   BIN RESOLUTION RANGE HIGH           :  2.074
REMARK   3   BIN RESOLUTION RANGE LOW            :  2.128
REMARK   3   REFLECTION IN BIN     (WORKING SET) :      0
REMARK   3   BIN COMPLETENESS (WORKING+TEST) (%) :   0.00
REMARK   3   BIN R VALUE           (WORKING SET) :  0.000
REMARK   3   BIN FREE R VALUE SET COUNT          :      0
REMARK   3   BIN FREE R VALUE                    :  0.000
REMARK   3
REMARK   3  NUMBER OF NON-HYDROGEN ATOMS USED IN REFINEMENT.
REMARK   3   ALL ATOMS                 :     6854
REMARK   3
REMARK   3  B VALUES.
REMARK   3   FROM WILSON PLOT           (A**2) :  NULL
REMARK   3   MEAN B VALUE      (OVERALL, A**2) : 27.640
REMARK   3   OVERALL ANISOTROPIC B VALUE.
REMARK   3    B11 (A**2) :      0.78
REMARK   3    B22 (A**2) :    -14.79
REMARK   3    B33 (A**2) :     14.01
REMARK   3    B12 (A**2) :      0.00
REMARK   3    B13 (A**2) :      0.00
REMARK   3    B23 (A**2) :      0.00
REMARK   3
REMARK   3  ESTIMATED OVERALL COORDINATE ERROR.
REMARK   3   ESU BASED ON R VALUE                    (A):   0.065
REMARK   3   ESU BASED ON FREE R VALUE               (A):   0.049
REMARK   3   ESU BASED ON MAXIMUM LIKELIHOOD         (A):   0.145
REMARK   3   ESU FOR B VALUES BASED ON MAXIMUM LIKELIHOOD (A**2):   5.932
REMARK   3
REMARK   3 CORRELATION COEFFICIENTS.
REMARK   3   CORRELATION COEFFICIENT FO-FC      :  0.938
REMARK   3   CORRELATION COEFFICIENT FO-FC FREE :  0.910
REMARK   3
```

FIG. 4A

```
REMARK   3    RMS DEVIATIONS FROM IDEAL VALUES          COUNT    RMS    WEIGHT
REMARK   3     BOND LENGTHS REFINED ATOMS       (A):    6698 ; 0.022 ; 0.022
REMARK   3     BOND LENGTHS OTHERS              (A):    4778 ; 0.001 ; 0.020
REMARK   3     BOND ANGLES REFINED ATOMS  (DEGREES):    8994 ; 1.850 ; 1.963
REMARK   3     BOND ANGLES OTHERS         (DEGREES):   11525 ; 1.010 ; 3.000
REMARK   3     TORSION ANGLES, PERIOD 1   (DEGREES):     766 ; 6.495 ; 5.000
REMARK   3     TORSION ANGLES, PERIOD 2   (DEGREES):     349 ;35.595 ;23.352
REMARK   3     TORSION ANGLES, PERIOD 3   (DEGREES):    1240 ;18.483 ;15.000
REMARK   3     TORSION ANGLES, PERIOD 4   (DEGREES):      60 ;18.609 ;15.000
REMARK   3     CHIRAL-CENTER RESTRAINTS       (A**3):    956 ; 0.112 ; 0.200
REMARK   3     GENERAL PLANES REFINED ATOMS     (A):    7283 ; 0.008 ; 0.020
REMARK   3     GENERAL PLANES OTHERS            (A):    1473 ; 0.001 ; 0.020
REMARK   3
REMARK   3    ISOTROPIC THERMAL FACTOR RESTRAINTS.     COUNT    RMS    WEIGHT
REMARK   3     MAIN-CHAIN BOND REFINED ATOMS  (A**2):   3872 ; 1.139 ; 1.500
REMARK   3     MAIN-CHAIN BOND OTHER ATOMS    (A**2):   1558 ; 0.276 ; 1.500
REMARK   3     MAIN-CHAIN ANGLE REFINED ATOMS (A**2):   6267 ; 2.034 ; 2.000
REMARK   3     SIDE-CHAIN BOND REFINED ATOMS  (A**2):   2826 ; 3.019 ; 3.000
REMARK   3     SIDE-CHAIN ANGLE REFINED ATOMS (A**2):   2727 ; 4.650 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  :    2
REMARK   3      TWIN DOMAIN   :   1
REMARK   3      TWIN OPERATOR :  H,   K,   L
REMARK   3      TWIN FRACTION : 0.945
REMARK   3      TWIN DOMAIN   :   2
REMARK   3      TWIN OPERATOR : -H,   L,   K
REMARK   3      TWIN FRACTION : 0.055
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3   HYDROGENS HAVE BEEN ADDED IN THE RIDING POSITIONS
REMARK   3   U VALUES      : REFINED INDIVIDUALLY
REMARK   3
LINKR              GLU A   64                ASN A   69                 gap
LINKR              LYS A  139                GLU A  141                 gap
LINKR              GLY B   66                PRO B   68                 gap
LINKR              ILE B  138                GLU B  141                 gap
LINKR              ILE C  138                GLU C  141                 gap
LINKR              GLU D   64                ASN D   69                 gap
CRYST1   56.590  120.810  128.200  90.00  90.00  90.00 P 21 21 21
SCALE1      0.017671  0.000000  0.000000        0.00000
SCALE2      0.000000  0.008277  0.000000        0.00000
SCALE3      0.000000  0.000000  0.007800        0.00000
ATOM      1  N   ALA A   0      15.963 -18.335 -14.296  1.00 30.50           N
ATOM      2  CA  ALA A   0      14.952 -19.442 -14.473  1.00 30.30           C
ATOM      4  CB  ALA A   0      15.422 -20.671 -13.830  1.00 29.96           C
ATOM      8  C   ALA A   0      13.538 -19.079 -13.941  1.00 29.59           C
ATOM      9  O   ALA A   0      13.372 -18.413 -12.924  1.00 30.09           O
```

FIG. 4B

```
ATOM     13  N   MET A   1      12.518 -19.561 -14.619  1.00 29.48           N
ATOM     14  CA  MET A   1      11.155 -19.136 -14.334  1.00 28.52           C
ATOM     16  CB  MET A   1      10.237 -19.764 -15.358  1.00 27.94           C
ATOM     19  CG  MET A   1       8.765 -19.272 -15.196  1.00 26.77           C
ATOM     22  SD  MET A   1       8.519 -17.513 -15.422  1.00 27.05           S
ATOM     23  CE  MET A   1       8.337 -17.593 -17.243  1.00 26.50           C
ATOM     27  C   MET A   1      10.626 -19.394 -12.868  1.00 28.59           C
ATOM     28  O   MET A   1       9.933 -18.569 -12.293  1.00 27.16           O
ATOM     30  N   GLU A   2      10.950 -20.533 -12.294  1.00 29.03           N
ATOM     31  CA  GLU A   2      10.517 -20.864 -10.922  1.00 30.60           C
ATOM     33  CB  GLU A   2      11.001 -22.260 -10.531  1.00 31.63           C
ATOM     36  CG  GLU A   2      10.547 -22.757  -9.123  1.00 34.24           C
ATOM     39  CD  GLU A   2      11.264 -24.025  -8.697  1.00 36.34           C
ATOM     40  OE1 GLU A   2      11.848 -24.675  -9.596  1.00 45.20           O
ATOM     41  OE2 GLU A   2      11.260 -24.386  -7.486  1.00 37.19           O
ATOM     42  C   GLU A   2      11.006 -19.834  -9.935  1.00 29.96           C
ATOM     43  O   GLU A   2      10.207 -19.319  -9.169  1.00 31.97           O
ATOM     45  N   ASP A   3      12.278 -19.449  -9.991  1.00 30.03           N
ATOM     46  CA  ASP A   3      12.747 -18.326  -9.148  1.00 30.22           C
ATOM     48  CB  ASP A   3      14.259 -18.093  -9.235  1.00 31.49           C
ATOM     51  CG  ASP A   3      15.114 -19.239  -8.654  1.00 35.34           C
ATOM     52  OD1 ASP A   3      14.590 -20.236  -8.135  1.00 37.70           O
ATOM     53  OD2 ASP A   3      16.358 -19.105  -8.749  1.00 40.48           O
ATOM     54  C   ASP A   3      12.111 -16.969  -9.536  1.00 28.85           C
ATOM     55  O   ASP A   3      11.971 -16.100  -8.682  1.00 28.74           O
ATOM     57  N   PHE A   4      11.858 -16.743 -10.826  1.00 25.92           N
ATOM     58  CA  PHE A   4      11.240 -15.514 -11.231  1.00 25.14           C
ATOM     60  CB  PHE A   4      10.940 -15.516 -12.720  1.00 26.12           C
ATOM     63  CG  PHE A   4      10.199 -14.303 -13.176  1.00 25.82           C
ATOM     64  CD1 PHE A   4      10.855 -13.109 -13.350  1.00 31.54           C
ATOM     66  CE1 PHE A   4      10.157 -11.973 -13.740  1.00 31.11           C
ATOM     68  CZ  PHE A   4       8.812 -12.050 -13.953  1.00 28.26           C
ATOM     70  CE2 PHE A   4       8.162 -13.233 -13.770  1.00 23.22           C
ATOM     72  CD2 PHE A   4       8.850 -14.346 -13.394  1.00 26.07           C
ATOM     74  C   PHE A   4       9.891 -15.372 -10.514  1.00 24.20           C
ATOM     75  O   PHE A   4       9.533 -14.318 -10.059  1.00 21.92           O
ATOM     77  N   VAL A   5       9.136 -16.461 -10.509  1.00 24.87           N
ATOM     78  CA  VAL A   5       7.761 -16.494  -9.947  1.00 24.17           C
ATOM     80  CB  VAL A   5       7.008 -17.814 -10.302  1.00 23.63           C
ATOM     82  CG1 VAL A   5       5.663 -17.929  -9.575  1.00 23.20           C
ATOM     86  CG2 VAL A   5       6.735 -17.799 -11.792  1.00 21.82           C
ATOM     90  C   VAL A   5       7.864 -16.229  -8.510  1.00 23.21           C
ATOM     91  O   VAL A   5       7.154 -15.412  -7.992  1.00 23.26           O
ATOM     93  N   ARG A   6       8.818 -16.835  -7.861  1.00 25.02           N
ATOM     94  CA  ARG A   6       8.922 -16.611  -6.423  1.00 26.02           C
ATOM     96  CB  ARG A   6       9.688 -17.753  -5.745  1.00 26.67           C
ATOM     99  CG  ARG A   6       8.864 -18.980  -5.620  1.00 30.23           C
ATOM    102  CD  ARG A   6       9.219 -19.915  -4.467  1.00 35.47           C
ATOM    105  NE  ARG A   6       9.975 -20.992  -5.049  1.00 37.99           N
ATOM    107  CZ  ARG A   6       9.522 -22.173  -5.425  1.00 34.04           C
ATOM    108  NH1 ARG A   6       8.282 -22.582  -5.180  1.00 32.65           N
ATOM    111  NH2 ARG A   6      10.395 -22.984  -5.996  1.00 32.12           N
ATOM    114  C   ARG A   6       9.446 -15.228  -6.012  1.00 25.83           C
ATOM    115  O   ARG A   6       9.177 -14.769  -4.860  1.00 26.33           O
ATOM    117  N   GLN A   7      10.141 -14.526  -6.899  1.00 23.76           N
ATOM    118  CA  GLN A   7      10.517 -13.140  -6.602  1.00 24.38           C
ATOM    120  CB  GLN A   7      11.882 -12.791  -7.229  1.00 25.78           C
ATOM    123  CG  GLN A   7      12.479 -11.400  -6.824  1.00 26.59           C
ATOM    126  CD  GLN A   7      14.014 -11.233  -7.185  1.00 30.80           C
ATOM    127  OE1 GLN A   7      14.741 -12.195  -7.386  1.00 34.92           O
ATOM    128  NE2 GLN A   7      14.459  -9.986  -7.298  1.00 35.42           N
ATOM    131  C   GLN A   7       9.474 -12.173  -7.147  1.00 23.65           C
ATOM    132  O   GLN A   7       9.284 -11.078  -6.628  1.00 23.50           O
```

FIG. 4C

| | | | | | | | | | | |
|---|---|---|---|---|---|---|---|---|---|---|
|ATOM|134|N|CYS|A|8|8.780|-12.560|-8.203|1.00 22.57|N|
|ATOM|135|CA|CYS|A|8|7.796|-11.650|-8.814|1.00 23.37|C|
|ATOM|137|CB|CYS|A|8|7.479|-12.116|-10.255|1.00 24.09|C|
|ATOM|140|SG|CYS|A|8|6.220|-11.130|-11.142|1.00 27.30|S|
|ATOM|142|C|CYS|A|8|6.500|-11.537|-7.998|1.00 22.00|C|
|ATOM|143|O|CYS|A|8|5.918|-10.447|-7.846|1.00 23.07|O|
|ATOM|145|N|PHE|A|9|6.028|-12.639|-7.447|1.00 21.92|N|
|ATOM|146|CA|PHE|A|9|4.689|-12.596|-6.875|1.00 21.00|C|
|ATOM|148|CB|PHE|A|9|3.886|-13.712|-7.416|1.00 21.08|C|
|ATOM|151|CG|PHE|A|9|3.607|-13.610|-8.851|1.00 17.90|C|
|ATOM|152|CD1|PHE|A|9|2.545|-12.874|-9.297|1.00 18.87|C|
|ATOM|154|CE1|PHE|A|9|2.245|-12.799|-10.672|1.00 18.19|C|
|ATOM|156|CZ|PHE|A|9|2.940|-13.523|-11.520|1.00 15.03|C|
|ATOM|158|CE2|PHE|A|9|4.006|-14.302|-11.070|1.00 15.44|C|
|ATOM|160|CD2|PHE|A|9|4.321|-14.334|-9.747|1.00 15.21|C|
|ATOM|162|C|PHE|A|9|4.693|-12.688|-5.361|1.00 21.04|C|
|ATOM|163|O|PHE|A|9|5.569|-13.276|-4.744|1.00 21.34|O|
|ATOM|165|N|ASN|A|10|3.707|-12.099|-4.743|1.00 21.70|N|
|ATOM|166|CA|ASN|A|10|3.634|-12.130|-3.299|1.00 22.00|C|
|ATOM|168|CB|ASN|A|10|2.566|-11.109|-2.839|1.00 23.91|C|
|ATOM|171|CG|ASN|A|10|1.908|-11.475|-1.549|1.00 30.75|C|
|ATOM|172|OD1|ASN|A|10|1.257|-12.491|-1.470|1.00 37.96|O|
|ATOM|173|ND2|ASN|A|10|2.097|-10.641|-0.502|1.00 37.10|N|
|ATOM|176|C|ASN|A|10|3.517|-13.585|-2.766|1.00 21.84|C|
|ATOM|177|O|ASN|A|10|2.930|-14.486|-3.428|1.00 22.22|O|
|ATOM|179|N|PRO|A|11|4.136|-13.866|-1.599|1.00 20.03|N|
|ATOM|180|CA|PRO|A|11|4.201|-15.225|-1.070|1.00 20.02|C|
|ATOM|182|CB|PRO|A|11|4.963|-15.068|0.275|1.00 21.83|C|
|ATOM|185|CG|PRO|A|11|5.196|-13.582|0.501|1.00 21.21|C|
|ATOM|188|CD|PRO|A|11|4.829|-12.857|-0.762|1.00 21.14|C|
|ATOM|191|C|PRO|A|11|2.847|-15.966|-0.856|1.00 18.60|C|
|ATOM|192|O|PRO|A|11|2.763|-17.208|-0.994|1.00 17.01|O|
|ATOM|193|N|MET|A|12|1.785|-15.228|-0.565|1.00 16.84|N|
|ATOM|194|CA|MET|A|12|0.486|-15.852|-0.393|1.00 18.09|C|
|ATOM|196|CB|MET|A|12|-0.513|-14.835|0.188|1.00 18.65|C|
|ATOM|199|CG|MET|A|12|-1.898|-15.447|0.458|1.00 23.68|C|
|ATOM|202|SD|MET|A|12|-2.937|-14.278|1.382|1.00 36.48|S|
|ATOM|203|CE|MET|A|12|-3.437|-13.193|0.081|1.00 33.14|C|
|ATOM|207|C|MET|A|12|-0.029|-16.421|-1.720|1.00 15.57|C|
|ATOM|208|O|MET|A|12|-0.432|-17.563|-1.765|1.00 14.91|O|
|ATOM|210|N|ILE|A|13|0.112|-15.639|-2.800|1.00 15.96|N|
|ATOM|211|CA|ILE|A|13|-0.230|-16.078|-4.170|1.00 15.35|C|
|ATOM|213|CB|ILE|A|13|-0.047|-14.949|-5.174|1.00 16.08|C|
|ATOM|215|CG1|ILE|A|13|-1.072|-13.902|-4.833|1.00 17.49|C|
|ATOM|218|CD1|ILE|A|13|-0.931|-12.604|-5.521|1.00 19.74|C|
|ATOM|222|CG2|ILE|A|13|-0.243|-15.506|-6.689|1.00 17.69|C|
|ATOM|226|C|ILE|A|13|0.572|-17.309|-4.520|1.00 14.39|C|
|ATOM|227|O|ILE|A|13|0.006|-18.360|-4.810|1.00 15.26|O|
|ATOM|229|N|VAL|A|14|1.886|-17.278|-4.309|1.00 14.68|N|
|ATOM|230|CA|VAL|A|14|2.727|-18.390|-4.684|1.00 13.57|C|
|ATOM|232|CB|VAL|A|14|4.237|-18.043|-4.472|1.00 15.21|C|
|ATOM|234|CG1|VAL|A|14|5.095|-19.212|-4.794|1.00 8.84|C|
|ATOM|238|CG2|VAL|A|14|4.665|-16.779|-5.309|1.00 13.78|C|
|ATOM|242|C|VAL|A|14|2.377|-19.664|-3.884|1.00 15.27|C|
|ATOM|243|O|VAL|A|14|2.302|-20.753|-4.454|1.00 12.96|O|
|ATOM|245|N|GLU|A|15|2.122|-19.526|-2.565|1.00 15.49|N|
|ATOM|246|CA|GLU|A|15|1.706|-20.650|-1.766|1.00 14.48|C|
|ATOM|248|CB|GLU|A|15|1.616|-20.326|-0.250|1.00 14.05|C|
|ATOM|251|CG|GLU|A|15|2.960|-20.368|0.476|1.00 19.20|C|
|ATOM|254|CD|GLU|A|15|2.886|-20.021|1.993|1.00 21.09|C|
|ATOM|255|OE1|GLU|A|15|3.961|-19.852|2.610|1.00 15.17|O|
|ATOM|256|OE2|GLU|A|15|1.770|-20.029|2.554|1.00 21.26|O|
|ATOM|257|C|GLU|A|15|0.389|-21.260|-2.228|1.00 14.35|C|

FIG. 4D

| ATOM | 258 | O | GLU | A | 15 | 0.237 | -22.465 | -2.210 | 1.00 | 16.19 | O |
|------|-----|-----|-----|---|----|-------|---------|--------|------|-------|---|
| ATOM | 260 | N | LEU | A | 16 | -0.572 | -20.456 | -2.601 | 1.00 | 14.17 | N |
| ATOM | 261 | CA | LEU | A | 16 | -1.826 | -20.994 | -3.128 | 1.00 | 13.85 | C |
| ATOM | 263 | CB | LEU | A | 16 | -2.839 | -19.882 | -3.277 | 1.00 | 13.31 | C |
| ATOM | 266 | CG | LEU | A | 16 | -3.389 | -19.207 | -1.980 | 1.00 | 14.08 | C |
| ATOM | 268 | CD1 | LEU | A | 16 | -4.060 | -17.913 | -2.331 | 1.00 | 13.26 | C |
| ATOM | 272 | CD2 | LEU | A | 16 | -4.383 | -20.157 | -1.260 | 1.00 | 15.28 | C |
| ATOM | 276 | C | LEU | A | 16 | -1.598 | -21.713 | -4.456 | 1.00 | 15.22 | C |
| ATOM | 277 | O | LEU | A | 16 | -2.117 | -22.822 | -4.694 | 1.00 | 15.20 | O |
| ATOM | 279 | N | ALA | A | 17 | -0.757 | -21.116 | -5.292 | 1.00 | 16.69 | N |
| ATOM | 280 | CA | ALA | A | 17 | -0.555 | -21.666 | -6.630 | 1.00 | 18.69 | C |
| ATOM | 282 | CB | ALA | A | 17 | 0.212 | -20.598 | -7.558 | 1.00 | 19.05 | C |
| ATOM | 286 | C | ALA | A | 17 | 0.181 | -23.025 | -6.513 | 1.00 | 18.76 | C |
| ATOM | 287 | O | ALA | A | 17 | -0.225 | -24.027 | -7.189 | 1.00 | 18.40 | O |
| ATOM | 289 | N | GLU | A | 18 | 1.121 | -23.120 | -5.558 | 1.00 | 17.99 | N |
| ATOM | 290 | CA | GLU | A | 18 | 1.886 | -24.363 | -5.325 | 1.00 | 18.12 | C |
| ATOM | 292 | CB | GLU | A | 18 | 2.985 | -24.281 | -4.223 | 1.00 | 17.68 | C |
| ATOM | 295 | CG | GLU | A | 18 | 4.225 | -23.578 | -4.596 | 1.00 | 19.29 | C |
| ATOM | 298 | CD | GLU | A | 18 | 5.052 | -23.100 | -3.420 | 1.00 | 20.38 | C |
| ATOM | 299 | OE1 | GLU | A | 18 | 4.592 | -23.126 | -2.244 | 1.00 | 23.14 | O |
| ATOM | 300 | OE2 | GLU | A | 18 | 6.155 | -22.587 | -3.655 | 1.00 | 19.15 | O |
| ATOM | 301 | C | GLU | A | 18 | 1.007 | -25.519 | -4.926 | 1.00 | 17.38 | C |
| ATOM | 302 | O | GLU | A | 18 | 1.116 | -26.598 | -5.483 | 1.00 | 16.57 | O |
| ATOM | 304 | N | LYS | A | 19 | 0.167 | -25.278 | -3.938 | 1.00 | 17.85 | N |
| ATOM | 305 | CA | LYS | A | 19 | -0.759 | -26.288 | -3.498 | 1.00 | 18.53 | C |
| ATOM | 307 | CB | LYS | A | 19 | -1.541 | -25.834 | -2.284 | 1.00 | 17.80 | C |
| ATOM | 310 | CG | LYS | A | 19 | -0.670 | -25.718 | -1.056 | 1.00 | 20.23 | C |
| ATOM | 313 | CD | LYS | A | 19 | -1.572 | -25.295 | 0.179 | 1.00 | 15.69 | C |
| ATOM | 316 | CE | LYS | A | 19 | -0.769 | -24.910 | 1.388 | 1.00 | 13.48 | C |
| ATOM | 319 | NZ | LYS | A | 19 | 0.134 | -26.026 | 1.972 | 1.00 | 10.75 | N |
| ATOM | 323 | C | LYS | A | 19 | -1.736 | -26.729 | -4.586 | 1.00 | 18.63 | C |
| ATOM | 324 | O | LYS | A | 19 | -2.098 | -27.881 | -4.626 | 1.00 | 18.44 | O |
| ATOM | 326 | N | ALA | A | 20 | -2.217 | -25.786 | -5.392 | 1.00 | 18.75 | N |
| ATOM | 327 | CA | ALA | A | 20 | -3.192 | -26.100 | -6.404 | 1.00 | 17.98 | C |
| ATOM | 329 | CB | ALA | A | 20 | -3.642 | -24.858 | -7.067 | 1.00 | 15.83 | C |
| ATOM | 333 | C | ALA | A | 20 | -2.556 | -27.061 | -7.417 | 1.00 | 18.39 | C |
| ATOM | 334 | O | ALA | A | 20 | -3.141 | -28.112 | -7.800 | 1.00 | 18.30 | O |
| ATOM | 336 | N | MET | A | 21 | -1.322 | -26.771 | -7.772 | 1.00 | 19.18 | N |
| ATOM | 337 | CA | MET | A | 21 | -0.586 | -27.606 | -8.701 | 1.00 | 20.29 | C |
| ATOM | 339 | CB | MET | A | 21 | 0.697 | -26.909 | -9.160 | 1.00 | 19.78 | C |
| ATOM | 342 | CG | MET | A | 21 | 0.450 | -25.855 | -10.135 | 1.00 | 20.69 | C |
| ATOM | 345 | SD | MET | A | 21 | 1.970 | -24.975 | -10.717 | 1.00 | 22.66 | S |
| ATOM | 346 | CE | MET | A | 21 | 2.404 | -26.127 | -12.032 | 1.00 | 19.16 | C |
| ATOM | 350 | C | MET | A | 21 | -0.351 | -29.008 | -8.138 | 1.00 | 21.58 | C |
| ATOM | 351 | O | MET | A | 21 | -0.736 | -30.040 | -8.751 | 1.00 | 21.61 | O |
| ATOM | 353 | N | LYS | A | 22 | 0.199 | -29.097 | -6.945 | 1.00 | 23.10 | N |
| ATOM | 354 | CA | LYS | A | 22 | 0.494 | -30.405 | -6.400 | 1.00 | 22.72 | C |
| ATOM | 356 | CB | LYS | A | 22 | 1.209 | -30.264 | -5.088 | 1.00 | 24.05 | C |
| ATOM | 359 | CG | LYS | A | 22 | 2.676 | -29.875 | -5.156 | 1.00 | 29.28 | C |
| ATOM | 362 | CD | LYS | A | 22 | 3.453 | -31.198 | -5.148 | 1.00 | 35.51 | C |
| ATOM | 365 | CE | LYS | A | 22 | 4.970 | -31.082 | -5.288 | 1.00 | 38.58 | C |
| ATOM | 368 | NZ | LYS | A | 22 | 5.474 | -32.448 | -5.775 | 1.00 | 41.37 | N |
| ATOM | 372 | C | LYS | A | 22 | -0.781 | -31.220 | -6.216 | 1.00 | 23.34 | C |
| ATOM | 373 | O | LYS | A | 22 | -0.823 | -32.425 | -6.486 | 1.00 | 22.04 | O |
| ATOM | 375 | N | GLU | A | 23 | -1.837 | -30.586 | -5.748 | 1.00 | 22.65 | N |
| ATOM | 376 | CA | GLU | A | 23 | -3.014 | -31.344 | -5.458 | 1.00 | 23.24 | C |
| ATOM | 378 | CB | GLU | A | 23 | -3.973 | -30.500 | -4.634 | 1.00 | 23.90 | C |
| ATOM | 381 | CG | GLU | A | 23 | -3.500 | -30.170 | -3.160 | 1.00 | 26.16 | C |
| ATOM | 384 | CD | GLU | A | 23 | -4.359 | -29.026 | -2.569 | 1.00 | 29.31 | C |
| ATOM | 385 | OE1 | GLU | A | 23 | -4.044 | -28.459 | -1.484 | 1.00 | 32.31 | O |
| ATOM | 386 | OE2 | GLU | A | 23 | -5.347 | -28.699 | -3.248 | 1.00 | 29.57 | O |
| ATOM | 387 | C | GLU | A | 23 | -3.683 | -31.902 | -6.729 | 1.00 | 23.54 | C |
| ATOM | 388 | O | GLU | A | 23 | -4.340 | -32.940 | -6.676 | 1.00 | 22.41 | O |

FIG. 4E

```
ATOM   390  N    TYR A  24    -3.470 -31.237  -7.864  1.00 24.01           N
ATOM   391  CA   TYR A  24    -3.936 -31.723  -9.126  1.00 24.70           C
ATOM   393  CB   TYR A  24    -4.410 -30.569 -10.016  1.00 24.71           C
ATOM   396  CG   TYR A  24    -5.791 -30.035  -9.623  1.00 25.44           C
ATOM   397  CD1  TYR A  24    -5.929 -29.075  -8.642  1.00 23.12           C
ATOM   399  CE1  TYR A  24    -7.149 -28.592  -8.292  1.00 26.13           C
ATOM   401  CZ   TYR A  24    -8.289 -29.081  -8.898  1.00 27.35           C
ATOM   402  OH   TYR A  24    -9.483 -28.561  -8.531  1.00 31.77           O
ATOM   404  CE2  TYR A  24    -8.206 -30.051  -9.853  1.00 28.19           C
ATOM   406  CD2  TYR A  24    -6.955 -30.535 -10.215  1.00 26.70           C
ATOM   408  C    TYR A  24    -2.927 -32.564  -9.858  1.00 25.45           C
ATOM   409  O    TYR A  24    -3.130 -32.862 -11.042  1.00 25.67           O
ATOM   411  N    GLY A  25    -1.864 -32.973  -9.169  1.00 26.36           N
ATOM   412  CA   GLY A  25    -0.879 -33.817  -9.751  1.00 27.66           C
ATOM   415  C    GLY A  25     0.226 -33.141 -10.533  1.00 29.55           C
ATOM   416  O    GLY A  25     0.979 -33.849 -11.198  1.00 30.50           O
ATOM   418  N    GLU A  26     0.356 -31.807 -10.486  1.00 30.09           N
ATOM   419  CA   GLU A  26     1.419 -31.129 -11.219  1.00 30.84           C
ATOM   421  CB   GLU A  26     0.841 -29.965 -12.030  1.00 31.77           C
ATOM   424  CG   GLU A  26    -0.240 -30.318 -13.001  1.00 34.86           C
ATOM   427  CD   GLU A  26    -1.061 -29.103 -13.387  1.00 39.14           C
ATOM   428  OE1  GLU A  26    -0.696 -27.991 -12.961  1.00 43.75           O
ATOM   429  OE2  GLU A  26    -2.087 -29.249 -14.078  1.00 42.46           O
ATOM   430  C    GLU A  26     2.515 -30.541 -10.315  1.00 30.90           C
ATOM   431  O    GLU A  26     2.301 -30.132  -9.163  1.00 31.68           O
ATOM   433  N    ASP A  27     3.691 -30.446 -10.870  1.00 29.80           N
ATOM   434  CA   ASP A  27     4.805 -29.937 -10.148  1.00 29.02           C
ATOM   436  CB   ASP A  27     5.978 -30.882 -10.304  1.00 29.29           C
ATOM   439  CG   ASP A  27     7.109 -30.501  -9.393  1.00 33.70           C
ATOM   440  OD1  ASP A  27     7.678 -29.403  -9.568  1.00 36.24           O
ATOM   441  OD2  ASP A  27     7.399 -31.272  -8.469  1.00 42.25           O
ATOM   442  C    ASP A  27     5.192 -28.541 -10.664  1.00 27.83           C
ATOM   443  O    ASP A  27     5.462 -28.378 -11.856  1.00 26.63           O
ATOM   445  N    PRO A  28     5.218 -27.549  -9.778  1.00 26.63           N
ATOM   446  CA   PRO A  28     5.559 -26.203 -10.233  1.00 27.90           C
ATOM   448  CB   PRO A  28     5.303 -25.341  -9.001  1.00 26.61           C
ATOM   451  CG   PRO A  28     5.227 -26.272  -7.879  1.00 27.36           C
ATOM   454  CD   PRO A  28     4.734 -27.546  -8.384  1.00 26.55           C
ATOM   457  C    PRO A  28     7.022 -26.035 -10.712  1.00 28.98           C
ATOM   458  O    PRO A  28     7.316 -25.137 -11.518  1.00 28.72           O
ATOM   459  N    LYS A  29     7.898 -26.895 -10.206  1.00 30.22           N
ATOM   460  CA   LYS A  29     9.298 -26.962 -10.607  1.00 32.09           C
ATOM   462  CB   LYS A  29    10.078 -27.837  -9.606  1.00 32.86           C
ATOM   465  CG   LYS A  29    11.406 -28.413 -10.105  1.00 36.73           C
ATOM   468  CD   LYS A  29    12.332 -28.853  -8.910  1.00 40.09           C
ATOM   471  CE   LYS A  29    12.943 -27.692  -8.123  1.00 42.70           C
ATOM   474  NZ   LYS A  29    12.991 -28.049  -6.652  1.00 44.13           N
ATOM   478  C    LYS A  29     9.445 -27.486 -12.055  1.00 33.14           C
ATOM   479  O    LYS A  29    10.377 -27.108 -12.754  1.00 33.57           O
ATOM   481  N    ILE A  30     8.488 -28.302 -12.509  1.00 33.67           N
ATOM   482  CA   ILE A  30     8.451 -28.810 -13.866  1.00 33.42           C
ATOM   484  CB   ILE A  30     7.975 -30.286 -13.837  1.00 33.81           C
ATOM   486  CG1  ILE A  30     8.980 -31.147 -13.057  1.00 35.38           C
ATOM   489  CD1  ILE A  30     8.594 -32.629 -12.901  1.00 31.76           C
ATOM   493  CG2  ILE A  30     7.769 -30.831 -15.251  1.00 36.17           C
ATOM   497  C    ILE A  30     7.564 -27.943 -14.798  1.00 32.85           C
ATOM   498  O    ILE A  30     7.999 -27.482 -15.864  1.00 33.05           O
ATOM   500  N    GLU A  31     6.332 -27.659 -14.410  1.00 31.24           N
ATOM   501  CA   GLU A  31     5.496 -26.840 -15.278  1.00 30.25           C
ATOM   503  CB   GLU A  31     4.063 -27.280 -15.207  1.00 30.90           C
ATOM   506  CG   GLU A  31     3.864 -28.748 -15.091  1.00 34.36           C
ATOM   509  CD   GLU A  31     2.908 -29.213 -16.150  1.00 40.95           C
ATOM   510  OE1  GLU A  31     3.323 -29.141 -17.335  1.00 41.41           O
```

FIG. 4F

```
ATOM   511  OE2 GLU A  31      1.766  -29.608 -15.801  1.00 42.33           O
ATOM   512  C   GLU A  31      5.567  -25.402 -14.858  1.00 28.18           C
ATOM   513  O   GLU A  31      4.597  -24.870 -14.297  1.00 28.99           O
ATOM   515  N   THR A  32      6.676  -24.749 -15.155  1.00 25.71           N
ATOM   516  CA  THR A  32      6.956  -23.398 -14.638  1.00 25.35           C
ATOM   518  CB  THR A  32      8.492  -23.076 -14.720  1.00 24.96           C
ATOM   520  OG1 THR A  32      8.961  -23.182 -16.086  1.00 31.47           O
ATOM   522  CG2 THR A  32      9.204  -24.048 -13.930  1.00 27.43           C
ATOM   526  C   THR A  32      6.181  -22.258 -15.245  1.00 23.24           C
ATOM   527  O   THR A  32      5.908  -21.258 -14.593  1.00 22.09           O
ATOM   529  N   ASN A  33      5.899  -22.351 -16.521  1.00 23.72           N
ATOM   530  CA  ASN A  33      5.052  -21.370 -17.207  1.00 23.16           C
ATOM   532  CB  ASN A  33      5.071  -21.580 -18.735  1.00 22.31           C
ATOM   535  CG  ASN A  33      6.425  -21.261 -19.351  1.00 25.75           C
ATOM   536  OD1 ASN A  33      7.084  -20.270 -18.997  1.00 24.11           O
ATOM   537  ND2 ASN A  33      6.875  -22.132 -20.270  1.00 26.78           N
ATOM   540  C   ASN A  33      3.634  -21.468 -16.658  1.00 22.02           C
ATOM   541  O   ASN A  33      2.970  -20.450 -16.488  1.00 21.98           O
ATOM   543  N   LYS A  34      3.173  -22.691 -16.395  1.00 22.17           N
ATOM   544  CA  LYS A  34      1.847  -22.873 -15.826  1.00 21.65           C
ATOM   546  CB  LYS A  34      1.473  -24.323 -15.817  1.00 22.10           C
ATOM   549  CG  LYS A  34     -0.025  -24.621 -15.808  1.00 27.83           C
ATOM   552  CD  LYS A  34     -0.241  -26.144 -16.124  1.00 32.95           C
ATOM   555  CE  LYS A  34     -1.387  -26.441 -17.048  1.00 36.23           C
ATOM   558  NZ  LYS A  34     -1.246  -27.808 -17.750  1.00 39.17           N
ATOM   562  C   LYS A  34      1.841  -22.274 -14.401  1.00 20.72           C
ATOM   563  O   LYS A  34      0.930  -21.565 -14.056  1.00 19.72           O
ATOM   565  N   PHE A  35      2.899  -22.526 -13.622  1.00 20.54           N
ATOM   566  CA  PHE A  35      3.101  -21.895 -12.316  1.00 20.15           C
ATOM   568  CB  PHE A  35      4.448  -22.357 -11.805  1.00 20.75           C
ATOM   571  CG  PHE A  35      4.814  -21.957 -10.417  1.00 20.43           C
ATOM   572  CD1 PHE A  35      6.149  -21.716 -10.134  1.00 16.84           C
ATOM   574  CE1 PHE A  35      6.594  -21.428  -8.813  1.00 20.67           C
ATOM   576  CZ  PHE A  35      5.690  -21.356  -7.767  1.00 18.61           C
ATOM   578  CE2 PHE A  35      4.325  -21.604  -8.017  1.00 15.74           C
ATOM   580  CD2 PHE A  35      3.888  -21.950  -9.354  1.00 19.43           C
ATOM   582  C   PHE A  35      2.914  -20.377 -12.367  1.00 21.24           C
ATOM   583  O   PHE A  35      2.133  -19.809 -11.592  1.00 18.39           O
ATOM   585  N   ALA A  36      3.574  -19.720 -13.340  1.00 21.28           N
ATOM   586  CA  ALA A  36      3.533  -18.267 -13.504  1.00 19.46           C
ATOM   588  CB  ALA A  36      4.616  -17.811 -14.518  1.00 19.96           C
ATOM   592  C   ALA A  36      2.159  -17.788 -14.006  1.00 19.48           C
ATOM   593  O   ALA A  36      1.692  -16.693 -13.644  1.00 17.95           O
ATOM   595  N   ALA A  37      1.520  -18.613 -14.813  1.00 16.92           N
ATOM   596  CA  ALA A  37      0.172  -18.304 -15.269  1.00 18.30           C
ATOM   598  CB  ALA A  37     -0.241  -19.183 -16.477  1.00 15.61           C
ATOM   602  C   ALA A  37     -0.885  -18.397 -14.134  1.00 17.24           C
ATOM   603  O   ALA A  37     -1.848  -17.624 -14.127  1.00 19.08           O
ATOM   605  N   ILE A  38     -0.749  -19.384 -13.271  1.00 17.39           N
ATOM   606  CA  ILE A  38     -1.649  -19.549 -12.145  1.00 17.68           C
ATOM   608  CB  ILE A  38     -1.476  -20.891 -11.443  1.00 19.04           C
ATOM   610  CG1 ILE A  38     -2.016  -21.972 -12.357  1.00 20.82           C
ATOM   613  CD1 ILE A  38     -1.258  -23.262 -12.299  1.00 24.99           C
ATOM   617  CG2 ILE A  38     -2.228  -20.960 -10.079  1.00 15.86           C
ATOM   621  C   ILE A  38     -1.483  -18.377 -11.205  1.00 17.31           C
ATOM   622  O   ILE A  38     -2.482  -17.778 -10.805  1.00 16.97           O
ATOM   624  N   CYS A  39     -0.253  -17.965 -10.948  1.00 16.99           N
ATOM   625  CA  CYS A  39      0.008  -16.819 -10.052  1.00 15.61           C
ATOM   627  CB  CYS A  39      1.494  -16.653  -9.761  1.00 15.70           C
ATOM   630  SG  CYS A  39      2.197  -17.917  -8.780  1.00 19.73           S
ATOM   632  C   CYS A  39     -0.515  -15.557 -10.589  1.00 15.45           C
ATOM   633  O   CYS A  39     -1.049  -14.745  -9.846  1.00 14.82           O
ATOM   635  N   THR A  40     -0.380  -15.360 -11.912  1.00 16.20           N
```

FIG. 4G

```
ATOM  636  CA   THR A  40    -0.825 -14.165 -12.577  1.00 13.99      C
ATOM  638  CB   THR A  40    -0.433 -14.203 -14.065  1.00 13.35      C
ATOM  640  OG1  THR A  40     0.951 -14.263 -14.179  1.00 16.39      O
ATOM  642  CG2  THR A  40    -0.833 -12.979 -14.746  1.00 12.50      C
ATOM  646  C    THR A  40    -2.332 -13.992 -12.586  1.00 13.71      C
ATOM  647  O    THR A  40    -2.821 -12.903 -12.367  1.00 13.31      O
ATOM  649  N    HIS A  41    -3.047 -15.069 -12.867  1.00 14.67      N
ATOM  650  CA   HIS A  41    -4.516 -15.058 -12.866  1.00 14.29      C
ATOM  652  CB   HIS A  41    -5.064 -16.389 -13.362  1.00 12.92      C
ATOM  655  CG   HIS A  41    -6.557 -16.530 -13.256  1.00 17.06      C
ATOM  656  ND1  HIS A  41    -7.164 -17.161 -12.193  1.00 12.13      N
ATOM  658  CE1  HIS A  41    -8.474 -17.135 -12.361  1.00 19.25      C
ATOM  660  NE2  HIS A  41    -8.741 -16.538 -13.508  1.00 18.10      N
ATOM  662  CD2  HIS A  41    -7.560 -16.144 -14.087  1.00 18.11      C
ATOM  664  C    HIS A  41    -4.990 -14.752 -11.440  1.00 15.56      C
ATOM  665  O    HIS A  41    -5.877 -13.883 -11.229  1.00 15.77      O
ATOM  667  N    LEU A  42    -4.462 -15.486 -10.475  1.00 15.04      N
ATOM  668  CA   LEU A  42    -4.766 -15.193  -9.073  1.00 16.63      C
ATOM  670  CB   LEU A  42    -3.878 -16.077  -8.182  1.00 17.22      C
ATOM  673  CG   LEU A  42    -4.357 -16.984  -7.049  1.00 22.42      C
ATOM  675  CD1  LEU A  42    -5.839 -17.309  -6.971  1.00 25.30      C
ATOM  679  CD2  LEU A  42    -3.511 -18.291  -7.104  1.00 26.49      C
ATOM  683  C    LEU A  42    -4.493 -13.743  -8.695  1.00 15.22      C
ATOM  684  O    LEU A  42    -5.318 -13.055  -8.065  1.00 14.84      O
ATOM  686  N    GLU A  43    -3.300 -13.263  -9.011  1.00 14.76      N
ATOM  687  CA   GLU A  43    -3.040 -11.869  -8.782  1.00 15.62      C
ATOM  689  CB   GLU A  43    -1.707 -11.496  -9.298  1.00 16.05      C
ATOM  692  CG   GLU A  43    -1.282 -10.105  -8.900  1.00 24.48      C
ATOM  695  CD   GLU A  43     0.165  -9.855  -9.234  1.00 31.12      C
ATOM  696  OE1  GLU A  43     0.956  -9.726  -8.311  1.00 32.89      O
ATOM  697  OE2  GLU A  43     0.501  -9.820 -10.448  1.00 36.99      O
ATOM  698  C    GLU A  43    -4.023 -10.894  -9.393  1.00 15.59      C
ATOM  699  O    GLU A  43    -4.269  -9.880  -8.807  1.00 14.48      O
ATOM  701  N    VAL A  44    -4.520 -11.156 -10.603  1.00 15.61      N
ATOM  702  CA   VAL A  44    -5.430 -10.180 -11.261  1.00 15.94      C
ATOM  704  CB   VAL A  44    -5.615 -10.527 -12.794  1.00 15.90      C
ATOM  706  CG1  VAL A  44    -6.797  -9.766 -13.426  1.00 12.56      C
ATOM  710  CG2  VAL A  44    -4.286 -10.170 -13.496  1.00 17.14      C
ATOM  714  C    VAL A  44    -6.778 -10.239 -10.596  1.00 15.13      C
ATOM  715  O    VAL A  44    -7.419  -9.227 -10.476  1.00 17.66      O
ATOM  717  N    CYS A  45    -7.203 -11.412 -10.177  1.00 15.15      N
ATOM  718  CA   CYS A  45    -8.476 -11.540  -9.456  1.00 16.24      C
ATOM  720  CB   CYS A  45    -8.797 -12.980  -9.152  1.00 14.89      C
ATOM  723  SG   CYS A  45    -9.209 -14.110 -10.579  1.00 18.03      S
ATOM  725  C    CYS A  45    -8.456 -10.752  -8.124  1.00 17.43      C
ATOM  726  O    CYS A  45    -9.463 -10.120  -7.775  1.00 18.28      O
ATOM  728  N    PHE A  46    -7.334 -10.841  -7.394  1.00 16.26      N
ATOM  729  CA   PHE A  46    -7.170 -10.063  -6.204  1.00 17.98      C
ATOM  731  CB   PHE A  46    -5.942 -10.518  -5.389  1.00 17.25      C
ATOM  734  CG   PHE A  46    -5.992 -11.947  -4.921  1.00 18.26      C
ATOM  735  CD1  PHE A  46    -7.115 -12.735  -5.072  1.00 22.19      C
ATOM  737  CE1  PHE A  46    -7.146 -14.026  -4.628  1.00 20.50      C
ATOM  739  CZ   PHE A  46    -6.053 -14.544  -3.978  1.00 20.22      C
ATOM  741  CE2  PHE A  46    -4.942 -13.796  -3.856  1.00 21.94      C
ATOM  743  CD2  PHE A  46    -4.916 -12.492  -4.334  1.00 19.78      C
ATOM  745  C    PHE A  46    -7.065  -8.567  -6.525  1.00 18.86      C
ATOM  746  O    PHE A  46    -7.673  -7.745  -5.856  1.00 19.42      O
ATOM  748  N    MET A  47    -6.302  -8.204  -7.555  1.00 19.81      N
ATOM  749  CA   MET A  47    -6.217  -6.789  -7.951  1.00 19.89      C
ATOM  751  CB   MET A  47    -5.219  -6.492  -9.058  1.00 19.83      C
ATOM  754  CG   MET A  47    -3.771  -6.811  -8.755  1.00 23.47      C
ATOM  757  SD   MET A  47    -2.626  -6.263 -10.034  1.00 24.82      S
ATOM  758  CE   MET A  47    -2.935  -4.506  -9.996  1.00 21.80      C
```

FIG. 4H

```
ATOM    762  C   MET A  47      -7.577  -6.288  -8.369  1.00 19.33           C
ATOM    763  O   MET A  47      -7.919  -5.136  -8.070  1.00 19.94           O
ATOM    765  N   TYR A  48      -8.354  -7.123  -9.027  1.00 19.10           N
ATOM    766  CA  TYR A  48      -9.680  -6.725  -9.488  1.00 20.16           C
ATOM    768  CB  TYR A  48     -10.330  -7.853 -10.304  1.00 19.64           C
ATOM    771  CG  TYR A  48     -11.384  -7.475 -11.329  1.00 18.21           C
ATOM    772  CD1 TYR A  48     -11.117  -7.558 -12.693  1.00 15.64           C
ATOM    774  CE1 TYR A  48     -12.080  -7.229 -13.631  1.00 14.20           C
ATOM    776  CZ  TYR A  48     -13.294  -6.843 -13.250  1.00 17.43           C
ATOM    777  OH  TYR A  48     -14.243  -6.489 -14.259  1.00 17.51           O
ATOM    779  CE2 TYR A  48     -13.589  -6.701 -11.847  1.00 12.11           C
ATOM    781  CD2 TYR A  48     -12.657  -7.074 -10.943  1.00 18.69           C
ATOM    783  C   TYR A  48     -10.572  -6.350  -8.282  1.00 22.24           C
ATOM    784  O   TYR A  48     -11.295  -5.349  -8.336  1.00 23.14           O
ATOM    786  N   SER A  49     -10.539  -7.112  -7.201  1.00 24.64           N
ATOM    787  CA  SER A  49     -11.342  -6.715  -5.981  1.00 28.17           C
ATOM    789  CB  SER A  49     -11.687  -7.886  -5.049  1.00 26.81           C
ATOM    792  OG  SER A  49     -10.691  -8.878  -5.111  1.00 33.40           O
ATOM    794  C   SER A  49     -10.751  -5.588  -5.144  1.00 30.07           C
ATOM    795  O   SER A  49     -11.500  -4.830  -4.544  1.00 31.68           O
ATOM    797  N   ASP A  50      -9.427  -5.448  -5.126  1.00 33.58           N
ATOM    798  CA  ASP A  50      -8.745  -4.559  -4.172  1.00 35.29           C
ATOM    800  CB  ASP A  50      -7.207  -4.647  -4.351  1.00 36.94           C
ATOM    803  CG  ASP A  50      -6.591  -5.777  -3.513  1.00 38.10           C
ATOM    804  OD1 ASP A  50      -7.324  -6.461  -2.764  1.00 41.46           O
ATOM    805  OD2 ASP A  50      -5.370  -5.988  -3.608  1.00 44.96           O
ATOM    806  C   ASP A  50      -9.215  -3.122  -4.220  1.00 35.74           C
ATOM    807  O   ASP A  50      -9.446  -2.576  -5.278  1.00 36.08           O
ATOM    809  N   PHE A  51      -9.375  -2.518  -3.036  1.00 36.46           N
ATOM    810  CA  PHE A  51      -9.741  -1.093  -2.893  1.00 35.69           C
ATOM    812  CB  PHE A  51      -8.895  -0.148  -3.771  1.00 36.43           C
ATOM    815  CG  PHE A  51      -7.434  -0.370  -3.703  1.00 39.21           C
ATOM    816  CD1 PHE A  51      -6.775  -0.514  -2.469  1.00 42.51           C
ATOM    818  CE1 PHE A  51      -5.383  -0.694  -2.415  1.00 42.42           C
ATOM    820  CZ  PHE A  51      -4.666  -0.716  -3.575  1.00 44.11           C
ATOM    822  CE2 PHE A  51      -5.318  -0.547  -4.817  1.00 42.67           C
ATOM    824  CD2 PHE A  51      -6.681  -0.365  -4.872  1.00 40.16           C
ATOM    826  C   PHE A  51     -11.165  -0.748  -3.233  1.00 34.79           C
ATOM    827  O   PHE A  51     -11.519   0.430  -3.153  1.00 35.95           O
ATOM    829  N   HIS A  52     -11.987  -1.720  -3.616  1.00 33.61           N
ATOM    830  CA  HIS A  52     -13.339  -1.425  -4.090  1.00 32.70           C
ATOM    832  CB  HIS A  52     -13.633  -2.213  -5.382  1.00 32.49           C
ATOM    835  CG  HIS A  52     -12.716  -1.820  -6.477  1.00 35.73           C
ATOM    836  ND1 HIS A  52     -11.546  -2.495  -6.737  1.00 39.01           N
ATOM    838  CE1 HIS A  52     -10.877  -1.860  -7.692  1.00 39.74           C
ATOM    840  NE2 HIS A  52     -11.563  -0.788  -8.042  1.00 37.46           N
ATOM    842  CD2 HIS A  52     -12.706  -0.723  -7.277  1.00 38.30           C
ATOM    844  C   HIS A  52     -14.353  -1.722  -3.014  1.00 30.80           C
ATOM    845  O   HIS A  52     -14.510  -2.844  -2.597  1.00 28.92           O
ATOM    847  N   PHE A  53     -15.072  -0.699  -2.598  1.00 29.95           N
ATOM    848  CA  PHE A  53     -16.109  -0.874  -1.601  1.00 29.74           C
ATOM    850  CB  PHE A  53     -15.641  -0.239  -0.292  1.00 29.37           C
ATOM    853  CG  PHE A  53     -14.370  -0.825   0.197  1.00 29.01           C
ATOM    854  CD1 PHE A  53     -14.367  -1.960   0.969  1.00 31.98           C
ATOM    856  CE1 PHE A  53     -13.172  -2.517   1.404  1.00 32.29           C
ATOM    858  CZ  PHE A  53     -11.985  -1.975   1.048  1.00 31.74           C
ATOM    860  CE2 PHE A  53     -11.983  -0.860   0.243  1.00 35.12           C
ATOM    862  CD2 PHE A  53     -13.185  -0.295  -0.178  1.00 31.45           C
ATOM    864  C   PHE A  53     -17.396  -0.294  -2.086  1.00 29.76           C
ATOM    865  O   PHE A  53     -17.477   0.178  -3.197  1.00 28.42           O
ATOM    867  N   ILE A  54     -18.406  -0.342  -1.232  1.00 30.62           N
ATOM    868  CA  ILE A  54     -19.725   0.193  -1.550  1.00 30.36           C
ATOM    870  CB  ILE A  54     -20.850  -0.879  -1.489  1.00 29.74           C
```

FIG. 4I

```
ATOM    872  CG1 ILE A  54     -20.465  -2.125  -2.288  1.00 29.55           C
ATOM    875  CD1 ILE A  54     -20.790  -2.049  -3.677  1.00 31.07           C
ATOM    879  CG2 ILE A  54     -22.222  -0.272  -1.953  1.00 29.02           C
ATOM    883  C   ILE A  54     -19.983   1.158  -0.422  1.00 31.02           C
ATOM    884  O   ILE A  54     -19.790   0.764   0.724  1.00 29.51           O
ATOM    886  N   ASP A  55     -20.389   2.399  -0.753  1.00 32.46           N
ATOM    887  CA  ASP A  55     -20.611   3.461   0.252  1.00 33.38           C
ATOM    889  CB  ASP A  55     -20.168   4.839  -0.264  1.00 33.28           C
ATOM    892  CG  ASP A  55     -21.113   5.438  -1.328  1.00 35.07           C
ATOM    893  OD1 ASP A  55     -22.137   4.800  -1.699  1.00 34.63           O
ATOM    894  OD2 ASP A  55     -20.811   6.570  -1.810  1.00 34.87           O
ATOM    895  C   ASP A  55     -22.063   3.485   0.674  1.00 34.60           C
ATOM    896  O   ASP A  55     -22.862   2.633   0.286  1.00 32.29           O
ATOM    898  N   GLU A  56     -22.396   4.473   1.490  1.00 36.97           N
ATOM    899  CA  GLU A  56     -23.736   4.560   2.064  1.00 39.09           C
ATOM    901  CB  GLU A  56     -23.792   5.715   3.084  1.00 39.40           C
ATOM    904  CG  GLU A  56     -23.009   5.340   4.371  1.00 41.09           C
ATOM    907  CD  GLU A  56     -22.944   6.455   5.397  1.00 42.83           C
ATOM    908  OE1 GLU A  56     -22.309   7.461   5.099  1.00 46.74           O
ATOM    909  OE2 GLU A  56     -23.531   6.332   6.501  1.00 45.11           O
ATOM    910  C   GLU A  56     -24.833   4.630   0.974  1.00 39.80           C
ATOM    911  O   GLU A  56     -25.883   4.044   1.144  1.00 40.55           O
ATOM    913  N   ARG A  57     -24.538   5.260  -0.168  1.00 40.80           N
ATOM    914  CA  ARG A  57     -25.448   5.318  -1.327  1.00 40.68           C
ATOM    916  CB  ARG A  57     -24.983   6.410  -2.303  1.00 40.79           C
ATOM    919  CG  ARG A  57     -24.801   7.815  -1.758  1.00 39.77           C
ATOM    922  CD  ARG A  57     -24.097   8.679  -2.807  1.00 38.90           C
ATOM    925  NE  ARG A  57     -22.697   8.302  -2.948  1.00 38.83           N
ATOM    927  CZ  ARG A  57     -21.917   8.583  -3.997  1.00 40.06           C
ATOM    928  NH1 ARG A  57     -22.360   9.261  -5.042  1.00 38.85           N
ATOM    931  NH2 ARG A  57     -20.665   8.163  -4.011  1.00 40.10           N
ATOM    934  C   ARG A  57     -25.562   4.031  -2.174  1.00 41.31           C
ATOM    935  O   ARG A  57     -26.278   4.025  -3.184  1.00 42.62           O
ATOM    937  N   GLY A  58     -24.848   2.957  -1.862  1.00 40.49           N
ATOM    938  CA  GLY A  58     -24.848   1.810  -2.812  1.00 39.29           C
ATOM    941  C   GLY A  58     -23.957   2.045  -4.030  1.00 37.83           C
ATOM    942  O   GLY A  58     -23.980   1.276  -4.989  1.00 36.76           O
ATOM    944  N   GLU A  59     -23.160   3.114  -3.997  1.00 37.02           N
ATOM    945  CA  GLU A  59     -22.234   3.423  -5.093  1.00 36.11           C
ATOM    947  CB  GLU A  59     -22.101   4.939  -5.263  1.00 36.60           C
ATOM    950  CG  GLU A  59     -23.368   5.649  -5.722  1.00 37.72           C
ATOM    953  CD  GLU A  59     -23.748   5.344  -7.188  1.00 42.53           C
ATOM    954  OE1 GLU A  59     -22.836   5.093  -8.022  1.00 38.87           O
ATOM    955  OE2 GLU A  59     -24.963   5.347  -7.480  1.00 44.08           O
ATOM    956  C   GLU A  59     -20.841   2.792  -4.886  1.00 36.10           C
ATOM    957  O   GLU A  59     -20.432   2.514  -3.741  1.00 34.00           O
ATOM    959  N   SER A  60     -20.133   2.555  -6.008  1.00 36.08           N
ATOM    960  CA  SER A  60     -18.803   1.965  -5.997  1.00 36.64           C
ATOM    962  CB  SER A  60     -18.379   1.429  -7.374  1.00 36.60           C
ATOM    965  OG  SER A  60     -17.185   0.633  -7.259  1.00 38.00           O
ATOM    967  C   SER A  60     -17.877   3.062  -5.593  1.00 37.06           C
ATOM    968  O   SER A  60     -17.976   4.156  -6.126  1.00 39.81           O
ATOM    970  N   ILE A  61     -16.982   2.804  -4.660  1.00 36.48           N
ATOM    971  CA  ILE A  61     -15.957   3.792  -4.334  1.00 36.52           C
ATOM    973  CB  ILE A  61     -16.244   4.524  -2.960  1.00 36.18           C
ATOM    975  CG1 ILE A  61     -16.331   3.515  -1.803  1.00 35.09           C
ATOM    978  CD1 ILE A  61     -16.023   4.122  -0.441  1.00 37.25           C
ATOM    982  CG2 ILE A  61     -17.505   5.320  -3.041  1.00 36.52           C
ATOM    986  C   ILE A  61     -14.652   3.045  -4.254  1.00 36.45           C
ATOM    987  O   ILE A  61     -14.641   1.824  -4.157  1.00 36.79           O
ATOM    989  N   ILE A  62     -13.561   3.796  -4.301  1.00 38.15           N
ATOM    990  CA  ILE A  62     -12.195   3.285  -4.169  1.00 38.42           C
ATOM    992  CB  ILE A  62     -11.327   3.686  -5.393  1.00 38.22           C
```

FIG. 4J

| | | | | | | | | | |
|---|---|---|---|---|---|---|---|---|---|
| ATOM | 994 | CG1 | ILE | A | 62 | -11.674 | 2.834 | -6.617 | 1.00 39.63 | C |
| ATOM | 997 | CD1 | ILE | A | 62 | -11.127 | 3.420 | -7.948 | 1.00 39.20 | C |
| ATOM | 1001 | CG2 | ILE | A | 62 | -9.827 | 3.502 | -5.116 | 1.00 37.26 | C |
| ATOM | 1005 | C | ILE | A | 62 | -11.573 | 3.836 | -2.866 | 1.00 38.94 | C |
| ATOM | 1006 | O | ILE | A | 62 | -11.695 | 5.027 | -2.561 | 1.00 38.86 | O |
| ATOM | 1008 | N | VAL | A | 63 | -10.944 | 2.960 | -2.096 | 1.00 39.30 | N |
| ATOM | 1009 | CA | VAL | A | 63 | -10.259 | 3.371 | -0.885 | 1.00 40.85 | C |
| ATOM | 1011 | CB | VAL | A | 63 | -11.128 | 3.252 | 0.397 | 1.00 40.45 | C |
| ATOM | 1013 | CG1 | VAL | A | 63 | -10.287 | 3.695 | 1.603 | 1.00 40.89 | C |
| ATOM | 1017 | CG2 | VAL | A | 63 | -12.362 | 4.110 | 0.291 | 1.00 41.72 | C |
| ATOM | 1021 | C | VAL | A | 63 | -8.994 | 2.558 | -0.643 | 1.00 41.66 | C |
| ATOM | 1022 | O | VAL | A | 63 | -9.044 | 1.352 | -0.400 | 1.00 40.46 | O |
| ATOM | 1024 | N | GLU | A | 64 | -7.864 | 3.247 | -0.664 | 1.00 44.26 | N |
| ATOM | 1025 | CA | GLU | A | 64 | -6.581 | 2.589 | -0.586 | 1.00 46.11 | C |
| ATOM | 1027 | CB | GLU | A | 64 | -5.793 | 2.808 | -1.878 | 1.00 46.95 | C |
| ATOM | 1030 | CG | GLU | A | 64 | -5.387 | 4.252 | -2.157 | 1.00 50.19 | C |
| ATOM | 1033 | CD | GLU | A | 64 | -4.832 | 4.421 | -3.555 | 1.00 55.07 | C |
| ATOM | 1034 | OE1 | GLU | A | 64 | -5.160 | 3.568 | -4.422 | 1.00 58.64 | O |
| ATOM | 1035 | OE2 | GLU | A | 64 | -4.068 | 5.396 | -3.791 | 1.00 56.49 | O |
| ATOM | 1036 | C | GLU | A | 64 | -5.817 | 3.089 | 0.605 | 1.00 46.65 | C |
| ATOM | 1037 | O | GLU | A | 64 | -4.871 | 2.416 | 1.025 | 1.00 48.61 | O |
| ATOM | 1039 | N | ASN | A | 69 | -9.699 | -5.137 | 4.836 | 1.00 50.30 | N |
| ATOM | 1040 | CA | ASN | A | 69 | -9.802 | -5.461 | 6.261 | 1.00 50.93 | C |
| ATOM | 1042 | CB | ASN | A | 69 | -8.423 | -5.348 | 6.949 | 1.00 51.20 | C |
| ATOM | 1045 | CG | ASN | A | 69 | -7.534 | -6.523 | 6.676 | 1.00 53.81 | C |
| ATOM | 1046 | OD1 | ASN | A | 69 | -7.366 | -6.926 | 5.520 | 1.00 56.28 | O |
| ATOM | 1047 | ND2 | ASN | A | 69 | -6.929 | -7.086 | 7.744 | 1.00 55.89 | N |
| ATOM | 1050 | C | ASN | A | 69 | -10.804 | -4.548 | 6.991 | 1.00 49.52 | C |
| ATOM | 1051 | O | ASN | A | 69 | -12.024 | -4.770 | 6.940 | 1.00 50.35 | O |
| ATOM | 1053 | N | ALA | A | 70 | -10.273 | -3.493 | 7.610 | 1.00 47.79 | N |
| ATOM | 1054 | CA | ALA | A | 70 | -11.027 | -2.551 | 8.482 | 1.00 46.02 | C |
| ATOM | 1056 | CB | ALA | A | 70 | -10.095 | -1.393 | 8.917 | 1.00 45.20 | C |
| ATOM | 1060 | C | ALA | A | 70 | -12.329 | -1.993 | 7.853 | 1.00 43.84 | C |
| ATOM | 1061 | O | ALA | A | 70 | -13.152 | -1.387 | 8.550 | 1.00 45.49 | O |
| ATOM | 1063 | N | LEU | A | 71 | -12.506 | -2.208 | 6.553 | 1.00 40.70 | N |
| ATOM | 1064 | CA | LEU | A | 71 | -13.664 | -1.724 | 5.808 | 1.00 38.26 | C |
| ATOM | 1066 | CB | LEU | A | 71 | -13.178 | -0.799 | 4.679 | 1.00 37.81 | C |
| ATOM | 1069 | CG | LEU | A | 71 | -14.076 | 0.322 | 4.165 | 1.00 35.97 | C |
| ATOM | 1071 | CD1 | LEU | A | 71 | -14.811 | 1.089 | 5.312 | 1.00 30.90 | C |
| ATOM | 1075 | CD2 | LEU | A | 71 | -13.167 | 1.269 | 3.355 | 1.00 31.34 | C |
| ATOM | 1079 | C | LEU | A | 71 | -14.414 | -2.950 | 5.275 | 1.00 36.69 | C |
| ATOM | 1080 | O | LEU | A | 71 | -13.859 | -3.751 | 4.506 | 1.00 36.93 | O |
| ATOM | 1082 | N | LEU | A | 72 | -15.655 | -3.107 | 5.706 | 1.00 34.62 | N |
| ATOM | 1083 | CA | LEU | A | 72 | -16.363 | -4.380 | 5.567 | 1.00 33.79 | C |
| ATOM | 1085 | CB | LEU | A | 72 | -17.089 | -4.697 | 6.873 | 1.00 34.75 | C |
| ATOM | 1088 | CG | LEU | A | 72 | -16.263 | -4.782 | 8.171 | 1.00 36.57 | C |
| ATOM | 1090 | CD1 | LEU | A | 72 | -17.229 | -5.172 | 9.290 | 1.00 36.78 | C |
| ATOM | 1094 | CD2 | LEU | A | 72 | -15.123 | -5.823 | 8.033 | 1.00 34.27 | C |
| ATOM | 1098 | C | LEU | A | 72 | -17.374 | -4.392 | 4.398 | 1.00 31.42 | C |
| ATOM | 1099 | O | LEU | A | 72 | -17.904 | -5.442 | 4.051 | 1.00 30.18 | O |
| ATOM | 1101 | N | LYS | A | 73 | -17.659 | -3.246 | 3.810 | 1.00 29.50 | N |
| ATOM | 1102 | CA | LYS | A | 73 | -18.592 | -3.226 | 2.651 | 1.00 29.77 | C |
| ATOM | 1104 | CB | LYS | A | 73 | -19.534 | -2.034 | 2.709 | 1.00 30.39 | C |
| ATOM | 1107 | CG | LYS | A | 73 | -20.853 | -2.377 | 3.466 | 1.00 32.55 | C |
| ATOM | 1110 | CD | LYS | A | 73 | -21.774 | -3.200 | 2.533 | 1.00 38.94 | C |
| ATOM | 1113 | CE | LYS | A | 73 | -23.291 | -2.935 | 2.766 | 1.00 44.43 | C |
| ATOM | 1116 | NZ | LYS | A | 73 | -24.173 | -3.378 | 1.609 | 1.00 47.06 | N |
| ATOM | 1120 | C | LYS | A | 73 | -17.902 | -3.396 | 1.284 | 1.00 27.45 | C |
| ATOM | 1121 | O | LYS | A | 73 | -17.762 | -2.455 | 0.523 | 1.00 27.16 | O |
| ATOM | 1123 | N | HIS | A | 74 | -17.478 | -4.624 | 1.032 | 1.00 25.84 | N |
| ATOM | 1124 | CA | HIS | A | 74 | -16.683 | -5.005 | -0.157 | 1.00 26.65 | C |
| ATOM | 1126 | CB | HIS | A | 74 | -16.084 | -6.403 | 0.045 | 1.00 26.92 | C |
| ATOM | 1129 | CG | HIS | A | 74 | -15.125 | -6.465 | 1.176 | 1.00 31.99 | C |

FIG. 4K

| | | | | | | | | | | |
|---|---|---|---|---|---|---|---|---|---|---|
| ATOM | 1130 | ND1 | HIS | A | 74 | -14.808 | -7.627 | 1.840 | 1.00 34.39 | N |
| ATOM | 1132 | CE1 | HIS | A | 74 | -13.914 | -7.366 | 2.780 | 1.00 35.49 | C |
| ATOM | 1134 | NE2 | HIS | A | 74 | -13.646 | -6.076 | 2.754 | 1.00 35.02 | N |
| ATOM | 1136 | CD2 | HIS | A | 74 | -14.395 | -5.492 | 1.761 | 1.00 35.96 | C |
| ATOM | 1138 | C | HIS | A | 74 | -17.525 | -5.072 | -1.391 | 1.00 23.93 | C |
| ATOM | 1139 | O | HIS | A | 74 | -18.553 | -5.692 | -1.375 | 1.00 24.65 | O |
| ATOM | 1141 | N | ARG | A | 75 | -17.074 | -4.493 | -2.480 | 1.00 23.49 | N |
| ATOM | 1142 | CA | ARG | A | 75 | -17.809 | -4.603 | -3.765 | 1.00 22.29 | C |
| ATOM | 1144 | CB | ARG | A | 75 | -17.343 | -3.542 | -4.803 | 1.00 22.01 | C |
| ATOM | 1147 | CG | ARG | A | 75 | -18.051 | -3.752 | -6.184 | 1.00 23.60 | C |
| ATOM | 1150 | CD | ARG | A | 75 | -17.769 | -2.714 | -7.198 | 1.00 24.27 | C |
| ATOM | 1153 | NE | ARG | A | 75 | -18.534 | -2.960 | -8.405 | 1.00 27.56 | N |
| ATOM | 1155 | CZ | ARG | A | 75 | -18.511 | -2.213 | -9.502 | 1.00 24.04 | C |
| ATOM | 1156 | NH1 | ARG | A | 75 | -17.780 | -1.126 | -9.587 | 1.00 28.81 | N |
| ATOM | 1159 | NH2 | ARG | A | 75 | -19.259 | -2.557 | -10.496 | 1.00 27.51 | N |
| ATOM | 1162 | C | ARG | A | 75 | -17.779 | -6.002 | -4.362 | 1.00 21.43 | C |
| ATOM | 1163 | O | ARG | A | 75 | -18.765 | -6.429 | -4.938 | 1.00 23.45 | O |
| ATOM | 1165 | N | PHE | A | 76 | -16.651 | -6.709 | -4.270 | 1.00 21.36 | N |
| ATOM | 1166 | CA | PHE | A | 76 | -16.536 | -8.069 | -4.821 | 1.00 21.10 | C |
| ATOM | 1168 | CB | PHE | A | 76 | -15.330 | -8.131 | -5.771 | 1.00 19.96 | C |
| ATOM | 1171 | CG | PHE | A | 76 | -15.412 | -7.153 | -6.852 | 1.00 21.31 | C |
| ATOM | 1172 | CD1 | PHE | A | 76 | -16.231 | -7.399 | -7.962 | 1.00 19.74 | C |
| ATOM | 1174 | CE1 | PHE | A | 76 | -16.364 | -6.446 | -8.985 | 1.00 19.45 | C |
| ATOM | 1176 | CZ | PHE | A | 76 | -15.753 | -5.300 | -8.906 | 1.00 16.56 | C |
| ATOM | 1178 | CE2 | PHE | A | 76 | -14.922 | -5.017 | -7.808 | 1.00 18.83 | C |
| ATOM | 1180 | CD2 | PHE | A | 76 | -14.791 | -5.939 | -6.751 | 1.00 19.24 | C |
| ATOM | 1182 | C | PHE | A | 76 | -16.338 | -9.143 | -3.748 | 1.00 20.61 | C |
| ATOM | 1183 | O | PHE | A | 76 | -15.537 | -8.934 | -2.848 | 1.00 20.88 | O |
| ATOM | 1185 | N | GLU | A | 77 | -17.030 | -10.273 | -3.877 | 1.00 20.45 | N |
| ATOM | 1186 | CA | GLU | A | 77 | -16.632 | -11.489 | -3.184 | 1.00 20.69 | C |
| ATOM | 1188 | CB | GLU | A | 77 | -17.797 | -12.436 | -2.940 | 1.00 21.46 | C |
| ATOM | 1191 | CG | GLU | A | 77 | -17.538 | -13.402 | -1.730 | 1.00 23.66 | C |
| ATOM | 1194 | CD | GLU | A | 77 | -17.471 | -12.674 | -0.396 | 1.00 26.23 | C |
| ATOM | 1195 | OE1 | GLU | A | 77 | -18.410 | -11.952 | -0.052 | 1.00 34.43 | O |
| ATOM | 1196 | OE2 | GLU | A | 77 | -16.479 | -12.817 | 0.329 | 1.00 31.80 | O |
| ATOM | 1197 | C | GLU | A | 77 | -15.590 | -12.208 | -4.015 | 1.00 21.50 | C |
| ATOM | 1198 | O | GLU | A | 77 | -15.820 | -12.502 | -5.177 | 1.00 20.48 | O |
| ATOM | 1200 | N | ILE | A | 78 | -14.468 | -12.538 | -3.392 | 1.00 21.53 | N |
| ATOM | 1201 | CA | ILE | A | 78 | -13.438 | -13.321 | -4.057 | 1.00 22.68 | C |
| ATOM | 1203 | CB | ILE | A | 78 | -12.091 | -13.044 | -3.458 | 1.00 23.45 | C |
| ATOM | 1205 | CG1 | ILE | A | 78 | -10.991 | -13.951 | -4.034 | 1.00 24.51 | C |
| ATOM | 1208 | CD1 | ILE | A | 78 | -10.754 | -13.790 | -5.423 | 1.00 24.46 | C |
| ATOM | 1212 | CG2 | ILE | A | 78 | -12.092 | -13.324 | -1.979 | 1.00 24.26 | C |
| ATOM | 1216 | C | ILE | A | 78 | -13.740 | -14.805 | -3.933 | 1.00 22.92 | C |
| ATOM | 1217 | O | ILE | A | 78 | -13.859 | -15.293 | -2.811 | 1.00 23.85 | O |
| ATOM | 1219 | N | ILE | A | 79 | -13.931 | -15.494 | -5.085 | 1.00 21.80 | N |
| ATOM | 1220 | CA | ILE | A | 79 | -14.250 | -16.923 | -5.158 | 1.00 19.88 | C |
| ATOM | 1222 | CB | ILE | A | 79 | -15.485 | -17.209 | -6.069 | 1.00 20.09 | C |
| ATOM | 1224 | CG1 | ILE | A | 79 | -16.745 | -16.541 | -5.481 | 1.00 20.63 | C |
| ATOM | 1227 | CD1 | ILE | A | 79 | -17.744 | -16.082 | -6.465 | 1.00 23.17 | C |
| ATOM | 1231 | CG2 | ILE | A | 79 | -15.783 | -18.773 | -6.198 | 1.00 16.69 | C |
| ATOM | 1235 | C | ILE | A | 79 | -12.981 | -17.745 | -5.550 | 1.00 20.44 | C |
| ATOM | 1236 | O | ILE | A | 79 | -12.751 | -18.790 | -4.980 | 1.00 19.75 | O |
| ATOM | 1238 | N | GLU | A | 80 | -12.139 | -17.242 | -6.450 | 1.00 19.89 | N |
| ATOM | 1239 | CA | GLU | A | 80 | -10.868 | -17.885 | -6.810 | 1.00 20.47 | C |
| ATOM | 1241 | CB | GLU | A | 80 | -10.116 | -17.073 | -7.936 | 1.00 21.83 | C |
| ATOM | 1244 | CG | GLU | A | 80 | -8.984 | -17.851 | -8.730 | 1.00 22.70 | C |
| ATOM | 1247 | CD | GLU | A | 80 | -9.368 | -19.280 | -9.169 | 1.00 26.61 | C |
| ATOM | 1248 | OE1 | GLU | A | 80 | -9.892 | -19.522 | -10.337 | 1.00 26.94 | O |
| ATOM | 1249 | OE2 | GLU | A | 80 | -9.164 | -20.176 | -8.333 | 1.00 25.79 | O |
| ATOM | 1250 | C | GLU | A | 80 | -9.957 | -17.918 | -5.642 | 1.00 20.93 | C |
| ATOM | 1251 | O | GLU | A | 80 | -9.918 | -16.978 | -4.850 | 1.00 20.60 | O |
| ATOM | 1253 | N | GLY | A | 81 | -9.226 | -19.011 | -5.523 | 1.00 19.93 | N |

FIG. 4L

```
ATOM   1254  CA  GLY A  81      -8.220 -19.122  -4.550  1.00 19.78           C
ATOM   1257  C   GLY A  81      -8.748 -20.015  -3.479  1.00 20.64           C
ATOM   1258  O   GLY A  81      -7.981 -20.616  -2.795  1.00 21.05           O
ATOM   1260  N   ARG A  82     -10.073 -20.103  -3.309  1.00 21.77           N
ATOM   1261  CA  ARG A  82     -10.638 -21.006  -2.275  1.00 21.34           C
ATOM   1263  CB  ARG A  82     -12.043 -20.525  -1.906  1.00 21.09           C
ATOM   1266  CG  ARG A  82     -12.135 -19.091  -1.313  1.00 19.98           C
ATOM   1269  CD  ARG A  82     -13.552 -18.784  -1.148  1.00 20.28           C
ATOM   1272  NE  ARG A  82     -13.925 -17.401  -0.934  1.00 21.64           N
ATOM   1274  CZ  ARG A  82     -14.331 -16.883   0.224  1.00 19.55           C
ATOM   1275  NH1 ARG A  82     -14.271 -17.565   1.337  1.00 17.21           N
ATOM   1278  NH2 ARG A  82     -14.665 -15.624   0.284  1.00 22.68           N
ATOM   1281  C   ARG A  82     -10.690 -22.443  -2.762  1.00 21.95           C
ATOM   1282  O   ARG A  82     -10.862 -22.668  -3.956  1.00 21.32           O
ATOM   1284  N   ASP A  83     -10.566 -23.444  -1.868  1.00 22.70           N
ATOM   1285  CA  ASP A  83     -11.013 -24.810  -2.189  1.00 22.14           C
ATOM   1287  CB  ASP A  83     -10.708 -25.780  -1.053  1.00 24.64           C
ATOM   1290  CG  ASP A  83     -11.499 -25.490   0.220  1.00 29.11           C
ATOM   1291  OD1 ASP A  83     -12.691 -25.853   0.285  1.00 34.82           O
ATOM   1292  OD2 ASP A  83     -10.905 -24.912   1.183  1.00 38.03           O
ATOM   1293  C   ASP A  83     -12.501 -24.887  -2.650  1.00 22.32           C
ATOM   1294  O   ASP A  83     -13.264 -23.926  -2.433  1.00 21.71           O
ATOM   1296  N   ARG A  84     -12.847 -25.968  -3.402  1.00 21.87           N
ATOM   1297  CA  ARG A  84     -14.170 -26.164  -3.982  1.00 21.71           C
ATOM   1299  CB  ARG A  84     -14.200 -27.352  -4.958  1.00 22.42           C
ATOM   1302  CG  ARG A  84     -13.356 -27.108  -6.234  1.00 24.99           C
ATOM   1305  CD  ARG A  84     -13.705 -27.915  -7.495  1.00 33.08           C
ATOM   1308  NE  ARG A  84     -12.898 -29.121  -7.539  1.00 37.24           N
ATOM   1310  CZ  ARG A  84     -12.403 -29.720  -8.617  1.00 35.66           C
ATOM   1311  NH1 ARG A  84     -12.622 -29.278  -9.868  1.00 39.32           N
ATOM   1314  NH2 ARG A  84     -11.718 -30.840  -8.426  1.00 35.09           N
ATOM   1317  C   ARG A  84     -15.340 -26.231  -2.959  1.00 21.04           C
ATOM   1318  O   ARG A  84     -16.415 -25.747  -3.240  1.00 20.23           O
ATOM   1320  N   ILE A  85     -15.085 -26.730  -1.768  1.00 20.61           N
ATOM   1321  CA  ILE A  85     -16.091 -26.779  -0.717  1.00 21.35           C
ATOM   1323  CB  ILE A  85     -15.551 -27.556   0.555  1.00 22.56           C
ATOM   1325  CG1 ILE A  85     -15.196 -28.982   0.166  1.00 20.56           C
ATOM   1328  CD1 ILE A  85     -14.091 -29.593   1.026  1.00 21.78           C
ATOM   1332  CG2 ILE A  85     -16.544 -27.523   1.708  1.00 22.29           C
ATOM   1336  C   ILE A  85     -16.507 -25.396  -0.344  1.00 20.16           C
ATOM   1337  O   ILE A  85     -17.699 -25.074  -0.351  1.00 20.10           O
ATOM   1339  N   MET A  86     -15.515 -24.553  -0.062  1.00 19.64           N
ATOM   1340  CA  MET A  86     -15.770 -23.208   0.368  1.00 18.69           C
ATOM   1342  CB  MET A  86     -14.548 -22.623   1.097  1.00 19.83           C
ATOM   1345  CG  MET A  86     -14.434 -23.111   2.573  1.00 22.33           C
ATOM   1348  SD  MET A  86     -15.951 -22.818   3.515  1.00 36.97           S
ATOM   1349  CE  MET A  86     -16.285 -21.118   3.278  1.00 16.27           C
ATOM   1353  C   MET A  86     -16.172 -22.311  -0.785  1.00 18.74           C
ATOM   1354  O   MET A  86     -16.992 -21.401  -0.584  1.00 16.67           O
ATOM   1356  N   ALA A  87     -15.593 -22.548  -1.984  1.00 17.76           N
ATOM   1357  CA  ALA A  87     -16.033 -21.848  -3.153  1.00 17.60           C
ATOM   1359  CB  ALA A  87     -15.181 -22.271  -4.417  1.00 18.74           C
ATOM   1363  C   ALA A  87     -17.522 -22.070  -3.388  1.00 17.40           C
ATOM   1364  O   ALA A  87     -18.247 -21.106  -3.619  1.00 18.53           O
ATOM   1366  N   TRP A  88     -17.977 -23.312  -3.360  1.00 18.16           N
ATOM   1367  CA  TRP A  88     -19.399 -23.592  -3.573  1.00 19.10           C
ATOM   1369  CB  TRP A  88     -19.647 -25.082  -3.898  1.00 18.82           C
ATOM   1372  CG  TRP A  88     -19.387 -25.425  -5.278  1.00 16.31           C
ATOM   1373  CD1 TRP A  88     -18.378 -26.203  -5.776  1.00 13.37           C
ATOM   1375  NE1 TRP A  88     -18.462 -26.239  -7.146  1.00 16.31           N
ATOM   1377  CE2 TRP A  88     -19.468 -25.428  -7.552  1.00 14.82           C
ATOM   1378  CD2 TRP A  88     -20.065 -24.891  -6.391  1.00 16.25           C
ATOM   1379  CE3 TRP A  88     -21.130 -24.021  -6.531  1.00 16.53           C
```

FIG. 4M

```
ATOM   1381  CZ3 TRP A  88     -21.587 -23.720  -7.816  1.00 16.31           C
ATOM   1383  CH2 TRP A  88     -20.966 -24.246  -8.942  1.00 14.98           C
ATOM   1385  CZ2 TRP A  88     -19.890 -25.095  -8.831  1.00 17.58           C
ATOM   1387  C   TRP A  88     -20.282 -23.149  -2.407  1.00 18.61           C
ATOM   1388  O   TRP A  88     -21.392 -22.765  -2.629  1.00 20.91           O
ATOM   1390  N   THR A  89     -19.783 -23.213  -1.180  1.00 18.27           N
ATOM   1391  CA  THR A  89     -20.462 -22.627  -0.029  1.00 18.10           C
ATOM   1393  CB  THR A  89     -19.672 -22.939   1.273  1.00 18.78           C
ATOM   1395  OG1 THR A  89     -19.491 -24.336   1.411  1.00 15.81           O
ATOM   1397  CG2 THR A  89     -20.341 -22.403   2.572  1.00 19.57           C
ATOM   1401  C   THR A  89     -20.706 -21.117  -0.207  1.00 18.81           C
ATOM   1402  O   THR A  89     -21.814 -20.596   0.097  1.00 19.84           O
ATOM   1404  N   VAL A  90     -19.698 -20.391  -0.685  1.00 19.00           N
ATOM   1405  CA  VAL A  90     -19.826 -18.964  -0.906  1.00 18.31           C
ATOM   1407  CB  VAL A  90     -18.449 -18.241  -1.155  1.00 19.43           C
ATOM   1409  CG1 VAL A  90     -18.661 -16.721  -1.475  1.00 17.31           C
ATOM   1413  CG2 VAL A  90     -17.618 -18.314   0.069  1.00 20.21           C
ATOM   1417  C   VAL A  90     -20.799 -18.688  -2.006  1.00 17.64           C
ATOM   1418  O   VAL A  90     -21.691 -17.879  -1.803  1.00 17.18           O
ATOM   1420  N   VAL A  91     -20.690 -19.387  -3.152  1.00 18.06           N
ATOM   1421  CA  VAL A  91     -21.669 -19.218  -4.258  1.00 17.21           C
ATOM   1423  CB  VAL A  91     -21.376 -20.129  -5.440  1.00 17.76           C
ATOM   1425  CG1 VAL A  91     -22.589 -20.184  -6.384  1.00 16.67           C
ATOM   1429  CG2 VAL A  91     -20.145 -19.600  -6.162  1.00 16.76           C
ATOM   1433  C   VAL A  91     -23.143 -19.449  -3.790  1.00 18.15           C
ATOM   1434  O   VAL A  91     -24.033 -18.671  -4.096  1.00 14.83           O
ATOM   1436  N   ASN A  92     -23.350 -20.517  -3.036  1.00 19.48           N
ATOM   1437  CA  ASN A  92     -24.653 -20.841  -2.514  1.00 21.21           C
ATOM   1439  CB  ASN A  92     -24.562 -22.133  -1.722  1.00 21.93           C
ATOM   1442  CG  ASN A  92     -24.618 -23.354  -2.612  1.00 28.79           C
ATOM   1443  OD1 ASN A  92     -24.601 -23.238  -3.860  1.00 36.94           O
ATOM   1444  ND2 ASN A  92     -24.680 -24.544  -1.995  1.00 31.11           N
ATOM   1447  C   ASN A  92     -25.250 -19.799  -1.608  1.00 20.96           C
ATOM   1448  O   ASN A  92     -26.395 -19.438  -1.726  1.00 20.73           O
ATOM   1450  N   SER A  93     -24.468 -19.335  -0.662  1.00 22.18           N
ATOM   1451  CA  SER A  93     -24.883 -18.242   0.235  1.00 22.20           C
ATOM   1453  CB  SER A  93     -23.823 -18.090   1.320  1.00 21.57           C
ATOM   1456  OG  SER A  93     -23.813 -16.817   1.872  1.00 27.30           O
ATOM   1458  C   SER A  93     -25.207 -16.908  -0.529  1.00 22.52           C
ATOM   1459  O   SER A  93     -26.212 -16.213  -0.235  1.00 19.76           O
ATOM   1461  N   ILE A  94     -24.400 -16.569  -1.527  1.00 22.32           N
ATOM   1462  CA  ILE A  94     -24.707 -15.425  -2.362  1.00 22.22           C
ATOM   1464  CB  ILE A  94     -23.553 -15.081  -3.388  1.00 22.50           C
ATOM   1466  CG1 ILE A  94     -22.321 -14.560  -2.680  1.00 22.23           C
ATOM   1469  CD1 ILE A  94     -21.084 -14.589  -3.556  1.00 19.61           C
ATOM   1473  CG2 ILE A  94     -24.011 -14.069  -4.435  1.00 20.41           C
ATOM   1477  C   ILE A  94     -26.002 -15.660  -3.143  1.00 22.46           C
ATOM   1478  O   ILE A  94     -26.846 -14.817  -3.164  1.00 22.87           O
ATOM   1480  N   CYS A  95     -26.160 -16.762  -3.836  1.00 24.44           N
ATOM   1481  CA  CYS A  95     -27.452 -17.048  -4.483  1.00 26.05           C
ATOM   1483  CB  CYS A  95     -27.415 -18.426  -5.131  1.00 26.83           C
ATOM   1486  SG  CYS A  95     -26.204 -18.541  -6.527  1.00 28.09           S
ATOM   1488  C   CYS A  95     -28.679 -16.925  -3.462  1.00 26.95           C
ATOM   1489  O   CYS A  95     -29.652 -16.193  -3.689  1.00 25.51           O
ATOM   1491  N   ASN A  96     -28.550 -17.605  -2.337  1.00 27.06           N
ATOM   1492  CA  ASN A  96     -29.481 -17.488  -1.228  1.00 27.69           C
ATOM   1494  CB  ASN A  96     -28.972 -18.174   0.062  1.00 26.25           C
ATOM   1497  CG  ASN A  96     -29.018 -19.689  -0.008  1.00 26.75           C
ATOM   1498  OD1 ASN A  96     -29.531 -20.260  -0.973  1.00 27.85           O
ATOM   1499  ND2 ASN A  96     -28.442 -20.362   1.010  1.00 22.79           N
ATOM   1502  C   ASN A  96     -29.851 -16.062  -0.942  1.00 28.01           C
ATOM   1503  O   ASN A  96     -31.032 -15.800  -0.825  1.00 28.33           O
ATOM   1505  N   THR A  97     -28.889 -15.138  -0.907  1.00 28.06           N
```

FIG. 4N

```
ATOM   1506  CA   THR A  97    -29.174 -13.806  -0.423  1.00 27.85           C
ATOM   1508  CB   THR A  97    -28.054 -13.215   0.562  1.00 28.24           C
ATOM   1510  OG1  THR A  97    -27.298 -12.176  -0.069  1.00 32.96           O
ATOM   1512  CG2  THR A  97    -27.163 -14.189   1.054  1.00 23.90           C
ATOM   1516  C    THR A  97    -29.471 -12.749  -1.475  1.00 27.72           C
ATOM   1517  O    THR A  97    -30.047 -11.754  -1.146  1.00 29.22           O
ATOM   1519  N    THR A  98    -29.021 -12.896  -2.704  1.00 27.28           N
ATOM   1520  CA   THR A  98    -29.289 -11.899  -3.744  1.00 26.68           C
ATOM   1522  CB   THR A  98    -28.001 -11.558  -4.526  1.00 26.80           C
ATOM   1524  OG1  THR A  98    -27.577 -12.711  -5.266  1.00 24.60           O
ATOM   1526  CG2  THR A  98    -26.870 -11.158  -3.537  1.00 26.11           C
ATOM   1530  C    THR A  98    -30.290 -12.425  -4.719  1.00 26.65           C
ATOM   1531  O    THR A  98    -30.740 -11.703  -5.557  1.00 27.58           O
ATOM   1533  N    GLY A  99    -30.630 -13.699  -4.627  1.00 27.19           N
ATOM   1534  CA   GLY A  99    -31.450 -14.312  -5.636  1.00 27.70           C
ATOM   1537  C    GLY A  99    -30.864 -14.417  -7.041  1.00 28.93           C
ATOM   1538  O    GLY A  99    -31.576 -14.865  -7.924  1.00 27.61           O
ATOM   1540  N    VAL A 100    -29.581 -14.105  -7.301  1.00 29.69           N
ATOM   1541  CA   VAL A 100    -29.070 -14.467  -8.651  1.00 29.83           C
ATOM   1543  CB   VAL A 100    -27.649 -13.943  -8.974  1.00 30.24           C
ATOM   1545  CG1  VAL A 100    -27.638 -12.444  -9.003  1.00 33.39           C
ATOM   1549  CG2  VAL A 100    -26.661 -14.494  -7.998  1.00 28.50           C
ATOM   1553  C    VAL A 100    -29.013 -15.968  -8.833  1.00 29.97           C
ATOM   1554  O    VAL A 100    -28.908 -16.747  -7.893  1.00 28.90           O
ATOM   1556  N    GLU A 101    -29.022 -16.347 -10.098  1.00 31.73           N
ATOM   1557  CA   GLU A 101    -29.019 -17.731 -10.575  1.00 32.51           C
ATOM   1559  CB   GLU A 101    -29.275 -17.620 -12.082  1.00 34.61           C
ATOM   1562  CG   GLU A 101    -29.647 -18.878 -12.833  1.00 40.79           C
ATOM   1565  CD   GLU A 101    -29.851 -18.595 -14.350  1.00 44.48           C
ATOM   1566  OE1  GLU A 101    -29.096 -19.175 -15.161  1.00 48.94           O
ATOM   1567  OE2  GLU A 101    -30.724 -17.765 -14.714  1.00 47.68           O
ATOM   1568  C    GLU A 101    -27.678 -18.410 -10.315  1.00 31.48           C
ATOM   1569  O    GLU A 101    -26.634 -17.788 -10.445  1.00 31.03           O
ATOM   1571  N    LYS A 102    -27.714 -19.675  -9.931  1.00 31.74           N
ATOM   1572  CA   LYS A 102    -26.538 -20.434  -9.531  1.00 32.82           C
ATOM   1574  CB   LYS A 102    -26.958 -21.667  -8.721  1.00 32.25           C
ATOM   1577  CG   LYS A 102    -25.854 -22.316  -7.911  1.00 33.10           C
ATOM   1580  CD   LYS A 102    -26.308 -23.663  -7.265  1.00 34.79           C
ATOM   1583  CE   LYS A 102    -27.071 -23.472  -5.945  1.00 36.05           C
ATOM   1586  NZ   LYS A 102    -27.818 -24.722  -5.568  1.00 35.64           N
ATOM   1590  C    LYS A 102    -25.798 -20.870 -10.779  1.00 33.19           C
ATOM   1591  O    LYS A 102    -26.340 -21.613 -11.581  1.00 35.22           O
ATOM   1593  N    PRO A 103    -24.558 -20.411 -10.963  1.00 33.42           N
ATOM   1594  CA   PRO A 103    -23.861 -20.827 -12.199  1.00 33.38           C
ATOM   1596  CB   PRO A 103    -22.579 -19.991 -12.170  1.00 33.40           C
ATOM   1599  CG   PRO A 103    -22.256 -19.841 -10.665  1.00 32.31           C
ATOM   1602  CD   PRO A 103    -23.619 -19.918  -9.929  1.00 33.43           C
ATOM   1605  C    PRO A 103    -23.543 -22.320 -12.143  1.00 33.18           C
ATOM   1606  O    PRO A 103    -23.588 -22.919 -11.078  1.00 32.89           O
ATOM   1607  N    LYS A 104    -23.242 -22.954 -13.267  1.00 33.97           N
ATOM   1608  CA   LYS A 104    -22.902 -24.390 -13.177  1.00 34.76           C
ATOM   1610  CB   LYS A 104    -23.428 -25.172 -14.359  1.00 35.87           C
ATOM   1613  CG   LYS A 104    -24.969 -25.171 -14.468  1.00 39.54           C
ATOM   1616  CD   LYS A 104    -25.631 -26.419 -13.849  1.00 41.86           C
ATOM   1619  CE   LYS A 104    -27.006 -26.709 -14.510  1.00 45.68           C
ATOM   1622  NZ   LYS A 104    -27.195 -28.167 -14.830  1.00 48.38           N
ATOM   1626  C    LYS A 104    -21.411 -24.609 -13.008  1.00 33.55           C
ATOM   1627  O    LYS A 104    -21.025 -25.616 -12.423  1.00 34.79           O
ATOM   1629  N    PHE A 105    -20.572 -23.682 -13.481  1.00 32.04           N
ATOM   1630  CA   PHE A 105    -19.128 -23.710 -13.095  1.00 31.60           C
ATOM   1632  CB   PHE A 105    -18.265 -23.565 -14.343  1.00 33.09           C
ATOM   1635  CG   PHE A 105    -18.624 -24.511 -15.427  1.00 35.88           C
ATOM   1636  CD1  PHE A 105    -18.454 -25.869 -15.257  1.00 40.92           C
```

FIG. 4O

```
ATOM   1638  CE1 PHE A 105     -18.801 -26.753 -16.258  1.00 41.97           C
ATOM   1640  CZ  PHE A 105     -19.309 -26.308 -17.431  1.00 39.96           C
ATOM   1642  CE2 PHE A 105     -19.511 -24.967 -17.617  1.00 42.33           C
ATOM   1644  CD2 PHE A 105     -19.159 -24.059 -16.613  1.00 40.48           C
ATOM   1646  C   PHE A 105     -18.725 -22.579 -12.097  1.00 28.22           C
ATOM   1647  O   PHE A 105     -19.356 -21.501 -12.064  1.00 27.52           O
ATOM   1649  N   LEU A 106     -17.663 -22.788 -11.334  1.00 24.93           N
ATOM   1650  CA  LEU A 106     -17.241 -21.751 -10.371  1.00 23.49           C
ATOM   1652  CB  LEU A 106     -16.153 -22.262  -9.438  1.00 23.80           C
ATOM   1655  CG  LEU A 106     -16.607 -23.265  -8.425  1.00 22.14           C
ATOM   1657  CD1 LEU A 106     -15.361 -23.908  -7.734  1.00 18.98           C
ATOM   1661  CD2 LEU A 106     -17.485 -22.415  -7.457  1.00 16.61           C
ATOM   1665  C   LEU A 106     -16.688 -20.544 -11.061  1.00 22.77           C
ATOM   1666  O   LEU A 106     -15.827 -20.685 -11.904  1.00 21.46           O
ATOM   1668  N   PRO A 107     -17.208 -19.340 -10.716  1.00 22.55           N
ATOM   1669  CA  PRO A 107     -16.619 -18.120 -11.178  1.00 20.85           C
ATOM   1671  CB  PRO A 107     -17.789 -17.133 -11.147  1.00 20.47           C
ATOM   1674  CG  PRO A 107     -18.621 -17.581 -10.120  1.00 22.95           C
ATOM   1677  CD  PRO A 107     -18.456 -19.074  -9.979  1.00 23.33           C
ATOM   1680  C   PRO A 107     -15.489 -17.684 -10.294  1.00 18.23           C
ATOM   1681  O   PRO A 107     -15.055 -18.381  -9.418  1.00 17.05           O
ATOM   1682  N   ASP A 108     -14.997 -16.504 -10.583  1.00 18.35           N
ATOM   1683  CA  ASP A 108     -13.814 -16.028  -9.984  1.00 16.38           C
ATOM   1685  CB  ASP A 108     -12.964 -15.326 -11.003  1.00 14.64           C
ATOM   1688  CG  ASP A 108     -12.096 -16.272 -11.866  1.00 14.48           C
ATOM   1689  OD1 ASP A 108     -11.953 -15.977 -13.050  1.00 16.75           O
ATOM   1690  OD2 ASP A 108     -11.510 -17.237 -11.408  1.00 14.43           O
ATOM   1691  C   ASP A 108     -14.189 -15.040  -8.894  1.00 16.04           C
ATOM   1692  O   ASP A 108     -13.495 -15.007  -7.857  1.00 15.86           O
ATOM   1694  N   LEU A 109     -15.173 -14.191  -9.213  1.00 16.67           N
ATOM   1695  CA  LEU A 109     -15.614 -13.070  -8.357  1.00 16.75           C
ATOM   1697  CB  LEU A 109     -15.039 -11.759  -8.805  1.00 17.47           C
ATOM   1700  CG  LEU A 109     -13.511 -11.535  -8.861  1.00 17.53           C
ATOM   1702  CD1 LEU A 109     -13.197 -10.316  -9.670  1.00 21.08           C
ATOM   1706  CD2 LEU A 109     -12.987 -11.405  -7.452  1.00 19.67           C
ATOM   1710  C   LEU A 109     -17.164 -12.956  -8.360  1.00 17.15           C
ATOM   1711  O   LEU A 109     -17.817 -13.467  -9.222  1.00 18.18           O
ATOM   1713  N   TYR A 110     -17.739 -12.296  -7.348  1.00 19.32           N
ATOM   1714  CA  TYR A 110     -19.106 -11.836  -7.371  1.00 18.38           C
ATOM   1716  CB  TYR A 110     -20.010 -12.574  -6.329  1.00 19.15           C
ATOM   1719  CG  TYR A 110     -21.457 -12.104  -6.434  1.00 19.24           C
ATOM   1720  CD1 TYR A 110     -22.249 -12.529  -7.483  1.00 20.32           C
ATOM   1722  CE1 TYR A 110     -23.551 -12.125  -7.630  1.00 15.06           C
ATOM   1724  CZ  TYR A 110     -24.080 -11.225  -6.751  1.00 21.81           C
ATOM   1725  OH  TYR A 110     -25.374 -10.866  -6.953  1.00 21.28           O
ATOM   1727  CE2 TYR A 110     -23.334 -10.742  -5.664  1.00 17.41           C
ATOM   1729  CD2 TYR A 110     -21.995 -11.163  -5.543  1.00 21.83           C
ATOM   1731  C   TYR A 110     -19.113 -10.349  -7.147  1.00 18.92           C
ATOM   1732  O   TYR A 110     -18.457  -9.833  -6.246  1.00 18.02           O
ATOM   1734  N   ASP A 111     -19.885  -9.646  -7.970  1.00 20.94           N
ATOM   1735  CA  ASP A 111     -19.949  -8.185  -7.962  1.00 22.09           C
ATOM   1737  CB  ASP A 111     -19.850  -7.650  -9.396  1.00 22.02           C
ATOM   1740  CG  ASP A 111     -20.084  -6.162  -9.519  1.00 23.79           C
ATOM   1741  OD1 ASP A 111     -20.492  -5.449  -8.554  1.00 22.21           O
ATOM   1742  OD2 ASP A 111     -19.910  -5.689 -10.637  1.00 24.62           O
ATOM   1743  C   ASP A 111     -21.279  -7.833  -7.349  1.00 24.14           C
ATOM   1744  O   ASP A 111     -22.315  -8.026  -7.999  1.00 24.35           O
ATOM   1746  N   TYR A 112     -21.249  -7.403  -6.080  1.00 25.61           N
ATOM   1747  CA  TYR A 112     -22.462  -6.953  -5.363  1.00 26.29           C
ATOM   1749  CB  TYR A 112     -22.150  -6.732  -3.859  1.00 25.98           C
ATOM   1752  CG  TYR A 112     -21.866  -7.964  -3.050  1.00 27.30           C
ATOM   1753  CD1 TYR A 112     -20.550  -8.363  -2.758  1.00 26.81           C
ATOM   1755  CE1 TYR A 112     -20.299  -9.484  -2.008  1.00 27.21           C
```

FIG. 4P

| | | | | | | | | | |
|---|---|---|---|---|---|---|---|---|---|
| ATOM | 1757 | CZ | TYR | A | 112 | -21.366 | -10.237 | -1.550 | 1.00 28.73 | C |
| ATOM | 1758 | OH | TYR | A | 112 | -21.130 | -11.370 | -0.831 | 1.00 31.55 | O |
| ATOM | 1760 | CE2 | TYR | A | 112 | -22.657 | -9.869 | -1.823 | 1.00 27.89 | C |
| ATOM | 1762 | CD2 | TYR | A | 112 | -22.906 | -8.744 | -2.558 | 1.00 28.83 | C |
| ATOM | 1764 | C | TYR | A | 112 | -23.057 | -5.645 | -5.930 | 1.00 27.21 | C |
| ATOM | 1765 | O | TYR | A | 112 | -24.160 | -5.274 | -5.532 | 1.00 27.86 | O |
| ATOM | 1767 | N | LYS | A | 113 | -22.358 | -4.884 | -6.791 | 1.00 28.62 | N |
| ATOM | 1768 | CA | LYS | A | 113 | -23.036 | -3.703 | -7.406 | 1.00 28.75 | C |
| ATOM | 1770 | CB | LYS | A | 113 | -22.103 | -2.530 | -7.793 | 1.00 29.51 | C |
| ATOM | 1773 | CG | LYS | A | 113 | -22.911 | -1.285 | -8.187 | 1.00 29.92 | C |
| ATOM | 1776 | CD | LYS | A | 113 | -22.077 | -0.013 | -8.355 | 1.00 34.77 | C |
| ATOM | 1779 | CE | LYS | A | 113 | -22.549 | 0.884 | -9.559 | 1.00 35.34 | C |
| ATOM | 1782 | NZ | LYS | A | 113 | -21.356 | 1.197 | -10.524 | 1.00 37.61 | N |
| ATOM | 1786 | C | LYS | A | 113 | -23.889 | -4.014 | -8.599 | 1.00 29.07 | C |
| ATOM | 1787 | O | LYS | A | 113 | -24.989 | -3.468 | -8.726 | 1.00 29.19 | O |
| ATOM | 1789 | N | GLU | A | 114 | -23.408 | -4.859 | -9.505 | 1.00 29.27 | N |
| ATOM | 1790 | CA | GLU | A | 114 | -24.210 | -5.278 | -10.662 | 1.00 28.26 | C |
| ATOM | 1792 | CB | GLU | A | 114 | -23.294 | -5.453 | -11.843 | 1.00 29.03 | C |
| ATOM | 1795 | CG | GLU | A | 114 | -22.385 | -4.270 | -12.059 | 1.00 30.44 | C |
| ATOM | 1798 | CD | GLU | A | 114 | -23.092 | -3.092 | -12.681 | 1.00 37.26 | C |
| ATOM | 1799 | OE1 | GLU | A | 114 | -24.235 | -3.278 | -13.193 | 1.00 38.37 | O |
| ATOM | 1800 | OE2 | GLU | A | 114 | -22.496 | -1.978 | -12.620 | 1.00 40.87 | O |
| ATOM | 1801 | C | GLU | A | 114 | -24.999 | -6.557 | -10.480 | 1.00 28.88 | C |
| ATOM | 1802 | O | GLU | A | 114 | -25.766 | -6.975 | -11.373 | 1.00 28.68 | O |
| ATOM | 1804 | N | ASN | A | 115 | -24.774 | -7.219 | -9.343 | 1.00 29.17 | N |
| ATOM | 1805 | CA | ASN | A | 115 | -25.381 | -8.506 | -9.006 | 1.00 28.97 | C |
| ATOM | 1807 | CB | ASN | A | 115 | -26.877 | -8.350 | -8.587 | 1.00 29.39 | C |
| ATOM | 1810 | CG | ASN | A | 115 | -27.003 | -7.869 | -7.171 | 1.00 32.64 | C |
| ATOM | 1811 | OD1 | ASN | A | 115 | -27.393 | -6.719 | -6.926 | 1.00 36.46 | O |
| ATOM | 1812 | ND2 | ASN | A | 115 | -26.550 | -8.702 | -6.216 | 1.00 30.25 | N |
| ATOM | 1815 | C | ASN | A | 115 | -25.171 | -9.577 | -10.048 | 1.00 27.50 | C |
| ATOM | 1816 | O | ASN | A | 115 | -26.110 | -10.227 | -10.527 | 1.00 27.57 | O |
| ATOM | 1818 | N | ARG | A | 116 | -23.900 | -9.795 | -10.349 | 1.00 26.76 | N |
| ATOM | 1819 | CA | ARG | A | 116 | -23.485 | -10.851 | -11.260 | 1.00 24.38 | C |
| ATOM | 1821 | CB | ARG | A | 116 | -23.465 | -10.333 | -12.691 | 1.00 24.02 | C |
| ATOM | 1824 | CG | ARG | A | 116 | -22.458 | -9.243 | -12.891 | 1.00 24.22 | C |
| ATOM | 1827 | CD | ARG | A | 116 | -22.724 | -8.473 | -14.123 | 1.00 24.86 | C |
| ATOM | 1830 | NE | ARG | A | 116 | -21.691 | -7.456 | -14.356 | 1.00 27.78 | N |
| ATOM | 1832 | CZ | ARG | A | 116 | -21.816 | -6.451 | -15.231 | 1.00 28.23 | C |
| ATOM | 1833 | NH1 | ARG | A | 116 | -22.943 | -6.289 | -15.954 | 1.00 27.75 | N |
| ATOM | 1836 | NH2 | ARG | A | 116 | -20.842 | -5.579 | -15.348 | 1.00 24.86 | N |
| ATOM | 1839 | C | ARG | A | 116 | -22.117 | -11.426 | -10.905 | 1.00 21.72 | C |
| ATOM | 1840 | O | ARG | A | 116 | -21.272 | -10.766 | -10.368 | 1.00 20.29 | O |
| ATOM | 1842 | N | PHE | A | 117 | -21.945 | -12.691 | -11.233 | 1.00 20.91 | N |
| ATOM | 1843 | CA | PHE | A | 117 | -20.654 | -13.338 | -11.202 | 1.00 19.71 | C |
| ATOM | 1845 | CB | PHE | A | 117 | -20.829 | -14.805 | -11.225 | 1.00 18.91 | C |
| ATOM | 1848 | CG | PHE | A | 117 | -21.511 | -15.335 | -10.028 | 1.00 20.54 | C |
| ATOM | 1849 | CD1 | PHE | A | 117 | -20.823 | -15.466 | -8.819 | 1.00 24.79 | C |
| ATOM | 1851 | CE1 | PHE | A | 117 | -21.439 | -15.936 | -7.686 | 1.00 23.52 | C |
| ATOM | 1853 | CZ | PHE | A | 117 | -22.741 | -16.334 | -7.749 | 1.00 25.41 | C |
| ATOM | 1855 | CE2 | PHE | A | 117 | -23.449 | -16.234 | -8.937 | 1.00 25.83 | C |
| ATOM | 1857 | CD2 | PHE | A | 117 | -22.827 | -15.738 | -10.087 | 1.00 23.53 | C |
| ATOM | 1859 | C | PHE | A | 117 | -19.796 | -12.914 | -12.366 | 1.00 19.90 | C |
| ATOM | 1860 | O | PHE | A | 117 | -20.316 | -12.421 | -13.353 | 1.00 18.65 | O |
| ATOM | 1862 | N | ILE | A | 118 | -18.477 | -13.097 | -12.200 | 1.00 18.22 | N |
| ATOM | 1863 | CA | ILE | A | 118 | -17.502 | -12.619 | -13.138 | 1.00 18.37 | C |
| ATOM | 1865 | CB | ILE | A | 118 | -16.708 | -11.373 | -12.601 | 1.00 17.99 | C |
| ATOM | 1867 | CG1 | ILE | A | 118 | -17.622 | -10.220 | -12.350 | 1.00 18.21 | C |
| ATOM | 1870 | CD1 | ILE | A | 118 | -16.994 | -9.029 | -11.736 | 1.00 16.51 | C |
| ATOM | 1874 | CG2 | ILE | A | 118 | -15.682 | -10.949 | -13.592 | 1.00 19.63 | C |
| ATOM | 1878 | C | ILE | A | 118 | -16.478 | -13.681 | -13.331 | 1.00 17.25 | C |
| ATOM | 1879 | O | ILE | A | 118 | -16.003 | -14.271 | -12.365 | 1.00 17.71 | O |
| ATOM | 1881 | N | GLU | A | 119 | -16.146 | -13.944 | -14.581 | 1.00 17.50 | N |

FIG. 4Q

```
ATOM   1882  CA   GLU A 119     -15.076 -14.847 -14.880  1.00 18.83           C
ATOM   1884  CB   GLU A 119     -15.582 -15.938 -15.835  1.00 19.64           C
ATOM   1887  CG   GLU A 119     -14.423 -16.668 -16.517  1.00 21.62           C
ATOM   1890  CD   GLU A 119     -13.691 -17.560 -15.560  1.00 27.20           C
ATOM   1891  OE1  GLU A 119     -14.396 -18.319 -14.810  1.00 26.78           O
ATOM   1892  OE2  GLU A 119     -12.415 -17.489 -15.556  1.00 29.28           O
ATOM   1893  C    GLU A 119     -13.938 -14.023 -15.504  1.00 17.40           C
ATOM   1894  O    GLU A 119     -14.151 -13.323 -16.505  1.00 16.54           O
ATOM   1896  N    ILE A 120     -12.738 -14.153 -14.922  1.00 16.83           N
ATOM   1897  CA   ILE A 120     -11.570 -13.406 -15.342  1.00 16.12           C
ATOM   1899  CB   ILE A 120     -10.760 -12.847 -14.160  1.00 16.33           C
ATOM   1901  CG1  ILE A 120     -11.573 -11.819 -13.361  1.00 17.76           C
ATOM   1904  CD1  ILE A 120     -12.263 -10.786 -14.228  1.00 27.36           C
ATOM   1908  CG2  ILE A 120      -9.446 -12.146 -14.581  1.00 13.88           C
ATOM   1912  C    ILE A 120     -10.658 -14.381 -16.053  1.00 15.76           C
ATOM   1913  O    ILE A 120     -10.410 -15.463 -15.565  1.00 13.37           O
ATOM   1915  N    GLY A 121     -10.068 -13.902 -17.139  1.00 15.55           N
ATOM   1916  CA   GLY A 121      -9.004 -14.619 -17.879  1.00 14.19           C
ATOM   1919  C    GLY A 121      -7.871 -13.662 -18.171  1.00 13.81           C
ATOM   1920  O    GLY A 121      -8.075 -12.459 -18.299  1.00 13.14           O
ATOM   1922  N    VAL A 122      -6.651 -14.190 -18.201  1.00 14.17           N
ATOM   1923  CA   VAL A 122      -5.510 -13.370 -18.488  1.00 14.51           C
ATOM   1925  CB   VAL A 122      -4.570 -13.211 -17.237  1.00 14.04           C
ATOM   1927  CG1  VAL A 122      -3.317 -12.479 -17.552  1.00 13.22           C
ATOM   1931  CG2  VAL A 122      -5.291 -12.518 -16.063  1.00 15.86           C
ATOM   1935  C    VAL A 122      -4.811 -14.164 -19.565  1.00 16.23           C
ATOM   1936  O    VAL A 122      -4.467 -15.282 -19.309  1.00 14.98           O
ATOM   1938  N    THR A 123      -4.605 -13.595 -20.770  1.00 17.75           N
ATOM   1939  CA   THR A 123      -4.065 -14.381 -21.872  1.00 18.91           C
ATOM   1941  CB   THR A 123      -5.123 -14.590 -23.041  1.00 17.81           C
ATOM   1943  OG1  THR A 123      -4.618 -15.580 -23.949  1.00 22.42           O
ATOM   1945  CG2  THR A 123      -5.441 -13.327 -23.772  1.00 18.47           C
ATOM   1949  C    THR A 123      -2.787 -13.805 -22.487  1.00 19.65           C
ATOM   1950  O    THR A 123      -2.577 -12.642 -22.453  1.00 21.50           O
ATOM   1952  N    ARG A 124      -1.984 -14.641 -23.095  1.00 22.23           N
ATOM   1953  CA   ARG A 124      -0.904 -14.190 -23.959  1.00 25.61           C
ATOM   1955  CB   ARG A 124       0.480 -14.652 -23.417  1.00 26.74           C
ATOM   1958  CG   ARG A 124       0.532 -16.005 -22.949  1.00 30.80           C
ATOM   1961  CD   ARG A 124       1.086 -16.246 -21.527  1.00 29.87           C
ATOM   1964  NE   ARG A 124       0.205 -17.242 -20.884  1.00 28.22           N
ATOM   1966  CZ   ARG A 124       0.467 -18.494 -20.529  1.00 27.99           C
ATOM   1967  NH1  ARG A 124       1.648 -19.122 -20.695  1.00 29.17           N
ATOM   1970  NH2  ARG A 124      -0.515 -19.148 -19.966  1.00 28.47           N
ATOM   1973  C    ARG A 124      -1.145 -14.530 -25.479  1.00 26.60           C
ATOM   1974  O    ARG A 124      -0.254 -14.329 -26.297  1.00 25.75           O
ATOM   1976  N    ARG A 125      -2.382 -14.968 -25.793  1.00 27.09           N
ATOM   1977  CA   ARG A 125      -2.911 -15.193 -27.136  1.00 26.52           C
ATOM   1979  CB   ARG A 125      -3.541 -16.555 -27.256  1.00 26.05           C
ATOM   1982  CG   ARG A 125      -2.623 -17.769 -27.241  1.00 27.91           C
ATOM   1985  CD   ARG A 125      -3.468 -19.012 -27.295  1.00 29.20           C
ATOM   1988  NE   ARG A 125      -4.248 -19.132 -26.075  1.00 34.62           N
ATOM   1990  CZ   ARG A 125      -5.215 -20.023 -25.832  1.00 37.80           C
ATOM   1991  NH1  ARG A 125      -5.569 -20.963 -26.732  1.00 38.27           N
ATOM   1994  NH2  ARG A 125      -5.823 -19.973 -24.639  1.00 38.09           N
ATOM   1997  C    ARG A 125      -3.969 -14.101 -27.457  1.00 26.64           C
ATOM   1998  O    ARG A 125      -4.356 -13.300 -26.620  1.00 27.37           O
ATOM   2000  N    GLU A 126      -4.388 -14.029 -28.708  1.00 26.40           N
ATOM   2001  CA   GLU A 126      -5.385 -13.067 -29.129  1.00 25.30           C
ATOM   2003  CB   GLU A 126      -5.936 -13.469 -30.532  1.00 24.50           C
ATOM   2006  CG   GLU A 126      -7.479 -13.282 -30.656  1.00 23.62           C
ATOM   2009  CD   GLU A 126      -7.684 -11.957 -30.933  1.00 24.93           C
ATOM   2010  OE1  GLU A 126      -6.622 -11.430 -31.048  1.00 29.31           O
ATOM   2011  OE2  GLU A 126      -8.780 -11.393 -31.035  1.00 28.68           O
```

FIG. 4R

```
ATOM   2012  C   GLU A 126      -6.514 -13.156 -28.109  1.00 24.21           C
ATOM   2013  O   GLU A 126      -6.951 -14.256 -27.854  1.00 24.01           O
ATOM   2015  N   VAL A 127      -7.063 -12.024 -27.664  1.00 24.98           N
ATOM   2016  CA  VAL A 127      -8.099 -11.982 -26.580  1.00 26.27           C
ATOM   2018  CB  VAL A 127      -8.417 -10.519 -26.115  1.00 27.43           C
ATOM   2020  CG1 VAL A 127      -7.293  -9.961 -25.368  1.00 27.23           C
ATOM   2024  CG2 VAL A 127      -8.762  -9.559 -27.338  1.00 28.59           C
ATOM   2028  C   VAL A 127      -9.445 -12.655 -26.865  1.00 25.98           C
ATOM   2029  O   VAL A 127     -10.172 -13.036 -25.916  1.00 25.27           O
ATOM   2031  N   HIS A 128      -9.828 -12.763 -28.150  1.00 24.52           N
ATOM   2032  CA  HIS A 128     -11.054 -13.426 -28.473  1.00 23.35           C
ATOM   2034  CB  HIS A 128     -11.414 -13.288 -29.971  1.00 25.33           C
ATOM   2037  CG  HIS A 128     -11.856 -11.914 -30.322  1.00 19.06           C
ATOM   2038  ND1 HIS A 128     -10.958 -10.907 -30.575  1.00 18.80           N
ATOM   2040  CE1 HIS A 128     -11.611  -9.781 -30.798  1.00 20.84           C
ATOM   2042  NE2 HIS A 128     -12.912 -10.024 -30.667  1.00 19.44           N
ATOM   2044  CD2 HIS A 128     -13.089 -11.352 -30.359  1.00 19.96           C
ATOM   2046  C   HIS A 128     -10.983 -14.851 -28.132  1.00 22.89           C
ATOM   2047  O   HIS A 128     -11.983 -15.442 -27.833  1.00 22.14           O
ATOM   2049  N   ILE A 129      -9.787 -15.411 -28.132  1.00 23.38           N
ATOM   2050  CA  ILE A 129      -9.648 -16.819 -27.902  1.00 23.32           C
ATOM   2052  CB  ILE A 129      -8.255 -17.309 -28.283  1.00 22.59           C
ATOM   2054  CG1 ILE A 129      -8.059 -17.188 -29.808  1.00 22.07           C
ATOM   2057  CD1 ILE A 129      -6.676 -17.757 -30.271  1.00 22.28           C
ATOM   2061  CG2 ILE A 129      -8.104 -18.755 -27.806  1.00 23.75           C
ATOM   2065  C   ILE A 129     -10.005 -17.231 -26.471  1.00 24.22           C
ATOM   2066  O   ILE A 129     -10.868 -18.100 -26.265  1.00 24.33           O
ATOM   2068  N   TYR A 130      -9.359 -16.633 -25.472  1.00 24.98           N
ATOM   2069  CA  TYR A 130      -9.770 -16.956 -24.077  1.00 26.34           C
ATOM   2071  CB  TYR A 130      -8.910 -16.194 -23.090  1.00 26.88           C
ATOM   2074  CG  TYR A 130      -8.737 -16.845 -21.740  1.00 32.11           C
ATOM   2075  CD1 TYR A 130      -7.494 -17.325 -21.336  1.00 34.68           C
ATOM   2077  CE1 TYR A 130      -7.323 -17.891 -20.115  1.00 35.80           C
ATOM   2079  CZ  TYR A 130      -8.379 -17.955 -19.235  1.00 36.03           C
ATOM   2080  OH  TYR A 130      -8.189 -18.527 -18.005  1.00 41.73           O
ATOM   2082  CE2 TYR A 130      -9.621 -17.465 -19.572  1.00 35.71           C
ATOM   2084  CD2 TYR A 130      -9.795 -16.896 -20.811  1.00 35.79           C
ATOM   2086  C   TYR A 130     -11.258 -16.648 -23.880  1.00 25.18           C
ATOM   2087  O   TYR A 130     -11.986 -17.447 -23.289  1.00 24.90           O
ATOM   2089  N   TYR A 131     -11.723 -15.510 -24.404  1.00 25.15           N
ATOM   2090  CA  TYR A 131     -13.136 -15.160 -24.341  1.00 24.93           C
ATOM   2092  CB  TYR A 131     -13.427 -13.860 -25.084  1.00 24.59           C
ATOM   2095  CG  TYR A 131     -14.808 -13.403 -24.819  1.00 24.95           C
ATOM   2096  CD1 TYR A 131     -15.065 -12.450 -23.856  1.00 24.13           C
ATOM   2098  CE1 TYR A 131     -16.305 -12.076 -23.546  1.00 23.50           C
ATOM   2100  CZ  TYR A 131     -17.395 -12.653 -24.173  1.00 28.67           C
ATOM   2101  OH  TYR A 131     -18.690 -12.187 -23.856  1.00 27.17           O
ATOM   2103  CE2 TYR A 131     -17.193 -13.588 -25.164  1.00 30.09           C
ATOM   2105  CD2 TYR A 131     -15.897 -13.975 -25.478  1.00 30.21           C
ATOM   2107  C   TYR A 131     -14.038 -16.269 -24.892  1.00 26.90           C
ATOM   2108  O   TYR A 131     -15.006 -16.614 -24.240  1.00 25.95           O
ATOM   2110  N   LEU A 132     -13.713 -16.839 -26.076  1.00 28.42           N
ATOM   2111  CA  LEU A 132     -14.509 -17.966 -26.664  1.00 28.97           C
ATOM   2113  CB  LEU A 132     -13.956 -18.362 -28.056  1.00 29.43           C
ATOM   2116  CG  LEU A 132     -14.117 -17.291 -29.136  1.00 31.58           C
ATOM   2118  CD1 LEU A 132     -13.623 -17.752 -30.546  1.00 27.53           C
ATOM   2122  CD2 LEU A 132     -15.575 -16.857 -29.145  1.00 25.39           C
ATOM   2126  C   LEU A 132     -14.449 -19.211 -25.822  1.00 29.28           C
ATOM   2127  O   LEU A 132     -15.463 -19.895 -25.573  1.00 27.68           O
ATOM   2129  N   GLU A 133     -13.249 -19.553 -25.390  1.00 31.42           N
ATOM   2130  CA  GLU A 133     -13.129 -20.787 -24.589  1.00 33.34           C
ATOM   2132  CB  GLU A 133     -11.704 -21.086 -24.169  1.00 33.37           C
ATOM   2135  CG  GLU A 133     -10.854 -21.366 -25.370  1.00 38.04           C
```

FIG. 4S

```
ATOM   2138  CD   GLU A 133      -9.387 -21.656 -25.073  1.00 42.78           C
ATOM   2139  OE1  GLU A 133      -8.977 -21.697 -23.880  1.00 45.36           O
ATOM   2140  OE2  GLU A 133      -8.651 -21.867 -26.072  1.00 47.10           O
ATOM   2141  C    GLU A 133     -14.031 -20.721 -23.402  1.00 33.96           C
ATOM   2142  O    GLU A 133     -14.672 -21.716 -23.062  1.00 35.17           O
ATOM   2144  N    LYS A 134     -14.129 -19.553 -22.792  1.00 34.78           N
ATOM   2145  CA   LYS A 134     -14.964 -19.403 -21.631  1.00 36.41           C
ATOM   2147  CB   LYS A 134     -14.381 -18.372 -20.614  1.00 36.53           C
ATOM   2150  CG   LYS A 134     -13.061 -18.869 -19.908  1.00 38.50           C
ATOM   2153  CD   LYS A 134     -13.230 -20.269 -19.209  1.00 43.08           C
ATOM   2156  CE   LYS A 134     -11.924 -21.067 -18.997  1.00 44.84           C
ATOM   2159  NZ   LYS A 134     -12.187 -22.562 -18.962  1.00 48.99           N
ATOM   2163  C    LYS A 134     -16.443 -19.181 -21.924  1.00 37.46           C
ATOM   2164  O    LYS A 134     -17.277 -19.657 -21.144  1.00 36.37           O
ATOM   2166  N    ALA A 135     -16.788 -18.470 -23.004  1.00 38.60           N
ATOM   2167  CA   ALA A 135     -18.215 -18.370 -23.414  1.00 39.74           C
ATOM   2169  CB   ALA A 135     -18.416 -17.303 -24.520  1.00 39.13           C
ATOM   2173  C    ALA A 135     -18.811 -19.733 -23.862  1.00 41.19           C
ATOM   2174  O    ALA A 135     -20.034 -19.971 -23.749  1.00 40.43           O
ATOM   2176  N    ASN A 136     -17.954 -20.617 -24.367  1.00 43.50           N
ATOM   2177  CA   ASN A 136     -18.398 -21.936 -24.833  1.00 46.08           C
ATOM   2179  CB   ASN A 136     -17.261 -22.693 -25.550  1.00 46.15           C
ATOM   2182  CG   ASN A 136     -17.037 -22.200 -26.993  1.00 48.34           C
ATOM   2183  OD1  ASN A 136     -17.824 -21.402 -27.523  1.00 49.55           O
ATOM   2184  ND2  ASN A 136     -15.932 -22.672 -27.635  1.00 50.97           N
ATOM   2187  C    ASN A 136     -19.022 -22.784 -23.722  1.00 47.77           C
ATOM   2188  O    ASN A 136     -20.081 -23.375 -23.923  1.00 48.03           O
ATOM   2190  N    LYS A 137     -18.381 -22.809 -22.555  1.00 50.42           N
ATOM   2191  CA   LYS A 137     -18.894 -23.517 -21.371  1.00 52.35           C
ATOM   2193  CB   LYS A 137     -17.724 -23.793 -20.423  1.00 53.15           C
ATOM   2196  CG   LYS A 137     -16.865 -25.004 -20.836  1.00 55.37           C
ATOM   2199  CD   LYS A 137     -15.544 -24.603 -21.505  1.00 57.57           C
ATOM   2202  CE   LYS A 137     -14.375 -25.810 -22.180  1.00 60.15           C
ATOM   2205  NZ   LYS A 137     -13.428 -25.568 -22.481  1.00 62.86           N
ATOM   2209  C    LYS A 137     -20.031 -22.798 -20.608  1.00 53.64           C
ATOM   2210  O    LYS A 137     -20.954 -23.434 -20.087  1.00 53.80           O
ATOM   2212  N    ILE A 138     -19.960 -21.476 -20.554  1.00 54.94           N
ATOM   2213  CA   ILE A 138     -20.962 -20.644 -19.882  1.00 56.34           C
ATOM   2215  CB   ILE A 138     -20.400 -19.202 -19.722  1.00 56.27           C
ATOM   2217  CG1  ILE A 138     -19.567 -19.117 -18.442  1.00 56.21           C
ATOM   2220  CD1  ILE A 138     -18.643 -17.902 -18.383  1.00 55.28           C
ATOM   2224  CG2  ILE A 138     -21.502 -18.147 -19.754  1.00 57.01           C
ATOM   2228  C    ILE A 138     -22.342 -20.603 -20.563  1.00 57.52           C
ATOM   2229  O    ILE A 138     -23.352 -20.244 -19.919  1.00 58.75           O
ATOM   2231  N    LYS A 139     -22.384 -20.972 -21.843  1.00 58.47           N
ATOM   2232  CA   LYS A 139     -23.606 -20.937 -22.677  1.00 59.03           C
ATOM   2234  CB   LYS A 139     -24.283 -22.314 -22.714  1.00 59.40           C
ATOM   2237  CG   LYS A 139     -23.567 -23.375 -23.583  1.00 61.60           C
ATOM   2240  CD   LYS A 139     -23.664 -23.086 -25.117  1.00 63.74           C
ATOM   2243  CE   LYS A 139     -23.146 -24.277 -25.948  1.00 65.00           C
ATOM   2246  NZ   LYS A 139     -22.573 -23.906 -27.284  1.00 66.48           N
ATOM   2250  C    LYS A 139     -24.616 -19.863 -22.259  1.00 58.99           C
ATOM   2251  O    LYS A 139     -25.540 -20.123 -21.483  1.00 58.89           O
ATOM   2253  N    GLU A 141     -25.979 -18.214 -19.379  1.00 50.86           N
ATOM   2254  CA   GLU A 141     -24.832 -17.298 -19.464  1.00 50.54           C
ATOM   2256  CB   GLU A 141     -24.517 -16.940 -20.936  1.00 51.64           C
ATOM   2259  CG   GLU A 141     -25.745 -16.809 -21.884  1.00 54.93           C
ATOM   2262  CD   GLU A 141     -26.562 -15.516 -21.730  1.00 58.27           C
ATOM   2263  OE1  GLU A 141     -26.960 -14.961 -22.789  1.00 60.97           O
ATOM   2264  OE2  GLU A 141     -26.847 -15.077 -20.585  1.00 60.03           O
ATOM   2265  C    GLU A 141     -24.989 -16.005 -18.666  1.00 48.69           C
ATOM   2266  O    GLU A 141     -24.764 -14.905 -19.184  1.00 49.48           O
ATOM   2268  N    LYS A 142     -25.337 -16.107 -17.396  1.00 46.08           N
```

FIG. 4T

```
ATOM   2269  CA   LYS A 142     -25.369 -14.877 -16.589  1.00 43.51           C
ATOM   2271  CB   LYS A 142     -26.465 -15.005 -15.535  1.00 43.94           C
ATOM   2274  CG   LYS A 142     -27.855 -15.247 -16.199  1.00 46.65           C
ATOM   2277  CD   LYS A 142     -28.984 -14.426 -15.531  1.00 51.06           C
ATOM   2280  CE   LYS A 142     -29.126 -12.991 -16.116  1.00 52.66           C
ATOM   2283  NZ   LYS A 142     -30.332 -12.857 -17.031  1.00 51.94           N
ATOM   2287  C    LYS A 142     -23.992 -14.478 -16.003  1.00 39.86           C
ATOM   2288  O    LYS A 142     -23.857 -13.490 -15.238  1.00 38.77           O
ATOM   2290  N    THR A 143     -22.963 -15.244 -16.348  1.00 35.54           N
ATOM   2291  CA   THR A 143     -21.640 -14.964 -15.787  1.00 32.29           C
ATOM   2293  CB   THR A 143     -20.855 -16.223 -15.534  1.00 31.98           C
ATOM   2295  OG1  THR A 143     -21.482 -16.936 -14.461  1.00 32.43           O
ATOM   2297  CG2  THR A 143     -19.436 -15.916 -15.122  1.00 30.99           C
ATOM   2301  C    THR A 143     -20.965 -13.970 -16.736  1.00 30.44           C
ATOM   2302  O    THR A 143     -20.903 -14.187 -17.952  1.00 30.80           O
ATOM   2304  N    HIS A 144     -20.548 -12.835 -16.192  1.00 27.71           N
ATOM   2305  CA   HIS A 144     -19.849 -11.816 -16.974  1.00 26.31           C
ATOM   2307  CB   HIS A 144     -19.872 -10.499 -16.220  1.00 25.89           C
ATOM   2310  CG   HIS A 144     -19.848  -9.292 -17.110  1.00 25.95           C
ATOM   2311  ND1  HIS A 144     -20.985  -8.781 -17.691  1.00 23.29           N
ATOM   2313  CE1  HIS A 144     -20.674  -7.684 -18.363  1.00 25.31           C
ATOM   2315  NE2  HIS A 144     -19.381  -7.455 -18.224  1.00 20.55           N
ATOM   2317  CD2  HIS A 144     -18.837  -8.462 -17.464  1.00 24.29           C
ATOM   2319  C    HIS A 144     -18.401 -12.215 -17.187  1.00 25.34           C
ATOM   2320  O    HIS A 144     -17.779 -12.650 -16.225  1.00 24.19           O
ATOM   2322  N    ILE A 145     -17.866 -12.048 -18.417  1.00 22.58           N
ATOM   2323  CA   ILE A 145     -16.508 -12.466 -18.758  1.00 20.97           C
ATOM   2325  CB   ILE A 145     -16.464 -13.312 -20.082  1.00 21.27           C
ATOM   2327  CG1  ILE A 145     -17.378 -14.497 -20.022  1.00 21.49           C
ATOM   2330  CD1  ILE A 145     -17.419 -15.334 -21.374  1.00 17.19           C
ATOM   2334  CG2  ILE A 145     -15.143 -13.876 -20.357  1.00 20.45           C
ATOM   2338  C    ILE A 145     -15.684 -11.219 -18.985  1.00 21.22           C
ATOM   2339  O    ILE A 145     -16.163 -10.323 -19.651  1.00 21.63           O
ATOM   2341  N    HIS A 146     -14.454 -11.149 -18.426  1.00 20.18           N
ATOM   2342  CA   HIS A 146     -13.550 -10.070 -18.670  1.00 19.45           C
ATOM   2344  CB   HIS A 146     -13.495  -9.132 -17.464  1.00 20.53           C
ATOM   2347  CG   HIS A 146     -12.856  -7.807 -17.730  1.00 19.65           C
ATOM   2348  ND1  HIS A 146     -13.235  -6.663 -17.065  1.00 19.96           N
ATOM   2350  CE1  HIS A 146     -12.503  -5.646 -17.489  1.00 21.90           C
ATOM   2352  NE2  HIS A 146     -11.643  -6.098 -18.385  1.00 18.30           N
ATOM   2354  CD2  HIS A 146     -11.837  -7.446 -18.544  1.00 20.67           C
ATOM   2356  C    HIS A 146     -12.208 -10.672 -18.859  1.00 20.19           C
ATOM   2357  O    HIS A 146     -11.674 -11.322 -17.921  1.00 19.48           O
ATOM   2359  N    ILE A 147     -11.620 -10.424 -20.035  1.00 19.77           N
ATOM   2360  CA   ILE A 147     -10.316 -10.989 -20.380  1.00 20.64           C
ATOM   2362  CB   ILE A 147     -10.316 -11.676 -21.781  1.00 22.08           C
ATOM   2364  CG1  ILE A 147     -11.479 -12.695 -21.908  1.00 23.83           C
ATOM   2367  CD1  ILE A 147     -11.275 -13.963 -21.095  1.00 28.34           C
ATOM   2371  CG2  ILE A 147      -8.954 -12.269 -22.059  1.00 18.00           C
ATOM   2375  C    ILE A 147      -9.322  -9.854 -20.438  1.00 20.39           C
ATOM   2376  O    ILE A 147      -9.612  -8.776 -20.940  1.00 19.54           O
ATOM   2378  N    PHE A 148      -8.139 -10.087 -19.914  1.00 20.81           N
ATOM   2379  CA   PHE A 148      -7.089  -9.101 -20.027  1.00 21.42           C
ATOM   2381  CB   PHE A 148      -6.520  -8.725 -18.647  1.00 20.44           C
ATOM   2384  CG   PHE A 148      -7.475  -7.995 -17.759  1.00 18.59           C
ATOM   2385  CD1  PHE A 148      -7.427  -6.623 -17.675  1.00 16.88           C
ATOM   2387  CE1  PHE A 148      -8.293  -5.907 -16.816  1.00 18.61           C
ATOM   2389  CZ   PHE A 148      -9.150  -6.574 -16.009  1.00 15.82           C
ATOM   2391  CE2  PHE A 148      -9.199  -7.949 -16.053  1.00 16.39           C
ATOM   2393  CD2  PHE A 148      -8.384  -8.673 -16.947  1.00 14.33           C
ATOM   2395  C    PHE A 148      -5.962  -9.766 -20.820  1.00 22.77           C
ATOM   2396  O    PHE A 148      -5.827 -10.947 -20.774  1.00 24.80           O
ATOM   2398  N    SER A 149      -5.094  -8.997 -21.441  1.00 25.54           N
```

FIG. 4U

```
ATOM   2399  CA   SER A 149      -4.004   -9.551  -22.218  1.00  27.57           C
ATOM   2401  CB   SER A 149      -4.324   -9.418  -23.730  1.00  28.36           C
ATOM   2404  OG   SER A 149      -3.237   -8.851  -24.430  1.00  31.65           O
ATOM   2406  C    SER A 149      -2.750   -8.815  -21.846  1.00  28.12           C
ATOM   2407  O    SER A 149      -2.798   -7.814  -21.170  1.00  29.37           O
ATOM   2409  N    PHE A 150      -1.613   -9.341  -22.242  1.00  29.44           N
ATOM   2410  CA   PHE A 150      -0.349   -8.768  -21.859  1.00  29.97           C
ATOM   2412  CB   PHE A 150       0.774   -9.853  -21.787  1.00  30.15           C
ATOM   2415  CG   PHE A 150       0.776  -10.720  -20.553  1.00  26.32           C
ATOM   2416  CD1  PHE A 150       1.529  -10.388  -19.475  1.00  25.66           C
ATOM   2418  CE1  PHE A 150       1.567  -11.161  -18.360  1.00  22.39           C
ATOM   2420  CZ   PHE A 150       0.849  -12.358  -18.302  1.00  23.54           C
ATOM   2422  CE2  PHE A 150       0.092  -12.712  -19.353  1.00  20.62           C
ATOM   2424  CD2  PHE A 150       0.065  -11.898  -20.495  1.00  26.99           C
ATOM   2426  C    PHE A 150      -0.005   -7.694  -22.910  1.00  31.85           C
ATOM   2427  O    PHE A 150       1.103   -7.209  -22.930  1.00  33.22           O
ATOM   2429  N    THR A 151      -0.943   -7.326  -23.783  1.00  32.17           N
ATOM   2430  CA   THR A 151      -0.667   -6.333  -24.841  1.00  32.67           C
ATOM   2432  CB   THR A 151      -1.199   -6.748  -26.287  1.00  32.13           C
ATOM   2434  OG1  THR A 151      -2.642   -6.863  -26.288  1.00  33.12           O
ATOM   2436  CG2  THR A 151      -0.640   -8.025  -26.738  1.00  31.02           C
ATOM   2440  C    THR A 151      -1.404   -5.062  -24.556  1.00  32.44           C
ATOM   2441  O    THR A 151      -1.257   -4.109  -25.292  1.00  32.41           O
ATOM   2443  N    GLY A 152      -2.246   -5.070  -23.526  1.00  32.32           N
ATOM   2444  CA   GLY A 152      -3.124   -3.936  -23.280  1.00  31.84           C
ATOM   2447  C    GLY A 152      -4.561   -4.041  -23.735  1.00  30.62           C
ATOM   2448  O    GLY A 152      -5.388   -3.226  -23.314  1.00  32.36           O
ATOM   2450  N    GLU A 153      -4.878   -4.990  -24.597  1.00  29.33           N
ATOM   2451  CA   GLU A 153      -6.244   -5.239  -25.050  1.00  28.81           C
ATOM   2453  CB   GLU A 153      -6.294   -6.144  -26.311  1.00  29.16           C
ATOM   2456  CG   GLU A 153      -5.528   -5.593  -27.515  1.00  34.39           C
ATOM   2459  CD   GLU A 153      -5.423   -6.598  -28.624  1.00  37.09           C
ATOM   2460  OE1  GLU A 153      -4.267   -6.948  -28.983  1.00  43.50           O
ATOM   2461  OE2  GLU A 153      -6.493   -7.050  -29.081  1.00  33.81           O
ATOM   2462  C    GLU A 153      -7.060   -5.928  -23.951  1.00  27.34           C
ATOM   2463  O    GLU A 153      -6.520   -6.690  -23.180  1.00  26.85           O
ATOM   2465  N    GLU A 154      -8.346   -5.624  -23.893  1.00  26.64           N
ATOM   2466  CA   GLU A 154      -9.294   -6.317  -23.056  1.00  28.17           C
ATOM   2468  CB   GLU A 154      -9.787   -5.434  -21.919  1.00  28.44           C
ATOM   2471  CG   GLU A 154      -8.784   -4.778  -21.031  1.00  29.35           C
ATOM   2474  CD   GLU A 154      -9.443   -3.680  -20.206  1.00  31.99           C
ATOM   2475  OE1  GLU A 154     -10.224   -4.006  -19.260  1.00  27.59           O
ATOM   2476  OE2  GLU A 154      -9.199   -2.480  -20.536  1.00  33.26           O
ATOM   2477  C    GLU A 154     -10.533   -6.690  -23.877  1.00  28.57           C
ATOM   2478  O    GLU A 154     -10.837   -6.067  -24.898  1.00  29.85           O
ATOM   2480  N    MET A 155     -11.249   -7.697  -23.416  1.00  28.27           N
ATOM   2481  CA   MET A 155     -12.542   -8.016  -23.954  1.00  27.95           C
ATOM   2483  CB   MET A 155     -12.397   -9.086  -25.045  1.00  28.61           C
ATOM   2486  CG   MET A 155     -13.695   -9.578  -25.605  1.00  29.85           C
ATOM   2489  SD   MET A 155     -13.473  -10.569  -27.093  1.00  32.63           S
ATOM   2490  CE   MET A 155     -13.281   -9.059  -28.068  1.00  35.44           C
ATOM   2494  C    MET A 155     -13.497   -8.465  -22.837  1.00  27.07           C
ATOM   2495  O    MET A 155     -13.233   -9.409  -22.106  1.00  25.23           O
ATOM   2497  N    ALA A 156     -14.594   -7.744  -22.720  1.00  27.17           N
ATOM   2498  CA   ALA A 156     -15.584   -7.970  -21.682  1.00  28.43           C
ATOM   2500  CB   ALA A 156     -15.657   -6.774  -20.687  1.00  27.43           C
ATOM   2504  C    ALA A 156     -16.906   -8.133  -22.356  1.00  28.18           C
ATOM   2505  O    ALA A 156     -17.134   -7.517  -23.406  1.00  28.26           O
ATOM   2507  N    THR A 157     -17.773   -8.963  -21.777  1.00  28.86           N
ATOM   2508  CA   THR A 157     -19.119   -9.076  -22.313  1.00  28.83           C
ATOM   2510  CB   THR A 157     -19.910  -10.291  -21.749  1.00  30.26           C
ATOM   2512  OG1  THR A 157     -21.272   -9.948  -21.377  1.00  32.79           O
ATOM   2514  CG2  THR A 157     -19.173  -10.901  -20.657  1.00  22.57           C
```

FIG. 4V

| | | | | | | | | | | |
|---|---|---|---|---|---|---|---|---|---|---|
|ATOM|2518|C  |THR|A|157|-19.902|-7.743|-22.383|1.00 29.08|C|
|ATOM|2519|O  |THR|A|157|-19.809|-6.874|-21.491|1.00 27.35|O|
|ATOM|2521|N  |LYS|A|158|-20.601|-7.606|-23.540|1.00 29.75|N|
|ATOM|2522|CA |LYS|A|158|-21.300|-6.405|-23.979|1.00 29.46|C|
|ATOM|2524|CB |LYS|A|158|-22.543|-6.143|-23.124|1.00 30.88|C|
|ATOM|2527|CG |LYS|A|158|-23.664|-7.067|-23.399|1.00 33.93|C|
|ATOM|2530|CD |LYS|A|158|-24.908|-6.587|-22.636|1.00 37.97|C|
|ATOM|2533|CE |LYS|A|158|-25.731|-7.723|-22.036|1.00 38.89|C|
|ATOM|2536|NZ |LYS|A|158|-26.962|-7.133|-21.386|1.00 44.09|N|
|ATOM|2540|C  |LYS|A|158|-20.439|-5.191|-23.925|1.00 29.29|C|
|ATOM|2541|O  |LYS|A|158|-20.965|-4.094|-23.775|1.00 29.22|O|
|ATOM|2543|N  |ALA|A|159|-19.124|-5.363|-24.025|1.00 28.23|N|
|ATOM|2544|CA |ALA|A|159|-18.214|-4.246|-23.875|1.00 27.72|C|
|ATOM|2546|CB |ALA|A|159|-18.268|-3.339|-25.125|1.00 27.45|C|
|ATOM|2550|C  |ALA|A|159|-18.417|-3.449|-22.575|1.00 26.99|C|
|ATOM|2551|O  |ALA|A|159|-18.112|-2.280|-22.480|1.00 26.15|O|
|ATOM|2553|N  |ASP|A|160|-18.892|-4.113|-21.539|1.00 27.50|N|
|ATOM|2554|CA |ASP|A|160|-19.009|-3.534|-20.201|1.00 26.58|C|
|ATOM|2556|CB |ASP|A|160|-20.297|-4.092|-19.616|1.00 28.34|C|
|ATOM|2559|CG |ASP|A|160|-20.612|-3.593|-18.226|1.00 28.80|C|
|ATOM|2560|OD1|ASP|A|160|-19.747|-2.968|-17.562|1.00 28.49|O|
|ATOM|2561|OD2|ASP|A|160|-21.779|-3.854|-17.820|1.00 31.47|O|
|ATOM|2562|C  |ASP|A|160|-17.766|-3.973|-19.379|1.00 26.86|C|
|ATOM|2563|O  |ASP|A|160|-17.569|-5.139|-19.037|1.00 25.77|O|
|ATOM|2565|N  |TYR|A|161|-16.913|-3.019|-19.048|1.00 26.95|N|
|ATOM|2566|CA |TYR|A|161|-15.658|-3.349|-18.414|1.00 27.50|C|
|ATOM|2568|CB |TYR|A|161|-14.587|-2.461|-19.006|1.00 26.48|C|
|ATOM|2571|CG |TYR|A|161|-14.366|-2.732|-20.454|1.00 30.05|C|
|ATOM|2572|CD1|TYR|A|161|-13.636|-3.830|-20.871|1.00 31.06|C|
|ATOM|2574|CE1|TYR|A|161|-13.416|-4.067|-22.232|1.00 36.48|C|
|ATOM|2576|CZ |TYR|A|161|-13.941|-3.164|-23.197|1.00 36.01|C|
|ATOM|2577|OH |TYR|A|161|-13.731|-3.378|-24.524|1.00 36.30|O|
|ATOM|2579|CE2|TYR|A|161|-14.682|-2.079|-22.805|1.00 33.71|C|
|ATOM|2581|CD2|TYR|A|161|-14.876|-1.849|-21.440|1.00 36.04|C|
|ATOM|2583|C  |TYR|A|161|-15.665|-3.310|-16.860|1.00 26.13|C|
|ATOM|2584|O  |TYR|A|161|-14.651|-3.519|-16.222|1.00 26.59|O|
|ATOM|2586|N  |THR|A|162|-16.833|-3.103|-16.284|1.00 26.72|N|
|ATOM|2587|CA |THR|A|162|-17.093|-3.127|-14.814|1.00 25.55|C|
|ATOM|2589|CB |THR|A|162|-16.799|-4.515|-14.188|1.00 26.01|C|
|ATOM|2591|OG1|THR|A|162|-17.667|-5.503|-14.752|1.00 24.29|O|
|ATOM|2593|CG2|THR|A|162|-17.003|-4.499|-12.642|1.00 24.98|C|
|ATOM|2597|C  |THR|A|162|-16.362|-2.064|-14.018|1.00 25.32|C|
|ATOM|2598|O  |THR|A|162|-16.975|-1.217|-13.407|1.00 24.39|O|
|ATOM|2600|N  |LEU|A|163|-15.037|-2.137|-13.988|1.00 25.35|N|
|ATOM|2601|CA |LEU|A|163|-14.223|-1.227|-13.180|1.00 24.16|C|
|ATOM|2603|CB |LEU|A|163|-12.871|-1.884|-12.978|1.00 23.47|C|
|ATOM|2606|CG |LEU|A|163|-12.849|-3.199|-12.193|1.00 20.40|C|
|ATOM|2608|CD1|LEU|A|163|-11.417|-3.756|-12.243|1.00 19.33|C|
|ATOM|2612|CD2|LEU|A|163|-13.268|-2.932|-10.827|1.00 16.61|C|
|ATOM|2616|C  |LEU|A|163|-13.998|0.119|-13.867|1.00 25.44|C|
|ATOM|2617|O  |LEU|A|163|-14.137|0.228|-15.113|1.00 26.02|O|
|ATOM|2619|N  |ASP|A|164|-13.612|1.122|-13.078|1.00 25.92|N|
|ATOM|2620|CA |ASP|A|164|-13.156|2.411|-13.611|1.00 27.67|C|
|ATOM|2622|CB |ASP|A|164|-12.812|3.383|-12.487|1.00 28.55|C|
|ATOM|2625|CG |ASP|A|164|-11.681|2.869|-11.595|1.00 32.34|C|
|ATOM|2626|OD1|ASP|A|164|-11.986|2.073|-10.684|1.00 36.78|O|
|ATOM|2627|OD2|ASP|A|164|-10.483|3.228|-11.801|1.00 38.62|O|
|ATOM|2628|C  |ASP|A|164|-11.889|2.283|-14.446|1.00 26.93|C|
|ATOM|2629|O  |ASP|A|164|-11.105|1.342|-14.270|1.00 26.55|O|
|ATOM|2631|N  |GLU|A|165|-11.655|3.277|-15.284|1.00 26.54|N|
|ATOM|2632|CA |GLU|A|165|-10.460|3.300|-16.110|1.00 27.41|C|
|ATOM|2634|CB |GLU|A|165|-10.345|4.579|-16.974|1.00 27.87|C|
|ATOM|2637|CG |GLU|A|165|-9.794|4.249|-18.441|1.00 32.49|C|

FIG. 4W

```
ATOM   2640  CD   GLU A 165      -9.346   5.481 -19.287  1.00 38.18           C
ATOM   2641  OE1  GLU A 165     -10.068   6.515 -19.249  1.00 40.83           O
ATOM   2642  OE2  GLU A 165      -8.269   5.404 -19.972  1.00 39.28           O
ATOM   2643  C    GLU A 165      -9.176   3.123 -15.309  1.00 26.49           C
ATOM   2644  O    GLU A 165      -8.269   2.385 -15.750  1.00 26.51           O
ATOM   2646  N    GLU A 166      -9.086   3.780 -14.144  1.00 25.65           N
ATOM   2647  CA   GLU A 166      -7.831   3.759 -13.367  1.00 24.90           C
ATOM   2649  CB   GLU A 166      -7.766   4.893 -12.308  1.00 25.89           C
ATOM   2652  CG   GLU A 166      -6.557   4.845 -11.256  1.00 27.20           C
ATOM   2655  CD   GLU A 166      -5.207   5.176 -11.884  1.00 31.46           C
ATOM   2656  OE1  GLU A 166      -5.196   5.320 -13.104  1.00 36.92           O
ATOM   2657  OE2  GLU A 166      -4.179   5.346 -11.188  1.00 33.28           O
ATOM   2658  C    GLU A 166      -7.513   2.366 -12.796  1.00 23.39           C
ATOM   2659  O    GLU A 166      -6.384   1.985 -12.800  1.00 23.57           O
ATOM   2661  N    SER A 167      -8.485   1.581 -12.362  1.00 21.96           N
ATOM   2662  CA   SER A 167      -8.196   0.262 -11.855  1.00 21.28           C
ATOM   2664  CB   SER A 167      -9.382  -0.289 -11.108  1.00 21.54           C
ATOM   2667  OG   SER A 167      -9.873   0.607 -10.137  1.00 23.03           O
ATOM   2669  C    SER A 167      -7.831  -0.732 -12.968  1.00 22.43           C
ATOM   2670  O    SER A 167      -7.006  -1.656 -12.776  1.00 20.55           O
ATOM   2672  N    ARG A 168      -8.438  -0.544 -14.146  1.00 22.10           N
ATOM   2673  CA   ARG A 168      -8.072  -1.372 -15.270  1.00 22.84           C
ATOM   2675  CB   ARG A 168      -9.055  -1.204 -16.427  1.00 22.98           C
ATOM   2678  CG   ARG A 168     -10.480  -1.746 -16.146  1.00 24.56           C
ATOM   2681  CD   ARG A 168     -11.169  -1.910 -17.448  1.00 29.37           C
ATOM   2684  NE   ARG A 168     -11.740  -0.691 -17.957  1.00 31.84           N
ATOM   2686  CZ   ARG A 168     -11.753  -0.301 -19.225  1.00 30.69           C
ATOM   2687  NH1  ARG A 168     -11.167  -0.969 -20.196  1.00 33.79           N
ATOM   2690  NH2  ARG A 168     -12.352   0.805 -19.514  1.00 29.78           N
ATOM   2693  C    ARG A 168      -6.627  -1.068 -15.710  1.00 21.35           C
ATOM   2694  O    ARG A 168      -5.887  -1.974 -16.070  1.00 19.69           O
ATOM   2696  N    ALA A 169      -6.240   0.196 -15.667  1.00 21.39           N
ATOM   2697  CA   ALA A 169      -4.874   0.579 -16.055  1.00 22.12           C
ATOM   2699  CB   ALA A 169      -4.806   2.114 -16.246  1.00 22.67           C
ATOM   2703  C    ALA A 169      -3.805   0.078 -15.052  1.00 21.58           C
ATOM   2704  O    ALA A 169      -2.678  -0.196 -15.400  1.00 22.14           O
ATOM   2706  N    ARG A 170      -4.197  -0.058 -13.805  1.00 22.87           N
ATOM   2707  CA   ARG A 170      -3.356  -0.591 -12.767  1.00 23.19           C
ATOM   2709  CB   ARG A 170      -4.077  -0.343 -11.469  1.00 25.00           C
ATOM   2712  CG   ARG A 170      -3.231  -0.432 -10.239  1.00 30.84           C
ATOM   2715  CD   ARG A 170      -3.998  -0.081  -8.958  1.00 37.81           C
ATOM   2718  NE   ARG A 170      -3.160  -0.405  -7.783  1.00 43.54           N
ATOM   2720  CZ   ARG A 170      -2.454   0.484  -7.052  1.00 47.99           C
ATOM   2721  NH1  ARG A 170      -2.485   1.793  -7.330  1.00 48.50           N
ATOM   2724  NH2  ARG A 170      -1.726   0.070  -6.002  1.00 47.36           N
ATOM   2727  C    ARG A 170      -3.065  -2.090 -12.998  1.00 22.30           C
ATOM   2728  O    ARG A 170      -1.890  -2.497 -13.034  1.00 22.41           O
ATOM   2730  N    ILE A 171      -4.115  -2.872 -13.257  1.00 21.20           N
ATOM   2731  CA   ILE A 171      -3.998  -4.261 -13.719  1.00 21.18           C
ATOM   2733  CB   ILE A 171      -5.406  -4.868 -14.032  1.00 21.39           C
ATOM   2735  CG1  ILE A 171      -6.249  -4.835 -12.743  1.00 21.48           C
ATOM   2738  CD1  ILE A 171      -7.609  -5.381 -12.762  1.00 21.47           C
ATOM   2742  CG2  ILE A 171      -5.268  -6.273 -14.685  1.00 19.89           C
ATOM   2746  C    ILE A 171      -3.131  -4.314 -14.962  1.00 22.08           C
ATOM   2747  O    ILE A 171      -2.183  -5.076 -15.048  1.00 22.01           O
ATOM   2749  N    LYS A 172      -3.426  -3.492 -15.953  1.00 23.68           N
ATOM   2750  CA   LYS A 172      -2.645  -3.570 -17.198  1.00 23.86           C
ATOM   2752  CB   LYS A 172      -3.266  -2.680 -18.237  1.00 24.88           C
ATOM   2755  CG   LYS A 172      -4.632  -3.113 -18.725  1.00 25.07           C
ATOM   2758  CD   LYS A 172      -5.317  -1.857 -19.226  1.00 25.86           C
ATOM   2761  CE   LYS A 172      -6.336  -2.104 -20.216  1.00 29.35           C
ATOM   2764  NZ   LYS A 172      -7.284  -0.864 -20.262  1.00 35.34           N
ATOM   2768  C    LYS A 172      -1.198  -3.144 -16.986  1.00 22.74           C
```

FIG. 4X

```
ATOM   2769  O   LYS A 172      -0.274  -3.716 -17.558  1.00 22.06           O
ATOM   2771  N   THR A 173      -0.982  -2.167 -16.112  1.00 22.31           N
ATOM   2772  CA  THR A 173       0.395  -1.877 -15.732  1.00 21.79           C
ATOM   2774  CB  THR A 173       0.510  -0.647 -14.861  1.00 22.72           C
ATOM   2776  OG1 THR A 173      -0.118   0.445 -15.546  1.00 24.08           O
ATOM   2778  CG2 THR A 173       1.945  -0.338 -14.663  1.00 21.78           C
ATOM   2782  C   THR A 173       1.067  -3.004 -15.064  1.00 20.73           C
ATOM   2783  O   THR A 173       2.243  -3.241 -15.300  1.00 23.71           O
ATOM   2785  N   ARG A 174       0.332  -3.797 -14.288  1.00 20.12           N
ATOM   2786  CA  ARG A 174       0.965  -4.886 -13.618  1.00 19.03           C
ATOM   2788  CB  ARG A 174       0.071  -5.428 -12.516  1.00 18.29           C
ATOM   2791  CG  ARG A 174       0.575  -6.661 -11.863  1.00 17.17           C
ATOM   2794  CD  ARG A 174       2.015  -6.519 -11.337  1.00 22.49           C
ATOM   2797  NE  ARG A 174       2.322  -7.691 -10.547  1.00 20.97           N
ATOM   2799  CZ  ARG A 174       3.509  -8.016 -10.083  1.00 20.69           C
ATOM   2800  NH1 ARG A 174       4.603  -7.305 -10.326  1.00 21.42           N
ATOM   2803  NH2 ARG A 174       3.586  -9.114  -9.400  1.00 24.76           N
ATOM   2806  C   ARG A 174       1.361  -5.935 -14.650  1.00 18.32           C
ATOM   2807  O   ARG A 174       2.474  -6.451 -14.641  1.00 14.85           O
ATOM   2809  N   LEU A 175       0.468  -6.217 -15.588  1.00 19.56           N
ATOM   2810  CA  LEU A 175       0.826  -7.165 -16.676  1.00 19.33           C
ATOM   2812  CB  LEU A 175      -0.431  -7.415 -17.508  1.00 19.46           C
ATOM   2815  CG  LEU A 175      -1.606  -7.965 -16.724  1.00 18.04           C
ATOM   2817  CD1 LEU A 175      -2.977  -7.864 -17.474  1.00 16.10           C
ATOM   2821  CD2 LEU A 175      -1.314  -9.363 -16.265  1.00 13.78           C
ATOM   2825  C   LEU A 175       1.980  -6.656 -17.585  1.00 21.22           C
ATOM   2826  O   LEU A 175       2.829  -7.429 -17.989  1.00 22.40           O
ATOM   2828  N   PHE A 176       2.005  -5.365 -17.911  1.00 23.21           N
ATOM   2829  CA  PHE A 176       3.109  -4.762 -18.729  1.00 24.74           C
ATOM   2831  CB  PHE A 176       2.841  -3.242 -18.909  1.00 26.23           C
ATOM   2834  CG  PHE A 176       3.946  -2.464 -19.651  1.00 29.22           C
ATOM   2835  CD1 PHE A 176       3.856  -2.248 -21.038  1.00 32.47           C
ATOM   2837  CE1 PHE A 176       4.887  -1.517 -21.726  1.00 33.44           C
ATOM   2839  CZ  PHE A 176       5.958  -0.986 -21.015  1.00 30.76           C
ATOM   2841  CE2 PHE A 176       6.031  -1.164 -19.646  1.00 30.78           C
ATOM   2843  CD2 PHE A 176       5.019  -1.891 -18.958  1.00 29.87           C
ATOM   2845  C   PHE A 176       4.484  -5.017 -18.072  1.00 24.93           C
ATOM   2846  O   PHE A 176       5.428  -5.441 -18.731  1.00 24.99           O
ATOM   2848  N   THR A 177       4.548  -4.831 -16.753  1.00 24.79           N
ATOM   2849  CA  THR A 177       5.743  -5.023 -15.952  1.00 24.17           C
ATOM   2851  CB  THR A 177       5.527  -4.549 -14.470  1.00 23.86           C
ATOM   2853  OG1 THR A 177       4.972  -3.251 -14.459  1.00 27.31           O
ATOM   2855  CG2 THR A 177       6.839  -4.507 -13.715  1.00 27.23           C
ATOM   2859  C   THR A 177       6.112  -6.453 -15.911  1.00 23.54           C
ATOM   2860  O   THR A 177       7.288  -6.806 -15.969  1.00 23.20           O
ATOM   2862  N   ILE A 178       5.114  -7.318 -15.738  1.00 23.34           N
ATOM   2863  CA  ILE A 178       5.418  -8.741 -15.709  1.00 21.32           C
ATOM   2865  CB  ILE A 178       4.185  -9.596 -15.446  1.00 20.37           C
ATOM   2867  CG1 ILE A 178       3.808  -9.591 -13.955  1.00 20.95           C
ATOM   2870  CD1 ILE A 178       2.363 -10.058 -13.752  1.00 16.61           C
ATOM   2874  CG2 ILE A 178       4.423 -11.014 -15.846  1.00 14.36           C
ATOM   2878  C   ILE A 178       6.052  -9.161 -17.063  1.00 22.00           C
ATOM   2879  O   ILE A 178       7.019  -9.928 -17.099  1.00 19.45           O
ATOM   2881  N   ARG A 179       5.506  -8.644 -18.151  1.00 23.00           N
ATOM   2882  CA  ARG A 179       6.051  -8.975 -19.500  1.00 25.50           C
ATOM   2884  CB  ARG A 179       5.155  -8.435 -20.612  1.00 25.34           C
ATOM   2887  CG  ARG A 179       5.608  -8.760 -21.993  1.00 30.92           C
ATOM   2890  CD  ARG A 179       4.982  -7.913 -23.090  1.00 37.60           C
ATOM   2893  NE  ARG A 179       5.477  -8.339 -24.410  1.00 45.25           N
ATOM   2895  CZ  ARG A 179       6.670  -8.027 -24.958  1.00 52.11           C
ATOM   2896  NH1 ARG A 179       7.564  -7.254 -24.333  1.00 54.21           N
ATOM   2899  NH2 ARG A 179       6.996  -8.512 -26.165  1.00 56.15           N
ATOM   2902  C   ARG A 179       7.467  -8.390 -19.651  1.00 25.34           C
```

FIG. 4Y

```
ATOM   2903  O    ARG A 179       8.403   -9.136  -19.995  1.00 24.83           O
ATOM   2905  N    GLN A 180       7.623   -7.095  -19.381  1.00 25.95           N
ATOM   2906  CA   GLN A 180       8.966   -6.439  -19.529  1.00 27.74           C
ATOM   2908  CB   GLN A 180       8.948   -4.991  -19.121  1.00 27.52           C
ATOM   2911  CG   GLN A 180       8.009   -4.054  -19.876  1.00 32.54           C
ATOM   2914  CD   GLN A 180       8.425   -3.792  -21.318  1.00 35.49           C
ATOM   2915  OE1  GLN A 180       8.133   -4.597  -22.223  1.00 39.28           O
ATOM   2916  NE2  GLN A 180       9.108   -2.669  -21.540  1.00 36.58           N
ATOM   2919  C    GLN A 180      10.089   -7.159  -18.730  1.00 28.07           C
ATOM   2920  O    GLN A 180      11.188   -7.365  -19.227  1.00 29.14           O
ATOM   2922  N    GLU A 181       9.799   -7.554  -17.501  1.00 28.48           N
ATOM   2923  CA   GLU A 181      10.764   -8.268  -16.657  1.00 28.66           C
ATOM   2925  CB   GLU A 181      10.322   -8.241  -15.190  1.00 28.88           C
ATOM   2928  CG   GLU A 181      10.140   -6.835  -14.600  1.00 28.54           C
ATOM   2931  CD   GLU A 181      11.495   -6.148  -14.269  1.00 31.19           C
ATOM   2932  OE1  GLU A 181      12.579   -6.734  -14.494  1.00 30.46           O
ATOM   2933  OE2  GLU A 181      11.465   -5.019  -13.813  1.00 33.08           O
ATOM   2934  C    GLU A 181      11.021   -9.694  -17.084  1.00 29.47           C
ATOM   2935  O    GLU A 181      12.150  -10.208  -16.930  1.00 31.66           O
ATOM   2937  N    MET A 182      10.019  -10.385  -17.603  1.00 29.58           N
ATOM   2938  CA   MET A 182      10.302  -11.692  -18.138  1.00 29.45           C
ATOM   2940  CB   MET A 182       9.044  -12.439  -18.547  1.00 29.37           C
ATOM   2943  CG   MET A 182       8.165  -13.014  -17.415  1.00 28.62           C
ATOM   2946  SD   MET A 182       6.731  -13.920  -18.081  1.00 24.07           S
ATOM   2947  CE   MET A 182       6.068  -14.615  -16.554  1.00 20.99           C
ATOM   2951  C    MET A 182      11.197  -11.537  -19.400  1.00 30.74           C
ATOM   2952  O    MET A 182      12.159  -12.315  -19.594  1.00 28.90           O
ATOM   2954  N    ALA A 183      10.851  -10.568  -20.255  1.00 31.32           N
ATOM   2955  CA   ALA A 183      11.575  -10.343  -21.553  1.00 33.08           C
ATOM   2957  CB   ALA A 183      10.921   -9.259  -22.386  1.00 31.94           C
ATOM   2961  C    ALA A 183      13.066  -10.017  -21.382  1.00 34.03           C
ATOM   2962  O    ALA A 183      13.913  -10.521  -22.110  1.00 35.32           O
ATOM   2964  N    SER A 184      13.379   -9.177  -20.412  1.00 35.01           N
ATOM   2965  CA   SER A 184      14.744   -8.819  -20.150  1.00 35.34           C
ATOM   2967  CB   SER A 184      14.781   -7.640  -19.219  1.00 35.27           C
ATOM   2970  OG   SER A 184      14.628   -8.162  -17.920  1.00 37.79           O
ATOM   2972  C    SER A 184      15.512   -9.973  -19.517  1.00 35.94           C
ATOM   2973  O    SER A 184      16.717   -9.861  -19.336  1.00 38.09           O
ATOM   2975  N    ARG A 185      14.833  -11.066  -19.165  1.00 34.89           N
ATOM   2976  CA   ARG A 185      15.495  -12.258  -18.676  1.00 34.32           C
ATOM   2978  CB   ARG A 185      14.947  -12.633  -17.295  1.00 34.77           C
ATOM   2981  CG   ARG A 185      15.251  -11.591  -16.255  1.00 36.90           C
ATOM   2984  CD   ARG A 185      14.500  -11.881  -14.962  1.00 39.45           C
ATOM   2987  NE   ARG A 185      14.853  -10.927  -13.907  1.00 41.21           N
ATOM   2989  CZ   ARG A 185      14.448   -9.653  -13.843  1.00 44.40           C
ATOM   2990  NH1  ARG A 185      13.659   -9.121  -14.769  1.00 45.96           N
ATOM   2993  NH2  ARG A 185      14.835   -8.892  -12.834  1.00 45.86           N
ATOM   2996  C    ARG A 185      15.377  -13.437  -19.617  1.00 33.06           C
ATOM   2997  O    ARG A 185      15.808  -14.504  -19.269  1.00 32.13           O
ATOM   2999  N    SER A 186      14.842  -13.221  -20.824  1.00 32.75           N
ATOM   3000  CA   SER A 186      14.653  -14.272  -21.833  1.00 33.07           C
ATOM   3002  CB   SER A 186      16.007  -14.899  -22.287  1.00 33.90           C
ATOM   3005  OG   SER A 186      16.829  -13.897  -22.872  1.00 36.07           O
ATOM   3007  C    SER A 186      13.668  -15.344  -21.441  1.00 32.43           C
ATOM   3008  O    SER A 186      13.792  -16.500  -21.888  1.00 32.01           O
ATOM   3010  N    LEU A 187      12.656  -14.955  -20.648  1.00 31.80           N
ATOM   3011  CA   LEU A 187      11.615  -15.867  -20.212  1.00 30.00           C
ATOM   3013  CB   LEU A 187      11.396  -15.692  -18.705  1.00 30.36           C
ATOM   3016  CG   LEU A 187      12.502  -16.242  -17.793  1.00 27.61           C
ATOM   3018  CD1  LEU A 187      12.357  -15.696  -16.463  1.00 29.76           C
ATOM   3022  CD2  LEU A 187      12.512  -17.744  -17.696  1.00 25.51           C
ATOM   3026  C    LEU A 187      10.305  -15.665  -20.987  1.00 29.92           C
ATOM   3027  O    LEU A 187       9.444  -16.570  -21.034  1.00 28.42           O
```

FIG. 4Z

```
ATOM   3029  N   TRP A 188      10.172 -14.516 -21.651  1.00 29.73           N
ATOM   3030  CA  TRP A 188       8.915 -14.160 -22.285  1.00 30.61           C
ATOM   3032  CB  TRP A 188       8.923 -12.731 -22.771  1.00 30.55           C
ATOM   3035  CG  TRP A 188       7.662 -12.343 -23.429  1.00 31.02           C
ATOM   3036  CD1 TRP A 188       7.506 -11.975 -24.743  1.00 28.67           C
ATOM   3038  NE1 TRP A 188       6.175 -11.658 -24.987  1.00 33.73           N
ATOM   3040  CE2 TRP A 188       5.436 -11.818 -23.833  1.00 31.22           C
ATOM   3041  CD2 TRP A 188       6.335 -12.251 -22.816  1.00 32.14           C
ATOM   3042  CE3 TRP A 188       5.842 -12.446 -21.516  1.00 31.23           C
ATOM   3044  CZ3 TRP A 188       4.452 -12.222 -21.274  1.00 32.46           C
ATOM   3046  CH2 TRP A 188       3.593 -11.807 -22.333  1.00 33.56           C
ATOM   3048  CZ2 TRP A 188       4.074 -11.598 -23.598  1.00 32.56           C
ATOM   3050  C   TRP A 188       8.501 -15.061 -23.431  1.00 31.67           C
ATOM   3051  O   TRP A 188       7.333 -15.477 -23.501  1.00 30.66           O
ATOM   3053  N   ASP A 189       9.445 -15.358 -24.330  1.00 32.87           N
ATOM   3054  CA  ASP A 189       9.135 -16.154 -25.546  1.00 33.62           C
ATOM   3056  CB  ASP A 189      10.389 -16.351 -26.430  1.00 34.77           C
ATOM   3059  CG  ASP A 189      10.723 -15.112 -27.250  1.00 39.04           C
ATOM   3060  OD1 ASP A 189       9.783 -14.367 -27.643  1.00 43.38           O
ATOM   3061  OD2 ASP A 189      11.933 -14.897 -27.516  1.00 45.77           O
ATOM   3062  C   ASP A 189       8.574 -17.515 -25.176  1.00 31.81           C
ATOM   3063  O   ASP A 189       7.530 -17.934 -25.671  1.00 32.23           O
ATOM   3065  N   SER A 190       9.265 -18.221 -24.309  1.00 29.34           N
ATOM   3066  CA  SER A 190       8.765 -19.516 -23.889  1.00 28.80           C
ATOM   3068  CB  SER A 190       9.840 -20.207 -23.033  1.00 28.07           C
ATOM   3071  OG  SER A 190       9.290 -21.332 -22.363  1.00 28.32           O
ATOM   3073  C   SER A 190       7.364 -19.383 -23.150  1.00 27.84           C
ATOM   3074  O   SER A 190       6.430 -20.169 -23.351  1.00 28.28           O
ATOM   3076  N   PHE A 191       7.206 -18.349 -22.336  1.00 27.26           N
ATOM   3077  CA  PHE A 191       5.949 -18.163 -21.590  1.00 26.62           C
ATOM   3079  CB  PHE A 191       6.080 -17.053 -20.524  1.00 24.94           C
ATOM   3082  CG  PHE A 191       4.796 -16.797 -19.719  1.00 19.84           C
ATOM   3083  CD1 PHE A 191       4.352 -17.700 -18.808  1.00 19.79           C
ATOM   3085  CE1 PHE A 191       3.164 -17.486 -18.091  1.00 18.95           C
ATOM   3087  CZ  PHE A 191       2.470 -16.327 -18.247  1.00 16.44           C
ATOM   3089  CE2 PHE A 191       2.912 -15.381 -19.121  1.00 16.60           C
ATOM   3091  CD2 PHE A 191       4.100 -15.634 -19.855  1.00 19.93           C
ATOM   3093  C   PHE A 191       4.847 -17.843 -22.575  1.00 27.88           C
ATOM   3094  O   PHE A 191       3.790 -18.415 -22.497  1.00 27.55           O
ATOM   3096  N   ARG A 192       5.112 -16.921 -23.492  1.00 30.82           N
ATOM   3097  CA  ARG A 192       4.123 -16.494 -24.525  1.00 33.38           C
ATOM   3099  CB  ARG A 192       4.678 -15.286 -25.356  1.00 35.13           C
ATOM   3102  CG  ARG A 192       4.043 -15.010 -26.770  1.00 38.94           C
ATOM   3105  CD  ARG A 192       4.669 -13.773 -27.530  1.00 45.61           C
ATOM   3108  NE  ARG A 192       3.897 -12.521 -27.314  1.00 52.10           N
ATOM   3110  CZ  ARG A 192       4.110 -11.329 -27.896  1.00 54.81           C
ATOM   3111  NH1 ARG A 192       5.099 -11.149 -28.776  1.00 57.29           N
ATOM   3114  NH2 ARG A 192       3.312 -10.303 -27.596  1.00 54.94           N
ATOM   3117  C   ARG A 192       3.668 -17.641 -25.439  1.00 33.69           C
ATOM   3118  O   ARG A 192       2.586 -17.587 -25.991  1.00 35.29           O
ATOM   3120  N   GLN A 193       4.468 -18.685 -25.589  1.00 34.34           N
ATOM   3121  CA  GLN A 193       4.113 -19.776 -26.504  1.00 35.14           C
ATOM   3123  CB  GLN A 193       5.358 -20.234 -27.285  1.00 36.40           C
ATOM   3126  CG  GLN A 193       5.895 -19.133 -28.248  1.00 38.81           C
ATOM   3129  CD  GLN A 193       7.264 -19.466 -28.862  1.00 44.26           C
ATOM   3130  OE1 GLN A 193       7.508 -20.604 -29.285  1.00 49.54           O
ATOM   3131  NE2 GLN A 193       8.154 -18.471 -28.920  1.00 45.12           N
ATOM   3134  C   GLN A 193       3.446 -20.936 -25.815  1.00 33.94           C
ATOM   3135  O   GLN A 193       2.791 -21.724 -26.472  1.00 32.24           O
ATOM   3137  N   SER A 194       3.529 -20.980 -24.482  1.00 33.88           N
ATOM   3138  CA  SER A 194       3.085 -22.143 -23.697  1.00 33.50           C
ATOM   3140  CB  SER A 194       3.872 -22.234 -22.378  1.00 34.18           C
ATOM   3143  OG  SER A 194       3.782 -21.015 -21.644  1.00 36.26           O
```

FIG. 4AA

```
ATOM   3145  C   SER A 194       1.598 -22.204 -23.359  1.00 33.28           C
ATOM   3146  O   SER A 194       1.142 -23.247 -22.895  1.00 32.79           O
ATOM   3148  N   GLU A 195       0.833 -21.130 -23.564  1.00 33.76           N
ATOM   3149  CA  GLU A 195      -0.606 -21.179 -23.200  1.00 35.56           C
ATOM   3151  CB  GLU A 195      -1.192 -19.783 -23.254  1.00 34.42           C
ATOM   3154  CG  GLU A 195      -2.669 -19.666 -22.814  1.00 31.19           C
ATOM   3157  CD  GLU A 195      -3.133 -18.225 -22.769  1.00 28.91           C
ATOM   3158  OE1 GLU A 195      -2.342 -17.330 -22.397  1.00 27.02           O
ATOM   3159  OE2 GLU A 195      -4.272 -17.934 -23.186  1.00 34.26           O
ATOM   3160  C   GLU A 195      -1.407 -22.098 -24.152  1.00 37.98           C
ATOM   3161  O   GLU A 195      -1.192 -22.064 -25.351  1.00 37.85           O
ATOM   3163  N   ARG A 196      -2.340 -22.897 -23.653  1.00 41.27           N
ATOM   3164  CA  ARG A 196      -3.202 -23.691 -24.598  1.00 44.13           C
ATOM   3166  CB  ARG A 196      -2.632 -25.092 -24.924  1.00 44.56           C
ATOM   3169  CG  ARG A 196      -1.340 -25.090 -25.665  1.00 46.98           C
ATOM   3172  CD  ARG A 196      -0.396 -26.126 -25.115  1.00 51.59           C
ATOM   3175  NE  ARG A 196       0.901 -26.111 -25.824  1.00 56.06           N
ATOM   3177  CZ  ARG A 196       1.977 -26.853 -25.504  1.00 58.69           C
ATOM   3178  NH1 ARG A 196       1.959 -27.695 -24.456  1.00 59.44           N
ATOM   3181  NH2 ARG A 196       3.097 -26.749 -26.238  1.00 58.42           N
ATOM   3184  C   ARG A 196      -4.655 -23.839 -24.121  1.00 44.90           C
ATOM   3185  O   ARG A 196      -4.994 -23.523 -22.960  1.00 43.59           O
ATOM   3187  N   GLY A 197      -5.499 -24.327 -25.034  1.00 45.89           N
ATOM   3188  CA  GLY A 197      -6.918 -24.546 -24.725  1.00 47.04           C
ATOM   3191  C   GLY A 197      -7.382 -25.915 -25.169  1.00 47.97           C
ATOM   3192  O   GLY A 197      -8.522 -26.060 -25.651  1.00 49.87           O
ATOM   3194  CL  CI2 A 801     -15.728 -22.157 -18.301  1.00 59.92          CL
ATOM   3195  CZB CI2 A 801     -14.908 -22.736 -16.812  1.00 55.31           C
ATOM   3196  CEB CI2 A 801     -14.510 -24.060 -16.666  1.00 53.54           C
ATOM   3198  CDB CI2 A 801     -13.900 -24.462 -15.490  1.00 51.40           C
ATOM   3200  CEA CI2 A 801     -14.701 -21.812 -15.796  1.00 53.54           C
ATOM   3202  CDA CI2 A 801     -14.109 -22.226 -14.621  1.00 53.52           C
ATOM   3204  CGA CI2 A 801     -13.681 -23.532 -14.477  1.00 49.32           C
ATOM   3205  CO  CI2 A 801     -13.076 -23.937 -13.177  1.00 45.66           C
ATOM   3208  CF  CI2 A 801     -11.643 -23.539 -12.821  1.00 43.95           C
ATOM   3209  CB  CI2 A 801     -11.425 -22.038 -12.875  1.00 35.87           C
ATOM   3210  CM  CI2 A 801     -10.757 -21.464 -14.059  1.00 30.39           C
ATOM   3212  CA  CI2 A 801     -10.456 -20.174 -14.315  1.00 30.57           C
ATOM   3213  CE  CI2 A 801      -9.778 -19.854 -15.595  1.00 31.60           C
ATOM   3214  OAO CI2 A 801      -9.659 -18.665 -15.946  1.00 30.40           O
ATOM   3215  OAN CI2 A 801      -9.354 -20.807 -16.303  1.00 33.34           O
ATOM   3216  O14 CI2 A 801     -10.714 -19.173 -13.533  1.00 22.32           O
ATOM   3218  O13 CI2 A 801     -11.767 -21.343 -11.934  1.00 35.37           O
ATOM   3219  CH  CI2 A 801     -10.664 -24.334 -13.706  1.00 43.59           C
ATOM   3222  CI  CI2 A 801      -9.513 -24.981 -12.927  1.00 43.92           C
ATOM   3225  NJ  CI2 A 801      -9.064 -24.273 -11.717  1.00 44.89           N
ATOM   3227  CK  CI2 A 801     -10.133 -23.961 -10.754  1.00 43.72           C
ATOM   3230  CG  CI2 A 801     -11.516 -24.037 -11.361  1.00 44.45           C
ATOM   3233  CP  CI2 A 801      -8.057 -25.042 -10.938  1.00 43.40           C
ATOM   3236  CGB CI2 A 801      -6.786 -25.369 -11.720  1.00 42.05           C
ATOM   3238  CD1 CI2 A 801      -5.548 -24.981 -10.878  1.00 41.01           C
ATOM   3241  CE1 CI2 A 801      -4.249 -25.642 -11.354  1.00 40.36           C
ATOM   3244  CZ  CI2 A 801      -4.382 -27.124 -11.626  1.00 39.96           C
ATOM   3247  CE2 CI2 A 801      -5.490 -27.358 -12.644  1.00 40.19           C
ATOM   3250  CD2 CI2 A 801      -6.820 -26.867 -12.069  1.00 40.71           C
ATOM   3253  MN  MN  A 901     -10.703 -17.245 -14.404  1.00 24.64          MN
ATOM   3254  MN  MN  A 902     -11.701 -19.336 -11.518  1.00 32.43          MN
ATOM   6571  O20 WAT A 910     -16.355  -6.528 -16.875  1.00 21.81        A  O
ATOM   6572  O21 WAT A 910     -19.399  -7.074 -12.901  0.01 27.10        A  O
ATOM   6573  O50 WAT A 911       2.434 -24.032  -0.834  1.00 25.92        A  O
ATOM   3255  OH2 WAT A 912     -12.701 -19.641  -9.315  1.00 21.06        A  O
ATOM   3258  OH2 WAT A 913     -13.728 -19.144 -12.466  1.00 20.27        A  O
ATOM   6574  OH2 WAT A 914       2.063 -10.125  -6.063  1.00 23.18        A  O
```

FIG. 4AB

```
ATOM   6575  OH2 WAT A 915     -19.399  -7.074 -12.901  1.00 27.10      A    O
ATOM   6576  OH2 WAT A 916      -5.118 -18.786 -10.812  1.00 25.47      A    O
ATOM   6578  OH2 WAT A 917     -19.803  -1.210 -12.980  1.00 26.51      A    O
ATOM   6580  OH2 WAT A 918     -12.079 -19.380   2.248  1.00 31.24      A    O
ATOM   6582  OH2 WAT A 919     -25.501  -7.311 -15.726  1.00 41.38      A    O
ATOM   6583  OH2 WAT A 920     -13.635   1.322 -17.485  1.00 30.53      A    O
ATOM   6584  OH2 WAT A 921      -8.119 -21.447 -11.560  1.00 40.66      A    O
ATOM   6585  OH2 WAT A 922     -13.999 -12.156  -0.739  1.00 26.43      A    O
ATOM   6586  OH2 WAT A 923     -16.887 -19.453 -14.787  1.00 25.99      A    O
ATOM   6587  OH2 WAT A 924     -23.343  -9.865 -17.567  1.00 38.22      A    O
ATOM   6588  OH2 WAT A 925     -23.435  -4.842 -19.324  1.00 39.09      A    O
ATOM   6589  OH2 WAT A 925     -20.248  -1.299 -15.398  1.00 37.28      A    O
ATOM   6590  OH2 WAT A 926     -26.917 -23.079  -1.691  1.00 37.24      A    O
ATOM   6591  OH2 WAT A 927       9.381 -19.345 -19.330  1.00 36.94      A    O
ATOM   6592  OH2 WAT A 928     -10.762 -27.509 -10.825  1.00 35.37      A    O
ATOM   6593  OH2 WAT A 929      -3.662  -8.088  -4.503  1.00 42.30      A    O
ATOM   6594  OH2 WAT A 930      -6.176 -26.098  -4.456  1.00 40.14      A    O
ATOM   6595  OH2 WAT A 931      12.331 -25.605 -11.961  1.00 45.87      A    O
ATOM   6596  OH2 WAT A 932      -7.467  -1.794 -22.654  1.00 31.36      A    O
END
```

FIG. 4AC

```
H1N1 polypeptide fragment (Chain A) with bound rUMP
HEADER    INFLUENZA POLYMERASE H1N1/2009 PA with bound rUMP
COMPND    ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :    2.05
REMARK   3   RESOLUTION RANGE LOW  (ANGSTROMS) :   41.70
REMARK   3   DATA CUTOFF            (SIGMA(F)) :    NONE
REMARK   3   COMPLETENESS FOR RANGE        (%) :   99.70
REMARK   3   NUMBER OF REFLECTIONS             :   51176
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE     (WORKING + TEST SET) :  0.20823
REMARK   3   R VALUE            (WORKING SET) :  0.20611
REMARK   3   FREE R VALUE                     :  0.24659
REMARK   3   FREE R VALUE TEST SET SIZE   (%) :    5.1
REMARK   3   FREE R VALUE TEST SET COUNT      :   2750
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :   2.049
REMARK   3   BIN RESOLUTION RANGE LOW            :   2.102
REMARK   3   REFLECTION IN BIN    (WORKING SET)  :    3657
REMARK   3   BIN COMPLETENESS (WORKING+TEST) (%) :   98.37
REMARK   3   BIN R VALUE           (WORKING SET) :   0.266
REMARK   3   BIN FREE R VALUE SET COUNT          :     202
REMARK   3   BIN FREE R VALUE                    :   0.342
REMARK   3
REMARK   3  NUMBER OF NON-HYDROGEN ATOMS USED IN REFINEMENT.
REMARK   3   ALL ATOMS                :    6703
REMARK   3
REMARK   3  B VALUES.
REMARK   3   FROM WILSON PLOT          (A**2) : NULL
REMARK   3   MEAN B VALUE      (OVERALL, A**2) :  32.525
REMARK   3   OVERALL ANISOTROPIC B VALUE.
REMARK   3    B11 (A**2) :    1.67
REMARK   3    B22 (A**2) :   -4.82
REMARK   3    B33 (A**2) :    3.15
REMARK   3    B12 (A**2) :    0.00
REMARK   3    B13 (A**2) :    0.00
REMARK   3    B23 (A**2) :    0.00
REMARK   3
REMARK   3  ESTIMATED OVERALL COORDINATE ERROR.
REMARK   3   ESU BASED ON R VALUE                    (A):   0.048
REMARK   3   ESU BASED ON FREE R VALUE               (A):   0.039
REMARK   3   ESU BASED ON MAXIMUM LIKELIHOOD         (A):   0.112
REMARK   3   ESU FOR B VALUES BASED ON MAXIMUM LIKELIHOOD (A**2):   4.400
REMARK   3
REMARK   3 CORRELATION COEFFICIENTS.
REMARK   3   CORRELATION COEFFICIENT FO-FC      :  0.950
REMARK   3   CORRELATION COEFFICIENT FO-FC FREE :  0.933
REMARK   3
REMARK   3 RMS DEVIATIONS FROM IDEAL VALUES        COUNT    RMS    WEIGHT
```

FIG. 5A

```
REMARK   3   BOND LENGTHS REFINED ATOMS        (A) :  6607 ; 0.022 ; 0.022
REMARK   3   BOND LENGTHS OTHERS               (A) :  4665 ; 0.001 ; 0.020
REMARK   3   BOND ANGLES REFINED ATOMS   (DEGREES):  8878 ; 1.802 ; 1.958
REMARK   3   BOND ANGLES OTHERS          (DEGREES): 11258 ; 0.969 ; 3.000
REMARK   3   TORSION ANGLES, PERIOD 1    (DEGREES):   761 ; 6.279 ; 5.000
REMARK   3   TORSION ANGLES, PERIOD 2    (DEGREES):   343 ;34.946 ;23.353
REMARK   3   TORSION ANGLES, PERIOD 3    (DEGREES):  1239 ;16.895 ;15.000
REMARK   3   TORSION ANGLES, PERIOD 4    (DEGREES):    58 ;19.417 ;15.000
REMARK   3   CHIRAL-CENTER RESTRAINTS       (A**3):   953 ; 0.109 ; 0.200
REMARK   3   GENERAL PLANES REFINED ATOMS     (A) :  7174 ; 0.008 ; 0.020
REMARK   3   GENERAL PLANES OTHERS            (A) :  1448 ; 0.001 ; 0.020
REMARK   3
REMARK   3   ISOTROPIC THERMAL FACTOR RESTRAINTS.   COUNT   RMS    WEIGHT
REMARK   3    MAIN-CHAIN BOND REFINED ATOMS  (A**2):  3827 ; 1.188 ; 1.500
REMARK   3    MAIN-CHAIN BOND OTHER ATOMS    (A**2):  1544 ; 0.279 ; 1.500
REMARK   3    MAIN-CHAIN ANGLE REFINED ATOMS (A**2):  6207 ; 2.129 ; 2.000
REMARK   3    SIDE-CHAIN BOND REFINED ATOMS  (A**2):  2780 ; 3.015 ; 3.000
REMARK   3    SIDE-CHAIN ANGLE REFINED ATOMS (A**2):  2671 ; 4.741 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3   HYDROGENS HAVE BEEN ADDED IN THE RIDING POSITIONS
REMARK   3   U VALUES       : REFINED INDIVIDUALLY
REMARK   3
CRYST1   54.940  120.110  128.050  90.00  90.00  90.00 P 21 21 21
SCALE1      0.018202  0.000000  0.000000        0.00000
SCALE2      0.000000  0.008326  0.000000        0.00000
SCALE3      0.000000  0.000000  0.007809        0.00000
ATOM   3300  N   MET A  -1      44.698  17.489   9.099  1.00 40.91           N
ATOM   3301  CA  MET A  -1      44.458  17.093  10.548  1.00 40.32           C
ATOM   3303  CB  MET A  -1      45.798  17.161  11.322  1.00 41.66           C
ATOM   3306  CG  MET A  -1      46.997  16.546  10.564  1.00 45.78           C
ATOM   3309  SD  MET A  -1      46.893  14.753  10.413  1.00 52.82           S
ATOM   3310  CE  MET A  -1      46.688  14.411   8.644  1.00 50.00           C
ATOM   3314  C   MET A  -1      43.379  17.909  11.321  1.00 38.01           C
ATOM   3315  O   MET A  -1      43.065  17.622  12.493  1.00 36.72           O
ATOM   3319  N   ALA A   0      42.842  18.953  10.706  1.00 34.89           N
ATOM   3320  CA  ALA A   0      41.910  19.785  11.419  1.00 33.46           C
ATOM   3322  CB  ALA A   0      41.918  21.220  10.891  1.00 32.88           C
ATOM   3326  C   ALA A   0      40.508  19.114  11.302  1.00 31.89           C
ATOM   3327  O   ALA A   0      40.300  18.100  10.623  1.00 30.47           O
ATOM   3329  N   MET A   1      39.583  19.632  12.066  1.00 30.44           N
ATOM   3330  CA  MET A   1      38.245  19.059  12.085  1.00 29.55           C
ATOM   3332  CB  MET A   1      37.342  19.793  13.103  1.00 28.89           C
ATOM   3335  CG  MET A   1      35.880  19.186  13.136  1.00 24.61           C
ATOM   3338  SD  MET A   1      35.730  17.443  13.354  1.00 27.64           S
```

FIG. 5B

| | | | | | | | | | | |
|---|---|---|---|---|---|---|---|---|---|---|
| ATOM | 3339 | CE | MET | A | 1 | 35.644 | 17.550 | 15.168 | 1.00 25.29 | C |
| ATOM | 3343 | C | MET | A | 1 | 37.646 | 19.099 | 10.659 | 1.00 29.07 | C |
| ATOM | 3344 | O | MET | A | 1 | 37.026 | 18.115 | 10.219 | 1.00 27.82 | O |
| ATOM | 3346 | N | GLU | A | 2 | 37.894 | 20.196 | 9.952 | 1.00 30.15 | N |
| ATOM | 3347 | CA | GLU | A | 2 | 37.405 | 20.362 | 8.585 | 1.00 31.45 | C |
| ATOM | 3349 | CB | GLU | A | 2 | 37.594 | 21.798 | 8.043 | 1.00 32.75 | C |
| ATOM | 3352 | CG | GLU | A | 2 | 39.027 | 22.336 | 7.945 | 1.00 37.90 | C |
| ATOM | 3355 | CD | GLU | A | 2 | 39.480 | 23.058 | 9.209 | 1.00 42.36 | C |
| ATOM | 3356 | OE1 | GLU | A | 2 | 39.147 | 22.631 | 10.342 | 1.00 41.20 | O |
| ATOM | 3357 | OE2 | GLU | A | 2 | 40.191 | 24.066 | 9.052 | 1.00 52.40 | O |
| ATOM | 3358 | C | GLU | A | 2 | 37.921 | 19.311 | 7.632 | 1.00 31.57 | C |
| ATOM | 3359 | O | GLU | A | 2 | 37.179 | 18.819 | 6.770 | 1.00 30.37 | O |
| ATOM | 3361 | N | ASP | A | 3 | 39.172 | 18.903 | 7.789 | 1.00 31.04 | N |
| ATOM | 3362 | CA | ASP | A | 3 | 39.704 | 17.947 | 6.872 | 1.00 29.76 | C |
| ATOM | 3364 | CB | ASP | A | 3 | 41.220 | 17.882 | 6.994 | 1.00 31.29 | C |
| ATOM | 3367 | CG | ASP | A | 3 | 41.842 | 19.240 | 6.902 | 1.00 33.01 | C |
| ATOM | 3368 | OD1 | ASP | A | 3 | 41.648 | 19.925 | 5.866 | 1.00 38.27 | O |
| ATOM | 3369 | OD2 | ASP | A | 3 | 42.456 | 19.657 | 7.896 | 1.00 36.12 | O |
| ATOM | 3370 | C | ASP | A | 3 | 39.070 | 16.612 | 7.203 | 1.00 29.57 | C |
| ATOM | 3371 | O | ASP | A | 3 | 38.671 | 15.872 | 6.321 | 1.00 30.25 | O |
| ATOM | 3373 | N | PHE | A | 4 | 38.972 | 16.293 | 8.474 | 1.00 28.06 | N |
| ATOM | 3374 | CA | PHE | A | 4 | 38.319 | 15.085 | 8.873 | 1.00 29.20 | C |
| ATOM | 3376 | CB | PHE | A | 4 | 38.271 | 15.021 | 10.382 | 1.00 29.95 | C |
| ATOM | 3379 | CG | PHE | A | 4 | 37.421 | 13.905 | 10.886 | 1.00 32.18 | C |
| ATOM | 3380 | CD1 | PHE | A | 4 | 37.762 | 12.583 | 10.604 | 1.00 38.76 | C |
| ATOM | 3382 | CE1 | PHE | A | 4 | 36.948 | 11.514 | 11.072 | 1.00 41.89 | C |
| ATOM | 3384 | CZ | PHE | A | 4 | 35.798 | 11.798 | 11.841 | 1.00 40.09 | C |
| ATOM | 3386 | CE2 | PHE | A | 4 | 35.480 | 13.120 | 12.115 | 1.00 37.85 | C |
| ATOM | 3388 | CD2 | PHE | A | 4 | 36.297 | 14.160 | 11.640 | 1.00 37.54 | C |
| ATOM | 3390 | C | PHE | A | 4 | 36.836 | 14.976 | 8.374 | 1.00 26.94 | C |
| ATOM | 3391 | O | PHE | A | 4 | 36.433 | 13.973 | 7.834 | 1.00 27.50 | O |
| ATOM | 3393 | N | VAL | A | 5 | 36.061 | 16.017 | 8.567 | 1.00 26.36 | N |
| ATOM | 3394 | CA | VAL | A | 5 | 34.659 | 16.030 | 8.029 | 1.00 25.59 | C |
| ATOM | 3396 | CB | VAL | A | 5 | 33.979 | 17.380 | 8.226 | 1.00 24.18 | C |
| ATOM | 3398 | CG1 | VAL | A | 5 | 32.585 | 17.500 | 7.406 | 1.00 24.01 | C |
| ATOM | 3402 | CG2 | VAL | A | 5 | 33.790 | 17.633 | 9.695 | 1.00 24.93 | C |
| ATOM | 3406 | C | VAL | A | 5 | 34.704 | 15.719 | 6.543 | 1.00 27.22 | C |
| ATOM | 3407 | O | VAL | A | 5 | 34.049 | 14.761 | 6.093 | 1.00 25.52 | O |
| ATOM | 3409 | N | ARG | A | 6 | 35.531 | 16.453 | 5.798 | 1.00 29.68 | N |
| ATOM | 3410 | CA | ARG | A | 6 | 35.568 | 16.304 | 4.336 | 1.00 33.09 | C |
| ATOM | 3412 | CB | ARG | A | 6 | 36.413 | 17.400 | 3.660 | 1.00 33.40 | C |
| ATOM | 3415 | CG | ARG | A | 6 | 35.813 | 18.727 | 3.765 | 1.00 36.20 | C |
| ATOM | 3418 | CD | ARG | A | 6 | 36.406 | 19.649 | 2.717 | 1.00 43.32 | C |
| ATOM | 3421 | NE | ARG | A | 6 | 37.721 | 20.133 | 3.111 | 1.00 45.97 | N |
| ATOM | 3423 | CZ | ARG | A | 6 | 37.937 | 21.249 | 3.807 | 1.00 50.61 | C |
| ATOM | 3424 | NH1 | ARG | A | 6 | 36.916 | 22.020 | 4.212 | 1.00 50.28 | N |
| ATOM | 3427 | NH2 | ARG | A | 6 | 39.195 | 21.599 | 4.104 | 1.00 49.54 | N |
| ATOM | 3430 | C | ARG | A | 6 | 36.035 | 14.980 | 3.811 | 1.00 34.75 | C |
| ATOM | 3431 | O | ARG | A | 6 | 35.563 | 14.527 | 2.754 | 1.00 35.03 | O |
| ATOM | 3433 | N | GLN | A | 7 | 36.953 | 14.345 | 4.527 | 1.00 37.42 | N |
| ATOM | 3434 | CA | GLN | A | 7 | 37.582 | 13.126 | 4.022 | 1.00 39.14 | C |
| ATOM | 3436 | CB | GLN | A | 7 | 38.833 | 12.780 | 4.862 | 1.00 40.63 | C |
| ATOM | 3439 | CG | GLN | A | 7 | 39.987 | 13.751 | 4.663 | 1.00 44.77 | C |
| ATOM | 3442 | CD | GLN | A | 7 | 41.119 | 13.532 | 5.640 | 1.00 49.32 | C |
| ATOM | 3443 | OE1 | GLN | A | 7 | 40.976 | 12.828 | 6.650 | 1.00 53.38 | O |
| ATOM | 3444 | NE2 | GLN | A | 7 | 42.262 | 14.134 | 5.340 | 1.00 49.61 | N |
| ATOM | 3447 | C | GLN | A | 7 | 36.659 | 11.958 | 4.147 | 1.00 39.73 | C |
| ATOM | 3448 | O | GLN | A | 7 | 36.621 | 11.078 | 3.240 | 1.00 41.23 | O |
| ATOM | 3450 | N | CYS | A | 8 | 35.963 | 11.957 | 5.304 | 1.00 38.83 | N |
| ATOM | 3451 | CA | CYS | A | 8 | 35.250 | 10.834 | 5.846 | 1.00 38.15 | C |
| ATOM | 3453 | CB | CYS | A | 8 | 35.656 | 10.617 | 7.296 | 1.00 38.88 | C |
| ATOM | 3456 | SG | CYS | A | 8 | 37.448 | 10.236 | 7.355 | 1.00 41.26 | S |
| ATOM | 3458 | C | CYS | A | 8 | 33.715 | 10.870 | 5.761 | 1.00 36.31 | C |

FIG. 5C

```
ATOM   3459  O    CYS A   8      33.128   9.806   5.630  1.00 36.01           O
ATOM   3461  N    PHE A   9      33.063  12.025   5.763  1.00 33.35           N
ATOM   3462  CA   PHE A   9      31.625  11.977   5.490  1.00 31.75           C
ATOM   3464  CB   PHE A   9      30.914  13.198   6.020  1.00 31.67           C
ATOM   3467  CG   PHE A   9      30.676  13.159   7.483  1.00 33.12           C
ATOM   3468  CD1  PHE A   9      29.559  12.548   7.999  1.00 34.29           C
ATOM   3470  CE1  PHE A   9      29.337  12.520   9.358  1.00 35.00           C
ATOM   3472  CZ   PHE A   9      30.249  13.097  10.205  1.00 36.38           C
ATOM   3474  CE2  PHE A   9      31.349  13.720   9.713  1.00 34.45           C
ATOM   3476  CD2  PHE A   9      31.586  13.723   8.355  1.00 35.44           C
ATOM   3478  C    PHE A   9      31.406  11.848   4.003  1.00 30.09           C
ATOM   3479  O    PHE A   9      32.194  12.313   3.202  1.00 28.69           O
ATOM   3481  N    ASN A  10      30.297  11.233   3.625  1.00 29.73           N
ATOM   3482  CA   ASN A  10      29.898  11.173   2.227  1.00 29.38           C
ATOM   3484  CB   ASN A  10      28.549  10.477   2.109  1.00 31.02           C
ATOM   3487  CG   ASN A  10      27.999  10.502   0.708  1.00 33.11           C
ATOM   3488  OD1  ASN A  10      27.393  11.479   0.271  1.00 39.21           O
ATOM   3489  ND2  ASN A  10      28.205   9.421  -0.006  1.00 42.47           N
ATOM   3492  C    ASN A  10      29.855  12.596   1.614  1.00 26.54           C
ATOM   3493  O    ASN A  10      29.391  13.563   2.236  1.00 25.97           O
ATOM   3495  N    PRO A  11      30.400  12.746   0.411  1.00 26.89           N
ATOM   3496  CA   PRO A  11      30.528  14.097  -0.108  1.00 24.69           C
ATOM   3498  CB   PRO A  11      31.265  13.922  -1.423  1.00 26.82           C
ATOM   3501  CG   PRO A  11      31.376  12.415  -1.663  1.00 29.01           C
ATOM   3504  CD   PRO A  11      31.108  11.724  -0.400  1.00 27.04           C
ATOM   3507  C    PRO A  11      29.149  14.758  -0.319  1.00 23.39           C
ATOM   3508  O    PRO A  11      29.058  15.951  -0.196  1.00 20.17           O
ATOM   3509  N    MET A  12      28.077  14.008  -0.611  1.00 21.62           N
ATOM   3510  CA   MET A  12      26.791  14.707  -0.761  1.00 22.43           C
ATOM   3512  CB   MET A  12      25.593  13.910  -1.314  1.00 23.96           C
ATOM   3515  CG   MET A  12      24.357  14.976  -1.680  1.00 24.53           C
ATOM   3518  SD   MET A  12      23.021  14.070  -2.475  1.00 42.59           S
ATOM   3519  CE   MET A  12      22.353  13.024  -1.154  1.00 34.73           C
ATOM   3523  C    MET A  12      26.397  15.303   0.580  1.00 20.83           C
ATOM   3524  O    MET A  12      25.914  16.411   0.619  1.00 21.28           O
ATOM   3526  N    ILE A  13      26.654  14.580   1.655  1.00 21.51           N
ATOM   3527  CA   ILE A  13      26.329  15.064   2.986  1.00 21.30           C
ATOM   3529  CB   ILE A  13      26.543  13.963   4.053  1.00 22.14           C
ATOM   3531  CG1  ILE A  13      25.321  13.012   4.020  1.00 27.29           C
ATOM   3534  CD1  ILE A  13      25.638  11.704   4.445  1.00 26.10           C
ATOM   3538  CG2  ILE A  13      26.685  14.650   5.457  1.00 21.85           C
ATOM   3542  C    ILE A  13      27.105  16.341   3.315  1.00 18.76           C
ATOM   3543  O    ILE A  13      26.524  17.342   3.823  1.00 20.01           O
ATOM   3545  N    VAL A  14      28.439  16.341   3.086  1.00 17.20           N
ATOM   3546  CA   VAL A  14      29.228  17.535   3.294  1.00 15.09           C
ATOM   3548  CB   VAL A  14      30.818  17.223   3.070  1.00 17.03           C
ATOM   3550  CG1  VAL A  14      31.559  18.390   3.439  1.00 17.67           C
ATOM   3554  CG2  VAL A  14      31.244  16.046   3.961  1.00 14.52           C
ATOM   3558  C    VAL A  14      28.777  18.766   2.484  1.00 16.48           C
ATOM   3559  O    VAL A  14      28.769  19.876   3.012  1.00 17.36           O
ATOM   3561  N    GLU A  15      28.399  18.605   1.225  1.00 17.56           N
ATOM   3562  CA   GLU A  15      27.882  19.711   0.381  1.00 17.94           C
ATOM   3564  CB   GLU A  15      27.723  19.312  -1.078  1.00 18.26           C
ATOM   3567  CG   GLU A  15      29.068  19.087  -1.759  1.00 23.15           C
ATOM   3570  CD   GLU A  15      29.034  19.173  -3.277  1.00 21.40           C
ATOM   3571  OE1  GLU A  15      27.972  19.446  -3.898  1.00 24.67           O
ATOM   3572  OE2  GLU A  15      30.090  18.923  -3.860  1.00 21.37           O
ATOM   3573  C    GLU A  15      26.548  20.273   0.864  1.00 17.81           C
ATOM   3574  O    GLU A  15      26.362  21.474   0.832  1.00 15.92           O
ATOM   3576  N    LEU A  16      25.722  19.397   1.430  1.00 18.53           N
ATOM   3577  CA   LEU A  16      24.393  19.784   2.036  1.00 18.74           C
ATOM   3579  CB   LEU A  16      23.550  18.549   2.208  1.00 18.19           C
ATOM   3582  CG   LEU A  16      23.052  17.889   0.914  1.00 20.78           C
```

FIG. 5D

```
ATOM  3584  CD1  LEU A  16    22.321  16.580   1.330  1.00  14.91           C
ATOM  3588  CD2  LEU A  16    22.126  18.762   0.088  1.00  21.73           C
ATOM  3592  C    LEU A  16    24.577  20.464   3.354  1.00  17.59           C
ATOM  3593  O    LEU A  16    23.927  21.448   3.644  1.00  17.80           O
ATOM  3595  N    ALA A  17    25.628  20.091   4.081  1.00  19.85           N
ATOM  3596  CA   ALA A  17    26.025  20.809   5.292  1.00  17.75           C
ATOM  3598  CB   ALA A  17    27.082  19.961   6.124  1.00  17.76           C
ATOM  3602  C    ALA A  17    26.531  22.196   5.031  1.00  19.62           C
ATOM  3603  O    ALA A  17    26.177  23.152   5.736  1.00  22.29           O
ATOM  3605  N    GLU A  18    27.376  22.330   4.011  1.00  20.93           N
ATOM  3606  CA   GLU A  18    27.886  23.589   3.573  1.00  20.59           C
ATOM  3608  CB   GLU A  18    28.936  23.434   2.482  1.00  19.91           C
ATOM  3611  CG   GLU A  18    30.189  22.772   3.004  1.00  20.80           C
ATOM  3614  CD   GLU A  18    31.204  22.356   1.896  1.00  28.00           C
ATOM  3615  OE1  GLU A  18    30.975  22.621   0.691  1.00  27.49           O
ATOM  3616  OE2  GLU A  18    32.296  21.882   2.257  1.00  27.65           O
ATOM  3617  C    GLU A  18    26.752  24.462   3.092  1.00  20.21           C
ATOM  3618  O    GLU A  18    26.683  25.614   3.479  1.00  20.68           O
ATOM  3620  N    LYS A  19    25.853  23.885   2.329  1.00  19.70           N
ATOM  3621  CA   LYS A  19    24.613  24.618   1.859  1.00  20.49           C
ATOM  3623  CB   LYS A  19    23.751  23.671   1.019  1.00  19.55           C
ATOM  3626  CG   LYS A  19    22.479  24.247   0.396  1.00  19.45           C
ATOM  3629  CD   LYS A  19    21.637  23.165  -0.383  1.00  24.26           C
ATOM  3632  CE   LYS A  19    20.832  22.282   0.535  1.00  25.00           C
ATOM  3635  NZ   LYS A  19    19.611  22.966   1.177  1.00  26.59           N
ATOM  3639  C    LYS A  19    23.800  25.134   3.018  1.00  21.30           C
ATOM  3640  O    LYS A  19    23.421  26.310   3.040  1.00  23.58           O
ATOM  3642  N    ALA A  20    23.520  24.273   3.995  1.00  22.46           N
ATOM  3643  CA   ALA A  20    22.776  24.699   5.191  1.00  23.28           C
ATOM  3645  CB   ALA A  20    22.424  23.437   6.066  1.00  22.23           C
ATOM  3649  C    ALA A  20    23.476  25.829   6.025  1.00  24.91           C
ATOM  3650  O    ALA A  20    22.866  26.876   6.421  1.00  22.86           O
ATOM  3652  N    MET A  21    24.789  25.674   6.238  1.00  23.58           N
ATOM  3653  CA   MET A  21    25.557  26.691   6.943  1.00  23.67           C
ATOM  3655  CB   MET A  21    26.965  26.176   7.239  1.00  23.36           C
ATOM  3658  CG   MET A  21    26.950  25.095   8.265  1.00  24.99           C
ATOM  3661  SD   MET A  21    28.628  24.595   8.865  1.00  27.42           S
ATOM  3662  CE   MET A  21    28.928  25.886  10.026  1.00  27.71           C
ATOM  3666  C    MET A  21    25.630  28.009   6.174  1.00  24.25           C
ATOM  3667  O    MET A  21    25.441  29.063   6.757  1.00  24.07           O
ATOM  3669  N    LYS A  22    25.805  27.967   4.872  1.00  24.70           N
ATOM  3670  CA   LYS A  22    25.623  29.171   4.088  1.00  26.29           C
ATOM  3672  CB   LYS A  22    25.970  28.918   2.652  1.00  26.62           C
ATOM  3675  CG   LYS A  22    25.948  30.174   1.832  1.00  31.39           C
ATOM  3678  CD   LYS A  22    26.633  29.962   0.506  1.00  38.31           C
ATOM  3681  CE   LYS A  22    26.536  31.214  -0.492  1.00  40.15           C
ATOM  3684  NZ   LYS A  22    26.927  30.772  -1.912  1.00  39.47           N
ATOM  3688  C    LYS A  22    24.167  29.753   4.159  1.00  26.21           C
ATOM  3689  O    LYS A  22    23.988  30.954   4.160  1.00  25.40           O
ATOM  3691  N    GLU A  23    23.137  28.929   4.212  1.00  25.78           N
ATOM  3692  CA   GLU A  23    21.777  29.511   4.336  1.00  26.23           C
ATOM  3694  CB   GLU A  23    20.709  28.430   4.187  1.00  25.11           C
ATOM  3697  CG   GLU A  23    19.290  29.003   4.192  1.00  26.74           C
ATOM  3700  CD   GLU A  23    18.256  27.915   4.191  1.00  29.44           C
ATOM  3701  OE1  GLU A  23    18.675  26.735   4.300  1.00  27.51           O
ATOM  3702  OE2  GLU A  23    17.047  28.250   4.089  1.00  28.84           O
ATOM  3703  C    GLU A  23    21.634  30.231   5.687  1.00  27.52           C
ATOM  3704  O    GLU A  23    21.062  31.319   5.788  1.00  26.79           O
ATOM  3706  N    TYR A  24    22.247  29.649   6.706  1.00  29.75           N
ATOM  3707  CA   TYR A  24    22.252  30.245   8.010  1.00  32.46           C
ATOM  3709  CB   TYR A  24    22.547  29.192   9.064  1.00  32.16           C
ATOM  3712  CG   TYR A  24    21.595  28.024   9.080  1.00  34.64           C
ATOM  3713  CD1  TYR A  24    22.029  26.756   9.471  1.00  36.69           C
```

FIG. 5E

| | | | | | | | | | | |
|---|---|---|---|---|---|---|---|---|---|---|
| ATOM | 3715 | CE1 | TYR | A | 24 | 21.140 | 25.650 | 9.508 | 1.00 39.66 | C |
| ATOM | 3717 | CZ | TYR | A | 24 | 19.812 | 25.840 | 9.151 | 1.00 40.75 | C |
| ATOM | 3718 | OH | TYR | A | 24 | 18.907 | 24.789 | 9.163 | 1.00 44.75 | O |
| ATOM | 3720 | CE2 | TYR | A | 24 | 19.368 | 27.100 | 8.752 | 1.00 40.65 | C |
| ATOM | 3722 | CD2 | TYR | A | 24 | 20.251 | 28.186 | 8.732 | 1.00 36.13 | C |
| ATOM | 3724 | C | TYR | A | 24 | 23.200 | 31.414 | 8.188 | 1.00 33.98 | C |
| ATOM | 3725 | O | TYR | A | 24 | 23.116 | 32.079 | 9.175 | 1.00 35.27 | O |
| ATOM | 3727 | N | GLY | A | 25 | 24.089 | 31.678 | 7.241 | 1.00 35.71 | N |
| ATOM | 3728 | CA | GLY | A | 25 | 25.142 | 32.658 | 7.467 | 1.00 35.78 | C |
| ATOM | 3731 | C | GLY | A | 25 | 26.261 | 32.239 | 8.429 | 1.00 37.15 | C |
| ATOM | 3732 | O | GLY | A | 25 | 26.957 | 33.101 | 8.959 | 1.00 37.79 | O |
| ATOM | 3734 | N | GLU | A | 26 | 26.475 | 30.934 | 8.634 | 1.00 36.80 | N |
| ATOM | 3735 | CA | GLU | A | 26 | 27.603 | 30.429 | 9.451 | 1.00 35.63 | C |
| ATOM | 3737 | CB | GLU | A | 26 | 27.072 | 29.339 | 10.397 | 1.00 37.55 | C |
| ATOM | 3740 | CG | GLU | A | 26 | 25.916 | 29.751 | 11.422 | 1.00 42.61 | C |
| ATOM | 3743 | CD | GLU | A | 26 | 24.872 | 28.631 | 11.728 | 1.00 51.24 | C |
| ATOM | 3744 | OE1 | GLU | A | 26 | 23.713 | 28.968 | 12.174 | 1.00 56.20 | O |
| ATOM | 3745 | OE2 | GLU | A | 26 | 25.173 | 27.405 | 11.509 | 1.00 55.98 | O |
| ATOM | 3746 | C | GLU | A | 26 | 28.672 | 29.843 | 8.493 | 1.00 33.96 | C |
| ATOM | 3747 | O | GLU | A | 26 | 28.330 | 29.224 | 7.478 | 1.00 31.11 | O |
| ATOM | 3749 | N | ASP | A | 27 | 29.956 | 29.987 | 8.819 | 1.00 32.67 | N |
| ATOM | 3750 | CA | ASP | A | 27 | 31.067 | 29.607 | 7.921 | 1.00 32.26 | C |
| ATOM | 3752 | CB | ASP | A | 27 | 32.161 | 30.683 | 8.023 | 1.00 33.82 | C |
| ATOM | 3755 | CG | ASP | A | 27 | 33.281 | 30.502 | 6.985 | 1.00 31.25 | C |
| ATOM | 3756 | OD1 | ASP | A | 27 | 33.499 | 29.386 | 6.502 | 1.00 31.52 | O |
| ATOM | 3757 | OD2 | ASP | A | 27 | 33.918 | 31.480 | 6.644 | 1.00 32.07 | O |
| ATOM | 3758 | C | ASP | A | 27 | 31.654 | 28.230 | 8.300 | 1.00 31.93 | C |
| ATOM | 3759 | O | ASP | A | 27 | 32.133 | 28.078 | 9.400 | 1.00 30.37 | O |
| ATOM | 3761 | N | PRO | A | 28 | 31.613 | 27.221 | 7.386 | 1.00 31.08 | N |
| ATOM | 3762 | CA | PRO | A | 28 | 32.150 | 25.910 | 7.664 | 1.00 32.11 | C |
| ATOM | 3764 | CB | PRO | A | 28 | 31.898 | 25.126 | 6.378 | 1.00 32.10 | C |
| ATOM | 3767 | CG | PRO | A | 28 | 30.760 | 25.807 | 5.785 | 1.00 33.26 | C |
| ATOM | 3770 | CD | PRO | A | 28 | 30.899 | 27.238 | 6.107 | 1.00 32.15 | C |
| ATOM | 3773 | C | PRO | A | 28 | 33.660 | 25.961 | 7.961 | 1.00 32.67 | C |
| ATOM | 3774 | O | PRO | A | 28 | 34.142 | 25.132 | 8.674 | 1.00 32.31 | O |
| ATOM | 3775 | N | LYS | A | 29 | 34.335 | 26.995 | 7.486 | 1.00 33.37 | N |
| ATOM | 3776 | CA | LYS | A | 29 | 35.787 | 27.156 | 7.747 | 1.00 35.20 | C |
| ATOM | 3778 | CB | LYS | A | 29 | 36.360 | 28.112 | 6.709 | 1.00 34.94 | C |
| ATOM | 3781 | CG | LYS | A | 29 | 36.020 | 27.628 | 5.262 | 1.00 37.58 | C |
| ATOM | 3784 | CD | LYS | A | 29 | 36.363 | 28.657 | 4.136 | 1.00 38.64 | C |
| ATOM | 3787 | CE | LYS | A | 29 | 37.801 | 29.104 | 4.268 | 1.00 40.39 | C |
| ATOM | 3790 | NZ | LYS | A | 29 | 38.400 | 29.308 | 2.978 | 1.00 37.87 | N |
| ATOM | 3794 | C | LYS | A | 29 | 36.072 | 27.617 | 9.186 | 1.00 34.80 | C |
| ATOM | 3795 | O | LYS | A | 29 | 37.108 | 27.305 | 9.732 | 1.00 35.64 | O |
| ATOM | 3797 | N | ILE | A | 30 | 35.112 | 28.303 | 9.819 | 1.00 35.20 | N |
| ATOM | 3798 | CA | ILE | A | 30 | 35.270 | 28.815 | 11.182 | 1.00 34.52 | C |
| ATOM | 3800 | CB | ILE | A | 30 | 34.716 | 30.220 | 11.318 | 1.00 35.55 | C |
| ATOM | 3802 | CG1 | ILE | A | 30 | 35.493 | 31.164 | 10.393 | 1.00 37.16 | C |
| ATOM | 3805 | CD1 | ILE | A | 30 | 34.949 | 32.583 | 10.305 | 1.00 40.89 | C |
| ATOM | 3809 | CG2 | ILE | A | 30 | 34.808 | 30.728 | 12.753 | 1.00 36.66 | C |
| ATOM | 3813 | C | ILE | A | 30 | 34.622 | 27.878 | 12.173 | 1.00 34.34 | C |
| ATOM | 3814 | O | ILE | A | 30 | 35.297 | 27.361 | 13.079 | 1.00 32.95 | O |
| ATOM | 3816 | N | GLU | A | 31 | 33.317 | 27.615 | 11.985 | 1.00 32.99 | N |
| ATOM | 3817 | CA | GLU | A | 31 | 32.569 | 26.844 | 12.960 | 1.00 32.08 | C |
| ATOM | 3819 | CB | GLU | A | 31 | 31.121 | 27.392 | 13.011 | 1.00 32.50 | C |
| ATOM | 3822 | CG | GLU | A | 31 | 30.975 | 28.714 | 13.857 | 1.00 36.73 | C |
| ATOM | 3825 | CD | GLU | A | 31 | 29.506 | 29.249 | 13.897 | 1.00 46.12 | C |
| ATOM | 3826 | OE1 | GLU | A | 31 | 28.783 | 29.008 | 14.908 | 1.00 49.86 | O |
| ATOM | 3827 | OE2 | GLU | A | 31 | 29.053 | 29.893 | 12.898 | 1.00 50.48 | O |
| ATOM | 3828 | C | GLU | A | 31 | 32.672 | 25.375 | 12.604 | 1.00 31.19 | C |
| ATOM | 3829 | O | GLU | A | 31 | 31.688 | 24.743 | 12.099 | 1.00 30.07 | O |
| ATOM | 3831 | N | THR | A | 32 | 33.864 | 24.820 | 12.855 | 1.00 28.87 | N |
| ATOM | 3832 | CA | THR | A | 32 | 34.233 | 23.553 | 12.306 | 1.00 28.77 | C |

FIG. 5F

```
ATOM   3834  CB   THR A   32      35.810  23.390  12.218  1.00 29.05           C
ATOM   3836  OG1  THR A   32      36.345  23.501  13.517  1.00 30.38           O
ATOM   3838  CG2  THR A   32      36.368  24.474  11.355  1.00 28.51           C
ATOM   3842  C    THR A   32      33.635  22.443  13.073  1.00 27.91           C
ATOM   3843  O    THR A   32      33.340  21.383  12.503  1.00 28.55           O
ATOM   3845  N    ASN A   33      33.471  22.632  14.362  1.00 26.97           N
ATOM   3846  CA   ASN A   33      32.753  21.647  15.167  1.00 27.78           C
ATOM   3848  CB   ASN A   33      32.901  21.951  16.651  1.00 27.61           C
ATOM   3851  CG   ASN A   33      34.220  21.427  17.205  1.00 34.08           C
ATOM   3852  OD1  ASN A   33      34.773  20.410  16.718  1.00 33.29           O
ATOM   3853  ND2  ASN A   33      34.761  22.142  18.169  1.00 31.62           N
ATOM   3856  C    ASN A   33      31.243  21.559  14.798  1.00 27.02           C
ATOM   3857  O    ASN A   33      30.725  20.482  14.721  1.00 29.90           O
ATOM   3859  N    LYS A   34      30.594  22.686  14.587  1.00 26.67           N
ATOM   3860  CA   LYS A   34      29.164  22.748  14.188  1.00 27.48           C
ATOM   3862  CB   LYS A   34      28.771  24.219  14.154  1.00 28.16           C
ATOM   3865  CG   LYS A   34      27.391  24.511  13.601  1.00 30.94           C
ATOM   3868  CD   LYS A   34      26.279  24.037  14.609  1.00 36.57           C
ATOM   3871  CE   LYS A   34      25.549  25.212  15.353  1.00 35.99           C
ATOM   3874  NZ   LYS A   34      25.371  26.473  14.534  1.00 37.66           N
ATOM   3878  C    LYS A   34      28.989  22.054  12.809  1.00 25.55           C
ATOM   3879  O    LYS A   34      28.154  21.184  12.622  1.00 25.90           O
ATOM   3881  N    PHE A   35      29.917  22.356  11.911  1.00 25.88           N
ATOM   3882  CA   PHE A   35      30.084  21.660  10.646  1.00 24.88           C
ATOM   3884  CB   PHE A   35      31.337  22.189   9.977  1.00 25.57           C
ATOM   3887  CG   PHE A   35      31.576  21.715   8.565  1.00 26.65           C
ATOM   3888  CD1  PHE A   35      30.509  21.442   7.670  1.00 25.74           C
ATOM   3890  CE1  PHE A   35      30.770  21.053   6.365  1.00 20.88           C
ATOM   3892  CZ   PHE A   35      32.106  20.952   5.929  1.00 24.97           C
ATOM   3894  CE2  PHE A   35      33.176  21.171   6.825  1.00 21.40           C
ATOM   3896  CD2  PHE A   35      32.918  21.528   8.120  1.00 24.71           C
ATOM   3898  C    PHE A   35      30.050  20.178  10.778  1.00 24.09           C
ATOM   3899  O    PHE A   35      29.175  19.546  10.170  1.00 23.97           O
ATOM   3901  N    ALA A   36      30.909  19.588  11.611  1.00 23.22           N
ATOM   3902  CA   ALA A   36      30.815  18.185  11.907  1.00 23.31           C
ATOM   3904  CB   ALA A   36      31.894  17.752  12.953  1.00 23.98           C
ATOM   3908  C    ALA A   36      29.461  17.760  12.465  1.00 21.84           C
ATOM   3909  O    ALA A   36      29.005  16.666  12.203  1.00 21.60           O
ATOM   3911  N    ALA A   37      28.887  18.561  13.336  1.00 21.88           N
ATOM   3912  CA   ALA A   37      27.649  18.133  13.999  1.00 21.44           C
ATOM   3914  CB   ALA A   37      27.350  19.027  15.213  1.00 20.06           C
ATOM   3918  C    ALA A   37      26.493  18.183  12.966  1.00 19.17           C
ATOM   3919  O    ALA A   37      25.615  17.369  12.978  1.00 21.53           O
ATOM   3921  N    ILE A   38      26.522  19.156  12.093  1.00 20.44           N
ATOM   3922  CA   ILE A   38      25.508  19.254  11.009  1.00 19.29           C
ATOM   3924  CB   ILE A   38      25.626  20.564  10.260  1.00 18.50           C
ATOM   3926  CG1  ILE A   38      25.142  21.636  11.216  1.00 20.39           C
ATOM   3929  CD1  ILE A   38      25.427  23.045  10.873  1.00 25.17           C
ATOM   3933  CG2  ILE A   38      24.808  20.544   8.898  1.00 18.73           C
ATOM   3937  C    ILE A   38      25.634  18.084  10.136  1.00 19.70           C
ATOM   3938  O    ILE A   38      24.640  17.422   9.856  1.00 17.66           O
ATOM   3940  N    CYS A   39      26.880  17.717   9.771  1.00 18.67           N
ATOM   3941  CA   CYS A   39      27.049  16.524   8.938  1.00 18.32           C
ATOM   3943  CB   CYS A   39      28.559  16.305   8.470  1.00 18.20           C
ATOM   3946  SG   CYS A   39      29.211  17.518   7.360  1.00 23.17           S
ATOM   3948  C    CYS A   39      26.525  15.264   9.605  1.00 17.79           C
ATOM   3949  O    CYS A   39      25.835  14.456   8.981  1.00 18.02           O
ATOM   3951  N    THR A   40      26.865  15.082  10.884  1.00 17.25           N
ATOM   3952  CA   THR A   40      26.475  13.945  11.640  1.00 18.06           C
ATOM   3954  CB   THR A   40      27.049  14.050  13.007  1.00 20.01           C
ATOM   3956  OG1  THR A   40      28.484  14.100  12.864  1.00 23.15           O
ATOM   3958  CG2  THR A   40      26.685  12.824  13.845  1.00 19.86           C
ATOM   3962  C    THR A   40      24.938  13.819  11.761  1.00 17.94           C
```

FIG. 5G

```
ATOM   3963  O    THR A  40      24.439  12.774  11.588  1.00 17.27           O
ATOM   3965  N    HIS A  41      24.292  14.931  12.077  1.00 19.50           N
ATOM   3966  CA   HIS A  41      22.842  15.007  12.276  1.00 19.81           C
ATOM   3968  CB   HIS A  41      22.432  16.388  12.814  1.00 19.82           C
ATOM   3971  CG   HIS A  41      20.952  16.664  12.758  1.00 20.37           C
ATOM   3972  ND1  HIS A  41      20.339  17.302  11.700  1.00 21.48           N
ATOM   3974  CE1  HIS A  41      19.041  17.429  11.962  1.00 22.42           C
ATOM   3976  NE2  HIS A  41      18.805  16.912  13.150  1.00 23.82           N
ATOM   3978  CD2  HIS A  41      19.989  16.484  13.690  1.00 18.08           C
ATOM   3980  C    HIS A  41      22.224  14.710  10.937  1.00 18.88           C
ATOM   3981  O    HIS A  41      21.294  13.919  10.903  1.00 19.64           O
ATOM   3983  N    LEU A  42      22.761  15.283   9.831  1.00 18.01           N
ATOM   3984  CA   LEU A  42      22.189  14.974   8.517  1.00 18.86           C
ATOM   3986  CB   LEU A  42      22.807  15.848   7.376  1.00 20.46           C
ATOM   3989  CG   LEU A  42      22.161  15.809   5.987  1.00 24.61           C
ATOM   3991  CD1  LEU A  42      20.616  16.114   6.039  1.00 25.14           C
ATOM   3995  CD2  LEU A  42      22.827  16.886   5.102  1.00 31.06           C
ATOM   3999  C    LEU A  42      22.347  13.512   8.210  1.00 19.21           C
ATOM   4000  O    LEU A  42      21.405  12.844   7.701  1.00 19.82           O
ATOM   4002  N    GLU A  43      23.540  12.984   8.467  1.00 19.50           N
ATOM   4003  CA   GLU A  43      23.734  11.592   8.266  1.00 20.69           C
ATOM   4005  CB   GLU A  43      25.223  11.209   8.489  1.00 22.31           C
ATOM   4008  CG   GLU A  43      25.350   9.825   7.982  1.00 27.94           C
ATOM   4011  CD   GLU A  43      26.715   9.334   7.937  1.00 30.82           C
ATOM   4012  OE1  GLU A  43      26.925   8.463   7.114  1.00 43.59           O
ATOM   4013  OE2  GLU A  43      27.560   9.792   8.675  1.00 33.88           O
ATOM   4014  C    GLU A  43      22.781  10.741   9.124  1.00 20.20           C
ATOM   4015  O    GLU A  43      22.208   9.800   8.621  1.00 18.66           O
ATOM   4017  N    VAL A  44      22.488  11.131  10.371  1.00 19.84           N
ATOM   4018  CA   VAL A  44      21.521  10.329  11.153  1.00 20.97           C
ATOM   4020  CB   VAL A  44      21.570  10.698  12.675  1.00 21.29           C
ATOM   4022  CG1  VAL A  44      20.456  10.080  13.447  1.00 21.90           C
ATOM   4026  CG2  VAL A  44      22.984  10.268  13.386  1.00 24.03           C
ATOM   4030  C    VAL A  44      20.068  10.409  10.585  1.00 21.37           C
ATOM   4031  O    VAL A  44      19.314   9.403  10.565  1.00 21.88           O
ATOM   4033  N    CYS A  45      19.646  11.606  10.174  1.00 21.03           N
ATOM   4034  CA   CYS A  45      18.296  11.785   9.544  1.00 21.16           C
ATOM   4036  CB   CYS A  45      18.088  13.231   9.152  1.00 18.88           C
ATOM   4039  SG   CYS A  45      17.930  14.217  10.522  1.00 20.57           S
ATOM   4041  C    CYS A  45      18.157  10.855   8.323  1.00 22.81           C
ATOM   4042  O    CYS A  45      17.151  10.092   8.203  1.00 23.44           O
ATOM   4044  N    PHE A  46      19.194  10.836   7.483  1.00 22.85           N
ATOM   4045  CA   PHE A  46      19.223   9.915   6.361  1.00 26.26           C
ATOM   4047  CB   PHE A  46      20.445  10.179   5.493  1.00 26.97           C
ATOM   4050  CG   PHE A  46      20.397  11.481   4.689  1.00 27.31           C
ATOM   4051  CD1  PHE A  46      19.450  12.456   4.902  1.00 27.51           C
ATOM   4053  CE1  PHE A  46      19.449  13.626   4.142  1.00 30.33           C
ATOM   4055  CZ   PHE A  46      20.401  13.827   3.186  1.00 27.29           C
ATOM   4057  CE2  PHE A  46      21.352  12.926   2.996  1.00 29.34           C
ATOM   4059  CD2  PHE A  46      21.347  11.715   3.736  1.00 29.82           C
ATOM   4061  C    PHE A  46      19.195   8.414   6.763  1.00 26.98           C
ATOM   4062  O    PHE A  46      18.445   7.634   6.142  1.00 28.73           O
ATOM   4064  N    MET A  47      19.990   7.997   7.765  1.00 26.04           N
ATOM   4065  CA   MET A  47      19.944   6.582   8.216  1.00 27.74           C
ATOM   4067  CB   MET A  47      21.066   6.272   9.205  1.00 28.12           C
ATOM   4070  CG   MET A  47      22.453   6.608   8.674  1.00 29.74           C
ATOM   4073  SD   MET A  47      23.783   6.300   9.814  1.00 34.67           S
ATOM   4074  CE   MET A  47      23.511   4.549  10.197  1.00 27.14           C
ATOM   4078  C    MET A  47      18.608   6.268   8.849  1.00 28.19           C
ATOM   4079  O    MET A  47      18.052   5.162   8.703  1.00 29.11           O
ATOM   4081  N    TYR A  48      18.059   7.247   9.549  1.00 27.66           N
ATOM   4082  CA   TYR A  48      16.780   7.030  10.187  1.00 27.82           C
ATOM   4084  CB   TYR A  48      16.401   8.265  10.959  1.00 25.59           C
```

FIG. 5H

| | | | | | | | | | | |
|---|---|---|---|---|---|---|---|---|---|---|
|ATOM|4087|CG|TYR|A|48|15.429|8.073|12.090|1.00 25.74|C|
|ATOM|4088|CD1|TYR|A|48|15.833|8.175|13.405|1.00 22.42|C|
|ATOM|4090|CE1|TYR|A|48|14.938|8.030|14.445|1.00 24.87|C|
|ATOM|4092|CZ|TYR|A|48|13.596|7.800|14.216|1.00 26.71|C|
|ATOM|4093|OH|TYR|A|48|12.717|7.671|15.318|1.00 24.81|O|
|ATOM|4095|CE2|TYR|A|48|13.155|7.668|12.933|1.00 27.06|C|
|ATOM|4097|CD2|TYR|A|48|14.075|7.810|11.856|1.00 26.71|C|
|ATOM|4099|C|TYR|A|48|15.696|6.670|9.165|1.00 29.27|C|
|ATOM|4100|O|TYR|A|48|14.869|5.790|9.378|1.00 26.64|O|
|ATOM|4102|N|SER|A|49|15.736|7.339|8.030|1.00 32.83|N|
|ATOM|4103|CA|SER|A|49|14.783|7.093|6.948|1.00 35.43|C|
|ATOM|4105|CB|SER|A|49|14.690|8.314|6.035|1.00 35.64|C|
|ATOM|4108|OG|SER|A|49|13.905|7.940|4.900|1.00 36.39|O|
|ATOM|4110|C|SER|A|49|15.091|5.876|6.073|1.00 37.95|C|
|ATOM|4111|O|SER|A|49|14.155|5.202|5.581|1.00 40.05|O|
|ATOM|4113|N|ASP|A|50|16.367|5.581|5.874|1.00 40.93|N|
|ATOM|4114|CA|ASP|A|50|16.801|4.547|4.909|1.00 44.18|C|
|ATOM|4116|CB|ASP|A|50|18.353|4.437|4.799|1.00 44.74|C|
|ATOM|4119|CG|ASP|A|50|18.963|5.590|3.997|1.00 46.66|C|
|ATOM|4120|OD1|ASP|A|50|20.206|5.775|4.030|1.00 51.65|O|
|ATOM|4121|OD2|ASP|A|50|18.182|6.351|3.358|1.00 50.32|O|
|ATOM|4122|C|ASP|A|50|16.230|3.184|5.192|1.00 45.66|C|
|ATOM|4123|O|ASP|A|50|16.137|2.758|6.351|1.00 47.11|O|
|ATOM|4125|N|PHE|A|51|15.823|2.521|4.117|1.00 47.20|N|
|ATOM|4126|CA|PHE|A|51|15.291|1.168|4.160|1.00 48.87|C|
|ATOM|4128|CB|PHE|A|51|16.265|0.175|4.872|1.00 48.96|C|
|ATOM|4131|CG|PHE|A|51|17.707|0.312|4.467|1.00 52.30|C|
|ATOM|4132|CD1|PHE|A|51|18.081|0.217|3.117|1.00 55.97|C|
|ATOM|4134|CE1|PHE|A|51|19.425|0.343|2.737|1.00 57.47|C|
|ATOM|4136|CZ|PHE|A|51|20.407|0.582|3.733|1.00 58.95|C|
|ATOM|4138|CE2|PHE|A|51|20.030|0.662|5.089|1.00 55.32|C|
|ATOM|4140|CD2|PHE|A|51|18.703|0.519|5.443|1.00 53.55|C|
|ATOM|4142|C|PHE|A|51|13.899|1.030|4.796|1.00 49.11|C|
|ATOM|4143|O|PHE|A|51|13.422|-0.077|4.888|1.00 49.98|O|
|ATOM|4145|N|HIS|A|52|13.238|2.104|5.225|1.00 49.71|N|
|ATOM|4146|CA|HIS|A|52|11.891|1.980|5.787|1.00 49.81|C|
|ATOM|4148|CB|HIS|A|52|11.780|2.734|7.099|1.00 50.49|C|
|ATOM|4151|CG|HIS|A|52|12.629|2.144|8.177|1.00 51.72|C|
|ATOM|4152|ND1|HIS|A|52|13.791|2.742|8.617|1.00 53.36|N|
|ATOM|4154|CE1|HIS|A|52|14.350|1.973|9.537|1.00 54.13|C|
|ATOM|4156|NE2|HIS|A|52|13.605|0.893|9.694|1.00 53.31|N|
|ATOM|4158|CD2|HIS|A|52|12.527|0.971|8.846|1.00 52.73|C|
|ATOM|4160|C|HIS|A|52|10.790|2.384|4.838|1.00 50.48|C|
|ATOM|4161|O|HIS|A|52|10.791|3.486|4.284|1.00 49.74|O|
|ATOM|4163|N|PHE|A|53|9.847|1.462|4.651|1.00 51.60|N|
|ATOM|4164|CA|PHE|A|53|8.869|1.556|3.590|1.00 53.19|C|
|ATOM|4166|CB|PHE|A|53|9.300|0.668|2.425|1.00 53.76|C|
|ATOM|4169|CG|PHE|A|53|10.480|1.201|1.643|1.00 53.69|C|
|ATOM|4170|CD1|PHE|A|53|10.307|2.155|0.679|1.00 53.29|C|
|ATOM|4172|CE1|PHE|A|53|11.377|2.639|-0.042|1.00 55.70|C|
|ATOM|4174|CZ|PHE|A|53|12.652|2.162|0.196|1.00 56.82|C|
|ATOM|4176|CE2|PHE|A|53|12.836|1.188|1.148|1.00 56.35|C|
|ATOM|4178|CD2|PHE|A|53|11.754|0.715|1.867|1.00 55.39|C|
|ATOM|4180|C|PHE|A|53|7.503|1.153|4.108|1.00 54.70|C|
|ATOM|4181|O|PHE|A|53|7.398|0.526|5.142|1.00 53.81|O|
|ATOM|4183|N|ILE|A|54|6.444|1.562|3.419|1.00 57.24|N|
|ATOM|4184|CA|ILE|A|54|5.089|1.171|3.818|1.00 58.97|C|
|ATOM|4186|CB|ILE|A|54|4.281|2.349|4.455|1.00 58.93|C|
|ATOM|4188|CG1|ILE|A|54|4.550|3.674|3.743|1.00 58.38|C|
|ATOM|4191|CD1|ILE|A|54|3.806|4.853|4.359|1.00 56.17|C|
|ATOM|4195|CG2|ILE|A|54|4.614|2.476|5.934|1.00 59.10|C|
|ATOM|4199|C|ILE|A|54|4.331|0.556|2.636|1.00 61.05|C|
|ATOM|4200|O|ILE|A|54|4.235|1.163|1.564|1.00 60.93|O|

FIG. 5I

```
ATOM   4202  N    ASP A  55       3.796  -0.649   2.849  1.00 63.73           N
ATOM   4203  CA   ASP A  55       3.250  -1.472   1.758  1.00 65.98           C
ATOM   4205  CB   ASP A  55       3.105  -2.958   2.172  1.00 66.36           C
ATOM   4208  CG   ASP A  55       2.077  -3.188   3.269  1.00 67.76           C
ATOM   4209  OD1  ASP A  55       2.250  -4.178   4.015  1.00 71.29           O
ATOM   4210  OD2  ASP A  55       1.103  -2.408   3.396  1.00 70.42           O
ATOM   4211  C    ASP A  55       1.949  -0.933   1.132  1.00 67.80           C
ATOM   4212  O    ASP A  55       1.460  -1.492   0.132  1.00 68.87           O
ATOM   4214  N    ASP A  56       1.390   0.128   1.719  1.00 69.38           N
ATOM   4215  CA   ASP A  56       0.330   0.915   1.074  1.00 70.37           C
ATOM   4217  CB   ASP A  56      -1.024   0.187   1.157  1.00 70.91           C
ATOM   4220  CG   ASP A  56      -2.058   0.742   0.178  1.00 72.59           C
ATOM   4221  OD1  ASP A  56      -1.944   1.917  -0.257  1.00 74.34           O
ATOM   4222  OD2  ASP A  56      -3.003  -0.008  -0.155  1.00 76.69           O
ATOM   4223  C    ASP A  56       0.231   2.295   1.730  1.00 70.77           C
ATOM   4224  O    ASP A  56       0.004   2.402   2.943  1.00 71.00           O
ATOM   4226  N    GLY A  58       0.587  -1.157   6.263  1.00 81.38           N
ATOM   4227  CA   GLY A  58       1.600  -1.539   7.247  1.00 81.46           C
ATOM   4230  C    GLY A  58       2.991  -1.331   6.679  1.00 81.74           C
ATOM   4231  O    GLY A  58       3.138  -1.095   5.472  1.00 81.77           O
ATOM   4233  N    GLU A  59       4.019  -1.422   7.527  1.00 81.75           N
ATOM   4234  CA   GLU A  59       5.391  -1.072   7.101  1.00 81.67           C
ATOM   4236  CB   GLU A  59       6.076  -0.095   8.085  1.00 81.61           C
ATOM   4239  CG   GLU A  59       6.951  -0.720   9.176  1.00 81.33           C
ATOM   4242  CD   GLU A  59       6.136  -1.423  10.247  1.00 80.59           C
ATOM   4243  OE1  GLU A  59       5.322  -2.303   9.900  1.00 81.03           O
ATOM   4244  OE2  GLU A  59       6.301  -1.093  11.440  1.00 77.96           O
ATOM   4245  C    GLU A  59       6.264  -2.289   6.848  1.00 81.47           C
ATOM   4246  O    GLU A  59       5.885  -3.414   7.152  1.00 81.51           O
ATOM   4248  N    SER A  60       7.436  -2.032   6.279  1.00 81.57           N
ATOM   4249  CA   SER A  60       8.369  -3.072   5.890  1.00 81.64           C
ATOM   4251  CB   SER A  60       7.881  -3.798   4.634  1.00 81.53           C
ATOM   4254  OG   SER A  60       7.444  -2.889   3.646  1.00 80.41           O
ATOM   4256  C    SER A  60       9.759  -2.492   5.657  1.00 82.25           C
ATOM   4257  O    SER A  60       9.920  -1.312   5.327  1.00 81.91           O
ATOM   4259  N    ILE A  61      10.746  -3.365   5.820  1.00 83.15           N
ATOM   4260  CA   ILE A  61      12.172  -3.035   5.807  1.00 83.98           C
ATOM   4262  CB   ILE A  61      12.824  -3.573   7.126  1.00 84.00           C
ATOM   4264  CG1  ILE A  61      11.974  -3.152   8.347  1.00 84.28           C
ATOM   4267  CD1  ILE A  61      12.623  -3.382   9.701  1.00 83.44           C
ATOM   4271  CG2  ILE A  61      14.255  -3.105   7.253  1.00 83.90           C
ATOM   4275  C    ILE A  61      12.838  -3.678   4.563  1.00 84.60           C
ATOM   4276  O    ILE A  61      12.521  -4.827   4.229  1.00 85.06           O
ATOM   4278  N    ILE A  62      13.729  -2.950   3.871  1.00 85.09           N
ATOM   4279  CA   ILE A  62      14.450  -3.481   2.676  1.00 85.39           C
ATOM   4281  CB   ILE A  62      14.074  -2.722   1.367  1.00 85.47           C
ATOM   4283  CG1  ILE A  62      12.570  -2.830   1.082  1.00 85.98           C
ATOM   4286  CD1  ILE A  62      12.129  -2.183  -0.273  1.00 85.70           C
ATOM   4290  CG2  ILE A  62      14.839  -3.290   0.169  1.00 85.59           C
ATOM   4294  C    ILE A  62      15.983  -3.474   2.872  1.00 85.49           C
ATOM   4295  O    ILE A  62      16.765  -3.150   1.962  1.00 85.65           O
ATOM   4297  N    LYS A  73       6.938   2.964  -1.660  1.00 48.05           N
ATOM   4298  CA   LYS A  73       6.539   4.123  -0.839  1.00 48.25           C
ATOM   4300  CB   LYS A  73       5.067   3.954  -0.459  1.00 49.02           C
ATOM   4303  CG   LYS A  73       4.385   5.133   0.229  1.00 53.20           C
ATOM   4306  CD   LYS A  73       2.844   4.863   0.197  1.00 56.19           C
ATOM   4309  CE   LYS A  73       1.921   6.006   0.697  1.00 57.81           C
ATOM   4312  NZ   LYS A  73       0.509   5.455   0.873  1.00 56.71           N
ATOM   4316  C    LYS A  73       7.395   4.315   0.444  1.00 46.21           C
ATOM   4317  O    LYS A  73       7.399   3.441   1.331  1.00 45.27           O
ATOM   4319  N    HIS A  74       8.047   5.478   0.570  1.00 42.54           N
ATOM   4320  CA   HIS A  74       8.901   5.755   1.732  1.00 41.51           C
ATOM   4322  CB   HIS A  74       9.773   7.001   1.502  1.00 41.99           C
```

FIG. 5J

```
ATOM   4325  CG   HIS A  74      10.794   6.828   0.424  1.00 45.77           C
ATOM   4326  ND1  HIS A  74      11.882   7.666   0.278  1.00 51.13           N
ATOM   4328  CE1  HIS A  74      12.613   7.272  -0.747  1.00 50.19           C
ATOM   4330  NE2  HIS A  74      12.053   6.192  -1.257  1.00 49.77           N
ATOM   4332  CD2  HIS A  74      10.909   5.900  -0.551  1.00 48.34           C
ATOM   4334  C    HIS A  74       8.053   5.945   2.990  1.00 38.11           C
ATOM   4335  O    HIS A  74       7.068   6.687   2.971  1.00 39.13           O
ATOM   4337  N    ARG A  75       8.432   5.286   4.078  1.00 33.28           N
ATOM   4338  CA   ARG A  75       7.790   5.529   5.383  1.00 31.40           C
ATOM   4340  CB   ARG A  75       8.310   4.536   6.419  1.00 30.88           C
ATOM   4343  CG   ARG A  75       7.838   4.843   7.806  1.00 32.49           C
ATOM   4346  CD   ARG A  75       8.088   3.752   8.788  1.00 29.37           C
ATOM   4349  NE   ARG A  75       7.641   4.211  10.076  1.00 32.59           N
ATOM   4351  CZ   ARG A  75       7.726   3.528  11.208  1.00 35.96           C
ATOM   4352  NH1  ARG A  75       8.254   2.326  11.229  1.00 40.55           N
ATOM   4355  NH2  ARG A  75       7.309   4.078  12.327  1.00 38.41           N
ATOM   4358  C    ARG A  75       7.998   6.972   5.893  1.00 29.60           C
ATOM   4359  O    ARG A  75       7.136   7.555   6.553  1.00 29.98           O
ATOM   4361  N    PHE A  76       9.131   7.552   5.569  1.00 27.87           N
ATOM   4362  CA   PHE A  76       9.510   8.814   6.132  1.00 27.42           C
ATOM   4364  CB   PHE A  76      10.811   8.665   6.904  1.00 27.96           C
ATOM   4367  CG   PHE A  76      10.705   7.775   8.089  1.00 25.71           C
ATOM   4368  CD1  PHE A  76      10.062   8.207   9.226  1.00 24.03           C
ATOM   4370  CE1  PHE A  76       9.966   7.392  10.311  1.00 26.98           C
ATOM   4372  CZ   PHE A  76      10.511   6.175  10.276  1.00 24.68           C
ATOM   4374  CE2  PHE A  76      11.176   5.725   9.176  1.00 26.92           C
ATOM   4376  CD2  PHE A  76      11.281   6.528   8.084  1.00 29.01           C
ATOM   4378  C    PHE A  76       9.738   9.838   5.041  1.00 26.82           C
ATOM   4379  O    PHE A  76      10.435   9.552   4.078  1.00 28.59           O
ATOM   4381  N    GLU A  77       9.205  11.041   5.206  1.00 25.46           N
ATOM   4382  CA   GLU A  77       9.584  12.135   4.363  1.00 24.88           C
ATOM   4384  CB   GLU A  77       8.437  13.136   4.297  1.00 26.37           C
ATOM   4387  CG   GLU A  77       8.775  14.311   3.354  1.00 29.27           C
ATOM   4390  CD   GLU A  77       8.802  13.849   1.933  1.00 30.94           C
ATOM   4391  OE1  GLU A  77       9.772  14.104   1.188  1.00 38.76           O
ATOM   4392  OE2  GLU A  77       7.870  13.122   1.617  1.00 33.73           O
ATOM   4393  C    GLU A  77      10.833  12.818   4.985  1.00 25.17           C
ATOM   4394  O    GLU A  77      10.836  13.070   6.172  1.00 25.52           O
ATOM   4396  N    ILE A  78      11.868  13.153   4.212  1.00 23.90           N
ATOM   4397  CA   ILE A  78      13.028  13.832   4.801  1.00 24.27           C
ATOM   4399  CB   ILE A  78      14.384  13.395   4.193  1.00 26.03           C
ATOM   4401  CG1  ILE A  78      14.548  11.854   4.322  1.00 28.41           C
ATOM   4404  CD1  ILE A  78      15.529  11.142   3.285  1.00 29.47           C
ATOM   4408  CG2  ILE A  78      15.522  14.075   4.953  1.00 25.15           C
ATOM   4412  C    ILE A  78      12.861  15.359   4.682  1.00 22.51           C
ATOM   4413  O    ILE A  78      12.699  15.869   3.638  1.00 23.77           O
ATOM   4415  N    ILE A  79      12.775  16.053   5.791  1.00 21.51           N
ATOM   4416  CA   ILE A  79      12.680  17.524   5.836  1.00 20.74           C
ATOM   4418  CB   ILE A  79      11.719  17.834   6.936  1.00 20.06           C
ATOM   4420  CG1  ILE A  79      10.335  17.217   6.505  1.00 23.77           C
ATOM   4423  CD1  ILE A  79       9.431  17.082   7.599  1.00 25.23           C
ATOM   4427  CG2  ILE A  79      11.557  19.343   7.135  1.00 18.11           C
ATOM   4431  C    ILE A  79      14.063  18.196   5.974  1.00 19.32           C
ATOM   4432  O    ILE A  79      14.410  19.151   5.254  1.00 18.63           O
ATOM   4434  N    GLU A  80      14.873  17.649   6.850  1.00 18.99           N
ATOM   4435  CA   GLU A  80      16.261  18.154   7.077  1.00 19.21           C
ATOM   4437  CB   GLU A  80      16.902  17.361   8.223  1.00 19.58           C
ATOM   4440  CG   GLU A  80      18.266  17.872   8.736  1.00 21.39           C
ATOM   4443  CD   GLU A  80      18.271  19.248   9.206  1.00 21.69           C
ATOM   4444  OE1  GLU A  80      17.943  19.564  10.330  1.00 27.20           O
ATOM   4445  OE2  GLU A  80      18.622  20.130   8.457  1.00 26.69           O
ATOM   4446  C    GLU A  80      17.038  17.953   5.817  1.00 18.98           C
ATOM   4447  O    GLU A  80      16.826  16.974   5.126  1.00 19.55           O
```

FIG. 5K

```
ATOM   4449  N    GLY A  81      17.961  18.865   5.521  1.00 21.49           N
ATOM   4450  CA   GLY A  81      18.735  18.863   4.276  1.00 20.61           C
ATOM   4453  C    GLY A  81      18.147  19.780   3.223  1.00 21.59           C
ATOM   4454  O    GLY A  81      18.865  20.256   2.335  1.00 20.89           O
ATOM   4456  N    ARG A  82      16.841  20.039   3.318  1.00 21.56           N
ATOM   4457  CA   ARG A  82      16.174  20.983   2.435  1.00 22.08           C
ATOM   4459  CB   ARG A  82      14.643  20.698   2.362  1.00 22.60           C
ATOM   4462  CG   ARG A  82      14.384  19.272   1.930  1.00 21.62           C
ATOM   4465  CD   ARG A  82      13.003  18.619   2.219  1.00 31.85           C
ATOM   4468  NE   ARG A  82      12.520  18.520   0.905  1.00 35.87           N
ATOM   4470  CZ   ARG A  82      12.224  17.517   0.130  1.00 27.09           C
ATOM   4471  NH1  ARG A  82      11.988  16.259   0.455  1.00 27.90           N
ATOM   4474  NH2  ARG A  82      12.075  17.918  -1.087  1.00 29.02           N
ATOM   4477  C    ARG A  82      16.454  22.385   2.890  1.00 21.61           C
ATOM   4478  O    ARG A  82      16.526  22.619   4.030  1.00 21.64           O
ATOM   4480  N    ASP A  83      16.529  23.362   1.993  1.00 23.18           N
ATOM   4481  CA   ASP A  83      16.443  24.742   2.466  1.00 24.33           C
ATOM   4483  CB   ASP A  83      16.859  25.761   1.367  1.00 25.29           C
ATOM   4486  CG   ASP A  83      15.830  25.943   0.262  1.00 29.71           C
ATOM   4487  OD1  ASP A  83      14.707  25.406   0.276  1.00 33.99           O
ATOM   4488  OD2  ASP A  83      16.167  26.685  -0.640  1.00 39.38           O
ATOM   4489  C    ASP A  83      15.048  25.062   3.081  1.00 23.94           C
ATOM   4490  O    ASP A  83      14.131  24.238   3.020  1.00 22.18           O
ATOM   4492  N    ARG A  84      14.921  26.239   3.678  1.00 23.12           N
ATOM   4493  CA   ARG A  84      13.766  26.490   4.515  1.00 23.78           C
ATOM   4495  CB   ARG A  84      13.879  27.780   5.304  1.00 23.86           C
ATOM   4498  CG   ARG A  84      14.665  27.726   6.571  1.00 25.58           C
ATOM   4501  CD   ARG A  84      14.592  29.049   7.254  1.00 25.51           C
ATOM   4504  NE   ARG A  84      15.303  29.032   8.540  1.00 30.29           N
ATOM   4506  CZ   ARG A  84      16.408  29.722   8.799  1.00 32.03           C
ATOM   4507  NH1  ARG A  84      16.949  30.502   7.870  1.00 31.92           N
ATOM   4510  NH2  ARG A  84      16.991  29.639   9.994  1.00 35.40           N
ATOM   4513  C    ARG A  84      12.546  26.540   3.617  1.00 24.57           C
ATOM   4514  O    ARG A  84      11.480  26.093   4.009  1.00 24.75           O
ATOM   4516  N    ILE A  85      12.706  27.115   2.433  1.00 23.26           N
ATOM   4517  CA   ILE A  85      11.607  27.261   1.537  1.00 23.31           C
ATOM   4519  CB   ILE A  85      11.979  28.167   0.400  1.00 24.01           C
ATOM   4521  CG1  ILE A  85      12.224  29.574   0.954  1.00 25.10           C
ATOM   4524  CD1  ILE A  85      13.111  30.416  -0.093  1.00 33.55           C
ATOM   4528  CG2  ILE A  85      10.892  28.156  -0.692  1.00 23.45           C
ATOM   4532  C    ILE A  85      11.032  25.951   1.080  1.00 23.83           C
ATOM   4533  O    ILE A  85       9.799  25.728   1.232  1.00 23.01           O
ATOM   4535  N    MET A  86      11.880  25.047   0.594  1.00 23.70           N
ATOM   4536  CA   MET A  86      11.453  23.706   0.240  1.00 24.04           C
ATOM   4538  CB   MET A  86      12.552  22.913  -0.480  1.00 25.61           C
ATOM   4541  CG   MET A  86      12.822  23.410  -1.922  1.00 29.68           C
ATOM   4544  SD   MET A  86      11.329  23.275  -2.901  1.00 38.30           S
ATOM   4545  CE   MET A  86      11.932  24.152  -4.366  1.00 44.18           C
ATOM   4549  C    MET A  86      10.973  22.895   1.436  1.00 23.56           C
ATOM   4550  O    MET A  86       9.939  22.184   1.343  1.00 22.21           O
ATOM   4552  N    ALA A  87      11.647  23.030   2.569  1.00 20.43           N
ATOM   4553  CA   ALA A  87      11.207  22.367   3.790  1.00 20.21           C
ATOM   4555  CB   ALA A  87      12.126  22.651   4.934  1.00 19.24           C
ATOM   4559  C    ALA A  87       9.730  22.784   4.199  1.00 19.78           C
ATOM   4560  O    ALA A  87       8.900  21.935   4.518  1.00 18.95           O
ATOM   4562  N    TRP A  88       9.447  24.054   4.200  1.00 20.65           N
ATOM   4563  CA   TRP A  88       8.053  24.500   4.559  1.00 21.04           C
ATOM   4565  CB   TRP A  88       8.023  25.960   4.796  1.00 21.58           C
ATOM   4568  CG   TRP A  88       8.508  26.312   6.146  1.00 18.17           C
ATOM   4569  CD1  TRP A  88       9.592  27.069   6.449  1.00 20.94           C
ATOM   4571  NE1  TRP A  88       9.730  27.182   7.781  1.00 24.67           N
ATOM   4573  CE2  TRP A  88       8.689  26.540   8.395  1.00 23.58           C
ATOM   4574  CD2  TRP A  88       7.883  25.997   7.378  1.00 18.52           C
```

FIG. 5L

```
ATOM   4575  CE3 TRP A  88       6.746  25.251   7.733  1.00 20.25           C
ATOM   4577  CZ3 TRP A  88       6.448  25.093   9.039  1.00 22.47           C
ATOM   4579  CH2 TRP A  88       7.274  25.653  10.060  1.00 26.37           C
ATOM   4581  CZ2 TRP A  88       8.402  26.373   9.750  1.00 26.62           C
ATOM   4583  C   TRP A  88       7.069  24.096   3.498  1.00 21.67           C
ATOM   4584  O   TRP A  88       5.957  23.688   3.812  1.00 22.18           O
ATOM   4586  N   THR A  89       7.535  24.024   2.254  1.00 21.88           N
ATOM   4587  CA  THR A  89       6.691  23.547   1.176  1.00 22.15           C
ATOM   4589  CB  THR A  89       7.405  23.610  -0.167  1.00 21.30           C
ATOM   4591  OG1 THR A  89       7.803  24.932  -0.361  1.00 21.89           O
ATOM   4593  CG2 THR A  89       6.491  23.236  -1.421  1.00 25.31           C
ATOM   4597  C   THR A  89       6.247  22.158   1.508  1.00 22.56           C
ATOM   4598  O   THR A  89       5.039  21.808   1.356  1.00 19.63           O
ATOM   4600  N   VAL A  90       7.219  21.327   1.925  1.00 22.06           N
ATOM   4601  CA  VAL A  90       6.956  19.943   2.169  1.00 22.93           C
ATOM   4603  CB  VAL A  90       8.279  19.123   2.270  1.00 24.11           C
ATOM   4605  CG1 VAL A  90       8.045  17.790   2.870  1.00 25.20           C
ATOM   4609  CG2 VAL A  90       8.902  18.931   0.886  1.00 27.88           C
ATOM   4613  C   VAL A  90       6.080  19.790   3.427  1.00 21.81           C
ATOM   4614  O   VAL A  90       5.127  19.031   3.408  1.00 20.95           O
ATOM   4616  N   VAL A  91       6.400  20.533   4.486  1.00 20.25           N
ATOM   4617  CA  VAL A  91       5.663  20.469   5.719  1.00 19.92           C
ATOM   4619  CB  VAL A  91       6.315  21.321   6.791  1.00 20.85           C
ATOM   4621  CG1 VAL A  91       5.403  21.463   8.018  1.00 17.94           C
ATOM   4625  CG2 VAL A  91       7.751  20.664   7.174  1.00 20.42           C
ATOM   4629  C   VAL A  91       4.193  20.917   5.464  1.00 20.56           C
ATOM   4630  O   VAL A  91       3.262  20.259   5.914  1.00 19.15           O
ATOM   4632  N   ASN A  92       4.029  21.980   4.706  1.00 21.42           N
ATOM   4633  CA  ASN A  92       2.711  22.489   4.435  1.00 23.06           C
ATOM   4635  CB  ASN A  92       2.824  23.766   3.639  1.00 23.94           C
ATOM   4638  CG  ASN A  92       3.210  24.892   4.454  1.00 25.31           C
ATOM   4639  OD1 ASN A  92       3.365  24.790   5.696  1.00 26.26           O
ATOM   4640  ND2 ASN A  92       3.312  26.060   3.795  1.00 31.85           N
ATOM   4643  C   ASN A  92       1.864  21.506   3.694  1.00 23.30           C
ATOM   4644  O   ASN A  92       0.733  21.255   4.085  1.00 23.77           O
ATOM   4646  N   SER A  93       2.439  20.884   2.672  1.00 23.36           N
ATOM   4647  CA  SER A  93       1.746  19.906   1.866  1.00 23.47           C
ATOM   4649  CB  SER A  93       2.687  19.507   0.737  1.00 23.42           C
ATOM   4652  OG  SER A  93       2.219  18.458  -0.044  1.00 26.35           O
ATOM   4654  C   SER A  93       1.285  18.677   2.697  1.00 25.02           C
ATOM   4655  O   SER A  93       0.131  18.189   2.604  1.00 22.83           O
ATOM   4657  N   ILE A  94       2.179  18.198   3.559  1.00 24.78           N
ATOM   4658  CA  ILE A  94       1.880  17.107   4.421  1.00 23.76           C
ATOM   4660  CB  ILE A  94       3.130  16.675   5.220  1.00 24.01           C
ATOM   4662  CG1 ILE A  94       4.079  15.862   4.356  1.00 24.64           C
ATOM   4665  CD1 ILE A  94       5.475  15.728   5.021  1.00 21.78           C
ATOM   4669  CG2 ILE A  94       2.731  15.884   6.456  1.00 20.87           C
ATOM   4673  C   ILE A  94       0.737  17.460   5.426  1.00 24.70           C
ATOM   4674  O   ILE A  94      -0.172  16.623   5.618  1.00 24.12           O
ATOM   4676  N   CYS A  95       0.819  18.629   6.074  1.00 22.49           N
ATOM   4677  CA  CYS A  95      -0.214  19.057   6.999  1.00 24.70           C
ATOM   4679  CB  CYS A  95       0.165  20.366   7.692  1.00 23.51           C
ATOM   4682  SG  CYS A  95       1.627  20.123   8.837  1.00 26.20           S
ATOM   4684  C   CYS A  95      -1.584  19.178   6.317  1.00 25.37           C
ATOM   4685  O   CYS A  95      -2.582  18.683   6.860  1.00 27.30           O
ATOM   4687  N   ASN A  96      -1.589  19.743   5.115  1.00 25.91           N
ATOM   4688  CA  ASN A  96      -2.819  19.958   4.350  1.00 27.86           C
ATOM   4690  CB  ASN A  96      -2.520  20.768   3.075  1.00 27.67           C
ATOM   4693  CG  ASN A  96      -2.179  22.197   3.357  1.00 31.54           C
ATOM   4694  OD1 ASN A  96      -2.443  22.722   4.457  1.00 36.77           O
ATOM   4695  ND2 ASN A  96      -1.603  22.877   2.341  1.00 32.47           N
ATOM   4698  C   ASN A  96      -3.476  18.633   4.003  1.00 28.53           C
ATOM   4699  O   ASN A  96      -4.684  18.421   4.140  1.00 26.67           O
```

FIG. 5M

```
ATOM   4701  N    THR A  97      -2.625  17.725   3.578  1.00 29.23           N
ATOM   4702  CA   THR A  97      -2.958  16.414   3.104  1.00 31.24           C
ATOM   4704  CB   THR A  97      -1.773  16.031   2.220  1.00 32.02           C
ATOM   4706  OG1  THR A  97      -1.988  16.668   0.933  1.00 38.24           O
ATOM   4708  CG2  THR A  97      -1.551  14.653   2.113  1.00 33.72           C
ATOM   4712  C    THR A  97      -3.277  15.324   4.165  1.00 31.50           C
ATOM   4713  O    THR A  97      -4.028  14.426   3.876  1.00 31.45           O
ATOM   4715  N    THR A  98      -2.746  15.425   5.380  1.00 30.49           N
ATOM   4716  CA   THR A  98      -2.925  14.408   6.412  1.00 30.11           C
ATOM   4718  CB   THR A  98      -1.563  13.981   7.029  1.00 29.99           C
ATOM   4720  OG1  THR A  98      -0.999  15.135   7.642  1.00 25.52           O
ATOM   4722  CG2  THR A  98      -0.642  13.365   5.996  1.00 29.30           C
ATOM   4726  C    THR A  98      -3.737  14.879   7.583  1.00 31.24           C
ATOM   4727  O    THR A  98      -4.207  14.054   8.359  1.00 31.90           O
ATOM   4729  N    GLY A  99      -3.864  16.186   7.741  1.00 32.43           N
ATOM   4730  CA   GLY A  99      -4.546  16.782   8.879  1.00 33.28           C
ATOM   4733  C    GLY A  99      -3.662  16.923  10.121  1.00 33.98           C
ATOM   4734  O    GLY A  99      -4.112  17.455  11.117  1.00 35.59           O
ATOM   4736  N    VAL A 100      -2.413  16.455  10.095  1.00 33.92           N
ATOM   4737  CA   VAL A 100      -1.538  16.717  11.259  1.00 33.90           C
ATOM   4739  CB   VAL A 100      -0.118  16.037  11.163  1.00 33.99           C
ATOM   4741  CG1  VAL A 100      -0.297  14.580  11.342  1.00 33.72           C
ATOM   4745  CG2  VAL A 100       0.618  16.372   9.801  1.00 32.56           C
ATOM   4749  C    VAL A 100      -1.357  18.182  11.504  1.00 33.22           C
ATOM   4750  O    VAL A 100      -1.251  18.974  10.596  1.00 32.99           O
ATOM   4752  N    GLU A 101      -1.331  18.510  12.776  1.00 34.14           N
ATOM   4753  CA   GLU A 101      -1.006  19.834  13.309  1.00 35.00           C
ATOM   4755  CB   GLU A 101      -0.882  19.699  14.859  1.00 36.13           C
ATOM   4758  CG   GLU A 101      -0.204  20.878  15.637  1.00 40.70           C
ATOM   4761  CD   GLU A 101      -0.190  20.628  17.154  1.00 48.59           C
ATOM   4762  OE1  GLU A 101      -1.295  20.645  17.806  1.00 51.01           O
ATOM   4763  OE2  GLU A 101       0.928  20.390  17.694  1.00 53.90           O
ATOM   4764  C    GLU A 101       0.293  20.398  12.716  1.00 33.10           C
ATOM   4765  O    GLU A 101       1.286  19.684  12.550  1.00 32.12           O
ATOM   4767  N    LYS A 102       0.261  21.665  12.351  1.00 32.11           N
ATOM   4768  CA   LYS A 102       1.386  22.248  11.710  1.00 31.98           C
ATOM   4770  CB   LYS A 102       0.959  23.431  10.909  1.00 32.96           C
ATOM   4773  CG   LYS A 102       2.188  24.058  10.219  1.00 33.83           C
ATOM   4776  CD   LYS A 102       1.787  25.023   9.206  1.00 36.21           C
ATOM   4779  CE   LYS A 102       0.973  24.404   8.111  1.00 32.75           C
ATOM   4782  NZ   LYS A 102       0.724  25.545   7.167  1.00 29.74           N
ATOM   4786  C    LYS A 102       2.425  22.663  12.725  1.00 30.91           C
ATOM   4787  O    LYS A 102       2.139  23.447  13.601  1.00 30.99           O
ATOM   4789  N    PRO A 103       3.645  22.148  12.615  1.00 30.60           N
ATOM   4790  CA   PRO A 103       4.657  22.542  13.633  1.00 30.96           C
ATOM   4792  CB   PRO A 103       5.916  21.724  13.264  1.00 31.44           C
ATOM   4795  CG   PRO A 103       5.696  21.202  11.868  1.00 31.26           C
ATOM   4798  CD   PRO A 103       4.189  21.301  11.552  1.00 31.28           C
ATOM   4801  C    PRO A 103       4.969  24.028  13.550  1.00 30.24           C
ATOM   4802  O    PRO A 103       4.737  24.626  12.516  1.00 29.18           O
ATOM   4803  N    LYS A 104       5.461  24.607  14.642  1.00 30.63           N
ATOM   4804  CA   LYS A 104       5.923  26.017  14.646  1.00 31.79           C
ATOM   4806  CB   LYS A 104       5.792  26.637  16.037  1.00 33.81           C
ATOM   4809  CG   LYS A 104       4.372  26.720  16.545  1.00 38.65           C
ATOM   4812  CD   LYS A 104       3.581  27.852  15.799  1.00 42.44           C
ATOM   4815  CE   LYS A 104       2.159  27.987  16.401  1.00 46.56           C
ATOM   4818  NZ   LYS A 104       2.184  28.941  17.582  1.00 47.58           N
ATOM   4822  C    LYS A 104       7.385  26.136  14.192  1.00 30.83           C
ATOM   4823  O    LYS A 104       7.790  27.188  13.734  1.00 29.36           O
ATOM   4825  N    PHE A 105       8.144  25.040  14.272  1.00 29.59           N
ATOM   4826  CA   PHE A 105       9.482  24.994  13.736  1.00 29.63           C
ATOM   4828  CB   PHE A 105      10.501  24.953  14.899  1.00 31.16           C
ATOM   4831  CG   PHE A 105      10.191  25.941  16.009  1.00 33.67           C
```

FIG. 5N

```
ATOM   4832  CD1 PHE A 105      10.709  27.232  15.972  1.00 37.41           C
ATOM   4834  CE1 PHE A 105      10.372  28.145  16.966  1.00 38.82           C
ATOM   4836  CZ  PHE A 105       9.495  27.770  18.002  1.00 36.70           C
ATOM   4838  CE2 PHE A 105       8.965  26.517  18.026  1.00 36.76           C
ATOM   4840  CD2 PHE A 105       9.304  25.601  17.039  1.00 34.31           C
ATOM   4842  C   PHE A 105       9.636  23.750  12.843  1.00 27.42           C
ATOM   4843  O   PHE A 105       8.995  22.711  13.063  1.00 29.07           O
ATOM   4845  N   LEU A 106      10.543  23.855  11.909  1.00 25.19           N
ATOM   4846  CA  LEU A 106      10.824  22.816  10.977  1.00 25.00           C
ATOM   4848  CB  LEU A 106      11.827  23.279   9.936  1.00 25.27           C
ATOM   4851  CG  LEU A 106      11.338  24.314   8.903  1.00 24.10           C
ATOM   4853  CD1 LEU A 106      12.616  24.876   8.179  1.00 22.92           C
ATOM   4857  CD2 LEU A 106      10.362  23.685   7.888  1.00 20.32           C
ATOM   4861  C   LEU A 106      11.361  21.596  11.725  1.00 24.06           C
ATOM   4862  O   LEU A 106      12.305  21.692  12.484  1.00 23.08           O
ATOM   4864  N   PRO A 107      10.719  20.441  11.524  1.00 23.01           N
ATOM   4865  CA  PRO A 107      11.221  19.229  12.105  1.00 21.52           C
ATOM   4867  CB  PRO A 107       9.976  18.354  12.238  1.00 21.18           C
ATOM   4870  CG  PRO A 107       9.005  18.884  11.261  1.00 24.05           C
ATOM   4873  CD  PRO A 107       9.438  20.241  10.824  1.00 23.47           C
ATOM   4876  C   PRO A 107      12.160  18.624  11.123  1.00 20.29           C
ATOM   4877  O   PRO A 107      12.350  19.163  10.011  1.00 19.85           O
ATOM   4878  N   ASP A 108      12.616  17.430  11.450  1.00 19.68           N
ATOM   4879  CA  ASP A 108      13.500  16.725  10.564  1.00 19.49           C
ATOM   4881  CB  ASP A 108      14.489  16.014  11.446  1.00 19.69           C
ATOM   4884  CG  ASP A 108      15.403  16.964  12.116  1.00 19.29           C
ATOM   4885  OD1 ASP A 108      15.795  18.026  11.495  1.00 18.08           O
ATOM   4886  OD2 ASP A 108      15.687  16.644  13.284  1.00 14.86           O
ATOM   4887  C   ASP A 108      12.965  15.691   9.621  1.00 18.52           C
ATOM   4888  O   ASP A 108      13.547  15.523   8.551  1.00 17.83           O
ATOM   4890  N   LEU A 109      11.916  14.961  10.082  1.00 19.44           N
ATOM   4891  CA  LEU A 109      11.272  13.891   9.386  1.00 18.77           C
ATOM   4893  CB  LEU A 109      11.781  12.534   9.873  1.00 18.44           C
ATOM   4896  CG  LEU A 109      13.263  12.120   9.679  1.00 17.95           C
ATOM   4898  CD1 LEU A 109      13.491  10.795  10.239  1.00 25.66           C
ATOM   4902  CD2 LEU A 109      13.695  12.110   8.230  1.00 14.62           C
ATOM   4906  C   LEU A 109       9.753  13.971   9.602  1.00 18.72           C
ATOM   4907  O   LEU A 109       9.298  14.650  10.518  1.00 18.75           O
ATOM   4909  N   TYR A 110       9.031  13.346   8.690  1.00 19.56           N
ATOM   4910  CA  TYR A 110       7.621  12.948   8.872  1.00 20.42           C
ATOM   4912  CB  TYR A 110       6.705  13.767   7.964  1.00 21.85           C
ATOM   4915  CG  TYR A 110       5.235  13.432   8.170  1.00 22.08           C
ATOM   4916  CD1 TYR A 110       4.529  13.962   9.272  1.00 23.99           C
ATOM   4918  CE1 TYR A 110       3.191  13.642   9.493  1.00 24.06           C
ATOM   4920  CZ  TYR A 110       2.550  12.774   8.601  1.00 22.57           C
ATOM   4921  OH  TYR A 110       1.234  12.512   8.805  1.00 25.86           O
ATOM   4923  CE2 TYR A 110       3.203  12.255   7.526  1.00 24.34           C
ATOM   4925  CD2 TYR A 110       4.587  12.576   7.316  1.00 17.59           C
ATOM   4927  C   TYR A 110       7.435  11.452   8.629  1.00 21.88           C
ATOM   4928  O   TYR A 110       7.881  10.892   7.643  1.00 24.70           O
ATOM   4930  N   ASP A 111       6.771  10.823   9.571  1.00 22.57           N
ATOM   4931  CA  ASP A 111       6.555   9.412   9.647  1.00 24.85           C
ATOM   4933  CB  ASP A 111       6.730   8.999  11.109  1.00 22.59           C
ATOM   4936  CG  ASP A 111       6.476   7.507  11.343  1.00 28.35           C
ATOM   4937  OD1 ASP A 111       5.940   6.820  10.436  1.00 29.11           O
ATOM   4938  OD2 ASP A 111       6.872   7.017  12.428  1.00 25.75           O
ATOM   4939  C   ASP A 111       5.108   9.171   9.176  1.00 25.94           C
ATOM   4940  O   ASP A 111       4.141   9.533   9.872  1.00 24.93           O
ATOM   4942  N   TYR A 112       4.973   8.699   7.958  1.00 29.67           N
ATOM   4943  CA  TYR A 112       3.642   8.476   7.400  1.00 32.79           C
ATOM   4945  CB  TYR A 112       3.649   8.215   5.880  1.00 33.41           C
ATOM   4948  CG  TYR A 112       3.973   9.441   5.010  1.00 33.52           C
ATOM   4949  CD1 TYR A 112       3.015  10.366   4.627  1.00 34.66           C
```

FIG. 5O

```
ATOM   4951  CE1  TYR A 112       3.373  11.469   3.804  1.00 34.31           C
ATOM   4953  CZ   TYR A 112       4.717  11.591   3.438  1.00 36.36           C
ATOM   4954  OH   TYR A 112       5.277  12.534   2.633  1.00 34.77           O
ATOM   4956  CE2  TYR A 112       5.614  10.664   3.838  1.00 36.92           C
ATOM   4958  CD2  TYR A 112       5.233   9.617   4.572  1.00 33.66           C
ATOM   4960  C    TYR A 112       2.997   7.280   8.083  1.00 35.76           C
ATOM   4961  O    TYR A 112       1.817   7.103   7.925  1.00 36.77           O
ATOM   4963  N    LYS A 113       3.751   6.414   8.778  1.00 37.26           N
ATOM   4964  CA   LYS A 113       3.103   5.277   9.437  1.00 38.17           C
ATOM   4966  CB   LYS A 113       4.066   4.140   9.704  1.00 38.53           C
ATOM   4969  CG   LYS A 113       3.447   2.932  10.408  1.00 41.42           C
ATOM   4972  CD   LYS A 113       4.520   2.151  11.195  1.00 44.74           C
ATOM   4975  CE   LYS A 113       3.970   0.799  11.740  1.00 48.17           C
ATOM   4978  NZ   LYS A 113       3.745  -0.277  10.637  1.00 46.49           N
ATOM   4982  C    LYS A 113       2.469   5.769  10.707  1.00 38.53           C
ATOM   4983  O    LYS A 113       1.315   5.465  10.998  1.00 40.27           O
ATOM   4985  N    GLU A 114       3.184   6.568  11.471  1.00 37.48           N
ATOM   4986  CA   GLU A 114       2.637   7.026  12.734  1.00 36.27           C
ATOM   4988  CB   GLU A 114       3.759   7.201  13.732  1.00 36.48           C
ATOM   4991  CG   GLU A 114       4.431   5.914  14.134  1.00 39.44           C
ATOM   4994  CD   GLU A 114       3.696   5.136  15.241  1.00 43.74           C
ATOM   4995  OE1  GLU A 114       2.798   5.703  15.895  1.00 44.63           O
ATOM   4996  OE2  GLU A 114       4.043   3.945  15.446  1.00 47.49           O
ATOM   4997  C    GLU A 114       1.867   8.316  12.578  1.00 34.69           C
ATOM   4998  O    GLU A 114       1.199   8.758  13.478  1.00 33.45           O
ATOM   5000  N    ASN A 115       1.982   8.929  11.414  1.00 34.33           N
ATOM   5001  CA   ASN A 115       1.404  10.244  11.156  1.00 33.81           C
ATOM   5003  CB   ASN A 115      -0.107  10.163  10.908  1.00 35.90           C
ATOM   5006  CG   ASN A 115      -0.405   9.640   9.501  1.00 39.18           C
ATOM   5007  OD1  ASN A 115      -0.881   8.528   9.395  1.00 42.57           O
ATOM   5008  ND2  ASN A 115      -0.020  10.405   8.408  1.00 37.31           N
ATOM   5011  C    ASN A 115       1.821  11.294  12.163  1.00 31.77           C
ATOM   5012  O    ASN A 115       0.995  11.947  12.814  1.00 30.79           O
ATOM   5014  N    ARG A 116       3.154  11.515  12.199  1.00 29.00           N
ATOM   5015  CA   ARG A 116       3.729  12.517  13.060  1.00 26.39           C
ATOM   5017  CB   ARG A 116       3.853  11.991  14.457  1.00 27.63           C
ATOM   5020  CG   ARG A 116       4.810  10.866  14.648  1.00 28.83           C
ATOM   5023  CD   ARG A 116       4.485  10.128  15.957  1.00 29.50           C
ATOM   5026  NE   ARG A 116       5.452   9.033  16.179  1.00 31.02           N
ATOM   5028  CZ   ARG A 116       5.386   8.136  17.181  1.00 33.08           C
ATOM   5029  NH1  ARG A 116       4.393   8.174  18.064  1.00 34.43           N
ATOM   5032  NH2  ARG A 116       6.335   7.195  17.322  1.00 29.98           N
ATOM   5035  C    ARG A 116       5.085  12.974  12.582  1.00 24.57           C
ATOM   5036  O    ARG A 116       5.819  12.227  11.942  1.00 22.78           O
ATOM   5038  N    PHE A 117       5.385  14.218  12.898  1.00 22.64           N
ATOM   5039  CA   PHE A 117       6.705  14.750  12.590  1.00 22.98           C
ATOM   5041  CB   PHE A 117       6.659  16.257  12.563  1.00 21.78           C
ATOM   5044  CG   PHE A 117       5.946  16.794  11.385  1.00 22.84           C
ATOM   5045  CD1  PHE A 117       6.548  16.822  10.186  1.00 20.76           C
ATOM   5047  CE1  PHE A 117       5.860  17.320   9.030  1.00 21.40           C
ATOM   5049  CZ   PHE A 117       4.564  17.707   9.145  1.00 23.52           C
ATOM   5051  CE2  PHE A 117       3.927  17.649  10.412  1.00 22.69           C
ATOM   5053  CD2  PHE A 117       4.618  17.224  11.502  1.00 20.29           C
ATOM   5055  C    PHE A 117       7.665  14.267  13.661  1.00 22.43           C
ATOM   5056  O    PHE A 117       7.226  13.905  14.783  1.00 23.34           O
ATOM   5058  N    ILE A 118       8.960  14.280  13.320  1.00 22.57           N
ATOM   5059  CA   ILE A 118      10.012  13.863  14.258  1.00 21.68           C
ATOM   5061  CB   ILE A 118      10.638  12.501  13.857  1.00 22.40           C
ATOM   5063  CG1  ILE A 118       9.600  11.453  13.660  1.00 24.98           C
ATOM   5066  CD1  ILE A 118      10.183  10.160  13.058  1.00 23.03           C
ATOM   5070  CG2  ILE A 118      11.684  12.014  14.939  1.00 21.73           C
ATOM   5074  C    ILE A 118      11.096  14.882  14.188  1.00 20.97           C
ATOM   5075  O    ILE A 118      11.529  15.308  13.074  1.00 20.64           O
```

FIG. 5P

```
ATOM   5077  N   GLU A 119      11.562  15.230  15.386  1.00 20.99           N
ATOM   5078  CA  GLU A 119      12.715  16.021  15.620  1.00 20.79           C
ATOM   5080  CB  GLU A 119      12.433  17.127  16.674  1.00 20.86           C
ATOM   5083  CG  GLU A 119      13.679  17.989  17.035  1.00 23.81           C
ATOM   5086  CD  GLU A 119      14.379  18.631  15.829  1.00 28.19           C
ATOM   5087  OE1 GLU A 119      13.661  19.191  14.981  1.00 28.89           O
ATOM   5088  OE2 GLU A 119      15.637  18.571  15.732  1.00 31.88           O
ATOM   5089  C   GLU A 119      13.807  15.104  16.131  1.00 21.33           C
ATOM   5090  O   GLU A 119      13.647  14.420  17.143  1.00 22.44           O
ATOM   5092  N   ILE A 120      14.901  15.049  15.379  1.00 21.35           N
ATOM   5093  CA  ILE A 120      16.000  14.171  15.679  1.00 19.98           C
ATOM   5095  CB  ILE A 120      16.636  13.623  14.409  1.00 21.39           C
ATOM   5097  CG1 ILE A 120      15.683  12.670  13.677  1.00 20.96           C
ATOM   5100  CD1 ILE A 120      15.279  11.486  14.397  1.00 26.55           C
ATOM   5104  CG2 ILE A 120      17.943  12.912  14.706  1.00 20.43           C
ATOM   5108  C   ILE A 120      17.012  15.012  16.354  1.00 20.11           C
ATOM   5109  O   ILE A 120      17.336  16.107  15.887  1.00 19.50           O
ATOM   5111  N   GLY A 121      17.556  14.527  17.454  1.00 20.99           N
ATOM   5112  CA  GLY A 121      18.675  15.210  18.076  1.00 20.91           C
ATOM   5115  C   GLY A 121      19.884  14.315  18.144  1.00 20.94           C
ATOM   5116  O   GLY A 121      19.739  13.120  18.384  1.00 20.56           O
ATOM   5118  N   VAL A 122      21.074  14.880  17.934  1.00 21.69           N
ATOM   5119  CA  VAL A 122      22.308  14.072  18.065  1.00 23.58           C
ATOM   5121  CB  VAL A 122      23.055  13.779  16.772  1.00 25.29           C
ATOM   5123  CG1 VAL A 122      24.420  13.036  17.114  1.00 23.52           C
ATOM   5127  CG2 VAL A 122      22.312  12.875  15.858  1.00 22.13           C
ATOM   5131  C   VAL A 122      23.236  14.871  19.017  1.00 23.55           C
ATOM   5132  O   VAL A 122      23.485  16.010  18.792  1.00 22.71           O
ATOM   5134  N   THR A 123      23.536  14.268  20.154  1.00 24.16           N
ATOM   5135  CA  THR A 123      24.111  14.971  21.284  1.00 26.23           C
ATOM   5137  CB  THR A 123      23.125  15.206  22.463  1.00 25.44           C
ATOM   5139  OG1 THR A 123      23.761  16.103  23.393  1.00 25.14           O
ATOM   5141  CG2 THR A 123      22.757  13.968  23.147  1.00 26.59           C
ATOM   5145  C   THR A 123      25.359  14.317  21.863  1.00 27.75           C
ATOM   5146  O   THR A 123      25.461  13.086  21.927  1.00 27.75           O
ATOM   5148  N   ARG A 124      26.285  15.191  22.238  1.00 30.85           N
ATOM   5149  CA  ARG A 124      27.501  14.861  22.983  1.00 32.89           C
ATOM   5151  CB  ARG A 124      28.606  15.773  22.454  1.00 33.22           C
ATOM   5154  CG  ARG A 124      28.831  15.761  20.939  1.00 35.45           C
ATOM   5157  CD  ARG A 124      29.434  17.052  20.435  1.00 37.68           C
ATOM   5160  NE  ARG A 124      28.434  17.724  19.671  1.00 38.87           N
ATOM   5162  CZ  ARG A 124      28.509  18.929  19.134  1.00 37.32           C
ATOM   5163  NH1 ARG A 124      29.571  19.738  19.271  1.00 36.52           N
ATOM   5166  NH2 ARG A 124      27.455  19.316  18.457  1.00 34.67           N
ATOM   5169  C   ARG A 124      27.324  15.188  24.485  1.00 34.45           C
ATOM   5170  O   ARG A 124      28.273  15.086  25.231  1.00 35.66           O
ATOM   5172  N   ARG A 125      26.178  15.752  24.870  1.00 35.36           N
ATOM   5173  CA  ARG A 125      25.840  16.009  26.273  1.00 35.64           C
ATOM   5175  CB  ARG A 125      25.160  17.381  26.433  1.00 35.56           C
ATOM   5178  CG  ARG A 125      26.059  18.578  26.306  1.00 35.38           C
ATOM   5181  CD  ARG A 125      25.271  19.859  26.363  1.00 37.73           C
ATOM   5184  NE  ARG A 125      24.263  19.915  25.294  1.00 38.35           N
ATOM   5186  CZ  ARG A 125      23.242  20.769  25.208  1.00 42.26           C
ATOM   5187  NH1 ARG A 125      23.032  21.704  26.127  1.00 42.33           N
ATOM   5190  NH2 ARG A 125      22.415  20.687  24.160  1.00 43.26           N
ATOM   5193  C   ARG A 125      24.908  14.935  26.790  1.00 35.73           C
ATOM   5194  O   ARG A 125      24.482  14.009  26.070  1.00 36.31           O
ATOM   5196  N   GLU A 126      24.582  15.027  28.065  1.00 36.52           N
ATOM   5197  CA  GLU A 126      23.645  14.080  28.655  1.00 36.81           C
ATOM   5199  CB  GLU A 126      23.424  14.460  30.138  1.00 37.31           C
ATOM   5202  CG  GLU A 126      23.034  13.241  30.999  1.00 39.80           C
ATOM   5205  CD  GLU A 126      21.622  12.866  30.788  1.00 35.83           C
ATOM   5206  OE1 GLU A 126      20.868  13.816  30.553  1.00 41.69           O
```

FIG. 5Q

```
ATOM   5207  OE2 GLU A 126      21.265  11.686  30.835  1.00 33.68           O
ATOM   5208  C   GLU A 126      22.324  14.036  27.814  1.00 35.45           C
ATOM   5209  O   GLU A 126      21.724  15.068  27.511  1.00 35.89           O
ATOM   5211  N   VAL A 127      21.877  12.837  27.463  1.00 35.07           N
ATOM   5212  CA  VAL A 127      20.745  12.630  26.561  1.00 33.41           C
ATOM   5214  CB  VAL A 127      20.515  11.111  26.306  1.00 34.98           C
ATOM   5216  CG1 VAL A 127      19.572  10.410  27.370  1.00 30.93           C
ATOM   5220  CG2 VAL A 127      20.028  10.851  24.856  1.00 33.48           C
ATOM   5224  C   VAL A 127      19.436  13.337  26.962  1.00 34.24           C
ATOM   5225  O   VAL A 127      18.696  13.779  26.070  1.00 32.79           O
ATOM   5227  N   HIS A 128      19.142  13.469  28.266  1.00 32.85           N
ATOM   5228  CA  HIS A 128      17.899  14.203  28.675  1.00 33.05           C
ATOM   5230  CB  HIS A 128      17.558  14.043  30.177  1.00 32.76           C
ATOM   5233  CG  HIS A 128      17.185  12.655  30.563  1.00 31.31           C
ATOM   5234  ND1 HIS A 128      18.122  11.702  30.874  1.00 36.05           N
ATOM   5236  CE1 HIS A 128      17.510  10.567  31.143  1.00 37.04           C
ATOM   5238  NE2 HIS A 128      16.208  10.756  31.022  1.00 35.99           N
ATOM   5240  CD2 HIS A 128      15.984  12.045  30.628  1.00 35.98           C
ATOM   5242  C   HIS A 128      17.974  15.689  28.375  1.00 32.21           C
ATOM   5243  O   HIS A 128      16.969  16.273  28.175  1.00 32.13           O
ATOM   5245  N   ILE A 129      19.163  16.279  28.352  1.00 32.38           N
ATOM   5246  CA  ILE A 129      19.314  17.721  28.164  1.00 33.03           C
ATOM   5248  CB  ILE A 129      20.796  18.156  28.389  1.00 34.00           C
ATOM   5250  CG1 ILE A 129      21.149  18.025  29.884  1.00 33.95           C
ATOM   5253  CD1 ILE A 129      22.553  18.290  30.237  1.00 34.74           C
ATOM   5257  CG2 ILE A 129      21.100  19.562  27.866  1.00 32.34           C
ATOM   5261  C   ILE A 129      18.798  18.161  26.802  1.00 33.61           C
ATOM   5262  O   ILE A 129      17.950  19.077  26.675  1.00 34.12           O
ATOM   5264  N   TYR A 130      19.220  17.455  25.771  1.00 32.85           N
ATOM   5265  CA  TYR A 130      18.885  17.883  24.457  1.00 32.65           C
ATOM   5267  CB  TYR A 130      19.769  17.159  23.431  1.00 34.68           C
ATOM   5270  CG  TYR A 130      19.979  17.920  22.150  1.00 37.22           C
ATOM   5271  CD1 TYR A 130      20.188  19.300  22.136  1.00 44.34           C
ATOM   5273  CE1 TYR A 130      20.382  19.981  20.918  1.00 46.32           C
ATOM   5275  CZ  TYR A 130      20.373  19.237  19.717  1.00 43.87           C
ATOM   5276  OH  TYR A 130      20.526  19.808  18.456  1.00 44.04           O
ATOM   5278  CE2 TYR A 130      20.184  17.922  19.764  1.00 42.09           C
ATOM   5280  CD2 TYR A 130      19.976  17.269  20.960  1.00 41.85           C
ATOM   5282  C   TYR A 130      17.414  17.620  24.242  1.00 31.94           C
ATOM   5283  O   TYR A 130      16.733  18.382  23.535  1.00 28.25           O
ATOM   5285  N   TYR A 131      16.913  16.588  24.942  1.00 30.99           N
ATOM   5286  CA  TYR A 131      15.552  16.181  24.782  1.00 31.03           C
ATOM   5288  CB  TYR A 131      15.210  14.896  25.581  1.00 30.32           C
ATOM   5291  CG  TYR A 131      13.724  14.596  25.493  1.00 30.23           C
ATOM   5292  CD1 TYR A 131      13.237  13.728  24.542  1.00 30.44           C
ATOM   5294  CE1 TYR A 131      11.914  13.511  24.390  1.00 35.11           C
ATOM   5296  CZ  TYR A 131      10.999  14.141  25.202  1.00 37.00           C
ATOM   5297  OH  TYR A 131       9.662  13.845  25.026  1.00 42.43           O
ATOM   5299  CE2 TYR A 131      11.424  15.008  26.175  1.00 32.98           C
ATOM   5301  CD2 TYR A 131      12.794  15.241  26.315  1.00 34.17           C
ATOM   5303  C   TYR A 131      14.747  17.354  25.292  1.00 30.93           C
ATOM   5304  O   TYR A 131      13.775  17.730  24.714  1.00 31.34           O
ATOM   5306  N   LEU A 132      15.197  17.935  26.395  1.00 32.82           N
ATOM   5307  CA  LEU A 132      14.443  18.962  27.097  1.00 32.46           C
ATOM   5309  CB  LEU A 132      14.950  19.076  28.544  1.00 32.00           C
ATOM   5312  CG  LEU A 132      14.423  18.024  29.520  1.00 31.87           C
ATOM   5314  CD1 LEU A 132      15.403  17.900  30.669  1.00 27.92           C
ATOM   5318  CD2 LEU A 132      12.966  18.327  30.013  1.00 31.96           C
ATOM   5322  C   LEU A 132      14.516  20.314  26.388  1.00 33.12           C
ATOM   5323  O   LEU A 132      13.491  21.014  26.271  1.00 32.87           O
ATOM   5325  N   GLU A 133      15.691  20.675  25.880  1.00 34.26           N
ATOM   5326  CA  GLU A 133      15.813  21.873  24.990  1.00 35.13           C
ATOM   5328  CB  GLU A 133      17.220  22.011  24.434  1.00 35.77           C
```

FIG. 5R

| | | | | | | | | | |
|---|---|---|---|---|---|---|---|---|---|
| ATOM | 5331 | CG | GLU | A | 133 | 18.329 | 22.032 | 25.512 | 1.00 38.71 | C |
| ATOM | 5334 | CD | GLU | A | 133 | 19.701 | 22.450 | 24.973 | 1.00 42.35 | C |
| ATOM | 5335 | OE1 | GLU | A | 133 | 20.114 | 22.044 | 23.851 | 1.00 46.63 | O |
| ATOM | 5336 | OE2 | GLU | A | 133 | 20.396 | 23.179 | 25.689 | 1.00 41.91 | O |
| ATOM | 5337 | C | GLU | A | 133 | 14.853 | 21.791 | 23.796 | 1.00 35.24 | C |
| ATOM | 5338 | O | GLU | A | 133 | 14.162 | 22.736 | 23.477 | 1.00 34.78 | O |
| ATOM | 5340 | N | LYS | A | 134 | 14.811 | 20.633 | 23.150 | 1.00 36.33 | N |
| ATOM | 5341 | CA | LYS | A | 134 | 13.904 | 20.433 | 22.050 | 1.00 36.65 | C |
| ATOM | 5343 | CB | LYS | A | 134 | 14.105 | 19.081 | 21.371 | 1.00 37.06 | C |
| ATOM | 5346 | CG | LYS | A | 134 | 15.492 | 18.851 | 20.740 | 1.00 38.38 | C |
| ATOM | 5349 | CD | LYS | A | 134 | 15.709 | 19.662 | 19.463 | 1.00 38.57 | C |
| ATOM | 5352 | CE | LYS | A | 134 | 17.012 | 19.227 | 18.717 | 1.00 36.39 | C |
| ATOM | 5355 | NZ | LYS | A | 134 | 17.241 | 20.091 | 17.562 | 1.00 34.31 | N |
| ATOM | 5359 | C | LYS | A | 134 | 12.491 | 20.533 | 22.543 | 1.00 37.39 | C |
| ATOM | 5360 | O | LYS | A | 134 | 11.732 | 21.289 | 21.960 | 1.00 37.59 | O |
| ATOM | 5362 | N | ALA | A | 135 | 12.130 | 19.775 | 23.594 | 1.00 37.71 | N |
| ATOM | 5363 | CA | ALA | A | 135 | 10.733 | 19.804 | 24.080 | 1.00 39.89 | C |
| ATOM | 5365 | CB | ALA | A | 135 | 10.451 | 18.788 | 25.239 | 1.00 38.29 | C |
| ATOM | 5369 | C | ALA | A | 135 | 10.374 | 21.194 | 24.538 | 1.00 41.41 | C |
| ATOM | 5370 | O | ALA | A | 135 | 9.273 | 21.627 | 24.347 | 1.00 41.30 | O |
| ATOM | 5372 | N | ASN | A | 136 | 11.300 | 21.896 | 25.158 | 1.00 45.15 | N |
| ATOM | 5373 | CA | ASN | A | 136 | 10.964 | 23.237 | 25.514 | 1.00 48.79 | C |
| ATOM | 5375 | CB | ASN | A | 136 | 11.907 | 23.813 | 26.550 | 1.00 49.28 | C |
| ATOM | 5378 | CG | ASN | A | 136 | 11.394 | 25.138 | 27.082 | 1.00 52.63 | C |
| ATOM | 5379 | OD1 | ASN | A | 136 | 11.519 | 26.154 | 26.396 | 1.00 55.30 | O |
| ATOM | 5380 | ND2 | ASN | A | 136 | 10.767 | 25.131 | 28.286 | 1.00 53.15 | N |
| ATOM | 5383 | C | ASN | A | 136 | 10.881 | 24.124 | 24.265 | 1.00 51.27 | C |
| ATOM | 5384 | O | ASN | A | 136 | 9.877 | 24.796 | 24.077 | 1.00 51.97 | O |
| ATOM | 5386 | N | LYS | A | 137 | 11.904 | 24.090 | 23.403 | 1.00 54.54 | N |
| ATOM | 5387 | CA | LYS | A | 137 | 11.915 | 24.940 | 22.197 | 1.00 56.62 | C |
| ATOM | 5389 | CB | LYS | A | 137 | 13.105 | 24.672 | 21.271 | 1.00 56.82 | C |
| ATOM | 5392 | CG | LYS | A | 137 | 12.842 | 25.253 | 19.864 | 1.00 57.48 | C |
| ATOM | 5395 | CD | LYS | A | 137 | 14.030 | 25.240 | 18.949 | 1.00 59.50 | C |
| ATOM | 5398 | CE | LYS | A | 137 | 13.750 | 26.048 | 17.679 | 1.00 60.50 | C |
| ATOM | 5401 | NZ | LYS | A | 137 | 13.229 | 27.441 | 17.992 | 1.00 60.93 | N |
| ATOM | 5405 | C | LYS | A | 137 | 10.637 | 24.740 | 21.416 | 1.00 58.12 | C |
| ATOM | 5406 | O | LYS | A | 137 | 9.942 | 25.701 | 21.138 | 1.00 59.00 | O |
| ATOM | 5408 | N | ILE | A | 138 | 10.348 | 23.498 | 21.031 | 1.00 60.12 | N |
| ATOM | 5409 | CA | ILE | A | 138 | 9.099 | 23.224 | 20.328 | 1.00 61.65 | C |
| ATOM | 5411 | CB | ILE | A | 138 | 9.139 | 21.967 | 19.338 | 1.00 61.70 | C |
| ATOM | 5413 | CG1 | ILE | A | 138 | 9.009 | 20.611 | 20.060 | 1.00 61.14 | C |
| ATOM | 5416 | CD1 | ILE | A | 138 | 7.583 | 20.106 | 20.169 | 1.00 59.21 | C |
| ATOM | 5420 | CG2 | ILE | A | 138 | 10.376 | 22.005 | 18.459 | 1.00 61.29 | C |
| ATOM | 5424 | C | ILE | A | 138 | 8.089 | 23.021 | 21.402 | 1.00 63.14 | C |
| ATOM | 5425 | O | ILE | A | 138 | 8.441 | 22.845 | 22.559 | 1.00 64.78 | O |
| ATOM | 5460 | N | GLU | A | 141 | 3.876 | 19.557 | 21.554 | 1.00 59.21 | N |
| ATOM | 5461 | CA | GLU | A | 141 | 3.782 | 18.176 | 21.160 | 1.00 57.45 | C |
| ATOM | 5463 | CB | GLU | A | 141 | 3.028 | 17.314 | 22.216 | 1.00 57.96 | C |
| ATOM | 5466 | CG | GLU | A | 141 | 1.473 | 17.202 | 22.034 | 1.00 59.82 | C |
| ATOM | 5469 | CD | GLU | A | 141 | 0.681 | 17.478 | 23.312 | 1.00 63.12 | C |
| ATOM | 5470 | OE1 | GLU | A | 141 | -0.228 | 16.672 | 23.606 | 1.00 64.80 | O |
| ATOM | 5471 | OE2 | GLU | A | 141 | 0.957 | 18.492 | 24.013 | 1.00 64.58 | O |
| ATOM | 5472 | C | GLU | A | 141 | 3.181 | 18.029 | 19.770 | 1.00 54.78 | C |
| ATOM | 5473 | O | GLU | A | 141 | 3.192 | 18.958 | 18.942 | 1.00 54.77 | O |
| ATOM | 5475 | N | LYS | A | 142 | 2.667 | 16.826 | 19.544 | 1.00 50.93 | N |
| ATOM | 5476 | CA | LYS | A | 142 | 2.484 | 16.289 | 18.244 | 1.00 48.09 | C |
| ATOM | 5478 | CB | LYS | A | 142 | 1.578 | 17.164 | 17.381 | 1.00 48.08 | C |
| ATOM | 5481 | CG | LYS | A | 142 | 0.237 | 17.433 | 18.087 | 1.00 50.33 | C |
| ATOM | 5484 | CD | LYS | A | 142 | -0.578 | 16.144 | 18.293 | 1.00 53.05 | C |
| ATOM | 5487 | CE | LYS | A | 142 | -2.094 | 16.429 | 18.369 | 1.00 55.73 | C |
| ATOM | 5490 | NZ | LYS | A | 142 | -2.617 | 16.712 | 19.746 | 1.00 56.54 | N |
| ATOM | 5494 | C | LYS | A | 142 | 3.887 | 15.996 | 17.697 | 1.00 43.19 | C |
| ATOM | 5495 | O | LYS | A | 142 | 4.136 | 14.868 | 17.407 | 1.00 43.47 | O |

FIG. 5S

```
ATOM   5497  N    THR A 143       4.816  16.943  17.652  1.00 39.10           N
ATOM   5498  CA   THR A 143       6.159  16.569  17.163  1.00 35.58           C
ATOM   5500  CB   THR A 143       7.045  17.742  16.865  1.00 35.34           C
ATOM   5502  OG1  THR A 143       6.364  18.615  15.975  1.00 34.89           O
ATOM   5504  CG2  THR A 143       8.424  17.267  16.225  1.00 33.54           C
ATOM   5508  C    THR A 143       6.856  15.617  18.128  1.00 32.81           C
ATOM   5509  O    THR A 143       7.194  15.973  19.256  1.00 32.08           O
ATOM   5511  N    HIS A 144       7.104  14.412  17.646  1.00 30.83           N
ATOM   5512  CA   HIS A 144       7.873  13.396  18.380  1.00 29.52           C
ATOM   5514  CB   HIS A 144       7.661  12.082  17.674  1.00 28.83           C
ATOM   5517  CG   HIS A 144       7.736  10.904  18.577  1.00 29.31           C
ATOM   5518  ND1  HIS A 144       6.681  10.521  19.389  1.00 26.72           N
ATOM   5520  CE1  HIS A 144       7.032   9.446  20.061  1.00 30.35           C
ATOM   5522  NE2  HIS A 144       8.263   9.116  19.708  1.00 32.52           N
ATOM   5524  CD2  HIS A 144       8.714  10.005  18.771  1.00 29.00           C
ATOM   5526  C    HIS A 144       9.381  13.696  18.436  1.00 28.96           C
ATOM   5527  O    HIS A 144       9.951  14.079  17.444  1.00 30.10           O
ATOM   5529  N    ILE A 145      10.034  13.539  19.584  1.00 27.20           N
ATOM   5530  CA   ILE A 145      11.453  13.833  19.700  1.00 25.64           C
ATOM   5532  CB   ILE A 145      11.755  14.734  20.888  1.00 26.53           C
ATOM   5534  CG1  ILE A 145      11.049  16.080  20.720  1.00 28.31           C
ATOM   5537  CD1  ILE A 145      10.803  16.793  22.041  1.00 29.05           C
ATOM   5541  CG2  ILE A 145      13.254  14.968  21.086  1.00 21.92           C
ATOM   5545  C    ILE A 145      12.197  12.521  19.866  1.00 26.87           C
ATOM   5546  O    ILE A 145      11.795  11.665  20.685  1.00 28.32           O
ATOM   5548  N    HIS A 146      13.294  12.336  19.127  1.00 24.40           N
ATOM   5549  CA   HIS A 146      14.166  11.171  19.313  1.00 23.21           C
ATOM   5551  CB   HIS A 146      13.917  10.157  18.188  1.00 23.84           C
ATOM   5554  CG   HIS A 146      14.520   8.782  18.403  1.00 21.72           C
ATOM   5555  ND1  HIS A 146      14.045   7.666  17.746  1.00 24.44           N
ATOM   5557  CE1  HIS A 146      14.742   6.607  18.102  1.00 25.79           C
ATOM   5559  NE2  HIS A 146      15.694   6.993  18.941  1.00 26.04           N
ATOM   5561  CD2  HIS A 146      15.575   8.350  19.141  1.00 27.26           C
ATOM   5563  C    HIS A 146      15.595  11.668  19.301  1.00 23.84           C
ATOM   5564  O    HIS A 146      16.060  12.294  18.290  1.00 21.67           O
ATOM   5566  N    ILE A 147      16.280  11.437  20.427  1.00 23.11           N
ATOM   5567  CA   ILE A 147      17.584  11.931  20.679  1.00 22.94           C
ATOM   5569  CB   ILE A 147      17.690  12.630  22.000  1.00 22.97           C
ATOM   5571  CG1  ILE A 147      16.688  13.772  22.162  1.00 22.95           C
ATOM   5574  CD1  ILE A 147      16.835  14.950  21.198  1.00 21.64           C
ATOM   5578  CG2  ILE A 147      19.164  13.019  22.253  1.00 20.59           C
ATOM   5582  C    ILE A 147      18.546  10.755  20.752  1.00 25.00           C
ATOM   5583  O    ILE A 147      18.223   9.719  21.373  1.00 26.02           O
ATOM   5585  N    PHE A 148      19.704  10.886  20.127  1.00 24.41           N
ATOM   5586  CA   PHE A 148      20.727   9.841  20.143  1.00 26.58           C
ATOM   5588  CB   PHE A 148      21.107   9.331  18.768  1.00 25.84           C
ATOM   5591  CG   PHE A 148      20.027   8.628  18.052  1.00 24.60           C
ATOM   5592  CD1  PHE A 148      19.916   7.252  18.128  1.00 25.26           C
ATOM   5594  CE1  PHE A 148      18.912   6.544  17.449  1.00 24.20           C
ATOM   5596  CZ   PHE A 148      18.014   7.212  16.690  1.00 26.92           C
ATOM   5598  CE2  PHE A 148      18.104   8.616  16.601  1.00 25.66           C
ATOM   5600  CD2  PHE A 148      19.109   9.310  17.305  1.00 23.77           C
ATOM   5602  C    PHE A 148      21.965  10.524  20.679  1.00 27.81           C
ATOM   5603  O    PHE A 148      22.230  11.650  20.326  1.00 27.99           O
ATOM   5605  N    SER A 149      22.701   9.870  21.562  1.00 28.62           N
ATOM   5606  CA   SER A 149      23.991  10.413  21.944  1.00 30.88           C
ATOM   5608  CB   SER A 149      24.177  10.469  23.452  1.00 31.17           C
ATOM   5611  OG   SER A 149      24.505   9.186  23.871  1.00 34.53           O
ATOM   5613  C    SER A 149      25.101   9.570  21.377  1.00 31.23           C
ATOM   5614  O    SER A 149      24.887   8.434  20.985  1.00 33.07           O
ATOM   5616  N    PHE A 150      26.286  10.138  21.365  1.00 32.55           N
ATOM   5617  CA   PHE A 150      27.466   9.400  20.978  1.00 34.57           C
ATOM   5619  CB   PHE A 150      28.663  10.325  20.745  1.00 33.55           C
```

FIG. 5T

```
ATOM   5622  CG   PHE A 150      28.524  11.219  19.550  1.00 31.30           C
ATOM   5623  CD1  PHE A 150      27.896  12.435  19.667  1.00 28.52           C
ATOM   5625  CE1  PHE A 150      27.790  13.275  18.600  1.00 29.60           C
ATOM   5627  CZ   PHE A 150      28.285  12.888  17.354  1.00 33.22           C
ATOM   5629  CE2  PHE A 150      28.932  11.662  17.214  1.00 29.70           C
ATOM   5631  CD2  PHE A 150      29.033  10.843  18.297  1.00 31.31           C
ATOM   5633  C    PHE A 150      27.814   8.317  22.005  1.00 37.59           C
ATOM   5634  O    PHE A 150      28.628   7.464  21.697  1.00 38.78           O
ATOM   5636  N    THR A 151      27.187   8.310  23.189  1.00 39.50           N
ATOM   5637  CA   THR A 151      27.470   7.257  24.166  1.00 41.17           C
ATOM   5639  CB   THR A 151      27.163   7.680  25.603  1.00 42.21           C
ATOM   5641  OG1  THR A 151      25.735   7.694  25.763  1.00 44.81           O
ATOM   5643  CG2  THR A 151      27.744   9.026  25.920  1.00 42.12           C
ATOM   5647  C    THR A 151      26.594   6.049  23.950  1.00 41.24           C
ATOM   5648  O    THR A 151      26.752   5.071  24.655  1.00 43.10           O
ATOM   5650  N    GLY A 152      25.635   6.113  23.029  1.00 39.78           N
ATOM   5651  CA   GLY A 152      24.809   4.965  22.707  1.00 37.64           C
ATOM   5654  C    GLY A 152      23.445   5.034  23.337  1.00 36.58           C
ATOM   5655  O    GLY A 152      22.608   4.175  23.113  1.00 37.39           O
ATOM   5657  N    GLU A 153      23.217   6.038  24.155  1.00 35.57           N
ATOM   5658  CA   GLU A 153      21.942   6.177  24.852  1.00 35.12           C
ATOM   5660  CB   GLU A 153      22.137   7.014  26.105  1.00 35.59           C
ATOM   5663  CG   GLU A 153      23.104   6.361  27.126  1.00 40.05           C
ATOM   5666  CD   GLU A 153      22.996   6.976  28.550  1.00 43.31           C
ATOM   5667  OE1  GLU A 153      22.432   8.055  28.711  1.00 44.86           O
ATOM   5668  OE2  GLU A 153      23.438   6.338  29.537  1.00 50.12           O
ATOM   5669  C    GLU A 153      20.968   6.844  23.892  1.00 33.92           C
ATOM   5670  O    GLU A 153      21.381   7.468  22.915  1.00 31.33           O
ATOM   5672  N    GLU A 154      19.681   6.680  24.137  1.00 33.73           N
ATOM   5673  CA   GLU A 154      18.690   7.350  23.334  1.00 33.95           C
ATOM   5675  CB   GLU A 154      18.290   6.555  22.051  1.00 34.14           C
ATOM   5678  CG   GLU A 154      17.675   5.218  22.304  1.00 36.12           C
ATOM   5681  CD   GLU A 154      17.436   4.373  21.068  1.00 36.61           C
ATOM   5682  OE1  GLU A 154      17.069   4.856  19.973  1.00 30.15           O
ATOM   5683  OE2  GLU A 154      17.600   3.155  21.225  1.00 37.95           O
ATOM   5684  C    GLU A 154      17.541   7.681  24.272  1.00 35.16           C
ATOM   5685  O    GLU A 154      17.394   7.092  25.337  1.00 34.87           O
ATOM   5687  N    MET A 155      16.813   8.721  23.926  1.00 34.53           N
ATOM   5688  CA   MET A 155      15.613   9.063  24.583  1.00 34.55           C
ATOM   5690  CB   MET A 155      15.898  10.173  25.528  1.00 35.98           C
ATOM   5693  CG   MET A 155      14.684  10.641  26.185  1.00 40.29           C
ATOM   5696  SD   MET A 155      15.144  11.635  27.551  1.00 48.65           S
ATOM   5697  CE   MET A 155      13.454  11.711  28.268  1.00 47.98           C
ATOM   5701  C    MET A 155      14.668   9.577  23.518  1.00 33.54           C
ATOM   5702  O    MET A 155      15.088  10.320  22.603  1.00 32.14           O
ATOM   5704  N    ALA A 156      13.412   9.191  23.651  1.00 31.53           N
ATOM   5705  CA   ALA A 156      12.383   9.514  22.721  1.00 31.19           C
ATOM   5707  CB   ALA A 156      12.239   8.383  21.741  1.00 29.85           C
ATOM   5711  C    ALA A 156      11.053   9.764  23.483  1.00 32.17           C
ATOM   5712  O    ALA A 156      10.808   9.181  24.550  1.00 32.09           O
ATOM   5714  N    THR A 157      10.228  10.637  22.934  1.00 31.32           N
ATOM   5715  CA   THR A 157       8.879  10.907  23.437  1.00 33.56           C
ATOM   5717  CB   THR A 157       8.101  11.753  22.388  1.00 32.63           C
ATOM   5719  OG1  THR A 157       8.845  12.937  22.118  1.00 31.49           O
ATOM   5721  CG2  THR A 157       6.707  12.151  22.838  1.00 35.00           C
ATOM   5725  C    THR A 157       8.172   9.606  23.824  1.00 33.29           C
ATOM   5726  O    THR A 157       8.106   8.634  23.056  1.00 34.08           O
ATOM   5728  N    LYS A 158       7.752   9.567  25.077  1.00 36.21           N
ATOM   5729  CA   LYS A 158       7.024   8.410  25.655  1.00 36.17           C
ATOM   5731  CB   LYS A 158       5.719   8.258  24.934  1.00 36.36           C
ATOM   5734  CG   LYS A 158       4.851   9.513  25.033  1.00 38.77           C
ATOM   5737  CD   LYS A 158       3.633   9.378  24.118  1.00 41.45           C
ATOM   5740  CE   LYS A 158       2.366   9.796  24.825  1.00 45.12           C
```

FIG. 5U

```
ATOM   5743  NZ   LYS A 158       2.412  11.238  25.121  1.00 46.77           N
ATOM   5747  C    LYS A 158       7.753   7.129  25.511  1.00 36.28           C
ATOM   5748  O    LYS A 158       7.123   6.112  25.271  1.00 37.46           O
ATOM   5750  N    ALA A 159       9.081   7.161  25.582  1.00 36.45           N
ATOM   5751  CA   ALA A 159       9.905   5.962  25.305  1.00 35.35           C
ATOM   5753  CB   ALA A 159      10.007   5.044  26.560  1.00 36.36           C
ATOM   5757  C    ALA A 159       9.404   5.181  24.090  1.00 35.52           C
ATOM   5758  O    ALA A 159       9.529   3.949  24.038  1.00 33.91           O
ATOM   5760  N    ASP A 160       8.890   5.918  23.074  1.00 35.12           N
ATOM   5761  CA   ASP A 160       8.504   5.331  21.801  1.00 33.93           C
ATOM   5763  CB   ASP A 160       7.116   5.860  21.447  1.00 34.67           C
ATOM   5766  CG   ASP A 160       6.644   5.427  20.129  1.00 34.90           C
ATOM   5767  OD1  ASP A 160       7.329   4.661  19.439  1.00 36.96           O
ATOM   5768  OD2  ASP A 160       5.544   5.861  19.745  1.00 37.75           O
ATOM   5769  C    ASP A 160       9.611   5.701  20.785  1.00 34.19           C
ATOM   5770  O    ASP A 160       9.741   6.889  20.315  1.00 32.67           O
ATOM   5772  N    TYR A 161      10.416   4.685  20.458  1.00 32.93           N
ATOM   5773  CA   TYR A 161      11.664   4.863  19.684  1.00 32.18           C
ATOM   5775  CB   TYR A 161      12.738   3.875  20.196  1.00 32.82           C
ATOM   5778  CG   TYR A 161      13.091   4.101  21.663  1.00 32.93           C
ATOM   5779  CD1  TYR A 161      13.825   5.186  22.040  1.00 31.88           C
ATOM   5781  CE1  TYR A 161      14.101   5.442  23.336  1.00 38.00           C
ATOM   5783  CZ   TYR A 161      13.671   4.553  24.314  1.00 42.38           C
ATOM   5784  OH   TYR A 161      13.999   4.788  25.598  1.00 44.08           O
ATOM   5786  CE2  TYR A 161      12.959   3.434  23.970  1.00 42.24           C
ATOM   5788  CD2  TYR A 161      12.667   3.214  22.640  1.00 37.73           C
ATOM   5790  C    TYR A 161      11.421   4.696  18.168  1.00 31.18           C
ATOM   5791  O    TYR A 161      12.372   4.731  17.357  1.00 27.16           O
ATOM   5793  N    THR A 162      10.129   4.485  17.813  1.00 29.57           N
ATOM   5794  CA   THR A 162       9.659   4.426  16.452  1.00 29.27           C
ATOM   5796  CB   THR A 162      10.002   5.748  15.633  1.00 28.80           C
ATOM   5798  OG1  THR A 162       9.498   6.881  16.307  1.00 26.38           O
ATOM   5800  CG2  THR A 162       9.413   5.750  14.310  1.00 28.12           C
ATOM   5804  C    THR A 162      10.218   3.296  15.661  1.00 29.90           C
ATOM   5805  O    THR A 162       9.474   2.561  14.981  1.00 29.65           O
ATOM   5807  N    LEU A 163      11.545   3.233  15.610  1.00 30.60           N
ATOM   5808  CA   LEU A 163      12.189   2.292  14.761  1.00 31.31           C
ATOM   5810  CB   LEU A 163      13.541   2.829  14.343  1.00 30.83           C
ATOM   5813  CG   LEU A 163      13.591   4.104  13.492  1.00 31.84           C
ATOM   5815  CD1  LEU A 163      15.033   4.384  13.159  1.00 31.55           C
ATOM   5819  CD2  LEU A 163      12.743   4.007  12.212  1.00 29.01           C
ATOM   5823  C    LEU A 163      12.394   0.960  15.520  1.00 32.80           C
ATOM   5824  O    LEU A 163      12.337   0.940  16.753  1.00 32.75           O
ATOM   5826  N    ASP A 164      12.664  -0.099  14.754  1.00 34.26           N
ATOM   5827  CA   ASP A 164      13.129  -1.384  15.243  1.00 36.76           C
ATOM   5829  CB   ASP A 164      13.276  -2.390  14.089  1.00 37.95           C
ATOM   5832  CG   ASP A 164      14.189  -1.884  12.975  1.00 42.05           C
ATOM   5833  OD1  ASP A 164      13.788  -0.942  12.214  1.00 49.37           O
ATOM   5834  OD2  ASP A 164      15.330  -2.370  12.858  1.00 47.06           O
ATOM   5835  C    ASP A 164      14.511  -1.193  15.875  1.00 37.68           C
ATOM   5836  O    ASP A 164      15.244  -0.243  15.547  1.00 35.84           O
ATOM   5838  N    GLU A 165      14.892  -2.146  16.717  1.00 37.68           N
ATOM   5839  CA   GLU A 165      16.167  -2.082  17.428  1.00 38.72           C
ATOM   5841  CB   GLU A 165      16.216  -3.208  18.495  1.00 39.95           C
ATOM   5844  CG   GLU A 165      17.138  -2.904  19.703  1.00 43.37           C
ATOM   5847  CD   GLU A 165      17.045  -3.968  20.802  1.00 50.02           C
ATOM   5848  OE1  GLU A 165      15.915  -4.436  21.077  1.00 51.72           O
ATOM   5849  OE2  GLU A 165      18.097  -4.305  21.405  1.00 55.03           O
ATOM   5850  C    GLU A 165      17.400  -2.114  16.492  1.00 38.14           C
ATOM   5851  O    GLU A 165      18.398  -1.440  16.743  1.00 38.13           O
ATOM   5853  N    GLU A 166      17.323  -2.850  15.390  1.00 37.57           N
ATOM   5854  CA   GLU A 166      18.460  -2.963  14.486  1.00 37.34           C
ATOM   5856  CB   GLU A 166      18.258  -4.102  13.473  1.00 37.68           C
```

FIG. 5V

```
ATOM   5859  CG  GLU A 166      19.312  -4.182  12.324  1.00 39.46           C
ATOM   5862  CD  GLU A 166      20.695  -4.674  12.773  1.00 42.44           C
ATOM   5863  OE1 GLU A 166      20.955  -4.769  13.978  1.00 46.71           O
ATOM   5864  OE2 GLU A 166      21.542  -4.978  11.915  1.00 45.64           O
ATOM   5865  C   GLU A 166      18.674  -1.641  13.760  1.00 36.13           C
ATOM   5866  O   GLU A 166      19.796  -1.184  13.659  1.00 38.21           O
ATOM   5868  N   SER A 167      17.599  -1.005  13.318  1.00 34.14           N
ATOM   5869  CA  SER A 167      17.720   0.303  12.650  1.00 33.30           C
ATOM   5871  CB  SER A 167      16.374   0.828  12.222  1.00 32.17           C
ATOM   5874  OG  SER A 167      15.715  -0.099  11.377  1.00 34.51           O
ATOM   5876  C   SER A 167      18.393   1.283  13.571  1.00 30.87           C
ATOM   5877  O   SER A 167      19.278   1.992  13.134  1.00 31.49           O
ATOM   5879  N   ARG A 168      18.004   1.292  14.850  1.00 29.38           N
ATOM   5880  CA  ARG A 168      18.639   2.157  15.836  1.00 28.56           C
ATOM   5882  CB  ARG A 168      17.878   2.150  17.117  1.00 29.48           C
ATOM   5885  CG  ARG A 168      16.554   2.835  16.999  1.00 32.07           C
ATOM   5888  CD  ARG A 168      15.965   2.874  18.359  1.00 35.95           C
ATOM   5891  NE  ARG A 168      14.991   1.874  18.490  1.00 35.74           N
ATOM   5893  CZ  ARG A 168      14.726   1.168  19.590  1.00 36.73           C
ATOM   5894  NH1 ARG A 168      15.316   1.352  20.776  1.00 36.99           N
ATOM   5897  NH2 ARG A 168      13.784   0.300  19.477  1.00 34.77           N
ATOM   5900  C   ARG A 168      20.080   1.827  16.140  1.00 27.43           C
ATOM   5901  O   ARG A 168      20.873   2.702  16.442  1.00 23.27           O
ATOM   5903  N   ALA A 169      20.387   0.539  16.103  1.00 28.70           N
ATOM   5904  CA  ALA A 169      21.760   0.054  16.309  1.00 28.58           C
ATOM   5906  CB  ALA A 169      21.742  -1.535  16.398  1.00 29.63           C
ATOM   5910  C   ALA A 169      22.629   0.488  15.165  1.00 28.42           C
ATOM   5911  O   ALA A 169      23.743   0.765  15.365  1.00 27.79           O
ATOM   5913  N   ARG A 170      22.113   0.467  13.938  1.00 30.11           N
ATOM   5914  CA  ARG A 170      22.866   0.994  12.794  1.00 31.58           C
ATOM   5916  CB  ARG A 170      22.006   0.931  11.532  1.00 32.82           C
ATOM   5919  CG  ARG A 170      22.751   1.149  10.228  1.00 40.04           C
ATOM   5922  CD  ARG A 170      21.770   1.308   9.040  1.00 48.48           C
ATOM   5925  NE  ARG A 170      21.170   0.011   8.738  1.00 55.58           N
ATOM   5927  CZ  ARG A 170      21.846  -1.004   8.190  1.00 61.84           C
ATOM   5928  NH1 ARG A 170      23.139  -0.858   7.859  1.00 63.30           N
ATOM   5931  NH2 ARG A 170      21.237  -2.177   7.957  1.00 62.81           N
ATOM   5934  C   ARG A 170      23.353   2.424  13.076  1.00 30.18           C
ATOM   5935  O   ARG A 170      24.553   2.747  12.979  1.00 28.40           O
ATOM   5937  N   ILE A 171      22.420   3.279  13.497  1.00 29.52           N
ATOM   5938  CA  ILE A 171      22.735   4.681  13.852  1.00 28.02           C
ATOM   5940  CB  ILE A 171      21.440   5.476  14.225  1.00 28.40           C
ATOM   5942  CG1 ILE A 171      20.586   5.674  12.978  1.00 27.25           C
ATOM   5945  CD1 ILE A 171      18.989   6.056  13.237  1.00 25.06           C
ATOM   5949  CG2 ILE A 171      21.804   6.871  14.938  1.00 28.73           C
ATOM   5953  C   ILE A 171      23.719   4.780  15.001  1.00 28.08           C
ATOM   5954  O   ILE A 171      24.734   5.492  14.934  1.00 26.21           O
ATOM   5956  N   LYS A 172      23.448   4.064  16.078  1.00 28.36           N
ATOM   5957  CA  LYS A 172      24.382   4.088  17.208  1.00 29.21           C
ATOM   5959  CB  LYS A 172      23.871   3.176  18.319  1.00 29.60           C
ATOM   5962  CG  LYS A 172      22.531   3.591  18.882  1.00 32.46           C
ATOM   5965  CD  LYS A 172      22.010   2.576  19.817  1.00 34.70           C
ATOM   5968  CE  LYS A 172      20.754   3.100  20.479  1.00 37.65           C
ATOM   5971  NZ  LYS A 172      19.894   1.954  21.015  1.00 33.76           N
ATOM   5975  C   LYS A 172      25.776   3.586  16.781  1.00 27.84           C
ATOM   5976  O   LYS A 172      26.796   4.046  17.279  1.00 29.48           O
ATOM   5978  N   THR A 173      25.823   2.614  15.893  1.00 27.57           N
ATOM   5979  CA  THR A 173      27.105   2.097  15.452  1.00 28.51           C
ATOM   5981  CB  THR A 173      26.963   0.785  14.599  1.00 29.22           C
ATOM   5983  OG1 THR A 173      26.463  -0.272  15.431  1.00 34.02           O
ATOM   5985  CG2 THR A 173      28.321   0.268  14.032  1.00 28.21           C
ATOM   5989  C   THR A 173      27.792   3.227  14.704  1.00 28.01           C
ATOM   5990  O   THR A 173      28.975   3.501  14.387  1.00 28.49           O
```

FIG. 5W

```
ATOM   5992  N    ARG A 174      27.023    3.969   13.897  1.00  27.44           N
ATOM   5993  CA   ARG A 174      27.637    5.090   13.182  1.00  27.11           C
ATOM   5995  CB   ARG A 174      26.650    5.785   12.238  1.00  27.58           C
ATOM   5998  CG   ARG A 174      27.241    6.903   11.457  1.00  29.58           C
ATOM   6001  CD   ARG A 174      28.232    6.266   10.520  1.00  35.38           C
ATOM   6004  NE   ARG A 174      28.827    7.248    9.661  1.00  41.14           N
ATOM   6006  CZ   ARG A 174      29.542    6.955    8.585  1.00  47.71           C
ATOM   6007  NH1  ARG A 174      29.761    5.678    8.237  1.00  48.98           N
ATOM   6010  NH2  ARG A 174      30.059    7.944    7.867  1.00  50.34           N
ATOM   6013  C    ARG A 174      28.237    6.067   14.114  1.00  25.23           C
ATOM   6014  O    ARG A 174      29.363    6.523   13.875  1.00  22.94           O
ATOM   6016  N    LEU A 175      27.486    6.425   15.157  1.00  24.54           N
ATOM   6017  CA   LEU A 175      27.963    7.440   16.133  1.00  24.11           C
ATOM   6019  CB   LEU A 175      26.851    7.857   17.074  1.00  23.47           C
ATOM   6022  CG   LEU A 175      25.529    8.406   16.403  1.00  24.12           C
ATOM   6024  CD1  LEU A 175      24.436    8.769   17.378  1.00  23.42           C
ATOM   6028  CD2  LEU A 175      25.861    9.611   15.603  1.00  19.70           C
ATOM   6032  C    LEU A 175      29.152    6.967   16.977  1.00  26.04           C
ATOM   6033  O    LEU A 175      29.996    7.739   17.316  1.00  25.79           O
ATOM   6035  N    PHE A 176      29.159    5.707   17.358  1.00  28.13           N
ATOM   6036  CA   PHE A 176      30.308    5.113   18.090  1.00  30.90           C
ATOM   6038  CB   PHE A 176      29.962    3.653   18.364  1.00  31.38           C
ATOM   6041  CG   PHE A 176      31.038    2.854   19.041  1.00  37.70           C
ATOM   6042  CD1  PHE A 176      32.010    2.187   18.286  1.00  39.42           C
ATOM   6044  CE1  PHE A 176      33.007    1.437   18.911  1.00  40.80           C
ATOM   6046  CZ   PHE A 176      33.012    1.313   20.305  1.00  41.87           C
ATOM   6048  CE2  PHE A 176      32.038    1.931   21.066  1.00  43.88           C
ATOM   6050  CD2  PHE A 176      31.038    2.701   20.428  1.00  42.08           C
ATOM   6052  C    PHE A 176      31.568    5.251   17.219  1.00  31.17           C
ATOM   6053  O    PHE A 176      32.597    5.670   17.679  1.00  29.60           O
ATOM   6055  N    THR A 177      31.417    4.946   15.931  1.00  32.23           N
ATOM   6056  CA   THR A 177      32.519    4.966   14.983  1.00  32.30           C
ATOM   6058  CB   THR A 177      32.060    4.444   13.655  1.00  32.56           C
ATOM   6060  OG1  THR A 177      31.573    3.110   13.823  1.00  33.77           O
ATOM   6062  CG2  THR A 177      33.180    4.420   12.683  1.00  34.29           C
ATOM   6066  C    THR A 177      33.050    6.329   14.762  1.00  31.78           C
ATOM   6067  O    THR A 177      34.257    6.513   14.645  1.00  30.06           O
ATOM   6069  N    ILE A 178      32.146    7.319   14.694  1.00  31.31           N
ATOM   6070  CA   ILE A 178      32.555    8.683   14.494  1.00  29.31           C
ATOM   6072  CB   ILE A 178      31.349    9.587   14.228  1.00  31.07           C
ATOM   6074  CG1  ILE A 178      30.870    9.441   12.748  1.00  28.43           C
ATOM   6077  CD1  ILE A 178      29.386   10.059   12.500  1.00  28.35           C
ATOM   6081  CG2  ILE A 178      31.701   10.989   14.602  1.00  27.52           C
ATOM   6085  C    ILE A 178      33.306    9.190   15.713  1.00  31.15           C
ATOM   6086  O    ILE A 178      34.316    9.908   15.590  1.00  28.66           O
ATOM   6088  N    ARG A 179      32.817    8.863   16.900  1.00  30.03           N
ATOM   6089  CA   ARG A 179      33.498    9.271   18.083  1.00  31.68           C
ATOM   6091  CB   ARG A 179      32.663    8.898   19.291  1.00  32.08           C
ATOM   6094  CG   ARG A 179      33.357    8.981   20.664  1.00  35.09           C
ATOM   6097  CD   ARG A 179      32.474    8.196   21.636  1.00  42.45           C
ATOM   6100  NE   ARG A 179      32.544    8.615   23.039  1.00  50.82           N
ATOM   6102  CZ   ARG A 179      33.293    8.037   23.995  1.00  57.90           C
ATOM   6103  NH1  ARG A 179      34.115    7.004   23.739  1.00  58.57           N
ATOM   6106  NH2  ARG A 179      33.238    8.514   25.238  1.00  61.33           N
ATOM   6109  C    ARG A 179      34.898    8.553   18.176  1.00  33.24           C
ATOM   6110  O    ARG A 179      35.878    9.180   18.448  1.00  30.58           O
ATOM   6112  N    GLN A 180      34.959    7.255   17.969  1.00  36.01           N
ATOM   6113  CA   GLN A 180      36.294    6.597   18.031  1.00  39.30           C
ATOM   6115  CB   GLN A 180      36.150    5.101   17.822  1.00  39.90           C
ATOM   6118  CG   GLN A 180      35.443    4.390   19.003  1.00  46.03           C
ATOM   6121  CD   GLN A 180      36.186    4.482   20.354  1.00  52.50           C
ATOM   6122  OE1  GLN A 180      37.398    4.785   20.399  1.00  56.81           O
ATOM   6123  NE2  GLN A 180      35.454    4.203   21.469  1.00  54.63           N
```

FIG. 5X

```
ATOM   6126  C    GLN A 180      37.306   7.275  17.077  1.00 39.85           C
ATOM   6127  O    GLN A 180      38.433   7.669  17.483  1.00 41.27           O
ATOM   6129  N    GLU A 181      36.879   7.516  15.831  1.00 40.96           N
ATOM   6130  CA   GLU A 181      37.761   8.110  14.826  1.00 39.80           C
ATOM   6132  CB   GLU A 181      37.119   8.145  13.460  1.00 40.41           C
ATOM   6135  CG   GLU A 181      36.979   6.829  12.791  1.00 41.90           C
ATOM   6138  CD   GLU A 181      38.322   6.124  12.546  1.00 45.90           C
ATOM   6139  OE1  GLU A 181      39.341   6.806  12.241  1.00 46.42           O
ATOM   6140  OE2  GLU A 181      38.324   4.879  12.692  1.00 49.22           O
ATOM   6141  C    GLU A 181      38.160   9.503  15.187  1.00 40.61           C
ATOM   6142  O    GLU A 181      39.278   9.956  14.826  1.00 39.32           O
ATOM   6144  N    MET A 182      37.266  10.245  15.851  1.00 39.52           N
ATOM   6145  CA   MET A 182      37.613  11.608  16.256  1.00 38.77           C
ATOM   6147  CB   MET A 182      36.389  12.354  16.759  1.00 37.91           C
ATOM   6150  CG   MET A 182      35.416  12.823  15.688  1.00 37.77           C
ATOM   6153  SD   MET A 182      34.183  13.936  16.362  1.00 35.31           S
ATOM   6154  CE   MET A 182      33.315  14.409  14.804  1.00 34.42           C
ATOM   6158  C    MET A 182      38.675  11.566  17.383  1.00 39.15           C
ATOM   6159  O    MET A 182      39.660  12.326  17.380  1.00 38.70           O
ATOM   6161  N    ALA A 183      38.418  10.697  18.342  1.00 39.85           N
ATOM   6162  CA   ALA A 183      39.359  10.386  19.434  1.00 41.20           C
ATOM   6164  CB   ALA A 183      38.798   9.292  20.328  1.00 40.66           C
ATOM   6168  C    ALA A 183      40.740  10.022  18.879  1.00 41.54           C
ATOM   6169  O    ALA A 183      41.685  10.691  19.171  1.00 42.10           O
ATOM   6171  N    SER A 184      40.810   9.050  17.978  1.00 43.07           N
ATOM   6172  CA   SER A 184      42.041   8.737  17.237  1.00 43.27           C
ATOM   6174  CB   SER A 184      41.755   7.761  16.096  1.00 43.55           C
ATOM   6177  OG   SER A 184      41.410   6.515  16.639  1.00 47.00           O
ATOM   6179  C    SER A 184      42.769   9.882  16.592  1.00 43.28           C
ATOM   6180  O    SER A 184      43.941   9.719  16.261  1.00 41.85           O
ATOM   6182  N    ARG A 185      42.091  11.006  16.330  1.00 42.56           N
ATOM   6183  CA   ARG A 185      42.778  12.132  15.684  1.00 41.98           C
ATOM   6185  CB   ARG A 185      42.035  12.541  14.427  1.00 42.71           C
ATOM   6188  CG   ARG A 185      42.112  11.513  13.286  1.00 44.32           C
ATOM   6191  CD   ARG A 185      40.772  11.375  12.601  1.00 46.31           C
ATOM   6194  NE   ARG A 185      40.841  11.600  11.167  1.00 48.70           N
ATOM   6196  CZ   ARG A 185      40.855  10.662  10.232  1.00 50.47           C
ATOM   6197  NH1  ARG A 185      40.810   9.367  10.552  1.00 54.56           N
ATOM   6200  NH2  ARG A 185      40.915  11.028   8.954  1.00 51.36           N
ATOM   6203  C    ARG A 185      42.921  13.280  16.643  1.00 41.46           C
ATOM   6204  O    ARG A 185      43.389  14.357  16.255  1.00 42.04           O
ATOM   6206  N    SER A 186      42.559  13.049  17.907  1.00 40.15           N
ATOM   6207  CA   SER A 186      42.690  14.080  18.895  1.00 40.46           C
ATOM   6209  CB   SER A 186      44.168  14.565  18.967  1.00 41.03           C
ATOM   6212  OG   SER A 186      45.057  13.465  18.793  1.00 41.70           O
ATOM   6214  C    SER A 186      41.722  15.225  18.625  1.00 40.66           C
ATOM   6215  O    SER A 186      42.049  16.387  18.830  1.00 41.52           O
ATOM   6217  N    LEU A 187      40.516  14.903  18.137  1.00 40.17           N
ATOM   6218  CA   LEU A 187      39.545  15.937  17.811  1.00 39.38           C
ATOM   6220  CB   LEU A 187      39.071  15.792  16.342  1.00 37.70           C
ATOM   6223  CG   LEU A 187      40.052  16.060  15.231  1.00 35.50           C
ATOM   6225  CD1  LEU A 187      39.533  15.545  13.893  1.00 37.73           C
ATOM   6229  CD2  LEU A 187      40.413  17.519  15.118  1.00 34.91           C
ATOM   6233  C    LEU A 187      38.335  15.825  18.718  1.00 40.04           C
ATOM   6234  O    LEU A 187      37.467  16.714  18.680  1.00 40.14           O
ATOM   6236  N    TRP A 188      38.254  14.728  19.485  1.00 40.63           N
ATOM   6237  CA   TRP A 188      37.047  14.372  20.247  1.00 41.70           C
ATOM   6239  CB   TRP A 188      37.019  12.876  20.680  1.00 41.23           C
ATOM   6242  CG   TRP A 188      35.865  12.590  21.612  1.00 42.78           C
ATOM   6243  CD1  TRP A 188      35.933  12.377  22.974  1.00 43.61           C
ATOM   6245  NE1  TRP A 188      34.664  12.209  23.495  1.00 41.33           N
ATOM   6247  CE2  TRP A 188      33.745  12.333  22.489  1.00 43.56           C
ATOM   6248  CD2  TRP A 188      34.459  12.603  21.287  1.00 41.64           C
```

FIG. 5Y

```
ATOM   6249  CE3 TRP A 188      33.738  12.766  20.097  1.00 38.96           C
ATOM   6251  CZ3 TRP A 188      32.347  12.690  20.142  1.00 38.37           C
ATOM   6253  CH2 TRP A 188      31.658  12.452  21.351  1.00 40.60           C
ATOM   6255  CZ2 TRP A 188      32.331  12.261  22.533  1.00 42.31           C
ATOM   6257  C   TRP A 188      36.821  15.323  21.417  1.00 42.95           C
ATOM   6258  O   TRP A 188      35.773  15.966  21.514  1.00 42.21           O
ATOM   6260  N   ASP A 189      37.832  15.487  22.267  1.00 44.68           N
ATOM   6261  CA  ASP A 189      37.728  16.438  23.387  1.00 45.62           C
ATOM   6263  CB  ASP A 189      39.089  16.690  24.078  1.00 46.90           C
ATOM   6266  CG  ASP A 189      39.618  15.458  24.792  1.00 50.88           C
ATOM   6267  OD1 ASP A 189      38.856  14.464  24.951  1.00 57.27           O
ATOM   6268  OD2 ASP A 189      40.813  15.474  25.177  1.00 58.02           O
ATOM   6269  C   ASP A 189      37.125  17.765  22.978  1.00 44.63           C
ATOM   6270  O   ASP A 189      36.178  18.228  23.623  1.00 44.50           O
ATOM   6272  N   SER A 190      37.629  18.368  21.909  1.00 43.98           N
ATOM   6273  CA  SER A 190      37.135  19.698  21.536  1.00 43.64           C
ATOM   6275  CB  SER A 190      38.034  20.373  20.535  1.00 44.12           C
ATOM   6278  OG  SER A 190      37.320  21.490  19.984  1.00 42.51           O
ATOM   6280  C   SER A 190      35.721  19.664  20.921  1.00 43.14           C
ATOM   6281  O   SER A 190      34.929  20.549  21.165  1.00 44.73           O
ATOM   6283  N   PHE A 191      35.449  18.659  20.092  1.00 42.12           N
ATOM   6284  CA  PHE A 191      34.103  18.405  19.586  1.00 40.48           C
ATOM   6286  CB  PHE A 191      34.103  17.229  18.602  1.00 38.37           C
ATOM   6289  CG  PHE A 191      32.735  16.951  17.994  1.00 35.18           C
ATOM   6290  CD1 PHE A 191      32.162  17.840  17.115  1.00 31.73           C
ATOM   6292  CE1 PHE A 191      30.916  17.572  16.525  1.00 28.61           C
ATOM   6294  CZ  PHE A 191      30.249  16.436  16.850  1.00 28.17           C
ATOM   6296  CE2 PHE A 191      30.790  15.514  17.715  1.00 30.21           C
ATOM   6298  CD2 PHE A 191      32.039  15.784  18.293  1.00 34.28           C
ATOM   6300  C   PHE A 191      33.120  18.178  20.758  1.00 40.75           C
ATOM   6301  O   PHE A 191      32.107  18.871  20.872  1.00 41.14           O
ATOM   6303  N   ARG A 192      33.456  17.282  21.662  1.00 42.35           N
ATOM   6304  CA  ARG A 192      32.569  17.012  22.783  1.00 44.44           C
ATOM   6306  CB  ARG A 192      33.051  15.841  23.662  1.00 44.72           C
ATOM   6309  CG  ARG A 192      32.136  15.580  24.891  1.00 49.27           C
ATOM   6312  CD  ARG A 192      32.653  14.523  25.877  1.00 55.19           C
ATOM   6315  NE  ARG A 192      34.062  14.741  26.241  1.00 60.10           N
ATOM   6317  CZ  ARG A 192      34.508  15.720  27.034  1.00 64.70           C
ATOM   6318  NH1 ARG A 192      33.664  16.614  27.576  1.00 65.66           N
ATOM   6321  NH2 ARG A 192      35.817  15.824  27.271  1.00 64.46           N
ATOM   6324  C   ARG A 192      32.302  18.237  23.622  1.00 44.96           C
ATOM   6325  O   ARG A 192      31.224  18.349  24.187  1.00 45.11           O
ATOM   6327  N   GLN A 193      33.238  19.169  23.691  1.00 46.51           N
ATOM   6328  CA  GLN A 193      33.043  20.382  24.510  1.00 47.96           C
ATOM   6330  CB  GLN A 193      34.407  20.906  25.012  1.00 48.06           C
ATOM   6333  CG  GLN A 193      35.007  20.014  26.104  1.00 51.75           C
ATOM   6336  CD  GLN A 193      36.350  20.516  26.638  1.00 54.61           C
ATOM   6337  OE1 GLN A 193      37.410  19.937  26.341  1.00 56.62           O
ATOM   6338  NE2 GLN A 193      36.311  21.594  27.434  1.00 55.66           N
ATOM   6341  C   GLN A 193      32.253  21.552  23.879  1.00 48.24           C
ATOM   6342  O   GLN A 193      31.846  22.474  24.583  1.00 48.42           O
ATOM   6344  N   SER A 194      32.052  21.546  22.569  1.00 48.36           N
ATOM   6345  CA  SER A 194      31.495  22.723  21.896  1.00 48.16           C
ATOM   6347  CB  SER A 194      32.097  22.849  20.484  1.00 48.00           C
ATOM   6350  OG  SER A 194      32.187  21.578  19.842  1.00 48.78           O
ATOM   6352  C   SER A 194      29.972  22.751  21.789  1.00 47.98           C
ATOM   6353  O   SER A 194      29.428  23.698  21.243  1.00 48.12           O
ATOM   6355  N   GLU A 195      29.270  21.739  22.270  1.00 48.15           N
ATOM   6356  CA  GLU A 195      27.818  21.734  22.083  1.00 49.04           C
ATOM   6358  CB  GLU A 195      27.248  20.337  22.246  1.00 47.73           C
ATOM   6361  CG  GLU A 195      25.708  20.275  21.988  1.00 47.51           C
ATOM   6364  CD  GLU A 195      25.184  18.866  21.954  1.00 40.56           C
ATOM   6365  OE1 GLU A 195      25.951  17.957  21.535  1.00 38.62           O
```

FIG. 5Z

```
ATOM   6366  OE2  GLU A 195     24.018  18.661  22.355  1.00 41.85           O
ATOM   6367  C    GLU A 195     27.106  22.774  23.002  1.00 50.42           C
ATOM   6368  O    GLU A 195     27.407  22.858  24.191  1.00 50.12           O
ATOM   6370  N    ARG A 196     26.208  23.572  22.413  1.00 52.14           N
ATOM   6371  CA   ARG A 196     25.535  24.719  23.085  1.00 54.22           C
ATOM   6373  CB   ARG A 196     25.553  25.970  22.178  1.00 54.91           C
ATOM   6376  CG   ARG A 196     26.913  26.280  21.555  1.00 58.70           C
ATOM   6379  CD   ARG A 196     27.193  27.801  21.309  1.00 63.36           C
ATOM   6382  NE   ARG A 196     28.625  28.093  21.546  1.00 67.68           N
ATOM   6384  CZ   ARG A 196     29.219  29.289  21.466  1.00 69.92           C
ATOM   6385  NH1  ARG A 196     28.536  30.386  21.126  1.00 70.56           N
ATOM   6388  NH2  ARG A 196     30.526  29.380  21.728  1.00 70.21           N
ATOM   6391  C    ARG A 196     24.073  24.422  23.392  1.00 53.67           C
ATOM   6392  O    ARG A 196     23.387  23.853  22.541  1.00 53.86           O
ATOM   6394  MN   MN  A 495     17.177  17.733  14.554  1.00 27.34          MN
ATOM   6395  MN   MN  A 496     16.334  20.007  11.605  1.00 25.22          MN
ATOM   6396  P    U   A 910     18.219  20.415  14.571  1.00 27.05           P
ATOM   6397  O1P  U   A 910     17.604  21.673  15.082  1.00 23.04           O
ATOM   6398  O2P  U   A 910     18.577  19.263  15.469  1.00 31.98           O
ATOM   6399  O5*  U   A 910     19.574  21.020  13.967  1.00 23.57           O
ATOM   6400  C5*  U   A 910     20.367  20.247  13.117  1.00 24.39           C
ATOM   6403  C4*  U   A 910     21.784  20.705  13.215  1.00 28.06           C
ATOM   6405  O4*  U   A 910     21.815  21.996  12.589  1.00 26.37           O
ATOM   6406  C1*  U   A 910     22.248  22.933  13.474  1.00 30.01           C
ATOM   6408  N1   U   A 910     21.536  24.181  13.181  1.00 32.01           N
ATOM   6409  C2   U   A 910     22.256  25.356  12.994  1.00 32.20           C
ATOM   6410  O2   U   A 910     23.483  25.405  12.991  1.00 34.28           O
ATOM   6411  N3   U   A 910     21.467  26.454  12.746  1.00 28.48           N
ATOM   6413  C4   U   A 910     20.056  26.518  12.730  1.00 33.14           C
ATOM   6414  O4   U   A 910     19.445  27.586  12.504  1.00 34.24           O
ATOM   6415  C5   U   A 910     19.400  25.246  12.961  1.00 30.32           C
ATOM   6417  C6   U   A 910     20.134  24.159  13.139  1.00 31.66           C
ATOM   6419  C2*  U   A 910     22.008  22.384  14.874  1.00 31.55           C
ATOM   6421  O2*  U   A 910     22.837  23.039  15.841  1.00 37.61           O
ATOM   6423  C3*  U   A 910     22.338  20.935  14.627  1.00 30.46           C
ATOM   6425  O3*  U   A 910     23.743  20.749  14.670  1.00 31.33           O
ATOM   6426  O3P  U   A 910     17.461  19.664  13.515  1.00 23.08           O
ATOM   1588  OH2  WAT A   1     14.505  20.354  12.931  1.00 21.34       A   O
ATOM   1589  OH2  WAT A   2     14.846  20.240   9.761  1.00 23.05       A   O
ATOM   1591  OH2  WAT A   3     18.587  22.283   9.729  1.00 43.33       A   O
ATOM   1592  OH2  WAT A   4     16.862  22.040  11.589  1.00 22.93       A   O
ATOM   1593  OH2  WAT A   5     21.286  20.252   8.173  1.00 26.14       A   O
ATOM   1594  OH2  WAT A   6     27.845  21.923  17.662  1.00 36.53       A   O
ATOM   1595  OH2  WAT A   7     29.576  24.494  -0.774  1.00 26.71       A   O
ATOM   1597  OH2  WAT A   8     20.137  24.907   2.814  1.00 35.50       A   O
ATOM   1598  OH2  WAT A   9     16.624  30.565   4.822  1.00 24.94       A   O
ATOM   1599  OH2  WAT A  10     11.003   7.856  18.224  1.00 25.82       A   O
ATOM   1600  OH2  WAT A  11     21.990  18.523  10.066  1.00 21.07       A   O
ATOM   1601  OH2  WAT A  12     34.615  22.163   3.521  1.00 31.63       A   O
ATOM   1602  OH2  WAT A  13      3.807  28.657   3.719  1.00 24.89       A   O
ATOM   1603  OH2  WAT A  14      3.370  27.070   7.393  1.00 29.15       A   O
ATOM   1604  OH2  WAT A  15      7.739   8.326  14.326  1.00 33.16       A   O
ATOM   1605  OH2  WAT A  16     11.825  12.412   1.504  1.00 39.80       A   O
END
```

H1N1 PA structure (Chain A) native

H1N1 PA structure (Chain A) with EMBL-R05-3

EMBL-R05-3

H1N1 PA structure (Chain A) with EMBL-R05-3

H1N1 PA structure (Chain D) with EMBL-R05-3

H1N1 PA structure (Chain A) with ribo-Uridine Monophosphate

FIG. 10

```
H1N1 polypeptide fragment (chain A) with bound EMBL-R05-1
HEADER                                              XX-XXX-XX   xxxx
COMPND     ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   1.90
REMARK   3   RESOLUTION RANGE LOW  (ANGSTROMS) :  65.01
REMARK   3   DATA CUTOFF            (SIGMA(F)) :  NONE
REMARK   3   COMPLETENESS FOR RANGE        (%) :  99.79
REMARK   3   NUMBER OF REFLECTIONS             :  15580
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE     (WORKING + TEST SET)  : 0.20827
REMARK   3   R VALUE            (WORKING SET)  : 0.20610
REMARK   3   FREE R VALUE                      : 0.25114
REMARK   3   FREE R VALUE TEST SET SIZE    (%) : 5.1
REMARK   3   FREE R VALUE TEST SET COUNT       :    830
REMARK   3
REMARK   3  FIT IN THE HIGHEST RESOLUTION BIN.
REMARK   3   TOTAL NUMBER OF BINS USED         :     20
REMARK   3   BIN RESOLUTION RANGE HIGH         :  1.899
REMARK   3   BIN RESOLUTION RANGE LOW          :  1.949
REMARK   3   REFLECTION IN BIN     (WORKING SET) :  1092
REMARK   3   BIN COMPLETENESS (WORKING+TEST) (%) : 98.15
REMARK   3   BIN R VALUE           (WORKING SET) : 0.317
REMARK   3   BIN FREE R VALUE SET COUNT        :     77
REMARK   3   BIN FREE R VALUE                  :  0.355
REMARK   3
REMARK   3  NUMBER OF NON-HYDROGEN ATOMS USED IN REFINEMENT.
REMARK   3   ALL ATOMS                 :   1592
REMARK   3
REMARK   3  B VALUES.
REMARK   3   FROM WILSON PLOT           (A**2) : NULL
REMARK   3   MEAN B VALUE      (OVERALL, A**2) : 30.699
REMARK   3   OVERALL ANISOTROPIC B VALUE.
REMARK   3    B11 (A**2) :    2.00
REMARK   3    B22 (A**2) :    2.00
REMARK   3    B33 (A**2) :   -4.00
REMARK   3    B12 (A**2) :    0.00
REMARK   3    B13 (A**2) :    0.00
REMARK   3    B23 (A**2) :    0.00
REMARK   3
REMARK   3  ESTIMATED OVERALL COORDINATE ERROR.
REMARK   3   ESU BASED ON R VALUE                       (A):  0.035
REMARK   3   ESU BASED ON FREE R VALUE                  (A):  0.033
REMARK   3   ESU BASED ON MAXIMUM LIKELIHOOD            (A):  0.084
REMARK   3   ESU FOR B VALUES BASED ON MAXIMUM LIKELIHOOD (A**2):  3.129
REMARK   3
REMARK   3 CORRELATION COEFFICIENTS.
REMARK   3   CORRELATION COEFFICIENT FO-FC       :  0.952
REMARK   3   CORRELATION COEFFICIENT FO-FC FREE  :  0.939
REMARK   3
```

FIG. 15A

```
REMARK   3   RMS DEVIATIONS FROM IDEAL VALUES        COUNT    RMS   WEIGHT
REMARK   3    BOND LENGTHS REFINED ATOMS      (A):   1522 ; 0.022 ; 0.022
REMARK   3    BOND LENGTHS OTHERS             (A):   1075 ; 0.002 ; 0.020
REMARK   3    BOND ANGLES REFINED ATOMS  (DEGREES):  2045 ; 1.843 ; 1.966
REMARK   3    BOND ANGLES OTHERS         (DEGREES):  2588 ; 1.007 ; 3.000
REMARK   3    TORSION ANGLES, PERIOD 1   (DEGREES):   173 ; 5.556 ; 5.000
REMARK   3    TORSION ANGLES, PERIOD 2   (DEGREES):    78 ;34.734 ;23.333
REMARK   3    TORSION ANGLES, PERIOD 3   (DEGREES):   279 ;14.663 ;15.000
REMARK   3    TORSION ANGLES, PERIOD 4   (DEGREES):    13 ;17.969 ;15.000
REMARK   3    CHIRAL-CENTER RESTRAINTS       (A**3):  215 ; 0.111 ; 0.200
REMARK   3    GENERAL PLANES REFINED ATOMS     (A):  1658 ; 0.010 ; 0.020
REMARK   3    GENERAL PLANES OTHERS            (A):   340 ; 0.004 ; 0.020
REMARK   3
REMARK   3   ISOTROPIC THERMAL FACTOR RESTRAINTS.    COUNT    RMS   WEIGHT
REMARK   3    MAIN-CHAIN BOND REFINED ATOMS  (A**2):  878 ; 1.390 ; 1.500
REMARK   3    MAIN-CHAIN BOND OTHER ATOMS    (A**2):  353 ; 0.396 ; 1.500
REMARK   3    MAIN-CHAIN ANGLE REFINED ATOMS (A**2): 1418 ; 2.403 ; 2.000
REMARK   3    SIDE-CHAIN BOND REFINED ATOMS  (A**2):  644 ; 3.554 ; 3.000
REMARK   3    SIDE-CHAIN ANGLE REFINED ATOMS (A**2):  627 ; 5.783 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : REFINED INDIVIDUALLY
REMARK   3
LINKR             GLY A  52                 LYS A  73              gap
LINKR             LYS A 139                 GLU A 141              gap
CRYST1   75.060   75.060  120.050  90.00  90.00 120.00 P 62 2 2
SCALE1    0.013323  0.007692  0.000000      0.00000
SCALE2    0.000000  0.015384  0.000000      0.00000
SCALE3    0.000000  0.000000  0.008330      0.00000
ATOM      1  N   ALA A   0      32.705   9.904  20.915  1.00 46.80           N
ATOM      2  CA  ALA A   0      34.010  10.013  21.658  1.00 46.90           C
ATOM      4  CB  ALA A   0      34.129   8.971  22.756  1.00 46.72           C
ATOM      8  C   ALA A   0      35.274   9.961  20.738  1.00 45.78           C
ATOM      9  O   ALA A   0      35.571   8.954  20.084  1.00 48.51           O
ATOM     13  N   MET A   1      36.021  11.036  20.730  1.00 45.20           N
ATOM     14  CA  MET A   1      37.196  11.143  19.801  1.00 44.87           C
ATOM     16  CB  MET A   1      37.842  12.491  19.948  1.00 43.94           C
ATOM     19  CG  MET A   1      39.041  12.697  19.045  1.00 43.15           C
ATOM     22  SD  MET A   1      38.629  12.410  17.284  1.00 38.41           S
ATOM     23  CE  MET A   1      38.364  14.091  17.050  1.00 30.85           C
ATOM     27  C   MET A   1      38.222  10.049  20.005  1.00 44.30           C
ATOM     28  O   MET A   1      38.737   9.461  19.057  1.00 43.72           O
ATOM     30  N   GLU A   2      38.510   9.716  21.259  1.00 45.08           N
ATOM     31  CA  GLU A   2      39.458   8.627  21.499  1.00 45.07           C
```

FIG. 15B

| | | | | | | | | | | |
|---|---|---|---|---|---|---|---|---|---|---|
| ATOM | 33 | CB | GLU | A | 2 | 39.699 | 8.426 | 23.013 | 1.00 46.79 | C |
| ATOM | 36 | CG | GLU | A | 2 | 40.839 | 7.490 | 23.302 | 1.00 48.28 | C |
| ATOM | 39 | CD | GLU | A | 2 | 40.849 | 6.940 | 24.750 | 1.00 51.47 | C |
| ATOM | 40 | OE1 | GLU | A | 2 | 40.318 | 7.609 | 25.663 | 1.00 51.73 | O |
| ATOM | 41 | OE2 | GLU | A | 2 | 41.412 | 5.837 | 24.937 | 1.00 53.93 | O |
| ATOM | 42 | C | GLU | A | 2 | 39.015 | 7.339 | 20.841 | 1.00 44.15 | C |
| ATOM | 43 | O | GLU | A | 2 | 39.817 | 6.682 | 20.212 | 1.00 44.18 | O |
| ATOM | 45 | N | ASP | A | 3 | 37.736 | 6.958 | 20.961 | 1.00 43.00 | N |
| ATOM | 46 | CA | ASP | A | 3 | 37.230 | 5.748 | 20.260 | 1.00 42.31 | C |
| ATOM | 48 | CB | ASP | A | 3 | 35.831 | 5.336 | 20.768 | 1.00 43.36 | C |
| ATOM | 51 | CG | ASP | A | 3 | 35.898 | 4.734 | 22.204 | 1.00 46.34 | C |
| ATOM | 52 | OD1 | ASP | A | 3 | 36.548 | 3.673 | 22.411 | 1.00 45.20 | O |
| ATOM | 53 | OD2 | ASP | A | 3 | 35.375 | 5.402 | 23.096 | 1.00 51.42 | O |
| ATOM | 54 | C | ASP | A | 3 | 37.187 | 5.895 | 18.727 | 1.00 39.54 | C |
| ATOM | 55 | O | ASP | A | 3 | 37.526 | 5.003 | 18.015 | 1.00 36.33 | O |
| ATOM | 57 | N | PHE | A | 4 | 36.740 | 7.029 | 18.230 | 1.00 40.01 | N |
| ATOM | 58 | CA | PHE | A | 4 | 37.014 | 7.336 | 16.828 | 1.00 39.34 | C |
| ATOM | 60 | CB | PHE | A | 4 | 36.748 | 8.784 | 16.542 | 1.00 39.01 | C |
| ATOM | 63 | CG | PHE | A | 4 | 37.007 | 9.100 | 15.139 | 1.00 40.24 | C |
| ATOM | 64 | CD1 | PHE | A | 4 | 36.113 | 8.658 | 14.181 | 1.00 42.88 | C |
| ATOM | 66 | CE1 | PHE | A | 4 | 36.362 | 8.860 | 12.834 | 1.00 43.41 | C |
| ATOM | 68 | CZ | PHE | A | 4 | 37.548 | 9.481 | 12.450 | 1.00 40.84 | C |
| ATOM | 70 | CE2 | PHE | A | 4 | 38.445 | 9.923 | 13.390 | 1.00 39.99 | C |
| ATOM | 72 | CD2 | PHE | A | 4 | 38.206 | 9.697 | 14.741 | 1.00 38.67 | C |
| ATOM | 74 | C | PHE | A | 4 | 38.447 | 6.982 | 16.287 | 1.00 38.41 | C |
| ATOM | 75 | O | PHE | A | 4 | 38.632 | 6.188 | 15.326 | 1.00 37.84 | O |
| ATOM | 77 | N | VAL | A | 5 | 39.459 | 7.552 | 16.929 | 1.00 39.80 | N |
| ATOM | 78 | CA | VAL | A | 5 | 40.863 | 7.302 | 16.532 | 1.00 39.12 | C |
| ATOM | 80 | CB | VAL | A | 5 | 41.832 | 7.994 | 17.471 | 1.00 40.00 | C |
| ATOM | 82 | CG1 | VAL | A | 5 | 43.292 | 7.610 | 17.120 | 1.00 34.65 | C |
| ATOM | 86 | CG2 | VAL | A | 5 | 41.597 | 9.515 | 17.449 | 1.00 36.50 | C |
| ATOM | 90 | C | VAL | A | 5 | 41.203 | 5.854 | 16.534 | 1.00 40.24 | C |
| ATOM | 91 | O | VAL | A | 5 | 41.846 | 5.337 | 15.614 | 1.00 39.45 | O |
| ATOM | 93 | N | ARG | A | 6 | 40.734 | 5.130 | 17.555 | 1.00 41.95 | N |
| ATOM | 94 | CA | ARG | A | 6 | 40.971 | 3.692 | 17.573 | 1.00 42.22 | C |
| ATOM | 96 | CB | ARG | A | 6 | 40.695 | 3.128 | 18.979 | 1.00 42.67 | C |
| ATOM | 99 | CG | ARG | A | 6 | 41.687 | 3.685 | 19.986 | 1.00 45.01 | C |
| ATOM | 102 | CD | ARG | A | 6 | 41.385 | 3.360 | 21.445 | 1.00 46.86 | C |
| ATOM | 105 | NE | ARG | A | 6 | 42.179 | 4.217 | 22.335 | 1.00 46.22 | N |
| ATOM | 107 | CZ | ARG | A | 6 | 43.471 | 4.043 | 22.607 | 1.00 43.79 | C |
| ATOM | 108 | NH1 | ARG | A | 6 | 44.140 | 3.040 | 22.057 | 1.00 44.27 | N |
| ATOM | 111 | NH2 | ARG | A | 6 | 44.098 | 4.892 | 23.461 | 1.00 49.15 | N |
| ATOM | 114 | C | ARG | A | 6 | 40.257 | 2.919 | 16.459 | 1.00 42.70 | C |
| ATOM | 115 | O | ARG | A | 6 | 40.715 | 1.864 | 16.046 | 1.00 43.47 | O |
| ATOM | 117 | N | GLN | A | 7 | 39.157 | 3.442 | 15.934 | 1.00 43.72 | N |
| ATOM | 118 | CA | GLN | A | 7 | 38.462 | 2.741 | 14.826 | 1.00 43.50 | C |
| ATOM | 120 | CB | GLN | A | 7 | 36.942 | 2.884 | 14.934 | 1.00 44.41 | C |
| ATOM | 123 | CG | GLN | A | 7 | 36.334 | 4.286 | 14.587 | 1.00 49.44 | C |
| ATOM | 126 | CD | GLN | A | 7 | 35.161 | 4.240 | 13.571 | 1.00 56.61 | C |
| ATOM | 127 | OE1 | GLN | A | 7 | 34.923 | 3.214 | 12.911 | 1.00 62.15 | O |
| ATOM | 128 | NE2 | GLN | A | 7 | 34.412 | 5.350 | 13.459 | 1.00 62.20 | N |
| ATOM | 131 | C | GLN | A | 7 | 38.908 | 3.198 | 13.416 | 1.00 42.71 | C |
| ATOM | 132 | O | GLN | A | 7 | 38.763 | 2.473 | 12.455 | 1.00 41.90 | O |
| ATOM | 134 | N | CYS | A | 8 | 39.418 | 4.408 | 13.322 | 1.00 41.81 | N |
| ATOM | 135 | CA | CYS | A | 8 | 39.768 | 5.063 | 12.016 | 1.00 40.76 | C |
| ATOM | 137 | CB | CYS | A | 8 | 39.579 | 6.568 | 12.224 | 1.00 40.40 | C |
| ATOM | 140 | SG | CYS | A | 8 | 40.073 | 7.732 | 10.854 | 1.00 42.15 | S |
| ATOM | 142 | C | CYS | A | 8 | 41.186 | 4.710 | 11.485 | 1.00 39.98 | C |
| ATOM | 143 | O | CYS | A | 8 | 41.409 | 4.496 | 10.282 | 1.00 40.49 | O |
| ATOM | 145 | N | PHE | A | 9 | 42.141 | 4.563 | 12.396 | 1.00 39.04 | N |
| ATOM | 146 | CA | PHE | A | 9 | 43.501 | 4.272 | 12.052 | 1.00 37.93 | C |
| ATOM | 148 | CB | PHE | A | 9 | 44.375 | 5.256 | 12.812 | 1.00 38.19 | C |
| ATOM | 151 | CG | PHE | A | 9 | 44.104 | 6.657 | 12.432 | 1.00 31.90 | C |

FIG. 15C

```
ATOM   152  CD1  PHE A    9      44.692    7.190   11.317  1.00 32.40           C
ATOM   154  CE1  PHE A    9      44.454    8.473   10.986  1.00 27.02           C
ATOM   156  CZ   PHE A    9      43.652    9.216   11.685  1.00 32.18           C
ATOM   158  CE2  PHE A    9      43.036    8.710   12.814  1.00 32.36           C
ATOM   160  CD2  PHE A    9      43.299    7.436   13.182  1.00 30.81           C
ATOM   162  C    PHE A    9      43.937    2.872   12.361  1.00 40.11           C
ATOM   163  O    PHE A    9      43.472    2.232   13.305  1.00 38.23           O
ATOM   165  N    ASN A   10      44.867    2.401   11.579  1.00 41.36           N
ATOM   166  CA   ASN A   10      45.299    1.074   11.753  1.00 43.17           C
ATOM   168  CB   ASN A   10      46.002    0.568   10.504  1.00 45.30           C
ATOM   171  CG   ASN A   10      47.485    0.770   10.490  1.00 49.13           C
ATOM   172  OD1  ASN A   10      48.109    1.231   11.457  1.00 55.05           O
ATOM   173  ND2  ASN A   10      48.086    0.394    9.355  1.00 56.56           N
ATOM   176  C    ASN A   10      46.059    0.920   13.068  1.00 43.49           C
ATOM   177  O    ASN A   10      46.443    1.924   13.716  1.00 41.30           O
ATOM   179  N    PRO A   11      46.174   -0.332   13.524  1.00 43.22           N
ATOM   180  CA   PRO A   11      46.665   -0.469   14.876  1.00 42.66           C
ATOM   182  CB   PRO A   11      46.538   -1.983   15.155  1.00 43.18           C
ATOM   185  CG   PRO A   11      45.578   -2.512   14.138  1.00 44.32           C
ATOM   188  CD   PRO A   11      45.433   -1.529   13.059  1.00 43.91           C
ATOM   191  C    PRO A   11      48.094   -0.021   15.037  1.00 40.71           C
ATOM   192  O    PRO A   11      48.399    0.518   16.080  1.00 40.83           O
ATOM   193  N    MET A   12      48.949   -0.280   14.039  1.00 39.97           N
ATOM   194  CA   MET A   12      50.332    0.177   14.063  1.00 39.17           C
ATOM   196  CB   MET A   12      51.046   -0.192   12.782  1.00 40.79           C
ATOM   199  CG   MET A   12      52.432    0.498   12.579  1.00 46.56           C
ATOM   202  SD   MET A   12      53.061    0.207   10.883  1.00 62.60           S
ATOM   203  CE   MET A   12      51.840    1.130    9.888  1.00 60.09           C
ATOM   207  C    MET A   12      50.401    1.686   14.309  1.00 37.46           C
ATOM   208  O    MET A   12      51.213    2.141   15.092  1.00 35.55           O
ATOM   210  N    ILE A   13      49.532    2.436   13.634  1.00 35.53           N
ATOM   211  CA   ILE A   13      49.544    3.896   13.670  1.00 35.50           C
ATOM   213  CB   ILE A   13      48.616    4.513   12.594  1.00 33.84           C
ATOM   215  CG1  ILE A   13      49.112    4.292   11.162  1.00 36.54           C
ATOM   218  CD1  ILE A   13      50.209    5.154   10.801  1.00 40.55           C
ATOM   222  CG2  ILE A   13      48.304    6.056   12.857  1.00 33.81           C
ATOM   226  C    ILE A   13      49.114    4.326   15.061  1.00 34.57           C
ATOM   227  O    ILE A   13      49.746    5.203   15.694  1.00 34.50           O
ATOM   229  N    VAL A   14      48.037    3.727   15.564  1.00 33.15           N
ATOM   230  CA   VAL A   14      47.560    4.085   16.871  1.00 34.21           C
ATOM   232  CB   VAL A   14      46.238    3.382   17.252  1.00 34.30           C
ATOM   234  CG1  VAL A   14      45.764    3.804   18.648  1.00 33.03           C
ATOM   238  CG2  VAL A   14      45.143    3.737   16.259  1.00 35.73           C
ATOM   242  C    VAL A   14      48.637    3.828   17.927  1.00 35.71           C
ATOM   243  O    VAL A   14      48.869    4.682   18.779  1.00 36.45           O
ATOM   245  N    GLU A   15      49.309    2.691   17.838  1.00 37.13           N
ATOM   246  CA   GLU A   15      50.369    2.354   18.800  1.00 39.91           C
ATOM   248  CB   GLU A   15      51.026    0.998   18.463  1.00 40.71           C
ATOM   251  CG   GLU A   15      50.412   -0.243   19.100  1.00 48.93           C
ATOM   254  CD   GLU A   15      51.305   -1.515   18.976  1.00 55.78           C
ATOM   255  OE1  GLU A   15      52.425   -1.469   18.368  1.00 57.79           O
ATOM   256  OE2  GLU A   15      50.855   -2.578   19.489  1.00 60.50           O
ATOM   257  C    GLU A   15      51.471    3.447   18.744  1.00 39.79           C
ATOM   258  O    GLU A   15      51.893    3.961   19.781  1.00 38.30           O
ATOM   260  N    LEU A   16      51.949    3.743   17.527  1.00 40.41           N
ATOM   261  CA   LEU A   16      53.006    4.748   17.359  1.00 40.78           C
ATOM   263  CB   LEU A   16      53.446    4.889   15.911  1.00 41.25           C
ATOM   266  CG   LEU A   16      54.075    3.611   15.380  1.00 42.02           C
ATOM   268  CD1  LEU A   16      54.294    3.737   13.894  1.00 41.89           C
ATOM   272  CD2  LEU A   16      55.363    3.242   16.153  1.00 42.80           C
ATOM   276  C    LEU A   16      52.596    6.085   17.905  1.00 40.38           C
ATOM   277  O    LEU A   16      53.429    6.760   18.567  1.00 39.11           O
ATOM   279  N    ALA A   17      51.343    6.469   17.669  1.00 38.39           N
```

FIG. 15D

```
ATOM   280  CA   ALA A  17      50.814   7.733  18.214  1.00 39.46           C
ATOM   282  CB   ALA A  17      49.439   8.076  17.652  1.00 38.01           C
ATOM   286  C    ALA A  17      50.776   7.753  19.760  1.00 40.24           C
ATOM   287  O    ALA A  17      51.120   8.751  20.408  1.00 38.60           O
ATOM   289  N    GLU A  18      50.360   6.646  20.349  1.00 42.22           N
ATOM   290  CA   GLU A  18      50.302   6.592  21.813  1.00 43.95           C
ATOM   292  CB   GLU A  18      49.642   5.305  22.265  1.00 44.73           C
ATOM   295  CG   GLU A  18      48.140   5.305  22.036  1.00 46.92           C
ATOM   298  CD   GLU A  18      47.446   4.139  22.729  1.00 48.80           C
ATOM   299  OE1  GLU A  18      47.661   3.013  22.289  1.00 49.43           O
ATOM   300  OE2  GLU A  18      46.703   4.360  23.721  1.00 53.91           O
ATOM   301  C    GLU A  18      51.716   6.727  22.394  1.00 44.65           C
ATOM   302  O    GLU A  18      51.903   7.477  23.336  1.00 44.11           O
ATOM   304  N    LYS A  19      52.680   6.030  21.794  1.00 46.00           N
ATOM   305  CA   LYS A  19      54.089   6.073  22.208  1.00 47.58           C
ATOM   307  CB   LYS A  19      54.899   5.094  21.380  1.00 48.56           C
ATOM   310  CG   LYS A  19      54.717   3.593  21.687  1.00 51.09           C
ATOM   313  CD   LYS A  19      55.743   2.795  20.830  1.00 55.89           C
ATOM   316  CE   LYS A  19      55.447   1.282  20.716  1.00 59.14           C
ATOM   319  NZ   LYS A  19      56.675   0.552  20.235  1.00 59.08           N
ATOM   323  C    LYS A  19      54.721   7.477  22.045  1.00 48.06           C
ATOM   324  O    LYS A  19      55.474   7.937  22.906  1.00 47.61           O
ATOM   326  N    ALA A  20      54.436   8.136  20.930  1.00 46.96           N
ATOM   327  CA   ALA A  20      54.903   9.479  20.695  1.00 48.49           C
ATOM   329  CB   ALA A  20      54.526   9.998  19.225  1.00 47.84           C
ATOM   333  C    ALA A  20      54.338  10.402  21.752  1.00 49.19           C
ATOM   334  O    ALA A  20      55.038  11.276  22.241  1.00 49.21           O
ATOM   336  N    MET A  21      53.084  10.198  22.131  1.00 50.73           N
ATOM   337  CA   MET A  21      52.445  11.108  23.057  1.00 52.02           C
ATOM   339  CB   MET A  21      50.950  10.867  23.139  1.00 51.42           C
ATOM   342  CG   MET A  21      50.267  11.467  21.923  1.00 49.73           C
ATOM   345  SD   MET A  21      48.495  11.479  21.966  1.00 44.10           S
ATOM   346  CE   MET A  21      48.082  13.087  22.545  1.00 41.49           C
ATOM   350  C    MET A  21      53.126  11.039  24.413  1.00 54.84           C
ATOM   351  O    MET A  21      53.518  12.079  24.964  1.00 55.52           O
ATOM   353  N    LYS A  22      53.354   9.824  24.890  1.00 57.57           N
ATOM   354  CA   LYS A  22      53.987   9.630  26.193  1.00 59.31           C
ATOM   356  CB   LYS A  22      53.859   8.177  26.603  1.00 60.30           C
ATOM   359  CG   LYS A  22      52.368   7.746  26.726  1.00 63.31           C
ATOM   362  CD   LYS A  22      52.229   6.314  27.283  1.00 67.07           C
ATOM   365  CE   LYS A  22      50.800   5.752  27.151  1.00 68.81           C
ATOM   368  NZ   LYS A  22      50.629   4.591  28.075  1.00 70.93           N
ATOM   372  C    LYS A  22      55.440  10.148  26.216  1.00 59.45           C
ATOM   373  O    LYS A  22      55.781  10.969  27.083  1.00 59.33           O
ATOM   375  N    GLU A  23      56.245   9.735  25.223  1.00 59.22           N
ATOM   376  CA   GLU A  23      57.616  10.256  24.998  1.00 59.66           C
ATOM   378  CB   GLU A  23      58.186   9.782  23.618  1.00 59.02           C
ATOM   381  CG   GLU A  23      59.705   9.948  23.441  1.00 60.52           C
ATOM   384  CD   GLU A  23      60.265   9.386  22.104  1.00 61.02           C
ATOM   385  OE1  GLU A  23      59.536   9.342  21.091  1.00 63.65           O
ATOM   386  OE2  GLU A  23      61.447   9.008  22.063  1.00 61.08           O
ATOM   387  C    GLU A  23      57.679  11.781  25.099  1.00 59.34           C
ATOM   388  O    GLU A  23      58.688  12.358  25.503  1.00 59.71           O
ATOM   390  N    TYR A  24      56.583  12.429  24.748  1.00 59.76           N
ATOM   391  CA   TYR A  24      56.513  13.871  24.706  1.00 59.92           C
ATOM   393  CB   TYR A  24      56.107  14.290  23.290  1.00 60.13           C
ATOM   396  CG   TYR A  24      56.570  15.662  22.869  1.00 61.52           C
ATOM   397  CD1  TYR A  24      57.901  15.900  22.553  1.00 62.62           C
ATOM   399  CE1  TYR A  24      58.332  17.177  22.150  1.00 64.21           C
ATOM   401  CZ   TYR A  24      57.416  18.225  22.052  1.00 63.87           C
ATOM   402  OH   TYR A  24      57.846  19.480  21.655  1.00 65.64           O
ATOM   404  CE2  TYR A  24      56.082  18.010  22.357  1.00 63.99           C
ATOM   406  CD2  TYR A  24      55.662  16.726  22.756  1.00 63.49           C
```

FIG. 15E

```
ATOM    408  C    TYR A  24      55.545  14.403  25.765  1.00 59.58           C
ATOM    409  O    TYR A  24      55.087  15.534  25.666  1.00 59.96           O
ATOM    411  N    GLY A  25      55.242  13.571  26.764  1.00 59.90           N
ATOM    412  CA   GLY A  25      54.493  13.986  27.971  1.00 59.81           C
ATOM    415  C    GLY A  25      52.975  13.809  28.081  1.00 59.97           C
ATOM    416  O    GLY A  25      52.454  13.843  29.209  1.00 60.51           O
ATOM    418  N    GLU A  26      52.282  13.554  26.952  1.00 59.10           N
ATOM    419  CA   GLU A  26      50.803  13.738  26.812  1.00 58.30           C
ATOM    421  CB   GLU A  26      50.511  14.338  25.424  1.00 58.29           C
ATOM    424  CG   GLU A  26      51.224  15.617  25.096  1.00 58.31           C
ATOM    427  CD   GLU A  26      50.792  16.726  25.993  1.00 59.07           C
ATOM    428  OE1  GLU A  26      49.566  16.850  26.204  1.00 62.18           O
ATOM    429  OE2  GLU A  26      51.666  17.476  26.481  1.00 59.44           O
ATOM    430  C    GLU A  26      49.911  12.484  26.935  1.00 58.16           C
ATOM    431  O    GLU A  26      50.320  11.351  26.616  1.00 58.80           O
ATOM    433  N    ASP A  27      48.659  12.703  27.329  1.00 57.04           N
ATOM    434  CA   ASP A  27      47.728  11.607  27.544  1.00 56.23           C
ATOM    436  CB   ASP A  27      46.989  11.777  28.873  1.00 56.36           C
ATOM    439  CG   ASP A  27      45.982  10.649  29.149  1.00 58.44           C
ATOM    440  OD1  ASP A  27      45.917   9.653  28.376  1.00 59.06           O
ATOM    441  OD2  ASP A  27      45.240  10.742  30.157  1.00 62.08           O
ATOM    442  C    ASP A  27      46.696  11.564  26.402  1.00 54.78           C
ATOM    443  O    ASP A  27      45.894  12.491  26.277  1.00 53.52           O
ATOM    445  N    PRO A  28      46.676  10.462  25.627  1.00 53.87           N
ATOM    446  CA   PRO A  28      45.700  10.276  24.528  1.00 53.60           C
ATOM    448  CB   PRO A  28      46.037   8.879  23.983  1.00 53.21           C
ATOM    451  CG   PRO A  28      46.822   8.218  25.035  1.00 54.25           C
ATOM    454  CD   PRO A  28      47.586   9.300  25.725  1.00 53.63           C
ATOM    457  C    PRO A  28      44.264  10.261  24.976  1.00 53.18           C
ATOM    458  O    PRO A  28      43.363  10.578  24.198  1.00 52.05           O
ATOM    459  N    LYS A  29      44.048   9.894  26.238  1.00 53.31           N
ATOM    460  CA   LYS A  29      42.709   9.864  26.790  1.00 53.08           C
ATOM    462  CB   LYS A  29      42.678   8.987  28.050  1.00 53.95           C
ATOM    465  CG   LYS A  29      42.953   7.491  27.783  1.00 57.43           C
ATOM    468  CD   LYS A  29      42.406   6.593  28.927  1.00 62.00           C
ATOM    471  CE   LYS A  29      41.955   5.187  28.437  1.00 62.89           C
ATOM    474  NZ   LYS A  29      41.360   4.375  29.540  1.00 61.45           N
ATOM    478  C    LYS A  29      42.165  11.277  27.056  1.00 51.76           C
ATOM    479  O    LYS A  29      40.972  11.479  27.102  1.00 51.40           O
ATOM    481  N    ILE A  30      43.035  12.262  27.187  1.00 50.90           N
ATOM    482  CA   ILE A  30      42.615  13.618  27.477  1.00 50.42           C
ATOM    484  CB   ILE A  30      43.505  14.239  28.616  1.00 51.21           C
ATOM    486  CG1  ILE A  30      43.253  13.532  29.953  1.00 53.48           C
ATOM    489  CD1  ILE A  30      43.921  14.213  31.165  1.00 55.34           C
ATOM    493  CG2  ILE A  30      43.261  15.776  28.768  1.00 51.82           C
ATOM    497  C    ILE A  30      42.713  14.501  26.246  1.00 48.45           C
ATOM    498  O    ILE A  30      41.763  15.195  25.886  1.00 48.91           O
ATOM    500  N    GLU A  31      43.887  14.489  25.619  1.00 46.18           N
ATOM    501  CA   GLU A  31      44.183  15.345  24.505  1.00 44.26           C
ATOM    503  CB   GLU A  31      45.683  15.708  24.473  1.00 45.81           C
ATOM    506  CG   GLU A  31      46.152  16.676  25.618  1.00 48.19           C
ATOM    509  CD   GLU A  31      45.103  17.734  25.877  1.00 52.01           C
ATOM    510  OE1  GLU A  31      44.886  18.554  24.952  1.00 51.03           O
ATOM    511  OE2  GLU A  31      44.449  17.713  26.959  1.00 53.86           O
ATOM    512  C    GLU A  31      43.769  14.468  23.314  1.00 42.26           C
ATOM    513  O    GLU A  31      44.612  13.862  22.649  1.00 40.25           O
ATOM    515  N    THR A  32      42.467  14.347  23.109  1.00 39.04           N
ATOM    516  CA   THR A  32      41.988  13.407  22.131  1.00 37.70           C
ATOM    518  CB   THR A  32      40.578  12.869  22.416  1.00 38.00           C
ATOM    520  OG1  THR A  32      39.651  13.931  22.420  1.00 39.31           O
ATOM    522  CG2  THR A  32      40.544  12.091  23.782  1.00 39.07           C
ATOM    526  C    THR A  32      42.119  14.005  20.747  1.00 35.54           C
ATOM    527  O    THR A  32      42.374  13.291  19.814  1.00 34.64           O
```

FIG. 15F

```
ATOM   529  N    ASN A   33      42.047  15.311  20.619  1.00 34.52           N
ATOM   530  CA   ASN A   33      42.145  15.911  19.313  1.00 33.77           C
ATOM   532  CB   ASN A   33      41.674  17.313  19.304  1.00 33.95           C
ATOM   535  CG   ASN A   33      40.179  17.452  19.360  1.00 35.32           C
ATOM   536  OD1  ASN A   33      39.715  18.561  19.587  1.00 38.41           O
ATOM   537  ND2  ASN A   33      39.418  16.381  19.074  1.00 32.64           N
ATOM   540  C    ASN A   33      43.580  15.840  18.857  1.00 34.12           C
ATOM   541  O    ASN A   33      43.853  15.485  17.733  1.00 32.00           O
ATOM   543  N    LYS A   34      44.500  16.115  19.765  1.00 34.79           N
ATOM   544  CA   LYS A   34      45.919  15.927  19.490  1.00 34.89           C
ATOM   546  CB   LYS A   34      46.721  16.362  20.702  1.00 36.54           C
ATOM   549  CG   LYS A   34      48.206  16.161  20.584  1.00 39.36           C
ATOM   552  CD   LYS A   34      48.870  16.791  21.860  1.00 47.58           C
ATOM   555  CE   LYS A   34      48.868  18.335  21.853  1.00 50.27           C
ATOM   558  NZ   LYS A   34      48.393  18.882  23.193  1.00 55.33           N
ATOM   562  C    LYS A   34      46.265  14.502  19.096  1.00 33.45           C
ATOM   563  O    LYS A   34      46.964  14.323  18.101  1.00 31.93           O
ATOM   565  N    PHE A   35      45.730  13.501  19.826  1.00 32.58           N
ATOM   566  CA   PHE A   35      45.875  12.063  19.493  1.00 32.48           C
ATOM   568  CB   PHE A   35      44.996  11.244  20.484  1.00 31.76           C
ATOM   571  CG   PHE A   35      45.077   9.740  20.379  1.00 31.60           C
ATOM   572  CD1  PHE A   35      46.201   9.067  19.980  1.00 30.51           C
ATOM   574  CE1  PHE A   35      46.237   7.661  19.937  1.00 32.27           C
ATOM   576  CZ   PHE A   35      45.177   6.935  20.348  1.00 37.25           C
ATOM   578  CE2  PHE A   35      44.039   7.583  20.762  1.00 35.15           C
ATOM   580  CD2  PHE A   35      44.009   8.981  20.824  1.00 36.86           C
ATOM   582  C    PHE A   35      45.411  11.797  18.025  1.00 31.14           C
ATOM   583  O    PHE A   35      46.058  11.081  17.267  1.00 30.28           O
ATOM   585  N    ALA A   36      44.271  12.387  17.665  1.00 31.50           N
ATOM   586  CA   ALA A   36      43.759  12.234  16.292  1.00 30.02           C
ATOM   588  CB   ALA A   36      42.380  12.805  16.164  1.00 29.01           C
ATOM   592  C    ALA A   36      44.697  12.898  15.276  1.00 29.95           C
ATOM   593  O    ALA A   36      44.958  12.329  14.209  1.00 29.06           O
ATOM   595  N    ALA A   37      45.231  14.082  15.617  1.00 27.72           N
ATOM   596  CA   ALA A   37      46.127  14.794  14.720  1.00 27.19           C
ATOM   598  CB   ALA A   37      46.406  16.237  15.252  1.00 26.52           C
ATOM   602  C    ALA A   37      47.420  14.046  14.511  1.00 27.00           C
ATOM   603  O    ALA A   37      47.950  14.030  13.399  1.00 27.38           O
ATOM   605  N    ILE A   38      47.954  13.461  15.573  1.00 27.10           N
ATOM   606  CA   ILE A   38      49.239  12.726  15.521  1.00 28.20           C
ATOM   608  CB   ILE A   38      49.710  12.324  16.925  1.00 30.03           C
ATOM   610  CG1  ILE A   38      50.129  13.588  17.683  1.00 31.11           C
ATOM   613  CD1  ILE A   38      50.240  13.306  19.252  1.00 33.33           C
ATOM   617  CG2  ILE A   38      50.866  11.234  16.864  1.00 26.80           C
ATOM   621  C    ILE A   38      49.068  11.492  14.675  1.00 28.32           C
ATOM   622  O    ILE A   38      49.911  11.222  13.811  1.00 27.19           O
ATOM   624  N    CYS A   39      47.929  10.791  14.825  1.00 26.33           N
ATOM   625  CA   CYS A   39      47.654   9.640  13.946  1.00 27.24           C
ATOM   627  CB   CYS A   39      46.325   8.957  14.327  1.00 28.57           C
ATOM   630  SG   CYS A   39      46.482   8.073  15.870  1.00 32.84           S
ATOM   632  C    CYS A   39      47.574  10.045  12.485  1.00 24.91           C
ATOM   633  O    CYS A   39      48.128   9.399  11.634  1.00 25.54           O
ATOM   635  N    THR A   40      46.834  11.091  12.214  1.00 25.66           N
ATOM   636  CA   THR A   40      46.624  11.561  10.853  1.00 25.89           C
ATOM   638  CB   THR A   40      45.742  12.791  10.851  1.00 26.03           C
ATOM   640  OG1  THR A   40      44.458  12.490  11.452  1.00 26.97           O
ATOM   642  CG2  THR A   40      45.513  13.288   9.457  1.00 25.07           C
ATOM   646  C    THR A   40      47.987  11.888  10.237  1.00 25.84           C
ATOM   647  O    THR A   40      48.301  11.509   9.111  1.00 26.38           O
ATOM   649  N    HIS A   41      48.749  12.681  10.943  1.00 24.88           N
ATOM   650  CA   HIS A   41      50.096  13.100  10.454  1.00 25.98           C
ATOM   652  CB   HIS A   41      50.710  14.208  11.363  1.00 26.34           C
ATOM   655  CG   HIS A   41      52.135  14.537  11.071  1.00 24.61           C
```

FIG. 15G

```
ATOM    656  ND1 HIS A   41      53.166  13.780  11.564  1.00 24.99           N
ATOM    658  CE1 HIS A   41      54.313  14.295  11.172  1.00 27.54           C
ATOM    660  NE2 HIS A   41      54.069  15.346  10.413  1.00 22.92           N
ATOM    662  CD2 HIS A   41      52.714  15.546  10.361  1.00 26.94           C
ATOM    664  C   HIS A   41      51.027  11.898  10.262  1.00 25.39           C
ATOM    665  O   HIS A   41      51.700  11.744   9.231  1.00 24.47           O
ATOM    667  N   LEU A   42      51.033  10.999  11.214  1.00 25.11           N
ATOM    668  CA  LEU A   42      51.739   9.740  10.958  1.00 27.52           C
ATOM    670  CB  LEU A   42      51.675   8.772  12.137  1.00 27.69           C
ATOM    673  CG  LEU A   42      52.538   8.928  13.366  1.00 31.80           C
ATOM    675  CD1 LEU A   42      51.909   8.078  14.530  1.00 34.67           C
ATOM    679  CD2 LEU A   42      53.984   8.476  13.059  1.00 34.51           C
ATOM    683  C   LEU A   42      51.287   9.045   9.702  1.00 26.25           C
ATOM    684  O   LEU A   42      52.099   8.585   8.909  1.00 27.53           O
ATOM    686  N   GLU A   43      49.985   8.943   9.477  1.00 26.61           N
ATOM    687  CA  GLU A   43      49.543   8.160   8.321  1.00 26.85           C
ATOM    689  CB  GLU A   43      47.996   7.994   8.340  1.00 28.03           C
ATOM    692  CG  GLU A   43      47.566   7.084   7.311  1.00 32.44           C
ATOM    695  CD  GLU A   43      46.169   6.480   7.510  1.00 39.32           C
ATOM    696  OE1 GLU A   43      45.851   5.546   6.765  1.00 43.40           O
ATOM    697  OE2 GLU A   43      45.385   6.966   8.312  1.00 43.91           O
ATOM    698  C   GLU A   43      49.955   8.865   7.033  1.00 26.06           C
ATOM    699  O   GLU A   43      50.295   8.232   6.029  1.00 26.34           O
ATOM    701  N   VAL A   44      49.909  10.185   7.020  1.00 23.78           N
ATOM    702  CA  VAL A   44      50.323  10.911   5.811  1.00 21.96           C
ATOM    704  CB  VAL A   44      49.966  12.383   5.908  1.00 22.48           C
ATOM    706  CG1 VAL A   44      50.695  13.245   4.839  1.00 22.23           C
ATOM    710  CG2 VAL A   44      48.441  12.534   5.884  1.00 23.28           C
ATOM    714  C   VAL A   44      51.794  10.701   5.538  1.00 22.90           C
ATOM    715  O   VAL A   44      52.186  10.414   4.392  1.00 23.74           O
ATOM    717  N   CYS A   45      52.595  10.761   6.581  1.00 22.26           N
ATOM    718  CA  CYS A   45      54.021  10.450   6.426  1.00 23.67           C
ATOM    720  CB  CYS A   45      54.761  10.631   7.732  1.00 23.37           C
ATOM    723  SG  CYS A   45      54.877  12.405   8.328  1.00 25.99           S
ATOM    725  C   CYS A   45      54.280   9.033   5.830  1.00 23.51           C
ATOM    726  O   CYS A   45      55.125   8.860   4.964  1.00 23.06           O
ATOM    728  N   PHE A   46      53.627   8.026   6.362  1.00 25.19           N
ATOM    729  CA  PHE A   46      53.761   6.714   5.852  1.00 26.03           C
ATOM    731  CB  PHE A   46      53.050   5.689   6.734  1.00 27.99           C
ATOM    734  CG  PHE A   46      53.596   5.627   8.169  1.00 31.74           C
ATOM    735  CD1 PHE A   46      52.924   4.903   9.133  1.00 42.03           C
ATOM    737  CE1 PHE A   46      53.407   4.838  10.463  1.00 42.43           C
ATOM    739  CZ  PHE A   46      54.558   5.469  10.790  1.00 43.17           C
ATOM    741  CE2 PHE A   46      55.220   6.209   9.834  1.00 41.76           C
ATOM    743  CD2 PHE A   46      54.740   6.269   8.538  1.00 37.20           C
ATOM    745  C   PHE A   46      53.252   6.601   4.434  1.00 27.54           C
ATOM    746  O   PHE A   46      53.902   5.987   3.603  1.00 27.30           O
ATOM    748  N   MET A   47      52.127   7.221   4.119  1.00 28.70           N
ATOM    749  CA  MET A   47      51.658   7.197   2.735  1.00 28.78           C
ATOM    751  CB  MET A   47      50.304   7.827   2.597  1.00 28.05           C
ATOM    754  CG  MET A   47      49.155   7.042   3.260  1.00 30.76           C
ATOM    757  SD  MET A   47      47.646   8.044   3.112  1.00 31.27           S
ATOM    758  CE  MET A   47      47.341   7.951   1.406  1.00 30.23           C
ATOM    762  C   MET A   47      52.602   7.921   1.775  1.00 29.96           C
ATOM    763  O   MET A   47      52.790   7.463   0.631  1.00 31.63           O
ATOM    765  N   TYR A   48      53.183   9.028   2.226  1.00 28.93           N
ATOM    766  CA  TYR A   48      54.063   9.828   1.433  1.00 28.12           C
ATOM    768  CB  TYR A   48      54.509  11.043   2.218  1.00 26.67           C
ATOM    771  CG  TYR A   48      54.988  12.219   1.405  1.00 26.63           C
ATOM    772  CD1 TYR A   48      54.207  13.365   1.308  1.00 25.62           C
ATOM    774  CE1 TYR A   48      54.660  14.471   0.711  1.00 20.45           C
ATOM    776  CZ  TYR A   48      55.859  14.446   0.020  1.00 24.91           C
ATOM    777  OH  TYR A   48      56.264  15.598  -0.589  1.00 26.73           O
```

FIG. 15H

```
ATOM    779  CE2 TYR A   48      56.652  13.337   0.068  1.00 24.50           C
ATOM    781  CD2 TYR A   48      56.230  12.242   0.801  1.00 23.89           C
ATOM    783  C   TYR A   48      55.235   8.951   1.073  1.00 28.14           C
ATOM    784  O   TYR A   48      55.702   8.943  -0.033  1.00 28.09           O
ATOM    786  N   SER A   49      55.713   8.283   2.074  1.00 31.34           N
ATOM    787  CA  SER A   49      56.873   7.448   1.973  1.00 35.16           C
ATOM    789  CB  SER A   49      57.364   7.048   3.319  1.00 34.36           C
ATOM    792  OG  SER A   49      58.502   6.211   3.091  1.00 40.09           O
ATOM    794  C   SER A   49      56.597   6.197   1.167  1.00 37.53           C
ATOM    795  O   SER A   49      57.432   5.810   0.383  1.00 38.85           O
ATOM    797  N   ASP A   50      55.415   5.611   1.302  1.00 41.01           N
ATOM    798  CA  ASP A   50      55.086   4.387   0.521  1.00 44.36           C
ATOM    800  CB  ASP A   50      53.871   3.670   1.158  1.00 44.72           C
ATOM    803  CG  ASP A   50      54.263   2.996   2.523  1.00 48.52           C
ATOM    804  OD1 ASP A   50      53.394   2.439   3.225  1.00 53.16           O
ATOM    805  OD2 ASP A   50      55.482   3.045   2.902  1.00 51.41           O
ATOM    806  C   ASP A   50      54.938   4.657  -0.978  1.00 46.30           C
ATOM    807  O   ASP A   50      55.223   3.805  -1.817  1.00 46.29           O
ATOM    809  N   PHE A   51      54.579   5.882  -1.314  1.00 49.65           N
ATOM    810  CA  PHE A   51      54.555   6.340  -2.711  1.00 52.45           C
ATOM    812  CB  PHE A   51      53.730   7.647  -2.795  1.00 51.92           C
ATOM    815  CG  PHE A   51      52.269   7.456  -2.432  1.00 53.76           C
ATOM    816  CD1 PHE A   51      51.590   8.378  -1.627  1.00 56.10           C
ATOM    818  CE1 PHE A   51      50.252   8.187  -1.302  1.00 52.71           C
ATOM    820  CZ  PHE A   51      49.579   7.085  -1.769  1.00 56.18           C
ATOM    822  CE2 PHE A   51      50.234   6.158  -2.596  1.00 56.57           C
ATOM    824  CD2 PHE A   51      51.567   6.345  -2.906  1.00 55.25           C
ATOM    826  C   PHE A   51      55.948   6.567  -3.310  1.00 53.76           C
ATOM    827  O   PHE A   51      56.169   7.579  -3.945  1.00 54.84           O
ATOM    829  N   GLY A   52      56.882   5.627  -3.135  1.00 55.39           N
ATOM    830  CA  GLY A   52      58.270   5.824  -3.623  1.00 55.86           C
ATOM    833  C   GLY A   52      59.124   4.584  -3.436  1.00 56.18           C
ATOM    834  O   GLY A   52      58.612   3.530  -3.011  1.00 57.12           O
ATOM    836  N   LYS A   73      63.661   2.892  -6.173  1.00 55.58           N
ATOM    837  CA  LYS A   73      63.127   1.698  -5.471  1.00 55.21           C
ATOM    839  CB  LYS A   73      64.266   0.696  -5.157  1.00 55.05           C
ATOM    846  C   LYS A   73      62.439   2.121  -4.171  1.00 54.02           C
ATOM    847  O   LYS A   73      61.217   1.927  -3.973  1.00 56.31           O
ATOM    849  N   HIS A   74      63.257   2.727  -3.306  1.00 51.19           N
ATOM    850  CA  HIS A   74      62.878   3.239  -2.005  1.00 48.42           C
ATOM    852  CB  HIS A   74      63.526   2.328  -0.948  1.00 48.86           C
ATOM    855  CG  HIS A   74      63.718   2.923   0.430  1.00 53.09           C
ATOM    856  ND1 HIS A   74      62.684   3.094   1.342  1.00 58.57           N
ATOM    858  CE1 HIS A   74      63.171   3.574   2.481  1.00 54.31           C
ATOM    860  NE2 HIS A   74      64.479   3.719   2.348  1.00 50.07           N
ATOM    862  CD2 HIS A   74      64.852   3.297   1.087  1.00 54.26           C
ATOM    864  C   HIS A   74      63.400   4.698  -2.015  1.00 44.69           C
ATOM    865  O   HIS A   74      64.551   4.967  -1.689  1.00 45.18           O
ATOM    867  N   ARG A   75      62.556   5.614  -2.489  1.00 39.40           N
ATOM    868  CA  ARG A   75      62.892   7.037  -2.567  1.00 35.64           C
ATOM    870  CB  ARG A   75      61.858   7.781  -3.390  1.00 34.06           C
ATOM    873  CG  ARG A   75      62.093   9.252  -3.420  1.00 33.10           C
ATOM    876  CD  ARG A   75      61.336   9.942  -4.532  1.00 30.93           C
ATOM    879  NE  ARG A   75      61.583  11.378  -4.556  1.00 29.38           N
ATOM    881  CZ  ARG A   75      61.059  12.226  -5.408  1.00 32.69           C
ATOM    882  NH1 ARG A   75      60.260  11.798  -6.389  1.00 38.25           N
ATOM    885  NH2 ARG A   75      61.328  13.504  -5.306  1.00 35.66           N
ATOM    888  C   ARG A   75      62.981   7.704  -1.191  1.00 31.56           C
ATOM    889  O   ARG A   75      63.714   8.681  -1.027  1.00 32.55           O
ATOM    891  N   PHE A   76      62.206   7.269  -0.210  1.00 30.32           N
ATOM    892  CA  PHE A   76      62.102   8.029   1.018  1.00 28.41           C
ATOM    894  CB  PHE A   76      60.675   8.503   1.272  1.00 28.48           C
ATOM    897  CG  PHE A   76      60.187   9.447   0.246  1.00 26.94           C
```

FIG. 15I

```
ATOM    898  CD1 PHE A  76      60.621  10.781   0.228  1.00 27.25           C
ATOM    900  CE1 PHE A  76      60.212  11.599  -0.762  1.00 26.70           C
ATOM    902  CZ  PHE A  76      59.388  11.142  -1.733  1.00 27.76           C
ATOM    904  CE2 PHE A  76      58.973   9.864  -1.711  1.00 27.83           C
ATOM    906  CD2 PHE A  76      59.379   9.023  -0.747  1.00 27.10           C
ATOM    908  C   PHE A  76      62.583   7.249   2.208  1.00 30.06           C
ATOM    909  O   PHE A  76      62.446   6.030   2.237  1.00 31.26           O
ATOM    911  N   GLU A  77      63.162   7.959   3.164  1.00 27.71           N
ATOM    912  CA  GLU A  77      63.458   7.371   4.502  1.00 28.00           C
ATOM    914  CB  GLU A  77      64.846   7.740   4.961  1.00 26.44           C
ATOM    917  CG  GLU A  77      65.305   7.028   6.186  1.00 28.16           C
ATOM    920  CD  GLU A  77      65.654   5.584   5.872  1.00 32.53           C
ATOM    921  OE1 GLU A  77      65.139   4.762   6.621  1.00 38.28           O
ATOM    922  OE2 GLU A  77      66.367   5.286   4.831  1.00 36.50           O
ATOM    923  C   GLU A  77      62.463   7.980   5.402  1.00 27.97           C
ATOM    924  O   GLU A  77      62.321   9.206   5.371  1.00 29.70           O
ATOM    926  N   ILE A  78      61.772   7.176   6.201  1.00 27.77           N
ATOM    927  CA  ILE A  78      60.738   7.699   7.101  1.00 28.41           C
ATOM    929  CB  ILE A  78      59.628   6.703   7.395  1.00 29.44           C
ATOM    931  CG1 ILE A  78      58.998   6.205   6.100  1.00 33.21           C
ATOM    934  CD1 ILE A  78      57.800   5.243   6.268  1.00 39.92           C
ATOM    938  CG2 ILE A  78      58.498   7.366   8.216  1.00 32.00           C
ATOM    942  C   ILE A  78      61.444   8.020   8.373  1.00 28.76           C
ATOM    943  O   ILE A  78      62.180   7.175   8.910  1.00 31.57           O
ATOM    945  N   ILE A  79      61.284   9.241   8.857  1.00 26.91           N
ATOM    946  CA  ILE A  79      61.910   9.628  10.085  1.00 26.42           C
ATOM    948  CB  ILE A  79      62.714  10.984   9.908  1.00 27.71           C
ATOM    950  CG1 ILE A  79      63.917  10.703   8.990  1.00 30.83           C
ATOM    953  CD1 ILE A  79      64.427  11.895   8.278  1.00 36.25           C
ATOM    957  CG2 ILE A  79      63.219  11.472  11.308  1.00 24.00           C
ATOM    961  C   ILE A  79      60.882   9.715  11.214  1.00 27.24           C
ATOM    962  O   ILE A  79      61.122   9.223  12.364  1.00 26.71           O
ATOM    964  N   GLU A  80      59.745  10.309  10.872  1.00 26.46           N
ATOM    965  CA  GLU A  80      58.575  10.339  11.707  1.00 28.25           C
ATOM    967  CB  GLU A  80      57.421  11.028  10.971  1.00 27.80           C
ATOM    970  CG  GLU A  80      56.166  11.382  11.846  1.00 32.66           C
ATOM    973  CD  GLU A  80      56.536  12.175  13.090  1.00 31.24           C
ATOM    974  OE1 GLU A  80      56.533  13.481  13.122  1.00 29.45           O
ATOM    975  OE2 GLU A  80      56.898  11.496  14.046  1.00 39.19           O
ATOM    976  C   GLU A  80      58.177   8.906  12.167  1.00 28.75           C
ATOM    977  O   GLU A  80      58.308   7.949  11.446  1.00 29.51           O
ATOM    979  N   GLY A  81      57.710   8.762  13.380  1.00 31.70           N
ATOM    980  CA  GLY A  81      57.310   7.417  13.827  1.00 32.58           C
ATOM    983  C   GLY A  81      58.398   6.644  14.534  1.00 33.97           C
ATOM    984  O   GLY A  81      58.123   5.643  15.231  1.00 37.29           O
ATOM    986  N   ARG A  82      59.638   7.060  14.383  1.00 33.41           N
ATOM    987  CA  ARG A  82      60.701   6.441  15.138  1.00 33.70           C
ATOM    989  CB  ARG A  82      61.994   6.577  14.372  1.00 33.53           C
ATOM    992  CG  ARG A  82      61.953   5.965  12.977  1.00 35.61           C
ATOM    995  CD  ARG A  82      63.226   6.193  12.351  1.00 37.85           C
ATOM    998  NE  ARG A  82      63.309   5.799  10.935  1.00 36.78           N
ATOM   1000  CZ  ARG A  82      63.724   4.627  10.493  1.00 42.41           C
ATOM   1001  NH1 ARG A  82      64.055   3.665  11.349  1.00 43.93           N
ATOM   1004  NH2 ARG A  82      63.808   4.421   9.185  1.00 45.62           N
ATOM   1007  C   ARG A  82      60.797   7.107  16.528  1.00 33.23           C
ATOM   1008  O   ARG A  82      60.483   8.284  16.685  1.00 33.61           O
ATOM   1010  N   ASP A  83      61.234   6.375  17.544  1.00 34.42           N
ATOM   1011  CA  ASP A  83      61.584   7.033  18.795  1.00 34.75           C
ATOM   1013  CB  ASP A  83      61.906   6.032  19.933  1.00 37.10           C
ATOM   1016  CG  ASP A  83      63.228   5.255  19.760  1.00 41.05           C
ATOM   1017  OD1 ASP A  83      64.295   5.849  19.496  1.00 42.23           O
ATOM   1018  OD2 ASP A  83      63.221   4.014  20.011  1.00 51.05           O
ATOM   1019  C   ASP A  83      62.722   8.029  18.544  1.00 34.57           C
```

FIG. 15J

```
ATOM   1020  O    ASP A   83      63.490   7.899  17.579  1.00 33.96           O
ATOM   1022  N    ARG A   84      62.864   8.971  19.445  1.00 35.28           N
ATOM   1023  CA   ARG A   84      63.754  10.123  19.275  1.00 35.45           C
ATOM   1025  CB   ARG A   84      63.729  10.987  20.547  1.00 36.54           C
ATOM   1028  CG   ARG A   84      63.558  12.438  20.330  1.00 39.98           C
ATOM   1031  CD   ARG A   84      63.533  13.125  21.692  1.00 41.59           C
ATOM   1034  NE   ARG A   84      62.870  14.417  21.723  1.00 47.97           N
ATOM   1036  CZ   ARG A   84      61.914  14.784  22.578  1.00 52.02           C
ATOM   1037  NH1  ARG A   84      61.460  13.970  23.520  1.00 55.25           N
ATOM   1040  NH2  ARG A   84      61.437  16.015  22.519  1.00 55.87           N
ATOM   1043  C    ARG A   84      65.179   9.761  18.939  1.00 34.18           C
ATOM   1044  O    ARG A   84      65.787  10.360  18.019  1.00 33.81           O
ATOM   1046  N    ILE A   85      65.724   8.763  19.630  1.00 32.73           N
ATOM   1047  CA   ILE A   85      67.098   8.353  19.418  1.00 31.80           C
ATOM   1049  CB   ILE A   85      67.539   7.375  20.510  1.00 34.16           C
ATOM   1051  CG1  ILE A   85      67.603   8.142  21.850  1.00 34.27           C
ATOM   1054  CD1  ILE A   85      67.623   7.273  23.022  1.00 38.78           C
ATOM   1058  CG2  ILE A   85      68.878   6.662  20.105  1.00 32.58           C
ATOM   1062  C    ILE A   85      67.337   7.729  18.065  1.00 32.35           C
ATOM   1063  O    ILE A   85      68.304   8.059  17.361  1.00 27.06           O
ATOM   1065  N    MET A   86      66.413   6.851  17.674  1.00 30.51           N
ATOM   1066  CA   MET A   86      66.456   6.287  16.346  1.00 32.48           C
ATOM   1068  CB   MET A   86      65.445   5.157  16.199  1.00 33.04           C
ATOM   1071  CG   MET A   86      65.931   3.934  16.997  1.00 40.81           C
ATOM   1074  SD   MET A   86      67.681   3.564  16.685  1.00 51.34           S
ATOM   1075  CE   MET A   86      67.698   3.446  14.868  1.00 41.58           C
ATOM   1079  C    MET A   86      66.295   7.308  15.258  1.00 29.80           C
ATOM   1080  O    MET A   86      66.954   7.182  14.234  1.00 29.70           O
ATOM   1082  N    ALA A   87      65.434   8.270  15.480  1.00 28.27           N
ATOM   1083  CA   ALA A   87      65.167   9.291  14.519  1.00 28.84           C
ATOM   1085  CB   ALA A   87      64.007  10.201  14.949  1.00 27.51           C
ATOM   1089  C    ALA A   87      66.464  10.077  14.243  1.00 29.11           C
ATOM   1090  O    ALA A   87      66.852  10.258  13.085  1.00 27.10           O
ATOM   1092  N    TRP A   88      67.120  10.512  15.311  1.00 28.23           N
ATOM   1093  CA   TRP A   88      68.350  11.231  15.181  1.00 28.62           C
ATOM   1095  CB   TRP A   88      68.699  11.958  16.481  1.00 28.73           C
ATOM   1098  CG   TRP A   88      67.926  13.220  16.669  1.00 27.17           C
ATOM   1099  CD1  TRP A   88      67.025  13.495  17.686  1.00 29.81           C
ATOM   1101  NE1  TRP A   88      66.504  14.751  17.531  1.00 29.27           N
ATOM   1103  CE2  TRP A   88      67.065  15.335  16.426  1.00 30.57           C
ATOM   1104  CD2  TRP A   88      67.975  14.398  15.861  1.00 28.98           C
ATOM   1105  CE3  TRP A   88      68.679  14.755  14.702  1.00 31.11           C
ATOM   1107  CZ3  TRP A   88      68.491  16.039  14.153  1.00 30.88           C
ATOM   1109  CH2  TRP A   88      67.568  16.952  14.743  1.00 32.87           C
ATOM   1111  CZ2  TRP A   88      66.871  16.617  15.891  1.00 32.84           C
ATOM   1113  C    TRP A   88      69.496  10.341  14.669  1.00 29.09           C
ATOM   1114  O    TRP A   88      70.376  10.844  13.988  1.00 29.20           O
ATOM   1116  N    THR A   89      69.513   9.051  14.992  1.00 28.39           N
ATOM   1117  CA   THR A   89      70.511   8.203  14.458  1.00 28.07           C
ATOM   1119  CB   THR A   89      70.351   6.780  15.025  1.00 30.45           C
ATOM   1121  OG1  THR A   89      70.403   6.829  16.472  1.00 30.47           O
ATOM   1123  CG2  THR A   89      71.375   5.852  14.445  1.00 27.45           C
ATOM   1127  C    THR A   89      70.363   8.163  12.951  1.00 27.73           C
ATOM   1128  O    THR A   89      71.364   8.202  12.254  1.00 29.24           O
ATOM   1130  N    VAL A   90      69.128   7.984  12.455  1.00 26.04           N
ATOM   1131  CA   VAL A   90      68.880   7.973  11.025  1.00 28.17           C
ATOM   1133  CB   VAL A   90      67.392   7.630  10.747  1.00 28.09           C
ATOM   1135  CG1  VAL A   90      67.116   7.760   9.270  1.00 32.79           C
ATOM   1139  CG2  VAL A   90      67.117   6.165  11.183  1.00 33.06           C
ATOM   1143  C    VAL A   90      69.294   9.304  10.332  1.00 25.29           C
ATOM   1144  O    VAL A   90      69.917   9.313   9.281  1.00 26.94           O
ATOM   1146  N    VAL A   91      68.920  10.413  10.941  1.00 24.78           N
ATOM   1147  CA   VAL A   91      69.194  11.703  10.388  1.00 26.03           C
```

FIG. 15K

```
ATOM   1149  CB   VAL A  91      68.555  12.844  11.211  1.00 26.73           C
ATOM   1151  CG1  VAL A  91      69.226  14.161  10.901  1.00 24.74           C
ATOM   1155  CG2  VAL A  91      67.028  12.902  11.061  1.00 26.13           C
ATOM   1159  C    VAL A  91      70.698  11.864  10.345  1.00 26.72           C
ATOM   1160  O    VAL A  91      71.220  12.272   9.344  1.00 25.76           O
ATOM   1162  N    ASN A  92      71.363  11.530  11.440  1.00 28.74           N
ATOM   1163  CA   ASN A  92      72.821  11.583  11.468  1.00 29.66           C
ATOM   1165  CB   ASN A  92      73.295  11.150  12.829  1.00 31.16           C
ATOM   1168  CG   ASN A  92      73.037  12.204  13.841  1.00 38.36           C
ATOM   1169  OD1  ASN A  92      72.486  13.261  13.498  1.00 40.90           O
ATOM   1170  ND2  ASN A  92      73.409  11.946  15.108  1.00 46.19           N
ATOM   1173  C    ASN A  92      73.514  10.765  10.410  1.00 29.41           C
ATOM   1174  O    ASN A  92      74.465  11.238   9.759  1.00 29.52           O
ATOM   1176  N    SER A  93      73.027   9.559  10.243  1.00 28.39           N
ATOM   1177  CA   SER A  93      73.528   8.654   9.251  1.00 29.99           C
ATOM   1179  CB   SER A  93      72.762   7.340   9.352  1.00 30.93           C
ATOM   1182  OG   SER A  93      73.330   6.429   8.454  1.00 38.77           O
ATOM   1184  C    SER A  93      73.381   9.231   7.849  1.00 28.47           C
ATOM   1185  O    SER A  93      74.335   9.186   7.015  1.00 28.29           O
ATOM   1187  N    ILE A  94      72.231   9.843   7.598  1.00 25.74           N
ATOM   1188  CA   ILE A  94      72.003  10.410   6.313  1.00 26.38           C
ATOM   1190  CB   ILE A  94      70.526  10.827   6.109  1.00 25.00           C
ATOM   1192  CG1  ILE A  94      69.641   9.573   5.895  1.00 27.06           C
ATOM   1195  CD1  ILE A  94      68.146   9.944   6.065  1.00 27.94           C
ATOM   1199  CG2  ILE A  94      70.440  11.755   4.881  1.00 23.67           C
ATOM   1203  C    ILE A  94      72.946  11.607   6.118  1.00 26.78           C
ATOM   1204  O    ILE A  94      73.590  11.779   5.052  1.00 28.05           O
ATOM   1206  N    CYS A  95      73.071  12.431   7.121  1.00 28.08           N
ATOM   1207  CA   CYS A  95      73.914  13.621   6.966  1.00 27.76           C
ATOM   1209  CB   CYS A  95      73.825  14.514   8.170  1.00 28.99           C
ATOM   1212  SG   CYS A  95      72.182  15.295   8.255  1.00 30.96           S
ATOM   1214  C    CYS A  95      75.391  13.222   6.771  1.00 28.81           C
ATOM   1215  O    CYS A  95      76.076  13.847   6.000  1.00 30.43           O
ATOM   1217  N    ASN A  96      75.805  12.165   7.428  1.00 30.19           N
ATOM   1218  CA   ASN A  96      77.155  11.638   7.326  1.00 30.99           C
ATOM   1220  CB   ASN A  96      77.390  10.648   8.409  1.00 31.98           C
ATOM   1223  CG   ASN A  96      77.529  11.285   9.703  1.00 34.09           C
ATOM   1224  OD1  ASN A  96      77.785  12.471   9.760  1.00 38.12           O
ATOM   1225  ND2  ASN A  96      77.443  10.505  10.777  1.00 37.79           N
ATOM   1228  C    ASN A  96      77.469  10.997   5.990  1.00 30.99           C
ATOM   1229  O    ASN A  96      78.632  10.916   5.608  1.00 32.53           O
ATOM   1231  N    THR A  97      76.458  10.584   5.241  1.00 31.87           N
ATOM   1232  CA   THR A  97      76.677   9.940   3.958  1.00 31.89           C
ATOM   1234  CB   THR A  97      75.918   8.581   3.922  1.00 33.06           C
ATOM   1236  OG1  THR A  97      74.547   8.804   4.168  1.00 30.94           O
ATOM   1238  CG2  THR A  97      76.432   7.624   4.993  1.00 37.08           C
ATOM   1242  C    THR A  97      76.274  10.796   2.784  1.00 32.52           C
ATOM   1243  O    THR A  97      76.406  10.371   1.632  1.00 34.10           O
ATOM   1245  N    THR A  98      75.752  11.999   3.017  1.00 32.16           N
ATOM   1246  CA   THR A  98      75.389  12.895   1.956  1.00 30.79           C
ATOM   1248  CB   THR A  98      73.850  13.080   1.925  1.00 31.93           C
ATOM   1250  OG1  THR A  98      73.465  13.807   3.105  1.00 28.31           O
ATOM   1252  CG2  THR A  98      73.141  11.726   1.783  1.00 28.96           C
ATOM   1256  C    THR A  98      75.966  14.277   2.059  1.00 32.23           C
ATOM   1257  O    THR A  98      75.926  15.075   1.083  1.00 33.52           O
ATOM   1259  N    GLY A  99      76.450  14.600   3.238  1.00 32.13           N
ATOM   1260  CA   GLY A  99      76.811  15.938   3.594  1.00 35.19           C
ATOM   1263  C    GLY A  99      75.688  16.961   3.648  1.00 35.47           C
ATOM   1264  O    GLY A  99      75.954  18.163   3.863  1.00 37.28           O
ATOM   1266  N    VAL A 100      74.436  16.554   3.397  1.00 34.98           N
ATOM   1267  CA   VAL A 100      73.326  17.477   3.629  1.00 34.52           C
ATOM   1269  CB   VAL A 100      71.940  16.785   3.368  1.00 33.48           C
ATOM   1271  CG1  VAL A 100      70.760  17.662   3.875  1.00 34.09           C
```

FIG. 15L

```
ATOM   1275  CG2 VAL A 100      71.806  16.509   1.922  1.00 34.00           C
ATOM   1279  C   VAL A 100      73.455  17.959   5.053  1.00 34.99           C
ATOM   1280  O   VAL A 100      73.786  17.220   5.937  1.00 35.13           O
ATOM   1282  N   GLU A 101      73.228  19.227   5.245  1.00 38.67           N
ATOM   1283  CA  GLU A 101      73.307  19.882   6.541  1.00 40.23           C
ATOM   1285  CB  GLU A 101      72.974  21.356   6.298  1.00 41.73           C
ATOM   1288  CG  GLU A 101      72.946  22.267   7.549  1.00 49.25           C
ATOM   1291  CD  GLU A 101      72.581  23.732   7.225  1.00 55.29           C
ATOM   1292  OE1 GLU A 101      72.233  24.471   8.179  1.00 57.93           O
ATOM   1293  OE2 GLU A 101      72.626  24.125   6.024  1.00 59.90           O
ATOM   1294  C   GLU A 101      72.313  19.279   7.592  1.00 39.87           C
ATOM   1295  O   GLU A 101      71.163  18.964   7.245  1.00 36.74           O
ATOM   1297  N   LYS A 102      72.755  19.161   8.851  1.00 40.02           N
ATOM   1298  CA  LYS A 102      71.892  18.586   9.906  1.00 40.48           C
ATOM   1300  CB  LYS A 102      72.636  18.175  11.173  1.00 42.28           C
ATOM   1303  CG  LYS A 102      72.525  16.685  11.437  1.00 46.45           C
ATOM   1306  CD  LYS A 102      73.005  16.258  12.827  1.00 50.39           C
ATOM   1309  CE  LYS A 102      74.493  16.040  12.865  1.00 51.80           C
ATOM   1312  NZ  LYS A 102      74.829  15.096  13.928  1.00 52.68           N
ATOM   1316  C   LYS A 102      70.808  19.553  10.275  1.00 38.78           C
ATOM   1317  O   LYS A 102      71.093  20.702  10.549  1.00 38.04           O
ATOM   1319  N   PRO A 103      69.549  19.092  10.274  1.00 36.34           N
ATOM   1320  CA  PRO A 103      68.519  20.053  10.566  1.00 34.63           C
ATOM   1322  CB  PRO A 103      67.227  19.361  10.090  1.00 35.11           C
ATOM   1325  CG  PRO A 103      67.552  17.966  10.133  1.00 34.09           C
ATOM   1328  CD  PRO A 103      68.992  17.865   9.710  1.00 35.93           C
ATOM   1331  C   PRO A 103      68.510  20.316  12.058  1.00 33.46           C
ATOM   1332  O   PRO A 103      68.935  19.464  12.829  1.00 31.01           O
ATOM   1333  N   LYS A 104      68.059  21.514  12.418  1.00 32.72           N
ATOM   1334  CA  LYS A 104      67.884  21.946  13.803  1.00 35.25           C
ATOM   1336  CB  LYS A 104      67.467  23.424  13.335  1.00 36.22           C
ATOM   1339  CG  LYS A 104      68.572  24.305  13.322  1.00 42.91           C
ATOM   1342  CD  LYS A 104      68.375  25.787  13.693  1.00 49.19           C
ATOM   1345  CE  LYS A 104      69.093  26.641  12.663  1.00 54.36           C
ATOM   1348  NZ  LYS A 104      69.130  28.087  13.047  1.00 60.95           N
ATOM   1352  C   LYS A 104      66.802  21.156  14.492  1.00 34.59           C
ATOM   1353  O   LYS A 104      66.902  20.889  15.686  1.00 34.61           O
ATOM   1355  N   PHE A 105      65.760  20.802  13.724  1.00 33.69           N
ATOM   1356  CA  PHE A 105      64.588  20.072  14.280  1.00 32.71           C
ATOM   1358  CB  PHE A 105      63.377  20.941  14.096  1.00 33.45           C
ATOM   1361  CG  PHE A 105      63.479  22.256  14.838  1.00 38.65           C
ATOM   1362  CD1 PHE A 105      63.467  22.272  16.239  1.00 44.18           C
ATOM   1364  CE1 PHE A 105      63.573  23.510  16.927  1.00 47.09           C
ATOM   1366  CZ  PHE A 105      63.683  24.702  16.211  1.00 43.63           C
ATOM   1368  CE2 PHE A 105      63.704  24.675  14.830  1.00 43.54           C
ATOM   1370  CD2 PHE A 105      63.619  23.463  14.150  1.00 40.08           C
ATOM   1372  C   PHE A 105      64.395  18.757  13.518  1.00 31.55           C
ATOM   1373  O   PHE A 105      64.729  18.701  12.357  1.00 29.93           O
ATOM   1375  N   LEU A 106      63.901  17.723  14.160  1.00 28.75           N
ATOM   1376  CA  LEU A 106      63.668  16.474  13.437  1.00 28.86           C
ATOM   1378  CB  LEU A 106      63.049  15.409  14.367  1.00 29.42           C
ATOM   1381  CG  LEU A 106      63.864  14.395  15.129  1.00 34.72           C
ATOM   1383  CD1 LEU A 106      62.880  13.291  15.671  1.00 34.63           C
ATOM   1387  CD2 LEU A 106      64.900  13.789  14.279  1.00 26.80           C
ATOM   1391  C   LEU A 106      62.705  16.690  12.294  1.00 26.40           C
ATOM   1392  O   LEU A 106      61.663  17.245  12.485  1.00 25.36           O
ATOM   1394  N   PRO A 107      63.028  16.276  11.079  1.00 25.21           N
ATOM   1395  CA  PRO A 107      62.022  16.372  10.006  1.00 24.80           C
ATOM   1397  CB  PRO A 107      62.916  16.504   8.771  1.00 26.70           C
ATOM   1400  CG  PRO A 107      64.078  15.644   9.118  1.00 27.32           C
ATOM   1403  CD  PRO A 107      64.334  15.842  10.564  1.00 27.04           C
ATOM   1406  C   PRO A 107      61.257  15.059   9.938  1.00 25.01           C
ATOM   1407  O   PRO A 107      61.460  14.178  10.812  1.00 25.42           O
```

FIG. 15M

| | | | | | | | | | |
|---|---|---|---|---|---|---|---|---|---|
| ATOM | 1408 | N | ASP | A | 108 | 60.466 | 14.890 | 8.893 | 1.00 23.40 | N |
| ATOM | 1409 | CA | ASP | A | 108 | 59.559 | 13.751 | 8.794 | 1.00 24.79 | C |
| ATOM | 1411 | CB | ASP | A | 108 | 58.193 | 14.244 | 8.337 | 1.00 23.28 | C |
| ATOM | 1414 | CG | ASP | A | 108 | 57.524 | 15.051 | 9.405 | 1.00 23.89 | C |
| ATOM | 1415 | OD1 | ASP | A | 108 | 57.552 | 14.593 | 10.575 | 1.00 23.84 | O |
| ATOM | 1416 | OD2 | ASP | A | 108 | 56.930 | 16.083 | 9.088 | 1.00 27.89 | O |
| ATOM | 1417 | C | ASP | A | 108 | 60.067 | 12.661 | 7.891 | 1.00 24.46 | C |
| ATOM | 1418 | O | ASP | A | 108 | 59.785 | 11.513 | 8.193 | 1.00 25.25 | O |
| ATOM | 1420 | N | LEU | A | 109 | 60.705 | 13.049 | 6.774 | 1.00 23.26 | N |
| ATOM | 1421 | CA | LEU | A | 109 | 61.250 | 12.171 | 5.748 | 1.00 23.65 | C |
| ATOM | 1423 | CB | LEU | A | 109 | 60.318 | 12.051 | 4.527 | 1.00 24.18 | C |
| ATOM | 1426 | CG | LEU | A | 109 | 58.818 | 11.678 | 4.749 | 1.00 27.31 | C |
| ATOM | 1428 | CD1 | LEU | A | 109 | 58.000 | 11.950 | 3.517 | 1.00 30.45 | C |
| ATOM | 1432 | CD2 | LEU | A | 109 | 58.641 | 10.255 | 5.224 | 1.00 27.38 | C |
| ATOM | 1436 | C | LEU | A | 109 | 62.597 | 12.680 | 5.223 | 1.00 23.28 | C |
| ATOM | 1437 | O | LEU | A | 109 | 62.890 | 13.883 | 5.336 | 1.00 24.26 | O |
| ATOM | 1439 | N | TYR | A | 110 | 63.329 | 11.800 | 4.547 | 1.00 22.76 | N |
| ATOM | 1440 | CA | TYR | A | 110 | 64.429 | 12.229 | 3.656 | 1.00 23.81 | C |
| ATOM | 1442 | CB | TYR | A | 110 | 65.803 | 11.706 | 4.129 | 1.00 23.81 | C |
| ATOM | 1445 | CG | TYR | A | 110 | 66.980 | 12.214 | 3.313 | 1.00 23.87 | C |
| ATOM | 1446 | CD1 | TYR | A | 110 | 67.413 | 13.498 | 3.439 | 1.00 26.85 | C |
| ATOM | 1448 | CE1 | TYR | A | 110 | 68.436 | 13.961 | 2.692 | 1.00 28.71 | C |
| ATOM | 1450 | CZ | TYR | A | 110 | 69.049 | 13.150 | 1.805 | 1.00 26.47 | C |
| ATOM | 1451 | OH | TYR | A | 110 | 70.128 | 13.601 | 1.049 | 1.00 29.18 | O |
| ATOM | 1453 | CE2 | TYR | A | 110 | 68.618 | 11.870 | 1.634 | 1.00 26.21 | C |
| ATOM | 1455 | CD2 | TYR | A | 110 | 67.593 | 11.413 | 2.387 | 1.00 24.74 | C |
| ATOM | 1457 | C | TYR | A | 110 | 64.119 | 11.708 | 2.277 | 1.00 25.22 | C |
| ATOM | 1458 | O | TYR | A | 110 | 63.721 | 10.539 | 2.101 | 1.00 26.47 | O |
| ATOM | 1460 | N | ASP | A | 111 | 64.304 | 12.577 | 1.304 | 1.00 23.71 | N |
| ATOM | 1461 | CA | ASP | A | 111 | 64.098 | 12.272 | -0.086 | 1.00 23.95 | C |
| ATOM | 1463 | CB | ASP | A | 111 | 63.483 | 13.478 | -0.715 | 1.00 23.51 | C |
| ATOM | 1466 | CG | ASP | A | 111 | 63.150 | 13.295 | -2.204 | 1.00 26.19 | C |
| ATOM | 1467 | OD1 | ASP | A | 111 | 63.722 | 12.431 | -2.905 | 1.00 24.46 | O |
| ATOM | 1468 | OD2 | ASP | A | 111 | 62.289 | 14.049 | -2.662 | 1.00 24.83 | O |
| ATOM | 1469 | C | ASP | A | 111 | 65.507 | 11.982 | -0.670 | 1.00 26.57 | C |
| ATOM | 1470 | O | ASP | A | 111 | 66.307 | 12.900 | -0.806 | 1.00 23.25 | O |
| ATOM | 1472 | N | TYR | A | 112 | 65.732 | 10.710 | -0.974 | 1.00 26.78 | N |
| ATOM | 1473 | CA | TYR | A | 112 | 67.010 | 10.213 | -1.566 | 1.00 29.95 | C |
| ATOM | 1475 | CB | TYR | A | 112 | 67.105 | 8.681 | -1.458 | 1.00 28.48 | C |
| ATOM | 1478 | CG | TYR | A | 112 | 67.357 | 8.175 | -0.088 | 1.00 32.03 | C |
| ATOM | 1479 | CD1 | TYR | A | 112 | 68.546 | 8.448 | 0.552 | 1.00 30.80 | C |
| ATOM | 1481 | CE1 | TYR | A | 112 | 68.783 | 8.007 | 1.833 | 1.00 30.92 | C |
| ATOM | 1483 | CZ | TYR | A | 112 | 67.865 | 7.231 | 2.485 | 1.00 32.17 | C |
| ATOM | 1484 | OH | TYR | A | 112 | 68.134 | 6.827 | 3.780 | 1.00 32.83 | O |
| ATOM | 1486 | CE2 | TYR | A | 112 | 66.665 | 6.929 | 1.867 | 1.00 32.64 | C |
| ATOM | 1488 | CD2 | TYR | A | 112 | 66.416 | 7.428 | 0.588 | 1.00 34.95 | C |
| ATOM | 1490 | C | TYR | A | 112 | 67.120 | 10.605 | -3.017 | 1.00 31.55 | C |
| ATOM | 1491 | O | TYR | A | 112 | 68.229 | 10.662 | -3.560 | 1.00 34.48 | O |
| ATOM | 1493 | N | LYS | A | 113 | 66.021 | 10.955 | -3.649 | 1.00 31.03 | N |
| ATOM | 1494 | CA | LYS | A | 113 | 66.136 | 11.436 | -5.022 | 1.00 32.58 | C |
| ATOM | 1496 | CB | LYS | A | 113 | 64.861 | 11.173 | -5.826 | 1.00 32.76 | C |
| ATOM | 1499 | CG | LYS | A | 113 | 64.985 | 11.582 | -7.320 | 1.00 36.49 | C |
| ATOM | 1502 | CD | LYS | A | 113 | 63.685 | 11.401 | -7.983 | 1.00 44.02 | C |
| ATOM | 1505 | CE | LYS | A | 113 | 63.790 | 11.452 | -9.517 | 1.00 47.29 | C |
| ATOM | 1508 | NZ | LYS | A | 113 | 62.618 | 10.654 | -10.007 | 1.00 52.44 | N |
| ATOM | 1512 | C | LYS | A | 113 | 66.528 | 12.874 | -5.113 | 1.00 32.02 | C |
| ATOM | 1513 | O | LYS | A | 113 | 67.505 | 13.200 | -5.798 | 1.00 31.77 | O |
| ATOM | 1515 | N | GLU | A | 114 | 65.843 | 13.749 | -4.396 | 1.00 29.70 | N |
| ATOM | 1516 | CA | GLU | A | 114 | 66.268 | 15.163 | -4.318 | 1.00 30.53 | C |
| ATOM | 1518 | CB | GLU | A | 114 | 65.061 | 16.089 | -4.047 | 1.00 31.86 | C |
| ATOM | 1521 | CG | GLU | A | 114 | 64.012 | 15.925 | -5.044 | 1.00 33.89 | C |
| ATOM | 1524 | CD | GLU | A | 114 | 64.247 | 16.698 | -6.340 | 1.00 40.59 | C |
| ATOM | 1525 | OE1 | GLU | A | 114 | 65.163 | 17.578 | -6.395 | 1.00 35.62 | O |

FIG. 15N

| ATOM | 1526 | OE2 | GLU | A | 114 | 63.476 | 16.385 | -7.296 | 1.00 | 43.51 | O |
| ATOM | 1527 | C | GLU | A | 114 | 67.323 | 15.477 | -3.304 | 1.00 | 29.79 | C |
| ATOM | 1528 | O | GLU | A | 114 | 67.813 | 16.593 | -3.281 | 1.00 | 32.38 | O |
| ATOM | 1530 | N | ASN | A | 115 | 67.699 | 14.512 | -2.485 | 1.00 | 29.15 | N |
| ATOM | 1531 | CA | ASN | A | 115 | 68.634 | 14.708 | -1.367 | 1.00 | 29.75 | C |
| ATOM | 1533 | CB | ASN | A | 115 | 70.072 | 14.728 | -1.936 | 1.00 | 30.28 | C |
| ATOM | 1536 | CG | ASN | A | 115 | 70.553 | 13.324 | -2.317 | 1.00 | 30.10 | C |
| ATOM | 1537 | OD1 | ASN | A | 115 | 70.645 | 12.971 | -3.492 | 1.00 | 34.49 | O |
| ATOM | 1538 | ND2 | ASN | A | 115 | 70.713 | 12.501 | -1.337 | 1.00 | 27.64 | N |
| ATOM | 1541 | C | ASN | A | 115 | 68.323 | 15.896 | -0.517 | 1.00 | 28.87 | C |
| ATOM | 1542 | O | ASN | A | 115 | 69.133 | 16.839 | -0.311 | 1.00 | 27.25 | O |
| ATOM | 1544 | N | ARG | A | 116 | 67.094 | 15.871 | 0.044 | 1.00 | 28.59 | N |
| ATOM | 1545 | CA | ARG | A | 116 | 66.681 | 16.835 | 0.994 | 1.00 | 25.83 | C |
| ATOM | 1547 | CB | ARG | A | 116 | 66.001 | 17.985 | 0.311 | 1.00 | 27.04 | C |
| ATOM | 1550 | CG | ARG | A | 116 | 64.665 | 17.601 | -0.372 | 1.00 | 26.90 | C |
| ATOM | 1553 | CD | ARG | A | 116 | 64.373 | 18.665 | -1.444 | 1.00 | 29.00 | C |
| ATOM | 1556 | NE | ARG | A | 116 | 63.155 | 18.330 | -2.105 | 1.00 | 28.73 | N |
| ATOM | 1558 | CZ | ARG | A | 116 | 62.725 | 18.858 | -3.256 | 1.00 | 29.84 | C |
| ATOM | 1559 | NH1 | ARG | A | 116 | 63.390 | 19.844 | -3.811 | 1.00 | 33.24 | N |
| ATOM | 1562 | NH2 | ARG | A | 116 | 61.565 | 18.440 | -3.768 | 1.00 | 30.97 | N |
| ATOM | 1565 | C | ARG | A | 116 | 65.722 | 16.258 | 2.024 | 1.00 | 25.38 | C |
| ATOM | 1566 | O | ARG | A | 116 | 65.030 | 15.281 | 1.755 | 1.00 | 24.92 | O |
| ATOM | 1568 | N | PHE | A | 117 | 65.772 | 16.789 | 3.213 | 1.00 | 24.74 | N |
| ATOM | 1569 | CA | PHE | A | 117 | 64.812 | 16.401 | 4.246 | 1.00 | 25.21 | C |
| ATOM | 1571 | CB | PHE | A | 117 | 65.299 | 16.777 | 5.616 | 1.00 | 24.84 | C |
| ATOM | 1574 | CG | PHE | A | 117 | 66.385 | 15.919 | 6.121 | 1.00 | 26.07 | C |
| ATOM | 1575 | CD1 | PHE | A | 117 | 66.112 | 14.682 | 6.606 | 1.00 | 25.75 | C |
| ATOM | 1577 | CE1 | PHE | A | 117 | 67.112 | 13.877 | 7.105 | 1.00 | 30.03 | C |
| ATOM | 1579 | CZ | PHE | A | 117 | 68.442 | 14.304 | 7.092 | 1.00 | 26.03 | C |
| ATOM | 1581 | CE2 | PHE | A | 117 | 68.736 | 15.523 | 6.581 | 1.00 | 27.23 | C |
| ATOM | 1583 | CD2 | PHE | A | 117 | 67.708 | 16.360 | 6.142 | 1.00 | 24.45 | C |
| ATOM | 1585 | C | PHE | A | 117 | 63.497 | 17.086 | 3.926 | 1.00 | 24.15 | C |
| ATOM | 1586 | O | PHE | A | 117 | 63.437 | 18.159 | 3.275 | 1.00 | 25.20 | O |
| ATOM | 1588 | N | ILE | A | 118 | 62.418 | 16.449 | 4.364 | 1.00 | 24.50 | N |
| ATOM | 1589 | CA | ILE | A | 118 | 61.081 | 16.993 | 4.177 | 1.00 | 24.40 | C |
| ATOM | 1591 | CB | ILE | A | 118 | 60.220 | 16.073 | 3.318 | 1.00 | 24.41 | C |
| ATOM | 1593 | CG1 | ILE | A | 118 | 60.801 | 15.888 | 1.924 | 1.00 | 27.44 | C |
| ATOM | 1596 | CD1 | ILE | A | 118 | 60.182 | 14.688 | 1.243 | 1.00 | 30.22 | C |
| ATOM | 1600 | CG2 | ILE | A | 118 | 58.808 | 16.625 | 3.101 | 1.00 | 22.98 | C |
| ATOM | 1604 | C | ILE | A | 118 | 60.342 | 17.124 | 5.514 | 1.00 | 23.65 | C |
| ATOM | 1605 | O | ILE | A | 118 | 60.311 | 16.195 | 6.326 | 1.00 | 24.27 | O |
| ATOM | 1607 | N | GLU | A | 119 | 59.668 | 18.249 | 5.675 | 1.00 | 24.65 | N |
| ATOM | 1608 | CA | GLU | A | 119 | 58.798 | 18.522 | 6.792 | 1.00 | 25.58 | C |
| ATOM | 1610 | CB | GLU | A | 119 | 59.029 | 19.893 | 7.475 | 1.00 | 25.17 | C |
| ATOM | 1613 | CG | GLU | A | 119 | 57.961 | 20.192 | 8.529 | 1.00 | 29.34 | C |
| ATOM | 1616 | CD | GLU | A | 119 | 57.827 | 19.121 | 9.619 | 1.00 | 29.67 | C |
| ATOM | 1617 | OE1 | GLU | A | 119 | 58.861 | 18.599 | 10.094 | 1.00 | 26.90 | O |
| ATOM | 1618 | OE2 | GLU | A | 119 | 56.688 | 18.876 | 10.074 | 1.00 | 27.14 | O |
| ATOM | 1619 | C | GLU | A | 119 | 57.360 | 18.457 | 6.214 | 1.00 | 25.13 | C |
| ATOM | 1620 | O | GLU | A | 119 | 57.036 | 19.157 | 5.294 | 1.00 | 24.01 | O |
| ATOM | 1622 | N | ILE | A | 120 | 56.588 | 17.522 | 6.729 | 1.00 | 23.31 | N |
| ATOM | 1623 | CA | ILE | A | 120 | 55.195 | 17.327 | 6.363 | 1.00 | 25.06 | C |
| ATOM | 1625 | CB | ILE | A | 120 | 54.854 | 15.838 | 6.355 | 1.00 | 24.51 | C |
| ATOM | 1627 | CG1 | ILE | A | 120 | 55.653 | 15.156 | 5.290 | 1.00 | 25.83 | C |
| ATOM | 1630 | CD1 | ILE | A | 120 | 55.366 | 15.654 | 4.029 | 1.00 | 25.16 | C |
| ATOM | 1634 | CG2 | ILE | A | 120 | 53.302 | 15.602 | 6.164 | 1.00 | 26.01 | C |
| ATOM | 1638 | C | ILE | A | 120 | 54.311 | 18.004 | 7.404 | 1.00 | 24.05 | C |
| ATOM | 1639 | O | ILE | A | 120 | 54.449 | 17.712 | 8.639 | 1.00 | 25.86 | O |
| ATOM | 1641 | N | GLY | A | 121 | 53.382 | 18.804 | 6.867 | 1.00 | 26.74 | N |
| ATOM | 1642 | CA | GLY | A | 121 | 52.413 | 19.536 | 7.659 | 1.00 | 25.86 | C |
| ATOM | 1645 | C | GLY | A | 121 | 51.010 | 19.088 | 7.280 | 1.00 | 25.17 | C |
| ATOM | 1646 | O | GLY | A | 121 | 50.707 | 18.934 | 6.118 | 1.00 | 24.93 | O |
| ATOM | 1648 | N | VAL | A | 122 | 50.192 | 18.836 | 8.280 | 1.00 | 23.76 | N |

FIG. 15O

```
ATOM   1649  CA   VAL A 122      48.749  18.577   8.099  1.00 23.87           C
ATOM   1651  CB   VAL A 122      48.341  17.149   8.504  1.00 25.39           C
ATOM   1653  CG1  VAL A 122      46.777  16.950   8.262  1.00 22.76           C
ATOM   1657  CG2  VAL A 122      49.165  16.116   7.717  1.00 24.40           C
ATOM   1661  C    VAL A 122      47.943  19.558   8.917  1.00 25.55           C
ATOM   1662  O    VAL A 122      48.085  19.597  10.138  1.00 27.28           O
ATOM   1664  N    THR A 123      47.110  20.361   8.278  1.00 27.69           N
ATOM   1665  CA   THR A 123      46.442  21.458   8.985  1.00 29.10           C
ATOM   1667  CB   THR A 123      46.983  22.854   8.510  1.00 30.55           C
ATOM   1669  OG1  THR A 123      46.353  23.946   9.208  1.00 32.05           O
ATOM   1671  CG2  THR A 123      46.716  23.090   7.018  1.00 29.90           C
ATOM   1675  C    THR A 123      44.938  21.435   8.745  1.00 29.70           C
ATOM   1676  O    THR A 123      44.500  21.161   7.678  1.00 25.46           O
ATOM   1678  N    ARG A 124      44.206  21.897   9.748  1.00 29.79           N
ATOM   1679  CA   ARG A 124      42.798  22.154   9.611  1.00 32.70           C
ATOM   1681  CB   ARG A 124      42.125  21.846  10.929  1.00 32.34           C
ATOM   1684  CG   ARG A 124      42.049  20.403  11.359  1.00 35.33           C
ATOM   1687  CD   ARG A 124      42.241  20.320  12.915  1.00 39.10           C
ATOM   1690  NE   ARG A 124      43.567  19.998  13.192  1.00 38.12           N
ATOM   1692  CZ   ARG A 124      44.110  19.738  14.364  1.00 37.82           C
ATOM   1693  NH1  ARG A 124      43.484  19.846  15.540  1.00 35.25           N
ATOM   1696  NH2  ARG A 124      45.367  19.427  14.324  1.00 35.38           N
ATOM   1699  C    ARG A 124      42.507  23.600   9.259  1.00 34.47           C
ATOM   1700  O    ARG A 124      41.348  23.974   9.180  1.00 36.83           O
ATOM   1702  N    ARG A 125      43.546  24.423   9.183  1.00 34.59           N
ATOM   1703  CA   ARG A 125      43.473  25.784   8.783  1.00 36.06           C
ATOM   1705  CB   ARG A 125      44.406  26.606   9.671  1.00 35.43           C
ATOM   1708  CG   ARG A 125      43.949  26.637  11.120  1.00 38.75           C
ATOM   1711  CD   ARG A 125      44.967  27.396  11.978  1.00 40.42           C
ATOM   1714  NE   ARG A 125      46.138  26.564  12.276  1.00 39.65           N
ATOM   1716  CZ   ARG A 125      47.320  27.021  12.674  1.00 45.69           C
ATOM   1717  NH1  ARG A 125      47.564  28.325  12.786  1.00 49.63           N
ATOM   1720  NH2  ARG A 125      48.291  26.161  12.940  1.00 49.30           N
ATOM   1723  C    ARG A 125      43.903  25.892   7.315  1.00 36.89           C
ATOM   1724  O    ARG A 125      44.077  24.878   6.617  1.00 37.27           O
ATOM   1726  N    GLU A 126      44.104  27.111   6.867  1.00 36.51           N
ATOM   1727  CA   GLU A 126      44.486  27.390   5.480  1.00 37.82           C
ATOM   1729  CB   GLU A 126      44.384  28.897   5.230  1.00 40.38           C
ATOM   1732  CG   GLU A 126      42.990  29.535   5.450  1.00 46.89           C
ATOM   1735  CD   GLU A 126      42.287  29.740   4.130  1.00 53.98           C
ATOM   1736  OE1  GLU A 126      41.958  28.703   3.509  1.00 54.03           O
ATOM   1737  OE2  GLU A 126      42.116  30.919   3.693  1.00 58.25           O
ATOM   1738  C    GLU A 126      45.952  26.978   5.315  1.00 36.18           C
ATOM   1739  O    GLU A 126      46.763  27.271   6.183  1.00 35.97           O
ATOM   1741  N    VAL A 127      46.269  26.287   4.229  1.00 34.74           N
ATOM   1742  CA   VAL A 127      47.626  25.793   3.986  1.00 34.58           C
ATOM   1744  CB   VAL A 127      47.730  24.908   2.713  1.00 32.34           C
ATOM   1746  CG1  VAL A 127      46.776  23.713   2.864  1.00 32.03           C
ATOM   1750  CG2  VAL A 127      47.458  25.708   1.360  1.00 33.77           C
ATOM   1754  C    VAL A 127      48.663  26.885   3.957  1.00 35.18           C
ATOM   1755  O    VAL A 127      49.707  26.707   4.522  1.00 35.08           O
ATOM   1757  N    HIS A 128      48.364  28.050   3.386  1.00 37.46           N
ATOM   1758  CA   HIS A 128      49.400  29.132   3.346  1.00 39.07           C
ATOM   1760  CB   HIS A 128      48.992  30.293   2.444  1.00 40.36           C
ATOM   1763  CG   HIS A 128      47.761  31.010   2.910  1.00 46.62           C
ATOM   1764  ND1  HIS A 128      46.524  30.837   2.319  1.00 53.49           N
ATOM   1766  CE1  HIS A 128      45.626  31.582   2.943  1.00 54.15           C
ATOM   1768  NE2  HIS A 128      46.235  32.225   3.928  1.00 53.93           N
ATOM   1770  CD2  HIS A 128      47.569  31.883   3.928  1.00 52.74           C
ATOM   1772  C    HIS A 128      49.758  29.606   4.734  1.00 38.82           C
ATOM   1773  O    HIS A 128      50.907  29.903   4.962  1.00 41.18           O
ATOM   1775  N    ILE A 129      48.786  29.629   5.649  1.00 38.08           N
ATOM   1776  CA   ILE A 129      48.950  29.995   7.056  1.00 38.75           C
```

FIG. 15P

```
ATOM   1778  CB   ILE A 129      47.513  30.106   7.719  1.00 40.14           C
ATOM   1780  CG1  ILE A 129      46.770  31.305   7.116  1.00 45.03           C
ATOM   1783  CD1  ILE A 129      45.423  31.608   7.784  1.00 50.51           C
ATOM   1787  CG2  ILE A 129      47.514  30.187   9.211  1.00 41.78           C
ATOM   1791  C    ILE A 129      49.854  29.019   7.813  1.00 36.91           C
ATOM   1792  O    ILE A 129      50.829  29.383   8.527  1.00 35.23           O
ATOM   1794  N    TYR A 130      49.519  27.738   7.679  1.00 34.42           N
ATOM   1795  CA   TYR A 130      50.326  26.744   8.319  1.00 32.26           C
ATOM   1797  CB   TYR A 130      49.571  25.424   8.285  1.00 33.12           C
ATOM   1800  CG   TYR A 130      50.105  24.423   9.227  1.00 29.16           C
ATOM   1801  CD1  TYR A 130      50.162  24.672  10.574  1.00 34.13           C
ATOM   1803  CE1  TYR A 130      50.665  23.754  11.457  1.00 34.09           C
ATOM   1805  CZ   TYR A 130      51.046  22.500  10.972  1.00 32.73           C
ATOM   1806  OH   TYR A 130      51.505  21.529  11.773  1.00 33.99           O
ATOM   1808  CE2  TYR A 130      50.999  22.244   9.650  1.00 31.35           C
ATOM   1810  CD2  TYR A 130      50.560  23.225   8.773  1.00 32.28           C
ATOM   1812  C    TYR A 130      51.714  26.640   7.665  1.00 30.92           C
ATOM   1813  O    TYR A 130      52.659  26.402   8.365  1.00 31.54           O
ATOM   1815  N    TYR A 131      51.819  26.837   6.364  1.00 31.50           N
ATOM   1816  CA   TYR A 131      53.103  26.832   5.673  1.00 32.79           C
ATOM   1818  CB   TYR A 131      52.966  27.138   4.179  1.00 32.33           C
ATOM   1821  CG   TYR A 131      54.325  27.104   3.461  1.00 35.34           C
ATOM   1822  CD1  TYR A 131      54.779  25.939   2.846  1.00 38.30           C
ATOM   1824  CE1  TYR A 131      56.009  25.877   2.217  1.00 37.73           C
ATOM   1826  CZ   TYR A 131      56.810  27.009   2.181  1.00 40.99           C
ATOM   1827  OH   TYR A 131      58.005  26.936   1.576  1.00 44.82           O
ATOM   1829  CE2  TYR A 131      56.410  28.182   2.789  1.00 40.13           C
ATOM   1831  CD2  TYR A 131      55.164  28.230   3.416  1.00 38.86           C
ATOM   1833  C    TYR A 131      54.035  27.861   6.321  1.00 33.95           C
ATOM   1834  O    TYR A 131      55.210  27.593   6.630  1.00 32.72           O
ATOM   1836  N    LEU A 132      53.481  29.059   6.533  1.00 35.56           N
ATOM   1837  CA   LEU A 132      54.252  30.196   7.096  1.00 37.00           C
ATOM   1839  CB   LEU A 132      53.369  31.476   7.106  1.00 37.41           C
ATOM   1842  CG   LEU A 132      53.206  32.108   5.722  1.00 40.82           C
ATOM   1844  CD1  LEU A 132      52.087  33.123   5.661  1.00 43.05           C
ATOM   1848  CD2  LEU A 132      54.485  32.793   5.376  1.00 42.60           C
ATOM   1852  C    LEU A 132      54.687  29.888   8.477  1.00 36.29           C
ATOM   1853  O    LEU A 132      55.849  30.096   8.852  1.00 38.30           O
ATOM   1855  N    GLU A 133      53.767  29.361   9.243  1.00 35.44           N
ATOM   1856  CA   GLU A 133      54.051  28.949  10.587  1.00 36.86           C
ATOM   1858  CB   GLU A 133      52.783  28.433  11.272  1.00 36.73           C
ATOM   1861  CG   GLU A 133      53.010  27.900  12.640  1.00 43.86           C
ATOM   1864  CD   GLU A 133      51.843  27.101  13.209  1.00 50.30           C
ATOM   1865  OE1  GLU A 133      50.686  27.594  13.126  1.00 55.46           O
ATOM   1866  OE2  GLU A 133      52.107  25.985  13.740  1.00 53.00           O
ATOM   1867  C    GLU A 133      55.180  27.913  10.659  1.00 35.70           C
ATOM   1868  O    GLU A 133      56.075  28.002  11.515  1.00 35.52           O
ATOM   1870  N    LYS A 134      55.173  26.950   9.743  1.00 36.10           N
ATOM   1871  CA   LYS A 134      56.178  25.919   9.742  1.00 36.22           C
ATOM   1873  CB   LYS A 134      55.813  24.780   8.769  1.00 36.51           C
ATOM   1876  CG   LYS A 134      54.829  23.807   9.356  1.00 40.26           C
ATOM   1879  CD   LYS A 134      55.496  22.994  10.439  1.00 43.13           C
ATOM   1882  CE   LYS A 134      54.779  21.666  10.663  1.00 43.25           C
ATOM   1885  NZ   LYS A 134      54.946  21.318  12.058  1.00 45.22           N
ATOM   1889  C    LYS A 134      57.520  26.480   9.314  1.00 35.70           C
ATOM   1890  O    LYS A 134      58.534  26.195   9.941  1.00 33.54           O
ATOM   1892  N    ALA A 135      57.515  27.165   8.168  1.00 37.54           N
ATOM   1893  CA   ALA A 135      58.702  27.714   7.566  1.00 37.54           C
ATOM   1895  CB   ALA A 135      58.335  28.490   6.291  1.00 38.38           C
ATOM   1899  C    ALA A 135      59.384  28.649   8.539  1.00 39.49           C
ATOM   1900  O    ALA A 135      60.618  28.638   8.660  1.00 37.56           O
ATOM   1902  N    ASN A 136      58.577  29.449   9.219  1.00 41.06           N
ATOM   1903  CA   ASN A 136      59.086  30.369  10.272  1.00 43.97           C
```

FIG. 15Q

```
ATOM   1905  CB   ASN A 136      57.975  31.265  10.849  1.00 42.31           C
ATOM   1908  CG   ASN A 136      58.525  32.236  11.892  1.00 44.84           C
ATOM   1909  OD1  ASN A 136      59.404  33.042  11.561  1.00 42.30           O
ATOM   1910  ND2  ASN A 136      58.043  32.152  13.147  1.00 39.73           N
ATOM   1913  C    ASN A 136      59.710  29.582  11.410  1.00 47.15           C
ATOM   1914  O    ASN A 136      60.811  29.920  11.915  1.00 47.98           O
ATOM   1916  N    LYS A 137      59.021  28.514  11.801  1.00 50.42           N
ATOM   1917  CA   LYS A 137      59.456  27.724  12.929  1.00 53.76           C
ATOM   1919  CB   LYS A 137      58.399  26.703  13.328  1.00 55.00           C
ATOM   1922  CG   LYS A 137      58.931  25.484  14.114  1.00 58.80           C
ATOM   1925  CD   LYS A 137      59.354  25.799  15.557  1.00 61.04           C
ATOM   1928  CE   LYS A 137      59.777  24.511  16.260  1.00 64.10           C
ATOM   1931  NZ   LYS A 137      59.915  24.664  17.745  1.00 65.54           N
ATOM   1935  C    LYS A 137      60.750  27.016  12.650  1.00 55.16           C
ATOM   1936  O    LYS A 137      61.562  26.898  13.552  1.00 55.31           O
ATOM   1938  N    ILE A 138      60.951  26.510  11.430  1.00 57.26           N
ATOM   1939  CA   ILE A 138      62.014  25.514  11.246  1.00 58.82           C
ATOM   1941  CB   ILE A 138      61.638  24.265  10.364  1.00 58.37           C
ATOM   1943  CG1  ILE A 138      61.470  24.598   8.891  1.00 57.40           C
ATOM   1946  CD1  ILE A 138      61.075  23.331   8.097  1.00 53.52           C
ATOM   1950  CG2  ILE A 138      60.398  23.521  10.909  1.00 59.17           C
ATOM   1954  C    ILE A 138      63.298  26.119  10.751  1.00 60.85           C
ATOM   1955  O    ILE A 138      64.373  25.690  11.188  1.00 62.53           O
ATOM   1957  N    LYS A 139      63.179  27.082   9.842  1.00 62.69           N
ATOM   1958  CA   LYS A 139      64.296  27.681   9.097  1.00 64.44           C
ATOM   1960  CB   LYS A 139      64.722  29.007   9.754  1.00 65.41           C
ATOM   1963  CG   LYS A 139      63.656  30.089   9.672  1.00 67.28           C
ATOM   1966  CD   LYS A 139      63.710  30.729   8.289  1.00 71.31           C
ATOM   1969  CE   LYS A 139      62.621  31.773   8.128  1.00 72.84           C
ATOM   1972  NZ   LYS A 139      62.877  33.018   8.930  1.00 73.64           N
ATOM   1976  C    LYS A 139      65.504  26.773   8.904  1.00 64.77           C
ATOM   1977  O    LYS A 139      66.589  27.072   9.406  1.00 65.82           O
ATOM   1979  N    GLU A 141      66.252  26.330   6.007  1.00 54.19           N
ATOM   1980  CA   GLU A 141      65.971  26.468   4.553  1.00 54.93           C
ATOM   1982  CB   GLU A 141      66.633  27.733   3.955  1.00 56.54           C
ATOM   1985  CG   GLU A 141      65.680  28.870   3.689  1.00 60.97           C
ATOM   1988  CD   GLU A 141      66.254  29.946   2.789  1.00 66.63           C
ATOM   1989  OE1  GLU A 141      67.437  29.847   2.350  1.00 70.47           O
ATOM   1990  OE2  GLU A 141      65.497  30.914   2.526  1.00 71.07           O
ATOM   1991  C    GLU A 141      66.455  25.315   3.660  1.00 52.30           C
ATOM   1992  O    GLU A 141      66.354  25.412   2.432  1.00 53.22           O
ATOM   1994  N    LYS A 142      67.056  24.268   4.208  1.00 48.76           N
ATOM   1995  CA   LYS A 142      67.351  23.156   3.312  1.00 45.83           C
ATOM   1997  CB   LYS A 142      68.699  22.518   3.630  1.00 46.92           C
ATOM   2000  CG   LYS A 142      69.914  23.416   3.212  1.00 48.41           C
ATOM   2003  CD   LYS A 142      69.975  23.689   1.694  1.00 49.50           C
ATOM   2006  CE   LYS A 142      71.273  24.477   1.335  1.00 52.43           C
ATOM   2009  NZ   LYS A 142      71.287  25.053  -0.054  1.00 54.98           N
ATOM   2013  C    LYS A 142      66.161  22.174   3.366  1.00 41.85           C
ATOM   2014  O    LYS A 142      65.904  21.483   2.391  1.00 42.59           O
ATOM   2016  N    THR A 143      65.424  22.204   4.466  1.00 37.79           N
ATOM   2017  CA   THR A 143      64.265  21.330   4.696  1.00 36.03           C
ATOM   2019  CB   THR A 143      63.871  21.227   6.185  1.00 35.63           C
ATOM   2021  OG1  THR A 143      64.958  20.676   6.941  1.00 36.26           O
ATOM   2023  CG2  THR A 143      62.639  20.237   6.370  1.00 34.75           C
ATOM   2027  C    THR A 143      63.078  21.784   3.858  1.00 34.21           C
ATOM   2028  O    THR A 143      62.558  22.884   4.067  1.00 34.89           O
ATOM   2030  N    HIS A 144      62.714  20.931   2.897  1.00 31.61           N
ATOM   2031  CA   HIS A 144      61.557  21.048   2.101  1.00 29.62           C
ATOM   2033  CB   HIS A 144      61.573  20.060   0.969  1.00 29.61           C
ATOM   2036  CG   HIS A 144      60.901  20.538  -0.260  1.00 31.00           C
ATOM   2037  ND1  HIS A 144      61.530  21.406  -1.146  1.00 30.50           N
ATOM   2039  CE1  HIS A 144      60.698  21.661  -2.148  1.00 32.11           C
```

FIG. 15R

```
ATOM   2041  NE2 HIS A 144      59.582  20.965  -1.968  1.00 31.10           N
ATOM   2043  CD2 HIS A 144      59.685  20.247  -0.805  1.00 26.87           C
ATOM   2045  C   HIS A 144      60.291  20.879   2.888  1.00 28.47           C
ATOM   2046  O   HIS A 144      60.116  19.879   3.541  1.00 27.79           O
ATOM   2048  N   ILE A 145      59.381  21.841   2.748  1.00 27.56           N
ATOM   2049  CA  ILE A 145      58.080  21.792   3.438  1.00 27.91           C
ATOM   2051  CB  ILE A 145      57.761  23.115   4.109  1.00 28.32           C
ATOM   2053  CG1 ILE A 145      58.790  23.402   5.167  1.00 28.36           C
ATOM   2056  CD1 ILE A 145      58.893  24.933   5.450  1.00 29.89           C
ATOM   2060  CG2 ILE A 145      56.325  23.070   4.881  1.00 27.62           C
ATOM   2064  C   ILE A 145      56.975  21.421   2.522  1.00 27.68           C
ATOM   2065  O   ILE A 145      56.886  21.927   1.415  1.00 28.64           O
ATOM   2067  N   HIS A 146      56.111  20.518   2.971  1.00 26.16           N
ATOM   2068  CA  HIS A 146      54.929  20.144   2.201  1.00 24.73           C
ATOM   2070  CB  HIS A 146      55.136  18.818   1.472  1.00 24.51           C
ATOM   2073  CG  HIS A 146      54.169  18.565   0.349  1.00 24.21           C
ATOM   2074  ND1 HIS A 146      54.447  17.723  -0.705  1.00 24.83           N
ATOM   2076  CE1 HIS A 146      53.403  17.658  -1.495  1.00 26.04           C
ATOM   2078  NE2 HIS A 146      52.438  18.410  -0.980  1.00 26.01           N
ATOM   2080  CD2 HIS A 146      52.892  18.996   0.161  1.00 23.03           C
ATOM   2082  C   HIS A 146      53.743  20.098   3.168  1.00 24.70           C
ATOM   2083  O   HIS A 146      53.741  19.318   4.118  1.00 25.50           O
ATOM   2085  N   ILE A 147      52.733  20.918   2.879  1.00 25.24           N
ATOM   2086  CA  ILE A 147      51.561  21.095   3.697  1.00 25.32           C
ATOM   2088  CB  ILE A 147      51.276  22.604   4.068  1.00 27.36           C
ATOM   2090  CG1 ILE A 147      52.496  23.287   4.709  1.00 24.22           C
ATOM   2093  CD1 ILE A 147      53.108  22.634   5.995  1.00 25.83           C
ATOM   2097  CG2 ILE A 147      50.020  22.683   4.958  1.00 24.95           C
ATOM   2101  C   ILE A 147      50.321  20.586   2.971  1.00 24.52           C
ATOM   2102  O   ILE A 147      50.121  20.813   1.767  1.00 26.06           O
ATOM   2104  N   PHE A 148      49.511  19.799   3.700  1.00 23.79           N
ATOM   2105  CA  PHE A 148      48.264  19.311   3.214  1.00 24.52           C
ATOM   2107  CB  PHE A 148      48.246  17.752   3.251  1.00 22.62           C
ATOM   2110  CG  PHE A 148      49.172  17.107   2.331  1.00 23.94           C
ATOM   2111  CD1 PHE A 148      48.826  16.363   1.009  1.00 24.02           C
ATOM   2113  CE1 PHE A 148      49.719  16.254   0.125  1.00 26.48           C
ATOM   2115  CZ  PHE A 148      50.943  15.861   0.585  1.00 24.27           C
ATOM   2117  CE2 PHE A 148      51.291  16.076   1.927  1.00 23.44           C
ATOM   2119  CD2 PHE A 148      50.429  16.705   2.787  1.00 23.79           C
ATOM   2121  C   PHE A 148      47.144  19.791   4.126  1.00 24.42           C
ATOM   2122  O   PHE A 148      47.348  19.816   5.362  1.00 25.05           O
ATOM   2124  N   SER A 149      45.977  20.084   3.547  1.00 25.10           N
ATOM   2125  CA  SER A 149      44.806  20.383   4.306  1.00 25.50           C
ATOM   2127  CB  SER A 149      44.099  21.644   3.774  1.00 26.08           C
ATOM   2130  OG  SER A 149      43.483  21.414   2.506  1.00 28.35           O
ATOM   2132  C   SER A 149      43.839  19.204   4.272  1.00 26.70           C
ATOM   2133  O   SER A 149      44.091  18.235   3.586  1.00 26.61           O
ATOM   2135  N   PHE A 150      42.741  19.313   5.008  1.00 26.45           N
ATOM   2136  CA  PHE A 150      41.639  18.391   4.875  1.00 27.80           C
ATOM   2138  CB  PHE A 150      40.931  18.288   6.218  1.00 28.57           C
ATOM   2141  CG  PHE A 150      41.767  17.653   7.309  1.00 26.93           C
ATOM   2142  CD1 PHE A 150      41.667  16.303   7.599  1.00 23.08           C
ATOM   2144  CE1 PHE A 150      42.369  15.751   8.576  1.00 24.02           C
ATOM   2146  CZ  PHE A 150      43.297  16.513   9.298  1.00 26.68           C
ATOM   2148  CE2 PHE A 150      43.443  17.857   9.016  1.00 28.79           C
ATOM   2150  CD2 PHE A 150      42.691  18.412   8.009  1.00 27.83           C
ATOM   2152  C   PHE A 150      40.650  18.836   3.765  1.00 29.06           C
ATOM   2153  O   PHE A 150      39.548  18.367   3.719  1.00 30.35           O
ATOM   2155  N   THR A 151      41.041  19.811   2.936  1.00 30.82           N
ATOM   2156  CA  THR A 151      40.217  20.378   1.901  1.00 31.77           C
ATOM   2158  CB  THR A 151      40.138  21.930   2.053  1.00 32.21           C
ATOM   2160  OG1 THR A 151      41.463  22.507   1.760  1.00 35.79           O
ATOM   2162  CG2 THR A 151      39.645  22.290   3.432  1.00 32.61           C
```

FIG. 15S

```
ATOM   2166  C   THR A 151      40.809  20.046   0.507  1.00 31.31           C
ATOM   2167  O   THR A 151      40.309  20.571  -0.475  1.00 31.21           O
ATOM   2169  N   GLY A 152      41.920  19.284   0.438  1.00 29.28           N
ATOM   2170  CA  GLY A 152      42.507  18.954  -0.837  1.00 30.05           C
ATOM   2173  C   GLY A 152      43.457  19.992  -1.298  1.00 30.16           C
ATOM   2174  O   GLY A 152      43.849  19.994  -2.482  1.00 28.81           O
ATOM   2176  N   GLU A 153      43.789  20.913  -0.395  1.00 28.76           N
ATOM   2177  CA  GLU A 153      44.788  21.894  -0.724  1.00 30.94           C
ATOM   2179  CB  GLU A 153      44.422  23.209  -0.098  1.00 30.70           C
ATOM   2182  CG  GLU A 153      43.191  23.755  -0.720  1.00 37.46           C
ATOM   2185  CD  GLU A 153      43.467  24.156  -2.172  1.00 48.47           C
ATOM   2186  OE1 GLU A 153      44.252  25.126  -2.392  1.00 55.74           O
ATOM   2187  OE2 GLU A 153      42.952  23.478  -3.098  1.00 55.29           O
ATOM   2188  C   GLU A 153      46.196  21.426  -0.313  1.00 29.71           C
ATOM   2189  O   GLU A 153      46.354  20.673   0.639  1.00 27.76           O
ATOM   2191  N   GLU A 154      47.198  21.945  -0.991  1.00 29.46           N
ATOM   2192  CA  GLU A 154      48.562  21.730  -0.576  1.00 30.45           C
ATOM   2194  CB  GLU A 154      49.126  20.443  -1.232  1.00 30.39           C
ATOM   2197  CG  GLU A 154      49.029  20.438  -2.711  1.00 30.47           C
ATOM   2200  CD  GLU A 154      49.543  19.158  -3.375  1.00 32.96           C
ATOM   2201  OE1 GLU A 154      49.165  18.974  -4.569  1.00 31.61           O
ATOM   2202  OE2 GLU A 154      50.338  18.351  -2.753  1.00 29.73           O
ATOM   2203  C   GLU A 154      49.358  22.958  -0.921  1.00 29.77           C
ATOM   2204  O   GLU A 154      48.999  23.718  -1.838  1.00 31.37           O
ATOM   2206  N   MET A 155      50.431  23.118  -0.202  1.00 29.24           N
ATOM   2207  CA  MET A 155      51.468  24.115  -0.452  1.00 30.22           C
ATOM   2209  CB  MET A 155      51.227  25.396   0.327  1.00 26.93           C
ATOM   2212  CG  MET A 155      52.217  26.532   0.009  1.00 32.34           C
ATOM   2215  SD  MET A 155      51.787  28.035   0.881  1.00 36.87           S
ATOM   2216  CE  MET A 155      50.684  28.665  -0.426  1.00 41.93           C
ATOM   2220  C   MET A 155      52.827  23.509  -0.074  1.00 29.88           C
ATOM   2221  O   MET A 155      52.967  22.893   0.970  1.00 30.17           O
ATOM   2223  N   ALA A 156      53.813  23.732  -0.939  1.00 31.46           N
ATOM   2224  CA  ALA A 156      55.135  23.141  -0.788  1.00 31.35           C
ATOM   2226  CB  ALA A 156      55.209  21.891  -1.695  1.00 31.85           C
ATOM   2230  C   ALA A 156      56.190  24.165  -1.143  1.00 32.96           C
ATOM   2231  O   ALA A 156      55.946  25.051  -2.001  1.00 32.16           O
ATOM   2233  N   THR A 157      57.344  24.081  -0.481  1.00 31.90           N
ATOM   2234  CA  THR A 157      58.473  24.916  -0.848  1.00 32.63           C
ATOM   2236  CB  THR A 157      59.719  24.392  -0.261  1.00 31.33           C
ATOM   2238  OG1 THR A 157      59.526  24.218   1.131  1.00 30.59           O
ATOM   2240  CG2 THR A 157      60.969  25.400  -0.589  1.00 33.92           C
ATOM   2244  C   THR A 157      58.627  24.965  -2.356  1.00 33.71           C
ATOM   2245  O   THR A 157      58.709  23.939  -2.983  1.00 33.41           O
ATOM   2247  N   LYS A 158      58.684  26.178  -2.926  1.00 35.63           N
ATOM   2248  CA  LYS A 158      59.037  26.426  -4.345  1.00 38.06           C
ATOM   2250  CB  LYS A 158      60.440  25.881  -4.720  1.00 38.52           C
ATOM   2253  CG  LYS A 158      61.548  26.813  -4.287  1.00 43.77           C
ATOM   2256  CD  LYS A 158      62.920  26.176  -4.451  1.00 50.12           C
ATOM   2259  CE  LYS A 158      63.968  26.696  -3.419  1.00 51.94           C
ATOM   2262  NZ  LYS A 158      65.303  25.978  -3.569  1.00 54.48           N
ATOM   2266  C   LYS A 158      57.947  25.882  -5.222  1.00 36.66           C
ATOM   2267  O   LYS A 158      58.120  25.633  -6.409  1.00 37.81           O
ATOM   2269  N   ALA A 159      56.778  25.672  -4.620  1.00 36.78           N
ATOM   2270  CA  ALA A 159      55.736  24.921  -5.290  1.00 35.33           C
ATOM   2272  CB  ALA A 159      54.976  25.840  -6.328  1.00 35.78           C
ATOM   2276  C   ALA A 159      56.247  23.630  -5.941  1.00 34.36           C
ATOM   2277  O   ALA A 159      55.789  23.215  -6.989  1.00 35.50           O
ATOM   2279  N   ASP A 160      57.194  22.962  -5.276  1.00 33.74           N
ATOM   2280  CA  ASP A 160      57.680  21.695  -5.702  1.00 32.65           C
ATOM   2282  CB  ASP A 160      59.195  21.657  -5.490  1.00 33.13           C
ATOM   2285  CG  ASP A 160      59.807  20.348  -5.880  1.00 33.72           C
ATOM   2286  OD1 ASP A 160      59.094  19.340  -6.149  1.00 37.99           O
```

FIG. 15T

```
ATOM   2287  OD2 ASP A 160      61.050  20.297  -5.922  1.00 36.13           O
ATOM   2288  C   ASP A 160      56.994  20.667  -4.813  1.00 31.04           C
ATOM   2289  O   ASP A 160      57.323  20.583  -3.656  1.00 30.14           O
ATOM   2291  N   TYR A 161      55.990  19.993  -5.356  1.00 31.54           N
ATOM   2292  CA  TYR A 161      55.150  19.039  -4.597  1.00 30.31           C
ATOM   2294  CB  TYR A 161      53.761  18.992  -5.205  1.00 31.64           C
ATOM   2297  CG  TYR A 161      53.080  20.350  -5.121  1.00 31.18           C
ATOM   2298  CD1 TYR A 161      52.722  20.893  -3.914  1.00 30.44           C
ATOM   2300  CE1 TYR A 161      52.067  22.143  -3.845  1.00 32.44           C
ATOM   2302  CZ  TYR A 161      51.843  22.853  -5.036  1.00 38.20           C
ATOM   2303  OH  TYR A 161      51.207  24.078  -5.056  1.00 39.66           O
ATOM   2305  CE2 TYR A 161      52.215  22.326  -6.234  1.00 34.66           C
ATOM   2307  CD2 TYR A 161      52.842  21.088  -6.278  1.00 37.13           C
ATOM   2309  C   TYR A 161      55.754  17.607  -4.494  1.00 29.93           C
ATOM   2310  O   TYR A 161      55.142  16.694  -3.932  1.00 26.52           O
ATOM   2312  N   THR A 162      56.976  17.440  -5.018  1.00 31.04           N
ATOM   2313  CA  THR A 162      57.783  16.227  -4.830  1.00 29.62           C
ATOM   2315  CB  THR A 162      58.114  15.930  -3.310  1.00 28.53           C
ATOM   2317  OG1 THR A 162      58.865  16.995  -2.757  1.00 27.24           O
ATOM   2319  CG2 THR A 162      58.884  14.666  -3.140  1.00 26.62           C
ATOM   2323  C   THR A 162      57.168  15.000  -5.450  1.00 30.35           C
ATOM   2324  O   THR A 162      57.798  14.372  -6.306  1.00 31.59           O
ATOM   2326  N   LEU A 163      55.952  14.588  -5.027  1.00 29.24           N
ATOM   2327  CA  LEU A 163      55.304  13.380  -5.504  1.00 28.46           C
ATOM   2329  CB  LEU A 163      54.302  12.829  -4.464  1.00 29.74           C
ATOM   2332  CG  LEU A 163      54.888  12.473  -3.103  1.00 30.65           C
ATOM   2334  CD1 LEU A 163      53.824  12.209  -2.055  1.00 30.87           C
ATOM   2338  CD2 LEU A 163      55.757  11.188  -3.301  1.00 27.81           C
ATOM   2342  C   LEU A 163      54.540  13.647  -6.821  1.00 29.29           C
ATOM   2343  O   LEU A 163      54.259  14.767  -7.177  1.00 30.11           O
ATOM   2345  N   ASP A 164      54.200  12.596  -7.508  1.00 30.22           N
ATOM   2346  CA  ASP A 164      53.320  12.707  -8.701  1.00 32.33           C
ATOM   2348  CB  ASP A 164      53.387  11.478  -9.605  1.00 32.82           C
ATOM   2351  CG  ASP A 164      52.827  10.191  -8.939  1.00 39.74           C
ATOM   2352  OD1 ASP A 164      52.212  10.249  -7.832  1.00 42.97           O
ATOM   2353  OD2 ASP A 164      53.018   9.089  -9.527  1.00 43.10           O
ATOM   2354  C   ASP A 164      51.889  12.990  -8.219  1.00 33.00           C
ATOM   2355  O   ASP A 164      51.568  12.945  -7.005  1.00 30.46           O
ATOM   2357  N   GLU A 165      51.038  13.304  -9.181  1.00 33.85           N
ATOM   2358  CA  GLU A 165      49.652  13.749  -8.914  1.00 35.10           C
ATOM   2360  CB  GLU A 165      48.959  14.137 -10.215  1.00 35.75           C
ATOM   2363  CG  GLU A 165      49.597  15.382 -10.844  1.00 38.75           C
ATOM   2366  CD  GLU A 165      49.198  16.668 -10.160  1.00 46.27           C
ATOM   2367  OE1 GLU A 165      48.227  16.711  -9.322  1.00 49.58           O
ATOM   2368  OE2 GLU A 165      49.853  17.682 -10.467  1.00 50.07           O
ATOM   2369  C   GLU A 165      48.836  12.687  -8.195  1.00 33.48           C
ATOM   2370  O   GLU A 165      48.088  13.029  -7.260  1.00 32.20           O
ATOM   2372  N   GLU A 166      49.008  11.434  -8.622  1.00 31.26           N
ATOM   2373  CA  GLU A 166      48.276  10.347  -8.047  1.00 32.53           C
ATOM   2375  CB  GLU A 166      48.427   9.052  -8.797  1.00 33.11           C
ATOM   2378  CG  GLU A 166      47.620   7.961  -8.149  1.00 38.83           C
ATOM   2381  CD  GLU A 166      47.435   6.732  -8.966  1.00 47.82           C
ATOM   2382  OE1 GLU A 166      47.707   6.766 -10.189  1.00 54.26           O
ATOM   2383  OE2 GLU A 166      46.991   5.718  -8.381  1.00 53.70           O
ATOM   2384  C   GLU A 166      48.597  10.128  -6.572  1.00 31.20           C
ATOM   2385  O   GLU A 166      47.704   9.799  -5.780  1.00 27.69           O
ATOM   2387  N   SER A 167      49.858  10.360  -6.200  1.00 30.33           N
ATOM   2388  CA  SER A 167      50.253  10.084  -4.831  1.00 30.62           C
ATOM   2390  CB  SER A 167      51.768  10.001  -4.697  1.00 31.04           C
ATOM   2393  OG  SER A 167      52.236   8.805  -5.296  1.00 32.02           O
ATOM   2395  C   SER A 167      49.643  11.154  -3.972  1.00 29.54           C
ATOM   2396  O   SER A 167      49.121  10.861  -2.878  1.00 28.16           O
ATOM   2398  N   ARG A 168      49.680  12.390  -4.468  1.00 27.80           N
```

FIG. 15U

```
ATOM   2399  CA   ARG A 168      49.181   13.483   -3.676  1.00 27.94           C
ATOM   2401  CB   ARG A 168      49.602   14.756   -4.289  1.00 27.61           C
ATOM   2404  CG   ARG A 168      51.052   15.132   -3.932  1.00 30.40           C
ATOM   2407  CD   ARG A 168      51.303   16.482   -4.557  1.00 40.05           C
ATOM   2410  NE   ARG A 168      51.643   16.311   -5.894  1.00 41.57           N
ATOM   2412  CZ   ARG A 168      51.408   17.095   -6.946  1.00 40.06           C
ATOM   2413  NH1  ARG A 168      50.701   18.206   -6.942  1.00 41.33           N
ATOM   2416  NH2  ARG A 168      51.920   16.648   -8.076  1.00 39.18           N
ATOM   2419  C    ARG A 168      47.650   13.374   -3.584  1.00 28.20           C
ATOM   2420  O    ARG A 168      47.074   13.630   -2.527  1.00 27.76           O
ATOM   2422  N    ALA A 169      47.032   13.007   -4.692  1.00 27.81           N
ATOM   2423  CA   ALA A 169      45.548   12.764   -4.693  1.00 28.27           C
ATOM   2425  CB   ALA A 169      45.087   12.409   -6.075  1.00 27.69           C
ATOM   2429  C    ALA A 169      45.112   11.696   -3.665  1.00 27.68           C
ATOM   2430  O    ALA A 169      44.105   11.874   -2.985  1.00 27.14           O
ATOM   2432  N    ARG A 170      45.856   10.605   -3.508  1.00 28.18           N
ATOM   2433  CA   ARG A 170      45.515    9.601   -2.535  1.00 28.85           C
ATOM   2435  CB   ARG A 170      46.323    8.331   -2.663  1.00 30.37           C
ATOM   2438  CG   ARG A 170      46.175    7.629   -4.044  1.00 38.79           C
ATOM   2441  CD   ARG A 170      46.727    6.173   -3.939  1.00 46.28           C
ATOM   2444  NE   ARG A 170      46.438    5.369   -5.143  1.00 56.73           N
ATOM   2446  CZ   ARG A 170      46.761    4.074   -5.288  1.00 61.83           C
ATOM   2447  NH1  ARG A 170      47.389    3.410   -4.301  1.00 61.96           N
ATOM   2450  NH2  ARG A 170      46.462    3.435   -6.426  1.00 63.35           N
ATOM   2453  C    ARG A 170      45.673   10.124   -1.113  1.00 27.52           C
ATOM   2454  O    ARG A 170      44.894    9.782   -0.225  1.00 25.16           O
ATOM   2456  N    ILE A 171      46.695   10.922   -0.882  1.00 24.59           N
ATOM   2457  CA   ILE A 171      46.852   11.521    0.453  1.00 23.95           C
ATOM   2459  CB   ILE A 171      48.202   12.243    0.559  1.00 22.75           C
ATOM   2461  CG1  ILE A 171      49.324   11.240    0.584  1.00 25.81           C
ATOM   2464  CD1  ILE A 171      50.712   11.862    0.201  1.00 27.61           C
ATOM   2468  CG2  ILE A 171      48.280   13.221    1.786  1.00 22.81           C
ATOM   2472  C    ILE A 171      45.669   12.493    0.739  1.00 23.85           C
ATOM   2473  O    ILE A 171      45.043   12.455    1.813  1.00 21.70           O
ATOM   2475  N    LYS A 172      45.352   13.311   -0.244  1.00 23.48           N
ATOM   2476  CA   LYS A 172      44.295   14.270   -0.114  1.00 23.54           C
ATOM   2478  CB   LYS A 172      44.202   15.135   -1.376  1.00 22.27           C
ATOM   2481  CG   LYS A 172      45.327   16.113   -1.474  1.00 24.79           C
ATOM   2484  CD   LYS A 172      45.367   16.711   -2.930  1.00 25.26           C
ATOM   2487  CE   LYS A 172      46.374   17.801   -3.082  1.00 28.91           C
ATOM   2490  NZ   LYS A 172      46.554   18.236   -4.533  1.00 29.28           N
ATOM   2494  C    LYS A 172      42.971   13.542    0.173  1.00 23.88           C
ATOM   2495  O    LYS A 172      42.165   14.030    1.010  1.00 22.00           O
ATOM   2497  N    THR A 173      42.757   12.416   -0.514  1.00 22.09           N
ATOM   2498  CA   THR A 173      41.527   11.632   -0.363  1.00 23.82           C
ATOM   2500  CB   THR A 173      41.394   10.515   -1.407  1.00 24.34           C
ATOM   2502  OG1  THR A 173      41.422   11.125   -2.696  1.00 23.99           O
ATOM   2504  CG2  THR A 173      40.096    9.695   -1.190  1.00 22.42           C
ATOM   2508  C    THR A 173      41.439   11.057    1.030  1.00 23.63           C
ATOM   2509  O    THR A 173      40.400   11.143    1.690  1.00 23.28           O
ATOM   2511  N    ARG A 174      42.540   10.554    1.524  1.00 23.86           N
ATOM   2512  CA   ARG A 174      42.509    9.975    2.870  1.00 23.67           C
ATOM   2514  CB   ARG A 174      43.814    9.284    3.146  1.00 23.50           C
ATOM   2517  CG   ARG A 174      43.920    8.746    4.577  1.00 24.93           C
ATOM   2520  CD   ARG A 174      42.896    7.651    4.897  1.00 26.22           C
ATOM   2523  NE   ARG A 174      43.107    7.214    6.290  1.00 28.64           N
ATOM   2525  CZ   ARG A 174      42.196    6.719    7.111  1.00 34.36           C
ATOM   2526  NH1  ARG A 174      40.900    6.626    6.767  1.00 32.44           N
ATOM   2529  NH2  ARG A 174      42.594    6.367    8.317  1.00 33.99           N
ATOM   2532  C    ARG A 174      42.214   11.052    3.922  1.00 23.15           C
ATOM   2533  O    ARG A 174      41.442   10.781    4.858  1.00 23.23           O
ATOM   2535  N    LEU A 175      42.907   12.223    3.853  1.00 22.25           N
ATOM   2536  CA   LEU A 175      42.683   13.315    4.791  1.00 22.73           C
```

FIG. 15V

```
ATOM   2538  CB  LEU A 175      43.562  14.486   4.428  1.00 23.20           C
ATOM   2541  CG  LEU A 175      45.052  14.243   4.736  1.00 21.29           C
ATOM   2543  CD1 LEU A 175      45.978  15.356   4.264  1.00 22.48           C
ATOM   2547  CD2 LEU A 175      45.154  14.117   6.277  1.00 20.52           C
ATOM   2551  C   LEU A 175      41.191  13.719   4.774  1.00 24.51           C
ATOM   2552  O   LEU A 175      40.549  13.806   5.814  1.00 23.15           O
ATOM   2554  N   PHE A 176      40.646  13.897   3.560  1.00 24.68           N
ATOM   2555  CA  PHE A 176      39.267  14.332   3.426  1.00 24.62           C
ATOM   2557  CB  PHE A 176      38.960  14.629   1.959  1.00 25.01           C
ATOM   2560  CG  PHE A 176      37.599  15.275   1.727  1.00 20.36           C
ATOM   2561  CD1 PHE A 176      37.441  16.648   1.745  1.00 28.35           C
ATOM   2563  CE1 PHE A 176      36.194  17.214   1.532  1.00 28.96           C
ATOM   2565  CZ  PHE A 176      35.148  16.389   1.345  1.00 26.10           C
ATOM   2567  CE2 PHE A 176      35.295  15.084   1.376  1.00 23.03           C
ATOM   2569  CD2 PHE A 176      36.503  14.497   1.593  1.00 24.15           C
ATOM   2571  C   PHE A 176      38.334  13.253   3.974  1.00 23.43           C
ATOM   2572  O   PHE A 176      37.286  13.587   4.580  1.00 24.90           O
ATOM   2574  N   THR A 177      38.669  12.001   3.790  1.00 24.64           N
ATOM   2575  CA  THR A 177      37.884  10.928   4.311  1.00 24.07           C
ATOM   2577  CB  THR A 177      38.364   9.607   3.764  1.00 26.26           C
ATOM   2579  OG1 THR A 177      38.215   9.651   2.345  1.00 26.99           O
ATOM   2581  CG2 THR A 177      37.616   8.416   4.360  1.00 27.14           C
ATOM   2585  C   THR A 177      37.876  10.951   5.852  1.00 26.03           C
ATOM   2586  O   THR A 177      36.823  10.815   6.481  1.00 24.89           O
ATOM   2588  N   ILE A 178      39.041  11.144   6.462  1.00 25.83           N
ATOM   2589  CA  ILE A 178      39.119  11.251   7.945  1.00 24.22           C
ATOM   2591  CB  ILE A 178      40.548  11.538   8.404  1.00 24.87           C
ATOM   2593  CG1 ILE A 178      41.441  10.290   8.145  1.00 21.54           C
ATOM   2596  CD1 ILE A 178      42.964  10.562   8.107  1.00 24.20           C
ATOM   2600  CG2 ILE A 178      40.539  12.106   9.885  1.00 25.42           C
ATOM   2604  C   ILE A 178      38.199  12.381   8.379  1.00 25.55           C
ATOM   2605  O   ILE A 178      37.462  12.227   9.347  1.00 28.89           O
ATOM   2607  N   ARG A 179      38.279  13.542   7.747  1.00 25.10           N
ATOM   2608  CA  ARG A 179      37.461  14.672   8.099  1.00 25.30           C
ATOM   2610  CB  ARG A 179      37.755  15.812   7.115  1.00 26.41           C
ATOM   2613  CG  ARG A 179      36.779  16.943   7.113  1.00 26.34           C
ATOM   2616  CD  ARG A 179      37.121  18.019   6.100  1.00 31.57           C
ATOM   2619  NE  ARG A 179      35.931  18.813   5.749  1.00 32.67           N
ATOM   2621  CZ  ARG A 179      35.889  19.741   4.834  1.00 36.55           C
ATOM   2622  NH1 ARG A 179      36.985  20.033   4.106  1.00 38.00           N
ATOM   2625  NH2 ARG A 179      34.744  20.380   4.606  1.00 39.70           N
ATOM   2628  C   ARG A 179      35.983  14.288   8.070  1.00 26.17           C
ATOM   2629  O   ARG A 179      35.218  14.604   8.998  1.00 25.08           O
ATOM   2631  N   GLN A 180      35.572  13.655   6.962  1.00 26.58           N
ATOM   2632  CA  GLN A 180      34.154  13.298   6.825  1.00 27.17           C
ATOM   2634  CB  GLN A 180      33.885  12.855   5.390  1.00 26.73           C
ATOM   2637  CG  GLN A 180      34.018  13.994   4.390  1.00 23.51           C
ATOM   2640  CD  GLN A 180      33.116  15.130   4.695  1.00 24.73           C
ATOM   2641  OE1 GLN A 180      31.982  14.953   5.153  1.00 26.56           O
ATOM   2642  NE2 GLN A 180      33.573  16.305   4.450  1.00 24.59           N
ATOM   2645  C   GLN A 180      33.730  12.203   7.835  1.00 28.34           C
ATOM   2646  O   GLN A 180      32.531  12.191   8.265  1.00 31.72           O
ATOM   2648  N   GLU A 181      34.614  11.263   8.183  1.00 27.65           N
ATOM   2649  CA  GLU A 181      34.296  10.254   9.194  1.00 29.16           C
ATOM   2651  CB  GLU A 181      35.316   9.122   9.257  1.00 28.63           C
ATOM   2654  CG  GLU A 181      35.324   8.306   7.968  1.00 33.56           C
ATOM   2657  CD  GLU A 181      36.360   7.231   7.983  1.00 37.89           C
ATOM   2658  OE1 GLU A 181      37.231   7.237   8.889  1.00 43.00           O
ATOM   2659  OE2 GLU A 181      36.346   6.376   7.073  1.00 45.13           O
ATOM   2660  C   GLU A 181      34.160  10.935  10.531  1.00 29.30           C
ATOM   2661  O   GLU A 181      33.228  10.619  11.313  1.00 29.71           O
ATOM   2663  N   MET A 182      34.974  11.960  10.774  1.00 28.89           N
ATOM   2664  CA  MET A 182      34.773  12.791  11.978  1.00 27.59           C
```

FIG. 15W

```
ATOM   2666  CB   MET A 182      35.909  13.781  12.237  1.00 26.73           C
ATOM   2669  CG   MET A 182      37.272  13.095  12.513  1.00 26.59           C
ATOM   2672  SD   MET A 182      38.431  14.392  12.816  1.00 30.86           S
ATOM   2673  CE   MET A 182      39.752  13.396  13.318  1.00 29.47           C
ATOM   2677  C    MET A 182      33.476  13.551  11.903  1.00 29.37           C
ATOM   2678  O    MET A 182      32.724  13.602  12.893  1.00 30.90           O
ATOM   2680  N    ALA A 183      33.170  14.128  10.732  1.00 29.41           N
ATOM   2681  CA   ALA A 183      31.936  14.879  10.585  1.00 29.66           C
ATOM   2683  CB   ALA A 183      31.840  15.655   9.208  1.00 28.42           C
ATOM   2687  C    ALA A 183      30.739  13.951  10.774  1.00 30.31           C
ATOM   2688  O    ALA A 183      29.721  14.382  11.300  1.00 32.63           O
ATOM   2690  N    SER A 184      30.857  12.711  10.379  1.00 33.09           N
ATOM   2691  CA   SER A 184      29.799  11.758  10.550  1.00 34.98           C
ATOM   2693  CB   SER A 184      30.210  10.395  10.093  1.00 34.44           C
ATOM   2696  OG   SER A 184      30.307  10.394   8.685  1.00 40.38           O
ATOM   2698  C    SER A 184      29.431  11.622  12.015  1.00 37.48           C
ATOM   2699  O    SER A 184      28.245  11.442  12.315  1.00 36.22           O
ATOM   2701  N    ARG A 185      30.460  11.607  12.867  1.00 38.38           N
ATOM   2702  CA   ARG A 185      30.344  11.463  14.314  1.00 40.16           C
ATOM   2704  CB   ARG A 185      31.492  10.558  14.820  1.00 41.09           C
ATOM   2707  CG   ARG A 185      31.447   9.154  14.176  1.00 45.67           C
ATOM   2710  CD   ARG A 185      32.420   8.085  14.767  1.00 53.28           C
ATOM   2713  NE   ARG A 185      32.377   8.033  16.256  1.00 59.10           N
ATOM   2715  CZ   ARG A 185      33.014   7.155  17.043  1.00 54.68           C
ATOM   2716  NH1  ARG A 185      33.727   6.155  16.537  1.00 55.85           N
ATOM   2719  NH2  ARG A 185      32.878   7.272  18.350  1.00 57.19           N
ATOM   2722  C    ARG A 185      30.252  12.759  15.082  1.00 39.45           C
ATOM   2723  O    ARG A 185      30.312  12.734  16.279  1.00 40.69           O
ATOM   2725  N    SER A 186      30.043  13.886  14.404  1.00 39.19           N
ATOM   2726  CA   SER A 186      29.988  15.215  14.994  1.00 39.62           C
ATOM   2728  CB   SER A 186      28.676  15.387  15.824  1.00 41.74           C
ATOM   2731  OG   SER A 186      27.524  15.263  14.982  1.00 41.75           O
ATOM   2733  C    SER A 186      31.236  15.598  15.809  1.00 39.62           C
ATOM   2734  O    SER A 186      31.153  16.349  16.794  1.00 39.05           O
ATOM   2736  N    LEU A 187      32.401  15.096  15.370  1.00 38.55           N
ATOM   2737  CA   LEU A 187      33.700  15.343  16.016  1.00 36.62           C
ATOM   2739  CB   LEU A 187      34.441  14.052  16.203  1.00 37.57           C
ATOM   2742  CG   LEU A 187      33.783  12.907  16.973  1.00 37.85           C
ATOM   2744  CD1  LEU A 187      34.698  11.790  16.843  1.00 34.83           C
ATOM   2748  CD2  LEU A 187      33.520  13.383  18.393  1.00 41.06           C
ATOM   2752  C    LEU A 187      34.606  16.302  15.239  1.00 36.62           C
ATOM   2753  O    LEU A 187      35.654  16.715  15.784  1.00 37.11           O
ATOM   2755  N    TRP A 188      34.238  16.642  13.988  1.00 35.45           N
ATOM   2756  CA   TRP A 188      35.060  17.477  13.113  1.00 35.47           C
ATOM   2758  CB   TRP A 188      34.489  17.537  11.668  1.00 35.76           C
ATOM   2761  CG   TRP A 188      35.171  18.570  10.882  1.00 31.25           C
ATOM   2762  CD1  TRP A 188      34.667  19.785  10.506  1.00 32.35           C
ATOM   2764  NE1  TRP A 188      35.623  20.513   9.849  1.00 32.61           N
ATOM   2766  CE2  TRP A 188      36.795  19.794   9.837  1.00 28.06           C
ATOM   2767  CD2  TRP A 188      36.545  18.568  10.487  1.00 28.00           C
ATOM   2768  CE3  TRP A 188      37.573  17.637  10.593  1.00 29.17           C
ATOM   2770  CZ3  TRP A 188      38.797  17.942  10.023  1.00 26.69           C
ATOM   2772  CH2  TRP A 188      39.019  19.174   9.408  1.00 23.86           C
ATOM   2774  CZ2  TRP A 188      38.014  20.111   9.302  1.00 26.86           C
ATOM   2776  C    TRP A 188      35.192  18.928  13.646  1.00 36.29           C
ATOM   2777  O    TRP A 188      36.256  19.491  13.693  1.00 35.22           O
ATOM   2779  N    ASP A 189      34.084  19.538  14.029  1.00 36.39           N
ATOM   2780  CA   ASP A 189      34.147  20.903  14.454  1.00 37.65           C
ATOM   2782  CB   ASP A 189      32.734  21.378  14.778  1.00 38.87           C
ATOM   2785  CG   ASP A 189      32.691  22.838  15.076  1.00 43.69           C
ATOM   2786  OD1  ASP A 189      32.547  23.642  14.113  1.00 51.93           O
ATOM   2787  OD2  ASP A 189      32.773  23.173  16.270  1.00 48.12           O
ATOM   2788  C    ASP A 189      35.131  21.123  15.650  1.00 36.44           C
```

FIG. 15X

```
ATOM   2789  O    ASP A 189      35.949  22.046  15.628  1.00 37.05           O
ATOM   2791  N    SER A 190      35.075  20.237  16.630  1.00 35.71           N
ATOM   2792  CA   SER A 190      35.958  20.251  17.781  1.00 36.18           C
ATOM   2794  CB   SER A 190      35.649  19.078  18.701  1.00 35.90           C
ATOM   2797  OG   SER A 190      36.657  18.917  19.700  1.00 36.76           O
ATOM   2799  C    SER A 190      37.396  20.128  17.297  1.00 36.17           C
ATOM   2800  O    SER A 190      38.274  20.997  17.564  1.00 35.59           O
ATOM   2802  N    PHE A 191      37.609  19.077  16.508  1.00 35.68           N
ATOM   2803  CA   PHE A 191      38.964  18.783  15.974  1.00 34.86           C
ATOM   2805  CB   PHE A 191      38.941  17.520  15.120  1.00 34.80           C
ATOM   2808  CG   PHE A 191      40.256  17.159  14.536  1.00 29.83           C
ATOM   2809  CD1  PHE A 191      41.267  16.608  15.319  1.00 27.51           C
ATOM   2811  CE1  PHE A 191      42.483  16.243  14.715  1.00 28.12           C
ATOM   2813  CZ   PHE A 191      42.660  16.403  13.371  1.00 28.30           C
ATOM   2815  CE2  PHE A 191      41.662  16.899  12.606  1.00 31.17           C
ATOM   2817  CD2  PHE A 191      40.469  17.308  13.186  1.00 30.35           C
ATOM   2819  C    PHE A 191      39.484  19.953  15.240  1.00 35.81           C
ATOM   2820  O    PHE A 191      40.635  20.377  15.468  1.00 39.04           O
ATOM   2822  N    ARG A 192      38.681  20.510  14.364  1.00 37.44           N
ATOM   2823  CA   ARG A 192      39.101  21.661  13.596  1.00 40.73           C
ATOM   2825  CB   ARG A 192      38.016  22.101  12.627  1.00 40.97           C
ATOM   2828  CG   ARG A 192      38.410  23.310  11.820  1.00 45.51           C
ATOM   2831  CD   ARG A 192      37.284  23.911  11.063  1.00 47.51           C
ATOM   2834  NE   ARG A 192      36.085  24.046  11.889  1.00 52.34           N
ATOM   2836  CZ   ARG A 192      35.718  25.145  12.543  1.00 55.03           C
ATOM   2837  NH1  ARG A 192      36.460  26.233  12.528  1.00 56.77           N
ATOM   2840  NH2  ARG A 192      34.594  25.149  13.239  1.00 57.12           N
ATOM   2843  C    ARG A 192      39.465  22.872  14.471  1.00 42.53           C
ATOM   2844  O    ARG A 192      40.391  23.620  14.168  1.00 42.73           O
ATOM   2846  N    GLN A 193      38.718  23.101  15.540  1.00 42.64           N
ATOM   2847  CA   GLN A 193      39.006  24.286  16.361  1.00 42.34           C
ATOM   2849  CB   GLN A 193      37.741  24.763  17.083  1.00 42.89           C
ATOM   2852  CG   GLN A 193      36.664  25.313  16.209  1.00 41.61           C
ATOM   2855  CD   GLN A 193      35.556  25.994  17.016  1.00 44.64           C
ATOM   2856  OE1  GLN A 193      35.743  27.085  17.557  1.00 39.07           O
ATOM   2857  NE2  GLN A 193      34.384  25.349  17.081  1.00 45.01           N
ATOM   2860  C    GLN A 193      40.210  24.107  17.307  1.00 44.01           C
ATOM   2861  O    GLN A 193      40.785  25.124  17.712  1.00 45.48           O
ATOM   2863  N    SER A 194      40.663  22.886  17.593  1.00 44.02           N
ATOM   2864  CA   SER A 194      41.803  22.698  18.519  1.00 45.95           C
ATOM   2866  CB   SER A 194      41.708  21.356  19.167  1.00 45.22           C
ATOM   2869  OG   SER A 194      41.505  20.452  18.153  1.00 49.40           O
ATOM   2871  C    SER A 194      43.218  22.837  17.948  1.00 47.09           C
ATOM   2872  O    SER A 194      44.201  22.407  18.561  1.00 48.16           O
ATOM   2874  N    GLU A 195      43.351  23.392  16.763  1.00 47.27           N
ATOM   2875  CA   GLU A 195      44.713  23.569  16.211  1.00 47.89           C
ATOM   2877  CB   GLU A 195      44.749  23.242  14.698  1.00 46.47           C
ATOM   2880  CG   GLU A 195      46.171  23.343  14.088  1.00 46.49           C
ATOM   2883  CD   GLU A 195      46.208  23.019  12.592  1.00 42.09           C
ATOM   2884  OE1  GLU A 195      45.667  21.977  12.213  1.00 39.80           O
ATOM   2885  OE2  GLU A 195      46.695  23.836  11.817  1.00 37.52           O
ATOM   2886  C    GLU A 195      45.098  25.032  16.431  1.00 48.18           C
ATOM   2887  O    GLU A 195      44.312  25.890  16.106  1.00 48.18           O
ATOM   2889  N    ARG A 196      46.316  25.274  16.904  1.00 50.67           N
ATOM   2890  CA   ARG A 196      46.898  26.649  17.239  1.00 52.34           C
ATOM   2892  CB   ARG A 196      48.434  26.548  17.169  1.00 51.78           C
ATOM   2901  C    ARG A 196      46.510  27.934  16.445  1.00 52.74           C
ATOM   2902  O    ARG A 196      45.357  28.154  16.021  1.00 55.25           O
ATOM   2904  O32  ci1 A 801      61.053  17.166  17.336  0.60 57.73           O
ATOM   2905  S30  ci1 A 801      60.183  16.043  17.508  0.60 56.27           S
ATOM   2906  O31  ci1 A 801      60.426  15.130  16.424  0.60 57.38           O
ATOM   2907  CP   ci1 A 801      60.634  15.277  18.941  1.00 56.91           C
ATOM   2910  CGB  ci1 A 801      59.951  13.939  19.141  1.00 57.03           C
```

FIG. 15Y

```
ATOM   2911  CD2 cil A 801      58.907  13.839  20.061  1.00 58.23           C
ATOM   2913  CE2 cil A 801      58.254  12.616  20.248  1.00 60.31           C
ATOM   2915  CZ  cil A 801      58.665  11.481  19.524  1.00 60.85           C
ATOM   2917  CE1 cil A 801      59.720  11.576  18.615  1.00 59.94           C
ATOM   2919  CD1 cil A 801      60.356  12.805  18.419  1.00 56.93           C
ATOM   2921  NJ  cil A 801      58.703  16.509  17.539  1.00 52.53           N
ATOM   2922  CI  cil A 801      58.427  17.933  17.855  1.00 51.58           C
ATOM   2925  CK  cil A 801      57.175  18.469  17.184  1.00 49.24           C
ATOM   2928  CG  cil A 801      56.064  17.431  17.352  1.00 48.54           C
ATOM   2931  CH  cil A 801      57.642  15.516  17.314  1.00 46.73           C
ATOM   2934  CF  cil A 801      56.410  16.120  16.631  1.00 45.93           C
ATOM   2935  CB  cil A 801      56.698  16.366  15.149  1.00 36.01           C
ATOM   2936  O13 cil A 801      57.678  15.835  14.580  1.00 32.50           O
ATOM   2937  CM  cil A 801      55.730  17.248  14.445  1.00 32.79           C
ATOM   2939  CA  cil A 801      55.509  17.325  13.110  1.00 32.20           C
ATOM   2940  O14 cil A 801      56.235  16.638  12.291  1.00 25.87           O
ATOM   2942  CE  cil A 801      54.451  18.222  12.629  1.00 33.27           C
ATOM   2943  OAN cil A 801      54.043  19.050  13.478  1.00 35.33           O
ATOM   2944  OAO cil A 801      54.071  18.295  11.450  1.00 30.90           O
ATOM   2945  CO  cil A 801      55.258  15.099  16.672  1.00 50.17           C
ATOM   2948  CGA cil A 801      54.568  15.044  18.019  1.00 53.47           C
ATOM   2949  CDB cil A 801      53.630  16.024  18.401  1.00 55.14           C
ATOM   2951  CEB cil A 801      53.018  15.968  19.658  1.00 57.71           C
ATOM   2953  CDA cil A 801      54.895  13.997  18.886  1.00 56.23           C
ATOM   2955  CEA cil A 801      54.261  13.934  20.128  1.00 58.00           C
ATOM   2957  CSB cil A 801      53.342  14.916  20.500  1.00 57.45           C
ATOM   2958  CL  cil A 801      52.552  14.795  22.088  1.00 65.61          CL
ATOM   2959  MN   MN A 901      55.441  17.121  10.259  1.00 26.23          MN
ATOM   2960  MN   MN A 902      57.695  15.256  12.553  1.00 32.69          MN
ATOM   2961  OH2 WAT A 903      59.083  16.811  11.845  1.00 30.18           O
ATOM   2964  OH2 WAT A 904      59.506  13.985  12.897  1.00 34.20           O
ATOM   2967  OH2 WAT Z   1      57.073  18.744  -1.578  1.00 27.97           O
ATOM   2970  OH2 WAT Z   2      61.259  16.436  -1.670  1.00 28.42           O
ATOM   2973  OH2 WAT Z   3      38.704  21.743  20.181  0.50 24.92           O
ATOM   2976  OH2 WAT Z   4      51.566  18.952  10.933  1.00 24.92           O
ATOM   2979  OH2 WAT Z   5      64.685  16.407  19.443  1.00 34.57           O
ATOM   2982  OH2 WAT Z   6      40.128   6.104   4.054  1.00 35.98           O
ATOM   2985  OH2 WAT Z   7      67.540  19.096   3.287  1.00 28.22           O
ATOM   2988  OH2 WAT Z   8      41.923  21.652   6.410  1.00 31.66           O
ATOM   2991  OH2 WAT Z   9      46.140  18.576  11.562  1.00 29.29           O
ATOM   2994  OH2 WAT Z  10      52.050  13.557 -11.851  1.00 42.71           O
ATOM   2997  OH2 WAT Z  11      30.038  16.498   6.206  1.00 30.20           O
ATOM   3000  OH2 WAT Z  12      47.655  16.197  11.836  1.00 29.72           O
ATOM   3003  OH2 WAT Z  13      55.304   9.756  -6.788  1.00 41.79           O
ATOM   3006  OH2 WAT Z  14      42.495  16.851   1.694  1.00 28.06           O
ATOM   3009  OH2 WAT Z  15      50.309  10.910 -11.312  1.00 42.43           O
ATOM   3012  OH2 WAT Z  16      45.497   3.737   9.204  1.00 37.30           O
ATOM   3015  OH2 WAT Z  18      65.343  22.138  10.865  1.00 36.86           O
ATOM   3018  OH2 WAT Z  19      59.976   5.414  -0.644  1.00 40.92           O
ATOM   3021  OH2 WAT Z  20      43.941  25.422   2.549  1.00 40.75           O
ATOM   3024  OH2 WAT Z  21      49.956  17.533  12.556  1.00 34.74           O
ATOM   3027  OH2 WAT Z  22      31.343  18.235  13.530  1.00 38.23           O
ATOM   3030  OH2 WAT Z  23      69.121  19.282   1.068  1.00 34.73           O
ATOM   3033  OH2 WAT Z  24      42.744  19.068  -4.776  1.00 32.18           O
ATOM   3036  OH2 WAT Z  25      71.088   5.741   6.557  1.00 42.30           O
ATOM   3039  OH2 WAT Z  26      40.961   7.159   1.472  1.00 41.68           O
ATOM   3042  OH2 WAT Z  27      73.968   7.591  13.017  1.00 38.60           O
ATOM   3045  OH2 WAT Z  29      60.643  15.295  -7.290  1.00 34.95           O
ATOM   3048  OH2 WAT Z  30      71.852  14.259  15.848  1.00 48.93           O
ATOM   3051  OH2 WAT Z  31      38.051  21.616  -1.639  1.00 42.27           O
ATOM   3054  OH2 WAT Z  32      55.765  19.517  -8.142  1.00 39.74           O
ATOM   3057  OH2 WAT Z  33      61.902   3.640  17.023  1.00 43.42           O
ATOM   3060  OH2 WAT Z  34      45.519  20.703  -4.713  1.00 44.57           O
```

FIG. 15Z

```
ATOM   3063  OH2 WAT Z  35      38.985    5.470    8.431  1.00 38.90       O
ATOM   3066  OH2 WAT Z  36      59.427   12.749   15.253  1.00 39.92       O
ATOM   3069  OH2 WAT Z  37      60.472   10.440   14.876  1.00 35.27       O
ATOM   3072  OH2 WAT Z  38      52.941   25.345   -3.209  1.00 36.14       O
ATOM   3075  OH2 WAT Z  39      32.646   18.717   17.216  1.00 38.32       O
ATOM   3078  OH2 WAT Z  40      48.706   23.747   -4.804  1.00 34.97       O
ATOM   3081  OH2 WAT Z  43      63.902   22.703   -1.026  1.00 39.80       O
ATOM   3084  OH2 WAT Z  44      47.086   15.488   -7.245  1.00 41.14       O
ATOM   3087  OH2 WAT Z  45      37.348   29.035   17.843  1.00 37.75       O
ATOM   3090  OH2 WAT Z  46      43.518    7.443   -0.088  1.00 41.34       O
ATOM   3093  OH2 WAT Z  47      35.474   23.141    8.204  1.00 43.91       O
ATOM   3096  OH2 WAT Z  48      62.625    4.491    6.219  1.00 46.42       O
ATOM   3099  OH2 WAT Z  49      55.363    3.527    4.813  1.00 53.74       O
ATOM   3102  OH2 WAT Z  50      29.097   17.237   11.257  1.00 40.71       O
ATOM   3105  OH2 WAT Z  52      46.450   23.495   -3.357  1.00 36.42       O
ATOM   3108  OH2 WAT Z  53      39.816   22.566    7.787  1.00 44.23       O
ATOM   3111  OH2 WAT Z  54      50.790   25.296   -7.626  1.00 47.59       O
ATOM   3114  OH2 WAT Z  55      33.752   18.740    7.662  1.00 38.93       O
ATOM   3117  OH2 WAT Z  56      54.946   28.181   -2.378  1.00 56.22       O
ATOM   3120  OH2 WAT Z  57      59.397   28.744   -1.513  1.00 44.95       O
ATOM   3123  OH2 WAT Z  58      37.750   23.261    6.502  1.00 48.53       O
ATOM   3126  OH2 WAT Z  59      35.300   12.965   21.863  1.00 57.82       O
ATOM   3129  OH2 WAT Z  60      37.614    7.381    1.350  1.00 36.73       O
ATOM   3132  OH2 WAT Z  61      63.498    3.175   14.610  1.00 53.27       O
ATOM   3135  OH2 WAT Z  62      42.301   24.286    4.864  1.00 42.97       O
ATOM   3138  OH2 WAT Z  63      63.366   18.279   16.941  1.00 39.55       O
ATOM   3141  OH2 WAT Z  64      31.100   18.979    7.375  1.00 44.42       O
ATOM   3144  OH2 WAT Z  65      45.337   18.138    1.047  1.00 40.67       O
ATOM   3147  OH2 WAT Z  66      52.657   12.351   13.992  1.00 35.16       O
ATOM   3150  OH2 WAT Z  67      42.874   29.165    8.279  1.00 45.65       O
ATOM   3153  OH2 WAT Z  68      56.220   29.847   13.406  1.00 45.04       O
ATOM   3156  OH2 WAT Z  69      62.411   22.567   -5.362  1.00 45.81       O
ATOM   3159  OH2 WAT Z  70      70.451    9.758   -2.164  1.00 39.56       O
ATOM   3162  OH2 WAT Z  71      66.063    3.607   -9.354  1.00 58.02       O
ATOM   3165  OH2 WAT Z  72      68.977   20.053    5.572  1.00 50.52       O
ATOM   3168  OH2 WAT Z  73      43.220    1.110   20.549  1.00 57.38       O
ATOM   3171  OH2 WAT Z  74      60.177   18.447   15.195  1.00 63.23       O
ATOM   3174  OH2 WAT Z  75      47.048   -0.137   18.643  1.00 41.49       O
ATOM   3177  OH2 WAT Z  76      30.889   18.926   11.147  1.00 49.30       O
ATOM   3180  OH2 WAT Z  77      35.546    5.848    2.440  1.00 51.27       O
ATOM   3183  OH2 WAT Z  78      42.310    8.977   -4.655  1.00 44.90       O
ATOM   3186  OH2 WAT Z  79      29.515   19.108   15.277  1.00 52.98       O
ATOM   3189  OH2 WAT Z  80      65.972   21.567   -0.154  1.00 54.82       O
ATOM   3192  OH2 WAT Z  81      63.611   19.972   10.280  1.00 34.36       O
ATOM   3195  OH2 WAT Z  84      70.312   14.978   -5.408  1.00 46.49       O
ATOM   3198  OH2 WAT Z  85      59.075   17.120   -8.006  1.00 36.47       O
ATOM   3201  OH2 WAT Z  86      61.218   19.761   10.732  1.00 35.24       O
ATOM   3204  OH2 WAT Z  87      34.505   22.643    2.888  1.00 43.76       O
ATOM   3207  OH2 WAT Z  88      70.603   23.278    9.934  1.00 58.37       O
ATOM   3210  OH2 WAT Z  89      42.605    6.965   -2.891  1.00 51.64       O
ATOM   3213  OH2 WAT Z  90      32.745    7.515   11.255  1.00 53.65       O
ATOM   3216  OH2 WAT Z  91      76.625    8.103   10.968  1.00 49.14       O
ATOM   3219  OH2 WAT Z  92      70.296   18.337   -2.321  1.00 43.04       O
ATOM   3222  OH2 WAT Z  93      51.113   31.653   10.198  1.00 45.47       O
ATOM   3225  OH2 WAT Z  94      35.555   17.473   21.332  1.00 46.53       O
ATOM   3228  OH2 WAT Z  95      45.909   28.788    1.826  1.00 40.43       O
ATOM   3231  OH2 WAT Z  96      69.218   11.585   -7.075  1.00 42.48       O
ATOM   3234  OH2 WAT Z 100      53.881   27.018   15.702  1.00 61.65       O
ATOM   3237  OH2 WAT Z 101      58.547    4.831   11.123  1.00 54.10       O
ATOM   3240  OH2 WAT Z 102      28.101    8.109   12.728  1.00 57.92       O
ATOM   3243  OH2 WAT Z 103      54.197   23.707   -9.308  1.00 51.65       O
ATOM   3246  OH2 WAT Z 104      44.604   -0.043   17.825  1.00 40.83       O
ATOM   3249  OH2 WAT Z 106      67.152   23.413   10.396  1.00 53.36       O
```

FIG. 15AA

```
ATOM   3252  OH2 WAT Z 107      47.292  19.642  16.716  1.00 59.73           O
ATOM   3255  OH2 WAT Z 111      50.477   6.557  -6.233  1.00 49.13           O
END
```

FIG. 15AB

```
H1N1 polypeptide fragment (chain A) with bound EGCG
HEADER      ----                                    XX-XXX-XX   xxxx
COMPND      ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :    2.60
REMARK   3   RESOLUTION RANGE LOW  (ANGSTROMS) :   42.78
REMARK   3   DATA CUTOFF            (SIGMA(F)) :    NONE
REMARK   3   COMPLETENESS FOR RANGE        (%) :   98.48
REMARK   3   NUMBER OF REFLECTIONS             :    7434
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE     (WORKING + TEST SET)  : 0.25191
REMARK   3   R VALUE            (WORKING SET)  : 0.24948
REMARK   3   FREE R VALUE                      : 0.30415
REMARK   3   FREE R VALUE TEST SET SIZE    (%) : 4.7
REMARK   3   FREE R VALUE TEST SET COUNT       : 363
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :   2.602
REMARK   3   BIN RESOLUTION RANGE LOW            :   2.669
REMARK   3   REFLECTION IN BIN     (WORKING SET) :     523
REMARK   3   BIN COMPLETENESS (WORKING+TEST) (%) :   97.35
REMARK   3   BIN R VALUE           (WORKING SET) :   0.340
REMARK   3   BIN FREE R VALUE SET COUNT          :      27
REMARK   3   BIN FREE R VALUE                    :   0.559
REMARK   3
REMARK   3  NUMBER OF NON-HYDROGEN ATOMS USED IN REFINEMENT.
REMARK   3   ALL ATOMS                : 1557
REMARK   3
REMARK   3  B VALUES.
REMARK   3   FROM WILSON PLOT           (A**2) : NULL
REMARK   3   MEAN B VALUE      (OVERALL, A**2) : 34.202
REMARK   3   OVERALL ANISOTROPIC B VALUE.
REMARK   3    B11 (A**2) :    9.15
REMARK   3    B22 (A**2) :    9.15
REMARK   3    B33 (A**2) :  -18.30
REMARK   3    B12 (A**2) :    0.00
REMARK   3    B13 (A**2) :    0.00
REMARK   3    B23 (A**2) :    0.00
REMARK   3
REMARK   3  ESTIMATED OVERALL COORDINATE ERROR.
REMARK   3   ESU BASED ON R VALUE                       (A):   0.160
REMARK   3   ESU BASED ON FREE R VALUE                  (A):   0.078
REMARK   3   ESU BASED ON MAXIMUM LIKELIHOOD            (A):   0.257
REMARK   3   ESU FOR B VALUES BASED ON MAXIMUM LIKELIHOOD (A**2):  13.175
REMARK   3
REMARK   3 CORRELATION COEFFICIENTS.
REMARK   3   CORRELATION COEFFICIENT FO-FC       : 0.902
REMARK   3   CORRELATION COEFFICIENT FO-FC FREE  : 0.868
REMARK   3
REMARK   3  RMS DEVIATIONS FROM IDEAL VALUES        COUNT    RMS    WEIGHT
```

FIG. 16A

```
REMARK   3    BOND LENGTHS REFINED ATOMS        (A):  1554 ;  0.009 ;  0.022
REMARK   3    BOND LENGTHS OTHERS               (A):  1094 ;  0.001 ;  0.020
REMARK   3    BOND ANGLES REFINED ATOMS   (DEGREES):  2088 ;  1.201 ;  1.973
REMARK   3    BOND ANGLES OTHERS          (DEGREES):  2634 ;  0.789 ;  3.000
REMARK   3    TORSION ANGLES, PERIOD 1    (DEGREES):   176 ;  5.150 ;  5.000
REMARK   3    TORSION ANGLES, PERIOD 2    (DEGREES):    79 ; 35.593 ; 23.165
REMARK   3    TORSION ANGLES, PERIOD 3    (DEGREES):   290 ; 16.970 ; 15.000
REMARK   3    TORSION ANGLES, PERIOD 4    (DEGREES):    14 ; 18.333 ; 15.000
REMARK   3    CHIRAL-CENTER RESTRAINTS       (A**3):   219 ;  0.058 ;  0.200
REMARK   3    GENERAL PLANES REFINED ATOMS     (A):  1686 ;  0.004 ;  0.020
REMARK   3    GENERAL PLANES OTHERS            (A):   342 ;  0.001 ;  0.020
REMARK   3
REMARK   3  ISOTROPIC THERMAL FACTOR RESTRAINTS.    COUNT    RMS    WEIGHT
REMARK   3   MAIN-CHAIN BOND REFINED ATOMS  (A**2):   889 ;  0.548 ;  1.500
REMARK   3   MAIN-CHAIN BOND OTHER ATOMS    (A**2):   359 ;  0.069 ;  1.500
REMARK   3   MAIN-CHAIN ANGLE REFINED ATOMS (A**2):  1438 ;  1.057 ;  2.000
REMARK   3   SIDE-CHAIN BOND REFINED ATOMS  (A**2):   665 ;  1.403 ;  3.000
REMARK   3   SIDE-CHAIN ANGLE REFINED ATOMS (A**2):   650 ;  2.392 ;  4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS    :  1.40
REMARK   3   ION PROBE RADIUS    :  0.80
REMARK   3   SHRINKAGE RADIUS    :  0.80
REMARK   3
REMARK   3  OTHER REFINEMENT REMARKS:
REMARK   3   HYDROGENS HAVE BEEN ADDED IN THE RIDING POSITIONS
REMARK   3   U VALUES      : REFINED INDIVIDUALLY
REMARK   3
LINKR           GLY A  52                  ALA A  70              gap
LINKR           LYS A 139                  GLU A 141              gap
CRYST1   99.940   99.940   82.730  90.00  90.00 120.00 P 64 2 2
SCALE1      0.010006  0.005777  0.000000        0.00000
SCALE2      0.000000  0.011554  0.000000        0.00000
SCALE3      0.000000  0.000000  0.012088        0.00000
ATOM      2  CA  ALA A   0      -2.958 -50.956  20.866  1.00 38.32           C
ATOM      4  CB  ALA A   0      -4.292 -50.809  20.158  1.00 38.65           C
ATOM      8  C   ALA A   0      -1.914 -50.172  20.100  1.00 38.49           C
ATOM      9  O   ALA A   0      -1.251 -50.707  19.213  1.00 38.54           O
ATOM     10  N   MET A   1      -1.797 -48.886  20.419  1.00 38.55           N
ATOM     11  CA  MET A   1      -0.896 -47.991  19.693  1.00 38.41           C
ATOM     13  CB  MET A   1      -1.116 -46.540  20.118  1.00 38.56           C
ATOM     16  CG  MET A   1      -0.069 -45.553  19.591  1.00 38.72           C
ATOM     19  SD  MET A   1      -0.064 -45.442  17.800  1.00 38.46           S
ATOM     20  CE  MET A   1      -1.234 -44.111  17.543  1.00 38.94           C
ATOM     24  C   MET A   1       0.562 -48.381  19.889  1.00 38.50           C
ATOM     25  O   MET A   1       1.389 -48.168  19.005  1.00 38.18           O
ATOM     27  N   GLU A   2       0.888 -48.956  21.038  1.00 38.78           N
ATOM     28  CA  GLU A   2       2.254 -49.380  21.251  1.00 39.20           C
ATOM     30  CB  GLU A   2       2.473 -49.950  22.654  1.00 39.51           C
ATOM     33  CG  GLU A   2       3.962 -50.141  22.975  1.00 39.86           C
```

FIG. 16B

| | | | | | | | | | | |
|---|---|---|---|---|---|---|---|---|---|---|
| ATOM | 36 | CD | GLU | A | 2 | 4.244 | -50.723 | 24.351 | 1.00 41.32 | C |
| ATOM | 37 | OE1 | GLU | A | 2 | 3.315 | -51.206 | 25.047 | 1.00 42.21 | O |
| ATOM | 38 | OE2 | GLU | A | 2 | 5.430 | -50.700 | 24.736 | 1.00 43.38 | O |
| ATOM | 39 | C | GLU | A | 2 | 2.616 | -50.410 | 20.205 | 1.00 39.33 | C |
| ATOM | 40 | O | GLU | A | 2 | 3.656 | -50.312 | 19.575 | 1.00 39.67 | O |
| ATOM | 42 | N | ASP | A | 3 | 1.742 | -51.387 | 20.001 | 1.00 39.74 | N |
| ATOM | 43 | CA | ASP | A | 3 | 2.044 | -52.518 | 19.106 | 1.00 39.73 | C |
| ATOM | 45 | CB | ASP | A | 3 | 1.003 | -53.621 | 19.292 | 1.00 40.00 | C |
| ATOM | 48 | CG | ASP | A | 3 | 1.006 | -54.180 | 20.706 | 1.00 42.56 | C |
| ATOM | 49 | OD1 | ASP | A | 3 | 2.114 | -54.449 | 21.244 | 1.00 46.13 | O |
| ATOM | 50 | OD2 | ASP | A | 3 | -0.091 | -54.336 | 21.290 | 1.00 45.10 | O |
| ATOM | 51 | C | ASP | A | 3 | 2.141 | -52.096 | 17.642 | 1.00 38.69 | C |
| ATOM | 52 | O | ASP | A | 3 | 2.936 | -52.639 | 16.870 | 1.00 38.86 | O |
| ATOM | 54 | N | PHE | A | 4 | 1.340 | -51.115 | 17.268 | 1.00 37.65 | N |
| ATOM | 55 | CA | PHE | A | 4 | 1.449 | -50.531 | 15.946 | 1.00 37.05 | C |
| ATOM | 57 | CB | PHE | A | 4 | 0.439 | -49.408 | 15.769 | 1.00 36.69 | C |
| ATOM | 60 | CG | PHE | A | 4 | 0.588 | -48.694 | 14.481 | 1.00 37.32 | C |
| ATOM | 61 | CD1 | PHE | A | 4 | 0.130 | -49.271 | 13.311 | 1.00 37.67 | C |
| ATOM | 63 | CE1 | PHE | A | 4 | 0.277 | -48.622 | 12.103 | 1.00 37.71 | C |
| ATOM | 65 | CZ | PHE | A | 4 | 0.897 | -47.386 | 12.057 | 1.00 38.26 | C |
| ATOM | 67 | CE2 | PHE | A | 4 | 1.376 | -46.800 | 13.224 | 1.00 36.88 | C |
| ATOM | 69 | CD2 | PHE | A | 4 | 1.226 | -47.455 | 14.421 | 1.00 37.64 | C |
| ATOM | 71 | C | PHE | A | 4 | 2.861 | -49.989 | 15.721 | 1.00 36.40 | C |
| ATOM | 72 | O | PHE | A | 4 | 3.539 | -50.387 | 14.773 | 1.00 36.25 | O |
| ATOM | 74 | N | VAL | A | 5 | 3.297 | -49.098 | 16.607 | 1.00 35.59 | N |
| ATOM | 75 | CA | VAL | A | 5 | 4.622 | -48.513 | 16.507 | 1.00 35.33 | C |
| ATOM | 77 | CB | VAL | A | 5 | 4.990 | -47.674 | 17.758 | 1.00 35.58 | C |
| ATOM | 79 | CG1 | VAL | A | 5 | 6.443 | -47.169 | 17.646 | 1.00 35.49 | C |
| ATOM | 83 | CG2 | VAL | A | 5 | 4.017 | -46.485 | 17.951 | 1.00 34.00 | C |
| ATOM | 87 | C | VAL | A | 5 | 5.697 | -49.586 | 16.253 | 1.00 35.25 | C |
| ATOM | 88 | O | VAL | A | 5 | 6.487 | -49.448 | 15.320 | 1.00 34.86 | O |
| ATOM | 90 | N | ARG | A | 6 | 5.678 | -50.673 | 17.025 | 1.00 34.99 | N |
| ATOM | 91 | CA | ARG | A | 6 | 6.731 | -51.687 | 16.946 | 1.00 35.30 | C |
| ATOM | 93 | CB | ARG | A | 6 | 6.811 | -52.561 | 18.219 | 1.00 35.55 | C |
| ATOM | 96 | CG | ARG | A | 6 | 6.306 | -51.916 | 19.512 | 1.00 36.75 | C |
| ATOM | 99 | CD | ARG | A | 6 | 6.714 | -52.703 | 20.745 | 1.00 37.93 | C |
| ATOM | 102 | NE | ARG | A | 6 | 8.038 | -52.291 | 21.188 | 1.00 40.77 | N |
| ATOM | 104 | CZ | ARG | A | 6 | 8.297 | -51.363 | 22.108 | 1.00 41.42 | C |
| ATOM | 105 | NH1 | ARG | A | 6 | 7.325 | -50.737 | 22.757 | 1.00 42.21 | N |
| ATOM | 108 | NH2 | ARG | A | 6 | 9.554 | -51.069 | 22.396 | 1.00 42.13 | N |
| ATOM | 111 | C | ARG | A | 6 | 6.579 | -52.605 | 15.735 | 1.00 35.22 | C |
| ATOM | 112 | O | ARG | A | 6 | 7.390 | -53.511 | 15.533 | 1.00 35.54 | O |
| ATOM | 114 | N | GLN | A | 7 | 5.520 | -52.421 | 14.961 | 1.00 34.97 | N |
| ATOM | 115 | CA | GLN | A | 7 | 5.358 | -53.141 | 13.697 | 1.00 34.58 | C |
| ATOM | 117 | CB | GLN | A | 7 | 3.942 | -53.733 | 13.586 | 1.00 35.12 | C |
| ATOM | 120 | CG | GLN | A | 7 | 3.617 | -54.842 | 14.604 | 1.00 36.29 | C |
| ATOM | 123 | CD | GLN | A | 7 | 2.111 | -54.980 | 14.879 | 1.00 38.16 | C |
| ATOM | 124 | OE1 | GLN | A | 7 | 1.284 | -54.470 | 14.121 | 1.00 40.59 | O |
| ATOM | 125 | NE2 | GLN | A | 7 | 1.758 | -55.653 | 15.974 | 1.00 36.63 | N |
| ATOM | 128 | C | GLN | A | 7 | 5.594 | -52.176 | 12.557 | 1.00 33.63 | C |
| ATOM | 129 | O | GLN | A | 7 | 6.157 | -52.545 | 11.545 | 1.00 33.98 | O |
| ATOM | 131 | N | CYS | A | 8 | 5.154 | -50.932 | 12.719 | 1.00 32.58 | N |
| ATOM | 132 | CA | CYS | A | 8 | 5.220 | -49.952 | 11.641 | 1.00 32.10 | C |
| ATOM | 134 | CB | CYS | A | 8 | 4.286 | -48.791 | 11.956 | 1.00 31.88 | C |
| ATOM | 137 | SG | CYS | A | 8 | 4.508 | -47.419 | 10.843 | 1.00 33.87 | S |
| ATOM | 139 | C | CYS | A | 8 | 6.636 | -49.414 | 11.372 | 1.00 31.12 | C |
| ATOM | 140 | O | CYS | A | 8 | 6.987 | -49.056 | 10.243 | 1.00 30.42 | O |
| ATOM | 142 | N | PHE | A | 9 | 7.434 | -49.342 | 12.426 | 1.00 30.32 | N |
| ATOM | 143 | CA | PHE | A | 9 | 8.717 | -48.676 | 12.363 | 1.00 29.67 | C |
| ATOM | 145 | CB | PHE | A | 9 | 8.768 | -47.548 | 13.405 | 1.00 29.41 | C |
| ATOM | 148 | CG | PHE | A | 9 | 7.812 | -46.413 | 13.114 | 1.00 28.23 | C |
| ATOM | 149 | CD1 | PHE | A | 9 | 8.093 | -45.501 | 12.095 | 1.00 28.80 | C |
| ATOM | 151 | CE1 | PHE | A | 9 | 7.223 | -44.444 | 11.809 | 1.00 28.14 | C |

FIG. 16C

| | | | | | | | | | | |
|---|---|---|---|---|---|---|---|---|---|---|
| ATOM | 153 | CZ | PHE | A | 9 | 6.052 | -44.311 | 12.549 | 1.00 27.84 | C |
| ATOM | 155 | CE2 | PHE | A | 9 | 5.764 | -45.224 | 13.571 | 1.00 26.77 | C |
| ATOM | 157 | CD2 | PHE | A | 9 | 6.639 | -46.262 | 13.840 | 1.00 26.84 | C |
| ATOM | 159 | C | PHE | A | 9 | 9.813 | -49.690 | 12.583 | 1.00 29.45 | C |
| ATOM | 160 | O | PHE | A | 9 | 9.621 | -50.671 | 13.298 | 1.00 29.14 | O |
| ATOM | 162 | N | ASN | A | 10 | 10.962 | -49.463 | 11.953 | 1.00 29.40 | N |
| ATOM | 163 | CA | ASN | A | 10 | 12.074 | -50.379 | 12.116 | 1.00 29.32 | C |
| ATOM | 165 | CB | ASN | A | 10 | 13.155 | -50.136 | 11.048 | 1.00 29.60 | C |
| ATOM | 168 | CG | ASN | A | 10 | 14.130 | -49.044 | 11.425 | 1.00 30.88 | C |
| ATOM | 169 | OD1 | ASN | A | 10 | 14.838 | -49.152 | 12.422 | 1.00 34.37 | O |
| ATOM | 170 | ND2 | ASN | A | 10 | 14.204 | -48.003 | 10.611 | 1.00 31.40 | N |
| ATOM | 173 | C | ASN | A | 10 | 12.601 | -50.288 | 13.561 | 1.00 28.82 | C |
| ATOM | 174 | O | ASN | A | 10 | 12.433 | -49.262 | 14.234 | 1.00 28.98 | O |
| ATOM | 176 | N | PRO | A | 11 | 13.210 | -51.366 | 14.054 | 1.00 27.98 | N |
| ATOM | 177 | CA | PRO | A | 11 | 13.616 | -51.390 | 15.452 | 1.00 28.02 | C |
| ATOM | 179 | CB | PRO | A | 11 | 14.245 | -52.786 | 15.602 | 1.00 28.00 | C |
| ATOM | 182 | CG | PRO | A | 11 | 13.689 | -53.585 | 14.484 | 1.00 27.59 | C |
| ATOM | 185 | CD | PRO | A | 11 | 13.491 | -52.638 | 13.370 | 1.00 27.90 | C |
| ATOM | 188 | C | PRO | A | 11 | 14.603 | -50.282 | 15.908 | 1.00 28.28 | C |
| ATOM | 189 | O | PRO | A | 11 | 14.509 | -49.839 | 17.057 | 1.00 27.65 | O |
| ATOM | 190 | N | MET | A | 12 | 15.522 | -49.847 | 15.037 | 1.00 28.46 | N |
| ATOM | 191 | CA | MET | A | 12 | 16.458 | -48.764 | 15.370 | 1.00 29.11 | C |
| ATOM | 193 | CB | MET | A | 12 | 17.460 | -48.497 | 14.214 | 1.00 30.11 | C |
| ATOM | 196 | CG | MET | A | 12 | 18.237 | -47.137 | 14.301 | 1.00 34.75 | C |
| ATOM | 199 | SD | MET | A | 12 | 19.622 | -46.832 | 13.106 | 1.00 45.22 | S |
| ATOM | 200 | CE | MET | A | 12 | 18.752 | -45.924 | 11.808 | 1.00 42.93 | C |
| ATOM | 204 | C | MET | A | 12 | 15.676 | -47.504 | 15.727 | 1.00 28.27 | C |
| ATOM | 205 | O | MET | A | 12 | 15.883 | -46.915 | 16.791 | 1.00 27.82 | O |
| ATOM | 207 | N | ILE | A | 13 | 14.777 | -47.107 | 14.831 | 1.00 27.74 | N |
| ATOM | 208 | CA | ILE | A | 13 | 13.888 | -45.963 | 15.043 | 1.00 27.50 | C |
| ATOM | 210 | CB | ILE | A | 13 | 12.812 | -45.867 | 13.916 | 1.00 27.79 | C |
| ATOM | 212 | CG1 | ILE | A | 13 | 13.453 | -45.462 | 12.590 | 1.00 28.46 | C |
| ATOM | 215 | CD1 | ILE | A | 13 | 14.177 | -44.171 | 12.667 | 1.00 31.66 | C |
| ATOM | 219 | CG2 | ILE | A | 13 | 11.711 | -44.885 | 14.272 | 1.00 26.30 | C |
| ATOM | 223 | C | ILE | A | 13 | 13.158 | -46.090 | 16.377 | 1.00 27.31 | C |
| ATOM | 224 | O | ILE | A | 13 | 13.194 | -45.183 | 17.218 | 1.00 27.14 | O |
| ATOM | 226 | N | VAL | A | 14 | 12.486 | -47.220 | 16.568 | 1.00 26.83 | N |
| ATOM | 227 | CA | VAL | A | 14 | 11.727 | -47.422 | 17.790 | 1.00 26.51 | C |
| ATOM | 229 | CB | VAL | A | 14 | 11.073 | -48.826 | 17.851 | 1.00 26.30 | C |
| ATOM | 231 | CG1 | VAL | A | 14 | 10.888 | -49.271 | 19.269 | 1.00 25.54 | C |
| ATOM | 235 | CG2 | VAL | A | 14 | 9.747 | -48.811 | 17.135 | 1.00 25.28 | C |
| ATOM | 239 | C | VAL | A | 14 | 12.655 | -47.199 | 18.966 | 1.00 26.65 | C |
| ATOM | 240 | O | VAL | A | 14 | 12.350 | -46.410 | 19.841 | 1.00 27.21 | O |
| ATOM | 242 | N | GLU | A | 15 | 13.806 | -47.860 | 18.956 | 1.00 26.55 | N |
| ATOM | 243 | CA | GLU | A | 15 | 14.763 | -47.767 | 20.057 | 1.00 26.50 | C |
| ATOM | 245 | CB | GLU | A | 15 | 15.994 | -48.643 | 19.759 | 1.00 26.92 | C |
| ATOM | 248 | CG | GLU | A | 15 | 17.055 | -48.645 | 20.831 | 1.00 28.10 | C |
| ATOM | 251 | CD | GLU | A | 15 | 16.546 | -49.161 | 22.138 | 1.00 30.86 | C |
| ATOM | 252 | OE1 | GLU | A | 15 | 15.821 | -50.179 | 22.118 | 1.00 32.95 | O |
| ATOM | 253 | OE2 | GLU | A | 15 | 16.870 | -48.560 | 23.187 | 1.00 33.11 | O |
| ATOM | 254 | C | GLU | A | 15 | 15.170 | -46.321 | 20.324 | 1.00 25.96 | C |
| ATOM | 255 | O | GLU | A | 15 | 15.196 | -45.888 | 21.470 | 1.00 26.34 | O |
| ATOM | 257 | N | LEU | A | 16 | 15.463 | -45.567 | 19.276 | 1.00 25.16 | N |
| ATOM | 258 | CA | LEU | A | 16 | 15.798 | -44.165 | 19.443 | 1.00 24.97 | C |
| ATOM | 260 | CB | LEU | A | 16 | 16.244 | -43.535 | 18.108 | 1.00 24.92 | C |
| ATOM | 263 | CG | LEU | A | 16 | 17.655 | -43.892 | 17.596 | 1.00 24.76 | C |
| ATOM | 265 | CD1 | LEU | A | 16 | 17.995 | -43.157 | 16.316 | 1.00 24.82 | C |
| ATOM | 269 | CD2 | LEU | A | 16 | 18.706 | -43.597 | 18.648 | 1.00 23.94 | C |
| ATOM | 273 | C | LEU | A | 16 | 14.629 | -43.377 | 20.041 | 1.00 25.24 | C |
| ATOM | 274 | O | LEU | A | 16 | 14.831 | -42.437 | 20.833 | 1.00 25.65 | O |
| ATOM | 276 | N | ALA | A | 17 | 13.408 | -43.744 | 19.669 | 1.00 25.24 | N |
| ATOM | 277 | CA | ALA | A | 17 | 12.228 | -43.077 | 20.214 | 1.00 25.17 | C |
| ATOM | 279 | CB | ALA | A | 17 | 10.972 | -43.559 | 19.525 | 1.00 24.97 | C |

FIG. 16D

```
ATOM    283  C   ALA A  17      12.132 -43.298  21.718  1.00 25.19           C
ATOM    284  O   ALA A  17      11.855 -42.361  22.464  1.00 24.69           O
ATOM    286  N   GLU A  18      12.384 -44.526  22.163  1.00 25.61           N
ATOM    287  CA  GLU A  18      12.268 -44.852  23.582  1.00 26.54           C
ATOM    289  CB  GLU A  18      12.446 -46.343  23.831  1.00 26.75           C
ATOM    292  CG  GLU A  18      11.279 -47.172  23.345  1.00 28.90           C
ATOM    295  CD  GLU A  18      11.627 -48.644  23.197  1.00 30.85           C
ATOM    296  OE1 GLU A  18      12.348 -49.014  22.244  1.00 35.60           O
ATOM    297  OE2 GLU A  18      11.176 -49.439  24.025  1.00 30.02           O
ATOM    298  C   GLU A  18      13.280 -44.081  24.406  1.00 26.76           C
ATOM    299  O   GLU A  18      12.914 -43.368  25.333  1.00 26.80           O
ATOM    301  N   LYS A  19      14.553 -44.221  24.062  1.00 27.19           N
ATOM    302  CA  LYS A  19      15.599 -43.493  24.761  1.00 27.72           C
ATOM    304  CB  LYS A  19      16.943 -43.745  24.075  1.00 28.13           C
ATOM    307  CG  LYS A  19      18.075 -42.844  24.515  1.00 30.88           C
ATOM    310  CD  LYS A  19      19.393 -43.274  23.846  1.00 35.40           C
ATOM    313  CE  LYS A  19      20.548 -42.341  24.229  1.00 38.04           C
ATOM    316  NZ  LYS A  19      21.565 -42.290  23.135  1.00 40.40           N
ATOM    320  C   LYS A  19      15.255 -41.991  24.838  1.00 27.32           C
ATOM    321  O   LYS A  19      15.385 -41.377  25.883  1.00 27.25           O
ATOM    323  N   ALA A  20      14.788 -41.417  23.738  1.00 27.29           N
ATOM    324  CA  ALA A  20      14.406 -40.008  23.712  1.00 27.47           C
ATOM    326  CB  ALA A  20      14.017 -39.594  22.305  1.00 27.28           C
ATOM    330  C   ALA A  20      13.271 -39.704  24.692  1.00 27.79           C
ATOM    331  O   ALA A  20      13.338 -38.729  25.440  1.00 28.10           O
ATOM    333  N   MET A  21      12.235 -40.541  24.704  1.00 28.05           N
ATOM    334  CA  MET A  21      11.116 -40.328  25.625  1.00 27.93           C
ATOM    336  CB  MET A  21       9.982 -41.310  25.361  1.00 27.92           C
ATOM    339  CG  MET A  21       9.211 -41.021  24.095  1.00 27.92           C
ATOM    342  SD  MET A  21       7.753 -42.077  23.918  1.00 27.49           S
ATOM    343  CE  MET A  21       6.684 -41.421  25.202  1.00 24.54           C
ATOM    347  C   MET A  21      11.578 -40.463  27.052  1.00 27.87           C
ATOM    348  O   MET A  21      11.203 -39.661  27.898  1.00 27.95           O
ATOM    350  N   LYS A  22      12.395 -41.476  27.319  1.00 27.99           N
ATOM    351  CA  LYS A  22      12.909 -41.696  28.668  1.00 28.41           C
ATOM    353  CB  LYS A  22      13.624 -43.047  28.768  1.00 28.43           C
ATOM    356  CG  LYS A  22      12.701 -44.266  28.780  1.00 28.34           C
ATOM    359  CD  LYS A  22      13.443 -45.537  29.204  1.00 28.21           C
ATOM    362  CE  LYS A  22      12.817 -46.786  28.586  1.00 28.68           C
ATOM    365  NZ  LYS A  22      13.112 -48.026  29.373  1.00 29.07           N
ATOM    369  C   LYS A  22      13.847 -40.569  29.145  1.00 28.80           C
ATOM    370  O   LYS A  22      13.923 -40.278  30.336  1.00 28.62           O
ATOM    372  N   GLU A  23      14.564 -39.931  28.230  1.00 29.39           N
ATOM    373  CA  GLU A  23      15.401 -38.805  28.624  1.00 30.07           C
ATOM    375  CB  GLU A  23      16.215 -38.281  27.453  1.00 30.38           C
ATOM    378  CG  GLU A  23      17.462 -39.073  27.187  1.00 31.17           C
ATOM    381  CD  GLU A  23      18.211 -38.579  25.977  1.00 32.82           C
ATOM    382  OE1 GLU A  23      18.295 -37.344  25.781  1.00 33.58           O
ATOM    383  OE2 GLU A  23      18.724 -39.441  25.227  1.00 35.98           O
ATOM    384  C   GLU A  23      14.551 -37.692  29.184  1.00 30.41           C
ATOM    385  O   GLU A  23      14.984 -36.954  30.063  1.00 29.86           O
ATOM    387  N   TYR A  24      13.326 -37.591  28.684  1.00 31.29           N
ATOM    388  CA  TYR A  24      12.436 -36.506  29.058  1.00 32.01           C
ATOM    390  CB  TYR A  24      11.680 -35.998  27.823  1.00 32.57           C
ATOM    393  CG  TYR A  24      12.421 -34.885  27.141  1.00 34.05           C
ATOM    394  CD1 TYR A  24      13.112 -35.091  25.952  1.00 35.94           C
ATOM    396  CE1 TYR A  24      13.811 -34.047  25.349  1.00 38.48           C
ATOM    398  CZ  TYR A  24      13.823 -32.794  25.964  1.00 39.58           C
ATOM    399  OH  TYR A  24      14.491 -31.727  25.425  1.00 43.50           O
ATOM    401  CE2 TYR A  24      13.159 -32.586  27.145  1.00 38.47           C
ATOM    403  CD2 TYR A  24      12.469 -33.625  27.726  1.00 36.71           C
ATOM    405  C   TYR A  24      11.485 -36.887  30.161  1.00 32.07           C
ATOM    406  O   TYR A  24      10.630 -36.093  30.535  1.00 32.09           O
```

FIG. 16E

```
ATOM    408  N    GLY A  25      11.645 -38.096  30.692  1.00 32.53           N
ATOM    409  CA   GLY A  25      10.838 -38.559  31.818  1.00 32.86           C
ATOM    412  C    GLY A  25       9.575 -39.324  31.463  1.00 33.29           C
ATOM    413  O    GLY A  25       8.864 -39.762  32.355  1.00 33.72           O
ATOM    415  N    GLU A  26       9.325 -39.532  30.174  1.00 33.69           N
ATOM    416  CA   GLU A  26       8.064 -40.092  29.697  1.00 34.32           C
ATOM    418  CB   GLU A  26       7.618 -39.372  28.423  1.00 34.42           C
ATOM    421  CG   GLU A  26       7.417 -37.866  28.630  1.00 34.93           C
ATOM    424  CD   GLU A  26       7.632 -37.040  27.379  1.00 36.22           C
ATOM    425  OE1  GLU A  26       7.048 -35.939  27.323  1.00 39.27           O
ATOM    426  OE2  GLU A  26       8.369 -37.460  26.454  1.00 36.41           O
ATOM    427  C    GLU A  26       8.172 -41.576  29.425  1.00 34.69           C
ATOM    428  O    GLU A  26       9.215 -42.067  29.009  1.00 35.07           O
ATOM    430  N    ASP A  27       7.076 -42.285  29.655  1.00 35.11           N
ATOM    431  CA   ASP A  27       7.045 -43.723  29.502  1.00 35.48           C
ATOM    433  CB   ASP A  27       6.205 -44.352  30.610  1.00 35.66           C
ATOM    436  CG   ASP A  27       6.389 -45.850  30.709  1.00 36.28           C
ATOM    437  OD1  ASP A  27       6.685 -46.510  29.686  1.00 36.77           O
ATOM    438  OD2  ASP A  27       6.221 -46.368  31.829  1.00 38.44           O
ATOM    439  C    ASP A  27       6.445 -44.053  28.153  1.00 35.74           C
ATOM    440  O    ASP A  27       5.270 -43.758  27.895  1.00 35.78           O
ATOM    442  N    PRO A  28       7.240 -44.675  27.277  1.00 36.14           N
ATOM    443  CA   PRO A  28       6.687 -45.024  25.970  1.00 36.38           C
ATOM    445  CB   PRO A  28       7.853 -45.751  25.265  1.00 36.24           C
ATOM    448  CG   PRO A  28       8.907 -45.959  26.290  1.00 36.08           C
ATOM    451  CD   PRO A  28       8.680 -44.975  27.379  1.00 36.08           C
ATOM    454  C    PRO A  28       5.408 -45.905  26.023  1.00 36.68           C
ATOM    455  O    PRO A  28       4.645 -45.909  25.052  1.00 36.76           O
ATOM    456  N    LYS A  29       5.194 -46.625  27.130  1.00 36.79           N
ATOM    457  CA   LYS A  29       4.002 -47.472  27.333  1.00 37.06           C
ATOM    459  CB   LYS A  29       4.247 -48.522  28.427  1.00 37.41           C
ATOM    462  CG   LYS A  29       5.280 -49.560  28.071  1.00 39.12           C
ATOM    465  CD   LYS A  29       5.366 -50.612  29.151  1.00 42.04           C
ATOM    468  CE   LYS A  29       6.753 -51.290  29.199  1.00 43.90           C
ATOM    471  NZ   LYS A  29       6.861 -52.266  30.348  1.00 45.30           N
ATOM    475  C    LYS A  29       2.737 -46.732  27.722  1.00 36.64           C
ATOM    476  O    LYS A  29       1.658 -47.291  27.606  1.00 37.00           O
ATOM    478  N    ILE A  30       2.852 -45.506  28.222  1.00 36.45           N
ATOM    479  CA   ILE A  30       1.667 -44.721  28.562  1.00 36.02           C
ATOM    481  CB   ILE A  30       1.803 -44.030  29.927  1.00 36.25           C
ATOM    483  CG1  ILE A  30       2.287 -45.018  31.003  1.00 36.11           C
ATOM    486  CD1  ILE A  30       1.499 -46.310  31.080  1.00 36.55           C
ATOM    490  CG2  ILE A  30       0.473 -43.339  30.317  1.00 35.94           C
ATOM    494  C    ILE A  30       1.403 -43.650  27.522  1.00 35.72           C
ATOM    495  O    ILE A  30       0.269 -43.449  27.115  1.00 36.26           O
ATOM    497  N    GLU A  31       2.441 -42.940  27.109  1.00 35.26           N
ATOM    498  CA   GLU A  31       2.273 -41.871  26.138  1.00 34.97           C
ATOM    500  CB   GLU A  31       3.210 -40.720  26.446  1.00 35.31           C
ATOM    503  CG   GLU A  31       2.981 -40.100  27.798  1.00 36.95           C
ATOM    506  CD   GLU A  31       2.764 -38.617  27.680  1.00 40.75           C
ATOM    507  OE1  GLU A  31       1.617 -38.238  27.320  1.00 43.96           O
ATOM    508  OE2  GLU A  31       3.730 -37.840  27.917  1.00 41.59           O
ATOM    509  C    GLU A  31       2.531 -42.417  24.746  1.00 34.31           C
ATOM    510  O    GLU A  31       3.514 -42.068  24.080  1.00 33.82           O
ATOM    512  N    THR A  32       1.605 -43.266  24.312  1.00 33.64           N
ATOM    513  CA   THR A  32       1.749 -44.027  23.082  1.00 32.92           C
ATOM    515  CB   THR A  32       0.766 -45.203  23.074  1.00 32.98           C
ATOM    517  OG1  THR A  32      -0.558 -44.717  23.315  1.00 32.87           O
ATOM    519  CG2  THR A  32       1.138 -46.200  24.170  1.00 32.57           C
ATOM    523  C    THR A  32       1.564 -43.165  21.835  1.00 32.43           C
ATOM    524  O    THR A  32       2.176 -43.427  20.800  1.00 31.95           O
ATOM    526  N    ASN A  33       0.740 -42.129  21.917  1.00 32.03           N
ATOM    527  CA   ASN A  33       0.617 -41.239  20.772  1.00 32.16           C
```

FIG. 16F

```
ATOM    529  CB  ASN A  33      -0.532 -40.248  20.949  1.00 32.51           C
ATOM    532  CG  ASN A  33      -1.905 -40.919  20.849  1.00 34.05           C
ATOM    533  OD1 ASN A  33      -2.073 -41.913  20.141  1.00 36.33           O
ATOM    534  ND2 ASN A  33      -2.886 -40.378  21.563  1.00 34.87           N
ATOM    537  C   ASN A  33       1.939 -40.523  20.516  1.00 31.51           C
ATOM    538  O   ASN A  33       2.489 -40.610  19.414  1.00 32.10           O
ATOM    540  N   LYS A  34       2.454 -39.849  21.546  1.00 30.49           N
ATOM    541  CA  LYS A  34       3.769 -39.209  21.499  1.00 29.32           C
ATOM    543  CB  LYS A  34       4.112 -38.635  22.870  1.00 29.26           C
ATOM    546  CG  LYS A  34       5.512 -38.037  22.957  1.00 30.64           C
ATOM    549  CD  LYS A  34       5.696 -37.126  24.195  1.00 31.23           C
ATOM    552  CE  LYS A  34       5.585 -35.640  23.859  1.00 32.05           C
ATOM    555  NZ  LYS A  34       6.238 -34.764  24.901  1.00 33.88           N
ATOM    559  C   LYS A  34       4.863 -40.180  21.021  1.00 28.15           C
ATOM    560  O   LYS A  34       5.655 -39.838  20.148  1.00 27.91           O
ATOM    562  N   PHE A  35       4.879 -41.395  21.568  1.00 26.76           N
ATOM    563  CA  PHE A  35       5.828 -42.434  21.143  1.00 26.05           C
ATOM    565  CB  PHE A  35       5.447 -43.793  21.778  1.00 25.73           C
ATOM    568  CG  PHE A  35       6.429 -44.926  21.528  1.00 24.67           C
ATOM    569  CD1 PHE A  35       6.014 -46.240  21.708  1.00 24.64           C
ATOM    571  CE1 PHE A  35       6.880 -47.318  21.516  1.00 24.84           C
ATOM    573  CZ  PHE A  35       8.200 -47.096  21.127  1.00 25.53           C
ATOM    575  CE2 PHE A  35       8.645 -45.788  20.949  1.00 25.67           C
ATOM    577  CD2 PHE A  35       7.753 -44.703  21.156  1.00 25.59           C
ATOM    579  C   PHE A  35       5.872 -42.524  19.627  1.00 25.88           C
ATOM    580  O   PHE A  35       6.952 -42.475  19.034  1.00 26.20           O
ATOM    582  N   ALA A  36       4.685 -42.630  19.021  1.00 25.55           N
ATOM    583  CA  ALA A  36       4.513 -42.758  17.578  1.00 25.05           C
ATOM    585  CB  ALA A  36       3.101 -43.221  17.272  1.00 25.33           C
ATOM    589  C   ALA A  36       4.782 -41.450  16.848  1.00 24.97           C
ATOM    590  O   ALA A  36       5.292 -41.448  15.720  1.00 24.71           O
ATOM    592  N   ALA A  37       4.409 -40.330  17.460  1.00 24.56           N
ATOM    593  CA  ALA A  37       4.827 -39.039  16.916  1.00 24.55           C
ATOM    595  CB  ALA A  37       4.384 -37.869  17.824  1.00 24.00           C
ATOM    599  C   ALA A  37       6.356 -39.043  16.751  1.00 24.28           C
ATOM    600  O   ALA A  37       6.866 -38.683  15.703  1.00 24.04           O
ATOM    602  N   ILE A  38       7.068 -39.492  17.784  1.00 24.05           N
ATOM    603  CA  ILE A  38       8.517 -39.364  17.814  1.00 24.02           C
ATOM    605  CB  ILE A  38       9.095 -39.711  19.211  1.00 24.10           C
ATOM    607  CG1 ILE A  38       8.771 -38.580  20.198  1.00 22.62           C
ATOM    610  CD1 ILE A  38       9.897 -38.962  21.658  1.00 20.65           C
ATOM    614  CG2 ILE A  38      10.620 -39.909  19.133  1.00 24.14           C
ATOM    618  C   ILE A  38       9.146 -40.221  16.733  1.00 24.02           C
ATOM    619  O   ILE A  38      10.007 -39.750  15.998  1.00 23.57           O
ATOM    621  N   CYS A  39       8.695 -41.469  16.631  1.00 24.20           N
ATOM    622  CA  CYS A  39       9.126 -42.363  15.551  1.00 24.21           C
ATOM    624  CB  CYS A  39       8.363 -43.683  15.603  1.00 24.23           C
ATOM    627  SG  CYS A  39       8.741 -44.707  17.021  1.00 23.25           S
ATOM    629  C   CYS A  39       8.925 -41.755  14.167  1.00 24.60           C
ATOM    630  O   CYS A  39       9.740 -41.993  13.265  1.00 25.04           O
ATOM    632  N   THR A  40       7.842 -40.995  13.985  1.00 24.47           N
ATOM    633  CA  THR A  40       7.545 -40.399  12.675  1.00 24.55           C
ATOM    635  CB  THR A  40       6.078 -39.851  12.581  1.00 24.67           C
ATOM    637  OG1 THR A  40       5.141 -40.934  12.550  1.00 24.71           O
ATOM    639  CG2 THR A  40       5.882 -39.021  11.335  1.00 24.61           C
ATOM    643  C   THR A  40       8.525 -39.278  12.340  1.00 24.61           C
ATOM    644  O   THR A  40       8.996 -39.191  11.203  1.00 24.74           O
ATOM    646  N   HIS A  41       8.800 -38.407  13.310  1.00 24.80           N
ATOM    647  CA  HIS A  41       9.762 -37.318  13.123  1.00 25.34           C
ATOM    649  CB  HIS A  41       9.794 -36.393  14.350  1.00 25.49           C
ATOM    652  CG  HIS A  41      10.878 -35.346  14.317  1.00 27.04           C
ATOM    653  ND1 HIS A  41      12.215 -35.646  14.493  1.00 28.09           N
ATOM    655  CE1 HIS A  41      12.923 -34.529  14.434  1.00 27.73           C
```

FIG. 16G

```
ATOM    657  NE2 HIS A   41      12.095 -33.515  14.262  1.00 26.35           N
ATOM    659  CD2 HIS A   41      10.811 -33.996  14.191  1.00 26.13           C
ATOM    661  C   HIS A   41      11.129 -37.940  12.859  1.00 25.49           C
ATOM    662  O   HIS A   41      11.822 -37.551  11.933  1.00 25.38           O
ATOM    664  N   LEU A   42      11.492 -38.928  13.666  1.00 25.95           N
ATOM    665  CA  LEU A   42      12.727 -39.667  13.460  1.00 26.48           C
ATOM    667  CB  LEU A   42      12.858 -40.826  14.465  1.00 26.51           C
ATOM    670  CG  LEU A   42      13.836 -40.745  15.658  1.00 26.43           C
ATOM    672  CD1 LEU A   42      14.571 -39.408  15.828  1.00 25.29           C
ATOM    676  CD2 LEU A   42      13.123 -41.119  16.939  1.00 26.61           C
ATOM    680  C   LEU A   42      12.819 -40.187  12.034  1.00 27.21           C
ATOM    681  O   LEU A   42      13.809 -39.915  11.350  1.00 27.76           O
ATOM    683  N   GLU A   43      11.804 -40.917  11.565  1.00 27.88           N
ATOM    684  CA  GLU A   43      11.883 -41.507  10.210  1.00 28.30           C
ATOM    686  CB  GLU A   43      10.735 -42.478   9.913  1.00 28.63           C
ATOM    689  CG  GLU A   43      10.925 -43.232   8.584  1.00 30.06           C
ATOM    692  CD  GLU A   43      10.083 -44.492   8.456  1.00 33.14           C
ATOM    693  OE1 GLU A   43      10.294 -45.275   7.495  1.00 35.19           O
ATOM    694  OE2 GLU A   43       9.197 -44.709   9.307  1.00 35.59           O
ATOM    695  C   GLU A   43      11.940 -40.461   9.103  1.00 28.09           C
ATOM    696  O   GLU A   43      12.699 -40.628   8.149  1.00 28.64           O
ATOM    698  N   VAL A   44      11.148 -39.396   9.202  1.00 27.56           N
ATOM    699  CA  VAL A   44      11.221 -38.348   8.188  1.00 27.48           C
ATOM    701  CB  VAL A   44      10.156 -37.241   8.381  1.00 27.51           C
ATOM    703  CG1 VAL A   44      10.482 -36.018   7.545  1.00 26.93           C
ATOM    707  CG2 VAL A   44       8.798 -37.763   7.983  1.00 28.07           C
ATOM    711  C   VAL A   44      12.620 -37.750   8.130  1.00 27.30           C
ATOM    712  O   VAL A   44      13.127 -37.529   7.062  1.00 27.85           O
ATOM    714  N   CYS A   45      13.248 -37.501   9.270  1.00 27.56           N
ATOM    715  CA  CYS A   45      14.614 -36.979   9.287  1.00 27.71           C
ATOM    717  CB  CYS A   45      15.094 -36.735  10.715  1.00 27.72           C
ATOM    720  SG  CYS A   45      14.293 -35.368  11.552  1.00 27.67           S
ATOM    722  C   CYS A   45      15.595 -37.897   8.575  1.00 28.00           C
ATOM    723  O   CYS A   45      16.425 -37.432   7.808  1.00 27.62           O
ATOM    725  N   PHE A   46      15.498 -39.198   8.819  1.00 28.77           N
ATOM    726  CA  PHE A   46      16.415 -40.127   8.179  1.00 29.80           C
ATOM    728  CB  PHE A   46      16.412 -41.496   8.852  1.00 29.70           C
ATOM    731  CG  PHE A   46      16.831 -41.489  10.309  1.00 30.79           C
ATOM    732  CD1 PHE A   46      17.366 -40.365  10.922  1.00 32.94           C
ATOM    734  CE1 PHE A   46      17.739 -40.398  12.267  1.00 33.58           C
ATOM    736  CZ  PHE A   46      17.602 -41.562  12.991  1.00 33.59           C
ATOM    738  CE2 PHE A   46      17.075 -42.677  12.392  1.00 33.18           C
ATOM    740  CD2 PHE A   46      16.703 -42.644  11.066  1.00 32.37           C
ATOM    742  C   PHE A   46      16.108 -40.283   6.696  1.00 30.78           C
ATOM    743  O   PHE A   46      17.011 -40.524   5.900  1.00 31.29           O
ATOM    745  N   MET A   47      14.847 -40.156   6.307  1.00 31.99           N
ATOM    746  CA  MET A   47      14.514 -40.254   4.889  1.00 33.04           C
ATOM    748  CB  MET A   47      13.002 -40.321   4.667  1.00 33.38           C
ATOM    751  CG  MET A   47      12.404 -41.707   4.804  1.00 34.59           C
ATOM    754  SD  MET A   47      10.606 -41.610   4.589  1.00 38.97           S
ATOM    755  CE  MET A   47      10.524 -41.399   2.805  1.00 37.18           C
ATOM    759  C   MET A   47      15.079 -39.044   4.177  1.00 33.39           C
ATOM    760  O   MET A   47      15.726 -39.168   3.144  1.00 33.49           O
ATOM    762  N   TYR A   48      14.810 -37.877   4.754  1.00 33.98           N
ATOM    763  CA  TYR A   48      15.295 -36.599   4.251  1.00 34.87           C
ATOM    765  CB  TYR A   48      14.890 -35.497   5.234  1.00 34.73           C
ATOM    768  CG  TYR A   48      14.804 -34.073   4.699  1.00 34.60           C
ATOM    769  CD1 TYR A   48      13.603 -33.363   4.742  1.00 34.57           C
ATOM    771  CE1 TYR A   48      13.528 -32.057   4.295  1.00 34.17           C
ATOM    773  CZ  TYR A   48      14.673 -31.443   3.804  1.00 34.27           C
ATOM    774  OH  TYR A   48      14.635 -30.137   3.349  1.00 34.35           O
ATOM    776  CE2 TYR A   48      15.863 -32.121   3.773  1.00 32.97           C
ATOM    778  CD2 TYR A   48      15.929 -33.415   4.224  1.00 34.11           C
```

FIG. 16H

```
ATOM    780  C   TYR A  48      16.817 -36.658   4.081  1.00 35.92           C
ATOM    781  O   TYR A  48      17.354 -36.181   3.085  1.00 35.93           O
ATOM    783  N   SER A  49      17.492 -37.266   5.059  1.00 37.24           N
ATOM    784  CA  SER A  49      18.933 -37.492   5.011  1.00 38.34           C
ATOM    786  CB  SER A  49      19.410 -38.209   6.284  1.00 38.66           C
ATOM    789  OG  SER A  49      20.564 -39.016   6.046  1.00 38.81           O
ATOM    791  C   SER A  49      19.343 -38.315   3.804  1.00 39.36           C
ATOM    792  O   SER A  49      20.182 -37.871   3.015  1.00 39.83           O
ATOM    794  N   ASP A  50      18.743 -39.500   3.663  1.00 40.23           N
ATOM    795  CA  ASP A  50      19.183 -40.483   2.665  1.00 41.03           C
ATOM    797  CB  ASP A  50      18.439 -41.811   2.825  1.00 41.26           C
ATOM    800  CG  ASP A  50      19.245 -42.842   3.613  1.00 42.74           C
ATOM    801  OD1 ASP A  50      20.087 -43.543   2.994  1.00 44.74           O
ATOM    802  OD2 ASP A  50      19.037 -42.959   4.845  1.00 44.45           O
ATOM    803  C   ASP A  50      19.103 -40.002   1.214  1.00 41.46           C
ATOM    804  O   ASP A  50      19.787 -40.555   0.352  1.00 41.38           O
ATOM    806  N   PHE A  51      18.282 -38.987   0.940  1.00 41.96           N
ATOM    807  CA  PHE A  51      18.325 -38.316  -0.363  1.00 42.54           C
ATOM    809  CB  PHE A  51      17.059 -37.472  -0.605  1.00 42.51           C
ATOM    812  CG  PHE A  51      15.766 -38.256  -0.491  1.00 41.89           C
ATOM    813  CD1 PHE A  51      14.701 -37.761   0.261  1.00 41.74           C
ATOM    815  CE1 PHE A  51      13.506 -38.478   0.376  1.00 41.45           C
ATOM    817  CZ  PHE A  51      13.370 -39.715  -0.256  1.00 41.44           C
ATOM    819  CE2 PHE A  51      14.427 -40.226  -0.999  1.00 41.90           C
ATOM    821  CD2 PHE A  51      15.621 -39.495  -1.114  1.00 41.38           C
ATOM    823  C   PHE A  51      19.590 -37.449  -0.417  1.00 43.16           C
ATOM    824  O   PHE A  51      19.659 -36.397   0.215  1.00 43.67           O
ATOM    826  N   GLY A  52      20.598 -37.914  -1.151  1.00 43.59           N
ATOM    827  CA  GLY A  52      21.914 -37.265  -1.174  1.00 43.70           C
ATOM    830  C   GLY A  52      23.017 -38.301  -1.175  1.00 43.78           C
ATOM    831  O   GLY A  52      22.773 -39.472  -1.481  1.00 43.78           O
ATOM    833  N   ALA A  70      24.774 -33.472  -7.196  1.00 61.12           N
ATOM    834  CA  ALA A  70      25.654 -34.263  -8.043  1.00 61.17           C
ATOM    836  CB  ALA A  70      25.413 -33.925  -9.517  1.00 61.15           C
ATOM    840  C   ALA A  70      27.133 -34.073  -7.668  1.00 61.08           C
ATOM    841  O   ALA A  70      27.929 -35.001  -7.808  1.00 61.30           O
ATOM    843  N   LEU A  71      27.497 -32.883  -7.185  1.00 60.92           N
ATOM    844  CA  LEU A  71      28.890 -32.597  -6.793  1.00 60.78           C
ATOM    846  CB  LEU A  71      29.097 -31.087  -6.586  1.00 60.80           C
ATOM    849  CG  LEU A  71      30.547 -30.618  -6.387  1.00 61.38           C
ATOM    851  CD1 LEU A  71      31.433 -31.044  -7.561  1.00 61.28           C
ATOM    855  CD2 LEU A  71      30.602 -29.107  -6.191  1.00 61.40           C
ATOM    859  C   LEU A  71      29.308 -33.366  -5.527  1.00 60.34           C
ATOM    860  O   LEU A  71      30.232 -34.188  -5.563  1.00 60.62           O
ATOM    862  N   LEU A  72      28.607 -33.102  -4.425  1.00 59.64           N
ATOM    863  CA  LEU A  72      28.912 -33.695  -3.115  1.00 58.90           C
ATOM    865  CB  LEU A  72      28.115 -32.971  -2.023  1.00 58.84           C
ATOM    868  CG  LEU A  72      28.349 -31.460  -1.881  1.00 58.58           C
ATOM    870  CD1 LEU A  72      27.079 -30.733  -1.437  1.00 57.55           C
ATOM    874  CD2 LEU A  72      29.518 -31.186  -0.930  1.00 58.09           C
ATOM    878  C   LEU A  72      28.581 -35.197  -3.080  1.00 58.23           C
ATOM    879  O   LEU A  72      27.828 -35.692  -3.933  1.00 58.38           O
ATOM    881  N   LYS A  73      29.141 -35.910  -2.096  1.00 57.05           N
ATOM    882  CA  LYS A  73      28.864 -37.351  -1.913  1.00 55.92           C
ATOM    884  CB  LYS A  73      30.087 -38.087  -1.350  1.00 56.13           C
ATOM    887  CG  LYS A  73      31.279 -38.109  -2.332  1.00 57.08           C
ATOM    890  CD  LYS A  73      32.401 -39.076  -1.906  1.00 58.07           C
ATOM    893  CE  LYS A  73      33.716 -38.794  -2.659  1.00 58.09           C
ATOM    896  NZ  LYS A  73      34.612 -39.985  -2.737  1.00 57.03           N
ATOM    900  C   LYS A  73      27.635 -37.558  -1.029  1.00 54.30           C
ATOM    901  O   LYS A  73      26.687 -38.236  -1.431  1.00 54.49           O
ATOM    903  N   HIS A  74      27.657 -36.965   0.163  1.00 52.21           N
ATOM    904  CA  HIS A  74      26.484 -36.901   1.036  1.00 50.51           C
```

FIG. 16I

```
ATOM    906  CB   HIS A  74      26.787 -37.469   2.426  1.00 50.51           C
ATOM    909  CG   HIS A  74      27.450 -38.810   2.412  1.00 52.26           C
ATOM    910  ND1  HIS A  74      26.741 -39.995   2.460  1.00 54.03           N
ATOM    912  CE1  HIS A  74      27.587 -41.011   2.446  1.00 54.64           C
ATOM    914  NE2  HIS A  74      28.818 -40.531   2.392  1.00 54.70           N
ATOM    916  CD2  HIS A  74      28.761 -39.156   2.375  1.00 53.75           C
ATOM    918  C    HIS A  74      26.107 -35.437   1.173  1.00 48.59           C
ATOM    919  O    HIS A  74      26.887 -34.655   1.718  1.00 48.33           O
ATOM    921  N    ARG A  75      24.928 -35.055   0.684  1.00 46.50           N
ATOM    922  CA   ARG A  75      24.495 -33.655   0.792  1.00 44.90           C
ATOM    924  CB   ARG A  75      23.347 -33.327  -0.168  1.00 44.90           C
ATOM    927  CG   ARG A  75      22.869 -31.875  -0.037  1.00 44.48           C
ATOM    930  CD   ARG A  75      21.760 -31.521  -0.991  1.00 44.37           C
ATOM    933  NE   ARG A  75      21.202 -30.227  -0.627  1.00 44.87           N
ATOM    935  CZ   ARG A  75      20.268 -29.579  -1.319  1.00 45.23           C
ATOM    936  NH1  ARG A  75      19.779 -30.101  -2.439  1.00 44.86           N
ATOM    939  NH2  ARG A  75      19.829 -28.393  -0.891  1.00 44.76           N
ATOM    942  C    ARG A  75      24.081 -33.283   2.215  1.00 43.31           C
ATOM    943  O    ARG A  75      24.117 -32.104   2.589  1.00 42.93           O
ATOM    945  N    PHE A  76      23.691 -34.278   3.007  1.00 41.50           N
ATOM    946  CA   PHE A  76      23.236 -34.002   4.362  1.00 40.11           C
ATOM    948  CB   PHE A  76      21.762 -34.350   4.493  1.00 39.96           C
ATOM    951  CG   PHE A  76      20.891 -33.560   3.571  1.00 39.79           C
ATOM    952  CD1  PHE A  76      20.608 -32.224   3.841  1.00 40.41           C
ATOM    954  CE1  PHE A  76      19.804 -31.475   2.983  1.00 39.78           C
ATOM    956  CZ   PHE A  76      19.288 -32.070   1.842  1.00 40.19           C
ATOM    958  CE2  PHE A  76      19.574 -33.406   1.565  1.00 39.39           C
ATOM    960  CD2  PHE A  76      20.375 -34.135   2.424  1.00 39.30           C
ATOM    962  C    PHE A  76      24.062 -34.698   5.426  1.00 38.82           C
ATOM    963  O    PHE A  76      24.587 -35.786   5.210  1.00 38.78           O
ATOM    965  N    GLU A  77      24.209 -34.033   6.565  1.00 37.43           N
ATOM    966  CA   GLU A  77      24.704 -34.679   7.762  1.00 36.49           C
ATOM    968  CB   GLU A  77      25.830 -33.856   8.406  1.00 36.48           C
ATOM    971  CG   GLU A  77      26.439 -34.455   9.679  1.00 37.14           C
ATOM    974  CD   GLU A  77      26.757 -35.947   9.578  1.00 39.38           C
ATOM    975  OE1  GLU A  77      27.526 -36.348   8.677  1.00 39.72           O
ATOM    976  OE2  GLU A  77      26.231 -36.730  10.408  1.00 41.46           O
ATOM    977  C    GLU A  77      23.506 -34.819   8.693  1.00 35.48           C
ATOM    978  O    GLU A  77      22.754 -33.856   8.880  1.00 35.25           O
ATOM    980  N    ILE A  78      23.329 -36.016   9.253  1.00 34.19           N
ATOM    981  CA   ILE A  78      22.249 -36.286  10.197  1.00 33.34           C
ATOM    983  CB   ILE A  78      21.824 -37.792  10.252  1.00 33.41           C
ATOM    985  CG1  ILE A  78      21.965 -38.479   8.894  1.00 34.00           C
ATOM    988  CD1  ILE A  78      21.409 -39.916   8.851  1.00 35.88           C
ATOM    992  CG2  ILE A  78      20.376 -37.908  10.758  1.00 33.46           C
ATOM    996  C    ILE A  78      22.702 -35.884  11.597  1.00 32.35           C
ATOM    997  O    ILE A  78      23.801 -36.242  12.028  1.00 32.27           O
ATOM    999  N    ILE A  79      21.840 -35.155  12.299  1.00 31.20           N
ATOM   1000  CA   ILE A  79      22.112 -34.670  13.646  1.00 30.26           C
ATOM   1002  CB   ILE A  79      22.172 -33.131  13.641  1.00 30.23           C
ATOM   1004  CG1  ILE A  79      23.380 -32.676  12.801  1.00 29.79           C
ATOM   1007  CD1  ILE A  79      23.128 -31.486  11.982  1.00 29.52           C
ATOM   1011  CG2  ILE A  79      22.277 -32.579  15.054  1.00 29.14           C
ATOM   1015  C    ILE A  79      21.061 -35.198  14.635  1.00 30.14           C
ATOM   1016  O    ILE A  79      21.383 -35.563  15.778  1.00 30.11           O
ATOM   1018  N    GLU A  80      19.807 -35.267  14.196  1.00 29.68           N
ATOM   1019  CA   GLU A  80      18.777 -35.948  14.978  1.00 29.13           C
ATOM   1021  CB   GLU A  80      17.404 -35.750  14.338  1.00 28.67           C
ATOM   1024  CG   GLU A  80      16.227 -36.286  15.152  1.00 27.69           C
ATOM   1027  CD   GLU A  80      16.084 -35.673  16.522  1.00 24.21           C
ATOM   1028  OE1  GLU A  80      15.340 -34.696  16.655  1.00 19.59           O
ATOM   1029  OE2  GLU A  80      16.716 -36.180  17.465  1.00 24.81           O
ATOM   1030  C    GLU A  80      19.122 -37.431  15.081  1.00 28.93           C
```

FIG. 16J

```
ATOM   1031  O    GLU A  80      19.790 -37.978  14.206  1.00 28.88           O
ATOM   1033  N    GLY A  81      18.702 -38.071  16.165  1.00 28.61           N
ATOM   1034  CA   GLY A  81      18.942 -39.506  16.328  1.00 28.77           C
ATOM   1037  C    GLY A  81      20.350 -39.872  16.766  1.00 28.87           C
ATOM   1038  O    GLY A  81      20.805 -41.004  16.587  1.00 29.88           O
ATOM   1040  N    ARG A  82      21.055 -38.918  17.351  1.00 28.47           N
ATOM   1041  CA   ARG A  82      22.362 -39.182  17.897  1.00 27.66           C
ATOM   1043  CB   ARG A  82      23.391 -38.304  17.208  1.00 27.67           C
ATOM   1046  CG   ARG A  82      23.679 -38.639  15.772  1.00 27.21           C
ATOM   1049  CD   ARG A  82      24.752 -37.707  15.303  1.00 27.78           C
ATOM   1052  NE   ARG A  82      25.171 -37.915  13.923  1.00 28.81           N
ATOM   1054  CZ   ARG A  82      26.069 -38.808  13.520  1.00 28.31           C
ATOM   1055  NH1  ARG A  82      26.654 -39.633  14.388  1.00 28.57           N
ATOM   1058  NH2  ARG A  82      26.370 -38.883  12.230  1.00 27.26           N
ATOM   1061  C    ARG A  82      22.286 -38.815  19.362  1.00 27.49           C
ATOM   1062  O    ARG A  82      21.506 -37.927  19.728  1.00 27.56           O
ATOM   1064  N    ASP A  83      23.081 -39.478  20.199  1.00 27.02           N
ATOM   1065  CA   ASP A  83      23.251 -39.025  21.569  1.00 27.25           C
ATOM   1067  CB   ASP A  83      24.171 -39.952  22.387  1.00 27.27           C
ATOM   1070  CG   ASP A  83      25.654 -39.734  22.089  1.00 30.15           C
ATOM   1071  OD1  ASP A  83      26.160 -40.198  21.032  1.00 29.66           O
ATOM   1072  OD2  ASP A  83      26.326 -39.101  22.944  1.00 35.18           O
ATOM   1073  C    ASP A  83      23.774 -37.594  21.522  1.00 26.74           C
ATOM   1074  O    ASP A  83      24.328 -37.146  20.512  1.00 26.66           O
ATOM   1076  N    ARG A  84      23.566 -36.860  22.602  1.00 26.74           N
ATOM   1077  CA   ARG A  84      23.844 -35.429  22.599  1.00 26.67           C
ATOM   1079  CB   ARG A  84      23.255 -34.777  23.826  1.00 27.25           C
ATOM   1082  CG   ARG A  84      21.765 -34.602  23.719  1.00 30.70           C
ATOM   1085  CD   ARG A  84      21.118 -34.753  25.075  1.00 35.33           C
ATOM   1088  NE   ARG A  84      21.055 -33.482  25.773  1.00 39.75           N
ATOM   1090  CZ   ARG A  84      19.926 -32.872  26.131  1.00 45.20           C
ATOM   1091  NH1  ARG A  84      18.735 -33.430  25.862  1.00 47.41           N
ATOM   1094  NH2  ARG A  84      19.983 -31.702  26.771  1.00 45.45           N
ATOM   1097  C    ARG A  84      25.313 -35.077  22.488  1.00 25.43           C
ATOM   1098  O    ARG A  84      25.639 -34.085  21.851  1.00 24.47           O
ATOM   1100  N    ILE A  85      26.179 -35.886  23.098  1.00 24.95           N
ATOM   1101  CA   ILE A  85      27.620 -35.670  23.018  1.00 24.78           C
ATOM   1103  CB   ILE A  85      28.438 -36.749  23.793  1.00 24.78           C
ATOM   1105  CG1  ILE A  85      28.068 -36.800  25.286  1.00 24.24           C
ATOM   1108  CD1  ILE A  85      27.601 -35.517  25.840  1.00 23.47           C
ATOM   1112  CG2  ILE A  85      29.928 -36.513  23.642  1.00 24.54           C
ATOM   1116  C    ILE A  85      28.053 -35.653  21.553  1.00 24.93           C
ATOM   1117  O    ILE A  85      28.682 -34.702  21.099  1.00 24.65           O
ATOM   1119  N    MET A  86      27.678 -36.688  20.811  1.00 25.38           N
ATOM   1120  CA   MET A  86      28.030 -36.785  19.387  1.00 26.03           C
ATOM   1122  CB   MET A  86      27.744 -38.194  18.837  1.00 26.65           C
ATOM   1125  CG   MET A  86      28.900 -39.200  19.039  1.00 29.33           C
ATOM   1128  SD   MET A  86      30.372 -38.922  17.989  1.00 35.60           S
ATOM   1129  CE   MET A  86      29.696 -38.027  16.600  1.00 33.20           C
ATOM   1133  C    MET A  86      27.320 -35.753  18.524  1.00 25.32           C
ATOM   1134  O    MET A  86      27.883 -35.270  17.546  1.00 26.22           O
ATOM   1136  N    ALA A  87      26.078 -35.438  18.850  1.00 24.52           N
ATOM   1137  CA   ALA A  87      25.333 -34.462  18.074  1.00 23.76           C
ATOM   1139  CB   ALA A  87      23.909 -34.284  18.641  1.00 23.37           C
ATOM   1143  C    ALA A  87      26.093 -33.142  18.073  1.00 23.09           C
ATOM   1144  O    ALA A  87      26.356 -32.564  17.018  1.00 23.05           O
ATOM   1146  N    TRP A  88      26.466 -32.678  19.255  1.00 22.72           N
ATOM   1147  CA   TRP A  88      27.188 -31.422  19.361  1.00 22.83           C
ATOM   1149  CB   TRP A  88      27.214 -30.939  20.792  1.00 22.74           C
ATOM   1152  CG   TRP A  88      25.943 -30.321  21.220  1.00 21.88           C
ATOM   1153  CD1  TRP A  88      25.040 -30.838  22.084  1.00 21.81           C
ATOM   1155  NE1  TRP A  88      23.990 -29.968  22.252  1.00 21.74           N
ATOM   1157  CE2  TRP A  88      24.203 -28.866  21.472  1.00 22.00           C
```

FIG. 16K

```
ATOM   1158  CD2 TRP A   88      25.438  -29.050  20.819  1.00 22.37           C
ATOM   1159  CE3 TRP A   88      25.900  -28.049  19.957  1.00 23.06           C
ATOM   1161  CZ3 TRP A   88      25.120  -26.905  19.779  1.00 22.32           C
ATOM   1163  CH2 TRP A   88      23.898  -26.747  20.457  1.00 22.11           C
ATOM   1165  CZ2 TRP A   88      23.422  -27.713  21.300  1.00 22.43           C
ATOM   1167  C   TRP A   88      28.612  -31.517  18.800  1.00 23.30           C
ATOM   1168  O   TRP A   88      29.142  -30.535  18.274  1.00 22.77           O
ATOM   1170  N   THR A   89      29.217  -32.701  18.882  1.00 23.62           N
ATOM   1171  CA  THR A   89      30.522  -32.913  18.266  1.00 23.72           C
ATOM   1173  CB  THR A   89      31.094  -34.322  18.532  1.00 23.67           C
ATOM   1175  OG1 THR A   89      31.402  -34.456  19.920  1.00 22.95           O
ATOM   1177  CG2 THR A   89      32.357  -34.557  17.692  1.00 22.34           C
ATOM   1181  C   THR A   89      30.398  -32.713  16.779  1.00 24.28           C
ATOM   1182  O   THR A   89      31.201  -31.987  16.192  1.00 24.53           O
ATOM   1184  N   VAL A   90      29.396  -33.350  16.172  1.00 24.74           N
ATOM   1185  CA  VAL A   90      29.158  -33.191  14.734  1.00 25.32           C
ATOM   1187  CB  VAL A   90      28.055  -34.146  14.209  1.00 25.51           C
ATOM   1189  CG1 VAL A   90      27.830  -33.943  12.730  1.00 24.97           C
ATOM   1193  CG2 VAL A   90      28.428  -35.604  14.462  1.00 25.28           C
ATOM   1197  C   VAL A   90      28.803  -31.731  14.406  1.00 25.79           C
ATOM   1198  O   VAL A   90      29.408  -31.114  13.537  1.00 25.15           O
ATOM   1200  N   VAL A   91      27.853  -31.164  15.131  1.00 26.67           N
ATOM   1201  CA  VAL A   91      27.490  -29.761  14.919  1.00 27.54           C
ATOM   1203  CB  VAL A   91      26.332  -29.343  15.852  1.00 27.45           C
ATOM   1205  CG1 VAL A   91      26.090  -27.856  15.796  1.00 27.80           C
ATOM   1209  CG2 VAL A   91      25.082  -30.077  15.459  1.00 27.65           C
ATOM   1213  C   VAL A   91      28.676  -28.788  15.069  1.00 28.44           C
ATOM   1214  O   VAL A   91      28.792  -27.852  14.293  1.00 28.27           O
ATOM   1216  N   ASN A   92      29.544  -29.006  16.057  1.00 29.67           N
ATOM   1217  CA  ASN A   92      30.720  -28.135  16.276  1.00 30.42           C
ATOM   1219  CB  ASN A   92      31.376  -28.387  17.641  1.00 30.16           C
ATOM   1222  CG  ASN A   92      30.654  -27.711  18.782  1.00 29.62           C
ATOM   1223  OD1 ASN A   92      30.317  -26.531  18.706  1.00 29.36           O
ATOM   1224  ND2 ASN A   92      30.434  -28.453  19.868  1.00 29.77           N
ATOM   1227  C   ASN A   92      31.774  -28.338  15.205  1.00 31.86           C
ATOM   1228  O   ASN A   92      32.441  -27.389  14.805  1.00 32.25           O
ATOM   1230  N   SER A   93      31.941  -29.585  14.767  1.00 33.42           N
ATOM   1231  CA  SER A   93      32.839  -29.910  13.656  1.00 34.58           C
ATOM   1233  CB  SER A   93      32.772  -31.417  13.354  1.00 34.62           C
ATOM   1236  OG  SER A   93      33.711  -31.839  12.387  1.00 34.43           O
ATOM   1238  C   SER A   93      32.444  -29.080  12.428  1.00 35.88           C
ATOM   1239  O   SER A   93      33.268  -28.339  11.890  1.00 36.78           O
ATOM   1241  N   ILE A   94      31.177  -29.194  12.016  1.00 36.99           N
ATOM   1242  CA  ILE A   94      30.605  -28.432  10.896  1.00 37.62           C
ATOM   1244  CB  ILE A   94      29.074  -28.692  10.772  1.00 37.60           C
ATOM   1246  CG1 ILE A   94      28.798  -30.044  10.096  1.00 38.01           C
ATOM   1249  CD1 ILE A   94      27.445  -30.681  10.487  1.00 37.00           C
ATOM   1253  CG2 ILE A   94      28.379  -27.570   9.998  1.00 37.52           C
ATOM   1257  C   ILE A   94      30.826  -26.921  11.039  1.00 38.56           C
ATOM   1258  O   ILE A   94      31.247  -26.250  10.099  1.00 38.63           O
ATOM   1260  N   CYS A   95      30.529  -26.384  12.214  1.00 39.56           N
ATOM   1261  CA  CYS A   95      30.689  -24.957  12.447  1.00 40.38           C
ATOM   1263  CB  CYS A   95      30.092  -24.571  13.790  1.00 40.24           C
ATOM   1266  SG  CYS A   95      28.303  -24.673  13.828  1.00 39.52           S
ATOM   1268  C   CYS A   95      32.156  -24.548  12.397  1.00 41.75           C
ATOM   1269  O   CYS A   95      32.508  -23.560  11.767  1.00 42.30           O
ATOM   1271  N   ASN A   96      33.016  -25.320  13.048  1.00 43.14           N
ATOM   1272  CA  ASN A   96      34.429  -24.979  13.111  1.00 44.09           C
ATOM   1274  CB  ASN A   96      35.157  -25.860  14.145  1.00 44.46           C
ATOM   1277  CG  ASN A   96      34.629  -25.659  15.596  1.00 46.19           C
ATOM   1278  OD1 ASN A   96      33.702  -24.871  15.851  1.00 48.05           O
ATOM   1279  ND2 ASN A   96      35.218  -26.396  16.540  1.00 47.62           N
ATOM   1282  C   ASN A   96      35.130  -25.059  11.751  1.00 44.38           C
```

FIG. 16L

```
ATOM   1283  O    ASN A  96      36.153 -24.416  11.568  1.00 44.60           O
ATOM   1285  N    THR A  97      34.585 -25.828  10.806  1.00 44.78           N
ATOM   1286  CA   THR A  97      35.242 -26.052   9.511  1.00 45.13           C
ATOM   1288  CB   THR A  97      35.372 -27.552   9.207  1.00 45.22           C
ATOM   1290  OG1  THR A  97      34.096 -28.063   8.822  1.00 45.02           O
ATOM   1292  CG2  THR A  97      35.900 -28.321  10.414  1.00 45.09           C
ATOM   1296  C    THR A  97      34.538 -25.435   8.295  1.00 45.62           C
ATOM   1297  O    THR A  97      35.025 -25.576   7.168  1.00 46.04           O
ATOM   1299  N    THR A  98      33.380 -24.812   8.510  1.00 45.85           N
ATOM   1300  CA   THR A  98      32.670 -24.063   7.465  1.00 45.77           C
ATOM   1302  CB   THR A  98      31.306 -24.703   7.122  1.00 45.97           C
ATOM   1304  OG1  THR A  98      30.401 -24.547   8.233  1.00 45.21           O
ATOM   1306  CG2  THR A  98      31.459 -26.185   6.750  1.00 45.92           C
ATOM   1310  C    THR A  98      32.372 -22.622   7.892  1.00 45.89           C
ATOM   1311  O    THR A  98      31.915 -21.822   7.073  1.00 46.24           O
ATOM   1313  N    GLY A  99      32.575 -22.308   9.170  1.00 45.62           N
ATOM   1314  CA   GLY A  99      32.351 -20.964   9.692  1.00 45.67           C
ATOM   1317  C    GLY A  99      30.921 -20.499   9.918  1.00 45.69           C
ATOM   1318  O    GLY A  99      30.715 -19.363  10.356  1.00 45.73           O
ATOM   1320  N    VAL A 100      29.927 -21.343   9.639  1.00 45.65           N
ATOM   1321  CA   VAL A 100      28.529 -20.953   9.871  1.00 45.60           C
ATOM   1323  CB   VAL A 100      27.510 -21.958   9.252  1.00 45.73           C
ATOM   1325  CG1  VAL A 100      27.853 -22.242   7.780  1.00 45.96           C
ATOM   1329  CG2  VAL A 100      27.461 -23.248  10.044  1.00 45.34           C
ATOM   1333  C    VAL A 100      28.279 -20.793  11.373  1.00 45.62           C
ATOM   1334  O    VAL A 100      28.953 -21.416  12.192  1.00 45.43           O
ATOM   1336  N    GLU A 101      27.321 -19.943  11.728  1.00 45.76           N
ATOM   1337  CA   GLU A 101      27.008 -19.676  13.135  1.00 45.87           C
ATOM   1339  CB   GLU A 101      26.001 -18.526  13.244  1.00 45.97           C
ATOM   1342  CG   GLU A 101      25.934 -17.911  14.649  1.00 47.57           C
ATOM   1345  CD   GLU A 101      24.684 -17.059  14.901  1.00 49.41           C
ATOM   1346  OE1  GLU A 101      23.724 -17.112  14.096  1.00 50.37           O
ATOM   1347  OE2  GLU A 101      24.661 -16.345  15.930  1.00 50.00           O
ATOM   1348  C    GLU A 101      26.467 -20.930  13.868  1.00 45.61           C
ATOM   1349  O    GLU A 101      25.748 -21.748  13.280  1.00 45.51           O
ATOM   1351  N    LYS A 102      26.818 -21.049  15.150  1.00 45.19           N
ATOM   1352  CA   LYS A 102      26.495 -22.207  15.974  1.00 44.90           C
ATOM   1354  CB   LYS A 102      27.503 -22.327  17.119  1.00 44.92           C
ATOM   1357  CG   LYS A 102      27.167 -23.380  18.177  1.00 45.81           C
ATOM   1360  CD   LYS A 102      28.370 -23.672  19.077  1.00 47.07           C
ATOM   1363  CE   LYS A 102      28.056 -24.760  20.101  1.00 48.07           C
ATOM   1366  NZ   LYS A 102      29.283 -25.225  20.821  1.00 48.42           N
ATOM   1370  C    LYS A 102      25.078 -22.093  16.535  1.00 44.59           C
ATOM   1371  O    LYS A 102      24.739 -21.084  17.145  1.00 44.77           O
ATOM   1373  N    PRO A 103      24.247 -23.132  16.339  1.00 44.06           N
ATOM   1374  CA   PRO A 103      22.878 -23.088  16.847  1.00 43.66           C
ATOM   1376  CB   PRO A 103      22.261 -24.400  16.336  1.00 43.85           C
ATOM   1379  CG   PRO A 103      23.186 -24.915  15.299  1.00 44.09           C
ATOM   1382  CD   PRO A 103      24.533 -24.390  15.624  1.00 44.10           C
ATOM   1385  C    PRO A 103      22.832 -23.066  18.367  1.00 43.12           C
ATOM   1386  O    PRO A 103      23.731 -23.611  19.002  1.00 42.87           O
ATOM   1387  N    LYS A 104      21.796 -22.439  18.931  1.00 42.34           N
ATOM   1388  CA   LYS A 104      21.566 -22.469  20.373  1.00 41.95           C
ATOM   1390  CB   LYS A 104      20.646 -21.326  20.804  1.00 42.29           C
ATOM   1393  CG   LYS A 104      21.334 -19.969  20.845  1.00 44.73           C
ATOM   1396  CD   LYS A 104      20.385 -18.854  21.320  1.00 47.70           C
ATOM   1399  CE   LYS A 104      21.032 -17.459  21.175  1.00 49.06           C
ATOM   1402  NZ   LYS A 104      20.091 -16.354  21.565  1.00 49.81           N
ATOM   1406  C    LYS A 104      20.976 -23.815  20.814  1.00 40.95           C
ATOM   1407  O    LYS A 104      21.213 -24.265  21.932  1.00 40.78           O
ATOM   1409  N    PHE A 105      20.196 -24.437  19.933  1.00 39.87           N
ATOM   1410  CA   PHE A 105      19.614 -25.754  20.182  1.00 39.25           C
ATOM   1412  CB   PHE A 105      18.093 -25.633  20.319  1.00 39.72           C
```

FIG. 16M

```
ATOM   1415  CG   PHE A 105      17.647 -24.831  21.528  1.00 41.82           C
ATOM   1416  CD1  PHE A 105      17.921 -25.279  22.820  1.00 43.75           C
ATOM   1418  CE1  PHE A 105      17.513 -24.545  23.940  1.00 44.10           C
ATOM   1420  CZ   PHE A 105      16.813 -23.361  23.769  1.00 43.68           C
ATOM   1422  CE2  PHE A 105      16.523 -22.908  22.485  1.00 43.88           C
ATOM   1424  CD2  PHE A 105      16.939 -23.640  21.374  1.00 43.40           C
ATOM   1426  C    PHE A 105      19.976 -26.714  19.038  1.00 37.58           C
ATOM   1427  O    PHE A 105      20.211 -26.271  17.916  1.00 37.07           O
ATOM   1429  N    LEU A 106      20.028 -28.017  19.322  1.00 35.46           N
ATOM   1430  CA   LEU A 106      20.329 -28.997  18.280  1.00 34.09           C
ATOM   1432  CB   LEU A 106      20.461 -30.413  18.851  1.00 34.01           C
ATOM   1435  CG   LEU A 106      21.754 -30.873  19.528  1.00 33.36           C
ATOM   1437  CD1  LEU A 106      21.567 -32.315  19.959  1.00 32.09           C
ATOM   1441  CD2  LEU A 106      22.967 -30.742  18.619  1.00 31.50           C
ATOM   1445  C    LEU A 106      19.235 -29.020  17.226  1.00 32.92           C
ATOM   1446  O    LEU A 106      18.078 -29.165  17.561  1.00 32.71           O
ATOM   1448  N    PRO A 107      19.598 -28.895  15.944  1.00 32.17           N
ATOM   1449  CA   PRO A 107      18.626 -29.063  14.885  1.00 31.74           C
ATOM   1451  CB   PRO A 107      19.138 -28.097  13.816  1.00 31.71           C
ATOM   1454  CG   PRO A 107      20.610 -28.086  14.005  1.00 31.66           C
ATOM   1457  CD   PRO A 107      20.924 -28.587  15.381  1.00 32.17           C
ATOM   1460  C    PRO A 107      18.629 -30.521  14.417  1.00 31.09           C
ATOM   1461  O    PRO A 107      19.133 -31.374  15.139  1.00 30.98           O
ATOM   1462  N    ASP A 108      18.078 -30.803  13.237  1.00 30.62           N
ATOM   1463  CA   ASP A 108      17.933 -32.179  12.749  1.00 30.37           C
ATOM   1465  CB   ASP A 108      16.505 -32.388  12.239  1.00 30.40           C
ATOM   1468  CG   ASP A 108      15.449 -32.136  13.322  1.00 30.54           C
ATOM   1469  OD1  ASP A 108      15.634 -32.602  14.477  1.00 27.46           O
ATOM   1470  OD2  ASP A 108      14.439 -31.465  13.005  1.00 30.39           O
ATOM   1471  C    ASP A 108      18.934 -32.569  11.656  1.00 30.46           C
ATOM   1472  O    ASP A 108      19.354 -33.714  11.595  1.00 30.14           O
ATOM   1474  N    LEU A 109      19.302 -31.624  10.790  1.00 30.79           N
ATOM   1475  CA   LEU A 109      20.242 -31.887   9.691  1.00 30.85           C
ATOM   1477  CB   LEU A 109      19.475 -32.231   8.415  1.00 30.72           C
ATOM   1480  CG   LEU A 109      18.466 -33.377   8.371  1.00 30.21           C
ATOM   1482  CD1  LEU A 109      17.591 -33.139   7.173  1.00 30.04           C
ATOM   1486  CD2  LEU A 109      19.121 -34.764   8.281  1.00 29.17           C
ATOM   1490  C    LEU A 109      21.152 -30.691   9.376  1.00 31.31           C
ATOM   1491  O    LEU A 109      20.917 -29.577   9.818  1.00 31.04           O
ATOM   1493  N    TYR A 110      22.197 -30.942   8.602  1.00 32.34           N
ATOM   1494  CA   TYR A 110      22.981 -29.870   7.989  1.00 33.22           C
ATOM   1496  CB   TYR A 110      24.423 -29.826   8.523  1.00 33.33           C
ATOM   1499  CG   TYR A 110      25.215 -28.662   7.954  1.00 33.07           C
ATOM   1500  CD1  TYR A 110      24.932 -27.359   8.333  1.00 33.36           C
ATOM   1502  CE1  TYR A 110      25.643 -26.278   7.809  1.00 34.08           C
ATOM   1504  CZ   TYR A 110      26.648 -26.495   6.898  1.00 34.55           C
ATOM   1505  OH   TYR A 110      27.344 -25.421   6.388  1.00 36.03           O
ATOM   1507  CE2  TYR A 110      26.951 -27.782   6.491  1.00 35.02           C
ATOM   1509  CD2  TYR A 110      26.227 -28.864   7.021  1.00 34.78           C
ATOM   1511  C    TYR A 110      23.032 -30.095   6.496  1.00 33.87           C
ATOM   1512  O    TYR A 110      23.252 -31.215   6.047  1.00 33.49           O
ATOM   1514  N    ASP A 111      22.842 -29.022   5.737  1.00 35.09           N
ATOM   1515  CA   ASP A 111      22.890 -29.087   4.284  1.00 36.18           C
ATOM   1517  CB   ASP A 111      21.758 -28.230   3.705  1.00 36.30           C
ATOM   1520  CG   ASP A 111      21.542 -28.465   2.219  1.00 36.33           C
ATOM   1521  OD1  ASP A 111      22.409 -29.106   1.577  1.00 35.59           O
ATOM   1522  OD2  ASP A 111      20.492 -28.013   1.696  1.00 35.58           O
ATOM   1523  C    ASP A 111      24.244 -28.580   3.781  1.00 37.05           C
ATOM   1524  O    ASP A 111      24.540 -27.387   3.862  1.00 36.92           O
ATOM   1526  N    TYR A 112      25.059 -29.482   3.250  1.00 38.34           N
ATOM   1527  CA   TYR A 112      26.397 -29.104   2.782  1.00 39.58           C
ATOM   1529  CB   TYR A 112      27.258 -30.343   2.538  1.00 39.64           C
ATOM   1532  CG   TYR A 112      27.802 -30.984   3.798  1.00 39.90           C
```

FIG. 16N

```
ATOM   1533  CD1  TYR A 112     27.340 -32.223   4.222  1.00 40.91           C
ATOM   1535  CE1  TYR A 112     27.839 -32.825   5.374  1.00 41.15           C
ATOM   1537  CZ   TYR A 112     28.806 -32.181   6.111  1.00 40.99           C
ATOM   1538  OH   TYR A 112     29.284 -32.781   7.246  1.00 41.18           O
ATOM   1540  CE2  TYR A 112     29.287 -30.946   5.708  1.00 40.68           C
ATOM   1542  CD2  TYR A 112     28.785 -30.358   4.555  1.00 40.03           C
ATOM   1544  C    TYR A 112     26.401 -28.224   1.521  1.00 40.71           C
ATOM   1545  O    TYR A 112     27.384 -27.536   1.243  1.00 41.24           O
ATOM   1547  N    LYS A 113     25.316 -28.260   0.753  1.00 41.88           N
ATOM   1548  CA   LYS A 113     25.241 -27.532  -0.508  1.00 42.22           C
ATOM   1550  CB   LYS A 113     24.270 -28.237  -1.471  1.00 42.45           C
ATOM   1553  CG   LYS A 113     23.912 -27.443  -2.738  1.00 43.40           C
ATOM   1556  CD   LYS A 113     23.015 -28.238  -3.687  1.00 43.70           C
ATOM   1559  CE   LYS A 113     22.563 -27.374  -4.874  1.00 44.50           C
ATOM   1562  NZ   LYS A 113     21.360 -27.929  -5.585  1.00 44.53           N
ATOM   1566  C    LYS A 113     24.825 -26.088  -0.245  1.00 42.47           C
ATOM   1567  O    LYS A 113     25.389 -25.166  -0.833  1.00 43.03           O
ATOM   1569  N    GLU A 114     23.850 -25.893   0.640  1.00 42.38           N
ATOM   1570  CA   GLU A 114     23.326 -24.566   0.925  1.00 42.25           C
ATOM   1572  CB   GLU A 114     21.804 -24.625   1.045  1.00 42.48           C
ATOM   1575  CG   GLU A 114     21.101 -25.211  -0.177  1.00 43.12           C
ATOM   1578  CD   GLU A 114     20.972 -24.245  -1.341  1.00 44.54           C
ATOM   1579  OE1  GLU A 114     21.635 -23.182  -1.349  1.00 45.47           O
ATOM   1580  OE2  GLU A 114     20.187 -24.558  -2.267  1.00 46.87           O
ATOM   1581  C    GLU A 114     23.918 -24.019   2.210  1.00 42.27           C
ATOM   1582  O    GLU A 114     23.530 -22.937   2.672  1.00 42.36           O
ATOM   1584  N    ASN A 115     24.841 -24.781   2.793  1.00 42.24           N
ATOM   1585  CA   ASN A 115     25.518 -24.420   4.037  1.00 42.33           C
ATOM   1587  CB   ASN A 115     26.706 -23.506   3.747  1.00 42.54           C
ATOM   1590  CG   ASN A 115     27.775 -24.201   2.913  1.00 44.14           C
ATOM   1591  OD1  ASN A 115     28.134 -23.730   1.822  1.00 47.65           O
ATOM   1592  ND2  ASN A 115     28.266 -25.345   3.403  1.00 43.77           N
ATOM   1595  C    ASN A 115     24.611 -23.819   5.102  1.00 41.99           C
ATOM   1596  O    ASN A 115     24.735 -22.644   5.468  1.00 42.22           O
ATOM   1598  N    ARG A 116     23.702 -24.649   5.601  1.00 41.33           N
ATOM   1599  CA   ARG A 116     22.796 -24.242   6.657  1.00 40.59           C
ATOM   1601  CB   ARG A 116     21.693 -23.370   6.084  1.00 40.85           C
ATOM   1604  CG   ARG A 116     20.850 -24.073   5.049  1.00 42.04           C
ATOM   1607  CD   ARG A 116     19.894 -23.108   4.403  1.00 43.56           C
ATOM   1610  NE   ARG A 116     19.078 -23.770   3.396  1.00 45.04           N
ATOM   1612  CZ   ARG A 116     18.320 -23.134   2.508  1.00 46.12           C
ATOM   1613  NH1  ARG A 116     18.263 -21.805   2.498  1.00 45.63           N
ATOM   1616  NH2  ARG A 116     17.611 -23.835   1.629  1.00 46.47           N
ATOM   1619  C    ARG A 116     22.169 -25.444   7.336  1.00 39.65           C
ATOM   1620  O    ARG A 116     22.084 -26.537   6.746  1.00 39.49           O
ATOM   1622  N    PHE A 117     21.720 -25.216   8.570  1.00 38.46           N
ATOM   1623  CA   PHE A 117     21.048 -26.229   9.365  1.00 37.48           C
ATOM   1625  CB   PHE A 117     21.268 -25.985  10.851  1.00 37.18           C
ATOM   1628  CG   PHE A 117     22.660 -26.297  11.303  1.00 36.90           C
ATOM   1629  CD1  PHE A 117     23.060 -27.612  11.488  1.00 35.87           C
ATOM   1631  CE1  PHE A 117     24.342 -27.908  11.891  1.00 35.89           C
ATOM   1633  CZ   PHE A 117     25.245 -26.886  12.122  1.00 35.53           C
ATOM   1635  CE2  PHE A 117     24.856 -25.569  11.939  1.00 36.00           C
ATOM   1637  CD2  PHE A 117     23.577 -25.279  11.533  1.00 36.26           C
ATOM   1639  C    PHE A 117     19.570 -26.245   9.060  1.00 37.05           C
ATOM   1640  O    PHE A 117     18.997 -25.225   8.649  1.00 36.82           O
ATOM   1642  N    ILE A 118     18.967 -27.419   9.253  1.00 36.44           N
ATOM   1643  CA   ILE A 118     17.545 -27.641   8.960  1.00 35.88           C
ATOM   1645  CB   ILE A 118     17.348 -28.632   7.801  1.00 35.62           C
ATOM   1647  CG1  ILE A 118     18.150 -28.199   6.567  1.00 35.28           C
ATOM   1650  CD1  ILE A 118     18.272 -29.271   5.489  1.00 33.61           C
ATOM   1654  CG2  ILE A 118     15.871 -28.765   7.470  1.00 35.12           C
ATOM   1658  C    ILE A 118     16.820 -28.200  10.185  1.00 35.61           C
```

FIG. 16O

```
ATOM  1659  O    ILE A 118      17.305 -29.147 10.836  1.00 35.73           O
ATOM  1661  N    GLU A 119      15.672 -27.607 10.499  1.00 34.98           N
ATOM  1662  CA   GLU A 119      14.801 -28.113 11.547  1.00 35.00           C
ATOM  1664  CB   GLU A 119      14.467 -27.017 12.570  1.00 35.24           C
ATOM  1667  CG   GLU A 119      13.432 -27.405 13.641  1.00 35.49           C
ATOM  1670  CD   GLU A 119      13.728 -28.715 14.333  1.00 35.78           C
ATOM  1671  OE1  GLU A 119      12.765 -29.474 14.574  1.00 37.24           O
ATOM  1672  OE2  GLU A 119      14.910 -28.990 14.629  1.00 35.45           O
ATOM  1673  C    GLU A 119      13.537 -28.664 10.898  1.00 34.57           C
ATOM  1674  O    GLU A 119      12.692 -27.901 10.431  1.00 34.20           O
ATOM  1676  N    ILE A 120      13.453 -29.996 10.854  1.00 34.05           N
ATOM  1677  CA   ILE A 120      12.318 -30.709 10.307  1.00 33.58           C
ATOM  1679  CB   ILE A 120      12.673 -32.156  9.965  1.00 33.46           C
ATOM  1681  CG1  ILE A 120      13.751 -32.220  8.883  1.00 34.02           C
ATOM  1684  CD1  ILE A 120      13.395 -31.531  7.587  1.00 34.17           C
ATOM  1688  CG2  ILE A 120      11.436 -32.925  9.549  1.00 33.36           C
ATOM  1692  C    ILE A 120      11.219 -30.752 11.357  1.00 33.80           C
ATOM  1693  O    ILE A 120      11.450 -31.129 12.506  1.00 33.34           O
ATOM  1695  N    GLY A 121      10.026 -30.344 10.950  1.00 34.18           N
ATOM  1696  CA   GLY A 121       8.836 -30.476 11.770  1.00 34.33           C
ATOM  1699  C    GLY A 121       7.862 -31.419 11.099  1.00 34.42           C
ATOM  1700  O    GLY A 121       7.762 -31.454  9.878  1.00 33.90           O
ATOM  1702  N    VAL A 122       7.170 -32.207 11.909  1.00 35.16           N
ATOM  1703  CA   VAL A 122       6.058 -33.020 11.451  1.00 35.47           C
ATOM  1705  CB   VAL A 122       6.397 -34.497 11.474  1.00 35.31           C
ATOM  1707  CG1  VAL A 122       5.261 -35.292 10.848  1.00 34.65           C
ATOM  1711  CG2  VAL A 122       7.716 -34.744 10.750  1.00 34.22           C
ATOM  1715  C    VAL A 122       4.887 -32.752 12.376  1.00 36.49           C
ATOM  1716  O    VAL A 122       5.006 -32.889 13.580  1.00 36.06           O
ATOM  1718  N    THR A 123       3.763 -32.334 11.812  1.00 38.25           N
ATOM  1719  CA   THR A 123       2.579 -32.030 12.606  1.00 39.75           C
ATOM  1721  CB   THR A 123       2.302 -30.519 12.644  1.00 39.76           C
ATOM  1723  OG1  THR A 123       1.369 -30.240 13.688  1.00 40.75           O
ATOM  1725  CG2  THR A 123       1.740 -30.008 11.307  1.00 39.49           C
ATOM  1729  C    THR A 123       1.388 -32.736 12.011  1.00 40.95           C
ATOM  1730  O    THR A 123       1.397 -33.051 10.833  1.00 40.89           O
ATOM  1732  N    ARG A 124       0.369 -32.991 12.820  1.00 42.67           N
ATOM  1733  CA   ARG A 124      -0.873 -33.583 12.300  1.00 44.25           C
ATOM  1735  CB   ARG A 124      -1.262 -34.879 13.053  1.00 44.20           C
ATOM  1738  CG   ARG A 124      -1.043 -34.891 14.572  1.00 43.73           C
ATOM  1741  CD   ARG A 124      -0.181 -36.060 15.073  1.00 42.41           C
ATOM  1744  NE   ARG A 124       0.776 -35.603 16.085  1.00 42.71           N
ATOM  1746  CZ   ARG A 124       0.789 -35.911 17.387  1.00 42.89           C
ATOM  1747  NH1  ARG A 124      -0.099 -36.727 17.936  1.00 43.49           N
ATOM  1750  NH2  ARG A 124       1.736 -35.394 18.162  1.00 43.09           N
ATOM  1753  C    ARG A 124      -1.993 -32.520 12.239  1.00 45.93           C
ATOM  1754  O    ARG A 124      -3.164 -32.819 11.957  1.00 45.97           O
ATOM  1756  N    ARG A 125      -1.585 -31.271 12.463  1.00 47.69           N
ATOM  1757  CA   ARG A 125      -2.415 -30.106 12.229  1.00 49.21           C
ATOM  1759  CB   ARG A 125      -2.260 -29.132 13.397  1.00 49.39           C
ATOM  1762  CG   ARG A 125      -2.830 -29.639 14.696  1.00 50.37           C
ATOM  1765  CD   ARG A 125      -2.641 -28.591 15.785  1.00 52.42           C
ATOM  1768  NE   ARG A 125      -1.401 -28.782 16.544  1.00 53.57           N
ATOM  1770  CZ   ARG A 125      -0.676 -27.807 17.098  1.00 53.86           C
ATOM  1771  NH1  ARG A 125      -1.030 -26.533 16.976  1.00 53.62           N
ATOM  1774  NH2  ARG A 125       0.433 -28.113 17.768  1.00 54.17           N
ATOM  1777  C    ARG A 125      -2.031 -29.439 10.890  1.00 50.38           C
ATOM  1778  O    ARG A 125      -1.513 -30.102  9.977  1.00 50.26           O
ATOM  1780  N    GLU A 126      -2.299 -28.135 10.776  1.00 51.87           N
ATOM  1781  CA   GLU A 126      -2.062 -27.375  9.544  1.00 52.89           C
ATOM  1783  CB   GLU A 126      -3.159 -26.323  9.357  1.00 53.10           C
ATOM  1786  CG   GLU A 126      -4.582 -26.846  9.556  1.00 54.37           C
ATOM  1789  CD   GLU A 126      -5.549 -25.734  9.907  1.00 56.25           C
```

FIG. 16P

```
ATOM   1790  OE1 GLU A 126     -5.627 -24.762   9.129  1.00 57.91           O
ATOM   1791  OE2 GLU A 126     -6.222 -25.819  10.959  1.00 57.22           O
ATOM   1792  C   GLU A 126     -0.687 -26.694   9.589  1.00 53.27           C
ATOM   1793  O   GLU A 126     -0.390 -25.930  10.518  1.00 53.08           O
ATOM   1795  N   VAL A 127      0.140 -26.997   8.587  1.00 53.87           N
ATOM   1796  CA  VAL A 127      1.521 -26.509   8.517  1.00 54.32           C
ATOM   1798  CB  VAL A 127      2.066 -26.550   7.065  1.00 54.30           C
ATOM   1800  CG1 VAL A 127      2.669 -27.906   6.752  1.00 54.92           C
ATOM   1804  CG2 VAL A 127      0.972 -26.217   6.056  1.00 54.54           C
ATOM   1808  C   VAL A 127      1.710 -25.096   9.072  1.00 54.78           C
ATOM   1809  O   VAL A 127      2.426 -24.906  10.053  1.00 54.69           O
ATOM   1811  N   HIS A 128      1.041 -24.122   8.459  1.00 55.54           N
ATOM   1812  CA  HIS A 128      1.350 -22.702   8.676  1.00 56.24           C
ATOM   1814  CB  HIS A 128      0.349 -21.774   7.955  1.00 56.67           C
ATOM   1817  CG  HIS A 128     -1.060 -21.872   8.463  1.00 58.76           C
ATOM   1818  ND1 HIS A 128     -1.852 -22.986   8.264  1.00 60.13           N
ATOM   1820  CE1 HIS A 128     -3.036 -22.786   8.815  1.00 60.50           C
ATOM   1822  NE2 HIS A 128     -3.048 -21.579   9.354  1.00 60.99           N
ATOM   1824  CD2 HIS A 128     -1.826 -20.985   9.145  1.00 60.28           C
ATOM   1826  C   HIS A 128      1.472 -22.326  10.146  1.00 56.07           C
ATOM   1827  O   HIS A 128      2.369 -21.566  10.506  1.00 56.30           O
ATOM   1829  N   ILE A 129      0.608 -22.881  10.994  1.00 55.81           N
ATOM   1830  CA  ILE A 129      0.647 -22.555  12.428  1.00 55.67           C
ATOM   1832  CB  ILE A 129     -0.656 -22.934  13.180  1.00 55.88           C
ATOM   1834  CG1 ILE A 129     -1.900 -22.732  12.290  1.00 56.67           C
ATOM   1837  CD1 ILE A 129     -3.237 -22.828  13.032  1.00 57.10           C
ATOM   1841  CG2 ILE A 129     -0.749 -22.119  14.478  1.00 55.39           C
ATOM   1845  C   ILE A 129      1.821 -23.238  13.135  1.00 55.29           C
ATOM   1846  O   ILE A 129      2.501 -22.619  13.952  1.00 55.20           O
ATOM   1848  N   TYR A 130      2.046 -24.516  12.830  1.00 55.01           N
ATOM   1849  CA  TYR A 130      3.141 -25.268  13.453  1.00 54.74           C
ATOM   1851  CB  TYR A 130      3.120 -26.749  13.053  1.00 54.46           C
ATOM   1854  CG  TYR A 130      4.114 -27.608  13.822  1.00 53.54           C
ATOM   1855  CD1 TYR A 130      3.840 -28.040  15.119  1.00 52.88           C
ATOM   1857  CE1 TYR A 130      4.748 -28.833  15.828  1.00 51.74           C
ATOM   1859  CZ  TYR A 130      5.941 -29.207  15.235  1.00 50.71           C
ATOM   1860  OH  TYR A 130      6.837 -29.994  15.923  1.00 47.79           O
ATOM   1862  CE2 TYR A 130      6.227 -28.799  13.948  1.00 50.99           C
ATOM   1864  CD2 TYR A 130      5.319 -28.003  13.249  1.00 52.18           C
ATOM   1866  C   TYR A 130      4.471 -24.642  13.078  1.00 54.65           C
ATOM   1867  O   TYR A 130      5.349 -24.505  13.915  1.00 54.47           O
ATOM   1869  N   TYR A 131      4.602 -24.255  11.817  1.00 54.85           N
ATOM   1870  CA  TYR A 131      5.757 -23.507  11.367  1.00 55.14           C
ATOM   1872  CB  TYR A 131      5.542 -23.029   9.932  1.00 54.97           C
ATOM   1875  CG  TYR A 131      6.691 -22.227   9.373  1.00 53.88           C
ATOM   1876  CD1 TYR A 131      7.614 -22.808   8.519  1.00 52.45           C
ATOM   1878  CE1 TYR A 131      8.668 -22.082   8.008  1.00 52.73           C
ATOM   1880  CZ  TYR A 131      8.811 -20.751   8.353  1.00 53.28           C
ATOM   1881  OH  TYR A 131      9.856 -20.015   7.849  1.00 53.98           O
ATOM   1883  CE2 TYR A 131      7.904 -20.147   9.202  1.00 53.18           C
ATOM   1885  CD2 TYR A 131      6.856 -20.883   9.709  1.00 53.29           C
ATOM   1887  C   TYR A 131      6.019 -22.316  12.292  1.00 55.97           C
ATOM   1888  O   TYR A 131      7.136 -22.126  12.772  1.00 55.86           O
ATOM   1890  N   LEU A 132      4.985 -21.520  12.546  1.00 57.07           N
ATOM   1891  CA  LEU A 132      5.140 -20.327  13.369  1.00 58.04           C
ATOM   1893  CB  LEU A 132      3.872 -19.464  13.343  1.00 58.13           C
ATOM   1896  CG  LEU A 132      3.549 -18.730  12.033  1.00 58.50           C
ATOM   1898  CD1 LEU A 132      2.332 -17.827  12.236  1.00 58.65           C
ATOM   1902  CD2 LEU A 132      4.739 -17.923  11.512  1.00 58.44           C
ATOM   1906  C   LEU A 132      5.523 -20.654  14.811  1.00 58.85           C
ATOM   1907  O   LEU A 132      6.281 -19.910  15.430  1.00 59.31           O
ATOM   1909  N   GLU A 133      5.005 -21.756  15.351  1.00 59.71           N
ATOM   1910  CA  GLU A 133      5.376 -22.181  16.705  1.00 60.14           C
```

FIG. 16Q

```
ATOM   1912  CB   GLU A 133       4.385  -23.218  17.251  1.00 60.24           C
ATOM   1915  CG   GLU A 133       2.961  -22.659  17.466  1.00 60.87           C
ATOM   1918  CD   GLU A 133       1.961  -23.690  18.018  1.00 61.61           C
ATOM   1919  OE1  GLU A 133       2.344  -24.858  18.247  1.00 62.42           O
ATOM   1920  OE2  GLU A 133       0.779  -23.331  18.219  1.00 61.07           O
ATOM   1921  C    GLU A 133       6.814  -22.710  16.729  1.00 60.43           C
ATOM   1922  O    GLU A 133       7.506  -22.592  17.742  1.00 60.50           O
ATOM   1924  N    LYS A 134       7.264  -23.272  15.607  1.00 60.82           N
ATOM   1925  CA   LYS A 134       8.660  -23.692  15.472  1.00 61.22           C
ATOM   1927  CB   LYS A 134       8.894  -24.505  14.192  1.00 61.09           C
ATOM   1930  CG   LYS A 134       8.749  -26.001  14.367  1.00 60.85           C
ATOM   1933  CD   LYS A 134       9.906  -26.617  15.147  1.00 59.97           C
ATOM   1936  CE   LYS A 134       9.756  -28.123  15.233  1.00 59.41           C
ATOM   1939  NZ   LYS A 134      10.467  -28.695  16.401  1.00 59.78           N
ATOM   1943  C    LYS A 134       9.575  -22.485  15.465  1.00 61.76           C
ATOM   1944  O    LYS A 134      10.472  -22.388  16.297  1.00 61.78           O
ATOM   1946  N    ALA A 135       9.337  -21.579  14.520  1.00 62.52           N
ATOM   1947  CA   ALA A 135      10.149  -20.370  14.353  1.00 63.28           C
ATOM   1949  CB   ALA A 135       9.513  -19.446  13.327  1.00 63.27           C
ATOM   1953  C    ALA A 135      10.376  -19.617  15.664  1.00 64.11           C
ATOM   1954  O    ALA A 135      11.512  -19.266  15.990  1.00 64.12           O
ATOM   1956  N    ASN A 136       9.303  -19.378  16.413  1.00 65.15           N
ATOM   1957  CA   ASN A 136       9.408  -18.693  17.708  1.00 66.21           C
ATOM   1959  CB   ASN A 136       8.048  -18.649  18.414  1.00 66.23           C
ATOM   1962  CG   ASN A 136       7.113  -17.611  17.820  1.00 66.63           C
ATOM   1963  OD1  ASN A 136       7.328  -17.108  16.711  1.00 66.81           O
ATOM   1964  ND2  ASN A 136       6.059  -17.285  18.561  1.00 67.06           N
ATOM   1967  C    ASN A 136      10.453  -19.304  18.650  1.00 66.97           C
ATOM   1968  O    ASN A 136      11.259  -18.583  19.232  1.00 67.21           O
ATOM   1970  N    LYS A 137      10.430  -20.627  18.791  1.00 67.87           N
ATOM   1971  CA   LYS A 137      11.375  -21.335  19.656  1.00 68.71           C
ATOM   1973  CB   LYS A 137      10.977  -22.815  19.765  1.00 68.85           C
ATOM   1976  CG   LYS A 137      12.044  -23.707  20.395  1.00 69.45           C
ATOM   1979  CD   LYS A 137      11.492  -25.045  20.875  1.00 70.12           C
ATOM   1982  CE   LYS A 137      12.631  -25.968  21.308  1.00 70.41           C
ATOM   1985  NZ   LYS A 137      12.148  -27.131  22.094  1.00 70.63           N
ATOM   1989  C    LYS A 137      12.841  -21.220  19.203  1.00 69.26           C
ATOM   1990  O    LYS A 137      13.752  -21.252  20.032  1.00 69.34           O
ATOM   1992  N    ILE A 138      13.059  -21.077  17.897  1.00 70.01           N
ATOM   1993  CA   ILE A 138      14.401  -21.134  17.302  1.00 70.47           C
ATOM   1995  CB   ILE A 138      14.391  -22.020  16.031  1.00 70.45           C
ATOM   1997  CG1  ILE A 138      13.905  -23.429  16.357  1.00 70.76           C
ATOM   2000  CD1  ILE A 138      13.693  -24.266  15.127  1.00 71.11           C
ATOM   2004  CG2  ILE A 138      15.764  -22.103  15.413  1.00 70.41           C
ATOM   2008  C    ILE A 138      14.930  -19.756  16.900  1.00 70.95           C
ATOM   2009  O    ILE A 138      14.448  -19.153  15.933  1.00 71.13           O
ATOM   2011  N    LYS A 139      15.925  -19.262  17.633  1.00 71.34           N
ATOM   2012  CA   LYS A 139      16.692  -18.093  17.195  1.00 71.67           C
ATOM   2014  CB   LYS A 139      16.520  -16.908  18.153  1.00 71.72           C
ATOM   2017  CG   LYS A 139      15.622  -15.804  17.599  1.00 71.82           C
ATOM   2020  CD   LYS A 139      15.766  -14.502  18.380  1.00 71.87           C
ATOM   2023  CE   LYS A 139      15.252  -13.315  17.575  1.00 71.74           C
ATOM   2026  NZ   LYS A 139      15.132  -12.089  18.406  1.00 71.74           N
ATOM   2030  C    LYS A 139      18.171  -18.446  17.030  1.00 71.93           C
ATOM   2031  O    LYS A 139      18.667  -18.556  15.903  1.00 72.13           O
ATOM   2033  N    GLU A 141      17.092  -18.759  14.096  1.00 56.22           N
ATOM   2034  CA   GLU A 141      16.583  -17.809  13.106  1.00 56.40           C
ATOM   2036  CB   GLU A 141      16.762  -16.357  13.579  1.00 56.67           C
ATOM   2039  CG   GLU A 141      16.675  -15.319  12.435  1.00 58.19           C
ATOM   2042  CD   GLU A 141      16.506  -13.876  12.902  1.00 59.66           C
ATOM   2043  OE1  GLU A 141      16.120  -13.641  14.073  1.00 60.52           O
ATOM   2044  OE2  GLU A 141      16.764  -12.974  12.070  1.00 60.27           O
ATOM   2045  C    GLU A 141      17.268  -17.997  11.761  1.00 55.75           C
```

FIG. 16R

```
ATOM   2046  O    GLU A 141      16.683 -17.703  10.718  1.00 55.89           O
ATOM   2048  N    LYS A 142      18.515 -18.459  11.798  1.00 54.98           N
ATOM   2049  CA   LYS A 142      19.285 -18.717  10.585  1.00 54.31           C
ATOM   2051  CB   LYS A 142      20.736 -18.286  10.791  1.00 54.42           C
ATOM   2054  CG   LYS A 142      20.869 -16.843  11.297  1.00 54.96           C
ATOM   2057  CD   LYS A 142      22.329 -16.434  11.466  1.00 55.72           C
ATOM   2060  CE   LYS A 142      22.990 -16.006  10.154  1.00 55.44           C
ATOM   2063  NZ   LYS A 142      24.472 -16.091  10.270  1.00 54.93           N
ATOM   2067  C    LYS A 142      19.194 -20.192  10.195  1.00 53.35           C
ATOM   2068  O    LYS A 142      19.723 -20.604   9.158  1.00 52.94           O
ATOM   2070  N    THR A 143      18.510 -20.972  11.033  1.00 52.37           N
ATOM   2071  CA   THR A 143      18.187 -22.366  10.738  1.00 51.54           C
ATOM   2073  CB   THR A 143      17.780 -23.128  12.012  1.00 51.60           C
ATOM   2075  OG1  THR A 143      18.867 -23.128  12.945  1.00 52.12           O
ATOM   2077  CG2  THR A 143      17.403 -24.560  11.684  1.00 51.66           C
ATOM   2081  C    THR A 143      17.009 -22.437   9.781  1.00 50.61           C
ATOM   2082  O    THR A 143      15.972 -21.839  10.030  1.00 50.42           O
ATOM   2084  N    HIS A 144      17.168 -23.185   8.700  1.00 49.59           N
ATOM   2085  CA   HIS A 144      16.083 -23.397   7.751  1.00 49.04           C
ATOM   2087  CB   HIS A 144      16.656 -23.927   6.434  1.00 49.09           C
ATOM   2090  CG   HIS A 144      15.766 -23.705   5.253  1.00 49.77           C
ATOM   2091  ND1  HIS A 144      15.778 -22.535   4.525  1.00 49.98           N
ATOM   2093  CE1  HIS A 144      14.906 -22.629   3.538  1.00 50.58           C
ATOM   2095  NE2  HIS A 144      14.328 -23.817   3.601  1.00 50.51           N
ATOM   2097  CD2  HIS A 144      14.852 -24.511   4.663  1.00 50.38           C
ATOM   2099  C    HIS A 144      15.049 -24.384   8.334  1.00 48.04           C
ATOM   2100  O    HIS A 144      15.405 -25.444   8.815  1.00 47.85           O
ATOM   2102  N    ILE A 145      13.776 -24.014   8.293  1.00 47.07           N
ATOM   2103  CA   ILE A 145      12.697 -24.836   8.836  1.00 46.29           C
ATOM   2105  CB   ILE A 145      11.751 -23.994   9.720  1.00 46.08           C
ATOM   2107  CG1  ILE A 145      12.510 -23.454  10.938  1.00 45.79           C
ATOM   2110  CD1  ILE A 145      11.753 -22.421  11.752  1.00 45.49           C
ATOM   2114  CG2  ILE A 145      10.546 -24.812  10.159  1.00 45.29           C
ATOM   2118  C    ILE A 145      11.896 -25.478   7.708  1.00 45.92           C
ATOM   2119  O    ILE A 145      11.712 -24.880   6.660  1.00 45.65           O
ATOM   2121  N    HIS A 146      11.429 -26.701   7.934  1.00 45.79           N
ATOM   2122  CA   HIS A 146      10.636 -27.439   6.946  1.00 45.53           C
ATOM   2124  CB   HIS A 146      11.562 -28.322   6.107  1.00 45.36           C
ATOM   2127  CG   HIS A 146      10.961 -28.786   4.819  1.00 44.92           C
ATOM   2128  ND1  HIS A 146      11.679 -28.837   3.644  1.00 44.45           N
ATOM   2130  CE1  HIS A 146      10.904 -29.296   2.678  1.00 44.56           C
ATOM   2132  NE2  HIS A 146       9.707 -29.535   3.181  1.00 44.13           N
ATOM   2134  CD2  HIS A 146       9.715 -29.224   4.519  1.00 44.35           C
ATOM   2136  C    HIS A 146       9.575 -28.296   7.653  1.00 45.49           C
ATOM   2137  O    HIS A 146       9.905 -29.269   8.325  1.00 45.24           O
ATOM   2139  N    ILE A 147       8.307 -27.916   7.521  1.00 45.44           N
ATOM   2140  CA   ILE A 147       7.223 -28.662   8.149  1.00 45.52           C
ATOM   2142  CB   ILE A 147       6.155 -27.735   8.758  1.00 45.50           C
ATOM   2144  CG1  ILE A 147       6.813 -26.626   9.580  1.00 46.11           C
ATOM   2147  CD1  ILE A 147       7.783 -27.133  10.634  1.00 45.97           C
ATOM   2151  CG2  ILE A 147       5.213 -28.515   9.646  1.00 44.84           C
ATOM   2155  C    ILE A 147       6.566 -29.590   7.130  1.00 45.87           C
ATOM   2156  O    ILE A 147       6.449 -29.259   5.949  1.00 45.65           O
ATOM   2158  N    PHE A 148       6.195 -30.778   7.592  1.00 46.20           N
ATOM   2159  CA   PHE A 148       5.323 -31.671   6.848  1.00 46.38           C
ATOM   2161  CB   PHE A 148       5.989 -33.014   6.596  1.00 46.34           C
ATOM   2164  CG   PHE A 148       7.155 -32.939   5.686  1.00 46.66           C
ATOM   2165  CD1  PHE A 148       7.001 -33.146   4.328  1.00 47.50           C
ATOM   2167  CE1  PHE A 148       8.095 -33.074   3.469  1.00 47.74           C
ATOM   2169  CZ   PHE A 148       9.354 -32.795   3.977  1.00 47.54           C
ATOM   2171  CE2  PHE A 148       9.514 -32.589   5.335  1.00 47.37           C
ATOM   2173  CD2  PHE A 148       8.416 -32.660   6.181  1.00 47.27           C
ATOM   2175  C    PHE A 148       4.106 -31.890   7.705  1.00 46.56           C
```

FIG. 16S

```
ATOM   2176  O    PHE A 148       4.142  -31.666   8.910  1.00 46.65           O
ATOM   2178  N    SER A 149       3.022  -32.324   7.084  1.00 46.95           N
ATOM   2179  CA   SER A 149       1.815  -32.649   7.827  1.00 47.08           C
ATOM   2181  CB   SER A 149       0.825  -31.489   7.772  1.00 47.20           C
ATOM   2184  OG   SER A 149       0.524  -31.175   6.421  1.00 48.80           O
ATOM   2186  C    SER A 149       1.195  -33.903   7.254  1.00 46.81           C
ATOM   2187  O    SER A 149       1.487  -34.285   6.119  1.00 46.80           O
ATOM   2189  N    PHE A 150       0.348  -34.545   8.050  1.00 46.57           N
ATOM   2190  CA   PHE A 150      -0.388  -35.712   7.587  1.00 46.60           C
ATOM   2192  CB   PHE A 150      -0.882  -36.538   8.775  1.00 46.47           C
ATOM   2195  CG   PHE A 150       0.192  -37.368   9.436  1.00 45.05           C
ATOM   2196  CD1  PHE A 150       0.402  -38.682   9.054  1.00 43.86           C
ATOM   2198  CE1  PHE A 150       1.378  -39.454   9.672  1.00 43.74           C
ATOM   2200  CZ   PHE A 150       2.153  -38.908  10.686  1.00 43.47           C
ATOM   2202  CE2  PHE A 150       1.952  -37.602  11.081  1.00 43.34           C
ATOM   2204  CD2  PHE A 150       0.975  -36.838  10.459  1.00 44.17           C
ATOM   2206  C    PHE A 150      -1.559  -35.319   6.666  1.00 46.94           C
ATOM   2207  O    PHE A 150      -2.227  -36.187   6.101  1.00 46.82           O
ATOM   2209  N    THR A 151      -1.800  -34.017   6.513  1.00 47.15           N
ATOM   2210  CA   THR A 151      -2.744  -33.520   5.515  1.00 47.38           C
ATOM   2212  CB   THR A 151      -3.248  -32.091   5.868  1.00 47.52           C
ATOM   2214  OG1  THR A 151      -2.190  -31.136   5.694  1.00 48.54           O
ATOM   2216  CG2  THR A 151      -3.769  -32.022   7.314  1.00 47.41           C
ATOM   2220  C    THR A 151      -2.133  -33.505   4.108  1.00 47.33           C
ATOM   2221  O    THR A 151      -2.806  -33.147   3.143  1.00 47.31           O
ATOM   2223  N    GLY A 152      -0.855  -33.870   4.002  1.00 47.40           N
ATOM   2224  CA   GLY A 152      -0.158  -33.967   2.717  1.00 47.31           C
ATOM   2227  C    GLY A 152       0.576  -32.690   2.351  1.00 47.49           C
ATOM   2228  O    GLY A 152       1.300  -32.636   1.342  1.00 47.67           O
ATOM   2230  N    GLU A 153       0.392  -31.659   3.171  1.00 47.43           N
ATOM   2231  CA   GLU A 153       0.999  -30.359   2.924  1.00 47.61           C
ATOM   2233  CB   GLU A 153       0.218  -29.279   3.682  1.00 47.73           C
ATOM   2236  CG   GLU A 153      -1.084  -28.906   3.025  1.00 48.08           C
ATOM   2239  CD   GLU A 153      -2.110  -28.339   3.987  1.00 48.76           C
ATOM   2240  OE1  GLU A 153      -1.735  -27.840   5.079  1.00 47.98           O
ATOM   2241  OE2  GLU A 153      -3.307  -28.402   3.625  1.00 49.67           O
ATOM   2242  C    GLU A 153       2.476  -30.295   3.335  1.00 47.64           C
ATOM   2243  O    GLU A 153       3.029  -31.243   3.910  1.00 47.48           O
ATOM   2245  N    GLU A 154       3.097  -29.158   3.022  1.00 47.60           N
ATOM   2246  CA   GLU A 154       4.407  -28.822   3.534  1.00 47.64           C
ATOM   2248  CB   GLU A 154       5.488  -29.464   2.684  1.00 47.55           C
ATOM   2251  CG   GLU A 154       5.330  -29.254   1.195  1.00 47.62           C
ATOM   2254  CD   GLU A 154       6.524  -29.753   0.415  1.00 46.94           C
ATOM   2255  OE1  GLU A 154       7.470  -30.256   1.049  1.00 46.23           O
ATOM   2256  OE2  GLU A 154       6.523  -29.634  -0.829  1.00 47.81           O
ATOM   2257  C    GLU A 154       4.600  -27.314   3.607  1.00 47.99           C
ATOM   2258  O    GLU A 154       3.764  -26.559   3.135  1.00 48.24           O
ATOM   2260  N    MET A 155       5.692  -26.888   4.235  1.00 48.34           N
ATOM   2261  CA   MET A 155       6.029  -25.477   4.356  1.00 48.49           C
ATOM   2263  CB   MET A 155       5.088  -24.775   5.336  1.00 48.57           C
ATOM   2266  CG   MET A 155       5.554  -23.365   5.694  1.00 49.76           C
ATOM   2269  SD   MET A 155       4.258  -22.235   6.206  1.00 51.85           S
ATOM   2270  CE   MET A 155       3.416  -21.995   4.633  1.00 51.21           C
ATOM   2274  C    MET A 155       7.477  -25.310   4.819  1.00 48.63           C
ATOM   2275  O    MET A 155       7.881  -25.926   5.803  1.00 48.67           O
ATOM   2277  N    ALA A 156       8.229  -24.454   4.115  1.00 48.88           N
ATOM   2278  CA   ALA A 156       9.649  -24.181   4.388  1.00 48.84           C
ATOM   2280  CB   ALA A 156      10.505  -24.910   3.391  1.00 48.79           C
ATOM   2284  C    ALA A 156       9.963  -22.680   4.342  1.00 49.16           C
ATOM   2285  O    ALA A 156       9.288  -21.925   3.639  1.00 49.18           O
ATOM   2287  N    THR A 157      10.988  -22.242   5.080  1.00 49.43           N
ATOM   2288  CA   THR A 157      11.311  -20.812   5.148  1.00 49.65           C
ATOM   2290  CB   THR A 157      12.572  -20.500   5.986  1.00 49.80           C
```

FIG. 16T

```
ATOM   2292  OG1 THR A 157      13.675 -21.279   5.505  1.00 51.08           O
ATOM   2294  CG2 THR A 157      12.354 -20.799   7.452  1.00 50.12           C
ATOM   2298  C   THR A 157      11.554 -20.280   3.752  1.00 49.49           C
ATOM   2299  O   THR A 157      12.238 -20.925   2.956  1.00 49.49           O
ATOM   2301  N   LYS A 158      10.980 -19.108   3.465  1.00 49.50           N
ATOM   2302  CA  LYS A 158      11.108 -18.449   2.163  1.00 49.29           C
ATOM   2304  CB  LYS A 158      12.537 -17.920   1.977  1.00 49.40           C
ATOM   2307  CG  LYS A 158      12.979 -16.904   3.032  1.00 50.03           C
ATOM   2310  CD  LYS A 158      14.455 -16.535   2.362  1.00 51.02           C
ATOM   2313  CE  LYS A 158      15.089 -16.043   4.165  1.00 52.04           C
ATOM   2316  NZ  LYS A 158      16.567 -16.317   4.217  1.00 52.29           N
ATOM   2320  C   LYS A 158      10.724 -19.373   0.998  1.00 48.93           C
ATOM   2321  O   LYS A 158      11.213 -19.203  -0.120  1.00 49.33           O
ATOM   2323  N   ALA A 159       9.852 -20.345   1.269  1.00 48.23           N
ATOM   2324  CA  ALA A 159       9.461 -21.358   0.295  1.00 47.78           C
ATOM   2326  CB  ALA A 159       8.446 -20.785  -0.684  1.00 47.65           C
ATOM   2330  C   ALA A 159      10.630 -21.984  -0.466  1.00 47.54           C
ATOM   2331  O   ALA A 159      10.533 -22.191  -1.673  1.00 48.06           O
ATOM   2333  N   ASP A 160      11.729 -22.273   0.227  1.00 46.99           N
ATOM   2334  CA  ASP A 160      12.820 -23.067  -0.349  1.00 46.60           C
ATOM   2336  CB  ASP A 160      14.176 -22.426  -0.042  1.00 46.49           C
ATOM   2339  CG  ASP A 160      15.346 -23.127  -0.743  1.00 46.39           C
ATOM   2340  OD1 ASP A 160      15.222 -24.300  -1.170  1.00 45.22           O
ATOM   2341  OD2 ASP A 160      16.413 -22.488  -0.851  1.00 46.18           O
ATOM   2342  C   ASP A 160      12.723 -24.463   0.271  1.00 46.37           C
ATOM   2343  O   ASP A 160      12.914 -24.619   1.482  1.00 46.41           O
ATOM   2345  N   TYR A 161      12.399 -25.466  -0.548  1.00 45.83           N
ATOM   2346  CA  TYR A 161      12.113 -26.810  -0.040  1.00 45.28           C
ATOM   2348  CB  TYR A 161      10.901 -27.411  -0.755  1.00 45.45           C
ATOM   2351  CG  TYR A 161       9.655 -26.583  -0.557  1.00 46.81           C
ATOM   2352  CD1 TYR A 161       9.106 -26.420   0.711  1.00 48.02           C
ATOM   2354  CE1 TYR A 161       7.976 -25.645   0.912  1.00 48.30           C
ATOM   2356  CZ  TYR A 161       7.369 -25.027  -0.158  1.00 48.63           C
ATOM   2357  OH  TYR A 161       6.243 -24.266   0.050  1.00 48.24           O
ATOM   2359  CE2 TYR A 161       7.891 -25.174  -1.433  1.00 48.64           C
ATOM   2361  CD2 TYR A 161       9.035 -25.946  -1.625  1.00 48.02           C
ATOM   2363  C   TYR A 161      13.322 -27.725  -0.149  1.00 44.58           C
ATOM   2364  O   TYR A 161      13.221 -28.929   0.114  1.00 44.46           O
ATOM   2366  N   THR A 162      14.469 -27.158  -0.525  1.00 43.50           N
ATOM   2367  CA  THR A 162      15.734 -27.875  -0.479  1.00 42.55           C
ATOM   2369  CB  THR A 162      16.044 -28.359   0.958  1.00 42.54           C
ATOM   2371  OG1 THR A 162      16.154 -27.227   1.825  1.00 41.69           O
ATOM   2373  CG2 THR A 162      17.322 -29.204   1.002  1.00 41.51           C
ATOM   2377  C   THR A 162      15.712 -29.071  -1.400  1.00 42.09           C
ATOM   2378  O   THR A 162      16.518 -29.172  -2.327  1.00 42.35           O
ATOM   2380  N   LEU A 163      14.797 -29.993  -1.132  1.00 41.33           N
ATOM   2381  CA  LEU A 163      14.695 -31.226  -1.881  1.00 40.86           C
ATOM   2383  CB  LEU A 163      13.922 -32.265  -1.073  1.00 40.74           C
ATOM   2386  CG  LEU A 163      14.601 -32.768   0.202  1.00 40.22           C
ATOM   2388  CD1 LEU A 163      13.633 -33.659   0.988  1.00 39.56           C
ATOM   2392  CD2 LEU A 163      15.895 -33.504  -0.127  1.00 38.43           C
ATOM   2396  C   LEU A 163      13.994 -30.990  -3.207  1.00 40.47           C
ATOM   2397  O   LEU A 163      13.321 -29.968  -3.401  1.00 40.41           O
ATOM   2399  N   ASP A 164      14.158 -31.941  -4.120  1.00 39.93           N
ATOM   2400  CA  ASP A 164      13.407 -31.922  -5.363  1.00 39.57           C
ATOM   2402  CB  ASP A 164      14.114 -32.769  -6.435  1.00 39.32           C
ATOM   2405  CG  ASP A 164      14.104 -34.257  -6.130  1.00 39.41           C
ATOM   2406  OD1 ASP A 164      13.323 -34.691  -5.272  1.00 40.02           O
ATOM   2407  OD2 ASP A 164      14.869 -35.010  -6.768  1.00 39.21           O
ATOM   2408  C   ASP A 164      11.960 -32.375  -5.065  1.00 39.44           C
ATOM   2409  O   ASP A 164      11.632 -32.706  -3.925  1.00 39.11           O
ATOM   2411  N   GLU A 165      11.089 -32.358  -6.073  1.00 39.55           N
ATOM   2412  CA  GLU A 165       9.694 -32.802  -5.888  1.00 39.27           C
```

FIG. 16U

```
ATOM   2414  CB   GLU A 165       8.822 -32.354  -7.069  1.00 39.27           C
ATOM   2417  CG   GLU A 165       7.307 -32.480  -6.836  1.00 39.15           C
ATOM   2420  CD   GLU A 165       6.769 -33.907  -7.054  1.00 39.46           C
ATOM   2421  OE1  GLU A 165       7.393 -34.708  -7.794  1.00 36.27           O
ATOM   2422  OE2  GLU A 165       5.707 -34.226  -6.477  1.00 38.42           O
ATOM   2423  C    GLU A 165       9.630 -34.320  -5.707  1.00 39.07           C
ATOM   2424  O    GLU A 165       8.838 -34.818  -4.923  1.00 38.30           O
ATOM   2426  N    GLU A 166      10.486 -35.040  -6.431  1.00 39.48           N
ATOM   2427  CA   GLU A 166      10.538 -36.504  -6.359  1.00 39.85           C
ATOM   2429  CB   GLU A 166      11.716 -37.053  -7.184  1.00 40.16           C
ATOM   2432  CG   GLU A 166      11.431 -38.312  -8.024  1.00 41.37           C
ATOM   2435  CD   GLU A 166      10.428 -39.254  -7.402  1.00 43.24           C
ATOM   2436  OE1  GLU A 166      10.741 -39.852  -6.356  1.00 45.39           O
ATOM   2437  OE2  GLU A 166       9.322 -39.405  -7.967  1.00 45.28           O
ATOM   2438  C    GLU A 166      10.685 -36.964  -4.910  1.00 39.58           C
ATOM   2439  O    GLU A 166       9.953 -37.839  -4.456  1.00 40.05           O
ATOM   2441  N    SER A 167      11.628 -36.351  -4.193  1.00 39.07           N
ATOM   2442  CA   SER A 167      12.011 -36.761  -2.847  1.00 38.68           C
ATOM   2444  CB   SER A 167      13.306 -36.041  -2.440  1.00 38.68           C
ATOM   2447  OG   SER A 167      14.400 -36.472  -3.242  1.00 38.61           O
ATOM   2449  C    SER A 167      10.922 -36.466  -1.824  1.00 38.49           C
ATOM   2450  O    SER A 167      10.638 -37.276  -0.951  1.00 38.05           O
ATOM   2452  N    ARG A 168      10.328 -35.286  -1.941  1.00 38.56           N
ATOM   2453  CA   ARG A 168       9.246 -34.868  -1.074  1.00 38.63           C
ATOM   2455  CB   ARG A 168       8.887 -33.428  -1.377  1.00 39.02           C
ATOM   2458  CG   ARG A 168       9.941 -32.454  -0.910  1.00 41.33           C
ATOM   2461  CD   ARG A 168       9.551 -31.031  -1.250  1.00 44.07           C
ATOM   2464  NE   ARG A 168      10.124 -30.579  -2.517  1.00 46.13           N
ATOM   2466  CZ   ARG A 168       9.627 -29.587  -3.254  1.00 48.23           C
ATOM   2467  NH1  ARG A 168       8.520 -28.935  -2.875  1.00 47.89           N
ATOM   2470  NH2  ARG A 168      10.238 -29.249  -4.387  1.00 49.04           N
ATOM   2473  C    ARG A 168       7.992 -35.732  -1.196  1.00 38.13           C
ATOM   2474  O    ARG A 168       7.341 -36.032  -0.195  1.00 38.30           O
ATOM   2476  N    ALA A 169       7.649 -36.130  -2.413  1.00 37.40           N
ATOM   2477  CA   ALA A 169       6.492 -36.984  -2.605  1.00 36.97           C
ATOM   2479  CB   ALA A 169       6.211 -37.180  -4.082  1.00 36.88           C
ATOM   2483  C    ALA A 169       6.688 -38.328  -1.909  1.00 36.77           C
ATOM   2484  O    ALA A 169       5.715 -38.956  -1.498  1.00 36.91           O
ATOM   2486  N    ARG A 170       7.938 -38.771  -1.778  1.00 36.50           N
ATOM   2487  CA   ARG A 170       8.230 -40.028  -1.086  1.00 36.39           C
ATOM   2489  CB   ARG A 170       9.653 -40.512  -1.369  1.00 36.90           C
ATOM   2492  CG   ARG A 170       9.822 -41.048  -2.772  1.00 39.59           C
ATOM   2495  CD   ARG A 170      11.186 -41.654  -3.012  1.00 43.56           C
ATOM   2498  NE   ARG A 170      11.427 -41.820  -4.450  1.00 47.71           N
ATOM   2500  CZ   ARG A 170      12.598 -42.155  -5.000  1.00 50.88           C
ATOM   2501  NH1  ARG A 170      13.675 -42.371  -4.236  1.00 52.20           N
ATOM   2504  NH2  ARG A 170      12.698 -42.269  -6.328  1.00 51.43           N
ATOM   2507  C    ARG A 170       8.016 -39.879   0.401  1.00 35.26           C
ATOM   2508  O    ARG A 170       7.486 -40.784   1.040  1.00 35.00           O
ATOM   2510  N    ILE A 171       8.432 -38.737   0.944  1.00 34.26           N
ATOM   2511  CA   ILE A 171       8.190 -38.421   2.354  1.00 33.56           C
ATOM   2513  CB   ILE A 171       8.914 -37.113   2.806  1.00 33.43           C
ATOM   2515  CG1  ILE A 171      10.422 -37.362   2.944  1.00 33.13           C
ATOM   2518  CD1  ILE A 171      11.238 -36.091   3.066  1.00 32.34           C
ATOM   2522  CG2  ILE A 171       8.347 -36.595   4.142  1.00 32.80           C
ATOM   2526  C    ILE A 171       6.687 -38.312   2.602  1.00 33.02           C
ATOM   2527  O    ILE A 171       6.183 -38.805   3.613  1.00 32.73           O
ATOM   2529  N    LYS A 172       5.982 -37.676   1.671  1.00 32.37           N
ATOM   2530  CA   LYS A 172       4.546 -37.475   1.806  1.00 32.17           C
ATOM   2532  CB   LYS A 172       4.036 -36.486   0.774  1.00 32.34           C
ATOM   2535  CG   LYS A 172       4.276 -35.045   1.144  1.00 33.47           C
ATOM   2538  CD   LYS A 172       4.162 -34.168  -0.082  1.00 35.92           C
ATOM   2541  CE   LYS A 172       4.518 -32.727   0.228  1.00 38.04           C
```

FIG. 16V

```
ATOM   2544  NZ   LYS A 172       4.926 -31.994  -1.022  1.00 39.72           N
ATOM   2548  C    LYS A 172       3.776 -38.776   1.683  1.00 31.57           C
ATOM   2549  O    LYS A 172       2.800 -38.985   2.407  1.00 31.40           O
ATOM   2551  N    THR A 173       4.204 -39.650   0.775  1.00 31.01           N
ATOM   2552  CA   THR A 173       3.568 -40.956   0.646  1.00 30.66           C
ATOM   2554  CB   THR A 173       4.229 -41.808  -0.408  1.00 30.42           C
ATOM   2556  OG1  THR A 173       4.246 -41.075  -1.630  1.00 31.59           O
ATOM   2558  CG2  THR A 173       3.478 -43.112  -0.604  1.00 28.72           C
ATOM   2562  C    THR A 173       3.655 -41.691   1.956  1.00 30.79           C
ATOM   2563  O    THR A 173       2.643 -42.172   2.465  1.00 31.04           O
ATOM   2565  N    ARG A 174       4.868 -41.747   2.504  1.00 30.80           N
ATOM   2566  CA   ARG A 174       5.139 -42.462   3.750  1.00 30.82           C
ATOM   2568  CB   ARG A 174       6.624 -42.342   4.121  1.00 30.93           C
ATOM   2571  CG   ARG A 174       7.042 -43.028   5.408  1.00 30.30           C
ATOM   2574  CD   ARG A 174       6.820 -44.537   5.399  1.00 30.20           C
ATOM   2577  NE   ARG A 174       7.206 -45.090   6.700  1.00 30.59           N
ATOM   2579  CZ   ARG A 174       6.703 -46.192   7.256  1.00 30.17           C
ATOM   2580  NH1  ARG A 174       5.775 -46.917   6.637  1.00 30.61           N
ATOM   2583  NH2  ARG A 174       7.132 -46.571   8.454  1.00 29.36           N
ATOM   2586  C    ARG A 174       4.268 -41.956   4.886  1.00 30.81           C
ATOM   2587  O    ARG A 174       3.783 -42.739   5.670  1.00 30.61           O
ATOM   2589  N    LEU A 175       4.075 -40.647   4.977  1.00 31.27           N
ATOM   2590  CA   LEU A 175       3.181 -40.092   5.991  1.00 31.49           C
ATOM   2592  CB   LEU A 175       3.164 -38.566   5.943  1.00 31.29           C
ATOM   2595  CG   LEU A 175       4.406 -37.866   6.486  1.00 32.29           C
ATOM   2597  CD1  LEU A 175       4.250 -36.336   6.439  1.00 33.56           C
ATOM   2601  CD2  LEU A 175       4.686 -38.311   7.914  1.00 33.38           C
ATOM   2605  C    LEU A 175       1.774 -40.631   5.795  1.00 31.82           C
ATOM   2606  O    LEU A 175       1.184 -41.170   6.734  1.00 32.27           O
ATOM   2608  N    PHE A 176       1.241 -40.499   4.578  1.00 32.00           N
ATOM   2609  CA   PHE A 176      -0.103 -40.994   4.274  1.00 32.00           C
ATOM   2611  CB   PHE A 176      -0.541 -40.649   2.846  1.00 32.08           C
ATOM   2614  CG   PHE A 176      -1.094 -39.252   2.691  1.00 31.82           C
ATOM   2615  CD1  PHE A 176      -0.532 -38.359   1.786  1.00 32.96           C
ATOM   2617  CE1  PHE A 176      -1.048 -37.070   1.643  1.00 32.60           C
ATOM   2619  CZ   PHE A 176      -2.128 -36.674   2.415  1.00 31.47           C
ATOM   2621  CE2  PHE A 176      -2.691 -37.562   3.306  1.00 30.41           C
ATOM   2623  CD2  PHE A 176      -2.176 -38.834   3.440  1.00 30.66           C
ATOM   2625  C    PHE A 176      -0.187 -42.499   4.486  1.00 32.30           C
ATOM   2626  O    PHE A 176      -1.203 -42.995   4.982  1.00 32.74           O
ATOM   2628  N    THR A 177       0.871 -43.229   4.133  1.00 32.09           N
ATOM   2629  CA   THR A 177       0.898 -44.660   4.405  1.00 32.03           C
ATOM   2631  CB   THR A 177       2.165 -45.330   3.867  1.00 32.06           C
ATOM   2633  OG1  THR A 177       2.290 -45.084   2.455  1.00 30.50           O
ATOM   2635  CG2  THR A 177       2.123 -46.826   4.138  1.00 30.92           C
ATOM   2639  C    THR A 177       0.770 -44.943   5.911  1.00 32.84           C
ATOM   2640  O    THR A 177       0.081 -45.881   6.304  1.00 33.30           O
ATOM   2642  N    ILE A 178       1.414 -44.133   6.752  1.00 33.26           N
ATOM   2643  CA   ILE A 178       1.328 -44.321   8.196  1.00 33.71           C
ATOM   2645  CB   ILE A 178       2.301 -43.404   8.977  1.00 33.68           C
ATOM   2647  CG1  ILE A 178       3.758 -43.806   8.729  1.00 33.87           C
ATOM   2650  CD1  ILE A 178       4.770 -42.747   9.141  1.00 31.58           C
ATOM   2654  CG2  ILE A 178       2.017 -43.475  10.472  1.00 33.34           C
ATOM   2658  C    ILE A 178      -0.088 -44.000   8.648  1.00 34.49           C
ATOM   2659  O    ILE A 178      -0.646 -44.678   9.510  1.00 34.24           O
ATOM   2661  N    ARG A 179      -0.645 -42.951   8.049  1.00 35.35           N
ATOM   2662  CA   ARG A 179      -1.970 -42.468   8.380  1.00 35.92           C
ATOM   2664  CB   ARG A 179      -2.264 -41.190   7.608  1.00 35.74           C
ATOM   2667  CG   ARG A 179      -3.700 -40.757   7.715  1.00 35.42           C
ATOM   2670  CD   ARG A 179      -3.938 -39.436   7.075  1.00 34.74           C
ATOM   2673  NE   ARG A 179      -5.224 -38.921   7.504  1.00 35.39           N
ATOM   2675  CZ   ARG A 179      -5.571 -37.641   7.498  1.00 36.51           C
ATOM   2676  NH1  ARG A 179      -4.725 -36.708   7.076  1.00 37.51           N
```

FIG. 16W

```
ATOM   2679  NH2 ARG A 179      -6.775 -37.293   7.925  1.00 36.68           N
ATOM   2682  C   ARG A 179      -3.070 -43.480   8.093  1.00 36.92           C
ATOM   2683  O   ARG A 179      -3.978 -43.642   8.906  1.00 37.30           O
ATOM   2685  N   GLN A 180      -3.020 -44.135   6.935  1.00 38.06           N
ATOM   2686  CA  GLN A 180      -4.070 -45.107   6.586  1.00 38.99           C
ATOM   2688  CB  GLN A 180      -4.068 -45.449   5.087  1.00 39.16           C
ATOM   2691  CG  GLN A 180      -3.512 -46.837   4.735  1.00 40.72           C
ATOM   2694  CD  GLN A 180      -3.364 -47.050   3.241  1.00 42.02           C
ATOM   2695  OE1 GLN A 180      -4.150 -46.524   2.449  1.00 42.40           O
ATOM   2696  NE2 GLN A 180      -2.345 -47.823   2.846  1.00 42.09           N
ATOM   2699  C   GLN A 180      -3.904 -46.361   7.446  1.00 39.24           C
ATOM   2700  O   GLN A 180      -4.879 -46.978   7.864  1.00 39.17           O
ATOM   2702  N   GLU A 181      -2.656 -46.718   7.721  1.00 39.78           N
ATOM   2703  CA  GLU A 181      -2.358 -47.867   8.577  1.00 40.30           C
ATOM   2705  CB  GLU A 181      -0.867 -48.178   8.522  1.00 40.73           C
ATOM   2708  CG  GLU A 181      -0.387 -48.673   7.157  1.00 42.79           C
ATOM   2711  CD  GLU A 181      -0.770 -50.112   6.871  1.00 46.05           C
ATOM   2712  OE1 GLU A 181      -1.321 -50.781   7.775  1.00 49.04           O
ATOM   2713  OE2 GLU A 181      -0.518 -50.574   5.732  1.00 48.35           O
ATOM   2714  C   GLU A 181      -2.811 -47.632  10.027  1.00 39.89           C
ATOM   2715  O   GLU A 181      -3.125 -48.577  10.754  1.00 39.81           O
ATOM   2717  N   MET A 182      -2.840 -46.368  10.438  1.00 39.35           N
ATOM   2718  CA  MET A 182      -3.399 -46.011  11.722  1.00 38.92           C
ATOM   2720  CB  MET A 182      -2.992 -44.589  12.136  1.00 38.53           C
ATOM   2723  CG  MET A 182      -1.592 -44.498  12.787  1.00 37.73           C
ATOM   2726  SD  MET A 182      -1.129 -42.822  13.310  1.00 34.01           S
ATOM   2727  CE  MET A 182       0.574 -43.048  13.786  1.00 34.19           C
ATOM   2731  C   MET A 182      -4.917 -46.148  11.615  1.00 39.25           C
ATOM   2732  O   MET A 182      -5.519 -47.010  12.272  1.00 39.36           O
ATOM   2734  N   ALA A 183      -5.519 -45.320  10.761  1.00 39.15           N
ATOM   2735  CA  ALA A 183      -6.974 -45.289  10.569  1.00 39.02           C
ATOM   2737  CB  ALA A 183      -7.326 -44.548   9.275  1.00 38.79           C
ATOM   2741  C   ALA A 183      -7.627 -46.683  10.596  1.00 38.82           C
ATOM   2742  O   ALA A 183      -8.561 -46.902  11.368  1.00 38.96           O
ATOM   2744  N   SER A 184      -7.116 -47.617   9.792  1.00 38.77           N
ATOM   2745  CA  SER A 184      -7.605 -49.014   9.749  1.00 38.98           C
ATOM   2747  CB  SER A 184      -6.678 -49.877   8.890  1.00 38.86           C
ATOM   2750  OG  SER A 184      -6.559 -49.351   7.586  1.00 39.28           O
ATOM   2752  C   SER A 184      -7.730 -49.708  11.108  1.00 39.27           C
ATOM   2753  O   SER A 184      -8.301 -50.781  11.200  1.00 39.52           O
ATOM   2755  N   ARG A 185      -7.152 -49.118  12.145  1.00 39.75           N
ATOM   2756  CA  ARG A 185      -7.150 -49.696  13.480  1.00 39.90           C
ATOM   2758  CB  ARG A 185      -5.725 -50.107  13.827  1.00 40.06           C
ATOM   2761  CG  ARG A 185      -5.047 -50.681  12.615  1.00 41.02           C
ATOM   2764  CD  ARG A 185      -3.666 -51.231  12.835  1.00 42.83           C
ATOM   2767  NE  ARG A 185      -3.146 -51.627  11.526  1.00 45.27           N
ATOM   2769  CZ  ARG A 185      -2.028 -52.312  11.316  1.00 46.99           C
ATOM   2770  NH1 ARG A 185      -1.255 -52.695  12.334  1.00 47.24           N
ATOM   2773  NH2 ARG A 185      -1.683 -52.612  10.069  1.00 47.68           N
ATOM   2776  C   ARG A 185      -7.696 -48.682  14.465  1.00 39.80           C
ATOM   2777  O   ARG A 185      -7.506 -48.802  15.670  1.00 39.41           O
ATOM   2779  N   SER A 186      -8.389 -47.681  13.932  1.00 40.05           N
ATOM   2780  CA  SER A 186      -9.030 -46.664  14.741  1.00 40.57           C
ATOM   2782  CB  SER A 186     -10.206 -47.281  15.541  1.00 40.69           C
ATOM   2785  OG  SER A 186     -11.017 -48.135  14.736  1.00 40.64           O
ATOM   2787  C   SER A 186      -8.050 -45.948  15.689  1.00 40.70           C
ATOM   2788  O   SER A 186      -8.476 -45.360  16.679  1.00 41.28           O
ATOM   2790  N   LEU A 187      -6.751 -45.986  15.384  1.00 40.68           N
ATOM   2791  CA  LEU A 187      -5.736 -45.307  16.194  1.00 40.33           C
ATOM   2793  CB  LEU A 187      -4.403 -46.057  16.133  1.00 40.08           C
ATOM   2796  CG  LEU A 187      -4.357 -47.541  16.534  1.00 39.09           C
ATOM   2798  CD1 LEU A 187      -3.067 -48.181  16.053  1.00 38.05           C
ATOM   2802  CD2 LEU A 187      -4.505 -47.732  18.021  1.00 37.25           C
```

FIG. 16X

```
ATOM   2806  C    LEU A 187      -5.532 -43.881  15.688  1.00 40.83           C
ATOM   2807  O    LEU A 187      -5.029 -43.024  16.414  1.00 41.20           O
ATOM   2809  N    TRP A 188      -5.920 -43.630  14.441  1.00 41.26           N
ATOM   2810  CA   TRP A 188      -5.656 -42.345  13.795  1.00 41.52           C
ATOM   2812  CB   TRP A 188      -6.150 -42.339  12.343  1.00 41.50           C
ATOM   2815  CG   TRP A 188      -6.158 -40.966  11.809  1.00 41.20           C
ATOM   2816  CD1  TRP A 188      -7.246 -40.187  11.564  1.00 41.75           C
ATOM   2818  NE1  TRP A 188      -6.854 -38.950  11.114  1.00 42.16           N
ATOM   2820  CE2  TRP A 188      -5.483 -38.908  11.087  1.00 42.58           C
ATOM   2821  CD2  TRP A 188      -5.014 -40.163  11.532  1.00 41.22           C
ATOM   2822  CE3  TRP A 188      -3.637 -40.383  11.606  1.00 41.13           C
ATOM   2824  CZ3  TRP A 188      -2.777 -39.363  11.228  1.00 41.93           C
ATOM   2826  CH2  TRP A 188      -3.271 -38.117  10.792  1.00 42.24           C
ATOM   2828  CZ2  TRP A 188      -4.615 -37.871  10.713  1.00 42.53           C
ATOM   2830  C    TRP A 188      -6.292 -41.168  14.514  1.00 41.88           C
ATOM   2831  O    TRP A 188      -5.659 -40.115  14.695  1.00 41.56           O
ATOM   2833  N    ASP A 189      -7.552 -41.342  14.894  1.00 42.52           N
ATOM   2834  CA   ASP A 189      -8.345 -40.228  15.412  1.00 43.24           C
ATOM   2836  CB   ASP A 189      -9.828 -40.605  15.492  1.00 43.54           C
ATOM   2839  CG   ASP A 189     -10.722 -39.489  15.019  1.00 45.48           C
ATOM   2840  OD1  ASP A 189     -11.025 -39.463  13.797  1.00 47.35           O
ATOM   2841  OD2  ASP A 189     -11.083 -38.618  15.854  1.00 47.65           O
ATOM   2842  C    ASP A 189      -7.820 -39.746  16.764  1.00 43.04           C
ATOM   2843  O    ASP A 189      -7.793 -38.551  17.034  1.00 42.91           O
ATOM   2845  N    SER A 190      -7.384 -40.684  17.596  1.00 43.12           N
ATOM   2846  CA   SER A 190      -6.683 -40.353  18.825  1.00 43.43           C
ATOM   2848  CB   SER A 190      -6.379 -41.629  19.605  1.00 43.34           C
ATOM   2851  OG   SER A 190      -5.852 -41.319  20.879  1.00 44.13           O
ATOM   2853  C    SER A 190      -5.380 -39.593  18.517  1.00 43.77           C
ATOM   2854  O    SER A 190      -5.183 -38.458  18.961  1.00 43.68           O
ATOM   2856  N    PHE A 191      -4.513 -40.227  17.733  1.00 44.05           N
ATOM   2857  CA   PHE A 191      -3.239 -39.649  17.347  1.00 44.52           C
ATOM   2859  CB   PHE A 191      -2.602 -40.522  16.265  1.00 44.54           C
ATOM   2862  CG   PHE A 191      -1.213 -40.111  15.864  1.00 43.80           C
ATOM   2863  CD1  PHE A 191      -0.143 -40.272  16.740  1.00 44.21           C
ATOM   2865  CE1  PHE A 191       1.145 -39.922  16.358  1.00 43.71           C
ATOM   2867  CZ   PHE A 191       1.379 -39.413  15.079  1.00 42.78           C
ATOM   2869  CE2  PHE A 191       0.330 -39.261  14.199  1.00 42.36           C
ATOM   2871  CD2  PHE A 191      -0.961 -39.616  14.589  1.00 42.74           C
ATOM   2873  C    PHE A 191      -3.418 -38.219  16.860  1.00 45.33           C
ATOM   2874  O    PHE A 191      -2.665 -37.342  17.254  1.00 45.14           O
ATOM   2876  N    ARG A 192      -4.426 -37.972  16.026  1.00 46.63           N
ATOM   2877  CA   ARG A 192      -4.671 -36.612  15.538  1.00 47.77           C
ATOM   2879  CB   ARG A 192      -5.832 -36.549  14.539  1.00 48.21           C
ATOM   2882  CG   ARG A 192      -5.687 -35.388  13.549  1.00 49.97           C
ATOM   2885  CD   ARG A 192      -7.011 -34.760  13.077  1.00 52.52           C
ATOM   2888  NE   ARG A 192      -6.735 -33.566  12.262  1.00 54.29           N
ATOM   2890  CZ   ARG A 192      -7.644 -32.844  11.606  1.00 54.80           C
ATOM   2891  NH1  ARG A 192      -8.935 -33.168  11.646  1.00 55.57           N
ATOM   2894  NH2  ARG A 192      -7.251 -31.785  10.903  1.00 54.56           N
ATOM   2897  C    ARG A 192      -4.955 -35.644  16.683  1.00 48.26           C
ATOM   2898  O    ARG A 192      -4.364 -34.566  16.741  1.00 48.45           O
ATOM   2900  N    GLN A 193      -5.842 -36.035  17.598  1.00 48.69           N
ATOM   2901  CA   GLN A 193      -6.274 -35.139  18.681  1.00 49.13           C
ATOM   2903  CB   GLN A 193      -7.613 -35.613  19.253  1.00 49.42           C
ATOM   2906  CG   GLN A 193      -8.767 -35.559  18.245  1.00 50.46           C
ATOM   2909  CD   GLN A 193     -10.039 -36.207  18.776  1.00 51.87           C
ATOM   2910  OE1  GLN A 193     -10.338 -36.119  19.972  1.00 52.98           O
ATOM   2911  NE2  GLN A 193     -10.796 -36.860  17.888  1.00 51.85           N
ATOM   2914  C    GLN A 193      -5.256 -34.950  19.822  1.00 49.03           C
ATOM   2915  O    GLN A 193      -5.313 -33.953  20.546  1.00 49.13           O
ATOM   2917  N    SER A 194      -4.325 -35.883  19.977  1.00 48.96           N
ATOM   2918  CA   SER A 194      -3.383 -35.935  21.102  1.00 49.13           C
```

FIG. 16Y

```
ATOM   2920  CB   SER A 194      -2.706 -37.200  21.295  1.00 49.05           C
ATOM   2923  OG   SER A 194      -1.924 -37.556  20.168  1.00 48.43           O
ATOM   2925  C    SER A 194      -2.318 -34.719  21.008  1.00 49.40           C
ATOM   2926  O    SER A 194      -1.701 -34.367  22.015  1.00 49.53           O
ATOM   2928  N    GLU A 195      -2.107 -34.160  19.820  1.00 49.59           N
ATOM   2929  CA   GLU A 195      -1.167 -33.060  19.656  1.00 49.84           C
ATOM   2931  CB   GLU A 195      -0.885 -32.832  18.168  1.00 49.58           C
ATOM   2934  CG   GLU A 195       0.398 -32.064  17.912  1.00 49.65           C
ATOM   2937  CD   GLU A 195       0.694 -31.811  16.441  1.00 48.50           C
ATOM   2938  OE1  GLU A 195       0.088 -32.456  15.572  1.00 47.38           O
ATOM   2939  OE2  GLU A 195       1.553 -30.956  16.152  1.00 48.72           O
ATOM   2940  C    GLU A 195      -1.711 -31.784  20.312  1.00 50.65           C
ATOM   2941  O    GLU A 195      -2.155 -30.867  19.625  1.00 50.92           O
ATOM   2943  N    ARG A 196      -1.684 -31.732  21.645  1.00 51.54           N
ATOM   2944  CA   ARG A 196      -2.200 -30.571  22.402  1.00 52.12           C
ATOM   2946  CB   ARG A 196      -3.042 -31.017  23.606  1.00 52.42           C
ATOM   2949  CG   ARG A 196      -4.243 -31.923  23.284  1.00 53.48           C
ATOM   2952  CD   ARG A 196      -4.777 -32.581  24.568  1.00 54.83           C
ATOM   2955  NE   ARG A 196      -5.630 -33.736  24.296  1.00 55.74           N
ATOM   2957  CZ   ARG A 196      -5.990 -34.655  25.195  1.00 57.08           C
ATOM   2958  NH1  ARG A 196      -5.583 -34.586  26.464  1.00 57.73           N
ATOM   2961  NH2  ARG A 196      -6.769 -35.664  24.819  1.00 57.50           N
ATOM   2964  C    ARG A 196      -1.047 -29.719  22.913  1.00 52.08           C
ATOM   2965  O    ARG A 196      -0.327 -30.128  23.829  1.00 52.03           O
ATOM   2967  O11  tte B 801      10.835 -36.373  17.796  1.00 42.05           O
ATOM   2968  C10  tte B 801      10.316 -35.557  18.550  1.00 40.00           C
ATOM   2969  C5   tte B 801       8.873 -35.153  18.337  1.00 39.47           C
ATOM   2970  C6   tte B 801       7.809 -35.410  19.226  1.00 39.38           C
ATOM   2972  C1   tte B 801       6.496 -35.030  18.895  1.00 39.35           C
ATOM   2973  O7   tte B 801       5.447 -35.260  19.747  1.00 38.95           O
ATOM   2975  C2   tte B 801       6.242 -34.403  17.681  1.00 38.89           C
ATOM   2976  O8   tte B 801       4.967 -34.019  17.368  1.00 38.97           O
ATOM   2978  C3   tte B 801       7.291 -34.164  16.799  1.00 38.72           C
ATOM   2979  O9   tte B 801       7.090 -33.549  15.599  1.00 38.53           O
ATOM   2981  C4   tte B 801       8.587 -34.545  17.128  1.00 38.93           C
ATOM   2983  O12  tte B 801      11.220 -35.067  19.560  1.00 40.90           O
ATOM   2984  C13  tte B 801      10.646 -34.543  20.741  1.00 41.82           C
ATOM   2986  C14  tte B 801      10.591 -32.999  20.659  1.00 42.19           C
ATOM   2988  C19  tte B 801      11.286 -32.627  19.406  1.00 41.36           C
ATOM   2989  C20  tte B 801      12.663 -32.838  19.328  1.00 41.52           C
ATOM   2991  C21  tte B 801      13.349 -32.548  18.152  1.00 41.30           C
ATOM   2992  O25  tte B 801      14.596 -32.713  18.106  1.00 40.42           O
ATOM   2993  C22  tte B 801      12.637 -32.067  17.056  1.00 40.80           C
ATOM   2994  O26  tte B 801      13.259 -31.813  16.006  1.00 39.62           O
ATOM   2995  C24  tte B 801      10.560 -32.161  18.303  1.00 40.37           C
ATOM   2997  C23  tte B 801      11.245 -31.870  17.117  1.00 41.43           C
ATOM   2998  O32  tte B 801      10.614 -31.426  16.117  1.00 39.59           O
ATOM   2999  C18  tte B 801      11.449 -35.083  21.917  1.00 40.77           C
ATOM   3002  C17  tte B 801      10.752 -34.444  23.085  1.00 41.20           C
ATOM   3003  C16  tte B 801      10.617 -33.070  22.993  1.00 41.65           C
ATOM   3004  O15  tte B 801      11.135 -32.467  21.865  1.00 41.79           O
ATOM   3005  C27  tte B 801      10.240 -35.151  24.162  1.00 40.94           C
ATOM   3006  O33  tte B 801      10.387 -36.498  24.231  1.00 39.60           O
ATOM   3008  C28  tte B 801       9.590 -34.451  25.183  1.00 42.18           C
ATOM   3010  C29  tte B 801       9.456 -33.054  25.106  1.00 42.77           C
ATOM   3011  O31  tte B 801       8.828 -32.352  26.102  1.00 42.73           O
ATOM   3013  C30  tte B 801       9.964 -32.366  24.001  1.00 41.87           C
ATOM   3015  MN   MN  D 901      12.532 -31.587  14.372  1.00 25.44          MN
ATOM   3016  MN   MN  D 902      15.458 -32.653  16.373  1.00 30.83          MN
ATOM   3017  OH2  HOH Z   2      13.415 -51.245  18.884  1.00 26.91           O
ATOM   3020  OH2  HOH Z   3      16.730 -33.917  -3.716  1.00 25.18           O
ATOM   3023  OH2  HOH Z   4       2.436 -30.369  -0.702  1.00 39.86           O
ATOM   3026  OH2  HOH Z   5      36.083 -30.269  12.439  1.00 58.91           O
```

FIG. 16Z

```
ATOM   3029  OH2 HOH Z    6      -5.686 -30.717  12.774  1.00 40.87           O
ATOM   3032  OH2 HOH Z    7       9.268 -52.765  11.043  1.00 29.78           O
ATOM   3035  OH2 HOH Z    8      16.565 -46.983  10.118  1.00 43.71           O
ATOM   3038  OH2 HOH Z   10      13.737 -26.906   3.048  1.00 36.56           O
ATOM   3041  OH2 HOH Z   11      13.318 -28.904  17.467  1.00 38.71           O
ATOM   3044  OH2 HOH Z   12      -2.332 -42.550  24.481  1.00 35.70           O
ATOM   3047  OH2 HOH Z   13      20.526 -35.810  18.407  1.00 23.17           O
ATOM   3050  OH2 HOH Z   14       2.036 -35.807  20.623  1.00 27.82           O
ATOM   3053  OH2 HOH Z   15      17.502 -51.219  12.607  1.00 31.36           O
ATOM   3056  OH2 HOH Z   17      10.285 -17.576   5.959  1.00 34.10           O
ATOM   3059  OH2 HOH Z   18      19.185 -28.489  22.437  1.00 31.79           O
ATOM   3062  OH2 HOH Z   19      -8.668 -42.953  17.301  1.00 33.17           O
ATOM   3065  OH2 HOH Z   20       1.902 -50.725  10.398  1.00 48.28           O
ATOM   3068  OH2 HOH Z   21       4.812 -40.883  30.946  1.00 36.95           O
ATOM   3071  OH2 HOH Z   23       0.803 -39.798  24.130  1.00 22.17           O
ATOM   3074  OH2 HOH Z   24      29.680 -32.800  22.760  1.00 24.02           O
ATOM   3077  OH2 HOH Z   26      10.321 -47.201   9.731  1.00 31.65           O
ATOM   3080  OH2 HOH Z   27      33.994 -31.256  17.131  1.00 26.61           O
ATOM   3083  OH2 HOH Z   28       9.636 -48.440  32.425  1.00 44.68           O
ATOM   3086  OH2 HOH Z   29      17.662 -32.975  16.700  1.00 25.53           O
ATOM   3089  OH2 HOH Z   30      11.999 -33.828  -8.615  1.00 33.84           O
ATOM   3092  OH2 HOH Z   31      15.640 -30.617  16.684  1.00 25.52           O
ATOM   3095  OH2 HOH Z   32       1.758 -19.230   9.258  1.00 52.92           O
ATOM   3098  OH2 HOH Z   33      -0.001 -23.575   5.431  1.00 46.79           O
ATOM   3101  OH2 HOH Z   34      12.384 -30.143  25.192  1.00 54.67           O
ATOM   3104  OH2 HOH Z   36      25.120 -37.878   8.328  1.00 36.86           O
ATOM   3107  OH2 HOH Z   37      13.744 -27.369  -4.131  1.00 46.71           O
ATOM   3110  OH2 HOH Z   38      18.892 -27.020   3.282  1.00 29.31           O
ATOM   3113  OH2 HOH Z   40       4.643 -45.577   1.211  1.00 43.16           O
```

FIG. 16AA

H1N1 PA structure with EMBL-R05-1 bound structure

FIG. 17

SEQUENCE LISTING

```
<160> NUMBER OF SEQ ID NOS: 16

<210> SEQ ID NO 1
<211> LENGTH: 2151
<212> TYPE: DNA
<213> ORGANISM: Influenza A pandemic H1N1 virus (A/California/04/2009)
<220> FEATURE:
<221> NAME/KEY: CDS
<222> LOCATION: (1)..(2151)
<223> OTHER INFORMATION: PA-subunit of the Influenza A pandemic H1N1
      virus (A/California/04/2009) RNA-dependent RNA polymerase

<400> SEQUENCE: 1 atg gaa gac ttt gtg cga caa tgc ttc aat cca atg atc gtc gag ctt      48
Met Glu Asp Phe Val Arg Gln Cys Phe Asn Pro Met Ile Val Glu Leu
1               5                   10                  15 gcg gaa aag gca atg aaa gaa tat ggg gaa gat ccg aaa atc gaa act      96
Ala Glu Lys Ala Met Lys Glu Tyr Gly Glu Asp Pro Lys Ile Glu Thr
            20                  25                  30
```

```
aac aag ttt gct gca ata tgc aca cat ttg gaa gtt tgt ttc atg tat        144
Asn Lys Phe Ala Ala Ile Cys Thr His Leu Glu Val Cys Phe Met Tyr
        35                  40                  45 tcg gat ttc cat ttc atc gac gaa cgg ggt gaa tca ata att gta gaa        192
Ser Asp Phe His Phe Ile Asp Glu Arg Gly Glu Ser Ile Ile Val Glu
 50                  55                  60 tct ggt gac ccg aat gca cta ttg aag cac cga ttt gag ata att gaa        240
Ser Gly Asp Pro Asn Ala Leu Leu Lys His Arg Phe Glu Ile Ile Glu
 65                  70                  75                  80 gga aga gac cga atc atg gcc tgg aca gtg gtg aac agt ata tgt aac        288
Gly Arg Asp Arg Ile Met Ala Trp Thr Val Val Asn Ser Ile Cys Asn
                 85                  90                  95 aca aca ggg gta gag aag cct aaa ttt ctt cct gat ttg tat gat tac        336
Thr Thr Gly Val Glu Lys Pro Lys Phe Leu Pro Asp Leu Tyr Asp Tyr
            100                 105                 110 aaa gag aac cgg ttc att gaa att gga gta aca cgg agg gaa gtc cac        384
Lys Glu Asn Arg Phe Ile Glu Ile Gly Val Thr Arg Arg Glu Val His
        115                 120                 125 ata tat tac cta gag aaa gcc aac aaa ata aaa tct gag aag aca cac        432
Ile Tyr Tyr Leu Glu Lys Ala Asn Lys Ile Lys Ser Glu Lys Thr His
130                 135                 140 att cac atc ttt tca ttc act gga gag gag atg gcc acc aaa gcg gac        480
Ile His Ile Phe Ser Phe Thr Gly Glu Glu Met Ala Thr Lys Ala Asp
145                 150                 155                 160 tac acc ctt gac gaa gag agc agg gca aga atc aaa act agg ctt ttc        528
Tyr Thr Leu Asp Glu Glu Ser Arg Ala Arg Ile Lys Thr Arg Leu Phe
                165                 170                 175 act ata aga caa gaa atg gcc agt agg agt cta tgg gat tcc ttt cgt        576
Thr Ile Arg Gln Glu Met Ala Ser Arg Ser Leu Trp Asp Ser Phe Arg
            180                 185                 190 cag tcc gaa aga ggc gaa gag aca att gaa gaa aaa ttt gag att aca        624
Gln Ser Glu Arg Gly Glu Glu Thr Ile Glu Glu Lys Phe Glu Ile Thr
        195                 200                 205 gga act atg cgc aag ctt gcc gac caa agt ctc cca ccg aac ttc ccc        672
Gly Thr Met Arg Lys Leu Ala Asp Gln Ser Leu Pro Pro Asn Phe Pro
210                 215                 220 agc ctt gaa aac ttt aga gcc tat gta gat gga ttc gag ccg aac ggc        720
Ser Leu Glu Asn Phe Arg Ala Tyr Val Asp Gly Phe Glu Pro Asn Gly
225                 230                 235                 240 tgc att gag ggc aag ctt tcc caa atg tca aaa gaa gtg aac gcc aaa        768
Cys Ile Glu Gly Lys Leu Ser Gln Met Ser Lys Glu Val Asn Ala Lys
                245                 250                 255 att gaa cca ttc ttg agg acg aca cca cgc ccc ctc aga ttg cct gat        816
Ile Glu Pro Phe Leu Arg Thr Thr Pro Arg Pro Leu Arg Leu Pro Asp
            260                 265                 270 ggg cct ctt tgc cat cag cgg tca aag ttc ctg ctg atg gat gct ctg        864
Gly Pro Leu Cys His Gln Arg Ser Lys Phe Leu Leu Met Asp Ala Leu
        275                 280                 285 aaa tta agt att gaa gac ccg agt cac gag ggg gag gga ata cca cta        912
Lys Leu Ser Ile Glu Asp Pro Ser His Glu Gly Glu Gly Ile Pro Leu
290                 295                 300 tat gat gca atc aaa tgc atg aag aca ttc ttt ggc tgg aaa gag cct        960
Tyr Asp Ala Ile Lys Cys Met Lys Thr Phe Phe Gly Trp Lys Glu Pro
305                 310                 315                 320 aac ata gtc aaa cca cat gag aaa ggc ata aat ccc aat tac ctc atg       1008
Asn Ile Val Lys Pro His Glu Lys Gly Ile Asn Pro Asn Tyr Leu Met
                325                 330                 335 gct tgg aag cag gtg cta gca gag cta cag gac att gaa aat gaa gag       1056
Ala Trp Lys Gln Val Leu Ala Glu Leu Gln Asp Ile Glu Asn Glu Glu
            340                 345                 350
```

```
aag atc cca agg aca aag aac atg aag aga aca agc caa ttg aag tgg    1104
Lys Ile Pro Arg Thr Lys Asn Met Lys Arg Thr Ser Gln Leu Lys Trp
            355                 360                 365 gca ctc ggt gaa aat atg gca cca gaa aaa gta gac ttt gat gac tgc    1152
Ala Leu Gly Glu Asn Met Ala Pro Glu Lys Val Asp Phe Asp Asp Cys
        370                 375                 380 aaa gat gtt gga gac ctt aaa cag tat gac agt gat gag cca gag ccc    1200
Lys Asp Val Gly Asp Leu Lys Gln Tyr Asp Ser Asp Glu Pro Glu Pro
385                 390                 395                 400 aga tct cta gca agc tgg gtc caa aat gaa ttc aat aag gca tgt gaa    1248
Arg Ser Leu Ala Ser Trp Val Gln Asn Glu Phe Asn Lys Ala Cys Glu
                405                 410                 415 ttg act gat tca agc tgg ata gaa ctt gat gaa ata gga gaa gat gtt    1296
Leu Thr Asp Ser Ser Trp Ile Glu Leu Asp Glu Ile Gly Glu Asp Val
            420                 425                 430 gcc ccg att gaa cat atc gca agc atg agg agg aac tat ttt aca gca    1344
Ala Pro Ile Glu His Ile Ala Ser Met Arg Arg Asn Tyr Phe Thr Ala
        435                 440                 445 gaa gtg tcc cac tgc agg gct act gaa tac ata atg aag gga gtg tac    1392
Glu Val Ser His Cys Arg Ala Thr Glu Tyr Ile Met Lys Gly Val Tyr
    450                 455                 460 ata aat acg gcc ttg ctc aat gca tcc tgt gca gcc atg gat gac ttt    1440
Ile Asn Thr Ala Leu Leu Asn Ala Ser Cys Ala Ala Met Asp Asp Phe
465                 470                 475                 480 cag ctg atc cca atg ata agc aaa tgt agg acc aaa gaa gga aga cgg    1488
Gln Leu Ile Pro Met Ile Ser Lys Cys Arg Thr Lys Glu Gly Arg Arg
                485                 490                 495 aaa aca aac ctg tat ggg ttc att ata aaa gga agg tct cat ttg aga    1536
Lys Thr Asn Leu Tyr Gly Phe Ile Ile Lys Gly Arg Ser His Leu Arg
            500                 505                 510 aat gat act gat gtg gtg aac ttt gta agt atg gag ttc tca ctc act    1584
Asn Asp Thr Asp Val Val Asn Phe Val Ser Met Glu Phe Ser Leu Thr
        515                 520                 525 gac ccg aga ctg gag cca cac aaa tgg gaa aaa tac tgt gtt ctt gaa    1632
Asp Pro Arg Leu Glu Pro His Lys Trp Glu Lys Tyr Cys Val Leu Glu
    530                 535                 540 ata gga gac atg ctc ttg agg act gcg ata ggc caa gtg tcg agg ccc    1680
Ile Gly Asp Met Leu Leu Arg Thr Ala Ile Gly Gln Val Ser Arg Pro
545                 550                 555                 560 atg ttc cta tat gtg aga acc aat gga acc tcc aag atc aag atg aaa    1728
Met Phe Leu Tyr Val Arg Thr Asn Gly Thr Ser Lys Ile Lys Met Lys
                565                 570                 575 tgg ggc atg gaa atg agg cgc tgc ctt ctt cag tct ctt cag cag att    1776
Trp Gly Met Glu Met Arg Arg Cys Leu Leu Gln Ser Leu Gln Gln Ile
            580                 585                 590 gag agc atg att gag gcc gag tct tct gtc aaa gag aaa gac atg acc    1824
Glu Ser Met Ile Glu Ala Glu Ser Ser Val Lys Glu Lys Asp Met Thr
        595                 600                 605 aag gaa ttc ttt gaa aac aaa tcg gaa aca tgg cca atc gga gag tca    1872
Lys Glu Phe Phe Glu Asn Lys Ser Glu Thr Trp Pro Ile Gly Glu Ser
    610                 615                 620 ccc agg gga gtg gag gaa ggc tct att ggg aaa gtg tgc agg acc tta    1920
Pro Arg Gly Val Glu Glu Gly Ser Ile Gly Lys Val Cys Arg Thr Leu
625                 630                 635                 640 ctg gca aaa tct gta ttc aac agt cta tat gcg tct cca caa ctt gag    1968
Leu Ala Lys Ser Val Phe Asn Ser Leu Tyr Ala Ser Pro Gln Leu Glu
                645                 650                 655 ggg ttt tcg gct gaa tct aga aaa ttg ctt ctc att gtt cag gca ctt    2016
Gly Phe Ser Ala Glu Ser Arg Lys Leu Leu Leu Ile Val Gln Ala Leu
```

```
                           660                 665                 670
agg gac aac ctg gaa cct gga acc ttc gat ctt ggg ggg cta tat gaa         2064
Arg Asp Asn Leu Glu Pro Gly Thr Phe Asp Leu Gly Gly Leu Tyr Glu
            675                 680                 685 gca atc gag gag tgc ctg att aat gat ccc tgg gtt ttg ctt aat gca         2112
Ala Ile Glu Glu Cys Leu Ile Asn Asp Pro Trp Val Leu Leu Asn Ala
        690                 695                 700 tct tgg ttc aac tcc ttc ctc aca cat gca ctg aag tag                     2151
Ser Trp Phe Asn Ser Phe Leu Thr His Ala Leu Lys
705                 710                 715

<210> SEQ ID NO 2
<211> LENGTH: 716
<212> TYPE: PRT
<213> ORGANISM: Influenza A pandemic H1N1 virus (A/California/04/2009)

<400> SEQUENCE: 2

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Pro
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300
```

```
Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715
```

```
<210> SEQ ID NO 3
<211> LENGTH: 6
<212> TYPE: PRT
<213> ORGANISM: artificial
<220> FEATURE:
<223> OTHER INFORMATION: synthetic sequence
<220> FEATURE:
<221> NAME/KEY: CHAIN
<222> LOCATION: (1)..(6)
<223> OTHER INFORMATION: amino-terminal linker

<400> SEQUENCE: 3

Met Gly Ser Gly Met Ala
1               5

<210> SEQ ID NO 4
<211> LENGTH: 11
<212> TYPE: PRT
<213> ORGANISM: Influenza A pandemic H1N1 virus (A/California/04/2009)
<220> FEATURE:
<221> NAME/KEY: peptide
<222> LOCATION: (1)..(11)
<223> OTHER INFORMATION: residues 20 to 30 of the PA-subunit of the
      Influenza A pandemic H1N1 virus (A/California/04/2009)
      RNA-dependent RNA polymerase

<400> SEQUENCE: 4

Ala Met Lys Glu Tyr Gly Glu Asp Pro Lys Ile
1               5                   10

<210> SEQ ID NO 5
<211> LENGTH: 9
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(9)
<223> OTHER INFORMATION: residues 32 to 40 of the PA-subunit of the
      Influenza A pandemic H1N1 virus (A/California/04/2009)
      RNA-dependent RNA polymerase

<400> SEQUENCE: 5

Thr Asn Lys Phe Ala Ala Ile Cys Thr
1               5

<210> SEQ ID NO 6
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 41 to 51 of the PA-subunit of the
      Influenza A pandemic H1N1 virus (A/California/04/2009)
      RNA-dependent RNA polymerase

<400> SEQUENCE: 6

His Leu Glu Val Cys Phe Met Tyr Ser Asp Phe
1               5                   10

<210> SEQ ID NO 7
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 80 to 90 of the PA-subunit of the
      Influenza A pandemic H1N1 virus (A/California/04/2009)
      RNA-dependent RNA polymerase
```

```
<400> SEQUENCE: 7

Glu Gly Arg Asp Arg Ile Met Ala Trp Thr Val
1               5                   10

<210> SEQ ID NO 8
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 100 to 110 of the PA-subunit of the
      Influenza A pandemic H1N1 virus (A/California/04/2009)
      RNA-dependent RNA polymerase

<400> SEQUENCE: 8

Val Glu Lys Pro Lys Phe Leu Pro Asp Leu Tyr
1               5                   10

<210> SEQ ID NO 9
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 115 to 125 of the PA-subunit of the
      Influenza A pandemic H1N1 virus (A/California/04/2009)
      RNA-dependent RNA polymerase

<400> SEQUENCE: 9

Asn Arg Phe Ile Glu Ile Gly Val Thr Arg Arg
1               5                   10

<210> SEQ ID NO 10
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(1)
<223> OTHER INFORMATION: residues 130 to 140 of the PA-subunit of the
      Influenza A pandemic H1N1 virus (A/California/04/2009)
      RNA-dependent RNA polymerase

<400> SEQUENCE: 10

Tyr Tyr Leu Glu Lys Ala Asn Lys Ile Lys Ser
1               5                   10

<210> SEQ ID NO 11
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 176 to 186 of the PA-subunit of the
      Influenza A pandemic H1N1 virus (A/California/04/2009)
      RNA-dependent RNA polymerase

<400> SEQUENCE: 11

Phe Thr Ile Arg Gln Glu Met Ala Ser Arg Ser
1               5                   10

<210> SEQ ID NO 12
<211> LENGTH: 7
<212> TYPE: PRT
<213> ORGANISM: artificial
<220> FEATURE:
```

```
<223> OTHER INFORMATION: synthetic
<220> FEATURE:
<221> NAME/KEY: PEPTIDE
<222> LOCATION: (1)..(7)
<223> OTHER INFORMATION: TEV protease recognition site

<400> SEQUENCE: 12

Glu Asn Leu Tyr Phe Gln Gly
1               5

<210> SEQ ID NO 13
<211> LENGTH: 198
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(198)
<223> OTHER INFORMATION: residues 1 to 198 of the PA-subunit of the
      Influenza A pandemic H1N1 virus (A/California/04/2009)
      RNA-dependent RNA polymerase

<400> SEQUENCE: 13

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu
        195

<210> SEQ ID NO 14
<211> LENGTH: 198
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(198)
<223> OTHER INFORMATION: residues 1-198 of the PA-subunit of the
      Influenza A pandemic H1N1 virus (A/California/04/2009)
      RNA-dependent RNA polymerase with residues 52-64 replaced with
      glycine

<400> SEQUENCE: 14
```

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
            35                  40                  45

Ser Asp Phe Gly Gly Gly Gly Gly Gly Gly Gly Gly Gly Gly Gly Gly
        50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
            115                 120                 125

Ile Tyr Tyr Leu Glu Lys Ala Asn Lys Ile Lys Ser Glu Lys Thr His
        130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu
        195

<210> SEQ ID NO 15
<211> LENGTH: 198
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(198)
<223> OTHER INFORMATION: amino acid residues 1-198 of PA-subunit of the
      Influenza A pandemic H1N1 virus (A/California/04/2009)
      RNA-dependent RNA polymerase with residues 52-72 replaced with
      Glycine

<400> SEQUENCE: 15

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
            35                  40                  45

Ser Asp Phe Gly Gly Gly Gly Gly Gly Gly Gly Gly Gly Gly Gly Gly
        50                  55                  60

Gly Gly Gly Gly Gly Gly Gly Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
            115                 120                 125

Ile Tyr Tyr Leu Glu Lys Ala Asn Lys Ile Lys Ser Glu Lys Thr His
```

```
                130               135                140
Ile His Ile Phe Ser Phe Thr Gly Glu Glu Met Ala Thr Lys Ala Asp
145                 150                155                160

Tyr Thr Leu Asp Glu Glu Ser Arg Ala Arg Ile Lys Thr Arg Leu Phe
                165                170                175

Thr Ile Arg Gln Glu Met Ala Ser Arg Ser Leu Trp Asp Ser Phe Arg
                180                185                190

Gln Ser Glu Arg Gly Glu
            195

<210> SEQ ID NO 16
<211> LENGTH: 198
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(198)
<223> OTHER INFORMATION: amino acid residues 1-198 of PA-subunit of the
      Influenza A pandemic H1N1 virus (A/California/04/2009)
      RNA-dependent RNA polymerase with residues 52-69 replaced with
      Glycine

<400> SEQUENCE: 16

Met Glu Asp Phe Val Arg Gln Cys Phe Asn Pro Met Ile Val Glu Leu
1               5                  10                 15

Ala Glu Lys Ala Met Lys Glu Tyr Gly Glu Asp Pro Lys Ile Glu Thr
                20                 25                 30

Asn Lys Phe Ala Ala Ile Cys Thr His Leu Glu Val Cys Phe Met Tyr
            35                 40                 45

Ser Asp Phe Gly Gly Gly Gly Gly Gly Gly Gly Gly Gly Gly Gly Gly
    50                 55                 60

Gly Gly Gly Gly Gly Ala Leu Leu Lys His Arg Phe Glu Ile Ile Glu
65                  70                 75                 80

Gly Arg Asp Arg Ile Met Ala Trp Thr Val Val Asn Ser Ile Cys Asn
                85                 90                 95

Thr Thr Gly Val Glu Lys Pro Lys Phe Leu Pro Asp Leu Tyr Asp Tyr
                100                105                110

Lys Glu Asn Arg Phe Ile Glu Ile Gly Val Thr Arg Arg Glu Val His
            115                120                125

Ile Tyr Tyr Leu Glu Lys Ala Asn Lys Ile Lys Ser Glu Lys Thr His
    130                135                140

Ile His Ile Phe Ser Phe Thr Gly Glu Glu Met Ala Thr Lys Ala Asp
145                 150                155                160

Tyr Thr Leu Asp Glu Glu Ser Arg Ala Arg Ile Lys Thr Arg Leu Phe
                165                170                175

Thr Ile Arg Gln Glu Met Ala Ser Arg Ser Leu Trp Asp Ser Phe Arg
                180                185                190

Gln Ser Glu Arg Gly Glu
            195
```

INFLUENZA A 2009 PANDEMIC H1N1 POLYPEPTIDE FRAGMENTS COMPRISING ENDONUCLEASE ACTIVITY AND THEIR USE

CROSS REFERENCES

This application is a divisional application to U.S. patent application Ser. No. 13/635,064, filed on Sep. 14, 2012, which is a National Stage filing of International Application Serial No. PCT/EP2011/001274, filed Mar. 15, 2011, which claims the benefit of U.S. Provisional Application Ser. No. 61/340,335 filed Mar. 16, 2010, the disclosures of which are expressly incorporated herein by reference.

TECHNICAL FIELD OF INVENTION

The present invention relates to polypeptide fragments comprising an amino-terminal fragment of the PA subunit of a viral RNA-dependent RNA polymerase possessing endonuclease activity, wherein said PA subunit is from Influenza A 2009 pandemic H1N1 virus or is a variant thereof. This invention also relates to (i) crystals of the polypeptide fragments which are suitable for structure determination of said polypeptide fragments using X-ray crystallography and (ii) computational methods using the structural coordinates of said polypeptide to screen for and design compounds that modulate, preferably inhibit the endonucleolytically active site within the polypeptide fragment. In addition, this invention relates to methods identifying compounds that bind to the PA polypeptide fragments possessing endonuclease activity and preferably inhibit said endonucleolytic activity, preferably in a high throughput setting. This invention also relates to compounds which are able to modulate, preferably to inhibit, the endonuclease activity of the PA subunit polypeptide fragment or variant thereof of the present invention and pharmaceutical compositions comprising said compounds for the treatment of disease conditions caused by viral infections with viruses of the Orthomyxoviridae family, Bunyaviridae family and/or Arenviridae family, preferably caused by viral infections with Influenza A 2009 pandemic H1N1 virus. Preferably, said compounds are identifiable by the methods disclosed herein or said pharmaceutical compositions are producible by the methods disclosed herein.

BACKGROUND OF THE INVENTION

Influenza is responsible for much morbidity and mortality in the world and is considered by many as belonging to the most significant viral threats to humans. Annual Influenza epidemics swipe the globe and occasional new virulent strains cause pandemics of great destructive power. At present the primary means of controlling Influenza virus epidemics is vaccination. However, mutant Influenza viruses are rapidly generated which escape the effects of vaccination. In the light of the fact that it takes approximately 6 months to generate a new Influenza vaccine, alternative therapeutic means, i.e., antiviral medication, are required especially as the first line of defense against a rapidly spreading pandemic.

An excellent starting point for the development of antiviral medication is structural data of essential viral proteins. Thus, the crystal structure determination of the Influenza virus surface antigen neuraminidase (von Itzstein et al., 1993, Nature 363:418-423) led directly to the development of neuraminidase inhibitors with anti-viral activity preventing the release of virus from the cells, however, not the virus production. These and their derivatives have subsequently developed into the anti-Influenza drugs, zanamivir (Glaxo) and oseltamivir (Roche), which are currently being stockpiled by many countries as a first line of defense against an eventual pandemic. However, these medicaments provide only a reduction in the duration of the clinical disease. Alternatively, other anti-Influenza compounds such as amantadine and rimantadine target an ion channel protein, i.e., the M2 protein, in the viral membrane interfering with the uncoating of the virus inside the cell. However, they have not been extensively used due to their side effects and the rapid development of resistant virus mutants (Magden et al., 2005, Appl. Microbiol. Biotechnol. 66:612-621). In addition, more unspecific viral drugs, such as ribavirin, have been shown to work for treatment of Influenza infections (Eriksson et al., 1977, Antimicrob. Agents Chemother. 11:946-951). However, ribavirin is only approved in a few countries, probably due to severe side effects (Furuta et al., 2005, Antimicrob. Agents Chemother. 49:981-986). Clearly, new antiviral compounds are needed, preferably directed against different targets.

Influenza virus A, B, C and Isavirus as well as Thogotovirus belong to the family of Orthomyxoviridae which, as well as the family of the Bunyaviridae, including the Hantavirus, Nairovirus, Orthobunyavirus, Phlebovirus, and Tospovirus, are negative stranded RNA viruses. Their genome is segmented and comes in ribonucleoprotein particles that include the RNA dependent RNA polymerase which carries out (i) the initial copying of the single-stranded virion RNA (vRNA) into viral mRNAs and (ii) the vRNA replication. For the generation of viral mRNA the polymerase makes use of the so called "cap-snatching" mechanism (Plotch et al., 1981, Cell 23:847-858; Kukkonen et al., 2005, Arch. Virol. 150:533-556; Leahy et al., 1997, J. Virol. 71:8347-8351; Noah and Krug, 2005, Adv. Virus Res. 65:121-145). The polymerase is composed of three subunits: PB1 (polymerase basic protein), PB2, and PA. For the cap-snatching mechanism, the viral polymerase binds via its PB2 subunit to the 5' RNA cap of cellular mRNA molecules which are cleaved at nucleotide 10 to 13 by the endonucleolytic activity of the polymerase. The capped RNA fragments serve as primers for the synthesis of viral mRNAs by the nucleotidyl-transferase center in the PB1 subunit (Li et al., 2001, EMBO J. 20:2078-2086). Finally, the viral mRNAs are 3'-end poly-adenylated by stuttering of the polymerase at an oligo-U motif at the 5'-end of the template. Recent studies have precisely defined the structural domain of PB2 responsible for cap-binding (Fechter et al., 2003, J. Biol. Chem. 278:20381-20388; Guilligay et al., 2008 Nat. Struct. Mol. Biol. 15:500-506). The endonucleolytic activity of the polymerase has hitherto been thought to reside in the PB1 subunit (Li et al, supra).

The polymerase complex seems to be an appropriate antiviral drug target since it is essential for synthesis of viral mRNA and viral replication and contains several functional active sites likely to be significantly different from those found in host cell proteins (Magden et al., supra). Thus, for example, there have been attempts to interfere with the assembly of polymerase subunits by a 25-amino-acid peptide resembling the PA-binding domain within PB1 (Ghanem et al., 2007, J. Virol. 81:7801-7804). Moreover, there have been attempts to interfere with viral transcription by nucleoside analogs, such as 2'-deoxy-2'-fluoroguanosine (Tisdale et al., 1995, Antimicrob. Agents Chemother. 39:2454-2458) and it has been shown that T-705, a substituted pyrazine compound may function as a specific inhibitor of Influenza virus RNA polymerase (Furuta et al., supra). Furthermore, the endonuclease activity of the polymerase has been targeted and a series of 4-substituted 2,4-dioxobutanoic acid compounds has been identified as selective inhibitors of this activity in Influenza viruses (Tomassini et al., 1994, Antimicrob. Agents Chemother. 38:2827-2837). In addition, flutimide, a substituted 2,6-diketopiperazine, identified in extracts of Delitschia confertaspora, a fungal species, has been shown to inhibit the endonuclease of Influenza virus (Tomassini et al., 1996, Antimicrob. Agents Chemother. 40:1189-1193). However, the inhibitory action of compounds on the endonucleolytic activity of the viral polymerase was hitherto only studied in the context of the entire trimeric complex of the polymerase.

The PA subunit of the polymerase is functionally the least well-characterised, although it has been implicated in both cap-binding and endonuclease activity, vRNA replication, and a controversial protease activity. PA (716 residues in influenza A) is separable by trypsination at residue 213. The recently determined crystal structure of the C-terminal two-thirds of PA bound to a PB1 N-terminal peptide provided the first structural insight into both a large part of the PA subunit, whose function, however, still remains unclear, and the exact nature of one of the critical inter-subunit interactions (He et al., 2008, Nature 454:1123-1126; Obayashi et al., 2008, Nature 454:1127-1131). Systematic mutation of conserved residues in the PA amino-terminal domain have identified residues important for protein stability, promoter binding, cap-binding and endonuclease activity of the polymerase complex (Hara et al., 2006, J. Virol. 80:7789-7798). The enzymology of the endonuclease within the context of intact viral ribonucleoprotein particles (RNPs) has been extensively studied.

It has been found recently that, contrary to the general opinion in the field, the endonucleolytic activity resides exclusively within the PA subunit of the RNA-dependent RNA polymerase of the Influenza A H3N2 virus (Dias et al., 2009).

The present inventors have now achieved to structurally characterize the PA domain of the Influenza A 2009 pandemic H1N1 virus by X-ray crystallography and identified the endonucleolytic active center within said domain. The present inventors surprisingly found that polypeptide fragments of the PA subunit of said virus readily crystallized and that, thus, said polypeptide fragments are very suitable to study the endonucleolytic activity of the RNA-dependent RNA polymerase of the Influenza A 2009 pandemic H1N1 virus in the context of said polypeptide fragments in order to simplify the development of new anti-viral compounds targeting the endonuclease activity of said viral polymerase as well as to optimize previously identified compounds.

The achievement of the present inventors to recombinantly produce PA polypeptide fragments possessing the endonucleolytic activity of the RNA-dependent RNA polymerase of the Influenza A 2009 pandemic H1N1 virus allows for performing in vitro high-throughput screening for inhibitors of a functional site on said viral polymerase using easily obtainable material from a straightforward expression system. Furthermore, the structural data of the endonucleolytic PA H1N1 polypeptide fragment as well as of the enzymatically active center therein allows for directed design of inhibitors and in silico screening for potentially therapeutic compounds.

The present inventors further managed, for the first time, the co-crystallization of a PA polypeptide fragment and of a variant thereof of the PA subunit of Influenza A 2009 pandemic H1N1 virus with a bound inhibitor and found that, thus, the development of new anti-viral compounds targeting the endonuclease activity of the RNA-dependent RNA polymerase of the Influenza A 2009 pandemic H1N1 virus can be improved. Particularly, the co-crystallization data show, for the first time, in detail which amino acids comprised in the active site of a PA polypeptide fragment of the PA subunit of Influenza A 2009 pandemic H1N1 virus are especially involved in compound binding. This new knowledge allows the optimized design of modifications to existing inhibitors in order to improve their potency or the design and optimization of novel inhibitors that effectively block endonuclease activity.

It is an object of the present invention to provide (i) high resolution structural data of the endonucleolytic amino-terminal domain of the viral polymerase H1N1 PA subunit by X-ray crystallography, (ii) high resolution structural data of the endonucleolytic amino-terminal domain of the viral polymerase H1N1 PA subunit co-crystallized with a known inhibitor by X-ray crystallography, (iii) computational as well as in vitro methods, preferably in a high-throughput setting, for identifying compounds that can modulate, preferably inhibit, the endonuclease activity of the viral polymerase of the Influenza A 2009 pandemic H1N1 virus, preferably by blocking the endonucleolytic active site within the H1N1 PA subunit, and (iv) pharmacological compositions comprising such compounds for the treatment of infectious diseases caused by viruses using the cap snatching mechanism for synthesis of viral mRNA.

SUMMARY OF THE INVENTION

In a first aspect, the present invention relates to a polypeptide fragment comprising an amino-terminal fragment of the PA subunit of a viral RNA-dependent RNA polymerase possessing endonuclease activity, wherein said PA subunit is from Influenza A pandemic 2009 H1N1 virus according to SEQ ID NO: 2 or is a variant thereof, wherein said variant comprises the amino acid serine at an amino acid position 186 according to SEQ ID NO: 2 or at an amino acid position corresponding thereto.

In a further aspect, the present invention relates to an isolated polynucleotide coding for an isolated polypeptide fragment according to the present invention.

In a further aspect, the present invention relates to a recombinant vector comprising the isolated polynucleotide according to the present invention.

In a further aspect, the present invention relates to a recombinant host cell comprising the isolated polynucleotide according to the present invention or the recombinant vector according to the present invention.

In a further aspect, the present invention relates to a method for identifying compounds, which modulate the endonuclease activity of the PA subunit of a RNA-dependent RNA polymerase from Influenza A 2009 pandemic H1N1 virus or a variant thereof comprising the steps of:
(a) constructing a computer model of the active site defined
   by (i) the structure coordinates of the polypeptide fragment according to the present invention as shown in FIG. 1, (ii) the structure coordinates of the polypeptide fragment according to the present invention as shown in FIG. 2, (iii) the structure coordinates of the polypeptide fragment according to the present invention as shown in FIG. 3, (iv) the structure coordinates of the polypeptide fragment according to the present invention as shown in FIG.

4, (v) the structure coordinates of the polypeptide fragment according to the present invention as shown in FIG. 5, (vi) the structure coordinates of the polypeptide fragment according to the present invention as shown in FIG. 15, or (vii) the structure coordinates of the polypeptide fragment according to the present invention as shown in FIG. 16, (b) selecting a potential modulating compound by a method selected from the group consisting of:
 (i) assembling molecular fragments into said compound,
 (ii) selecting a compound from a small molecule database, and
 (iii) de novo ligand design of said compound;

(c) employing computational means to perform a fitting program operation between computer models of the said compound and the said active site in order to provide an energy-minimized configuration of the said compound in the active site; and (d) evaluating the results of said fitting operation to quantify the association between the said compound and the active site model, whereby evaluating the ability of said compound to associate with the said active site.

In a further aspect, the present invention relates to a method for identifying compounds, which modulate the endonuclease activity of the PA subunit of a RNA-dependent RNA polymerase from Influenza A 2009 pandemic H1N1 virus or a variant thereof comprising the steps of:

(i) contacting the polypeptide fragment or variant thereof according to the present invention or the recombinant host cell according to the present invention with a test compound, and (ii) analyzing the ability of said test compound to modulate the endonuclease activity of said PA subunit polypeptide fragment or variant thereof.

In a further aspect, the present invention relates to a compound which is able to modulate, preferably to inhibit, the endonuclease activity of the PA subunit polypeptide fragment or variant thereof according to the present invention. Preferably, said compound is identifiable by the (in vitro) methods according to the present inventions.

In a further aspect, the present invention relates to a pharmaceutical composition comprising the compound of the present invention or a pharmaceutically acceptable salt thereof and one or more pharmaceutically acceptable excipient(s) and/or carrier(s). Preferably, said pharmaceutical composition is producible according to the (in vitro) methods of the present invention.

In a further aspect, the present invention relates to an antibody directed against the active site of the PA subunit of the Influenza A 2009 pandemic H1N1 virus according to SEQ ID NO: 2 or a variant thereof, wherein said variant comprises the amino acid serine at an amino acid position 186 according to SEQ ID NO: 2 or at an amino acid position corresponding thereto.

In a further aspect, the present invention relates to the use of a compound according to the present invention, a pharmaceutical composition according to the present invention, or an antibody according to the present invention for the manufacture of a medicament for treating, ameliorating, or preventing disease conditions caused by viral infections with viruses of the Orthomyxoviridae family, Bunyaviridae family and/or Arenviridae family, preferably caused by viral infections with Influenza A 2009 pandemic H1N1 virus.

In a further aspect, the present invention relates to the use of 4-[3-[(4-chlorophenyl)methyl]-1-(phenylmethyl)-3-piperidinyl]-2-hydroxy-4-oxo-2-butenoic acid (EMBL-R05-3), 4-[4-[(4-chlorophenyl)methyl]-1-(cyclohexylmethyl)-4-piperidinyl]-2-hydroxy-4-oxo-2-butenoic acid (EMBL-R05-2), 4-[3-[(4-chlorophenyl)methyl]-1-(phenylmethylsulpho)-3-piperidinyl]-2-hydroxy-4-oxo-2-butenoic acid (EMBL-R05-1), or [(2R,3R)-5,7-dihydroxy-2-(3,4,5-trihydroxyphenyl)chroman-3-yl]3,4,5-trihydroxybenzoate (EGCG) for the manufacture of a medicament for treating, ameliorating, or preventing disease conditions caused by viral infections with Influenza A 2009 pandemic H1N1 virus.

In a further aspect, the present invention relates to a compound according to the present invention, a pharmaceutical composition according to the present invention, or an antibody according to the present invention for treating, ameliorating, or preventing disease conditions caused by viral infections with viruses of the Orthomyxoviridae family, Bunyaviridae family and/or Arenviridae family, preferably caused by viral infections with Influenza A 2009 pandemic H1N1 virus.

In a further aspect, the present invention relates to 4-[3-[(4-chlorophenyl)methyl]-1-(phenylmethyl)-3-piperidinyl]-2-hydroxy-4-oxo-2-butenoic acid (EMBL-R05-3), 4-[4-[(4-chlorophenyl)methyl]-1-(cyclohexylmethyl)-4-piperidinyl]-2-hydroxy-4-oxo-2-butenoic acid (EMBL-R05-2), 4-[3-[(4-chlorophenyl)methyl]-1-(phenylmethylsulpho)-3-piperidinyl]-2-hydroxy-4-oxo-2-butenoic acid (EMBL-R05-1), or [(2R,3R)-5,7-dihydroxy-2-(3,4,5-trihydroxyphenyl)chroman-3-yl]3,4,5-trihydroxybenzoate (EGCG) for treating, ameliorating, or preventing disease conditions caused by viral infections with Influenza A 2009 pandemic H1N1 virus.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment the polypeptide fragment of the present invention corresponds to amino acids 1 to 198 of the amino acid sequence set forth in SEQ ID NO: 2 and in another preferred embodiment the PA polypeptide fragment according to the present invention may be tagged with a peptide-tag that is preferably cleavable from the PA polypeptide fragment, preferably using a TEV protease, it is a preferred embodiment of the invention that the polypeptide fragment corresponding to amino acids 1 to 198 of the amino acid sequence set forth in SEQ ID NO: 2 is tagged with a peptide-tag that is cleavable from the PA polypeptide using a TEV protease.

Preferably, the terms used herein are defined as described in "A multilingual glossary of biotechnological terms: (IUPAC Recommendations)", H. G. W. Leuenberger, B. Nagel, and H. Kolb', Eds., *Helvetica* Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Definitions

The term "polypeptide fragment" refers to a part of a protein which is composed of a single amino acid chain. The term "protein" comprises polypeptide fragments that resume a secondary and tertiary structure and additionally refers to proteins that are made up of several amino acid chains, i.e., several subunits, forming quaternary structures. The term "peptide" refers to short amino acid chains of up to 50 amino acids that do not necessarily assume secondary or tertiary structures. A "peptoid" is a peptidomimetic that results from the oligomeric assembly of N-substituted glycines.

Residues in two or more polypeptides are said to "correspond" to each other if the residues occupy an analogous position in the polypeptide structures. As is well known in the art, analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (see website at ebi.ac.uk/clustalw) or Align (see website at ebi.ac.uk/emboss/align/index.html) using standard settings, preferably for Align EMBOSS::needle, Matrix: Blosum62, Gap Open 10.0, Gap Extend 0.5. Those skilled in the art understand that it may be necessary to introduce gaps in either sequence to produce a satisfactory alignment. Residues in two or more PA subunits are said to "correspond" if the residues are aligned in the best sequence alignment. The "best sequence alignment" between two polypeptides is defined as the alignment that produces the largest number of aligned identical residues. The "region of best sequence alignment" ends and, thus, determines the metes and bounds of the length of the comparison sequence for the purpose of the determination of the similarity score, if the sequence similarity, preferably identity, between two aligned sequences drops to less than 30%, preferably less than 20%, more preferably less than 10% over a length of 10, 20 or 30 amino acids.

The present invention relates to Influenza A 2009 pandemic H1N1 virus RNA-dependent RNA polymerase PA subunit fragments possessing endonuclease activity. The term "RNA-dependent RNA polymerase PA subunit" refers to the PA subunit of Influenza A 2009 pandemic H1N1 virus having an amino acid sequence as set forth in SEQ ID NO: 2. The term "RNA-dependent RNA polymerase PA subunit variant" refers to a PA subunit variant of Influenza A 2009 pandemic H1N1 virus which comprises the amino acid serine at an amino acid position 186 according to SEQ ID NO: 2 or at an amino acid position corresponding thereto and preferably has at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid sequence set forth in SEQ ID NO: 2. It is preferred that when a PA subunit variant is aligned with a PA subunit according to SEQ ID NO: 2 that the alignment will be over the entire length of the two polypeptides and, thus, that the alignment score will be determined on this basis. It is, however, possible that the PA subunit variant may comprise C-terminal/N-terminal or internal deletions or additions, e.g., through N- or C-terminal fusions. In this case, only the best aligned region is used for the assessment of similarity and identity, respectively. Preferably, fragments derived from these variants show the indicated similarity and identity, respectively, preferably within the region required for endonuclease activity. Accordingly, any alignment between SEQ ID NO: 2 and a PA subunit variant should preferably comprise the endonuclease active site. Thus, the above sequence similarity and identity to SEQ ID NO: 2 occurs at least over a length of 80, 90, 100, 110, 120, 130, 140, 150, 160, 165, 170, 180, 190, 200, 210, 220, 230, 240, 250, 300 or more amino acids, preferably comprising the endonuclease active site.

The polypeptide fragments of the present invention are, thus, based on Influenza A 2009 pandemic H1N1 virus RNA-dependent RNA polymerase PA subunit or variants thereof as defined above. Accordingly, in the following specification, the terms "polypeptide fragment(s)" and "PA polypeptide fragment(s)" always comprise fragments derived both from the PA protein as set out in SEQ ID NO: 2 and from PA protein variants thereof, as set out above, possessing endonuclease activity.

However, the specification also uses the terms "PA polypeptide fragment variants" or "PA fragment variants" to specifically refer to PA polypeptide fragments or PA fragments possessing endonuclease activity that are derived from Influenza A 2009 pandemic H1N1 virus RNA-dependent RNA polymerase PA subunit variants. The PA polypeptide fragments of the present invention, thus, preferably comprise, essentially consist or consist of sequences of the naturally occurring Influenza A 2009 pandemic H1N1 virus PA subunit. It is, however, also envisioned that the PA polypeptide fragment variants comprise the amino acid serine at an amino acid position 186 according to SEQ ID NO: 2 or at an amino acid position corresponding thereto and preferably further contain amino acid substitutions at 1, 2, 3, 4, 5, 6, 7, 8, 9, 10, 11, 12, 13, 14, 15 or more amino acid positions, and/or have at least 60%, 65%, 70%, 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid sequence set forth in SEQ ID NO: 2. It is understood that PA fragments of the present invention may comprise additional amino acids not derived from PA, like, e.g., tags, enzymes etc., such additional amino acids will not be considered in such an alignment, i.e., are excluded from the calculation of the alignment score. In a preferred embodiment, the above indicated alignment score is obtained when aligning the sequence of the fragment with SEQ ID NO: 2 at least over a length of 70, 80, 90, 100, 110, 120, 130, 140, 150, 160, 165, 170, 180, or 190 amino acids, wherein the sequence of SEQ ID NO: 2 preferably comprises the endonuclease active site.

In a preferred embodiment, the PA polypeptide fragment variants comprise at least the amino acid residues corresponding to amino acids 1 to 190 of Influenza A 2009 pandemic H1N1 virus PA subunit according to SEQ ID NO: 2 or consist of amino acid residues 1 to 190 of Influenza A 2009 pandemic H1N1 virus PA subunit according to SEQ ID NO: 2 and have at least 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with amino acid residues 1 to 190 of the amino acid sequence set forth in SEQ ID NO: 2. More preferably, the PA polypeptide fragment variants comprise at least the amino acid residues corresponding to amino acid residues 1 to 198 of Influenza A 2009 pandemic H1N1 virus PA subunit according to SEQ ID NO: 2 or consist of amino acid residues 1 to 198 of Influenza A 2009 pandemic H1N1 virus PA subunit according to SEQ ID NO: 2 and have at least 70%, more preferably 75%, more preferably 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid residues 1 to 198 of the amino acid sequence set forth in SEQ ID NO: 2. It is also preferred that the PA polypeptide fragment variants comprise at least the amino acid residues corresponding to amino acid residues 1 to 200 of Influenza A 2009 pandemic H1N1 virus PA subunit according to SEQ ID NO: 2 or consist of amino acid residues 1 to 200 of Influenza A 2009 pandemic H1N1 virus PA subunit according to SEQ ID NO: 2 and have at least 60%, more preferably 65%, more preferably 70%, more preferably 75%, more preferably 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with amino acid residues 1 to 200 of the amino acid sequence set forth in SEQ ID NO: 2. It should be noted that all of the above mentioned preferred PA polypeptide fragment variants comprise the amino acid serine at an amino acid position 186 according to SEQ ID NO: 2 or at an amino acid position corresponding thereto.

In the context of the present invention, the term "PA-Nter" refers to a polypeptide fragment which consists of amino acid residues 1 to 198 of the amino acid sequence as set forth in SEQ ID NO: 2 (PA H1N1 1 to 198) and optionally of an additional amino-terminal linker, i.e. MGSGMA (SEQ ID NO: 3). In the context of the present invention, the term "PA-Nter mutant" refers to a polypeptide fragment (variant) which consists of amino acid residues 1 to 198 of the amino acid sequence as set forth in SEQ ID NO: 2 with amino acids 52 to 64 replaced by the amino acid glycine (PA H1N1 1 to 198 Δ52-64: Gly) and optionally of an additional amino-terminal linker, i.e. MGSGMA (SEQ ID NO: 3).

The term "sequence similarity" means that amino acids at the same position of the best sequence alignment are identical or similar, preferably identical. "Similar amino acids" possess similar characteristics, such as polarity, solubility, hydrophilicity, hydrophobicity, charge, or size. Similar amino acids are preferably leucine, isoleucine, and valine; phenylalanine, tryptophan, and tyrosine; lysine, arginine, and histidine; glutamic acid and aspartic acid; glycine, alanine, and serine; threonine, asparagine, glutamine, and methionine. The skilled person is well aware of sequence similarity searching tools, e.g., available on the World Wide Web (see website at ebi.ac.uk/Tools.similarity.html).

The term "soluble", as used herein, refers to a polypeptide fragment which remains in the supernatant after centrifugation for 30 min at 100,000×g in an aqueous buffer under physiologically isotonic conditions, for example, 0.14 M sodium chloride or sucrose, at a protein concentration of at least 200 µg/ml, preferably of at least 500 µg/ml, preferably of at least 1 mg/ml, more preferably of at least 2 mg/ml, even more preferably of at least 3 mg/ml, even more preferably of at least 4 mg/ml, most preferably of at least 5 mg/ml in the absence of denaturants such as guanidine or urea in effective concentrations. A protein fragment that is tested for its solubility is preferably expressed in one of the cellular expression systems indicated below.

The term "purified" in reference to a polypeptide, does not require absolute purity such as a homogenous preparation, rather it represents an indication that the polypeptide is relatively purer than in the natural environment. Generally, a purified polypeptide is substantially free of other proteins, lipids, carbohydrates, or other materials with which it is naturally associated, preferably at a functionally significant level, for example, at least 85% pure, more preferably at least 90% or 95% pure, most preferably at least 99% pure. The expression "purified to an extent to be suitable for crystallization" refers to a polypeptide that is 85% to 100%, preferably 90% to 100%, more preferably 95% to 100% or 98% to 100% pure and can be concentrated to higher than 3 mg/ml, preferably higher than 10 mg/ml, more preferably higher than 18 mg/ml without precipitation. A skilled artisan can purify a polypeptide using standard techniques for protein purification. A substantially pure polypeptide will yield a single major band on a non-reducing polyacrylamide gel.

The term "associate" as used in the context of identifying compounds with the methods of the present invention refers to a condition of proximity between a moiety (i.e., chemical entity or compound or portions or fragments thereof), and an endonuclease active site of the PA subunit. The association may be non-covalent, i.e., where the juxtaposition is energetically favored by, for example, hydrogen-bonding, van der Waals, electrostatic, or hydrophobic interactions, or it may be covalent.

The term "endonuclease activity" or "endonucleolytic activity" refers to an enzymatic activity which results in the cleavage of the phosphodiester bond within a polynucleotide chain. In the context of the present invention, the polypeptide fragments possess an endonucleolytic activity, which is preferably not selective for the polynucleotide type, i.e., the polypeptide fragments according to the present invention preferably exhibit endonucleolytic activity for DNA and RNA, preferably for single stranded DNA (ssDNA) or single stranded RNA (ssRNA). In this context, "Single stranded" means that a stretch of preferably at least 3 nucleotides, preferably at least 5 nucleotides, more preferably at least 10 nucleotides within the polynucleotide chain are single stranded, i.e., not base paired to another nucleotide. Preferably, the endonucleolytic activity of the polypeptide fragments according to the present invention is not dependent on recognition sites, i.e., specific nucleotide sequences, but results in unspecific cleavage of polynucleotide chains. For example, the skilled person may test for endonucleolytic activity of polypeptide fragments according to the present invention by incubating RNA or DNA substrates such as panhandle RNA or a linear or circular single stranded DNA, with or without the respective polypeptide fragment, for example, at 37° C. for a certain period of time such as for 5, 10, 20, 40, 60, or 80 minutes, and test for the integrity of the polynucleotides, for example, by gel electrophoresis.

The term "nucleotide" as used herein refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g., as described in Kornberg and Baker, DNA Replication, 2nd Ed. (Freeman, San Francisco, 1992) and further include, but are not limited to, synthetic nucleosides having modified base moieties and/or modified sugar moieties, e.g., described generally by Scheit, Nucleotide Analogs (John Wiley, N.Y., 1980).

The term "isolated polynucleotide" refers to polynucleotides that were (i) isolated from their natural environment, (ii) amplified by polymerase chain reaction, or (iii) wholly or partially synthesized, and means a single or double-stranded polymer of deoxyribonucleotide or ribonucleotide bases and includes DNA and RNA molecules, both sense and anti-sense strands. The term comprises cDNA, cRNA, genomic DNA, and recombinant DNA. A polynucleotide may consist of an entire gene, or a portion thereof.

The term "recombinant vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

"Recombinant host cell", as used herein, refers to a host cell that comprises a polynucleotide that codes for a polypeptide fragment of interest, i.e., the Influenz A pandemic H1N1 PA polypeptide fragment or variants thereof according to the invention. This polynucleotide may be found inside the host cell (i) freely dispersed as such, (ii) incorporated in a recombinant vector, or (iii) integrated into the host cell genome or mitochondrial DNA. The recombinant cell can be used for expression of a polynucleotide of interest or for amplification of the polynucleotide or the recombinant vector of the invention. The term "recombinant host cell" includes the progeny of the original cell which has been transformed, transfected, or infected with the polynucleotide or the recombinant vector of the invention. A recombinant host cell may be a bacterial cell such as an *E. coli* cell, a yeast cell such as *Saccharomyces cerevisiae* or *Pichia pastoris*, a plant cell, an insect cell such as SF9 or High Five cells, or a mammalian cell. Preferred examples of mammalian cells are Chinese hamster ovary (CHO) cells, green African monkey kidney (COS) cells, human embryonic kidney (HEK293) cells, HELA cells, and the like.

As used herein, the term "crystal" or "crystalline" means a structure (such as a three-dimensional solid aggregate) in which the plane faces intersect at definite angles and in which there is a regular structure (such as internal structure) of the constituent chemical species. The term "crystal" can include any one of: a solid physical crystal form such as an experimentally prepared crystal, a crystal structure derivable from the crystal (including secondary and/or tertiary and/or quaternary structural elements), a 2D and/or 3D model based on the crystal structure, a representation thereof such as a schematic representation thereof or a diagrammatic representation thereof, or a data set thereof for a computer. In one aspect, the crystal is usable in X-ray crystallography techniques. Here, the crystals used can withstand exposure to X-ray beams and are used to produce diffraction pattern data necessary to solve the X-ray crystallographic structure. A crystal may be characterized as being capable of diffracting X-rays in a pattern defined by one of the crystal forms depicted in T. L. Blundell and L. N. Johnson, "Protein Crystallography", Academic Press, New York (1976). The term "unit cell" refers to a basic cubic or parallelepiped shaped block. The entire volume of a crystal may be constructed by regular assembly of such blocks. Each unit cell comprises a complete representation of the unit of pattern, the repetition of which builds up the crystal.

The term "space group" refers to the arrangement of symmetry elements of a crystal. In a space group designation the capital letter indicates the lattice type and the other symbols represent symmetry operations that can be carried out on the contents of the asymmetric unit without changing its appearance.

The term "structure coordinates" refers to a set of values that define the position of one or more amino acid residues with reference to a system of axes. The term refers to a data set that defines the three-dimensional structure of a molecule or molecules (e.g., Cartesian coordinates, temperature factors, and occupancies). Structural coordinates can be slightly modified and still render nearly identical three-dimensional structures. A measure of a unique set of structural coordinates is the root mean square deviation of the resulting structure. Structural coordinates that render three-dimensional structures (in particular, a three-dimensional structure of an enzymatically active center) that deviate from one another by a root mean square deviation of less than 3 Å, 2 Å, 1.5 Å, 1.0 Å, or 0.5 Å may be viewed by a person of ordinary skill in the art as very similar.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a variant of the PA polypeptide fragment or the enzymatically active center therein from the backbone of the PA polypeptide fragment or the enzymatically active center therein as defined by the structure coordinates of the PA polypeptide fragment PA-Nter according to FIG. 1.

As used herein, the term "constructing a computer model" includes the quantitative and qualitative analysis of molecular structure and/or function based on atomic structural information and interaction models. The term "modeling" includes conventional numeric-based molecular dynamic and energy minimization models, interactive computer graphic models, modified molecular mechanics models, distance geometry, and other structure-based constraint models.

The term "fitting program operation" refers to an operation that utilizes the structure coordinates of a chemical entity, an enzymatically active center, a binding pocket, molecule or molecular complex, or portion thereof, to associate the chemical entity with the enzymatically active center, the binding pocket, molecule or molecular complex, or portion thereof. This may be achieved by positioning, rotating or translating the chemical entity in the enzymatically active center to match the shape and electrostatic complementarity of the enzymatically active center. Covalent interactions, non-covalent interactions such as hydrogen bond, electrostatic, hydrophobic, van der Waals interactions, and non-complementary electrostatic interactions such as repulsive charge-charge, dipole-dipole and charge-dipole interactions may be optimized. Alternatively, one may minimize the deformation energy of binding of the chemical entity to the enzymatically active center.

As used herein, the term "test compound" refers to an agent comprising a compound, molecule, or complex that is being tested for its ability to inhibit the endonucleolytic activity of the polypeptide fragment of interest, i.e., the PA polypeptide fragment of the invention or variants thereof possessing endonucleolytic acitvity. Test compounds can be any agents including, but not restricted to, peptides, peptoids, polypeptides, proteins (including antibodies), lipids, metals, nucleotides, nucleotide analogs, nucleosides, nucleic acids, small organic or inorganic molecules, chemical compounds, elements, saccharides, isotopes, carbohydrates, imaging agents, lipoproteins, glycoproteins, enzymes, analytical probes, polyamines, and combinations and derivatives thereof. The term "small molecules" refers to molecules that have a molecular weight between 50 and about 2,500 Daltons, preferably in the range of 200-800 Daltons. In addition, a test compound according to the present invention may optionally comprise a detectable label. Such labels include, but are not limited to, enzymatic labels, radioisotope or radioactive compounds or elements, fluorescent compounds or metals, chemiluminescent compounds and bioluminescent compounds. Well known methods may be used for attaching such a detectable label to a test compound. The test compound of the invention may also comprise complex mixtures of substances, such as extracts containing natural products, or the products of mixed combinatorial syntheses. These can also be tested and the component that inhibits the endonucleolytic activity of the target polypeptide fragment can be purified from the mixture in a subsequent step. Test compounds can be derived or selected from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant and animal cell and tissue extracts can be used. Additionally, test compounds can be synthetically produced using combinatorial chemistry either as individual compounds or as mixtures. A collection of compounds made using combinatorial chemistry is referred to herein as a combinatorial library.

In the context of the present invention, "a compound which modulates the endonucleolytic activity" may increase or decrease, preferably inhibit the endonucleolytic activity of the PA subunit of the Influenza A 2009 pandemic H1N1 virus or the Influenza A 2009 pandemic H1N1 virus RNA-dependent RNA polymerase or a variant thereof. Preferably, such a compound is specific for the endonucleolytic activity of the Influenza A 2009 pandemic H1N1 PA subunit or variant thereof and does not modulate, preferably decrease the endonucleolytic activity of other endonucleases, in particular mammalian endonucleases.

The term "a compound which decreases the endonucleolytic activity" means a compound which decreases the endonucleolytic activity of the PA subunit of the Influenza A 2009 pandemic H1N1 virus or the Influenza A 2009 pandemic H1N1 virus RNA-dependent RNA polymerase or a variant thereof by 50%, more preferably by 60%, even more preferably by 70%, even more preferably by 80%, even more preferably by 90%, and most preferably by 100% compared to the endonucleolytic activity of said PA subunit or a variant thereof without said compound but with otherwise the same reaction conditions, i.e., buffer conditions, reaction time and temperature.

It is most preferred that the compound which decreases the endonucleolytic activity of the PA subunit of the Influenza A 2009 pandemic H1N1 virus or a variant thereof inhibits said activity, i.e., decreases said activity by at least 95%, preferably by 100% compared to the activity without the compound. It is particularly preferred that the compound that decreases or inhibits the endonucleolytic activity of the PA subunit of the Influenza A 2009 pandemic H1N1 virus or a variant thereof specifically decreases or inhibits the endonucleolytic activity of said PA subunit or a variant thereof but does not inhibit the endonucleolytic activity of other endonucleases such as RNase H or restriction endonucleases to the same extent, preferably not at all. For example, the skilled person may set up the following samples with the same buffer and reaction conditions as well as substrate and endonuclease concentrations: (1) substrate such as panhandle RNA, endonucleolytically active PA H1N1 polypeptide fragment or variant thereof, (2) substrate such as panhandle RNA, endonucleolytically active PA H1N1 polypeptide fragment or variant thereof, test compound, (3) substrate such as panhandle RNA, reference endonuclease such as RNase H, (4) substrate such as panhandle RNA, reference nucleotide such as RNAse H, test compound. After incubation of the samples, the skilled person may analyze the substrate, for example, by gel electrophoresis. Test compounds which result in cleaved substrate in sample (4) and intact substrate in sample (2) are preferred.

The term "in a high-throughput setting" refers to high-throughput screening assays and techniques of various types which are used to screen libraries of test compounds for their ability to inhibit the endonuclease activity of the polypeptide fragment of interest. Typically, the high-throughput assays are performed in a multi-well format and include cell-free as well as cell-based assays.

The term "antibody" refers to both monoclonal and polyclonal antibodies, i.e., any immunoglobulin protein or portion thereof which is capable of recognizing an antigen or hapten, i.e., the Influenza A 2009 pandemic H1N1 PA polypeptide fragment possessing endonucleolytic activity or a peptide thereof. In a preferred embodiment, the antibody is capable of binding to the enzymatically (endonucleolytically) active center within the Influenza A 2009 pandemic H1N1 PA polypeptide fragment or variant thereof. Antigen-binding portions of the antibody may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies such as humanized antibodies, diabodies, and polypeptides that contain at least a portion of an antibody that is sufficient to confer specific antigen binding to the polypeptide.

The term "pharmaceutically acceptable salt" refers to a salt of a compound identifiable by the methods of the present invention or a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci. 66:1-19 (1977)).

The term "excipient" when used herein is intended to indicate all substances in a pharmaceutical formulation which are not active ingredients such as, e.g., carriers, binders, lubricants, thickeners, surface active agents, preservatives, emulsifiers, buffers, flavoring agents, or colorants.

The term "pharmaceutically acceptable carrier" includes, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

DETAILED DESCRIPTION

The present inventors surprisingly found that a small independently folded domain derived from the N-terminus of the PA subunit of Influenza A 2009 pandemic H1N1 virus RNA-dependent RNA polymerase exhibits the functional properties of the endonuclease reported for the trimeric complex, although this activity was thought to be detectable only in the trimeric complex. Moreover, the inventors found that this PA polypeptide fragment can easily be produced by recombinant means and, thus, is suitable for in vitro studies on the endonucleolytic activity and and its modulation. The present inventors surprisingly found that the domain derived from the N-terminus of the PA subunit of Influenza A 2009 pandemic H1N1 virus RNA-dependent RNA polymerase readily crystallized and that, thus, said domain is very dedicated for the identification, selection and design of new anti-viral compounds targeting the endonuclease activity of the Influenza A 2009 pandemic H1N1 polymerase as well as for the optimization of previously identified compounds by computer methods.

It is one aspect of the present invention to provide a polypeptide fragment comprising an amino-terminal fragment of the PA subunit of a viral RNA-dependent RNA polymerase possessing endonuclease activity, wherein said PA subunit is from Influenza A 2009 pandemic H1N1 virus according to SEQ ID NO: 2 or is a variant thereof, wherein said variant comprises the amino acid serine at an amino acid position 186 according to SEQ ID NO: 2 or at an amino acid position corresponding thereto.

In a preferred embodiment of the present invention, said variant comprises the amino acids 1 to 198 of the amino acid sequence set forth in SEQ ID NO: 2 with amino acids 52 to 64 replaced by the amino acid glycine (SEQ ID NO:14). In a further preferred embodiment of the present invention, said variant comprises the amino acids 1 to 198 of the amino acid sequence set forth in SEQ ID NO: 2 with amino acids 52 to 72 replaced by the amino acid glycine (SEQ ID NO:15). In another further preferred embodiment of the present invention, said variant comprises the amino acids 1 to 198 of the amino acid sequence set forth in SEQ ID NO: 2 with amino acids 52 to 69 replaced by the amino acid glycine (SEQ ID NO:16).

It is preferred that the polypeptide fragment according to the present invention is soluble, preferably in an aqueous solution. The minimal length of the polypeptide fragment of the present invention is determined by its ability to cleave polynucleotide chains such as panhandle RNA or single stranded DNA, i.e., the minimal length of the polypeptide is determined by its endonucleolytic activity. Preferably, the endonuclease activity is not dependent on the polynucleotide type, and thus, may be exerted on DNA and RNA, preferably on single stranded DNA and RNA. Preferably, the endonuclease activity is not dependent on specific recognition sites within the substrate polynucleotide.

In a preferred embodiment, the polypeptide fragment according to the present invention is suitable for crystallization, i.e., preferably the polypeptide fragment is crystallizable. Preferably, the crystals obtainable from the polypeptide fragment according to the invention are suitable for structure determination of the polypeptide fragment using X-ray crystallography. Preferably, said crystals are greater than 25 micron cubes and preferably are radiation stable enough to permit more than 85% diffraction data completeness at resolution of preferably 3.5 Å or better to be collected upon exposure to monochromatic X-rays.

In one embodiment, the polypeptide fragment is crystallizable using (i) an aqueous protein solution, i.e. the crystallization solution, with a protein concentration of 5 to 20 mg/ml, e.g. of 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mg/ml, preferably of 8 to 15 mg/ml, most preferably of 10 to 15 mg/ml in a buffer system such as HEPES or Tris-HCl at concentrations ranging from 10 mM to 3 M, preferably 10 mM to 2 M, more preferably 20 mM to 1 M, at pH 3 to pH 9, preferably pH 4 to pH 9, more preferably pH 7 to pH 9, and (ii) a precipitant/reservoir solution comprising one or more substances such as sodium formate, ammonium sulphate, lithium sulphate, magnesium acetate, manganese acetate, sodium chloride, glycerol or ethylene glycol.

Optionally, the protein solution may contain one or more salts such as monovalent salts, e.g., NaCl, KCl, or LiCl, preferably NaCl, at concentrations ranging from 10 mM to 1 M, preferably 20 mM to 500 mM, more preferably 50 mM to 200 mM, and/or divalent salts, e.g., $MnCl_2$, $CaCl_2$, $MgCl_2$, $ZnCl_2$, or $CoCl_2$, preferably $MgCl_2$ and $MnCl_2$, at concentrations ranging from 0.1 to 50 mM, preferably 0.5 to 25 mM, more preferably 1 to 10 mM or 1 to 5 mM.

Preferably, the precipitant/reservoir solution comprises sodium formate at concentrations ranging from 0.5 to 2 M, preferably 1 to 1.8 M, a buffer system such as HEPES at concentrations ranging from 10 mM to 1 M, preferably 50 mM to 500 mM, more preferably 75 to 150 mM, at preferably pH 4 to 8, more preferably pH 5 to 7, and/or ethylene glycol at concentrations ranging from 1% to 20%, preferably 2% to 8%, more preferably 2 to 5%.

The PA polypeptide fragment or variant thereof is preferably 85% to 100% pure, more preferably 90% to 100% pure, even more preferably 95% to 100% pure in the crystallization solution. To produce crystals, the protein solution suitable for crystallization may be mixed with an equal volume of the precipitant solution.

In a preferred embodiment, the crystallization medium comprises 0.05 to 2 µl, preferably 0.8 to 1.2 µl, of protein solution suitable for crystallization mixed with a similar, preferably equal volume of precipitant solution comprising 1.0 to 2.0 M sodium formate, 80 to 120 mM HEPES pH 6.5 to pH 7.5, and 2 to 5% glycol or glycerol.

In another embodiment, the precipitant solution comprises, preferably essentially consists of or consists of 1.6 M sodium formate, 0.1 M HEPES pH 7.0, and 5% glycol or glycerol, and the crystallization/protein solution comprises, preferably essentially consists or consists of 10 to 15 mg/ml in 20 mM HEPES pH 7.5, 150 mM NaCl, 2.0 mM $MnCl_2$, and 2.0 mM $MgCl_2$.

In another embodiment, the PA polypeptide fragment is co-crystallizable with a compound, preferably with a compound that modulates, preferably inhibits, the endonuclease activity of the PA polypeptide fragment, preferably with a compound according to Tables 1 or 2, using (i) an aqueous protein solution with a concentration of the PA polypeptide fragment of 5 to 20 mg/ml, e.g., 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mg/ml, preferably of 8 to 15 mg/ml, most preferably of 10 to 15 mg/ml in a buffer system such as HEPES or Tris-HCl at concentrations ranging from 10 mM to 3 M, preferably 10 mM to 2 M, more preferably 20 mM to 1 M, at pH 3 to pH 9, preferably pH 4 to pH 9, more preferably pH 7 to pH 9, and (ii) a precipitant/reservoir solution comprising one or more substances such as sodium formate, ammonium sulphate, lithium sulphate, magnesium acetate, manganese acetate, sodium chloride, ethylene glycol, glycerol, or PEG. For co-crystallization, a compound, preferably a compound that modulates, e.g. inhibits, the endonuclease activity of the PA polypeptide fragment, preferably a compound according to Tables 1 or 2, is added to the aqueous protein solution to a final concentration of between 0.5 and 5 mM, preferably of between 1.5 and 5 mM, i.e. 0.5, 1, 1.5, 2, 2.5, 3, 4.5 or 5 mM.

Optionally, the protein solution may contain one or more salts such as monovalent salts, e.g., NaCl, KCl, or LiCl, preferably NaCl, at concentrations ranging from 10 mM to 1 M, preferably 20 mM to 500 mM, more preferably 50 mM to 200 mM, and/or divalent salts, e.g., $MnCl_2$, $CaCl_2$, $MgCl_2$, $ZnCl_2$, or $CoCl_2$, preferably $MgCl_2$ and $MnCl_2$, at concentrations ranging from 0.1 to 50 mM, preferably 0.5 to 25 mM, more preferably 1 to 10 mM or 1 to 5 mM.

Preferably, the precipitant/reservoir solution comprises ammonium sulphate at concentrations ranging from 0.1 to 2.5 M, preferably 0.1 to 2.0 M, a buffer system such as Bis-Tris at concentrations ranging from 10 mM to 1 M, preferably 50 mM to 500 mM, more preferably 75 to 150 mM, at preferably pH 4 to 7, more preferably pH 5 to 6, and/or PEG such as PEG 3350 at concentrations ranging from 1% to 30%, preferably 15% to 30%, more preferably 20 to 25%.

The PA polypeptide fragment or variant thereof is preferably 85% to 100% pure, more preferably 90% to 100% pure, even more preferably 95% to 100% pure in the protein solution. For co-crystallization, the aqueous protein solution comprising the PA polypeptide fragment or variant thereof and the compound may be mixed with an equal volume of the precipitant solution.

In a preferred embodiment, the protein solution comprises, preferably essentially consists or consists of 10 to 15 mg/ml PA polypeptide fragment in 20 mM HEPES pH 7.5, 150 mM NaCl, 2.0 mM $MnCl_2$, and 2.0 mM $MgCl_2$ and 4-[3-[(4-chlorophenyl)methyl]-1-(phenylmethyl)-3-piperidinyl]-2-hydroxy-4-oxo-2-butenoic acid (EMBL-R05-3) in a final concentration of 1.5 mM, and the reservoir solution/precipitant solution comprises, preferably essentially consists of or consists of 2.0 M ammonium sulphate and 0.1M Bis-Tris pH5.5 (see also Table 1).

In another preferred embodiment, the protein solution comprises, preferably essentially consists or consists of 10 to 15 mg/ml PA polypeptide fragment in 20 mM HEPES pH 7.5, 150 mM NaCl, 2.0 mM $MnCl_2$, and 2.0 mM $MgCl_2$ and 4-[4-[(4-chlorophenyl)methyl]-1-(cyclohexylmethyl)-4-piperidinyl]-2-hydroxy-4-oxo-2-butenoic acid (EMBL-R05-2) in a final concentration of 1.5 mM, preferably soaked into crystals initially grown with ribo-Uridine Monophosphate (rUMP), and the reservoir solution/precipitant solution comprises, preferably essentially consists of or consists of 0.1 M ammonium sulphate, 0.1 M Bis-Tris pH5.5 and 25% (w/v) PEG 3350 (see also Table 1).

In a further preferred embodiment, the protein solution comprises, preferably essentially consists or consists of 10 to 15 mg/ml PA polypeptide fragment in 20 mM HEPES pH 7.5, 150 mM NaCl, 2.0 mM MnCl$_2$, and 2.0 mM MgCl$_2$ and ribo-Uridine Monophosphate (rUMP) in a final concentration of 5 mM, and the reservoir solution/precipitant solution comprises, preferably essentially consists of or consists of 0.1 M ammonium sulphate, 0.1 M Bis-Tris pH5.5 and 25% (w/v) PEG 3350 (see also Table 1).

Other preferred reservoir solutions/precipitant solutions for the co-crystallization of the PA polypeptide fragment or variant thereof, e.g. with 4-[3-[(4-chlorophenyl)methyl]-1-(phenylmethylsulpho)-3-piperidinyl]-2-hydroxy-4-oxo-2-butenoic acid (EMBL-R05-1) or with [(2R,3R)-5,7-dihydroxy-2-(3,4,5-trihydroxyphenyl)chroman-3-yl]3,4,5-trihydroxybenzoate (EGCG), can further be taken from Table 1.

Crystals can be grown by any method known to the person skilled in the art including, but not limited to, hanging and sitting drop techniques, sandwich-drop, dialysis, and micro-batch or microtube batch devices. It would be readily apparent to one of skill in the art to vary the crystallization conditions disclosed above to identify other crystallization conditions that would produce crystals of PA polypeptide fragments of the inventions or variants thereof alone or in complex with a compound. Such variations include, but are not limited to, adjusting pH, protein concentration and/or crystallization temperature, changing the identity or concentration of salt and/or precipitant used, using a different method for crystallization, or introducing additives such as detergents (e.g., TWEEN 20 (monolaurate), LDOA, Brij 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

Microseeding may be used to increase the size and quality of crystals. In brief, micro-crystals are crushed to yield a stock seed solution. The stock seed solution is diluted in series. Using a needle, glass rod or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

The manner of obtaining the structure coordinates as shown in FIGS. 1 to 5, interpretation of the coordinates and their utility in understanding the protein structure, as described herein, are commonly understood by the skilled person and by reference to standard texts such as J. Drenth, "Principles of protein X-ray crystallography", 2$^{nd}$ Ed., Springer Advanced Texts in Chemistry, New York (1999); and G. E. Schulz and R. H. Schirmer, "Principles of Protein Structure", Springer Verlag, New York (1985). For example, X-ray diffraction data is first acquired, often using cryoprotected (e.g., with 20% to 30% glycerol) crystals frozen to 100 K, e.g., using a beamline at a synchrotron facility or a rotating anode as an X-ray source. Then, the phase problem is solved by a generally known method, e.g., multiwavelength anomalous diffraction (MAD), multiple isomorphous replacement (MIR), single wavelength anomalous diffraction (SAD), or molecular replacement (MR). The substructure may be solved using SHELXD (Schneider and Sheldrick, 2002, Acta Crystallogr. D. Biol. Crystallogr. (Pt 10 Pt 2), 1772-1779), phases calculated with SHARP (Vonrhein et al., 2006, Methods Mol. Biol. 364:215-30), and improved with solvent flattening and non-crystallographic symmetry averaging, e.g., with RESOLVE (Terwilliger, 2000, Acta Cryst. D. Biol. Crystallogr. 56:965-972). Model autobuilding can be done, e.g., with ARP/wARP (Perrakis et al., 1999, Nat. Struct. Biol. 6:458-63) and refinement with, e.g. REFMAC (Murshudov, 1997, Acta Crystallogr. D. Biol. Crystallogr. 53: 240-255).

Preferably, the amino terminal PA fragment comprised within the polypeptide fragment according to the present invention corresponds to, preferably essentially consists or consists of, at least amino acids 1 to 190, preferably amino acids 1 to 198, preferably amino acids 1 to 200, of the PA subunit of the RNA-dependent RNA polymerase of Influenza A 2009 pandemic H1N1 virus according to SEQ ID NO: 2 or variants thereof.

In a preferred embodiment, the polypeptide fragment according to the present invention is purified to an extent to be suitable for crystallization, preferably it is 85% to 100%, more preferably 90% to 100%, most preferably 95% to 100% pure. In another preferred embodiment, the polypeptide fragment according to the present invention is purified to an extent to be suitable for co-crystallization, preferably it is 85% to 100%, more preferably 90% to 100%, most preferably 95% to 100% pure.

In another embodiment, the polypeptide fragment according to the present invention is capable of binding to divalent cations. Preferably, the polypeptide fragment according to the present invention is bound to one or more divalent cation(s), preferably it is bound to two divalent cations. In this context, the divalent cation is preferably selected form the group consisting of manganese, cobalt, calcium, magnesium, and zinc, and is more preferably manganese or cobalt, most preferably manganese and/or magnesium. Thus, in a preferred embodiment, the polypeptide fragment of the present invention is present in complex with (i) two manganese cations, (ii) two magnesium cations, or (iii) one manganese and one magnesium cation. In a preferred embodiment, the divalent cations are coordinated by amino acids corresponding to amino acids Glu80 and Asp108 (second cation) and amino acids corresponding to amino acids His41, Asp108, Ile120 and Glu119 (first cation) as set forth in SEQ ID NO: 2. In preferred embodiment, the divalent cation is manganese for site 1 and manganese or magnesium for site 2, i.e. manganese for site 1 and magnesium for site 2 (see FIG. 6) or manganese for site 1 and manganese for site 2 (see FIGS. 7 to 10, 17 and 18)

In a further embodiment, the polypeptide fragment according to the present invention is a polypeptide fragment, wherein the N-terminus is identical to or corresponds to amino acid position 15 or lower, e.g., at position 15, 14, 13, 12, 11, 10, 9, 8, 7, 6, 5, 4, 3, 2, or 1, and the C-terminus is identical to or corresponds to an amino acid at a position selected from positions 186 to 200, e.g., 186, 187, 188, 189, 190, 191, 192, 193, 194, 195, 196, 197, 198, 199, or 200 of the amino acid sequence of the PA subunit according to SEQ ID NO: 2, preferably the C-terminus is identical to or corresponds to an amino acid at a position selected from 190 to 200, more preferably 190 to 198 of the amino acid sequence of the PA subunit according to SEQ ID NO: 2, or is a variant thereof, wherein said variant comprises the amino acid serine at an amino acid position 186 according to SEQ ID NO: 2 or at an amino acid position corresponding thereto and retains the endonuclease activity.

In a preferred embodiment of the present invention, said variant comprises SEQ ID NO:14 (the amino acids 1 to 198 of the amino acid sequence set forth in SEQ ID NO: 2 with amino acids 52 to 64 replaced by the amino acid glycine). In a more preferred embodiment of the present invention, said variant consists of SEQ ID NO:14 (the amino acids 1 to 198 of the amino acid sequence set forth in SEQ ID NO: 2 with amino acids 52 to 64 replaced by the amino acid glycine) and optionally of an amino-terminal linker having the amino acid sequence MGSGMA (SEQ ID NO: 3).

In a further preferred embodiment of the present invention, said variant comprises SEQ ID NO:15 (the amino acids 1 to 198 of the amino acid sequence set forth in SEQ ID NO: 2 with amino acids 52 to 72 replaced by the amino acid glycine). In a more preferred embodiment of the present invention, said variant consists of SEQ ID NO:15 (the amino acids 1 to 198 of the amino acid sequence set forth in SEQ ID NO: 2 with amino acids 52 to 72 replaced by the amino acid glycine) and optionally of an amino-terminal linker having the amino acid sequence MGSGMA (SEQ ID NO: 3).

In another further preferred embodiment of the present invention, said variant comprises SEQ ID NO:16 (the amino acids 1 to 198 of the amino acid sequence set forth in SEQ ID NO: 2 with amino acids 52 to 69 replaced by the amino acid glycine). In a more preferred embodiment of the present invention, said variant consists of SEQ ID NO:16 (the amino acids 1 to 198 of the amino acid sequence set forth in SEQ ID NO: 2 with amino acids 52 to 69 replaced by the amino acid glycine) and optionally of an amino-terminal linker having the amino acid sequence MGSGMA (SEQ ID NO: 3).

Preferably, said polypeptide fragment has or corresponds to an amino acid sequence selected from the group of amino acid sequences consisting of amino acids 5 to 190, 10 to 190, 15 to 190, 20 to 190, 5 to 198, 10 to 198, 15 to 198, 20 to 198 of the amino acid sequence set forth in SEQ ID NO: 2 and variants thereof, wherein said variants comprises the amino acid serine at an amino acid position 186 according to SEQ ID NO: 2 or at an amino acid position corresponding thereto and retain the endonuclease activity.

In a further embodiment, the polypeptide fragment (variant) according to the present invention
(a) consists of SEQ ID NO:13 (amino acids 1 to 198 of the amino acid sequence set forth in SEQ ID NO: 2) and optionally of an amino-terminal linker having the amino acid sequence MGSGMA (SEQ ID NO: 3) and has the structure defined by (i) the structure coordinates as shown in FIG. 1, (ii) the structure coordinates as shown in FIG. 2, (iii) the structure coordinates as shown in FIG. 3, (iv) the structure coordinates as shown in FIG. 4, or (v) the structure coordinates as shown in FIG. 5, or
(b) consists of SEQ ID NO:14 (amino acids 1 to 198 of the amino acid sequence set forth in SEQ ID NO: 2 with amino acids 52 to 64 replaced by the amino acid glycine) and optionally of an amino-terminal linker having the amino acid sequence MGSGMA (SEQ ID NO: 3) and has the structure defined by (vi) the structure coordinates as shown in FIG. 15, or (vii) the structure coordinates as shown in FIG. 16.

It is preferred that said polypeptide fragment according to the present invention has the crystal structure defined by the structure coordinates as shown in FIG. 1 without co-crystallization with a compound (native structure).

It is further preferred that said polypeptide fragment (variant) according to the present invention has the crystal structure defined by the structure coordinates as shown in FIG. 2 to 5, 15 or 16 after co-crystallization with a compound, preferably with a compound that modulates, preferably inhibits, the endonuclease activity of said polypeptide fragment. It is particularly preferred that said polypeptide fragment (variant) has the structure defined by the structure coordinates as shown in FIG. 2 to 5, 15 or 16 after co-crystallization with a compound according to Tables 1 or 2, i.e. the structure defined by the structure coordinates as shown in FIGS. 2 and 3 after co-crystallization with 4-[3-[(4-chlorophenyl)methyl]-1-(phenylmethyl)-3-piperidinyl]-2-hydroxy-4-oxo-2-butenoic acid (EMBL-R05-3), the structure defined by the structure coordinates as shown in FIG. 4 after co-crystallization with 4-[4-[(4-chlorophenyl)methyl]-1-(cyclohexylmethyl)-4-piperidinyl]-2-hydroxy-4-oxo-2-butenoic acid, (EMBL-R05-2), the structure defined by the structure coordinates as shown in FIG. 5 after co-crystallization with ribo-uridine monophosphate (rUMP), the structure defined by the structure coordinates as shown in FIG. 15 after co-crystallization with 4-[3-[(4-chlorophenyl)methyl]-1-(phenylmethylsulpho)-3-piperidinyl]-2-hydroxy-4-oxo-2-butenoic acid (EMBL-R05-1), or the structure defined by the structure coordinates as shown in FIG. 16 after co-crystallization with [(2R,3R)-5,7-dihydroxy-2-(3,4,5-trihydroxyphenyl)chroman-3-yl]3,4,5-trihydroxybenzoate (EGCG).

Considering the above, the skilled person will readily understand that said polypeptide fragment (variant) has a crystal structure which is only defined by the structure coordinates of its amino acids and optionally of its bound divalent cations comprised in FIG. 1, 2 to 5, 15 or 16 and that it is not defined by the structure coordinates of the respective compound used for co-crystallization which are also comprised in FIG. 2 to 5, 15 or 16, i.e. the compound EMBL-R05-3 has the residue descriptor ci3 in FIGS. 2 and 3, the compound EMBL-R05-2 has the residue descriptor cit in FIG. 4, the compound rUMP has the residue descriptor U in FIG. 5, the compound EMBL-R05-1 has the residue descriptor ci1 in FIG. 15 and the compound EGCG has the residue descriptor tte in FIG. 16.

It is also preferred that said polypeptide fragment (variant) having the structure defined by the structure coordinates as shown in FIG. 1 has a crystalline form with space group C2 and unit cell dimensions of a=26.36 nm±0.5 nm, b=6.62 nm±0.3 nm, c=6.63 nm±0.3 nm, $\alpha$=90 deg, $\beta$=96±2 deg, $\gamma$=90 deg, having the structure defined by the structure coordinates as shown in FIGS. 2 to 5 has a crystalline form with space group $P2_12_12_1$ and unit cell dimensions of a=5.46±0.3 nm, b=12.25±0.4 nm, c=13.0±0.3 nm, $\alpha$=90 deg, $\beta$=90 deg, $\gamma$=90 deg, having the structure defined by the structure coordinates as shown in FIG. 15 has a crystalline form with space group $P 6_2 22$ and unit cell dimensions of a=7.50 nm±0.3 nm, b=7.50 nm±0.3 nm, c=12.00 nm±0.5 nm, $\alpha$=90 deg, $\beta$=90 deg, $\gamma$=120 deg, or having the structure defined by the structure coordinates as shown in FIG. 16 has a crystalline form with space group $P6_4 22$ and unit cell dimensions of a=9.99 nm±0.5 nm, b=9.99 nm±0.5 nm, c=8.27 nm±0.3 nm, $\alpha$=90 deg, $\beta$=90 deg, $\gamma$=120 deg.

Preferably, the crystal of the polypeptide fragment (variant) diffracts X-rays to a resolution of 2.8 Å or higher, preferably 2.6 Å or higher, more preferably 2.5 Å or higher, even more preferably 2.4 Å or higher, most preferably 2.1 Å or higher or 1.9 Å or higher. For example, the crystal of the polypeptide fragment (variant) diffracts X-rays to a resolution of 1.9, 2.0, 2.1, 2.2, 2.3, 2.4, 2.5, 2.6, 2.7, 2.8 Å or higher.

It is another aspect of the present invention to provide an isolated polynucleotide coding for the above-mentioned (isolated) PA polypeptide fragments and variants thereof according to the present invention.

In a preferred embodiment of the present invention, the isolated polynucleotide codes for the PA polypeptide fragment which comprises SEQ ID NO:13 (the amino acids 1 to 198 of the amino acid sequence set forth in SEQ ID NO: 2).

In another preferred embodiment of the present invention, the isolated polynucleotide codes for the PA polypeptide fragment variant which comprises SEQ ID NO:14 (the amino acids 1 to 198 of the amino acid sequence set forth in SEQ ID NO: 2 with amino acids 52 to 64 replaced by the amino acid glycine).

In a further preferred embodiment of the present invention, the isolated polynucleotide codes for the PA polypeptide fragment variant which comprises SEQ ID NO:15 (the amino acids 1 to 198 of the amino acid sequence set forth in SEQ ID NO: 2 with amino acids 52 to 72 replaced by the amino acid glycine).

In another further preferred embodiment of the present invention, the isolated polynucleotide codes for the PA polypeptide fragment variant which comprises SEQ ID NO:16 (the amino acids 1 to 198 of the amino acid sequence set forth in SEQ ID NO: 2 with amino acids 52 to 69 replaced by the amino acid glycine).

The molecular biology methods applied for obtaining such isolated nucleotide fragments are generally known to the person skilled in the art (for standard molecular biology methods see Sambrook et al., Eds., "Molecular Cloning: A Laboratory Manual", Cold Spring Harbor Laboratory Press, Cold Spring Harbor, N.Y. (1989), which is incorporated herein by reference). For example, RNA can be isolated from Influenza A 2009 pandemic H1N1 virus infected cells and cDNA generated applying reverse transcription polymerase chain reaction (RT-PCR) using either random primers (e.g., random hexamers of decamers) or primers specific for the generation of the fragments of interest. The fragments of interest can then be amplified by standard PCR using fragment specific primers.

The isolated polynucleotides coding for the Influenza A 2009 pandemic H1N1 virus RNA-dependent RNA polymerase PA subunit fragments are derived from SEQ ID NO: 1. In this context, "derived" refers to the fact that SEQ ID NO: 1 encodes the full-length PA polypeptide and, thus, polynucleotides coding for preferred PA polypeptide fragments may comprise deletions at the 3'- and/or 5'-ends of the polynucleotides as required by the respectively encoded PA polypeptide fragments.

In another aspect, the present invention relates to a recombinant vector comprising the isolated polynucleotide according to the present invention. The person skilled in the art is well aware of techniques used for the incorporation of polynucleotide sequences of interest into vectors (also see Sambrook et al., 1989, supra). Such vectors include any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors may be expression vectors suitable for prokaryotic or eukaryotic expression. Said plasmids may include an origin of replication (ori), a multiple cloning site, and regulatory sequences such as promoter (constitutive or inducible), transcription initiation site, ribosomal binding site, transcription termination site, polyadenylation signal, and selection marker such as antibiotic resistance or auxotrophic marker based on complementation of a mutation or deletion. In one embodiment the polynucleotide sequence of interest is operably linked to the regulatory sequences.

In another embodiment, said vector includes nucleotide sequences coding for epitope-, peptide-, or protein-tags that facilitate purification of polypeptide fragments of interest. Such epitope-, peptide-, or protein-tags include, but are not limited to, hemagglutinin-(HA-), FLAG-, myc-tag, poly-His-tag, glutathione-S-transferase-(GST-), maltose-binding-protein-(MBP-), NusA-, and thioredoxin-tag, or fluorescent protein-tags such as (enhanced) green fluorescent protein ((E)GFP), (enhanced) yellow fluorescent protein ((E)YFP), red fluorescent protein (RFP) derived from Discosoma species (DsRed) or monomeric (mRFP), cyan fluorescence protein (CFP), and the like. In a preferred embodiment, the epitope-, peptide-, or protein-tags can be cleaved off the polypeptide fragment of interest, for example, using a protease such as thrombin, Factor Xa, PreScission, TEV protease, and the like. Preferably, the tag can be cleaved of with a TEV protease. The recognition sites for such proteases are well known to the person skilled in the art. For example, the seven amino acid consensus sequence of the TEV protease recognition site is Glu-X-X-Tyr-X-Gln-Gly/Ser, wherein X may be any amino acid and is in the context of the present invention preferably Glu-Asn-Leu-Tyr-Phe-Gln-Gly (SEQ ID NO: 12). In another embodiment, the vector includes functional sequences that lead to secretion of the polypeptide fragment of interest into the culture medium of the recombinant host cells or into the periplasmic space of bacteria. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

In another aspect, the present invention provides a recombinant host cell comprising the isolated polynucleotide according to the present invention or the recombinant vector according to the present invention. The recombinant host cells may be prokaryotic cells such as archea and bacterial cells or eukaryotic cells such as yeast, plant, insect, or mammalian cells. In a preferred embodiment the host cell is a bacterial cell such as an *E. coli* cell. The person skilled in the art is well aware of methods for introducing said isolated polynucleotide or said recombinant vector into said host cell. For example, bacterial cells can be readily transformed using, for example, chemical transformation, e.g., the calcium chloride method, or electroporation. Yeast cells may be transformed, for example, using the lithium acetate transformation method or electroporation. Other eukaryotic cells can be transfected, for example, using commercially available liposome-based transfection kits such as Lipofectamine™ (Invitrogen), commercially available lipid-based transfection kits such as Fugene (Roche Diagnostics), polyethylene glycol-based transfection, calcium phosphate precipitation, gene gun (biolistic), electroporation, or viral infection. In a preferred embodiment of the invention, the recombinant host cell expresses the polynucleotide fragment of interest. In an even more preferred embodiment, said expression leads to soluble polypeptide fragments of the invention. These polypeptide fragments may be purified using protein purification methods well known to the person skilled in the art, optionally taking advantage of the above-mentioned epitope-, peptide-, or protein-tags.

In another aspect, the present invention relates to a method for identifying compounds, which modulate the endonuclease activity of the PA subunit of a RNA-dependent RNA polymerase from Influenza A 2009 pandemic H1N1 virus or a variant thereof comprising the steps of:

(a) constructing a computer model of the active site defined by (i) the structure coordinates of the polypeptide fragment according to the present invention as shown in FIG. 1, (ii) the structure coordinates of the polypeptide fragment according to the present invention as shown in FIG. 2, (iii) the structure coordinates of the polypeptide fragment according to the present invention as shown in FIG. 3, (iv) the structure coordinates of the polypeptide fragment according to the present invention as shown in FIG. 4, (v) the structure coordinates of the polypeptide fragment according to the present invention as shown in FIG. 5, (vi) the structure coordinates of the polypeptide fragment (variant) according to the present invention as shown in FIG. 15, and/or (vii) the structure coordinates of the polypeptide fragment (variant) according to the present invention as shown in FIG. 16,
(b) selecting a potential modulating compound by a method selected from the group consisting of:
  (i) assembling molecular fragments into said compound,
  (ii) selecting a compound from a small molecule database, and
  (iii) de novo ligand design of said compound;
(c) employing computational means to perform a fitting program operation between computer models of the said compound and the said active site in order to provide an energy-minimized configuration of the said compound in the active site; and
(d) evaluating the results of said fitting operation to quantify the association between the said compound and the active site model, whereby evaluating the ability of said compound to associate with the said active site.

In a preferred embodiment, a computer model of the active site defined by (i) the structure coordinates of the polypeptide fragment according to the present invention (i.e. amino acid structure coordinates) as shown in FIG. 1 and the structure coordinates of the divalent cations as shown in FIG. 1, (ii) the structure coordinates of the polypeptide fragment according to the present invention (i e amino acid structure coordinates) as shown in FIG. 2 and the structure coordinates of the divalent cations as shown in FIG. 2, (iii) the structure coordinates of the polypeptide fragment according to the present invention as shown in FIG. 3 and the structure coordinates of the divalent cations as shown in FIG. 3, (iv) the structure coordinates of the polypeptide fragment according to the present invention as shown in FIG. 4 and the structure coordinates of the divalent cations as shown in FIG. 4, (v) the structure coordinates of the polypeptide fragment according to the present invention as shown in FIG. 5 and the structure coordinates of the divalent cations as shown in FIG. 5, (vi) the structure coordinates of the polypeptide fragment (variant) according to the present invention (i e amino acid structure coordinates) as shown in FIG. 15 and the structure coordinates of the divalent cations as shown in FIG. 15, and/or (vii) the structure coordinates of the polypeptide fragment (variant) according to the present invention (i e amino acid structure coordinates) as shown in FIG. 16 and the structure coordinates of the divalent cations as shown in FIG. 16 is constructed in step a) of the method of the present invention.

Preferably, the modulating compound associates with, preferably binds to, the endonucleolytically active site within the PA subunit of a RNA-dependent RNA polymerase from Influenza A 2009 pandemic H1N1 virus or variant thereof. The modulating compound may increase or decrease, preferably decrease said endonucleolytic activity.

In a preferred embodiment of this aspect of the present invention, the compound that modulates the endonuclease activity of the PA subunit of a RNA-dependent RNA polymerase from Influenza A 2009 pandemic H1N1 virus or variant thereof decreases said activity, more preferably said compound inhibits said activity. Preferably, the compound decreases the endonucleolytic activity of the PA subunit of a RNA-dependent RNA polymerase from Influenza A 2009 pandemic H1N1 virus or variant thereof by 50%, more preferably by 60%, even more preferably by 70%, even more preferably by 80%, even more preferably by 90%, and most preferably by 100% compared to the endonucleolytic activity of said PA subunit or a variant thereof without said compound but with otherwise the same reaction conditions, i.e., buffer conditions, reaction time and temperature. It is particularly preferred that the compound specifically decreases or inhibits the endonucleolytic activity of the PA subunit of a RNA-dependent RNA polymerase from Influenza A 2009 pandemic H1N1 virus or variant thereof but does not decrease or inhibit the endonucleolytic activity of other endonucleases, in particular of mammalian endonucleases, to the same extent, preferably not at all.

The present invention permits the use of molecular design techniques to identify, select, or design compounds that potentially modulate the endonucleolytic activity of the PA subunit of a RNA-dependent RNA polymerase from Influenza A 2009 pandemic H1N1 virus or variant thereof, based on the structure coordinates of the (native) endonucleolytically active site according to FIG. 1. For the first time, the present invention further permits the optimized identification, selection and design of compounds that potentially modulate the endonucleolytic activity of the PA subunit of a RNA-dependent RNA polymerase from Influenza A 2009 pandemic H1N1 virus or variant thereof, based on the structure coordinates of the endonucleolytically active site according to FIG. 2 to 5, 15 or 16. Said structure coordinates have been achieved from polypeptide fragments (polypeptide fragment variants) according to the present invention which have been co-crystallized with a modulating compound, preferably with 4-[3-[(4-chlorophenyl)methyl]-1-(phenylmethyl)-3-piperidinyl]-2-hydroxy-4-oxo-2-butenoic acid (EMBL-R05-3) (see FIGS. 2 and 3), with 4-[4-[(4-chlorophenyl)methyl]-1-(cyclohexylmethyl)-4-piperidinyl]-2-hydroxy-4-oxo-2-butenoic acid (EMBL-R05-2) (see FIG. 4), with ribo-Uridine monophosphate (rUMP) (see FIG. 5), with 4-[3-[(4-chlorophenyl)methyl]-1-(phenylmethylsulpho)-3-piperidinyl]-2-hydroxy-4-oxo-2-butenoic acid (EMBL-R05-1) (see FIG. 15), or with [(2R,3R)-5,7-dihydroxy-2-(3,4,5-trihydroxyphenyl)chroman-3-yl]3,4,5-trihydroxybenzoate (EGCG) (see FIG. 16) (see also Tables 1 or 2). The present inventors have namely surprisingly found that the structure coordinates of the polypeptide fragment (variant) of the present invention without bound compound (i.e. native polypeptide fragment (variant)) (see, for example, FIG. 1) differ from the structure coordinates of the polypeptide fragment (variant) of the present invention with bound compound (see, for example, FIG. 2 to 5, 15 or 16) as said polypeptide fragment (variant) changes its conformation after compound binding. Thus, this new three-dimensional knowledge allows the optimized design of modifications to existing inhibitors in order to improve their potency or the design and optimization of novel inhibitors that effectively block endonuclease activity.

Such predictive models are valuable in light of the higher costs associated with the preparation and testing of the many diverse compounds that may possibly modulate the endonucleolytic activity. In order to use the structure coordinates generated for the Influenza A 2009 pandemic H1N1 PA polypeptide fragment (variant) it is necessary to convert the structure coordinates into a three-dimensional shape. This is achieved through the use of commercially available software that is capable of generating three-dimensional graphical representations of molecules or portions thereof from a set of structure coordinates. An example for such a computer program is MODELER (Sali and Blundell, 1993, J. Mol. Biol. 234:779-815 as implemented in the Insight II Homology software package (Insight II (97.0), Molecular Simulations Incorporated, San Diego, Calif.)).

One skilled in the art may use several methods to screen chemical entities or fragments for their ability to modulate the endonucleolytic activity of the Influenza A 2009 pandemic H1N1 PA subunit or Influenza A 2009 pandemic H1N1 PA subunit PA polypeptide variants. This process may begin by a visual inspection of, for example, a three-dimensional computer model of the endonucleolytically active site of PA based on the structural coordinates according to FIG. 1 to 5, 15 or 16. Selected fragments or chemical compounds may then be positioned in a variety of orientations or docked within the active site. Docking may be accomplished using software such as Cerius, Quanta, and Sybyl (Tripos Associates, St. Louis, Mo.), followed by energy minimization and molecular dynamics with standard molecular dynamics force fields such as OPLS-AA, CHARMM, and AMBER. Additional specialized computer programs that may assist the person skilled in the art in the process of selecting suitable compounds or fragments include, for example, (i) AUTODOCK (Goodsell et al., 1990, Proteins: Struct., Funct., Genet. 8: 195-202; AUTODOCK is available from The Scripps Research Institute, La Jolla, Calif.) and (ii) DOCK (Kuntz et al., 1982, J. Mol. Biol. 161:269-288; DOCK is available from the University of California, San Francisco, Calif.).

Once suitable compounds or fragments have been selected, they can be designed or assembled into a single compound or complex. This manual model building is performed using software such as Quanta or Sybyl. Useful programs aiding the skilled person in connecting individual compounds or fragments include, for example, (i) CAVEAT (Bartlett et al., 1989, in Molecular Recognition in Chemical and Biological Problems, Special Publication, Royal Chem. Soc. 78:182-196; Lauri and Bartlett, 1994, J. Comp. Aid. Mol. Des. 8:51-66; CAVEAT is available from the University of California, Berkley, Calif.), (ii) 3D Database systems such as ISIS (MDL Information Systems, San Leandro, Calif.; reviewed in Martin, 1992, J. Med. Chem. 35:2145-2154), and (iii) HOOK (Eisen et al., 1994, Proteins: Struct., Funct., Genet. 19:199-221; HOOK is available from Molecular Simulations Incorporated, San Diego, Calif.).

Another approach enabled by this invention, is the computational screening of small molecule databases for compounds that can bind in whole or part to the endonucleolytically active site of the Influenza A 2009 pandemic H1N1 PA subunit or active sites of Influenza A 2009 pandemic H1N1 PA polypeptide variants. In this screening, the quality of fit of such compounds to the active site may be judged either by shape complementarity or by estimated interaction energy (Meng et al., 1992, J. Comp. Chem. 13:505-524).

Alternatively, a potential modulator for the endonucleolytic activity of the Influenza A 2009 pandemic H1N1 PA subunit or Influenza A 2009 pandemic H1N1 polypeptide variant thereof, preferably an inhibitor of the endonucleolytic activity, may be designed de novo on the basis of the 3D structure of the PA polypeptide fragment according to FIGS. 1 to 5. There are various de novo ligand design methods available to the person skilled in the art. Such methods include (i) LUDI (Bohm, 1992, J. Comp. Aid. Mol. Des. 6:61-78; LUDI is available from Molecular Simulations Incorporated, San Diego, Calif.), (ii) LEGEND (Nishibata and Itai, Tetrahedron 47:8985-8990; LEGEND is available from Molecular Simulations Incorporated, San Diego, Calif.), (iii) LeapFrog (available from Tripos Associates, St. Louis, Mo.), (iv) SPROUT (Gillet et al., 1993, J. Comp. Aid. Mol. Des. 7:127-153; SPROUT is available from the University of Leeds, UK), (v) GROUPBUILD (Rotstein and Murcko, 1993, J. Med. Chem. 36:1700-1710), and (vi) GROW (Moon and Howe, 1991, Proteins 11:314-328).

In addition, several molecular modeling techniques (hereby incorporated by reference) that may support the person skilled in the art in de novo design and modeling of potential modulators and/or inhibitors of the endonucleolytically active site, preferably binding partners of the endonucleolytically active site, have been described and include, for example, Cohen et al., 1990, J. Med. Chem. 33:883-894; Navia and Murcko, 1992, Curr. Opin. Struct. Biol. 2:202-210; Balbes et al., 1994, Reviews in Computational Chemistry, Vol. 5, Lipkowitz and Boyd, Eds., VCH, New York, pp. 37-380; Guida, 1994, Curr. Opin. Struct. Biol. 4:777-781.

A molecule designed or selected as binding to the endonucleolytically active site of the Influenza A 2009 pandemic H1N1 PA subunit or variants thereof may be further computationally optimized so that in its bound state it preferably lacks repulsive electrostatic interaction with the target region. Such non-complementary (e.g., electrostatic) interactions include repulsive charge-charge, dipole-dipole and charge-dipole interactions. Specifically, the sum of all electrostatic interactions between the binding compound and the binding pocket in a bound state, preferably make a neutral or favorable contribution to the enthalpy of binding. Specific computer programs that can evaluate a compound deformation energy and electrostatic interaction are available in the art. Examples of suitable programs include (i) Gaussian 92, revision C (Frisch, Gaussian, Incorporated, Pittsburgh, Pa.), (ii) AMBER, version 4.0 (Kollman, University of California, San Francisco, Calif.), (iii) QUANTA/CHARMM (Molecular Simulations Incorporated, San Diego, Calif.), (iv) OPLS-AA (Jorgensen, 1998, Encyclopedia of Computational Chemistry, Schleyer, Ed., Wiley, New York, Vol. 3, pp. 1986-1989), and (v) Insight II/Discover (Biosysm Technologies Incorporated, San Diego, Calif.). These programs may be implemented, for instance, using a Silicon Graphics workstation, IRIS 4D/35 or IBM RISC/6000 workstation model 550. Other hardware systems and software packages are known to those skilled in the art.

Once a molecule of interest has been selected or designed, as described above, substitutions may then be made in some of its atoms or side groups in order to improve or modify its binding properties. Generally, initial substitutions are conservative, i.e., the replacement group will approximate the same size, shape, hydrophobicity and charge as the original group. It should, of course, be understood that components known in the art to alter conformation should be avoided. Such substituted chemical compounds may then be analyzed for efficiency of fit to the endonucleolytically active site of the Influenza A 2009 pandemic H1N1 PA subunit or variant thereof by the same computer methods described in detail above.

In one embodiment of the above-described method of the present invention, the endonucleolytically active site of the Influenza A 2009 pandemic H1N1 PA subunit or variant thereof comprises amino acids Glu80, Glu119, Asp108, Ile120, and His41 of the PA subunit according to SEQ ID NO: 2 or amino acids corresponding thereto. In another embodiment, said active site comprises amino acids Glu80, Glu119, Asp108, Ile120, His41 and Lys34 of the PA subunit according to SEQ ID NO: 2 or amino acids corresponding thereto. In another embodiment, said active site comprises amino acids Glu80, Glu119, Asp108, Ile120, His41 and Tyr24 of the PA subunit according to SEQ ID NO: 2 or amino acids corresponding thereto. In another embodiment, said active site comprises amino acids Glu80, Glu119, Asp108, Ile120, His41 and Arg84 of the PA subunit according to SEQ ID NO: 2 or amino acids corresponding thereto. In another embodiment, said active site comprises amino acids Glu80, Glu119, Asp108, Ile120, His41 and Phe105 of the PA subunit according to SEQ ID NO: 2 or amino acids corresponding thereto. In another embodiment, said active site comprises amino acids Glu80, Glu119, Asp108, Ile120, His41, and Tyr130 of the PA subunit according to SEQ ID NO: 2 or amino acids corresponding thereto. In another embodiment, said active site comprises amino acids Glu80, Glu119, Asp108, Ile120, His41, and Ile38 of the PA subunit according to SEQ ID NO: 2 or amino acids corresponding thereto. In another embodiment, said active site comprises amino acids Glu80, Glu119, Asp108, Ile120, His41, and Arg124 of the PA subunit according to SEQ ID NO: 2 or amino acids corresponding thereto. In another embodiment, said active site comprises amino acids Glu80, Glu119, Asp108, Ile120, His41, Lys34, and Tyr24 of the PA subunit according to SEQ ID NO: 2 or amino acids corresponding thereto. In another embodiment, said active site comprises amino acids Glu80, Glu119, Asp108, Ile120, His41, Lys34, Tyr24, and Arg84 of the PA subunit according to SEQ ID NO: 2 or amino acids corresponding thereto. In another embodiment, said active site comprises amino acids Glu80, Glu119, Asp108, Ile120, His41, Lys34, Tyr24, Arg84, and Phe105 of the PA subunit according to SEQ ID NO: 2 or amino acids corresponding thereto. In another embodiment, said active site comprises amino acids Glu80, Glu119, Asp108, Ile120, His41, Lys34, Tyr24, Arg84, Phe105, and Tyr130 of the PA subunit according to SEQ ID NO: 2 or amino acids corresponding thereto. In another embodiment, said active site comprises amino acids Glu80, Glu119, Asp108, Ile120, His41, Lys34, Tyr24, Arg84, Phe105, Tyr130, and Ile38 of the PA subunit according to SEQ ID NO: 2 or amino acids corresponding thereto. In another embodiment, said active site comprises amino acids Glu80, Glu119, Asp108, Ile120, His41, Lys34, Tyr24, Arg84, Phe105, Tyr130, Ile38 and Arg124 of the PA subunit according to SEQ ID NO: 2 or amino acids corresponding thereto.

In yet another embodiment, said active site comprises amino acids Glu80, Glu119, Asp108, Ile120, His41, Lys34, Tyr24, Arg84, Phe105, Tyr130, Ile38, and Glu26 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124 and Glu26 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, and Lys134 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, and Lys134 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, and Leu106 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, and Leu106 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, and Lys137 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Gly26 and Lys134 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Gly26 and Lys134 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Leu106, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Leu106, and Lys137 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Glu26, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Glu26, and Lys137 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Glu26, and Leu106 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Glu26, and Leu106 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Lys134, and Leu106 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Lys134, and Leu106 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Lys134, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Lys134, and Lys137 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Glu26, Lys134, and Leu106 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Glu26, Lys134, and Leu106 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Glu26, Lys134, Leu106, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Glu26, Lys134, Leu106, and Lys137 of the PA subunit according to SEQ ID NO: 2 or amino acids corresponding thereto.

In a further embodiment, said active site comprises amino acids Glu80, Glu119, Asp108, Ile120, His41, and Glu26 of the PA subunit according to SEQ ID NO: 2 or amino acids corresponding thereto. In a further embodiment, said active site comprises amino acids Glu80, Glu119, Asp108, Ile120, His41, and Lys134 of the PA subunit according to SEQ ID NO: 2 or amino acids corresponding thereto. In a further embodiment, said active site comprises amino acids Glu80, Glu119, Asp108, Ile120, His41, and Leu106 of the PA subunit according to SEQ ID NO: 2 or amino acids corresponding thereto. In a further embodiment, said active site comprises amino acids Glu80, Glu119, Asp108, Ile120, His41, and Lys137 of the PA subunit according to SEQ ID NO: 2 or amino acids corresponding thereto. In a further embodiment, said active site comprises amino acids Glu80, Glu119, Asp108, Ile120, His41, Glu26, and Lys134 of the PA subunit according to SEQ ID NO: 2 or amino acids corresponding thereto. In a further embodiment, said active site comprises amino acids Glu80, Glu119, Asp108, Ile120, His41, Glu26, Lys134, and Leu106 of the PA subunit according to SEQ ID NO: 2 or amino acids corresponding thereto. In a further embodiment, said active site comprises amino acids Glu80, Glu119, Asp108, Ile120, His41, Glu26, Lys134, Leu106, and Lys137 of the PA subunit according to SEQ ID NO: 2 or amino acids corresponding thereto.

In one embodiment of the above-described method of the invention, the endonucleolytically active site of the Influenza A 2009 pandemic H1N1 PA subunit or variant thereof is defined by the structure coordinates of the PA subunit SEQ ID NO: 2 amino acids Glu80, Glu119, Asp108, Ile120, and His41 according to FIGS. 1 to 5 or by the structure coordinates of the PA subunit amino acids Glu, Glu, Asp, Ile, and His corresponding to amino acids Glu80, Glu119, Asp108, Ile120, and His41 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Lys34 according to FIGS. 1 to 5 or by the structure coordinates of the PA subunit amino acids Glu, Glu, Asp, Ile, His and Lys corresponding to amino acids Glu80, Glu119, Asp108, Ile120, and His41 and Lys34 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Tyr24 according to FIGS. 1 to 5 or by the structure coordinates of the PA subunit amino acids Glu, Glu, Asp, Ile, His, and Tyr corresponding to amino acids Glu80, Glu119, Asp108, Ile120, His41 and Tyr24 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Arg84 according to FIGS. 1 to 5 or by the structure coordinates of the PA subunit amino acids Glu, Glu, Asp, Ile, His and Arg corresponding to amino acids Glu80, Glu119, Asp108, Ile120, His41 and Arg84 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Phe105 according to FIGS. 1 to 5 or by the structure coordinates of the PA subunit amino acids Glu, Glu, Asp, Ile, His and Phe corresponding to amino acids Glu80, Glu119, Asp108, Ile120, His41 and Phe105 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Tyr130 according to FIGS. 1 to 5 or by the structure coordinates of the PA subunit amino acids Glu, Glu, Asp, Ile, His and Tyr corresponding to amino acids Glu80, Glu119, Asp108, Ile120, His41 and Tyr130 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, and Ile38 according to FIGS. 1 to 5 or by the structure coordinates of the PA subunit amino acids Glu, Glu, Asp, Ile, His and Ile corresponding to amino acids Glu80, Glu119, Asp108, Ile120, His41 and Ile38 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, and Arg124 according to FIGS. 1 to 5 or by the structure coordinates of the PA subunit amino acids Glu, Glu, Asp, Ile, His, and Arg corresponding to amino acids Glu80, Glu119, Asp108, Ile120, His41, and Arg124 of SEQ ID NO: 2, respectively, according to FIG. 15 or 16.

In another embodiment, said active site is defined by the structure coordinates of the PA subunit SEQ ID NO: 2 amino acids Glu80, Glu119, Asp108, Ile120, His41, Lys34, and Tyr24 according to FIGS. 1 to 5 or by the structure coordinates of the PA subunit amino acids Glu, Glu, Asp, Ile, His, Lys, and Tyr corresponding to amino acids Glu80, Glu119, Asp108, Ile120, His41, Lys34, and Tyr24 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, and Arg84 according to FIGS. 1 to 5 or by the structure coordinates of the PA subunit amino acids Glu, Glu, Asp, Ile, His, Lys, Tyr, and Arg corresponding to amino acids Glu80, Glu119, Asp108, Ile120, His41, Lys34, Tyr24, and Arg84 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, Arg84, and Phe105 according to FIGS. 1 to 5 or by the structure coordinates of the PA subunit amino acids Glu, Glu, Asp, Ile, His, Lys, Tyr, Arg, and Phe corresponding to amino acids Glu80, Glu119, Asp108, Ile120, His41, Lys34, Tyr24, Arg84, and Phe105 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, Arg84, Phe105, and Tyr130 according to FIGS. 1 to 5 or by the structure coordinates of the PA subunit amino acids Glu, Glu, Asp, Ile, His, Lys, Tyr, Arg, Phe, and Tyr corresponding to amino acids Glu80, Glu119, Asp108, Ile120, His41, Lys34, Tyr24, Arg84, Phe105, and Tyr130 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, and Ile38 according to FIGS. 1 to 5 or by the structure coordinates of the PA subunit amino acids Glu, Glu, Asp, Ile, His, Lys, Tyr, Arg, Phe, Tyr, and Ile corresponding to amino acids Glu80, Glu119, Asp108, Ile120, His41, Lys34, Tyr24, Arg84, Phe105, Tyr130, and Ile38 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, and Arg124 according to FIGS. 1 to 5 or by the structure coordinates of the PA subunit amino acids Glu, Glu, Asp, Ile, His, Lys, Tyr, Arg, Phe, Tyr, Ile, and Arg corresponding to amino acids Glu80, Glu119, Asp108, Ile120, His41, Lys34, Tyr24, Arg84, Phe105, Tyr130, Ile38, and Arg124 of SEQ ID NO: 2, respectively, according to FIG. 15 or 16.

In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, and Glu26 according to FIGS. 1 to 5 or by the structure coordinates of the PA subunit amino acids Glu, Glu, Asp, Ile, His, Lys, Tyr, Arg, Phe, Tyr, Ile, and Glu corresponding to amino acids Glu80, Glu119, Asp108, Ile120, His41, Lys34, Tyr24, Arg84, Phe105, Tyr130, Ile38, and Glu26 of SEQ ID NO: 2, respectively, according to FIG. 15 or 16. In yet another embodiment, said active site is defined by the structure coordinates of the PA subunit SEQ ID NO: 2amino acids Glu80, Glu119, Asp108, Ile120, His41, Lys34, Tyr24, Arg84, Phe105, Tyr130, Ile38, and Lys134 according to FIGS. 1 to 5 or by the structure coordinates of the PA subunit amino acids Glu, Glu, Asp, Ile, His, Lys, Tyr, Arg, Phe, Tyr, Ile, and Lys corresponding to amino acids Glu80, Glu119, Asp108, Ile120, His41, Lys34, Tyr24, Arg84, Phe105, Tyr130, Ile38, and Lys134 of SEQ ID NO: 2, respectively, according to FIG. 15 or 16. In yet another embodiment, said active site is defined by the structure coordinates of the PA subunit SEQ ID NO: 2amino acids Glu80, Glu119, Asp108, Ile120, His41, Lys34, Tyr24, Arg84, Phe105, Tyr130, Ile38, and Leu106 according to FIGS. 1 to 5 or by the structure coordinates of the PA subunit amino acids Glu, Glu, Asp, Ile, His, Lys, Tyr, Arg, Phe, Tyr, Ile, and Leu corresponding to amino acids Glu80, Glu119, Asp108, Ile120, His41, Lys34, Tyr24, Arg84, Phe105, Tyr130, Ile38, and Leu106, of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, and Lys137 according to FIGS. 1 to 5 or by the structure coordinates of the PA subunit amino acids Glu, Glu, Asp, Ile, His, Lys, Tyr, Arg, Phe, Tyr, Ile, and Lys corresponding to amino acids Glu80, Glu119, Asp108, Ile120, His41, Lys34, Tyr24, Arg84, Phe105, Tyr130, Ile38, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Gly26 and Lys134 according to FIGS. 1 to 5 or by the structure coordinates of the PA subunit amino acids Glu, Glu, Asp, Ile, His, Lys, Tyr, Arg, Phe, Tyr, Ile, Glu, and Lys corresponding to amino acids Glu80, Glu119, Asp108, Ile120, His41, Lys34, Tyr24, Arg84, Phe105, Tyr130, Ile38, Glu26, and Lys134 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Leu106, and Lys137 according to FIGS. 1 to 5 or by the structure coordinates of the PA subunit amino acids Glu, Glu, Asp, Ile, His, Lys, Tyr, Arg, Phe, Tyr, Ile, Leu, and Lys corresponding to amino acids Glu80, Glu119, Asp108, Ile120, His41, Lys34, Tyr24, Arg84, Phe105, Tyr130, Ile38, Leu106, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Glu26, and Lys137 according to FIGS. 1 to 5 or by the structure coordinates of the PA subunit amino acids Glu, Glu, Asp, Ile, His, Lys, Tyr, Arg, Phe, Tyr, Ile, Glu, and Lys corresponding to amino acids Glu80, Glu119, Asp108, Ile120, His41, Lys34, Tyr24, Arg84, Phe105, Tyr130, Ile38, Glu26, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Glu26, and Leu106 according to FIGS. 1 to 5 or by the structure coordinates of the PA subunit amino acids Glu, Glu, Asp, Ile, His, Lys, Tyr, Arg, Phe, Tyr, Ile, Glu, and Leu, corresponding to amino acids Glu80, Glu119, Asp108, Ile120, His41, Lys34, Tyr24, Arg84, Phe105, Tyr130, Ile38, Glu26, and Leu106 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Lys134, and Leu106 according to FIGS. 1 to 5 or by the structure coordinates of the PA subunit amino acids Glu, Glu, Asp, Ile, His, Lys, Tyr, Arg, Phe, Tyr, Ile, Lys, and Leu corresponding to amino acids Glu80, Glu119, Asp108, Ile120, His41, Lys34, Tyr24, Arg84, Phe105, Tyr130, Ile38, Lys134, and Leu106 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Lys134, and Lys137 according to FIGS. 1 to 5 or by the structure coordinates of the PA subunit amino acids Glu, Glu, Asp, Ile, His, Lys, Tyr, Arg, Phe, Tyr, Ile, Lys, and Lys corresponding to amino acids Glu80, Glu119, Asp108, Ile120, His41, Lys34, Tyr24, Arg84, Phe105, Tyr130, Ile38, Lys134, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Glu26, Lys134, and Leu106 according to FIGS. 1 to 5 or by the structure coordinates of the PA subunit amino acids Glu, Glu, Asp, Ile, His, Lys, Tyr, Arg, Phe, Tyr, Ile, Glu, Lys, and Leu corresponding to amino acids Glu80, Glu119, Asp108, Ile120, His41, Lys34, Tyr24, Arg84, Phe105, Tyr130, Ile38, Glu26, Lys134, and Leu106 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Glu26, Lys134, Leu106, and Lys137 according to FIGS. 1 to 5 or by the structure coordinates of the PA subunit amino acids Glu, Glu, Asp, Ile, His, Lys, Tyr, Arg, Phe, Tyr, Ile, Glu, Lys, Leu, and Lys corresponding to amino acids Glu80, Glu119, Asp108, Ile120, His41, Lys34, Tyr24, Arg84, Phe105, Tyr130, Ile38, Glu26, Lys134, Leu106, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Arg124, Glu26, Lys134, Leu106, and Lys137 according to FIGS. 1 to 5 or by the structure coordinates of the PA subunit amino acids Glu, Glu, Asp, Ile, His, Lys, Tyr, Arg, Phe, Tyr, Ile, Arg, Glu, Lys, Leu, and Lys corresponding to amino acids Glu80, Glu119, Asp108, Ile120, His41, Lys34, Tyr24, Arg84, Phe105, Tyr130, Ile38, Arg124, Glu26, Lys134, Leu106, and Lys137 of SEQ ID NO: 2, respectively, according to FIG. 15 or 16.

In a further embodiment, said active site is defined by the structure coordinates of the PA subunit SEQ ID NO: 2 amino acids Glu80, Glu119, Asp108, Ile120, His41, and Glu26 according to FIGS. 1 to 5 or by the structure coordinates of the PA subunit amino acids Glu, Glu, Asp, Ile, His, and Glu corresponding to amino acids Glu80, Glu119, Asp108, Ile120, His41, and Glu26 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, and Lys134 according to FIGS. 1 to 5 or by the structure coordinates of the PA subunit amino acids Glu, Glu, Asp, Ile, His, and Lys corresponding to amino acids Glu80, Glu119, Asp108, Ile120, His41, and Lys134 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, and Leu106 according to FIGS. 1 to 5 or by the structure coordinates of the PA subunit amino acids Glu, Glu, Asp, Ile, His, and Leu corresponding to amino acids Glu80, Glu119, Asp108, Ile120, His41, and Leu106 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, and Lys137 according to FIGS. 1 to 5 or by the structure coordinates of the PA subunit amino acids Glu, Glu, Asp, Ile, His, and Lys corresponding to amino acids Glu80, Glu119, Asp108, Ile120, His41, and Lys137 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, Glu26, and Lys134 according to FIGS. 1 to 5 or by the structure coordinates of the PA subunit amino acids Glu, Glu, Asp, Ile, His, Glu, and Lys corresponding to amino acids Glu80, Glu119, Asp108, Ile120, His41, Glu26, and Lys134 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, Glu26, Lys134, and Leu106 according to FIGS. 1 to 5 or by the structure coordinates of the PA subunit amino acids Glu, Glu, Asp, Ile, His, Glu, Lys, and Leu corresponding to amino acids Glu80, Glu119, Asp108, Ile120, His41, Glu26, Lys134, and Leu106 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, Glu26, Lys134, Leu106, and Lys137 according to FIGS. 1 to 5 or by the structure coordinates of the PA subunit amino acids Glu, Glu, Asp, Ile, His, Glu, Lys, Leu, and Lys corresponding to amino acids Glu80, Glu119, Asp108, Ile120, His41, Glu26, Lys134, Leu106, and Lys137 of SEQ ID NO: 2, respectively, according to FIG. 15 or 16.

The inventors of the present invention have surprisingly found that the amino acids His 41, Glu80, Asp108, Glu119, and Ile120 according to SEQ ID NO: 2 within the active site of Influenza A 2009 pandemic H1N1 PA subunit are required for divalent cation binding (see for example FIGS. 1 and 6), while the amino acids Tyr24, Lys34, Ile38, Arg84, Phe105, and Tyr130 according to SEQ ID NO: 2 within the active site of Influenza A 2009 pandemic H1N1 PA subunit are required for compound (i.e. inhibitor) binding in the structures shown in FIGS. 2 to 5 (see also FIGS. 7 to 10 and Tables 1 and 2) and are those amino acids which conformation changes from the unligated structure (see FIGS. 1 and 6). In addition, the inventors of the present invention determined that the amino acid residues Leu106, Lys134, Lys137 and Glue26 according to SEQ ID NO: 2 within the active site of Influenza A 2009 pandemic H1N1 PA subunit are also required to make contacts with the tested compounds (see Tables 1 and 2, FIGS. 2 to 5 and FIGS. 7 to 10). See also FIGS. 15 to 19. In addition, the inventors of the present invention have found that the amino acid Arg124 within the active site of Influenza A 2009 pandemic H1N1 PA subunit is required for compound (i e inhibitor) interaction in the structures shown in FIGS. 16 and 18. This three-dimensional knowledge of the compound/ligand interacting residues and the plasticity of the active site is important for the optimised design of modifications to existing inhibitors in order to improve their potency. In addition, the design, identification and selection of new anti viral compounds that interact with these amino acids is, thus, highly preferable.

If computer modeling according to the methods described hereinabove indicates binding of a compound to the active site of the Influenza A 2009 pandemic H1N1 PA subunit or a variant thereof, said compound may be synthesized and optionally said compound or a pharmaceutically acceptable salt thereof may be formulated with one or more pharmaceutically acceptable excipient(s) and/or carrier(s). Thus, the above-described method may comprise the further step of (e) synthesizing said compound and optionally formulating said compound or a pharmaceutically acceptable salt thereof with one or more pharmaceutically acceptable excipient(s) and/or carrier(s).

Optionally, the ability of said compound or of a pharmaceutically acceptable salt thereof or of a formulation thereof to modulate, preferably decrease, more preferably inhibit, the endonucleolytic activity of the Influenza A 2009 pandemic H1N1 PA subunit or variant thereof may be tested in vitro or in vivo comprising the further step of (f) contacting said compound with the PA polypeptide fragment or variant thereof according to the present invention or the recombinant host cell according to the present invention and determine the ability of said compound to (i) bind to the active site and/or (ii) modulate, preferably decrease, more preferably inhibit, the endonucleolytic activity of the Influenza A 2009 pandemic H1N1 PA subunit polypeptide fragment or variant thereof. The quality of fit of such compounds to the active site may be judged either by shape complementarity or by estimated interaction energy (Meng et al., 1992, J. Comp. Chem. 13:505-524). Methods for synthesizing said compounds are well known to the person skilled in the art or such compounds may be commercially available.

It is another aspect of the present invention to provide a compound which is able to modulate, preferably to decrease, more preferably to inhibit, the endonuclease activity of the Influenza A 2009 pandemic H1N1 PA subunit or variant thereof according to the present invention. It is preferred that the compound is able to modulate, preferably to decrease, more preferably to inhibit, the endonuclease activity of the PA subunit or variant thereof according to the present invention by associating with, preferably by binding to, the endonucleolytically active site of said PA subunit or variant thereof.

It is also an aspect of the present invention to provide a compound which is able to modulate, preferably to decrease, more preferably to inhibit, the endonuclease activity of the Influenza A 2009 pandemic H1N1 PA subunit polypeptide fragment or variant thereof according to the present invention. It is preferred that the compound is able to modulate, preferably to decrease, more preferably to inhibit, the endonuclease activity of the PA subunit polypeptide fragment or variant thereof according to the present invention by associating with, preferably by binding to, the endonucleolytically active site of said PA subunit polypeptide fragment or variant thereof.

It is further an aspect of the present invention to provide a compound which is able to modulate, preferably to decrease, more preferably to inhibit, the endonuclease activity of the PA subunit of other viruses, preferably of viruses of the Orthomyxoviridae family, Bunyaviridae family and/or Arenviridae family. It is preferred that the compound is able to modulate, preferably to decrease, more preferably to inhibit, the endonuclease activity of the PA subunit of other viruses, preferably of viruses of the Orthomyxoviridae family, Bunyaviridae family and/or Arenviridae family, by associating with, preferably by binding to, the endonucleolytically active site of said PA subunit.

Preferably, the endonucleolytically active site of the above-mentioned PA subunits or variants thereof, or PA subunit polypeptide fragments or variants thereof has the structure as defined above.

Thus, it is preferred that said active site comprises amino acids Glu80, Glu119, Asp108, Ile120, and His41 of the PA subunit according to SEQ ID NO: 2 or amino acids corresponding thereto.

It is more preferred that said active site comprises amino acids Glu80, Glu119, Asp108, Ile120, His41, Lys34, Tyr24, Arg84, Phe105, Tyr130, and Ile38 of the PA subunit according to SEQ ID NO: 2 or amino acids corresponding thereto, or comprises amino acids Glu80, Glu119, Asp108, Ile120, His41 Lys34, Tyr24, Arg84, Phe105, Tyr130, Ile38, and Arg124 of the PA subunit according to SEQ ID NO: 2 or amino acids corresponding thereto.

It is also more preferred that said active site comprises amino acids Glu80, Glu119, Asp108, Ile120, His41, Glu26, Lys134, Leu106, and Lys137 of the PA subunit according to SEQ ID NO: 2 or amino acids corresponding thereto.

It is most preferred that said active side comprises amino acids Glu80, Glu119, Asp108, Ile120, His41 Lys34, Tyr24, Arg84, Phe105, Tyr130, Ile38, Glu26, Lys134, Leu106, and Lys137 of the PA subunit according to SEQ ID NO: 2 or amino acids corresponding thereto, or comprises amino acids Glu80, Glu119, Asp108, Ile120, His41 Lys34, Tyr24, Arg84, Phe105, Tyr130, Ile38, Arg124, Glu26, Lys134, Leu106, and Lys137 of the PA subunit according to SEQ ID NO: 2 or amino acids corresponding thereto.

Preferably, the endonucleolytically active site of the above-mentioned PA subunits or variants thereof, or PA subunit polypeptide fragments or variants thereof is defined by the structure coordinates of the PA subunit as mentioned above.

The ability of a compound to associate with, preferably to bind to, the endonucleolytically active site of the aforementioned PA subunit or variant thereof, or PA subunit polypeptide fragment or variant thereof, and/or to modulate, preferably to decrease, more preferably to inhibit the endonucleolytic activity of the PA subunit or variant thereof, or PA subunit polypeptide fragment or variant thereof can easily be assessed. For example, the purified PA subunit or PA subunit polypeptide fragment and a substrate thereof such as panhandle RNA or single stranded DNA are contacted in presence or absence of varying amounts of the test compound and incubated for a certain period of time, for example, for 5, 10, 15, 20, 30, 40, 60, or 90 minutes. The reaction conditions are chosen such that the PA subunit or PA subunit polypeptide fragment is endonucleolytically active without the test compound. The substrate is then analyzed for degradation/endonucleolytic cleavage, for example, by gel electrophoresis. Alternatively, such a test may comprise a labeled substrate molecule which provides a signal when the substrate molecule is endonucleolytically cleaved but does not provide a signal if it is intact. For example, the substrate polynucleotide chain may be labeled with fluorescent reporter molecule and a fluorescence quencher such that the fluorescent reporter is quenched as long as the substrate polynucleotide chain is intact. In case the substrate polynucleotide chain is cleaved, the fluorescent reporter and the quencher are separated, thus, the fluorescent reporter emits a signal which may be detected, for example, by an ELISA reader. Further suitable methods are described below.

Preferably, said compound is identifiable by the above-described method. More preferably, said compound is identified by the above-described method.

The compound identifiable by the above-described method may be able to modulate the endonuclease activity of the Influenza A 2009 pandemic H1N1 PA subunit or variant thereof. The compound identifiable by the above-described method may be able to modulate, preferably to decrease, more preferably to inhibit, the endonuclease activity of the Influenza A 2009 pandemic H1N1 PA subunit polypeptide fragment or variant thereof according to the present invention. It is also possible that the compound identifiable by the above-mentioned method may be able to modulate, preferably to decrease, most preferably to inhibit, the endonuclease activity of the PA subunit of other viruses, preferably of viruses of the Orthomyxoviridae family, Bunyaviridae family and/or Arenviridae family.

Compounds of the present invention can be any agents including, but not restricted to, peptides, peptoids, polypeptides, proteins (including antibodies), lipids, metals, nucleotides, nucleosides, nucleic acids, small organic or inorganic molecules, chemical compounds, elements, saccharides, isotopes, carbohydrates, imaging agents, lipoproteins, glycoproteins, enzymes, analytical probes, polyamines, and combinations and derivatives thereof. The term "small molecules" refers to molecules that have a molecular weight between 50 and about 2,500 Daltons, preferably in the range of 200-800 Daltons. In addition, a test compound according to the present invention may optionally comprise a detectable label. Such labels include, but are not limited to, enzymatic labels, radioisotope or radioactive compounds or elements, fluorescent compounds or metals, chemiluminescent compounds and bioluminescent compounds.

In a preferred embodiment of the compound according to the present invention, the compound is not a 4-substituted 2-dioxobutanoic acid, a 4-substituted 4-dioxobutanoic acid, a 4-substituted 2,4-dioxobutanoic acid, a 2,6-diketopiperazine or a derivative thereof, a substituted 2,6-diketopiperazine or a derivative thereof, pyrazine-2,6-dione or a substituted pyrazine-2,6-dione such as flutimide, an N-hydroxamic acid, or an N-hydroxymide.

In particular, the compound according to the present invention is not a compound according to Formula I:

Formula I

R¹ = Me, Et, Ph
R² = acyl, carbamoyl, sulfonyl.

In another preferred embodiment of the compound according to the present invention, the compound is not 4-[3-[(4-chlorophenyl)methyl]-1-(phenylmethyl)-3-piperidinyl]-2-hydroxy-4-oxo-2-butenoic acid, 4-[4-[(4-chlorophenyl)methyl]-1-(cyclohexylmethyl)-4-piperidinyl]-2-hydroxy-4-oxo-2-butenoic acid, 4-[3-[(4-chlorophenyl)methyl]-1-(phenylmethylsulpho)-3-piperidinyl]-2-hydroxy-4-oxo-2-butenoic acid, ribo-Uridine Monophosphate (rUMP), desoxy-thymidinmonophosphat (dTMP), or 2.4-dioxo-4-phenylbutanoic acid (DPBA).

In a further preferred embodiment of the compound according to the present invention, the compound is not a catechin, preferably not a (−)-epigallocatechin gallate (EGCG), such as [(2R,3R)-5,7-dihydroxy-2-(3,4,5-trihydroxyphenyl)chroman-3-yl]3,4,5-trihydroxybenzoate, a (−)-epicatechin gallate (ECG), (−)-epigallocatechin (EGC), (−)-epicatechin (EC), or gallic acid (GA). In another preferred embodiment of the compound of the present invention, the compound is not a phenethylphenylphthalimide, a phenethylphenylphthalimide analog derived from thalidomide or raltegravir (also a diketobutanoic acid derivative). In a further aspect, the present invention provides a (an in vitro) method for identifying compounds, which modulate, preferably decrease, more preferably inhibit, the endonuclease activity of the PA subunit of a RNA-dependent RNA polymerase from Influenza A 2009 pandemic H1N1 virus or a variant thereof comprising the steps of:

(i) contacting said polypeptide fragment or variant thereof according to the present invention or said recombinant host cell according to the present invention with a test compound, and (ii) analyzing the ability of said test compound to modulate, preferably to decrease, more preferably to inhibit, the endonuclease activity of said PA subunit polypeptide fragment or variant thereof.

It is preferred that said compounds modulate, preferably decrease, more preferably inhibit, the endonuclease activity of the PA subunit of a RNA-dependent RNA polymerase from Influenza A 2009 pandemic H1N1 virus or a variant thereof by associating with, preferably by binding to, the endonucleolytically active site of said PA subunit.

In another further aspect, the present invention provides a (an in vitro) method for identifying compounds, which bind to the endonucleolytically active site, (and) preferably modulate, more preferably decrease, most preferably inhibit, the endonuclease activity of the PA subunit of a RNA-dependent RNA polymerase from Influenza A 2009 pandemic H1N1 virus or a variant thereof comprising the steps of:

(i) contacting said polypeptide fragment or variant thereof according to the present invention or said recombinant host cell according to the present invention with a test compound, and (ii) analyzing the ability of said test compound to bind to the endonucleolytically site, (and) preferably to modulate, more preferably to decrease, most preferably to inhibit, the endonuclease activity of said PA subunit polypeptide fragment or variant thereof.

In one embodiment, the interaction between the Influenza A 2009 pandemic H1N1 PA polypeptide fragment or variant thereof and a test compound may be analyzed in form of a pull down assay. For example, the PA polypeptide fragment or variant thereof according to the invention may be purified and may be immobilized on beads. In one embodiment, the PA polypeptide fragment immobilized on beads may be contacted, for example, with (i) another purified protein, polypeptide fragment, or peptide, (ii) a mixture of proteins, polypeptide fragments, or peptides, or (iii) a cell or tissue extract, and binding of proteins, polypeptide fragments, or peptides may be verified by polyacrylamide gel electrophoresis in combination with coomassie staining or Western blotting. Unknown binding partners may be identified by mass spectrometric analysis.

In another embodiment, the interaction between the Influenza A 2009 pandemic H1N1 PA polypeptide fragment or variant thereof and a test compound may be analyzed in form of an enzyme-linked immunosorbent assay (ELISA)-based experiment. In one embodiment, the PA polypeptide fragment or variant thereof according to the invention may be immobilized on the surface of an ELISA plate and contacted with the test compound. Binding of the test compound may be verified, for example, for proteins, polypeptides, peptides, and epitope-tagged compounds by antibodies specific for the test compound or the epitope-tag. These antibodies might be directly coupled to an enzyme or detected with a secondary antibody coupled to said enzyme that—in combination with the appropriate substrates—carries out chemiluminescent reactions (e.g., horseradish peroxidase) or colorimetric reactions (e.g., alkaline phosphatase). In another embodiment, binding of compounds that cannot be detected by antibodies might be verified by labels directly coupled to the test compounds. Such labels may include enzymatic labels, radioisotope or radioactive compounds or elements, fluorescent compounds or metals, chemiluminescent compounds and bioluminescent compounds. In another embodiment, the test compounds might be immobilized on the ELISA plate and contacted with the PA polypeptide fragment or variants thereof according to the invention. Binding of said polypeptide may be verified by a PA polypeptide fragment specific antibody and chemiluminescence or colorimetric reactions as described above.

In a further embodiment, purified Influenza A 2009 pandemic H1N1 PA polypeptide fragments or variants may be incubated with a peptide array and binding of the PA polypeptide fragments to specific peptide spots corresponding to a specific peptide sequence may be analyzed, for example, by PA polypeptide specific antibodies, antibodies that are directed against an epitope-tag fused to the PA polypeptide fragment, or by a fluorescence signal emitted by a fluorescent tag coupled to the PA polypeptide fragment.

In another embodiment, the recombinant host cell according to the present invention is contacted with a test compound. This may be achieved by co-expression of test proteins or polypeptides and verification of interaction, for example, by fluorescence resonance energy transfer (FRET) or co-immunoprecipitation. In another embodiment, directly labeled test compounds may be added to the medium of the recombinant host cells. The potential of the test compound to penetrate membranes and bind to the PA polypeptide fragment may be, for example, verified by immunoprecipitation of said polypeptide and verification of the presence of the label.

In another embodiment, the ability of the test compound to modulate, preferably decrease, more preferably inhibit the endonucleolytic activity of the Influenza A 2009 pandemic H1N1 PA subunit polypeptide fragment or variant thereof is assessed. For example, the purified PA subunit polypeptide fragment and a substrate thereof such as panhandle RNA or single stranded DNA are contacted in presence or absence of varying amounts of the test compound and incubated for a certain period of time, for example, for 5, 10, 15, 20, 30, 40, 60, or 90 minutes. The reaction conditions are chosen such that the PA subunit polypeptide is endonucleolytically active without the test compound. The substrate is then analyzed for degradation/endonucleolytic cleavage, for example, by gel electrophoresis. Alternatively, such a test may comprise a labeled substrate molecule which provides a signal when the substrate molecule is endonucleolytically cleaved but does not provide a signal if it is intact. For example, the substrate polynucleotide chain may be labeled with fluorescent reporter molecule and a fluorescence quencher such that the fluorescent reporter is quenched as long as the substrate polynucleotide chain is intact. In case the substrate polynucleotide chain is cleaved, the fluorescent reporter and the quencher are separated, thus, the fluorescent reporter emits a signal which may be detected, for example, by an ELISA reader. This experimental setting may be applied in a multi-well plate format and is suitable for high throughput screening of compounds regarding their ability to modulate, decrease, or inhibit the endonuclease activity of the Influenza A 2009 pandemic H1N1 PA subunit polypeptide fragment or variants thereof.

Preferably, the ability of the test compound to inhibit the endonuclease activity of the Influenza A 2009 pandemic H1N1 PA subunit polypeptide fragment or variant thereof is analyzed in the above-described methods.

In a preferred embodiment, the above-described methods for identifying compounds which associate with, preferably bind to, the endonucleolytically active site, modulate, decrease, and/or inhibit the endonucleolytic activity of the Influenza A 2009 pandemic H1N1 PA subunit polypeptide fragment or variant thereof are performed in a high-throughput setting. In a preferred embodiment, said methods are carried out in a multi-well microtiter plate as described above using PA polypeptide fragments or variants thereof according to the present invention and labeled test compounds.

In a preferred embodiment, the test compounds are derived from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant, and animal extracts can be used. Additionally, test compounds can be synthetically produced using combinatorial chemistry either as individual compounds or as mixtures.

In another embodiment, the inhibitory effect of the identified compound on the Influenza A 2009 pandemic H1N1 virus life cycle may be tested in an in vivo setting. A cell line that is susceptible for Influenza virus infection such as 293T human embryonic kidney cells, Madin-Darby canine kidney cells, or chicken embryo fibroblasts may be infected with Influenza A 2009 pandemic H1N1 virus in presence or absence of the identified compound. In a preferred embodiment, the identified compound may be added to the culture medium of the cells in various concentrations. Viral plaque formation may be used as read out for the infectious capacity of the Influenza A 2009 pandemic H1N1 virus and may be compared between cells that have been treated with the identified compound and cells that have not been treated.

In a further embodiment of the invention, the test compound applied in any of the above described methods is a small molecule. In a preferred embodiment, said small molecule is derived from a library, e.g., a small molecule inhibitor library. In another embodiment, said test compound is a peptide or protein. In a preferred embodiment, said peptide or protein is derived from a peptide or protein library.

In another embodiment of the above-described methods for computational as well as in vitro identification of compounds that associate with, preferably bind to, the endonucleolytically active site, modulate, decrease, and/or inhibit the endonucleolytic activity of the Influenza A 2009 pandemic H1N1 PA subunit polypeptide fragment or variant thereof according to the present invention, said methods further comprise the step of formulating said compound or a pharmaceutically acceptable salt thereof with one or more pharmaceutically acceptable excipient(s) and/or carrier(s).

As already mentioned above, it is an aspect of the present invention to provide a compound which is able to modulate, preferably to decrease, more preferably to inhibit, the endonuclease activity of the Influenza A 2009 pandemic H1N1 PA subunit or variant thereof according to the present invention. It is preferred that the compound is able to modulate, preferably to decrease, more preferably to inhibit, the endonuclease activity of the PA subunit or variant thereof according to the present invention by associating with, preferably by binding to, the endonucleolytically active site of said PA subunit or variant thereof.

It is also an aspect of the present invention to provide a compound which is able to modulate, preferably to decrease, more preferably to inhibit, the endonuclease activity of the Influenza A 2009 pandemic H1N1 PA subunit polypeptide fragment or variant thereof according to the present invention. It is preferred that the compound is able to modulate, preferably to decrease, more preferably to inhibit, the endonuclease activity of the PA subunit polypeptide fragment or variant thereof according to the present invention by associating with, preferably by binding to, the endonucleolytically active site of said PA subunit polypeptide fragment or variant thereof.

It is further an aspect of the present invention to provide a compound which is able to modulate, preferably to decrease, more preferably to inhibit, the endonuclease activity of the PA subunit of other viruses, preferably of viruses of the Orthomyxoviridae family, Bunyaviridae family and/or Arenviridae family. It is preferred that the compound is able to modulate, preferably to decrease, more preferably to inhibit, the endonuclease activity of the PA subunit of other viruses, preferably of viruses of the Orthomyxoviridae family, Bunyaviridae family and/or Arenviridae family, by associating with, preferably by binding to, the endonucleolytically active site of said PA subunit.

The ability of a compound to associate with, preferably to bind to, the endonucleolytically active site of the aforementioned PA subunit or variant thereof, or PA subunit polypeptide fragment or variant thereof, and/or to modulate, preferably to decrease, more preferably to inhibit the endonucleolytic activity of the PA subunit or variant thereof, or PA subunit polypeptide fragment or variant thereof can easily be assessed. For example, the purified PA subunit or PA subunit polypeptide fragment and a substrate thereof such as panhandle RNA or single stranded DNA are contacted in presence or absence of varying amounts of the test compound and incubated for a certain period of time, for example, for 5, 10, 15, 20, 30, 40, 60, or 90 minutes. The reaction conditions are chosen such that the PA subunit or PA subunit polypeptide fragment is endonucleolytically active without the test compound. The substrate is then analyzed for degradation/endonucleolytic cleavage, for example, by gel electrophoresis. Alternatively, such a test may comprise a labeled substrate molecule which provides a signal when the substrate molecule is endonucleolytically cleaved but does not provide a signal if it is intact. For example, the substrate polynucleotide chain may be labeled with fluorescent reporter molecule and a fluorescence quencher such that the fluorescent reporter is quenched as long as the substrate polynucleotide chain is intact. In case the substrate polynucleotide chain is cleaved, the fluorescent reporter and the quencher are separated, thus, the fluorescent reporter emits a signal which may be detected, for example, by an ELISA reader. Further suitable methods are described below.

Preferably, said compound is identifiable by the above-described (in vitro) methods. More preferably, said compound is identified by the above-described (in vitro) methods.

The compound identifiable by the above described (in vitro) methods may be able to modulate the endonuclease activity of the Influenza A 2009 pandemic H1N1 PA subunit or variant thereof. The compound identifiable by the above-described (in vitro) methods may be able to modulate, preferably to decrease, more preferably to inhibit, the endonuclease activity of the Influenza A 2009 pandemic H1N1 PA subunit polypeptide fragment or variant thereof according to the present invention.

It is also possible that the compound identifiable by the above-described (in vitro) methods may be able to modulate, preferably to decrease, most preferably to inhibit, the endonuclease activity of the PA subunit of other viruses, preferably of viruses of the Orthomyxoviridae family, Bunyaviridae family and/or Arenviridae family.

Compounds of the present invention can be any agents as described above for the in silico screening methods. In a preferred embodiment of the compound according to the present invention, the compound is not a 4-substituted 2-dioxobutanoic acid, a 4-substituted 4-dioxobutanoic acid, a 4-substituted 2,4-dioxobutanoic acid, 2,6-diketopiperazine or a derivative thereof, a substituted 2,6-diketopiperazine or a derivative thereof, a pyrazine-2,6-dione or a substituted pyrazine-2,6-dione such as flutimide, an N-hydroxamic acid, or an N-hydroxymide.

In particular, the compound according to the present invention is not a compound according to Formula I:

Formula I

R¹ = Me, Et, Ph
R² = acyl, carbamoyl, sulfonyl.

In another preferred embodiment of the compound according to the present invention, the compound is not 4-[3-[(4-chlorophenyl)methyl]-1-(phenylmethyl)-3-piperidinyl]-2-hydroxy-4-oxo-2-butenoic acid, 4-[4-[(4-chlorophenyl)methyl]-1-(cyclohexylmethyl)-4-piperidinyl]-2-hydroxy-4-oxo-2-butenoic acid, 4-[3-[(4-chlorophenyl)methyl]-1-(phenylmethylsulpho)-3-piperidinyl]-2-hydroxy-4-oxo-2-butenoic acid, ribo-Uridine Monophosphate (rUMP), desoxy-thymidinmonophosphat (dTMP), or 2.4-dioxo-4-phenylbutanoic acid (DPBA).

In a further preferred embodiment of the compound according to the present invention, the compound is not a catechin, preferably not a (−)-epigallocatechin gallate (EGCG), such as [(2R,3R)-5,7-dihydroxy-2-(3,4,5-trihydroxyphenyl)chroman-3-yl]3,4,5-trihydroxybenzoate, a (−)-epicatechin gallate (ECG), (−)-epigallocatechin (EGC), (−)-epicatechin (EC), or gallic acid (GA). In another preferred embodiment of the compound of the present invention, the compound is not a phenethylphenylphthalimide, a phenethylphenylphthalimide analog derived from thalidomide or raltegravir (also a diketobutanoic acid derivative).

It is an aspect of the present invention to provide a pharmaceutical composition comprising the afore-mentioned compound of the present invention or a pharmaceutically acceptable salt thereof. It is also an aspect of the present invention to provide a pharmaceutical composition comprising the afore-mentioned compound of the present invention or a pharmaceutically acceptable salt thereof and one or more pharmaceutically acceptable excipient(s) and/or carrier(s).

As already mentioned above, the compound comprised in the pharmaceutical compositions of the present invention (i) is able to modulate, preferably to decrease, more preferably to inhibit, the endonuclease activity of the Influenza A 2009 pandemic H1N1 PA subunit or variant thereof according to the present invention, e.g. by binding to the endonucleolytically active site of said subunit or variant thereof, (ii) is able to modulate, preferably to decrease, more preferably to inhibit, the endonuclease activity of the Influenza A 2009 pandemic H1N1 PA subunit polypeptide fragment or variant thereof according to the present invention, e.g. by binding to the endonucleolytically active site of said polypeptide fragment or variant thereof, or (iii) is able to modulate, preferably to decrease, more preferably to inhibit, the endonuclease activity of the PA subunit of other viruses, preferably of viruses of the Orthomyxoviridae family, Bunyaviridae family and/or Arenviridae family, e.g. by binding to the endonucleolytically active site of said PA subunit. Preferably, the compound comprised in the pharmaceutical compositions of the present invention is identifiable by the above-described methods. More preferably, the compound comprised in the pharmaceutical compositions of the present invention is identified by the above-described methods.

Preferably, said pharmaceutical composition(s) is (are) producible according to the afore-mentioned methods.

A compound according to the present invention can be administered alone but, in human therapy, will generally be administered in admixture with a suitable pharmaceutical excipient, diluent, or carrier selected with regard to the intended route of administration and standard pharmaceutical practice (see hereinafter).

In the aspect of computational modeling or screening of a binding partner for the endonucleolytically active site, a modulator, and/or inhibitor of the endonucleolytic activity of the Influenza A 2009 pandemic H1N1 PA subunit polypeptide fragment or variant thereof according to the present invention, it may be possible to introduce into the molecule of interest, chemical moieties that may be beneficial for a molecule that is to be administered as a pharmaceutical. For example, it may be possible to introduce into or omit from the molecule of interest, chemical moieties that may not directly affect binding of the molecule to the target area but which contribute, for example, to the overall solubility of the molecule in a pharmaceutically acceptable carrier, the bioavailability of the molecule and/or the toxicity of the molecule. Considerations and methods for optimizing the pharmacology of the molecules of interest can be found, for example, in "Goodman and Gilman's The Pharmacological Basis of Therapeutics", $8^{th}$ Edition, Goodman, Gilman, Rall, Nies, & Taylor, Eds., Pergamon Press (1985); Jorgensen & Duffy, 2000, Bioorg. Med. Chem. Lett 10:1155-1158. Furthermore, the computer program "Qik Prop" can be used to provide rapid predictions for physically significant descriptions and pharmaceutically-relevant properties of an organic molecule of interest. A 'Rule of Five' probability scheme can be used to estimate oral absorption of the newly synthesized compounds (Lipinski et al., 1997, Adv. Drug Deliv. Rev. 23:3-25). Programs suitable for pharmacophore selection and design include (i) DISCO (Abbot Laboratories, Abbot Park, Ill.), (ii) Catalyst (Bio-CAD Corp., Mountain View, Calif.), and (iii) Chem DBS-3D (Chemical Design Ltd., Oxford, UK).

The pharmaceutical composition contemplated by the present invention may be formulated in various ways well known to one of skill in the art. For example, the pharmaceutical composition of the present invention may be in solid form such as in the form of tablets, pills, capsules (including soft gel capsules), cachets, lozenges, ovules, powder, granules, or suppositories, or in liquid form such as in the form of elixirs, solutions, emulsions, or suspensions.

Solid administration forms may contain excipients such as microcrystalline cellulose, lactose, sodium citrate, calcium carbonate, dibasic calcium phosphate, glycine, and starch (preferably corn, potato, or tapioca starch), disintegrants such as sodium starch glycolate, croscarmellose sodium, and certain complex silicates, and granulation binders such as polyvinylpyrrolidone, hydroxypropylmethyl cellulose (HPMC), hydroxypropylcellulose (HPC), sucrose, gelatin, and acacia. Additionally, lubricating agents such as magnesium stearate, stearic acid, glyceryl behenate, and talc may be included. Solid compositions of a similar type may also be employed as fillers in gelatin capsules. Preferred excipients in this regard include lactose, starch, a cellulose, milk sugar, or high molecular weight polyethylene glycols.

For aqueous suspensions, solutions, elixirs, and emulsions suitable for oral administration the compound may be combined with various sweetening or flavoring agents, coloring matter or dyes, with emulsifying and/or suspending agents and with diluents such as water, ethanol, propylene glycol, and glycerin, and combinations thereof.

The pharmaceutical composition of the present invention may contain release rate modifiers including, for example, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer, and mixtures thereof.

The pharmaceutical composition of the present invention may be in the form of fast dispersing or dissolving dosage formulations (FDDFs) and may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavoring, polyethylene glycol, fumed silica, silicon dioxide, sodium starch glycolate, sodium stearyl fumarate, sorbitol, xylitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

The pharmaceutical composition of the present invention suitable for parenteral administration is best used in the form of a sterile aqueous solution which may contain other substances, for example, enough salts or glucose to make the solution isotonic with blood. The aqueous solutions should be suitably buffered (preferably to a pH of from 3 to 9), if necessary.

The pharmaceutical composition suitable for intranasal administration and administration by inhalation is best delivered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide, or another suitable gas. The pressurized container, pump, spray or nebulizer may contain a solution or suspension of the active compound, e.g., using a mixture of ethanol and the propellant as the solvent, which may additionally contain a lubricant, e.g., sorbitan trioleate.

In another aspect, the present invention provides an antibody directed against the active site of the PA subunit of the Influenza A 2009 pandemic H1N1 virus according to SEQ ID NO: 2 or a variant thereof, wherein said variant comprises the amino acid serine at an amino acid position 186 according to SEQ ID NO: 2 or at an amino acid position corresponding thereto.

In a preferred embodiment, said antibody recognizes the endonuclease domain by recognition of a polypeptide fragment selected from the group of polypeptides defined by SEQ ID NO: 4 to 11, i.e., amino acids 20 to 30 (SEQ ID NO: 4), 32 to 40 (SEQ ID NO: 5), 41 to 51 (SEQ ID NO: 6), 80 to 90 (SEQ ID NO: 7), 100 to 110 (SEQ ID NO: 8), 115 to 125 (SEQ ID NO: 9), 130 to 140 (SEQ ID NO: 10), and 176 to 186 (SEQ ID NO: 11) of the amino acid sequence as set forth in SEQ ID NO: 2.

In particular, said antibody specifically binds to an epitope comprising one or more of above indicated amino acids, which define the active site. In this context, the term epitope has its art recognized meaning and preferably refers to stretches of 4 to 20 amino acids, preferably 5 to 18, 5 to 15, or 7 to 14 amino acids, e.g. stretches of 4, 5, 6, 7, 8, 9, 10, 11, 12, 13, 14, 15, 16, 17, 18, 19, or 20 amino acids. Accordingly, preferred epitopes have a length of 4 to 20, 5 to 18, preferably 5 to 15, or 7 to 14 amino acids, e.g. have a length of 4, 5, 6, 7, 8, 9, 10, 11, 12, 13, 14, 15, 16, 17, 18, 19, or 20 amino acids, and/or comprise one or more of Lys34, Glu26, Ile38, Tyr24, His41, Glu80, Arg84, Leu106, Asp108, Glu119, Ile120, Arg124, Tyr130, Lys134, Phe105, and Lys137 of SEQ ID NO: 2 or one or more corresponding amino acid(s). Thus, in a preferred embodiment, said antibody recognizes a polypeptide fragment of a length between 5 and 15 amino acids of the amino acid sequence as set forth in SEQ ID NO: 2, wherein the polypeptide fragment comprises one or more amino acid residues selected from the group consisting of Lys34, Glu26, Ile38, Tyr24, His41, Glu80, Arg84, Leu106, Asp108, Glu119, Ile120, Tyr130, Lys134, Phe105, Lys137, and Arg124.

The antibody of the present invention may be a monoclonal or polyclonal antibody or portions thereof. Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies such as humanized antibodies, diabodies, and polypeptides that contain at least a portion of an antibody that is sufficient to confer specific antigen binding to the polypeptide. The antibody of the present invention is generated according to standard protocols. For example, a polyclonal antibody may be generated by immunizing an animal such as mouse, rat, rabbit, goat, sheep, pig, cattle, or horse with the antigen of interest optionally in combination with an adjuvant such as Freund's complete or incomplete adjuvant, RIBI (muramyl dipeptides), or ISCOM (immunostimulating complexes) according to standard methods well known to the person skilled in the art. The polyclonal antiserum directed against the endonuclease domain of Influenza A 2009 pandemic H1N1 PA or fragments thereof is obtained from the animal by bleeding or sacrificing the immunized animal. The serum (i) may be used as it is obtained from the animal, (ii) an immunoglobulin fraction may be obtained from the serum, or (iii) the antibodies specific for the endonuclease domain of Influenza A 2009 pandemic H1N1 PA or fragments thereof may be purified from the serum. Monoclonal antibodies may be generated by methods well known to the person skilled in the art. In brief, the animal is sacrificed after immunization and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene Immortalized cells are screened using the H1N1 PA endonuclease domain or a fragment thereof. Cells that produce antibodies directed against the H1N1 PA endonuclease domain or a fragment thereof, e.g., hybridomas, are selected, cloned, and further screened for desirable characteristics including robust growth, high antibody production, and desirable antibody characteristics. Hybridomas can be expanded (i) in vivo in syngeneic animals, (ii) in animals that lack an immune system, e.g., nude mice, or (iii) in cell culture in vitro. Methods of selecting, cloning, and expanding hybridomas are well known to those of ordinary skill in the art. The skilled person may refer to standard texts such as "Antibodies: A Laboratory Manual", Harlow and Lane, Eds., Cold Spring Harbor Laboratory Press, Cold Spring Harbor, New York (1990), which is incorporated herein by reference, for support regarding generation of antibodies.

In another aspect, the present invention relates to the use of the compound(s) according the present invention, the pharmaceutical composition(s) according to the present invention, or the antibody according to the present invention for the manufacture of a medicament for treating, ameliorating, or preventing disease conditions caused by viral infections with viruses of the Orthomyxoviridae family, Bunyaviridae family and/or Arenviridae family, preferably caused by viral infections with Influenza A 2009 pandemic H1N1 virus.

Said compound (i) is able to modulate, preferably to decrease, more preferably to inhibit, the endonuclease activity of the Influenza A 2009 pandemic H1N1 PA subunit or variant thereof according to the present invention, e.g. by binding to the endonucleolytically active site of said PA subunit or variant thereof, (ii) is able to modulate, preferably to decrease, more preferably to inhibit, the endonuclease activity of the Influenza A 2009 pandemic H1N1 PA subunit polypeptide fragment or variant thereof according to the present invention, e.g. by binding to the endonucleolytically active site of said PA subunit polypeptide fragment or variant thereof, or (iii) is able to modulate, preferably to decrease, more preferably to inhibit, the endonuclease activity of the PA subunit of other viruses, preferably of viruses of the Orthomyxoviridae family, Bunyaviridae family and/or Arenviridae family, e.g. by binding to the endonucleolytically active site of said PA subunit.

It is preferred that said compound(s) is (are) identifiable by the above-described methods. It is further preferred that said pharmaceutical composition(s) is (are) producible according to the afore-mentioned methods. Thus, preferably, the present invention relates to the use of a compound identifiable by the above-described methods that is able to bind to the endonucleolytically active site of the Influenza A 2009 pandemic H1N1 PA subunit polypeptide fragment or variant thereof, and/or is able to modulate, preferably to decrease, more preferably to inhibit the endonucleolytic activity of the Influenza A 2009 pandemic H1N1 PA subunit polypeptide fragment or variant thereof, or the pharmaceutical composition producible according to the afore-mentioned methods for the manufacture of a medicament for treating, ameliorating, or preventing disease conditions caused by viral infections with viruses of the Orthomyxoviridae family Bunyaviridae family and/or Arenviridae family, preferably caused by viral infections with Influenza A 2009 pandemic H1N1 virus.

In a further aspect, the present invention relates to the compound(s) according the present invention, the pharmaceutical composition(s) according to the present invention, or the antibody according to the present invention for treating, ameliorating, or preventing disease conditions caused by viral infections with viruses of the Orthomyxoviridae family, Bunyaviridae family and/or Arenviridae family, preferably caused by viral infections with Influenza A 2009 pandemic H1N1 virus.

Said compound (i) is able to modulate, preferably to decrease, more preferably to inhibit, the endonuclease activity of the Influenza A 2009 pandemic H1N1 PA subunit or variant thereof according to the present invention, e.g. by binding to the endonucleolytically active site of said PA subunit or variant thereof, (ii) is able to modulate, preferably to decrease, more preferably to inhibit, the endonuclease activity of the Influenza A 2009 pandemic H1N1 PA subunit polypeptide fragment or variant thereof according to the present invention, e.g. by binding to the endonucleolytically active site of said PA subunit polypeptide fragment or variant thereof, or (iii) is able to modulate, preferably to decrease, more preferably to inhibit, the endonuclease activity of the PA subunit of other viruses, preferably of viruses of the Orthomyxoviridae family, Bunyaviridae family and/or Arenviridae family, e.g. by binding to the endonucleolytically active site of said PA subunit.

It is preferred that said compound(s) is (are) identifiable by the above-described methods. It is further preferred that said pharmaceutical composition(s) is (are) producible according to the afore-mentioned methods. Thus, preferably, the present invention relates to a compound identifiable by the above-described methods that is able to bind to the endonucleolytically active site of the Influenza A 2009 pandemic H1N1 PA subunit polypeptide fragment or variant thereof, and/or is able to modulate, preferably to decrease, more preferably to inhibit the endonucleolytic activity of the Influenza A 2009 pandemic H1N1 PA subunit polypeptide fragment or variant thereof, or the pharmaceutical composition producible according to the afore-mentioned methods for treating, ameliorating, or preventing disease conditions caused by viral infections with viruses of the Orthomyxoviridae family Bunyaviridae family and/or Arenviridae family, preferably caused by viral infections with Influenza A 2009 pandemic H1N1 virus.

In another aspect, the present invention relates to the use of the compound 4-[3-[(4-chlorophenyl)methyl]-1-(phenylmethyl)-3-piperidinyl]-2-hydroxy-4-oxo-2-butenoic acid (EMBL-R05-3), of the compound 4-[4-[(4-chlorophenyl)methyl]-1-(cyclohexylmethyl)-4-piperidinyl]-2-hydroxy-4-oxo-2-butenoic acid (EMBL-R05-2), of the compound 4-[3-[(4-chlorophenyl)methyl]-1-(phenylmethylsulpho)-3-piperidinyl]-2-hydroxy-4-oxo-2-butenoic acid (EMBL-R05-1), or of the compound [(2R,3R)-5,7-dihydroxy-2-(3,4,5-trihydroxyphenyl)chroman-3-yl]3,4,5-trihydroxybenzoate (EGCG) for the manufacture of a medicament for treating, ameliorating, or preventing disease conditions caused by viral infections with Influenza A 2009 pandemic H1N1 virus, as the inventors of the present invention have determined that said compounds are able to bind to the endonucleolytically active site of the Influenza A 2009 pandemic H1N1 PA subunit polypeptide fragment or variant thereof, and are able to modulate, i.e. to inhibit, the endonucleolytic activity of the Influenza A 2009 pandemic H1N1 PA subunit polypeptide fragment or variant thereof.

In an further aspect, the present invention relates to 4-[3-[(4-chlorophenyl)methyl]-1-(phenylmethyl)-3-piperidinyl]-2-hydroxy-4-oxo-2-butenoic acid (EMBL-R05-3), 4-[4-[(4-chlorophenyl)methyl]-1-(cyclohexylmethyl)-4-piperidinyl]-2-hydroxy-4-oxo-2-butenoic acid (EMBL-R05-2), 4-[3-[(4-chlorophenyl)methyl]-1-(phenylmethylsulpho)-3-piperidinyl]-2-hydroxy-4-oxo-2-butenoic acid (EMBL-R05-1), or [(2R,3R)-5,7-dihydroxy-2-(3,4,5-trihydroxyphenyl)chroman-3-yl]3,4,5-trihydroxybenzoate (EGCG) for treating, ameliorating, or preventing disease conditions caused by viral infections with Influenza A 2009 pandemic H1N1 virus.

In another aspect, the present invention relates to the use of a 4-substituted 2,4-dioxobutanoic acid compound or a green tea catechin for treating, ameliorating, or preventing disease conditions caused by viral infections with Influenza A 2009 pandemic H1N1 virus.

For treating, ameliorating, or preventing said disease conditions the medicament of the present invention can be administered to an animal patient, preferably a mammalian patient, preferably a human patient, orally, buccally, sublingually, intranasally, via pulmonary routes such as by inhalation, via rectal routes, or parenterally, for example, intracavernosally, intravenously, intra-arterially, intraperitoneally, intrathecally, intraventricularly, intra-urethrally intrasternally, intracranially, intramuscularly, or subcutaneously, they may be administered by infusion or needleless injection techniques.

The pharmaceutical compositions of the present invention may be formulated in various ways well known to one of skill in the art and as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation administered in the use of the present invention may be varied or adjusted from about 1 mg to about 1000 mg per $m^2$, preferably about 5 mg to about 150 mg/$m^2$ according to the particular application and the potency of the active component.

The compounds employed in the medical use of the invention are administered at an initial dosage of about 0.05 mg/kg to about 20 mg/kg daily. A daily dose range of about 0.05 mg/kg to about 2 mg/kg is preferred, with a daily dose range of about 0.05 mg/kg to about 1 mg/kg being most preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following figures and examples are merely illustrative of the present invention and should not be construed to limit the scope of the invention as indicated by the appended claims in any way.

BRIEF DESCRIPTION OF THE DRAWINGS

FIGS. 1-5 Refined atomic structure coordinates for PA polypeptide fragment amino acids 1 to 198 according to amino acids 1 to 198 of the amino acid sequence set forth in SEQ ID NO: 2 (PA H1N1 1 to 198), with or without bound compounds. For each structure there are generally four molecules in the crystallographic asymmetric unit (ASU) denoted A, B, C and D. In FIGS. 1 to 5, however, only one selected molecule is shown (see below). The file header gives information about the structure refinement. "Atom" refers to the element whose coordinates are measured. The first letter in the column defines the element. The 3-letter code of the respective amino acid is given and the amino acid sequence position. The first 3 values in the line "Atom" define the atomic position of the element as measured. The fourth value corresponds to the occupancy and the fifth (last) value is the temperature factor (B factor). The occupancy factor refers to the fraction of the molecules in which each atom occupies the position specified by the coordinates. A value of "1" indicates that each atom has the same conformation, i.e., the same position, in all equivalent molecules of the crystal. B is a thermal factor that measures movement of the atom around its atomic center. This nomenclature corresponds to the Protein Data Bank (PDB) format.

FIG. 1: (Sheets labelled FIG. 1A to FIG. 1AB) Structural co-ordinates of the native (i.e. without compound/ligand) H1N1 PA endonuclease domain in standard Protein Data Bank (PDB) format. Only the chain A (with associated divalent cations, i.e. one magnesium and one manganese ion, and water molecules) from the asymmetric unit is included. Chains B, C and D are very similar.

FIG. 2: (Sheets labelled FIG. 2A to FIG. 2AC) Structural co-ordinates of the H1N1 PA endonuclease domain with bound 4-[3-[(4-chlorophenyl)methyl]-1-(phenylmethyl)-3-piperidinyl]-2-hydroxy-4-oxo-2-butenoic acid (EMBL-R05-3) in standard Protein Data Bank (PDB) format. Only the chain A (with associated divalent cations, i.e. two manganese ions, and water molecules) from the asymmetric unit is included. The compound EMBL-R05-3 has residue descriptor ci3.

FIG. 3: (Sheets labelled FIG. 3A to FIG. 3AB) Structural co-ordinates of the H1N1 PA endonuclease domain with bound 4-[3-[(4-chlorophenyl)methyl]-1-(phenylmethyl)-3-piperidinyl]-2-hydroxy-4-oxo-2-butenoic acid (EMBL-R05-3) in standard Protein Data Bank (PDB) format. Only the chain D (with associated divalent cations, i.e. two manganese ions, and water molecules) from the asymmetric unit is included. The compound EMBL-05-03 has a different configuration than in chain A (FIG. 2). Said compound has residue descriptor ci3.

FIG. 4: (Sheets labelled FIG. 4A to FIG. 4AC) Structural co-ordinates of the H1N1 PA endonuclease domain with bound 4-[4-[(4-chlorophenyl)methyl]-1-(cyclohexylmethyl)-4-piperidinyl]-2-hydroxy-4-oxo-2-butenoic acid (EMBL-R05-2) in standard Protein Data Bank (PDB) format. Only the chain A (with associated divalent cations, i.e. two manganese ions, and water molecules) from the asymmetric unit is included. Chains B, C and D are very similar. The compound EMBL-R05-2 has residue descriptor cit.

FIG. 5: (Sheets labelled FIG. 5A to FIG. 5AA) Structural co-ordinates of the H1N1 PA endonuclease domain with bound ribo-Uridine Monophosphate (rUMP) in standard Protein Data Bank (PDB) format. Only the chain A (with associated divalent cations, i.e. two manganese ions, and water molecules) from the asymmetric unit is included. Chains B, C and D are very similar. The compound rUMP has residue descriptor U.

FIG. 6: Diagram using the structural co-ordinates of FIG. 1 illustrating the endonuclease active site (PA polypeptide fragment (chain A)), showing the divalent cations (one manganese and one magnesium) and key active site residues.

Figure 7A:
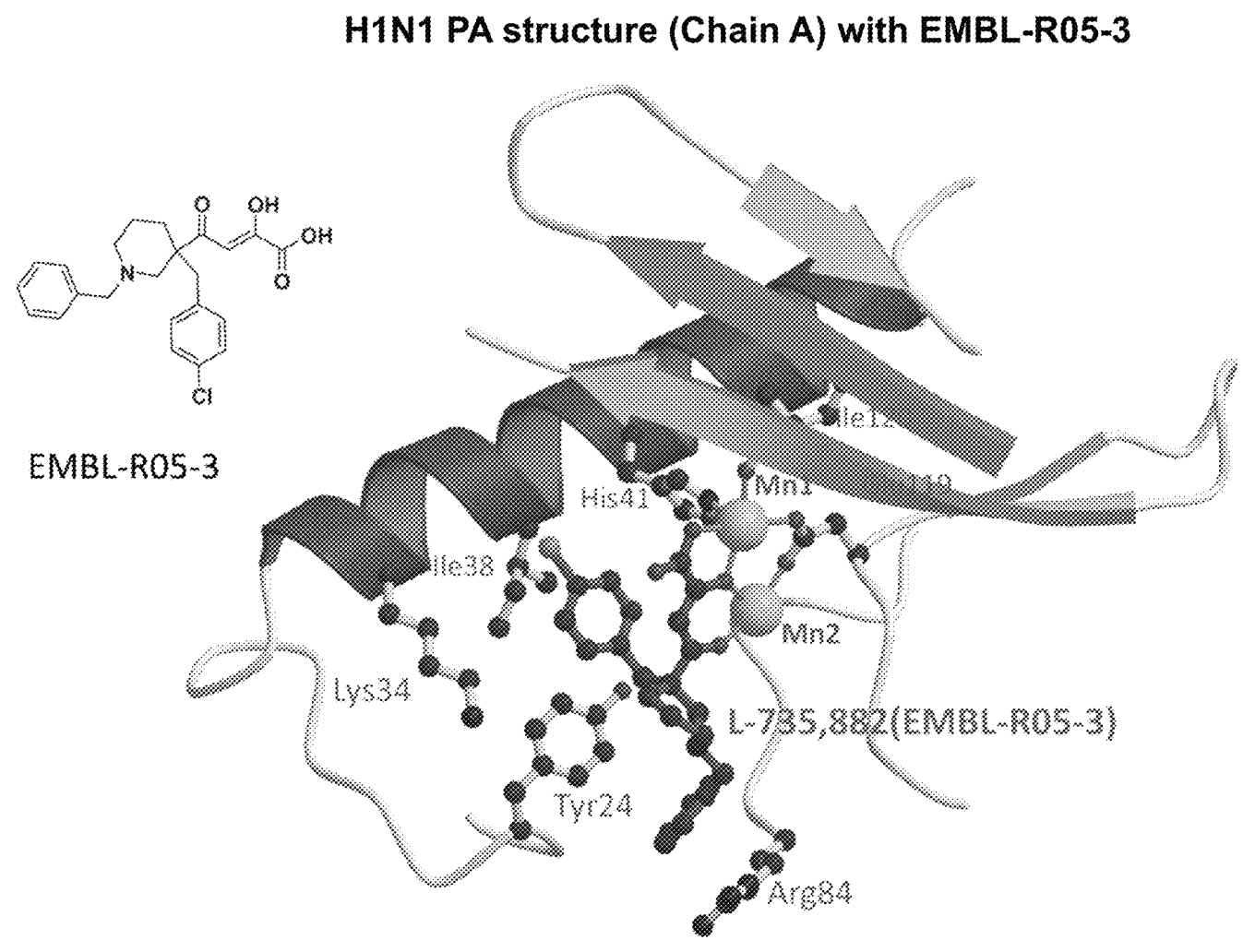
Figure 7B:
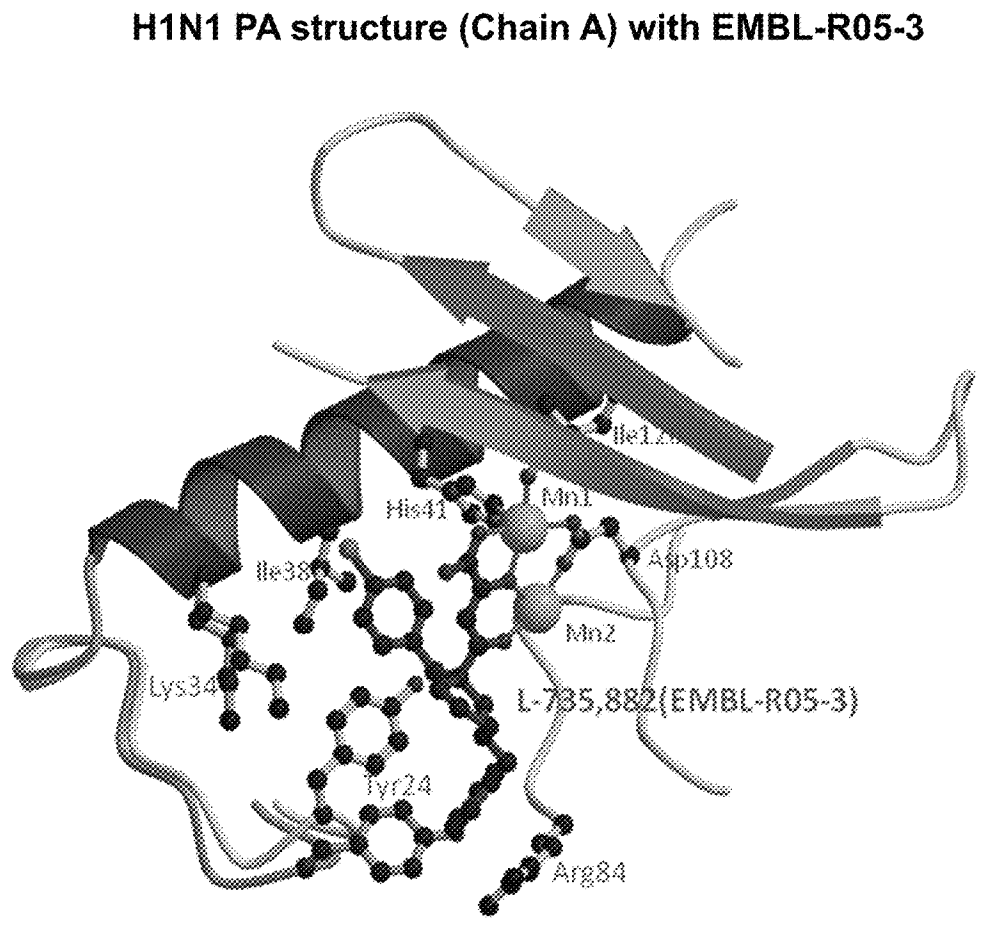

FIG. 7: (Sheets labelled FIG. 7A to 7B) (A) Diagram using the structural co-ordinates of FIG. 2 illustrating the endonuclease active site (PA polypeptide fragment (chain A)), showing the bound compound EMBL-R05-3, the divalent cations (two manganese) and key active site residues that interact with the compound (notably Arg84) or are close to it and (B) Diagram comparing the co-ordinates of FIG. 1 (chain subjacent on left hand side) and FIG. 2 showing change in conformation of the loop in the vicinity of Tyr24 upon binding of EMBL-R05-3 (chain A). Tyr24 side-chain moves to partially stack with the chlorobenzene of EMBL-R05-3.

FIG. 8: Diagram using the structural co-ordinates of FIG. 3 illustrating the endonuclease active site (PA polypeptide fragment (chain D)), showing the bound compound EMBL-R05-3, the divalent cations (two manganese) and key active site residues that interact with the compound (notably Tyr24 and Arg84) or are close to it.

Figure 9:
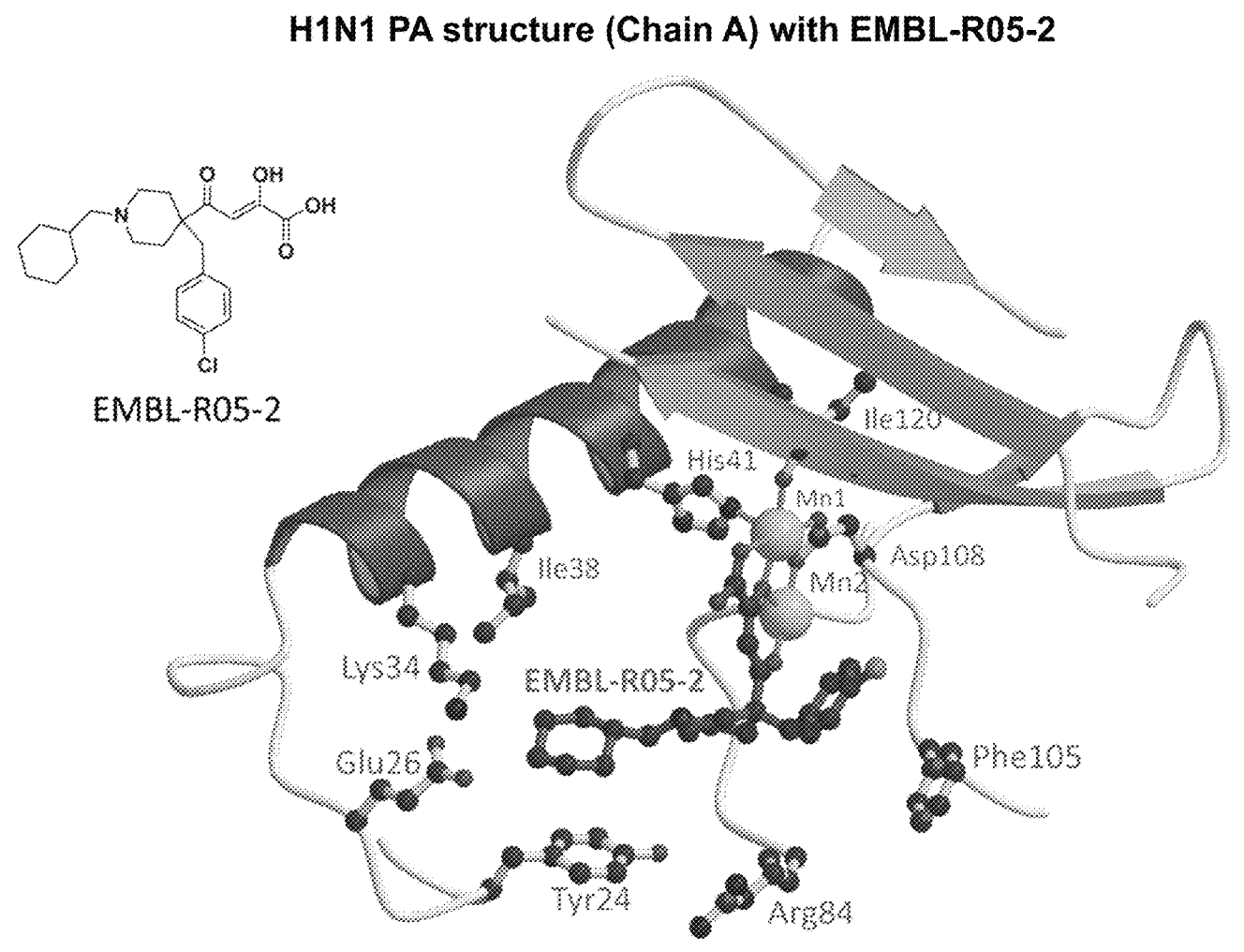

FIG. 9: Diagram using the structural co-ordinates of FIG. 4 illustrating the endonuclease active site (PA polypeptide fragment (chain A)), showing the bound compound EMBL-R05-2, the divalent cations (two manganese) and key active site residues that interact with the compound (notably Tyr24 and Phe105) or are close to it.

FIG. 10: Diagram using the structural co-ordinates of FIG. 5 illustrating the endonuclease active site (PA polypeptide fragment (chain A)), showing the bound compound rUMP, the divalent cations (two manganese) and key active site residues that interact with the compound (notably Tyr24 and Lys34) or are close to it.

FIGS. 11A, 11B, and 11C: 15% PAGE gels and gel filtration profile from a typical purification of H1N1 PA1-198 (SEQ ID NO:13). The arrow indicates faint traces of residual MBP.

FIG. 12: Frozen crystal of H1N1 PA-Nter co-crystallised with rUMP in the P212121 space-group.

FIG. 13: Divalent ion co-ordination in the native endonuclease structure.

FIG. 14: Electron density for rUMP and divalent cations (manganese, Mn1 and Mn2) in co-crystals with H1N1 PA-Nter. Refined 2Fo-Fc electron density contoured at 1.1 $\sigma$. Unbiased Fo-Fc electron density contoured at 2.8$\sigma$. Anomalous difference map contoured at 4$\sigma$.

FIGS. 15-16: Refined atomic structure coordinates for PA polypeptide fragment amino acids 1 to 198 of the amino acid sequence set forth in SEQ ID NO: 2 with amino acids 52 to 64 replaced by the amino acid glycine (PA H1N1 1 to 198 Δ52-64: Gly (SEQ ID NO:14) with bound compounds. For each structure there is one molecule in the crystallographic asymmetric unit (ASU). The file header gives information about the structure refinement. "Atom" refers to the element whose coordinates are measured. The first letter in the column defines the element. The 3-letter code of the respective amino acid is given and the amino acid sequence position. The first 3 values in the line "Atom" define the atomic position of the element as measured. The fourth value corresponds to the occupancy and the fifth (last) value is the temperature factor (B factor). The occupancy factor refers to the fraction of the molecules in which each atom occupies the position specified by the coordinates. A value of "1" indicates that each atom has the same conformation, i.e., the same position, in all equivalent molecules of the crystal. B is a thermal factor that measures movement of the atom around its atomic center. This nomenclature corresponds to the Protein Data Bank (PDB) format.

FIG. 15: (Sheets labelled FIG. 15A to FIG. 15AB) Structural co-ordinates of the H1N1 PA endonuclease domain with bound 4-[3-[(4-chlorophenyl)methyl]-1-(phenylmethylsulpho)-3-piperidinyl]-2-hydroxy-4-oxo-2-butenoic acid (EMBL-R05-1) in standard Protein Data Bank (PDB) format. The chain A (with associated divalent cations, i.e. two manganese ions, and water molecules) from the asymmetric unit is included. The compound EMBL-R05-1 has residue descriptor ci1.

FIG. 16: (Sheets labelled FIG. 16A to FIG. 16AA) Structural co-ordinates of the H1N1 PA endonuclease domain with bound epigallocatechin 3-gallate (EGCG) in standard Protein Data Bank (PDB) format. The chain A (with associated divalent cations, i.e. two manganese ions, and water molecules) from the asymmetric unit is included. The compound EGCG has residue descriptor tte.

FIG. 17: Diagram using the structural co-ordinates of FIG. 15 illustrating the endonuclease active site (PA polypeptide fragment), showing the bound compound EMBL-R05-1, the divalent cations (two manganese) and key active site residues that interact with the compound (notably Tyr24 and Arg84) or are close to it.

FIG. 18: (Sheets labelled FIG. 18A to FIG. 18B) Diagram using the structural co-ordinates of FIG. 16 illustrating the endonuclease active site (PA polypeptide fragment), showing the bound compound EGCG, the divalent cations (two manganese ions) and key active site residues that interact with the compound or are close to it. (B) Bound EGCG, the divalent cations (two manganese ions) and key active site residues that interact with the compound or are close to it. Interactions less than 3.3 Å (grey dotted lines), additional possible interactions less than 4 Å (dark grey dotted lines).

As shown in FIG. 19, the mode of binding of the three diketo inhibitors to the metals is conserved (although there is some variability in exact position) but the two 'arms' of each compound are inserted into different combinations of the pockets 1 to 4. EMBL-R05-1 has a similar configuration to EMBL-R05-3D, with the two arms occupying pockets 2 and 3. EMBL-R05-3A occupies pockets 2 and 4. EMBL-R05-2, which differs notably from R05-1 and R05-3 in the point of substitution on the piperidinyl ring (Table 2) occupies pocket 3 and uniquely pocket 1 (FIG. 7B). The green tea compound EGCG occupies pockets 3 and 4. More potent and specific compounds could be perhaps designed that occupy more than two of the pockets.

EXAMPLES

Figure 11A:
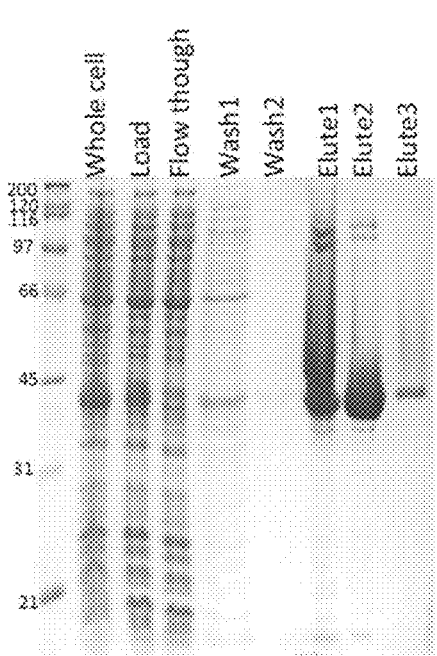
Figure 11B:
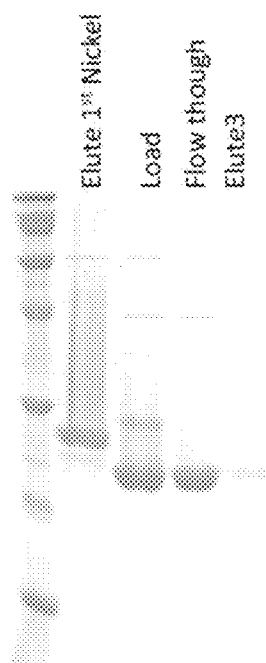
Figure 11C:
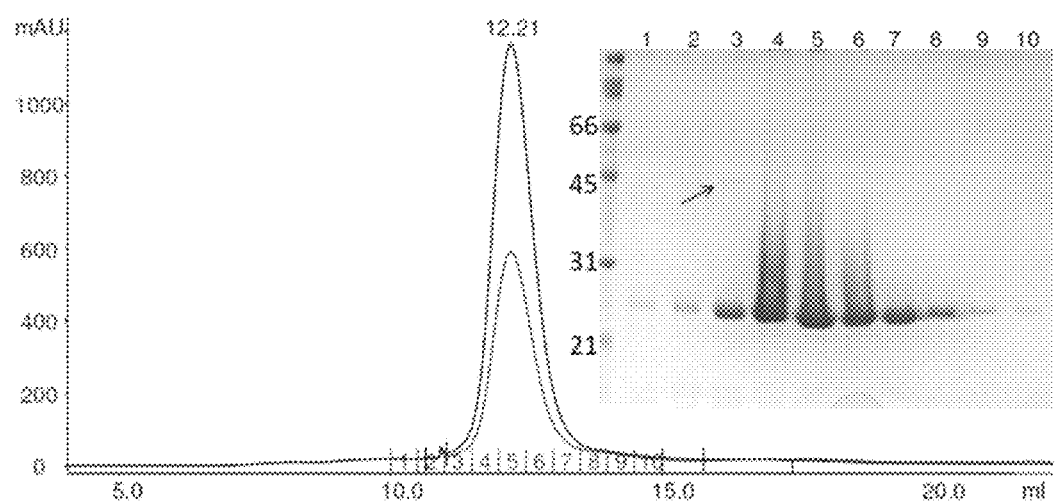
Figure 12:
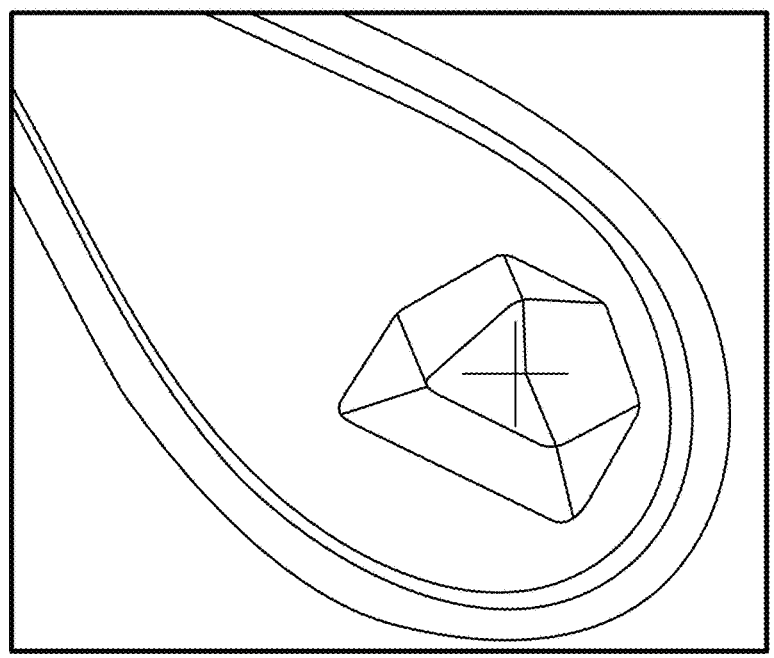

The Examples are designed in order to further illustrate the present invention and serve a better understanding. They are not to be construed as limiting the scope of the invention in any way.

1. Methods
1.1 Cloning, Expression and Purification of PA-Nter (PA H1N1 1 to 198 (SEQ ID NO:13)) and PA-Nter Mutant (PA H1N1 1 to 198 Δ52-64: Gly (SEQ ID NO:14)) from Influenza Strain a/California/04/2009-H1N1

The DNA coding for PA-Nter (residues 1-198 SEQ ID NO:13) (see SEQ ID NO: 1 and 2) from influenza strain A/California/04/2009-H1N1 was synthesized (PA H1N1 1 to 198 (SEQ ID NO:13)) and sub-cloned in the expression vector pESPRIT002 (EMBL) by GeneArt, Regensburg, Germany. The sequence was designed to contain a MGSGMA (SEQ ID NO: 3) polypeptide linker between the tobacco etch virus (TEV) cleavage site at the N-terminus to obtain 100% cleavage by TEV protease.

To further improve crystallisation properties, a deletion of part of the flexible loop (52-73) was engineered by site directed mutagenesis. To this end, a PCR amplification of the whole vector containing the wild-type gene was performed using two primers flanking the mutation site, one of them phosphorylated, and TurboPfu polymerase (Stratagene). Subsequently template vector was digested with DpnI (New England Biolabs) and the mutated vector was religated. In the PA-Nter mutant, the amino acid sequence encompassing amino acids 52-64 was replaced by a single glycine (PA H1N1 1 to 198 Δ52-64: Gly (SEQ ID NO:14)).

The wild-type and mutant plasmids were transformed to *E. coli* BL21(DE3) (Stratagene) and the protein was expressed in LB medium overnight at 20° C. after induction at an OD 0.8-1.0 with 0.2 mM isopropyl-β-thiogalactopyranoside (IPTG). The protein was purified by an immobilized metal affinity column (IMAC). A second IMAC step was performed after cleavage by the His-tagged TEV protease, followed by gel filtration on a Superdex 75 column (GE Healthcare). Finally, the protein was concentrated to 10-15 mg/ml. See FIG. 11.

1.2 Compounds

Compounds used for co-crystallisation are given in Table 2. Compound rUMP was purchased from Sigma. Compounds EMBL-R05-1, EMBL-R05-2, and EMBL-R05-3 (first described in {Tomassini, 1994 #397}) were custom synthesised by Shanghai ChemPartner. EGCG was purchased from Sigma (E4143).

1.3 Crystallization

Initial sitting drop screening was carried out at 20° C. mixing 100 nL of protein solution (15 mg/mL) with 100 nL of reservoir solution using a Cartesian robot at the EMBL Grenoble crystallization platform. Around 600 conditions were screened. Subsequently, larger crystals were obtained at 20° C. by the hanging drop method mixing protein and reservoir solutions in a ratio of 1:1. The protein solution contained 10-15 mg/mL of PA-N-ter in 20 mM HEPES pH 7.5, 150 mM NaCl, 2 mM $MnCl_2$, 2 mM $MgCl_2$. The refined reservoir compositions for native crystals and co-crystallization with different compounds/ligands are listed in Table 1. For co-crystallisations, compounds/ligands rUMP, EMBL-R05-3 and EGCG were added to the protein solution to final concentrations of 5 mM, 1.5 mM and 5 mM, respectively. Native crystals and those co-crystallized with EMBL-R05-3 and EGCG were flash frozen in liquid nitrogen in their reservoir solution with additional 25% glycerol as cryo-protectant. Co-crystals with rUMP were frozen in their reservoir solution with additonal rUMP at 10 mM concentration and additional 20% glycerol as cryoprotectant. The structure with EMBL-R05-2 was obtained by soaking co-crystals of PA-N-ter and rUMP for 2 h with reservoir solution containing 1.5 mM EMBL-R05-2 and no rUMP (the inhibitor displaces the rUMP) followed by cryo protection in reservoir solution containing 20% glycerol and 1.5 mM EMBL-R05-2. FIG. 12 shows a typical co-crystal with rUMP. The structure with EMBL-R05-1 was obtained by soaking co-crystals of PA-N-ter mutant and dTMP for 2 h with reservoir solution containing the inhibitor followed by cryo protection in reservoir solution containing 20% glycerol and the inhibitor. See also Table 2 for the compounds/ligands.

TABLE 1

Summary of crystallisation conditions and crystallographic parameters for various compounds

| Fragment/ FIG.(s) | Compound/ Ligand (final concentration) | Crystallisation reservoir condition | Space group and unit cell parameters | Resolution Refinement R-factor/R-free |
|---|---|---|---|---|
| PA H1N1 1 to 198 fragment (SEQ ID NO: 13) (chain A), see FIGS. 1 and 6 | No compound (native) | 1.6M sodium formate 0.1M HEPES pH 7 5% Glycerol | C2 4 Molecules/ASU 263.630 66.240 66.32 90.00 95.98 90.00 | 2.1 Å 0.222/0.268 |

TABLE 1-continued

Summary of crystallisation conditions and crystallographic parameters for various compounds

| Fragment/ FIG.(s) | Compound/ Ligand (final concentration) | Crystallisation reservoir condition | Space group and unit cell parameters | Resolution Refinement R-factor/R-free |
|---|---|---|---|---|
| PA H1N1 1 to 198 fragment (SEQ ID NO: 13) (chain A), see FIGS. 2 and 7 PA H1N1 fragment (chain D), see FIGS. 3 and 8 | EMBL-R05-3 (1.5 mM) | 2.0M ammonium sulphate 0.1M BisTris pH 5.5 | $P\,2_1\,2_1\,2_1$ 4 Molecules/ASU 54.57 122.54 129.78 90.00 90.00 90.00 | 2.5 Å 0.205/0.276 |
| PA H1N1 1 to 198 fragment (SEQ ID NO: 13) (chain A), see FIGS. 4 and 9 | EMBL-R05-2 (1.5 mM, soaked into crystals initially grown with rUMP) | 0.1M ammonium sulphate 0.1M Bis-Tris pH 5.5 25% (w/v) PEG 3350 | $P\,2_1\,2_1\,2_1$ 4 Molecules/ASU 56.59 120.81 128.20 90.00 90.00 90.00 | 2.07 Å 0.205/0.259 |
| PA H1N1 1 to 198 fragment (chain A), see FIGS. 5 and 10 | rUMP (5.0 mM) | 0.1M ammonium sulphate 0.1M Bis-Tris pH 5.5 25% (w/v) PEG 3350 | $P\,2_1\,2_1\,2_1$ 4 Molecules/ASU 54.94 120.11 128.05 90.00 90.00 90.00 | 2.05 Å 0.206/0.246 |
| PA H1N1 1-198 Δ52-64: Gly Fragment (SEQ ID NO: 14) (chain A) see FIGS. 15 and 17 | EMBL-R05-1 (1.5 mM, soaked into crystals initially grown with dTMP) | 25-30% PEG4K 0.1M Tris pH 8.5 0.2M NaCl | $P\,6_2 22$ (180) 1 molecule/ASU a = b = 75.06 c = 120.05 Å | 1.9 Å 0.201/0.251 |
| PA H1N1 1-198 Δ52-64: Gly Fragment (SEQ ID NO: 14) (chain A) see FIGS. 16 and 18 | EGCG (5 mM) | 10% peg 3350, 0.1M NaCl, 0.1M Hepes, pH 7.0 | $P6_4 22$ (181) 1 molecule/ASU a = b = 99.9 c = 82.7 Å | 2.65 Å 0.250/0.304 |

TABLE 2

Compounds used

| Compound | CA Index Name | Formula | Chemical structure |
|---|---|---|---|
| EMBL-R05-3 (Tomassini et al. Antimicrob Agents Chemother 1994, 38:2827-2837) | 4-[3-[(4-chlorophenyl)methyl]-1-(phenylmethyl)-3-piperidinyl]-2-hydroxy-4-oxo-2-butenoic acid | C23 H24 Cl N O4 | 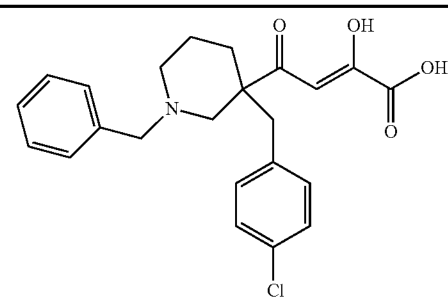 |

TABLE 2-continued

Compounds used

| Compound | CA Index Name | Formula | Chemical structure |
|---|---|---|---|
| EMBL-R05-2 (Tomassini et al. Antimicrob Agents Chemother 1994, 38:2827-2837) | 4-[4-[(4-chlorophenyl)methyl]-1-(cyclohexylmethyl)-4-piperidinyl]-2-hydroxy-4-oxo-2-butenoic acid | C23 H30 Cl N O4 | 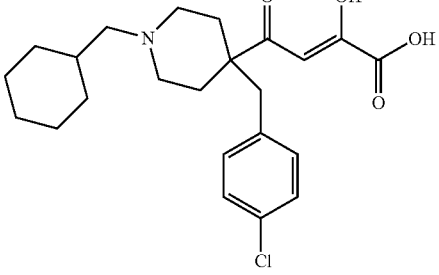 |
| rUMP (ribo-uridine monophosphate) | 5'-Uridylic acid | C9 H13 N2 O9 P | 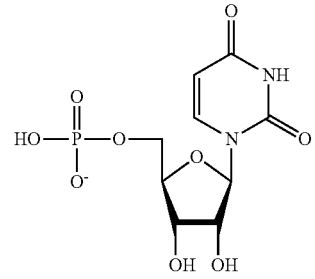 |
| EMBL-R05-1 (Tomassini et al. Antimicrob Agents Chemother 1994, 38:2827-2837) | 4-[3-[(4-chlorophenyl)methyl]-1-(phenylmethylsulpho)-3-piperidinyl]-2-hydroxy-4-oxo-2-butenoic acid | C23 H24 Cl N S O6 | 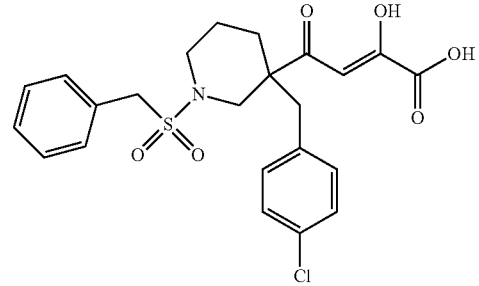 [SMILES: O=C(O)/C(O)=C/C(=O)C1(Cc2ccc(Cl)cc2)CCCN(S(=O)(=O)Cc2ccccc2)C1] |
| (−)-Epigallocatechin gallate (EGCG) | [(2R,3R)-5,7-dihydroxy-2-(3,4,5-trihydroxyphenyl)chroman-3-yl]3,4,5-trihydroxybenzoate | C22 H18 O11 | 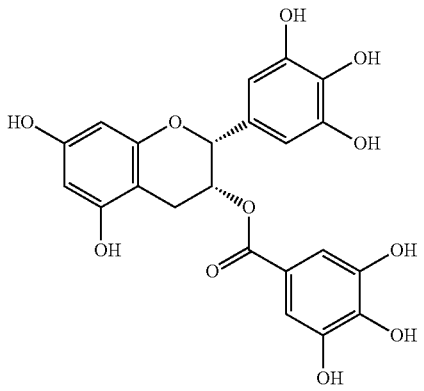 [SMILES: O=C(O[C@@H]1Cc2c(O)cc(O)cc2O[C@@H]1c1cc(O)c(O)c(O)c1)c1cc(O)c(O)c(O)c1] |

1.4 Crystal Structure Determination

Diffraction data were collected on various beamlines at the European Synchrotron Radiation Facility. Data sets were integrated with XDS and scaled with XSCALE. Subsequent data analysis was performed with the CCP4i programme suite. The initial H1N1 structure was solved with molecular replacement with PHASER using the previously determined H3N2 PA N-ter structure (Dias et al., Nature 2009). Subsequent co-crystal structures were determined with PHASER using the H1N1 structure. Refinement was carried out with REFMAC and/or model building with COOT or O. In the C2 and $P2_12_12_1$ crystal forms there are four molecules per asymmetric unit. However due to structural variations between the molecules due to plasticity (in particular the 53-73 region) and the generally good resolution, NCS restraints were not applied.

2. Results 2.1 PA H1N1 Polypeptide Fragment or PA H1N1 Polypeptide Fragment Variant Generation and Crystallisation The inventors of the present invention found that a polypeptide fragment comprising amino acids 1 to 198 of SEQ ID NO: 2 of influenza strain A/California/04/2009-

H1N1 (2009 pandemic strain) (PA H1N1 1 to 198) readily crystallised with and without relevant compounds/ligands (see FIGS. 1 to 10). Crystallisation properties could further be improved with a polypeptide fragment variant comprising amino acids 1 to 198 of SEQ ID NO: 2 of influenza strain A/California/04/2009-H1N1 (2009 pandemic strain) with amino acids 52 to 64 replaced by the amino acid glycine (PA H1N1 1 to 198 Δ52-64: Gly) (see FIGS. 15 to 18).

Thus, in contrast to the numerous unsuccessful attempts undertaken in the prior art, the inventors of the present invention were able to obtain structures of PA H1N1 polypeptide fragments or PA H1N1 polypeptide fragment variants with and without compounds/ligands.

The structures of PA H1N1 polypeptide fragments or PA H1N1 polypeptide fragment variants with and without compounds/ligands are described below. All these structures show in detail how these compounds/ligands bind directly to the metal ions as well as interacting with a number of residues in the active site. Furthermore several of the interacting residues change conformation upon ligand binding, information which was unavailable before. This three-dimensional knowledge of the ligand interacting residues and the regions of plasticity of the active site is critical for the optimised design of modifications to existing inhibitors to improve their potency or for structure based design and optimisation of novel inhibitors that effectively block endonuclease activity.

2.2 H1N1 PA Native Structure

Structural co-ordinates of the native (i.e. without compound/ligand) H1N1 PA endonuclease domain (PA H1N1 1 to 198(SEQ ID NO:13)) (chain A) in standard Protein Data Bank (PDB) format are shown in FIG. 1. Only the chain A (with associated divalent cations, i.e. one magnesium and one manganese ion, and water molecules) from the asymmetric unit is included. Chains B, C and D are very similar. A diagram using the structural co-ordinates of FIG. 1 illustrating the endonuclease active site (PA polypeptide fragment (chain A)) is shown in FIG. 6. It shows the divalent cations (one manganese and one magnesium) and key active site residues.

2.3 EMBL-R05-3-Bound Structure

Structural co-ordinates of the H1N1 PA endonuclease domain (PA H1N1 1 to 198(SEQ ID NO:13)) (chain A) with bound 4-[3-[(4-chlorophenyl)methyl]-1-(phenylmethyl)-3-piperidinyl]-2-hydroxy-4-oxo-2-butenoic acid (EMBL-R05-3) in standard Protein Data Bank (PDB) format are shown in FIG. 2. Only the chain A (with associated divalent cations, i.e. two manganese ions, and water molecules) from the asymmetric unit is included. The compound EMBL-R05-3 has residue descriptor ci3. A diagram using the structural co-ordinates of FIG. 2 illustrating the endonuclease active site (PA polypeptide fragment (chain A)) is shown in FIG. 7A. It shows the bound compound EMBL-R05-3, the divalent cations (two manganese) and key active site residues that interact with the compound (notably Arg84) or are close to it.

A diagram comparing the co-ordinates of FIG. 1 (chain subjacent on left hand side) and FIG. 2 showing change in conformation of the loop in the vicinity of Tyr24 upon binding of EMBL-R05-3 (chain A) is shown in FIG. 7B. The loop around Tyr24 is poorly ordered in the native structure. Tyr24 side-chain moves to partially stack with the chlorobenzene of EMBL-R05-3. This indicates a plasticity of the active site and an induced fit mode of ligand binding. An important conclusion for designing more potent inhibitors is to ensure that the extensions ('arms') to any ion-binding scaffold optimise interactions in one or more pocket(s).

Imperfect matching will lead to residual flexibility and sub-optimal potency, as seems to be the case for the current compounds, none of which exhibit very well defined, full occupancy binding modes.

Further, structural co-ordinates of the H1N1 PA endonuclease domain (PA H1N1 1 to 198(SEQ ID NO:13)) (chain D) with bound 4-[3-[(4-chlorophenyl)methyl]-1-(phenylmethyl)-3-piperidinyl]-2-hydroxy-4-oxo-2-butenoic acid (EMBL-R05-3) in standard Protein Data Bank (PDB) format are shown in FIG. 3. Only the chain D (with associated divalent cations, i.e. two manganese ions, and water molecules) from the asymmetric unit is included. The compound EMBL-05-3 has a different configuration than in chain A (FIG. 2). Said compound has residue descriptor ci3. A diagram using the structural co-ordinates of FIG. 3 illustrating the endonuclease active site (PA polypeptide fragment (chain D)) is shown in FIG. 8. It shows the bound compound EMBL-R05-3, the divalent cations (two manganese) and key active site residues that interact with the compound (notably Tyr24 and Arg84) or are close to it.

2.4 EMBL-R05-2-Bound Structure

Structural co-ordinates of the H1N1 PA endonuclease domain (PA H1N1 1 to 198 (SEQ ID NO:13)) (chain A) with bound 4-[4-[(4-chlorophenyl)methyl]-1-(cyclohexylmethyl)-4-piperidinyl]-2-hydroxy-4-oxo-2-butenoic acid (EMBL-R05-2) in standard Protein Data Bank (PDB) format are shown in FIG. 4. Only the chain A (with associated divalent cations, i.e. two manganese ions, and water molecules) from the asymmetric unit is included. Chains B, C and D are very similar. The compound EMBL-R05-2 has residue descriptor cit. A diagram using the structural co-ordinates of FIG. 4 illustrating the endonuclease active site (PA polypeptide fragment (chain A)) is shown in FIG. 9. It shows the bound compound EMBL-R05-2, the divalent cations (two manganese) and key active site residues that interact with the compound (notably Tyr24 and Phe105) or are close to it.

2.5 Ribo-Uridine Monosphosphate (rUMP)-Bound Structure

Structural co-ordinates of the H1N1 PA endonuclease domain (PA H1N1 1 to 198 (SEQ ID NO:13)) (chain A) with bound ribo-Uridine Monophosphate (rUMP) in standard Protein Data Bank (PDB) format are shown in FIG. 5. Only the chain A (with associated divalent cations, i.e. two manganese ions, and water molecules) from the asymmetric unit is included. Chains B, C and D are very similar. The compound rUMP has residue descriptor U.

Co-crystallisation trials with rUMP gave large, well-ordered crystals in a new orthorhombic space-group (FIGS. 12 and 14).

A diagram using the structural co-ordinates of FIG. 5 illustrating the endonuclease active site (PA polypeptide fragment (chain A)) is shown in FIG. 10. It shows the bound compound rUMP, the divalent cations (two manganese) and key active site residues that interact with the compound (notably Tyr24 and Lys34) or are close to it. The rUMP binds with two oxygens of the phosphate completing the co-ordination sphere of Mn1, one of them also co-ordinating Mn2. The base is well stacked on Tyr24 and Lys34 makes a hydrogen bond to the 02 position. The ribose hydroxyl groups do not make hydrogen bonds to the protein, consistent with the fact that deoxy ribose binds equally well and the protein is a DNAase as much as an RNAase {Dias, 2009 #448}.

The conformation observed for rUMP is quite different from that previously published (PDB entry 3hw3 {Zhao, 2009 #444}). The latter structure was obtained by soaking nucleotides into existing crystals of the endonuclease in the absence of manganese and the electron density is very poor. In this structure, a water molecule replaces Mn1 and a magnesium ion replaces Mn2. This difference in metal ligation is reflected in the altered conformation of Glu119. The ribose and base positions are quite different from the positions in the structure provided herein and unable to interact with Lys34 or Tyr24. The differences between the two structures may reflect firstly the lack of manganese and secondly the fact that soaking pre-grown crystals does not allow the active site to adapt to the ligand as is more likely the case for co-crystallisation.

2.6 EMBL-R05-1-Bound Structure

Figure 17:
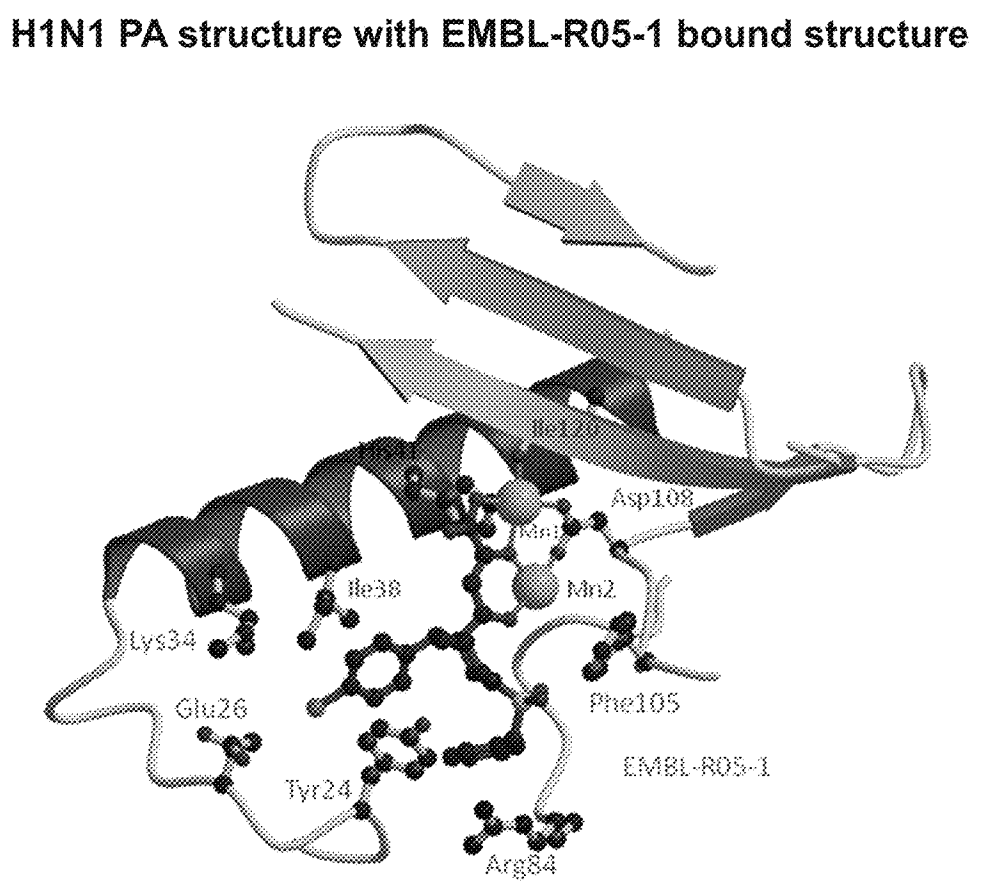

Structural co-ordinates of the H1N1 PA endonuclease domain (PA H1N1 1 to 198 Δ52-64: Gly (SEQ ID NO:14)) with bound 4-[3-[(4-chlorophenyl)methyl]-1-(phenylmethylsulpho)-3-piperidinyl]-2-hydroxy-4-oxo-2-butenoic acid (EMBL-R05-1) in standard Protein Data Bank (PDB) format are shown in FIG. 15. The chain (with associated divalent cations, i.e. two manganese ions, and water molecules) from the asymmetric unit is included. The compound EMBL-R05-1 has residue descriptor ci1. A diagram using the structural co-ordinates of FIG. 15 illustrating the endonuclease active site (PA polypeptide fragment) is shown in FIG. 17. It shows the bound compound EMBL-R05-1, the divalent cations (two manganese) and key active site residues that interact with the compound (notably Tyr24 and Arg84) or are close to it.

2.7 EGCG-Bound Structure

Epigallocatechin 3-gallate (EGCG), is the ester of epigallocatechin and gallic acid and is the most abundant catechin in green tea. It has recently been reported that EGCG inhibits the influenza endonuclease {Kuzuhara, 2009 #629}. Co-crystallisation of PA H1N1 1 to 198 Δ52-64: Gly (SEQ ID NO:14) with (–)-Epigallocatechin gallate gave a new crystal form (Table 1) diffracting to 2.65 Å resolution. The compound was clearly observed in the active site. Strong extra density also exists around a 2-fold crystallographic axis and most likely represents other EGCG molecules trapped by crystal packing.

Figure 18A:
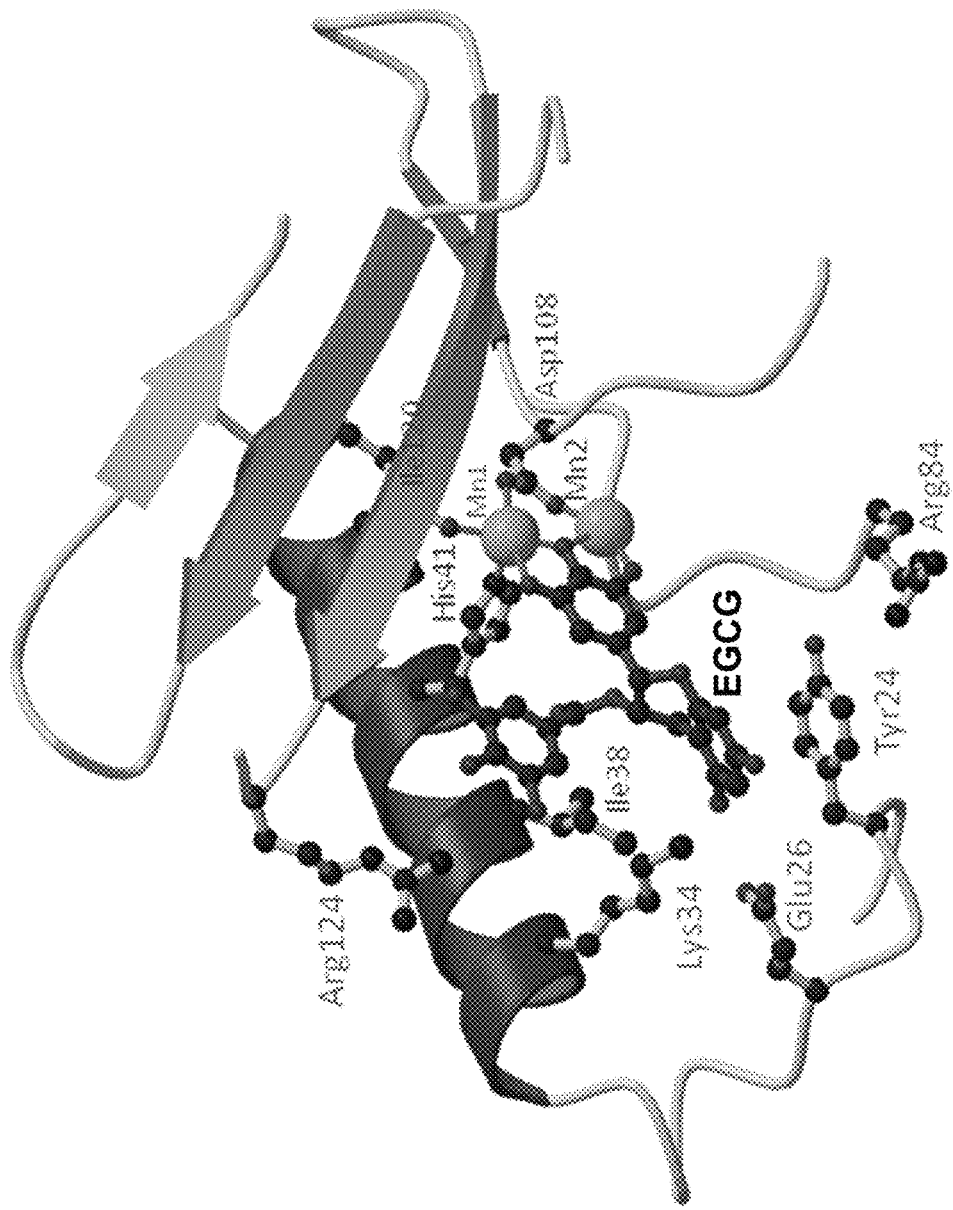
Figure 18B:
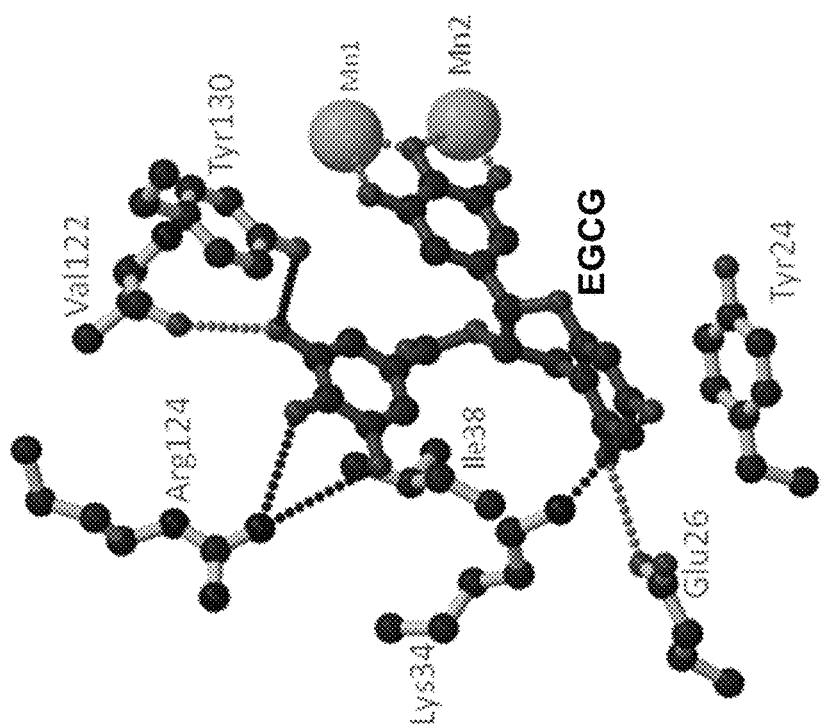

Structural co-ordinates of the H1N1 PA endonuclease domain (PA H1N1 1 to 198 Δ52-64: Gly (SEQ ID NO:14)) with bound epigallocatechin 3-gallate (EGCG) in standard Protein Data Bank (PDB) format is shown in FIG. 16. The chain (with associated divalent cations, i.e. two manganese ions, and water molecules) from the asymmetric unit is included. The compound EGCG has residue descriptor tte. A diagram using the structural co-ordinates of FIG. 16 illustrating the endonuclease active site (PA polypeptide fragment) is shown in FIG. 18A. It shows the bound compound EGCG, the divalent cations (two manganese ions) and key active site residues that interact with the compound or are close to it. FIG. 18B shows the bound EGCG, the divalent cations (two manganese ions) and key active site residues that interact with the compound or are close to it. Interactions less than 3.3 Å (grew dotted lines), additional possible interactions less than 4 Å (dark grey dotted lines) are shown.

2.8 Superposition of all Diketo Inhibitor Compounds

Figure 19:
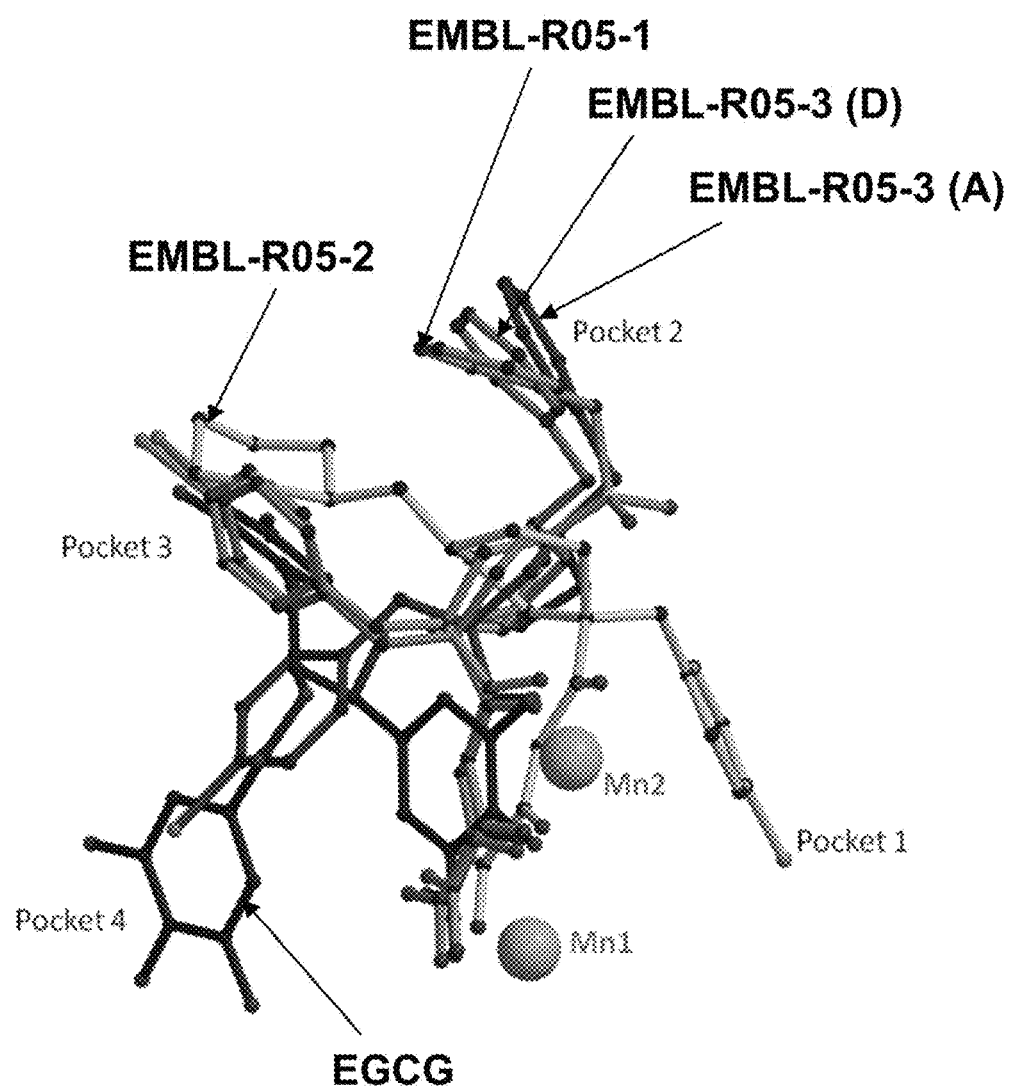
FIG. 19: Superposition of all diketo inhibitor compounds (EMBL-R05-1, EMBL-R05-2, and EMBL-R05-3A and D) and EGCG bound in PA active site.

A superposition of all diketo inhibitor compounds (EMBL-R05-1, EMBL-R05-2, and EMBL-R05-3A and D) and EGCG bound in PA active site is shown in FIG. 19. As shown in FIG. 19, the mode of binding of the three diketo inhibitors to the metals is conserved (although there is some variability in exact position) but the two 'arms' of each compound are inserted into different combinations of the pockets 1 to 4. EMBL-R05-1 has a similar configuration to EMBL-R05-3D, with the two arms occupying pockets 2 and 3. EMBL-R05-3A occupies pockets 2 and 4. EMBL-R05-2, which differs notably from R05-1 and R05-3 in the point of substitution on the piperidinyl ring (Table 2) occupies pocket 3 and uniquely pocket 1 (FIG. 7B). The green tea compound EGCG occupies pockets 3 and 4. More potent and specific compounds could be perhaps designed that occupy more than two of the pockets.

2.9 Divalent Cation Binding

Figure 13:
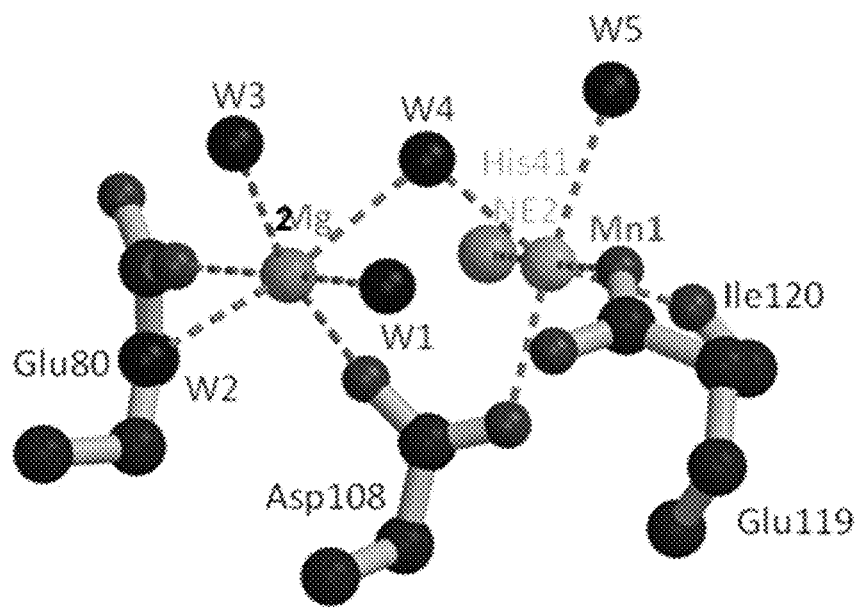
Figure 14:
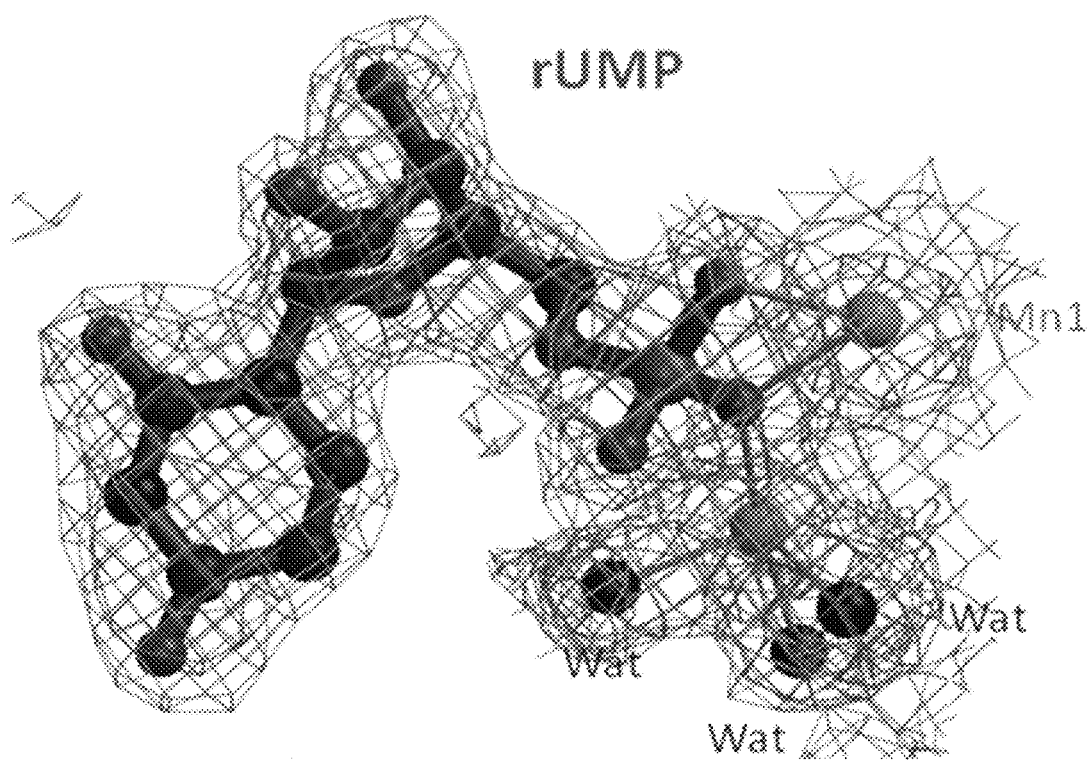

In the native structure (FIG. 1 and FIG. 6), two divalent cations are observed in the active site. These are identified (using magnitude of electron density and anomalous scattering, data not shown) to be a manganese atom in site 1 (Mn1 in FIG. 13), ligated by His41, Asp108, Glu119, Ile120 and two water molecules (W4 and W5) and a magnesium ion in site 2 (Mg2 in FIG. 13), ligated by Glu80 and Asp108 and four water molecules (W1, W2, W3 and W4). In the other structures (FIGS. 2-5 and FIGS. 7-10 as well as FIGS. 15-18) the ions in both site 1 and site 2 are manganese ions (Mn1 and Mn2), as identified by magnitude of electron density and anomalous scattering (e.g. for rUMP, see FIG. 14).

---

The invention claimed is:

1. A polypeptide fragment comprising an N-terminal fragment of the PA subunit of a viral RNA-dependent RNA polymerase possessing endonuclease activity, wherein said PA subunit has at least 95% sequence identity to SEQ ID NO: 2 having a maximum length of 240 amino acids, wherein the N-terminus is identical to or corresponds to amino acid position 1 and the C-terminus is identical to or corresponds to an amino acid at a position selected from positions 190 to 198 of the amino acid sequence of the PA subunit according to SEQ ID NO: 2, or is a variant thereof, wherein said variant comprises the amino acid serine at an amino acid position 186 according to SEQ ID NO: 2 or at an amino acid position corresponding thereto.

2. The polypeptide fragment of claim 1, which is soluble and remains in the supernatant after centrifugation for 30 min at 100,000×g in an aqueous buffer under physiologically isotonic conditions.

3. The polypeptide fragment of claim 1, which is crystallizable.

4. The polypeptide fragment of claim 1, wherein the N-terminal fragment has at least amino acids 1 to 190 of the PA subunit of the RNA-dependent RNA polymerase of Influenza A 2009 pandemic H1N1 virus according to SEQ ID NO: 2.

5. The polypeptide fragment of claim 1, wherein said polypeptide fragment is purified to an extent to be suitable for crystallization and is at least 85% pure.

6. The polypeptide fragment of claim 1 to which two divalent cations are bound.

7. The polypeptide fragment of claim 6, wherein the divalent cation is manganese and/or magnesium.

8. The polypeptide fragment of claim 1, which (a) consists of amino acids 1 to 198 of the amino acid sequence set forth in SEQ ID NO: 2 and of an N-terminal linker having the amino acid sequence MGSGMA (SEQ ID NO: 3) and which has the structure defined by (i) the structure coordinates as shown in FIG. 1, (ii) the structure coordinates as shown in FIG. 2, (iii) the structure coordinates as shown in FIG. 3, (iv) the structure coordinates as shown in FIG. 4, or (v) the structure coordinates as shown in FIG. 5, or (b) consists of amino acids 1 to 198 of the amino acid sequence set forth in SEQ ID NO: 2 with amino acids 52 to 64 replaced by the amino acid glycine and of an N-terminal linker having the amino acid sequence MGSGMA (SEQ ID NO: 3) and which has the structure defined by (vi) the structure coordinates as shown in FIG. 15, or (vii) the structure coordinates as shown in FIG. 16.

9. The polypeptide fragment of claim 8, wherein the polypeptide fragment having the structure defined by (i) has a crystalline form with space group C2 and unit cell dimensions of a=26.36 nm±0.5 nm, b=6.62 nm±0.3 nm, c=6.63 nm±0.3 nm, $\alpha$=90 deg, $\beta$=96±2 deg, $\gamma$=90 deg, (ii) to (v) has a crystalline form with space group $P2_12_12_1$ and unit cell dimensions of a=5.46±0.3 nm, b=12.25±0.4 nm, c=13.0±0.3 nm, $\alpha$=90 deg, $\beta$=90 deg, $\gamma$=90 deg, (vi) has a crystalline form with space group $P6_222$ and unit cell dimensions of a=7.50 nm±0.3 nm, b=7.50 nm±0.3 nm, c=12.00 nm±0.5 nm, $\alpha$=90 deg, $\beta$=90 deg, $\gamma$=120 deg, or (vii) has a crystalline form with space group $P6_422$ and unit cell dimensions of a=9.99 nm±0.5 nm, b=9.99 nm±0.5 nm, c=8.27 nm±0.3 nm, $\alpha$=90 deg, $\beta$=90 deg, $\gamma$=120 deg.

10. The polypeptide fragment of claim 8, wherein the crystal diffracts X-rays to a resolution of 2.6 Å, 2.1 Å, 1.9 Å or higher.

11. The polypeptide fragment of claim 8, wherein the polypeptide fragment has a crystalline form, and the crystal diffracts X-rays to a resolution of 2.1 Å or higher.

12. The polypeptide fragment of claim 8, wherein the polypeptide fragment has a crystalline form, and the crystal diffracts X-rays to a resolution of 1.9 Å or higher.

13. A polypeptide consisting of the amino acid sequence according to SEQ ID NO:14.

14. The polypeptide of claim 13, wherein the polypeptide is in a crystal form selected from the group consisting of a crystal in space group $P6_222$ with unit cell dimensions of a=75.0 Å±3 Å, b=75.0 Å±3 Å, c=120.0 Å±5 Å, $\alpha$=90 deg, $\beta$=90 deg, $\gamma$=120 deg, or a crystal in space group $P6_422$ with unit cell dimensions of a=99.9 Å±5 Å, b=99.9 Å±5 Å, c=82.7 Å±3 Å, $\alpha$=90 deg, $\beta$=90 deg, $\gamma$=120 deg.

* * * * *